(12) United States Patent
Ungashe et al.

(10) Patent No.: US 11,433,061 B2
(45) Date of Patent: *Sep. 6, 2022

(54) HETEROARYL SULFONAMIDES AND CCR2/CCR9

(71) Applicant: ChemoCentryx, Inc., Mountain View, CA (US)

(72) Inventors: Solomon Ungashe, Fremont, CA (US); Zheng Wei, Union City, CA (US); Arindrajit Basak, Mountain View, CA (US); Trevor T. Charvat, San Jose, CA (US); Wei Chen, Fremont, CA (US); Jeff Jin, Fremont, CA (US); Jimmie Moore, Redwood City, CA (US); Yibin Zeng, San Mateo, CA (US); Sreenivas Punna, Palo Alto, CA (US); Daniel Dairaghi, Palo Alto, CA (US); Derek Hansen, San Francisco, CA (US); Andrew M. K. Pennell, San Francisco, CA (US); John J. Wright, Redwood City, CA (US); Antoni Krasinski, Mountain View, CA (US); Qiang Wang, Sunnyvale, CA (US)

(73) Assignee: ChemoCentryx, Inc., San Carlos, CA (US)

(*) Notice: Subject to any disclaimer, the term of this patent is extended or adjusted under 35 U.S.C. 154(b) by 121 days.

This patent is subject to a terminal disclaimer.

(21) Appl. No.: 16/739,204

(22) Filed: Jan. 10, 2020

(65) Prior Publication Data

US 2020/0147066 A1 May 14, 2020

Related U.S. Application Data

(60) Continuation of application No. 16/272,401, filed on Feb. 11, 2019, now Pat. No. 10,532,044, which is a continuation of application No. 15/383,788, filed on Dec. 19, 2016, now Pat. No. 10,206,912, which is a division of application No. 13/938,119, filed on Jul. 9, 2013, now abandoned, which is a continuation of application No. 12/309,314, filed as application No. PCT/US2007/015893 on Jul. 12, 2007, now Pat. No. 8,519,135, which is a continuation-in-part of application No. 11/486,974, filed on Jul. 14, 2006, now Pat. No. 7,622,583.

(51) Int. Cl.
| | |
|---|---|
| A61K 31/444 | (2006.01) |
| C07C 311/21 | (2006.01) |
| C07D 213/75 | (2006.01) |
| C07D 241/22 | (2006.01) |
| C07D 401/06 | (2006.01) |
| C07D 401/10 | (2006.01) |
| C07D 407/04 | (2006.01) |
| C07D 409/12 | (2006.01) |
| C07D 413/06 | (2006.01) |
| C07D 417/12 | (2006.01) |
| C07D 471/04 | (2006.01) |
| C07D 498/04 | (2006.01) |
| A61K 31/437 | (2006.01) |
| A61K 31/4439 | (2006.01) |
| A61K 45/06 | (2006.01) |

(52) U.S. Cl.
CPC .......... *A61K 31/444* (2013.01); *A61K 31/437* (2013.01); *A61K 31/4439* (2013.01); *A61K 45/06* (2013.01); *C07C 311/21* (2013.01); *C07D 213/75* (2013.01); *C07D 241/22* (2013.01); *C07D 401/06* (2013.01); *C07D 401/10* (2013.01); *C07D 407/04* (2013.01); *C07D 409/12* (2013.01); *C07D 413/06* (2013.01); *C07D 417/12* (2013.01); *C07D 471/04* (2013.01); *C07D 498/04* (2013.01)

(58) Field of Classification Search
None
See application file for complete search history.

(56) References Cited

U.S. PATENT DOCUMENTS

| | | |
|---|---|---|
| 3,901,855 A | 8/1975 | Arnold |
| 4,166,452 A | 9/1979 | Generales |
| 4,256,108 A | 3/1981 | Theeuwes |
| 4,265,874 A | 5/1981 | Bonsen et al. |
| 5,292,758 A | 3/1994 | Yoshino et al. |
| 5,446,139 A | 8/1995 | Seela et al. |
| 5,571,775 A | 11/1996 | Van Heertum et al. |
| 5,780,488 A | 7/1998 | Bergman et al. |
| 5,973,148 A | 10/1999 | Ringer et al. |
| 6,380,206 B1 | 4/2002 | Pamukcu et al. |
| 6,403,607 B1 | 6/2002 | Hidaka et al. |
| 6,451,339 B2 | 9/2002 | Patel et al. |
| 6,479,527 B1 | 11/2002 | Barker et al. |
| 6,489,452 B1 | 12/2002 | Tateishi et al. |
| 6,939,885 B2 | 9/2005 | Ungashe et al. |
| 7,282,502 B2 | 10/2007 | Fleming et al. |
| 7,622,583 B2 | 11/2009 | Ungashe et al. |
| 7,884,110 B2 | 2/2011 | Krasinski et al. |
| 8,093,247 B2 | 1/2012 | Ungashe et al. |
| 8,519,135 B2 | 8/2013 | Chen et al. |

(Continued)

FOREIGN PATENT DOCUMENTS

| | | |
|---|---|---|
| DE | 3825041 A1 | 2/1990 |
| EP | 0472053 B1 | 6/1998 |

(Continued)

OTHER PUBLICATIONS

Amann et al., Diabetes Care, 26:2421-5 (2003).

(Continued)

*Primary Examiner* — Heidi Reese
(74) *Attorney, Agent, or Firm* — Barnes & Thornburg LLP; Ryan L. Marshall

(57) ABSTRACT

Compounds are provided that act as potent antagonists of the CCR2 receptor. Animal testing demonstrates that these compounds are useful for treating inflammation, a hallmark disease for CCR2. The compounds are generally aryl sulfonamide derivatives and are useful in pharmaceutical compositions, methods for the treatment of CCR2-mediated diseases, and as controls in assays for the identification of CCR2 antagonists.

16 Claims, 1 Drawing Sheet

(56) References Cited

U.S. PATENT DOCUMENTS

| | | |
|---|---|---|
| 2002/0052363 A1 | 5/2002 | Dinsmore et al. |
| 2002/0103202 A1 | 8/2002 | Pinto et al. |
| 2003/0229081 A1 | 12/2003 | Maduskuie |
| 2004/0023286 A1 | 2/2004 | Wei |
| 2004/0038976 A1 | 2/2004 | Fleming et al. |
| 2006/0173019 A1 | 8/2006 | Ungashe et al. |
| 2007/0021466 A1 | 1/2007 | Ungashe et al. |
| 2007/0037794 A1 | 2/2007 | Ungashe et al. |
| 2011/0319433 A1 | 12/2011 | Krasinski et al. |
| 2014/0100237 A1 | 4/2014 | Krasinski et al. |

FOREIGN PATENT DOCUMENTS

| | | |
|---|---|---|
| EP | 0937711 A1 | 8/1999 |
| EP | 1334719 A2 | 8/2003 |
| JP | 61113060 A2 | 5/1986 |
| JP | 04364168 A2 | 12/1992 |
| JP | 6135934 A2 | 5/1994 |
| JP | 06145145 A | 5/1994 |
| JP | 2000159665 A2 | 6/2000 |
| JP | 2001089412 A2 | 4/2001 |
| JP | 2003040726 A2 | 2/2003 |
| WO | 199420142 A1 | 9/1994 |
| WO | 1998011218 A1 | 3/1998 |
| WO | 9942439 A1 | 8/1999 |
| WO | 2000040560 A1 | 7/2000 |
| WO | 0100611 A1 | 1/2001 |
| WO | 2001002369 A2 | 1/2001 |
| WO | 0172744 A1 | 10/2001 |
| WO | 2002101350 A2 | 12/2002 |
| WO | 03032994 A2 | 4/2003 |
| WO | 03051870 A1 | 6/2003 |
| WO | 2003099773 A1 | 12/2003 |
| WO | 2004056774 A2 | 7/2004 |
| WO | 2004058164 A2 | 7/2004 |
| WO | 2004058265 A1 | 7/2004 |
| WO | 2004099127 A1 | 11/2004 |
| WO | 2004105794 A2 | 12/2004 |
| WO | 2005004810 A2 | 1/2005 |
| WO | 2005028445 A2 | 3/2005 |
| WO | 2005112925 A1 | 12/2005 |
| WO | 2006076644 A2 | 7/2006 |
| WO | 2007014008 A2 | 2/2007 |
| WO | 2007014054 A2 | 2/2007 |

OTHER PUBLICATIONS

Babu et al., Journal of Infectious Diseases, 191: 1018-26, (2005).
Baker, B.R., et al., "Puromycin. Synthetic studies. II. The position of glycosidation on the 6-dimethylaminopurine moiety," 19(4) J. Org. Chem. 638-645 (1954).
Beilstein Data XP002464251 (BRN:7928945) (2000).
Beilstein Data XP002464252 (BRN:7313089) (1995).
Beilstein Data XP002464253 (BRN:329227) (1949).
Beilstein Data XP002464254 (BRN:7102156) (1987).
Beilstein Data XP002464255 (BRN:6875780) (1983).
Bendele et al., Arthritis Rheum. 42:498-506 (1999).
Bendele et al., Toxicologic Pathol. 27:134-142 (1999).
Berman et al.,Immunol. Invest., 17, pp. 625-677,(1988).
Berqe, S.M. et ai, "Pharmaceutical Salts", J. Pharmaceutical Science, 66; pp. 1-19, (1977).
Bredereck, Hellmutt, et al., "Synthesen in der Purinreihe. XVI. Uber die Darstellung von 5-Alkyl-bzw.5-Arylsulfonylamino-4-aminouracilen, 4-Amino-5- alkylamino-uracilen und 4-Amino-5-[pyridiniomethylenamino]-uracil-chloriden," Chemische Berichte, 95:1902-1909 (1962).
Broek et al., Br. J. Cancer, 88(6): pp. 855-862, (2003).
Campbell, et al., J. Exp. Med., 195(1), pp. 135-141, (2002).
Christiansen T, et al., Int. J. Obes. (Lond). 29(1): pp. 146-150 (2005).
Dahinden, et al., J. Exp. Med., 179, pp. 751-756, (1994).
Dai et al., Chin. Med. J. (Engl), 114: pp. 864-868 (2001).
Davidson et al., J Exp Med., 184, pp. 241-251, (1996).
Deleuran et al., J. Dermatol. Sci., 13(3):228-36 (1996).
Diamond et al., Am. J. Physiol., 266: F926-33 (1994).
Eddy & Giachelli, Kidney Int., 47: pp. 1546-1557, (1995).
Ellingson, Rudolph C., et al., "Pyrazine chemistry. 111. Derivatives of 3- amino-5,6-dimethylpyrazinoic acid," 70(3) J. Am. Chem. Soc. 1257-1261 (1948).
Gillitzer et al., J. Invest. Dermatol., 101(2): pp. 127-131, (1993).
Gong et al., J. Exp. Med., 186: pp. 131-137, (1997).
Gonzalez-Cuadrado et al. Clin. Exp. Immunol., 106: pp. 518-522, (1996).
Hiroshi, Y., et al., "Novel Sulfonamides as potential systemically active antitumor agents," 35(13) J. Med. Chem. 2496-2497 (1992).
International Search Rept. App. No. PCT/US2007/015893 (2008).
Kavanaugh et al., J. Immunol., 146, pp. 4149-4156, (1991).
Kitaqawa et al., Am. J. Pathol., 165: DD. 237-46, (2004).
Kontoyiannis et al., Immunity, 10, DD. 387-398, (1999).
Kontoyiannis et al., J. Exp. Med., vol. 196, No. 12, (2002).
Kosiewicz et al., J Clin Invest., 107(6), pp. 695-702, (2001).
Kunkel, et al., J. Exp. Med. 192(5), pp. 761-767, (2000).
Kuse, Masaki, et al., "Novel synthetic route of aryl-aminopyrazine," Tetrahedron, 60:835-840 (2004).
Lloyd et al. J. Exp. Med., 185: pp. 1371-1380, (1997).
McDonald, Francis G., et al., "Pyrazine chemistry. II. Derivatives of 3- hydroxypyrazinoic acid," 69(5) J. Am. Chem. Soc 1034-1037 (1947).
Mine, et al., "Increased expression levels of monocyte CCR2 and monocyte chemoattractant protein-1 in patients with diabetes mellitus," Biochemical and Biophysical Research Communications, 344(3): pp. 780-785 (2006).
Morii et al., J Diabetes Complications, 17:11-5 (2003).
Murphy, Rev. Immun., 12, pp. 593-633, (1994).
Neote, et al., Cell, 72, pp. 415-125, (1993).
Ogata et al., J Pathol., 182:pp. 106-114, (1997).
Panwala, et al., J Immunol., 161(10), pp. 5733-5744, (1998).
Papadakis et al., Gastroenterology, 121(2): pp. 246-254 (2001).
Papadakis, et al., J Immunol., 165(9), pp. 5069-5076, (2000).
Plater-Zyberk et al., Immunol. Lett., 57: pp. 117-120, (1997).
Powrie et al., Int. Immunol., 5(11), pp. 1461-1471, (1993).
Qiuping Z et al., Cancer Res., 63, pp. 6469-6477, (2003).
Rivera-Nieves, et al., Gastroenterology, 131 (5): pp. 1518-1529, (2006).
Sartipy et al., Proc. Natl. Acad. Sci. U.S.A., 100: pp. 7265-7270. (2003).
Scaife et al., Rheumatology (Oxford), 43: pp. 1346-1352, (2004).
Schall, Cytokine, 3, pp. 165-183, (1991).
Schall, et al., Curr. Opin. Immunol., 6, pp. 865-873, (1994).
Science IP Search Results (Dec. 16, 2004).
Science IP Search Results (Mar. 29, 2006).
Scifinder Search Results (Jan. 24, 2006)—ether linker.
Scifinder Search Results (Jan. 24, 2006)—keto linker.
Segerer et al., J Am. Soc. Nephrol., 11:152-76 (2000).
Sell et al., "Monocyte Chemotactic Protein-1 Is a Potential Player in the Negative Cross-Talk between Adipose Tissue and Skeletal Muscle", Endocrinology, 2458-67 (2006).
Shadidi et al., Scand. J Immunol., 57:192-8 (2003).
Shimizu et al., J Am. Soc. Nephrol., 14:1496-505 (2003).
Sprecher, M., et al., "Methylated purines and pyrimidines. II. Synthesis and properties of 2,6-diamino-5-(methylamino)-4-pynmidinol," Biochemistry, 4(4):655-661 (1965).
Stephan et al., J Urol., 167:1497-502 (2002).
Takahashi K, et al., J Biol. Chem., 46654 (2003).
Targan et al., N Engl J Med., 337(15), pp. 1029-1035, (1997).
Taylor et al., Arthritis Rheum., 43:38-47 (2000).
Trentham et al., J. Exp. Med. 146(3):857-868 (1977).
Tucci et al., Biomed. Sci. Instrum., 34:169-74 (1997).
Uehara, et al., J. Immunol, 168(6), pp. 2811-2819, (2002).
Ueno et al., Clin. Cancer Res., 6(8):3282-9 (2001).
Van Riper, et al., J Exp. Med., 177, pp. 851-856, (1993).
Vervoordeldonk et al., Curr. Rheumatol. Rep., 4: pp. 208-217, (2002).
Vestergaard et al., Acta. Derm. Venereol., 84(5): pp. 353-358 (2004).

(56) References Cited

OTHER PUBLICATIONS

Villiger et al., J Immunol., 149: pp. 722-727 (1992).
Weisberg et al., J Clin. Invest., 112: pp. 1796-1808, (2003).
Weisberg SP, et al., J Clin. Invest., 115 (2006).
Wurbel, et al., Blood, 98(9), pp. 2626-2632, (2001).
Xu H, et al., J Clin. Invest.;112(12); pp. 1821-1830, (2003).
Yang et al., Zhonghua Yi Xue Za Zhi, 81: pp. 73-77, (2001).
Yogi, Seiichi, et al., "Synthesis of imido-substituted 3,8-diphenyl-1,2- diazacycloocta-2,4,6,8-tetraenes and their thermolysis," Bull. Chem. Soc. Jpn., 60:731-735 (1987).
Yoshimatsu, K., et al., "Mechanism of action of E7010, an orally active Su8lfonamideantitumor agent: Inhibition of mitosis by binding to the colchicine stie of tubulin," 57(15) Cancer Research, American Association for Cancer Research 3208-3213 (Jan. 1997).
Yoshino et al., J Med. Chem., vol. 35, pp. 2496-2497, (1992).
Youn BS, et al., Apoptosis, 7, pp. 271-276, (2002).
Zaballos, et al., J. Immunol., 162, pp. 5671-5675, (1999).
Zaragoza Dorwald, F., "Side Reactions in Organic Synthesis: A Guide to Successful Synthesis Desiqn" (2005) Wiley-VCH Verlaq GmbH & Co., KGaA, Weinheim.

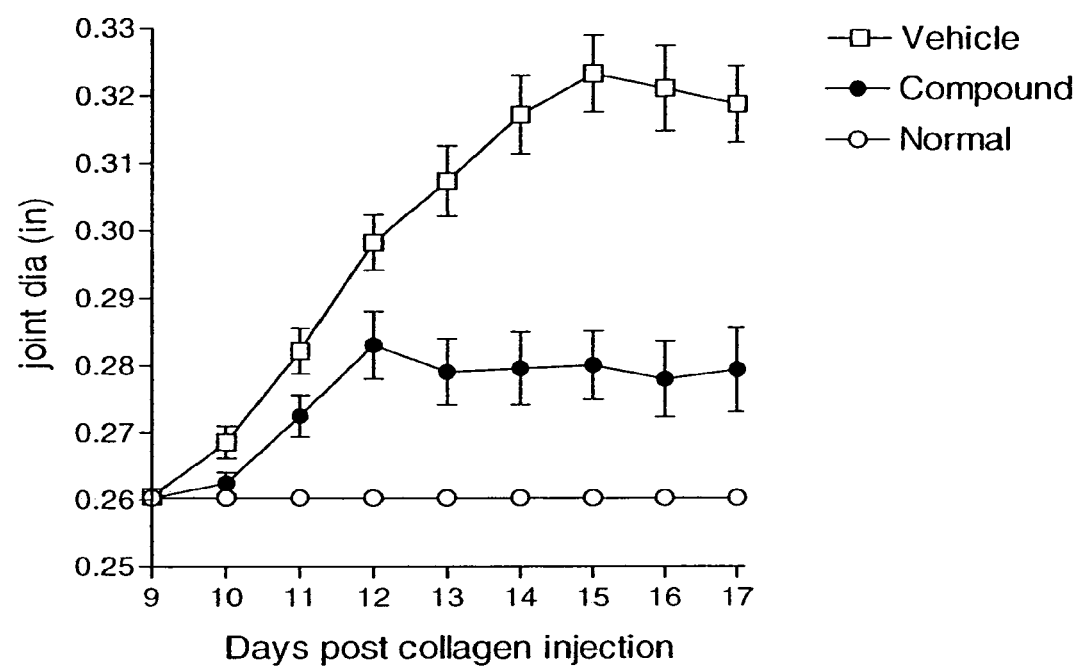

HETEROARYL SULFONAMIDES AND CCR2/CCR9

RELATED APPLICATIONS

This application is a continuation of U.S. application Ser. No. 16/272,401, filed Feb. 11, 2019, which is a continuation of U.S. application Ser. No. 15/383,788, filed Dec. 19, 2016, which is a divisional of U.S. application Ser. No. 13/938,119, filed Jul. 9, 2013, which is a continuation of U.S. application Ser. No. 12/309,314, filed Feb. 1, 2011, now U.S. Pat. No. 8,519,135, which issued Aug. 27, 2013, which is a 371 national phase of PCT/US2007/015893, filed Jul. 12, 2007, which is a continuation-in-part of U.S. application Ser. No. 11/486,974, filed Jul. 14, 2006, now U.S. Pat. No. 7,622,583, which issued Nov. 24, 2009. The disclosures of these priority applications are incorporated herein in their entirety.

FEDERALLY SPONSORED RESEARCH OR DEVELOPMENT

The present invention described herein was supported at least in part by NIH (U19-A1056690). The government has certain rights in the invention.

BACKGROUND

The present invention provides compounds, pharmaceutical compositions containing one or more of those compounds or their pharmaceutically acceptable salts, which are effective in inhibiting the binding or function of various chemokines to chemokine receptors. As antagonists or modulators of chemokine receptors, the compounds and compositions have utility in treating various immune disorder conditions and diseases.

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, Cytokine, 3:165-183 (1991), Schall et al., Curr. Opin. Immunol., 6:865-873 (1994)).

In addition to stimulating chemotaxis, chemokines can induce other changes in responsive cells, including changes in cell shape, granule exocytosis, integrin upregulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., J. Am. Soc. Nephrol., 11:152-76 (2000); Morii et al., J. Diabetes Complications, 17:11-5 (2003); Lloyd et al. J. Exp. Med., 185:1371-80 (1997); Gonzalez-Cuadrado et al. Clin. Exp. Immunol., 106:518-22 (1996); Eddy & Giachelli, Kidney Int., 47:1546-57 (1995); Diamond et al., Am. J. Physiol., 266:F926-33 (1994)). In humans, CCR2 and ligand MCP-1 are among the proteins expressed in renal fibrosis, and are correlated with the extent of macrophage infiltration into the interstitium (Yang et al., Zhonghua Yi Xue Za Zhi, 81:73-7 (2001); Stephan et al., J. Urol., 167:1497-502 (2002); Amann et al., Diabetes Care, 26:2421-5 (2003); Dai et al., Chin. Med. J. (Engl), 114: 864-8 (2001)). In animal models of renal fibrosis, blockade of CCR2 or MCP-1 leads to a marked reduction in severity of renal inflammation (Kitagawa et al., Am. J. Pathol., 165:237-46 (2004); Wada et al., Am. J. Pathol., 165:237-46 (2004); Shimizu et al., J. Am. Soc. Nephrol., 14:1496-505 (2003)).

Rheumatoid arthritis is a chronic disease of the joints characterized by synovial inflammation that leads to the destruction of cartilage and bone. Although the underlying causes of the disease are unknown, it is believed that macrophages and Th-1 type T cells play a key role in the initiation and perpetuation of the chronic inflammatory process (Vervoordeldonk et al., Curr. Rheumatol. Rep., 4:208-17 (2002)).

MCP-1 is among the several chemokines, including MIP-1α and IL-8, identified in rheumatoid synovium (Villiger et al., J. Immunol., 149:722-7 (1992); Scaife et al., Rheumatology (Oxford), 43:1346-52 (2004); Shadidi et al., Scand. J. Immunol., 57:192-8 (2003); Taylor et al., Arthritis Rheum., 43:38-47 (2000); Tucci et al., Biomed. Sci. Instrum., 34:169-74 (1997)). Chemokine receptors CCR1, CCR2, CCR3 and CCR5 are up-regulated in the joints from arthritic mice (Plater-Zyberk et al., Immunol. Lett., 57:117-20 (1997). Blockade of MCP-1 activity using a CCR2 antagonist or an antibody against MCP-1 have been shown efficacious in reducing joint inflammation in experimental models of rheumatoid arthritis (Gong et al., J. Exp. Med., 186:131-7 (1997); Ogata et al., J. Pathol., 182:106-14 (1997)).

Chemokine receptor-mediated infiltration of macrophages in the fat tissues may also contribute to the complications arising from obesity, a condition resulting from excessive storage of fat in the body. Obesity predisposes the affected individuals to many disorders, such as non-insulin-dependent diabetes, hypertension, stroke, and coronary artery disease. In obesity, adipose tissues have altered metabolic and endocrine functions that lead to an increased release of fatty acids, hormones, and pro-inflammatory molecules. Adipose tissue macrophages are believed to be a key source of pro-inflammatory cytokines including TNF-alpha, iNOS and IL-6 (Weisberg et al., J. Clin. Invest., 112:1796-808 (2003)). Recruitment of macrophages to the adipose tissue is likely mediated by MCP-1 produced by adipocytes (Christiansen T, et al., Int J Obes (Lond). 2005 January; 29(1): 146-50; Sartipy et al., Proc. Natl. Acad. Sci. U.S.A., 100: 7265-70 (2003)).

Elevated MCP-1 may induce adipocyte differentiation and insulin resistance, and contribute to pathologies associated with hyper-insulinemia and obesity. MCP-1 is over-expressed in plasma in obese mice compared to lean controls and white adipose is a major source. MCP-1 has also been shown to accelerate wound healing, and has a direct angiogenic effect on epithelial cells, and may play a direct role in the remodeling of adipose tissue in obesity. (Sartipy P, Loskutoff D J., Proc. Natl. Acad. Sci. U.S.A., 100:7265 (2003)).

MCP-1 plasma levels are substantially increased in Diet Induce Obesity (DIO) mice, and a strong correlation between plasma MCP-1 levels and body weight has been identified. Furthermore, elevation of MCP-1 induced by high fat diet causes changes in the CD11b positive monocyte population in DIO mice. (Takahashi K, et al., J. Biol. Chem., 46654 (2003)).

Furthermore, chronic inflammation in fat is thought to play a crucial role in the development of obesity-related insulin resistance (Xu H, et al., J Clin Invest. 2003 December; 112(12):1821-30). It has been proposed that obesity related insulin resistance is, at least in part, a chronic inflammatory disease initiated in adipose tissue. Many inflammation and macrophage specific genes are dramatically upregulated in white adipose tissue in mouse models of genetic and high fat diet-induced obesity (DIO), and this upregulation precedes a dramatic increase in circulating insulin.

Increased expression levels of monocyte CCR2 and monocyte chemoattractant protein-1 in patients with diabetes mellitus (Biochemical and Biophysical Research Communications, 344(3):780-5 (2006)) were found in a study involving diabetic patients. Serum MCP-1 concentrations and surface expression of CCR2 on monocytes in diabetic patients were significantly higher than in non-diabetics, and the serum MCP-1 levels correlated with HbA1c, triglycerides, BMI, hs-CRP. Surface expression levels of CD36 and CD68 on monocytes were significantly increased in diabetic patients and more unregulated by MCP-1 in diabetics, augmenting uptake of ox-LDL, and hence potentially foam cell transformation. Elevated serum MCP-1 and increased monocyte CCR2, CD36, CD68 expression correlated with poor blood glucose control and potentially correlate with increased vessel wall monocyte recruitment.

MCP-1 is a potential player in negative cross talk between adipose tissue and skeletal muscle (Bianco J J, et al., Endocrinology, 2458 (2006)). MCP-1 can significantly reduce insulin-stimulated glucose uptake, and is a prominent inducer of insulin resistance in human skeletal muscle cell. Adipose tissue is a major secretory and endocrine active organ producing bioactive proteins regulating energy metabolism and insulin sensitivity.

CCR2 modulates inflammatory and metabolic effects of high-fat feeding (Weisberg S P, et al., J. Clin. Invest., 115 (2006)). Genetic deficiency in CCR2 reduced food intake and attenuated the development of obesity in mice fed a high fat diet. In obese mice matched for adiposity, CCR2 deficiency reduced macrophage content and inflammatory profile of adipose tissue, increased adiponectin expression, and improved glucose homeostatis and insulin sensitivity. In lean animals, no effect of CCR2 genotype on metabolic trait was found. In high-fat diet mice, CCR2 genotype modulated feeding, the development of obesity and adipose tissue inflammation. Once established, short term antagonism was shown to attenuate macrophage accumulation in adipose tissue and insulin resistance.

Chemokine and chemokine receptors are the key regulators of immune cell trafficking. MCP-1 is a potent chemoattractant of monocytes and T cells; its expression is induced under inflammatory conditions including proinflammatory cytokine stimulations and hypoxia. The interaction between MCP-1 and CCR2 mediates migration of monocytes, macrophage as well as activated T cells and play a key role in the pathogenesis of many inflammatory diseases. Inhibition of CCR2 functions using small molecule antagonists described in this invention represents a new approach for the treatments of inflammatory disorders.

Psoriasis is a chronic inflammatory disease characterized by hyperproliferation of keratinocytes and pronounced leukocyte infiltration. It is known that keratinocytes from psoriasis lesion express abundant CCR2 ligand MCP-1, particularly when stimulated by proinflammatory cytokines such as TNF-α (Vestergaard et al., Acta. Derm. Venereol., 84(5):353-8 (2004); Gillitzer et al., J. Invest. Dermatol., 101(2):127-31 (1993); Deleuran et al., J. Dermatol. Sci., 13(3):228-36 (1996)). Since MCP-1 can attract migration of both macrophages and dendritic cells expressing CCR2 to the skin, this receptor and ligand pair is believed to be important in regulating the interaction between proliferating keratinocytes and dermal macrophage during the development of psoriasis. A small molecule antagonist may thus be useful in the treatment of psoriasis.

In addition to inflammatory diseases, chemokines and chemokine receptors have also been implicated in cancers (Broek et al., Br. J. Cancer, 88(6):855-62 (2003)). Tumor cells stimulate the formation of stroma that secretes various mediators pivotal for tumor growth, including growth factors, cytokines, and proteases. It is known that the level of MCP-1 is associated significantly with tumor-associated macrophage accumulation, and prognostic analysis reveals that high expression of MCP-1 is a significant indicator of early relapse in breast cancer (Ueno et al., Clin. Cancer Res., 6(8):3282-9 (2001)). A small molecule antagonist of a chemokine may thus be able to reduce the release of growth-stimulating cytokines by blocking accumulation of macrophages at sites of tumor formation.

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease causing T cells to the intestine. See for example, Zaballos et al., J. Immunol., 162(10):5671 5675 (1999); Kunkel et al., J. Exp. Med., 192(5):761-768 (2000); Papadakis et al., J. Immunol., 165 (9):5069-5076 (2000); Papadakis et al., Gastroenterology, 121(2):246-254 (2001); Campbell et al., J. Exp. Med., 195(1):135-141 (2002); Wurbel et al., Blood, 98(9):2626-2632 (2001); and Uehara et al., J. Immunol., 168(6):2811-2819 (2002). Rivera-Nieves, et al., Gastroenterology, 2006 November; 131(5):1518-29; and Kontoyiannis et al., J. Exp. Med., Vol. 196, Number 12, Dec. 16, 2002. In addition CCR9 bearing lymphocytes have been show to mediate the pathology of filariasis (lymphatic filarial disease) and inhibition of CCR9 has been correlated with reduction of the pathology associated with such conditions. See for example Babu et al., Journal of Infectious Diseases, 191: 1018-26, 2005.

PCT Published Application WO 2003/099773 (Millennium Pharmaceuticals, Inc.) discloses compounds which can bind to CCR9 receptors of the formula

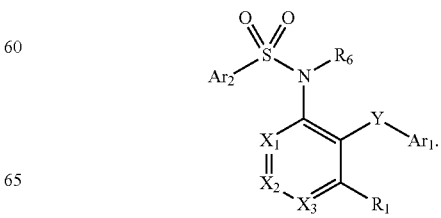

PCT Published Application WO 2005/004810 (Merck & Co., Inc.) discloses brandykinin B1 antagonists or inverse agonists of the formula

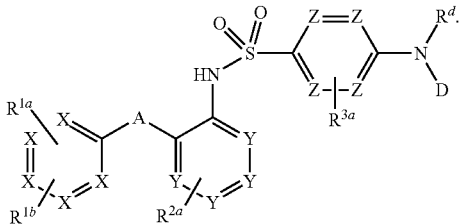

US Published Patent Application 2007/0037794 A1 (ChemoCentryx, Inc.) discloses CCR2 modulators of the formula

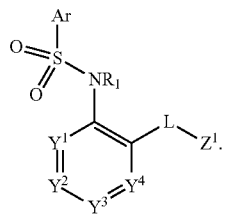

BRIEF SUMMARY

The present invention is directed to compounds and pharmaceutically acceptable salts thereof, compositions, and methods useful in modulating chemokine activity. The compounds and salts thereof, compositions, and methods described herein are useful in treating or preventing chemokine-mediated conditions or diseases, including certain inflammatory and immunoregulatory disorders and diseases.

The compounds of the present invention have been shown to modulate one or more of CCR2, CCR3, CCR4, CCR5, CCR6, CCR7, CCR8, CCR9, CCR10, CXCR3, CXCR4, CXCR5, and CX3CR1. In particular, various compounds of the present invention modulate CCR2 and CCR9 as shown in the examples.

In one embodiment, the present compound may be represented by formula (I) or salts thereof:

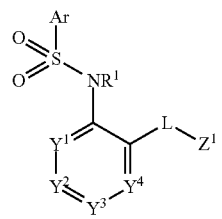

I where Ar, $R_1$, $Y_1$, $Y_2$, $Y_3$, $Y_4$, L, and $Z_1$ are as defined below.

In another aspect, the present invention provides compositions useful in modulating chemokine activity. In one embodiment, a composition according to the present invention comprises a compound according to the invention and a pharmaceutically acceptable carrier or excipient.

In yet another aspect, the present invention provides a method of modulating chemokine function in a cell, comprising contacting the cell with a therapeutically effective amount of a compound or composition according to the invention.

In still another aspect, the present invention provides a method for modulating chemokine function, comprising contacting a chemokine receptor with a therapeutically effective amount of a compound or composition according to the invention.

In still another aspect, the present invention provides a method for treating a chemokine-mediated condition or disease, comprising administering to a subject a safe and effective amount of a compound or composition according to the invention.

In addition to the compounds provided herein, the present invention further provides pharmaceutical compositions containing one or more of these compounds, as well as methods for the use of these compounds in therapeutic methods, primarily to treat diseases associated with chemokine signaling activity.

BRIEF DESCRIPTION OF THE DRAWINGS

FIG. 1 shows a plot of joint diameter measurements taken of Female Lewis rats (approximately 0.2 kilograms) using a compound of the invention as well as controls.

DETAILED DESCRIPTION

General

The present invention is directed to compounds and salts thereof, compositions and methods useful in the modulation of chemokine receptor function, particularly CCR2 or CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR2 or CCR9 receptor. Accordingly, the compounds of the present invention are compounds which modulate at least one function or characteristic of mammalian CCR2 or CCR9, for example, a human CCR2 or CCR9 protein. The ability of a compound to modulate the function of CCR2 or CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

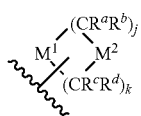

AA where formula (AA) is attached via a free valence on either $M^1$ or $M^2$; $M^1$ represents O, $NR^e$, or $S(O)_l$; $M^2$ represents $CR^fR^g$, O, $S(O)_l$, or $NR^e$; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^h$, —$CO_2R^h$, —$CONR^hR^i$, —$NR^hCOR^i$, —$SO_2R^h$, —$SO_2NR^hR^i$, —$NSO_2R^hR^i$—$NR^hR^i$, —$OR^h$, -$Q^1COR^h$, -$Q^1CO_2R^h$, $Q^1CONR^hR^i$, -$Q^1NR^hCOR^i$, -$Q^1SO_2R^{28}$, -$Q^1SO_2NR^hR^i$, -$Q^1NSO_2R^hR^i$, -$Q^1NR^hR^i$, -$Q^1OR^h$, wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of
halogen, —OH, —$OR^n$, —OC(O)$NHR^n$, —OC(O)$NR^nR^o$, —SH, —$SR^n$, —S(O)$R^n$, —$S(O)_2R^n$, —$SO_2NH_2$, —$S(O)_2NHR^n$, —$S(O)_2NR^nR^o$, —$NHS(O)_2R^n$, —$NR^nS(O)_2R^o$, —C(O)$NH_2$, —C(O)$NHR^n$, —C(O)$NR^nR^o$, —C(O)$R^n$, —NHC(O)$R^n$, —$NR^nC(O)R^o$, —NHC(O)$NH_2$, —$NR^nC(O)$ $NH_2$, —$NR^nC(O)NHR^o$, —NHC(O)$NHR^n$, —$NR^nC(O)$ $NR^oR^p$, —NHC(O)$NR^nR^o$, —$CO_2H$, —$CO_2R^n$, —$NHCO_2R^n$, —$NR^nCO_2R^o$, —CN, —$NO_2$, —$NH_2$, —$NHR^n$, —$NR^nR^o$, —$NR^nS(O)NH_2$ and —$NR^nS(O)_2$ $NHR^o$, wherein $R^n$, $R^o$ and $R^p$ are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In one preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —$COR^h$, —$CO_2R^h$, —$CONR^hR^h$, —$NR^hCOR^h$, —$SO_2R^h$, —$SO_2NR^hR^i$, —$NSO_2R^hR^i$, —$NR^hR^i$, and —$OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of
halogen, —OH, —$OR^n$, —OC(O)$NHR^n$, —OC(O)$NR^nR^o$, —SH, —$SR^n$, —S(O)$R^o$, —$S(O)_2R^n$, —$SO_2NH_2$, —$S(O)_2$ $NHR^n$, —$S(O)_2NR^nR^o$, —$NHS(O)_2R^n$, —$NR^nS(O)_2R^o$, —C(O)$NH_2$, —C(O)$NHR^n$, —C(O)$NR^nR^o$, —C(O)$R^n$, —NHC(O)$R^n$, —$NR^nC(O)R^o$, —NHC(O)$NH_2$, —$NR^nC(O)$ $NH_2$, —$NR^nC(O)NHR^o$, —NHC(O)$NHR^n$, —$NR^nC(O)$ $NR^oR^p$, —NHC(O)$NR^nR^o$, —$CO_2H$, —$CO_2R^n$, —$NHCO_2R^n$, —$NR^nCO_2R^o$, —CN, —$NO_2$, —$NH_2$, —$NHR^n$, —$NR^nR^o$, —$NR^nS(O)NH_2$ and —$NR^nS(O)_2$ $NHR^o$, wherein $R^n$, $R^o$ and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or —O$^-$), the resulting group may have either a carbonyl (—C(O)—) or a N-oxide (—N$^+$—O$^-$).

Suitable substituents for substituted alkyl, substituted alkenyl, and substituted alkynyl include halogen, —CN, —CO$_2$R', —C(O)R', —C(O)NR'R", oxo (=O or —O—), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'''C(O)NR'R", —NR'R", —NR'CO$_2$R", —NR'S(O)R", —NR'S(O)$_2$R''', —NR'S(O)NR'R", —NRS(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10 membered heterocyclyl. The number of possible substituents range from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6- or 7-membered ring.

Two of the substituents on adjacent atoms of an aryl or heteroaryl ring may optionally be replaced with a substituent of the formula -T-C(O)—(CH$_2$)$_q$—U—, wherein T and U are independently —NR''''—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, wherein A' and B' are independently —CH$_2$—, —O—, —NR''''—, —S—, —S(O)—, —S(O)$_2$—, —S(O)$_2$NR''''— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR''''—, —S—, —S(O)—, —S(O)$_2$—, or —S(O)$_2$NR'—. R'''' in is selected from hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds that Modulate CCR2 or CCR9 Activity

The present invention provides compounds that modulate at least one of CCR2 or CCR9 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the invention include, but are not limited to, the exemplary compounds provided herein and salts thereof.

For example, compounds of this invention act as potent CCR2 antagonists, and this antagonistic activity has been further confirmed in animal testing for inflammation, one of the hallmark disease states for CCR2. Accordingly, the compounds provided herein are useful in pharmaceutical compositions, methods for the treatment of CCR2-mediated diseases, and as controls in assays for the identification of competitive CCR2 antagonists.

The compounds of the invention are thought to interfere with inappropriate T-cell trafficking by specifically modulating or inhibiting a chemokine receptor function. Without intending to be bound by any particular theory, it is believed that the compounds provided herein interfere with the interaction between a chemokine receptor and one or more cognate ligands. In particular, it is believed that the compounds interfere with the interaction between CCR9 and a CCR9 ligand, such as TECK. Compounds contemplated by the invention include, but are not limited to, the exemplary compounds provided herein and salts thereof.

For example, compounds of this invention act as potent CCR9 antagonists, and this antagonistic activity has been further confirmed in animal testing for inflammation, one of the hallmark disease states for CCR9. Accordingly, the compounds provided herein are useful in pharmaceutical compositions, methods for the treatment of CCR9-mediated diseases, and as controls in assays for the identification of competitive CCR9 antagonists.

Compounds

In one embodiment, the compounds of the present invention are represented by formula (I), or salts thereof:

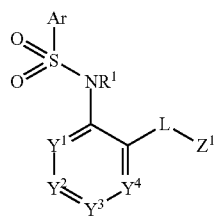
(I)

Ar is selected from the group consisting of substituted or unsubstituted $C_{6-10}$ aryl and substituted or unsubstituted 5- to 10-membered heteroaryl.

$R^1$ is selected from the group consisting of hydrogen, substituted or unsubstituted $C_{1-8}$ alkyl, substituted or unsubstituted $C_{2-6}$ alkenyl, substituted or unsubstituted $C_{2-6}$ alkynyl, and substituted or unsubstituted 3- to 10-membered heterocyclyl;

$Y^1$ is selected from the group consisting of —$CR^{2a}$—, —N—, and —$N^+(O)^-$—;

$Y^2$ is selected from the group consisting of —$CR^{2b}$—, —N—, and —$N^+(O)^-$—;

$Y^3$ is selected from the group consisting of —$CR^{2c}$—, —N—, and —$N^+(O)^-$—;

$Y^4$ is selected from the group consisting of —$CR^{2d}$—, —N—, and —$N^+(O)^-$—;

$R^{2a}$, $R^{2b}$, $R^{2c}$ and $R^{2d}$ are each independently selected from the group consisting of hydrogen, halogen, —CN, —C(O)$R^3$, —COO$_2R^3$, —C(O)NR$^3$R$^4$, —OR$^3$, —OC(O)R$^3$, —OC(O)NR$^3$R$^4$, —SR$^3$, —S(O)R$^3$, —S(O)$_2$R$^3$, —S(O)$_2$NR$^3$R$^4$, —NO$_2$, —NR$^3$R$^4$, —NR$^3$C(O)R$^4$, —NR$^3$C(O)OR$^4$, —NR$^3$S(O)$_2$R$^4$, —NR$^3$C(O)NR$^4$R$^5$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^3$, $R^4$, and $R^5$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^3$ and $R^4$, $R^4$ and $R^5$ or $R^3$ and $R^5$ may, together with the atoms to which they are attached, form a substituted or unsubstituted 5-, 6-, or 7-membered ring;

L is selected from the group consisting of a bond, —O—, —S—, —S(O)—, —S(O)$_2$—, —CR$^6$R$^7$—, —NR$^8$—, —C(O)—, —C(=N—O—R$^9$)—, —C(O)NR$^8$—, and —NR$^8$C(O)—;

$R^6$ and $R^7$ are each independently selected from the group consisting of hydrogen, halogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, —CN, —OR$^9$, —NR$^{10}$R$^{11}$, —S(O)R$^9$, and —S(O)$_2$R$^9$;

$R^6$ and $R^7$ may, together with the carbon atom to which they are attached, form substituted or unsubstituted $C_{3-8}$ cycloalkyl or substituted or unsubstituted 3- to 10-membered heterocyclic ring;

$R^9$ is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{10}$ and $R^{11}$ are each independently selected from the group consisting of substituted or unsubstituted $C_{1-8}$ alkyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted $C_{2-8}$ alkenyl, and substituted or unsubstituted $C_{2-8}$ alkynyl;

$R^{10}$ and $R^{11}$ of —NR$^{10}$R$^{11}$ may, together with the nitrogen, form substituted or unsubstituted 3- to 10-membered heterocyclyl;

$R^8$ is selected from the group consisting of hydrogen, C(O)R$^{12}$, S(O)$_2$R$^{12}$, CO$_2$R$^{12}$, substituted or unsubstituted $C_{1-8}$ alkyl, substituted or unsubstituted 3- to 10-membered heterocyclyl, substituted or unsubstituted $C_{2-6}$ alkenyl, and substituted or unsubstituted $C_{2-6}$ alkynyl;

$R^{12}$ is selected from the group consisting of substituted or unsubstituted $C_{1-8}$ alkyl, substituted or unsubstituted $C_{2-6}$ alkenyl, substituted or unsubstituted $C_{2-6}$ alkynyl, substituted or unsubstituted 3- to 10-membered heterocyclyl, substituted or unsubstituted $C_{6-10}$ aryl, and substituted or unsubstituted 5- to 10-membered heteroaryl;

$Z^1$ is selected from the group consisting of substituted or unsubstituted $C_{6-10}$ aryl, substituted or unsubstituted 5- to 10-membered heteroaryl, substituted or unsubstituted 3- to 10-membered heterocyclyl, and —NR$^{13}$R$^{14}$;

$R^{13}$ and $R^{14}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{13}$ and $R^{14}$ may, together with the nitrogen, form a substituted or unsubstituted 4-, 5-, 6-, or 7-membered heterocyclyl.

In one embodiment, the compounds of the present invention are represented by formula (I), or salts thereof:

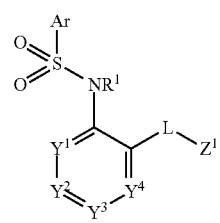
(I)

where Ar is substituted or unsubstituted $C_{6-10}$ aryl;

$R^1$ is selected from the group consisting of hydrogen or substituted or unsubstituted $C_{1-8}$ alkyl;

$Y^1$ is —$CR^{2a}$—;

$Y^2$ is —$CR^{2b}$—;

$Y^3$ is —$CR^{2c}$—;

$Y^4$ is selected from the group consisting of —$CR^{2d}$—, —N— and —$N^+(O)^-$—;

$R^{2a}$, $R^{2b}$, $R^{2c}$ and $R^{2d}$ are each independently selected from the group consisting of hydrogen, halogen, substituted or unsubstituted $C_{1-8}$ alkyl;

L is —C(O)—, —C(=N—O—$R^9$)—, or bond; and $Z^1$ is substituted or unsubstituted 3- to 10-membered heterocyclic or substituted or unsubstituted 5- to 10-membered heteroaryl.

In one embodiment of formula (I), the compound is of the formula (Ia) or a salt thereof:

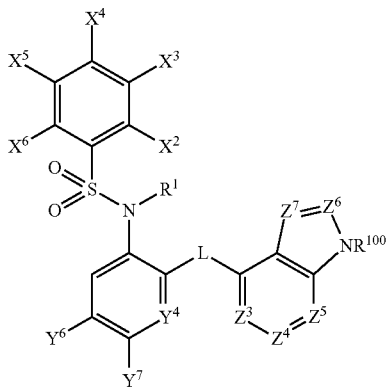

(Ia)

where $X^3$ and $X^4$ are each independently hydrogen, halogen, substituted or unsubstituted $C_{1-8}$ alkyl, —CN, or $C_{1-8}$ haloalkyl, provided that at least one of $X^3$ or $X^4$ is other than hydrogen;

each $X^2$, $X^5$, and $X^6$ is independently hydrogen, halogen, or substituted or unsubstituted $C_{1-4}$ alkyl;

$R^1$ is hydrogen or substituted or unsubstituted $C_{1-8}$ alkyl;

$Y^6$ is halogen or substituted or unsubstituted $C_{1-8}$ alkyl;

$Y^7$ is hydrogen or substituted or unsubstituted $C_{1-4}$ alkyl;

L is selected from the group consisting of a bond, —C(O)—, and —C(=N—O—$R^9$)—;

$Z^6$ and $Z^7$ are each independently selected from the group consisting of —$CR^{67}$—, —N—, and —$N^+(O)^-$—;

$Y^4$ is —$CR^{2a}$—, —N—, or —$N^+(O)^-$—;

$Z^3$ and $Z^5$ are —N—, or —$N^+(O)^-$—; and $Z^4$ is —$CR^{67}$—;

$R^{100}$ is selected from the group consisting of hydrogen, $C_{1-8}$ alkyl, $C_{2-8}$ alkenyl, $C_{2-8}$ alkynyl, substituted or unsubstituted $C_{6-10}$ aryl, substituted or unsubstituted 5- to 10-membered heteroaryl and substituted or unsubstituted 3- to 10-membered heterocycle;

each $R^{67}$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^{68}$, —$OC(O)R^{68}$, —$CO_2R^{68}$, —$C(O)R^{68}$, —C(O)$NR^{69}R^{68}$, —OC(O)$NR^{69}R^{68}$, —$NR^{70}C(O)R^{68}$, —$NR^{70}C(O)NR^{69}R^{68}$, —$NR^{69}R^{68}$, —$NR^{70}CO_2R^{68}$, —$SR^{68}$, —S(O)$R^{68}$, —$S(O)_2R^{68}$, —$S(O)_2NR^{69}R^{68}$, —$NR^{70}S(O)_2R^{68}$, substituted or unsubstituted $C_{6-10}$ aryl, substituted or unsubstituted 5- to 10-membered heteroaryl and substituted or unsubstituted 3- to 10-membered heterocyclyl;

each occurrence of $R^{68}$, $R^{69}$, and $R^{70}$ is independently selected from the group consisting of hydrogen, $C_{1-8}$ alkyl, $C_{2-8}$ alkenyl, $C_{2-8}$ alkynyl, aryl, or heteroaryl; or $R^{69}$ and $R^{68}$ or $R^{70}$ and $R^{68}$, together with the atom(s) to which they are attached, form an substituted or unsubstituted 5-, 6-, or 7-membered ring; and where $R^{2a}$ is as defined for formula (I).

In another embodiment of formula (I), the compound is of the formula (Ib) or a salt thereof:

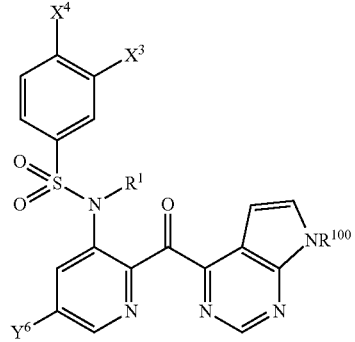

(Ib)

where $R^1$, $X^3$, $X^4$, $Y^6$, and $R^{100}$ are as described for formula (Ia).

In another embodiment of formula (I), the compound is of the formula (Ic) or a salt thereof:

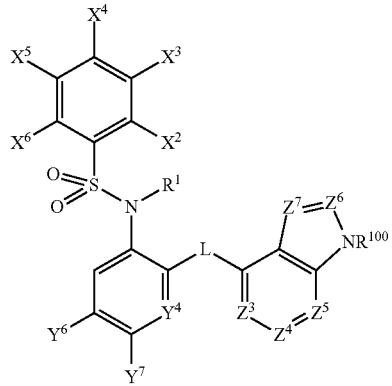

(Ic)

where $X^3$ and $X^4$ are each independently hydrogen, halogen, substituted or unsubstituted $C_{1-8}$ alkyl, —CN, or $C_{1-8}$ haloalkyl, provided that at least one of $X^3$ or $X^4$ is other than hydrogen;

each $X^2$, $X^5$, $X^6$ is independently hydrogen, halogen, or substituted or unsubstituted $C_{1-4}$ alkyl;

$R^1$ is hydrogen or substituted or unsubstituted $C_{1-8}$ alkyl;

$Y^6$ is halogen or substituted or unsubstituted $C_{1-8}$ alkyl;

$Y^7$ is hydrogen or substituted or unsubstituted $C_{1-4}$ alkyl;

$R^{100}$ is selected from the group consisting of hydrogen, substituted or unsubstituted $C_{1-8}$ alkyl, $C_{2-8}$ alkenyl, $C_{2-8}$ alkynyl, substituted or unsubstituted $C_{6-10}$ aryl, substituted or unsubstituted 5- to 10-membered heteroaryl and substituted or unsubstituted 3- to 10-membered heterocycle;

L is selected from the group consisting of a bond, —C(O)—, and —C(=N—O—$R^9$)—;

$Y^4$ is —$CR^{2a}$—, —N—, or —$N^+(O)^-$—;

$Z^4$ is —N—, or —$N^+(O)^-$—; and $Z^3$, $Z^5$, $Z^6$, and $Z^7$ are each independently —$CR^{67}$—;

where $R^{2a}$ and $R^{67}$ are as defined for formula (I).

In another embodiment of formula (I), the compound is of the formula (Id):

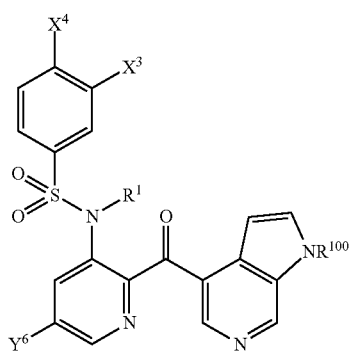

(Id)

where $X^3$, $X^4$, $R^1$, $Y^6$, and $R^{100}$ are as described for formula (Ic).

In another embodiment of formula (I), the compound of the formula (Ie) or a salt thereof:

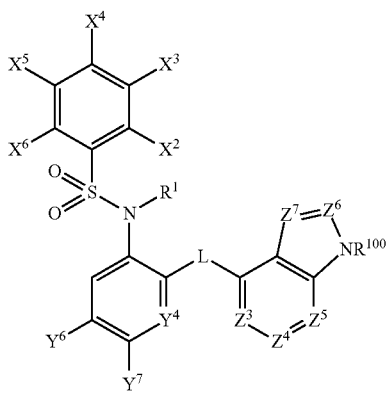

(Ie)

where $X^3$ and $X^4$ are each independently hydrogen, halogen, substituted or unsubstituted $C_{1-8}$ alkyl, —CN, or $C_{1-8}$ haloalkyl, provided that at least one of $X^3$ or $X^4$ is other than hydrogen;

each $X^2$, $X^5$, and $X^6$ is independently hydrogen, halogen, or substituted or unsubstituted $C_{1-4}$ alkyl;

$R^1$ is hydrogen or substituted or unsubstituted $C_{1-8}$ alkyl;

$Y^6$ is halogen or substituted or unsubstituted $C_{1-8}$ alkyl;

$Y^7$ is hydrogen or substituted or unsubstituted $C_{1-4}$ alkyl;

$R^{100}$ is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl and substituted or unsubstituted 3- to 10-membered heterocycle;

L is selected from the group consisting of a bond, —C(O)—, and —C(=N—O—$R^9$)—;

$Y^4$ is —$CR^{2a}$—, —N—, or —$N^+(O)^-$—;

$Z^3$ and $Z^4$ are each independently —$CR^{67}$—;

$Z^5$ is —N—, or —$N^+(O)^-$—;

$Z^6$ and $Z^7$ are each independently —$CR^{67}$—, —N—, or —$N^+(O)^-$—; and where $R^{2a}$ is as defined for formula (I) and $R^{67}$ is as defined for formula (Ia).

In another embodiment of formula (I), the compound is of the formula (If):

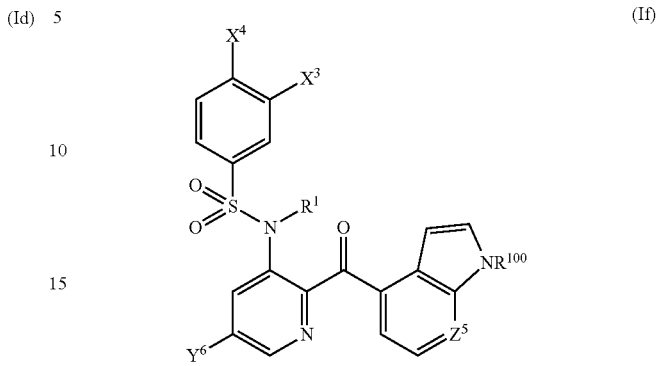

(If)

where $X^3$, $X^4$, $R^1$, $Y^6$, $R^{100}$ and $Z^5$ are as described for formula (Ie).

In another embodiment of formula (I), the compound is of the formula (Ig):

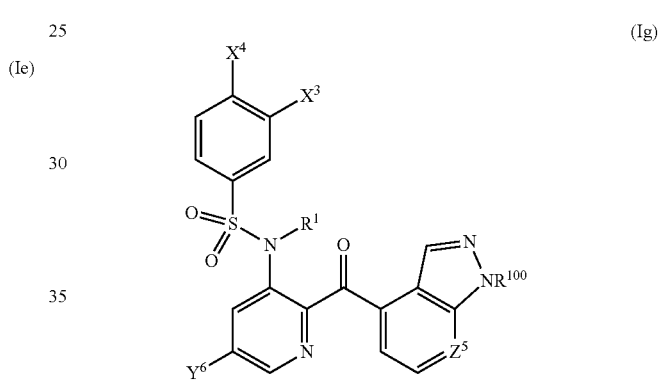

(Ig)

where $X^3$, $X^4$, $R^1$, $Y^6$, $R^{100}$ and $Z^5$ are as described for formula (Ie).

In a further embodiment, the compounds of the present invention are represented by formula (I), or salts thereof:

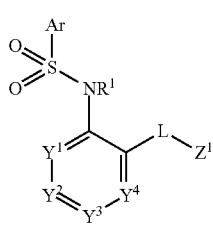

(I)

Ar is selected from the group consisting of substituted or unsubstituted $C_{6-10}$ aryl and substituted or unsubstituted 5- to 10-membered heteroaryl.

$R^1$ is selected from the group consisting of hydrogen, substituted or unsubstituted $C_{1-8}$ alkyl, substituted or unsubstituted $C_{2-6}$ alkenyl, substituted or unsubstituted $C_{2-6}$ alkynyl, and substituted or unsubstituted 3- to 10-membered heterocyclyl;

$Y^1$ is selected from the group consisting of —$CR^{2a}$—, —N—, and —$N^+(O)^-$—;

$Y^2$ is selected from the group consisting of —$CR^{2b}$—, —N—, and —$N^+(O)^-$—;

$Y^3$ is selected from the group consisting of —$CR^{2c}$—, —N—, and —$N^+(O)^-$—;

$R^{2a}$, $R^{2b}$, and $R^{2c}$ are each independently selected from the group consisting of hydrogen, halogen, —CN, —C(O)$R^3$, —CO$_2R^3$, —C(O)NR$^3R^4$, —OR$^3$, —OC(O)$R^3$, —OC(O)NR$^3R^4$, —SR$^3$, —S(O)$R^3$, —S(O)$_2R^3$, —S(O)$_2$NR$^3R^4$, —NO$_2$, —NR$^3R^4$, —NR$^3$C(O)$R^4$, —NR$^3$C(O)OR$^4$, —NR$^3$S(O)$_2R^4$, —NR$^3$C(O)NR$^4R^5$, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl;

$R^3$, $R^4$, and $R^5$ are each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl;

$R^3$ and $R^4$, $R^4$ and $R^5$ or $R^3$ and $R^5$ may, together with the atoms to which they are attached, form a substituted or unsubstituted 5-, 6-, or 7-membered ring;

$Y^4$ is selected from the group consisting of —N— and —N$^+$(O)$^-$—;

L is selected from the group consisting of a bond, —O—, —S—, —S(O)—, —S(O)$_2$—, —CR$^6R^7$—, —NR$^8$—, —C(O)—, —C(O)NR$^8$—, and —NR$^8$C(O)—;

$R^6$ and $R^7$ are each independently selected from the group consisting of hydrogen, halogen, substituted or unsubstituted C$_{1-8}$ alkyl, substituted or unsubstituted 3- to 10-membered heterocyclyl, substituted or unsubstituted C$_{2-6}$ alkenyl, substituted or unsubstituted C$_{2-6}$ alkynyl, —CN, —OR$^9$, —NR$^{10}R^{11}$, —S(O)$R^9$, and —S(O)$_2R^9$;

$R^6$ and $R^7$ may, together with the carbon atom to which they are attached, form substituted or unsubstituted C$_{3-8}$ cycloalkyl or substituted or unsubstituted 3- to 10-membered heterocyclic ring;

$R^9$ is selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl;

$R^{10}$ and $R^{11}$ are each independently selected from the group consisting of substituted or unsubstituted C$_{1-8}$ alkyl, substituted or unsubstituted 3- to 10-membered heterocyclyl, substituted or unsubstituted C$_{6-10}$ aryl, substituted or unsubstituted 5- to 10-membered heteroaryl, substituted or unsubstituted C$_{2-8}$ alkenyl, and substituted or unsubstituted C$_{2-8}$ alkynyl;

$R^{10}$ and $R^{11}$ of —NR$^{10}R^{11}$ may, together with the nitrogen, form substituted or unsubstituted 3- to 10-membered heterocyclyl;

$R^8$ is selected from the group consisting of hydrogen, C(O)$R^{12}$, S(O)$_2R^{12}$, COO$_2R^{12}$, substituted or unsubstituted C$_{1-8}$ alkyl, substituted or unsubstituted 3- to 10-membered heterocyclyl, substituted or unsubstituted C$_{2-6}$ alkenyl, and substituted or unsubstituted C$_{2-6}$ alkynyl;

$R^{12}$ is selected from the group consisting of substituted or unsubstituted C$_{1-8}$ alkyl, substituted or unsubstituted C$_{2-6}$ alkenyl, substituted or unsubstituted C$_{2-6}$ alkynyl, substituted or unsubstituted 3- to 10-membered heterocyclyl, substituted or unsubstituted C$_{6-10}$ aryl, and substituted or unsubstituted 5- to 10-membered heteroaryl;

$Z^1$ is selected from the group consisting of substituted or unsubstituted C$_{6-10}$ aryl, substituted or unsubstituted 5- to 10-membered heteroaryl, substituted or unsubstituted 3- to 10-membered heterocyclyl, and —NR$^{13}R^{14}$;

$R^{13}$ and $R^{14}$ are each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, substituted or unsubstituted 5- to 10-membered heteroaryl, substituted or unsubstituted (C$_{1-4}$ alkyl)-(C$_{6-10}$ aryl), and substituted or unsubstituted (C$_{1-4}$ alkyl)-(5- to 10-membered heteroaryl); and $R^{13}$ and $R^{14}$ may, together with the nitrogen, form a substituted or unsubstituted 4-, 5-, 6-, or 7-membered heterocyclyl.

In a further embodiment of formula (I), the compounds are represented by formula (II), or salts thereof:

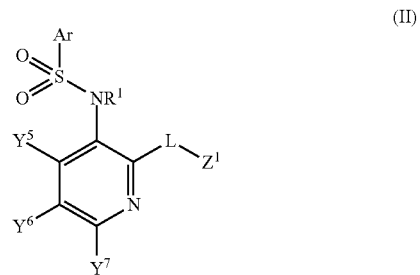

Ar, $R^1$, L and $Z^1$ are as defined above.

$Y^5$, $Y^6$ and $Y^7$ are each independently selected from the group consisting of hydrogen, halogen, —CN, —C(O)$R^{15}$, —CO$_2R^{15}$, —C(O)NR$^{15}R^{16}$, —OR$^{15}$, —OC(O)$R^{15}$, —OC(O)NR$^{15}R^{16}$, —SR$^{15}$, —S(O)$R^{15}$, —S(O)$_2R^{15}$, —S(O)$_2$NR$^{15}R^{16}$, —NO$_2$, —NR$^{15}R^{16}$, —NR$^{15}$C(O)$R^{16}$, —NR$^{15}$C(O)OR$^{16}$, —NR$^{15}$S(O)$_2R^{16}$, —NR$^{15}$C(O)NR$^{16}R^{17}$, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl;

$R^{15}$, $R^{16}$ and $R^{17}$ are each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl;

$R^{15}$ and $R^{16}$, $R^{16}$ and $R^{17}$ or $R^{15}$ and $R^{17}$ may, together with the atoms to which they are attached, form a substituted or unsubstituted 5-, 6-, or 7-membered ring.

In another embodiment of formula (I), the compounds are represented by formula (III), or salts thereof:

L and $Z^1$ are as defined above.

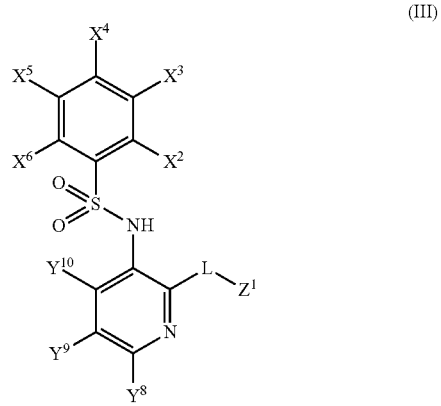

$X^2$, $X^3$, $X^4$, $X^5$, and $X^6$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —$NO_2$, —$C(O)R^{18}$, —$CO_2R^{18}$, —$C(O)NR^{18}R^{19}$, —$OR^{18}$, —$OC(O)R^{19}$, —$OC(O)NR^{18}R^{19}$, —$NO_2$, —$NR^{18}C(O)R^{19}$, —$NR^{18}C(O)NR^{19}R^{20}$, —$NR^{18}R^{19}$, —$NR^{18}CO_2R^{19}$, —$NR^{18}S(O)_2R^{19}$, —$SR^{18}$, —$S(O)R^{18}$, —$S(O)_2R^{18}$, —$S(O)_2NR^{18}R^{19}$, substituted or unsubstituted $C_{6-10}$ aryl, substituted or unsubstituted 5- to 10-membered heteroaryl, and substituted or unsubstituted 3- to 10-membered heterocyclyl;

$R^{18}$, $R^{19}$ and $R^{20}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{18}$ and $R^{19}$, $R^{19}$ and $R^{20}$ or $R^{18}$ and $R^{20}$ may, together with the atoms to which they are attached, form a substituted or unsubstituted 5-, 6-, or 7-membered ring;

$Y^8$, $Y^9$ and $Y^{10}$ are each independently selected from the group consisting of hydrogen, halogen, —CN, —$NO_2$, —$OR^{21}$, —$CO_2R^{21}$, —$OC(O)R^{21}$, —$OC(O)NR^{21}R^{22}$, —$C(O)NR^{21}R^{22}$, —$C(O)R^{21}$, —$SR^{21}$, —$S(O)R^{21}$, —$S(O)_2R^{21}$, —$NR^{21}R^{22}$, —$NR^{21}C(O)R^{22}$, —$NR^{21}C(O)_2R^{22}$, —$NR^{21}S(O)_2R^{22}$, —$NR^{21}C(O)NR^{22}R^{23}$, substituted or unsubstituted $C_{1-8}$ alkyl and substituted or unsubstituted 3- to 10-membered heterocyclyl, $R^{21}$, $R^{22}$ and $R^{23}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{21}$ and $R^{22}$, $R^{22}$ and $R^{23}$ or $R^{21}$ and $R^{23}$ may, together with the atoms to which they are attached, form a substituted or unsubstituted 5-, 6-, or 7-membered ring.

Known Compound

The compound of the formula (I) where Ar para-isopropoxy phenyl, $R^1$ is hydrogen, $Y^1$, $Y^2$, $Y^3$ are each —CH—, $Y^4$ is N, L is C=O, and $Z^1$ is phenyl, (also known as N-(2-benzoyl-pyridin-3-yl)-4-isopropoxy-benzenesulfonamide) is known, but not as a CCR2 antagonist.

3-[N-(2-Aminophenyl)methyl-N-(4-chlorobenzenesulfonyl)]amino-2-[2-(4-chlorophenyl)aminoethyl]aminopyridine is known, but not as CCR2

Preferred Compounds

In several preferred embodiments, the compounds may be represented by the following formulae, or salts thereof:

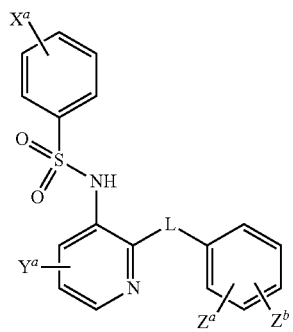

(IVa)

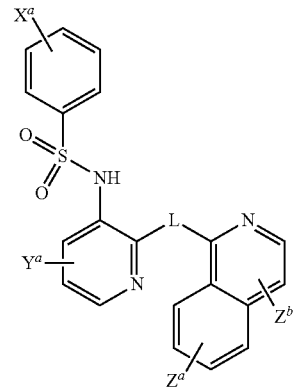

(IVb)

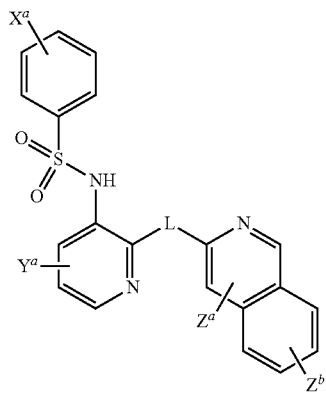

(IVc)

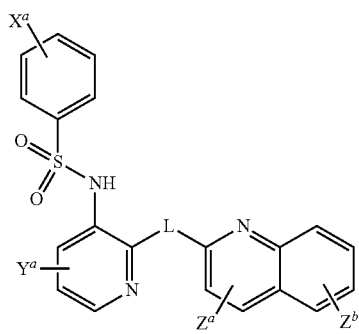

(IVd)

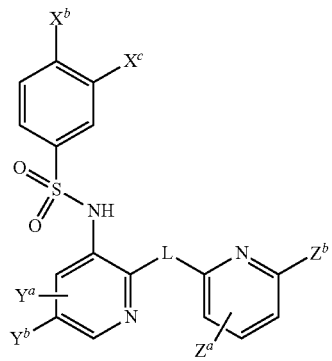

(V)

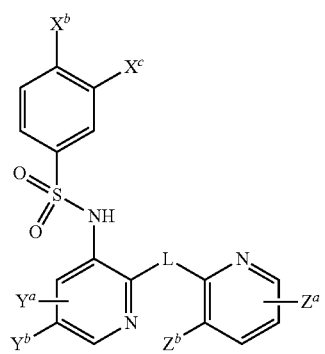
(VI)
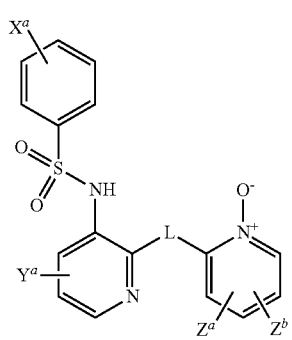
(VII)
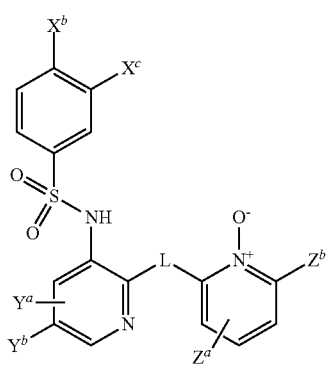
(VIII)
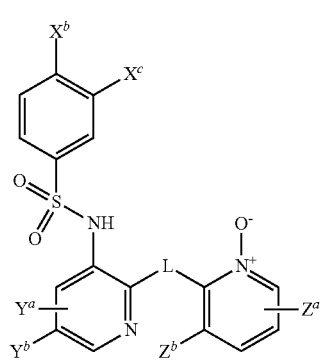
(IX)
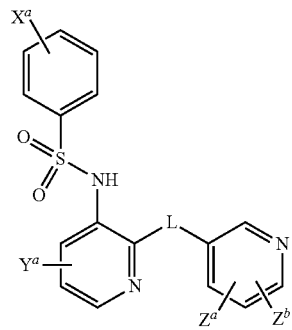
(Xa)
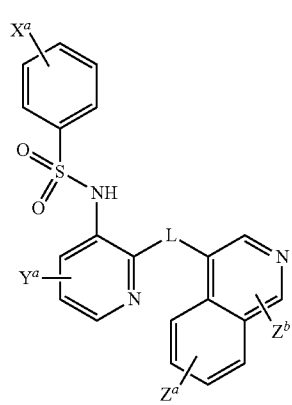
(Xb)
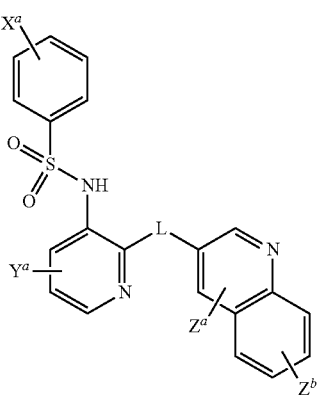
(Xc)
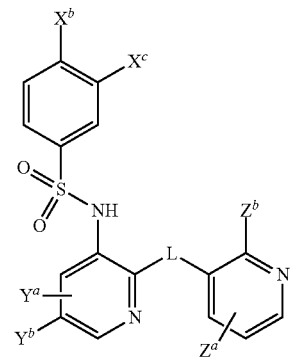
(XI)

(XII)
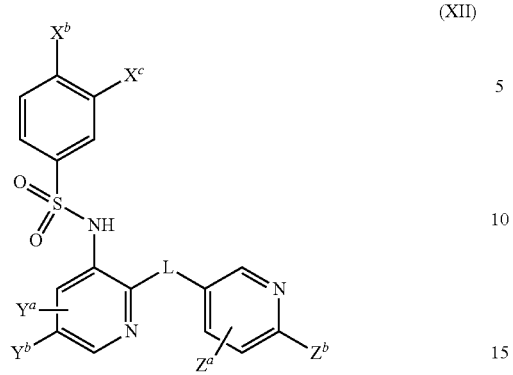
(XIII)
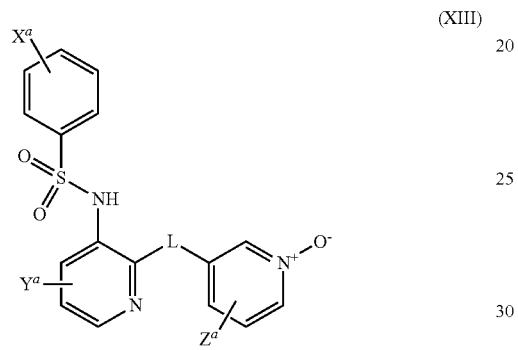
(XIV)
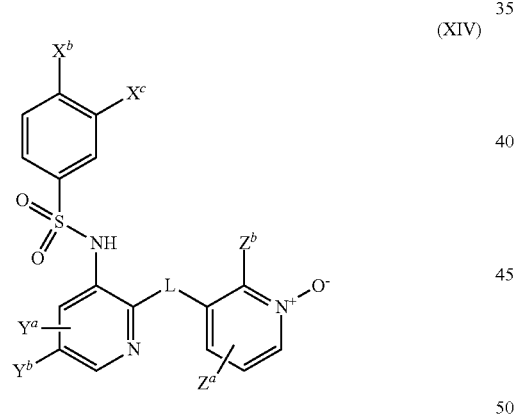
(XV)
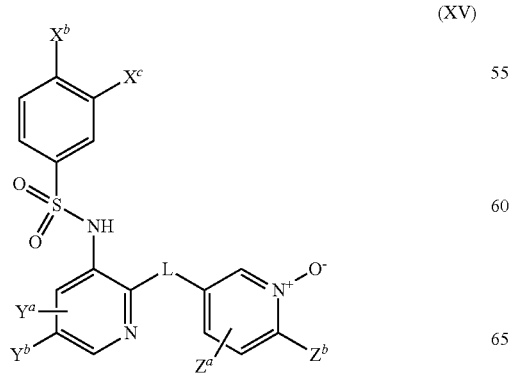
(XVIa)
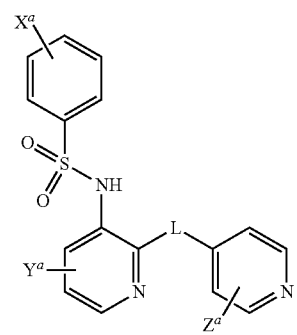
(XVIb)
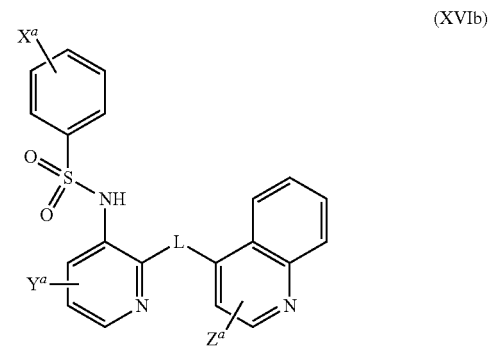
(XVII)
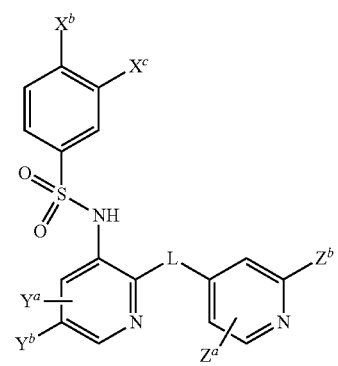
(XVIII)
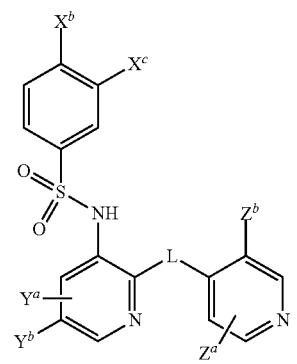

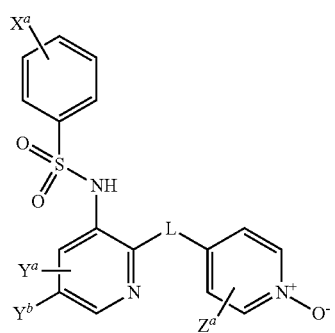 (XIX)
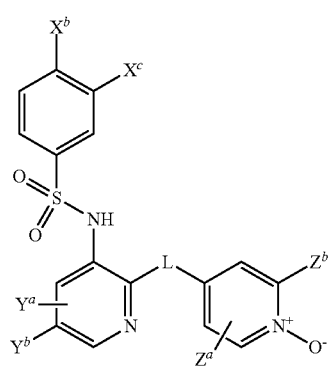 (XX)
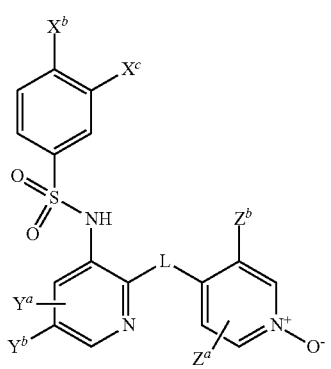 (XXI)
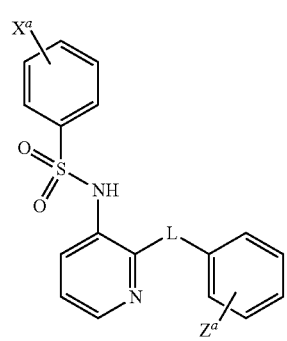 (XXIIa)
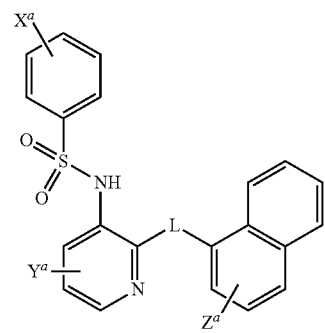 (XXIIb)
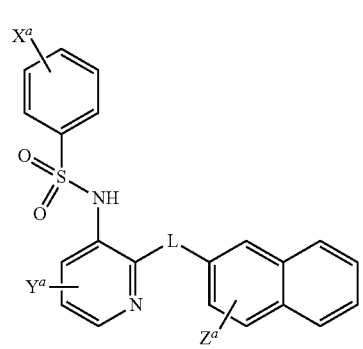 (XXIIc)
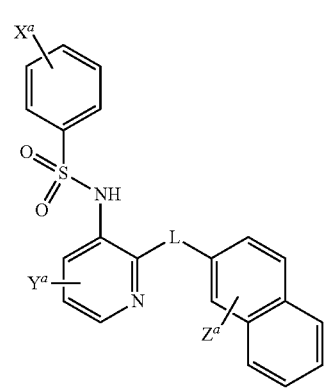 (XXIId)
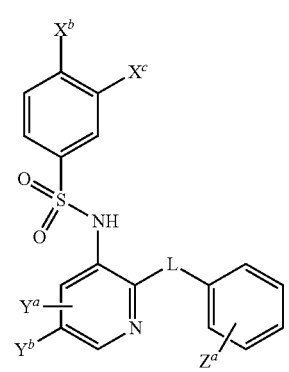 (XXIIIa)

-continued
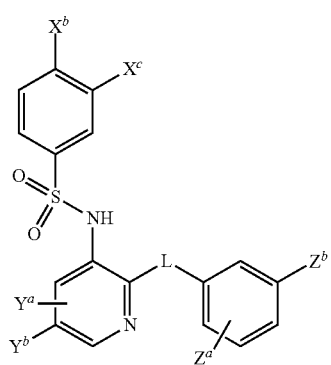
(XXIIIb)
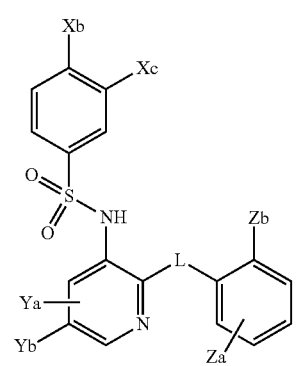
(XXIIIc)
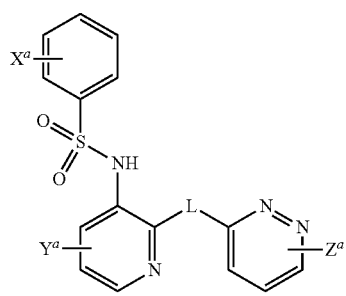
(XXIVa)
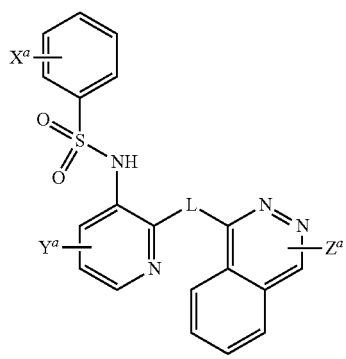
(XXIVb)
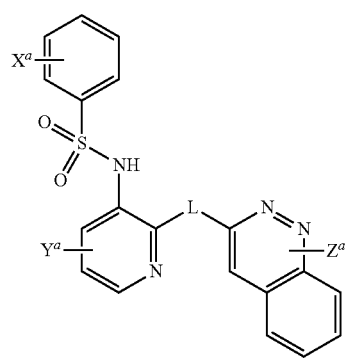
(XXIVc)
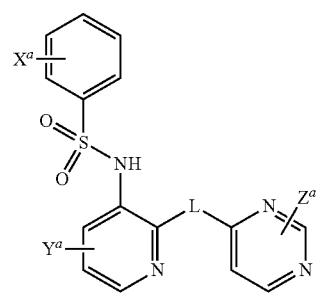
(XXVa)
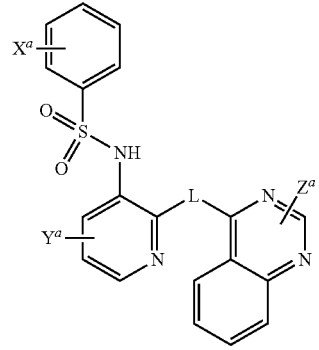
(XXVb)
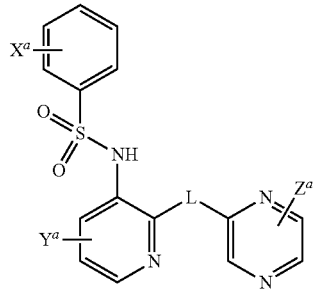
(XXVIa)
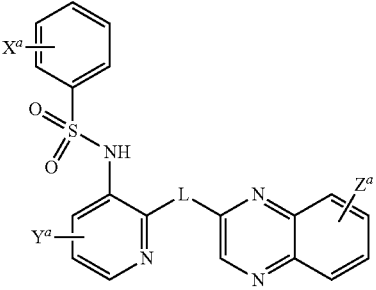
(XXVIb)

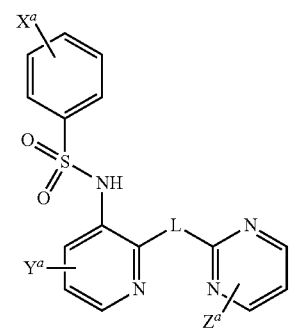
(XXVIIa)
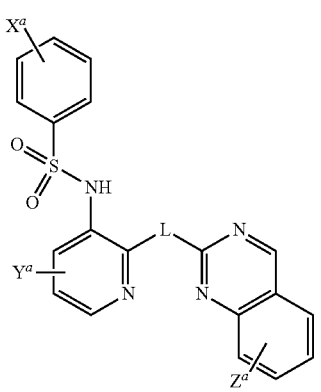
(XXVIIb)
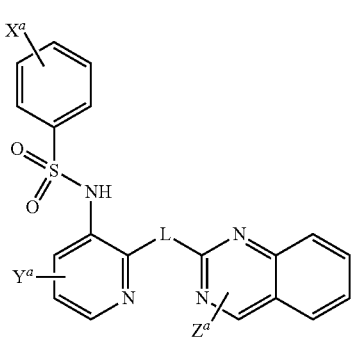
(XXVIIc)
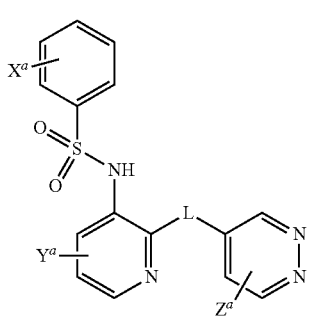
(XXVIIIa)
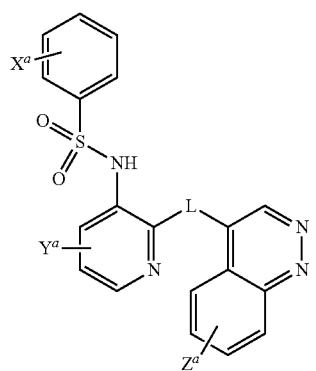
(XXVIIIb)
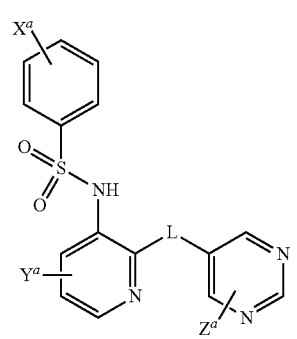
(XXIX)
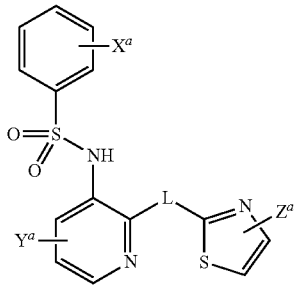
(XXXa)
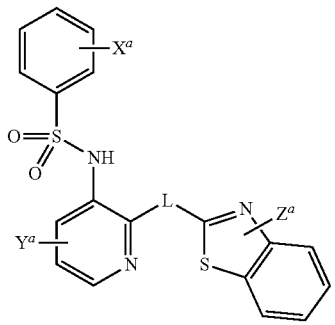
(XXXb)
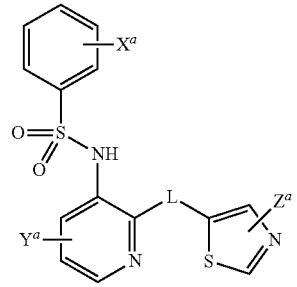
(XXXI)

(XXXIIa)
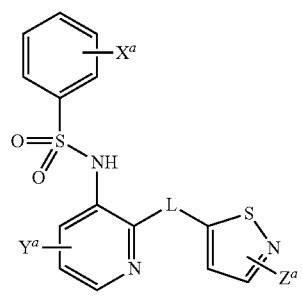
(XXXIIb)
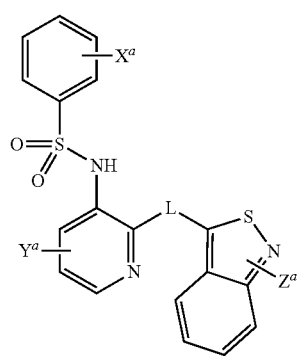
(XXXIIIa)
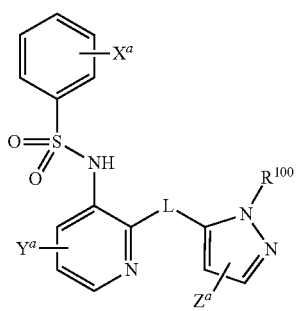
(XXXIIIb)
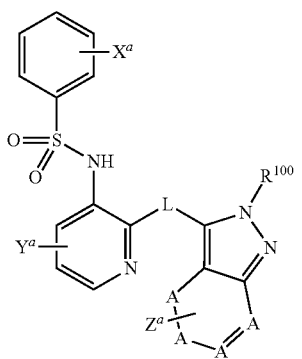
(XXXIIIc)
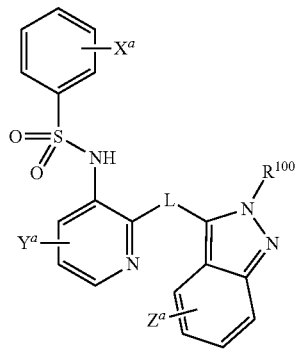
(XXXIIId)
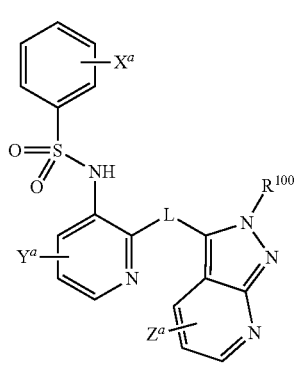
(XXXIVa)
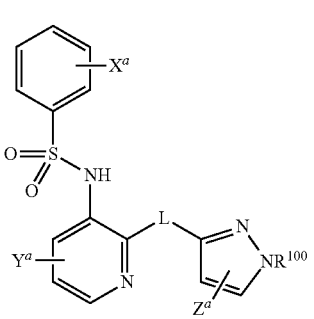
(XXXIVb)
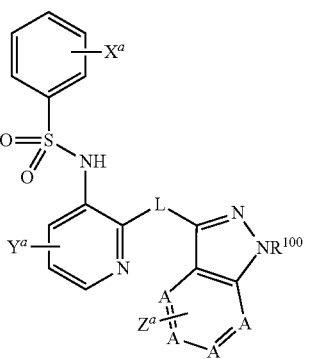

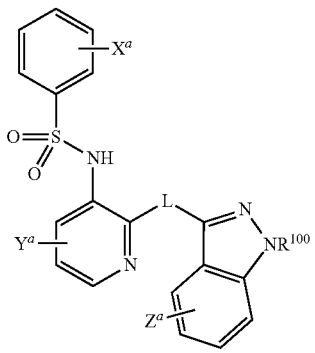 (XXXIVc)
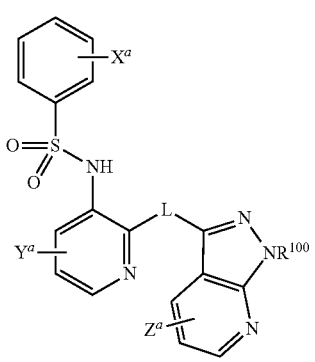 (XXXIVd)
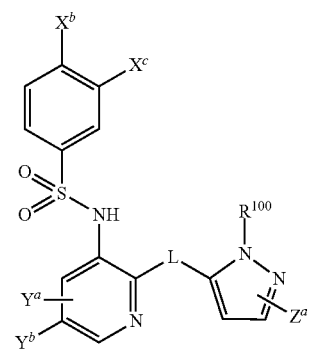 (XXXVa)
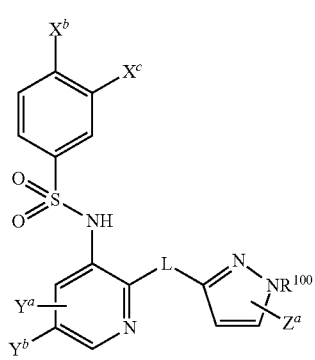 (XXXVb)
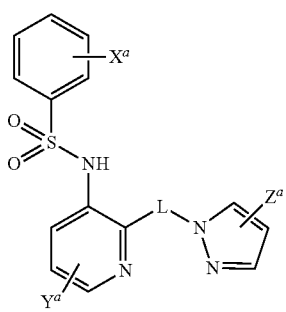 (XXXVIa)
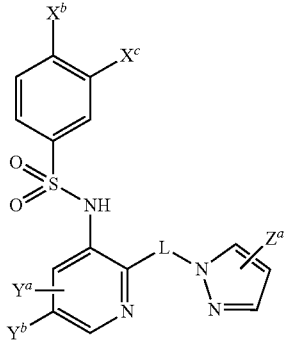 (XXXVIb)
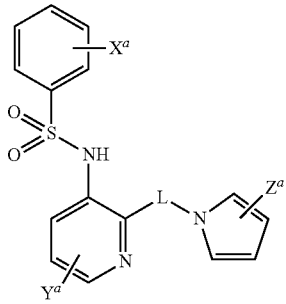 (XXXVIc)
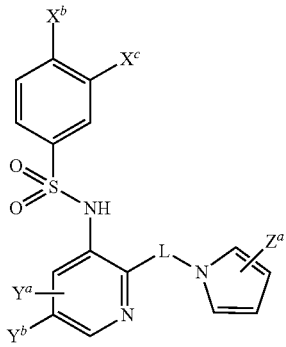 (XXXVId)
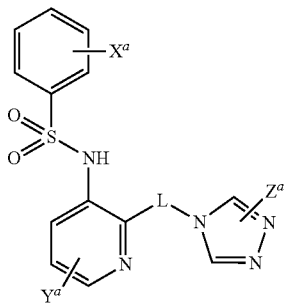 (XXXVIe)

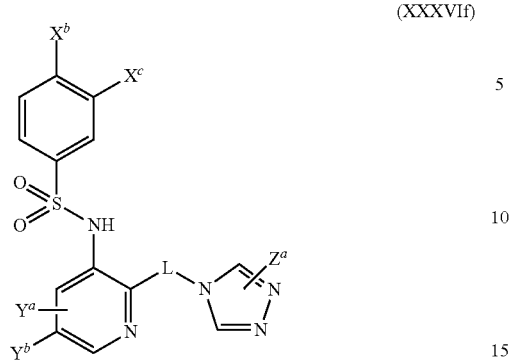
(XXXVIf)
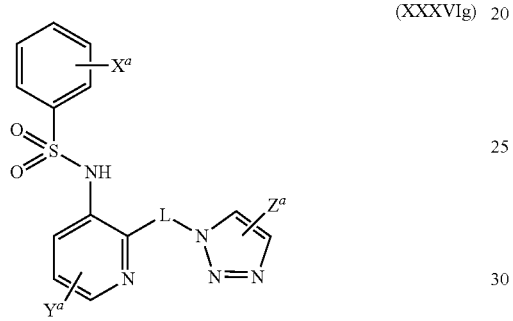
(XXXVIg)
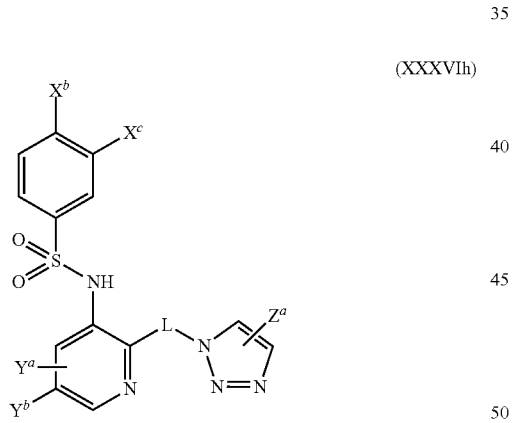
(XXXVIh)
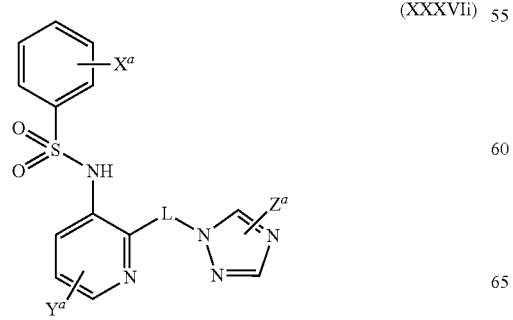
(XXXVIi)
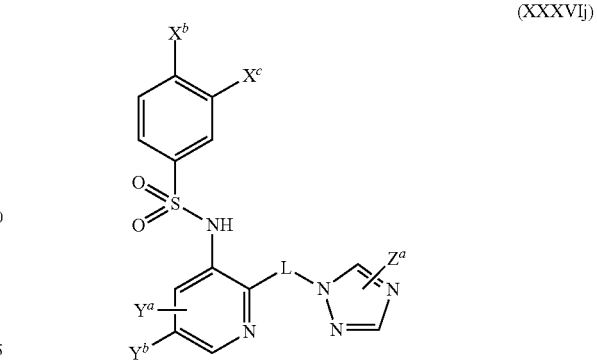
(XXXVIj)
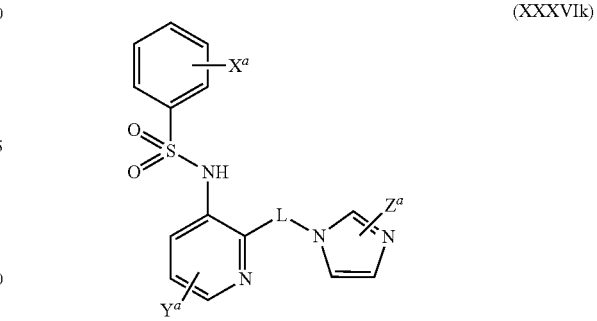
(XXXVIk)
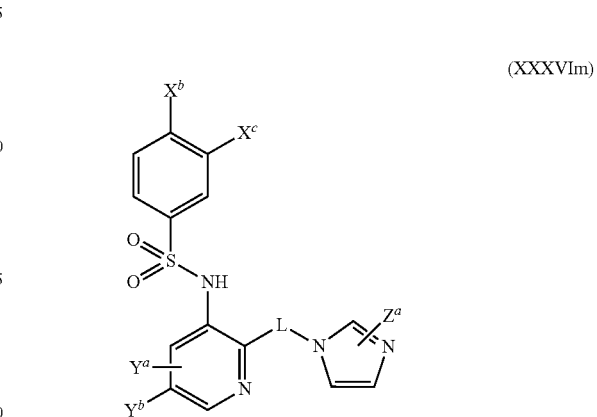
(XXXVIm)
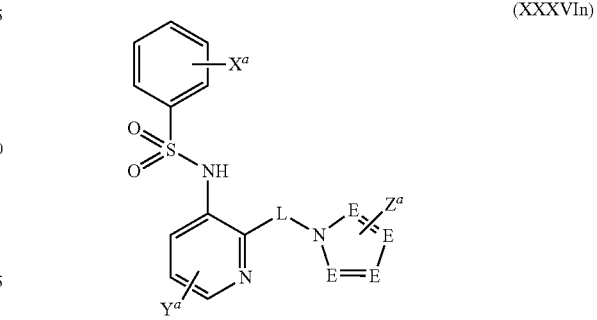
(XXXVIn)

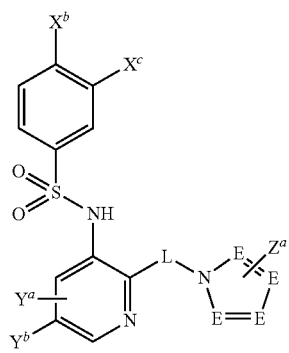
(XXXVIo)
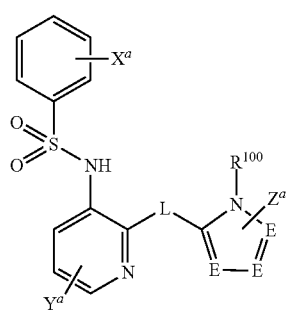
(XXXVIp)
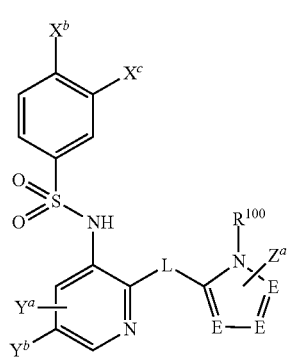
(XXXVIq)
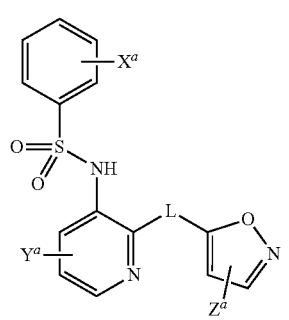
(XXXVIIa)
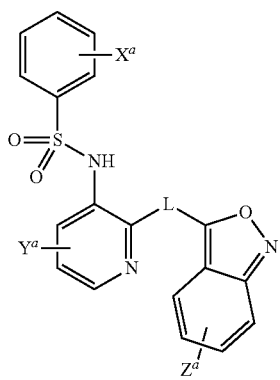
(XXXVIIb)
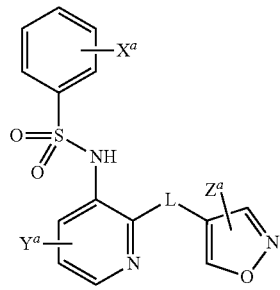
(XXXVIII)
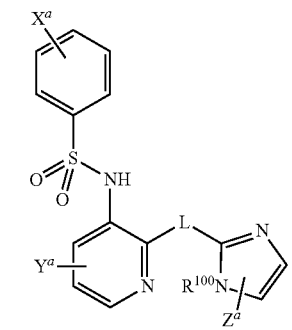
(XLIV)
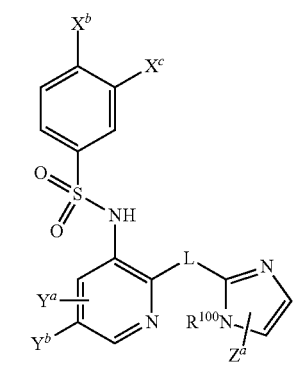
(XLV)

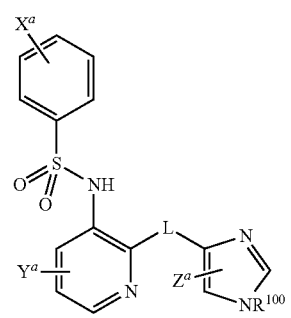 (XLVI)
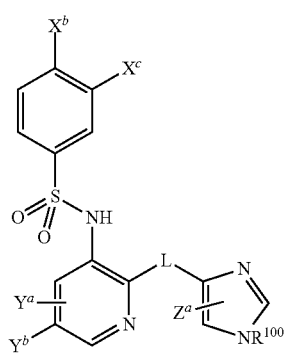 (XLVII)
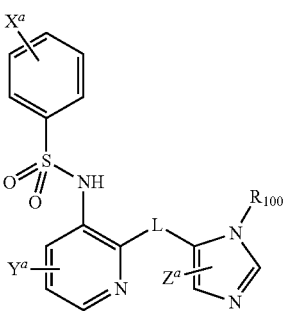 (XLVIII)
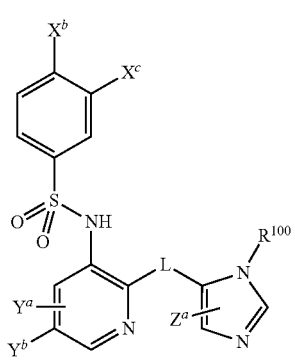 (XLIX)
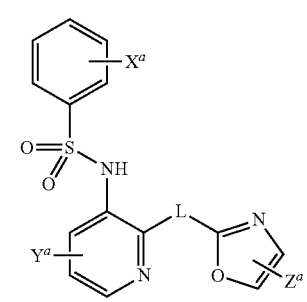 (La)
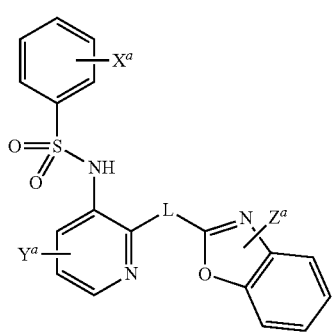 (Lb)
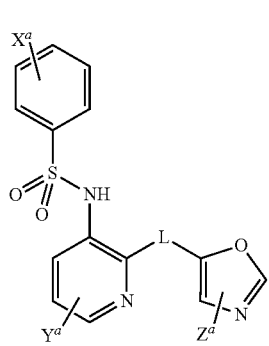 (LI)
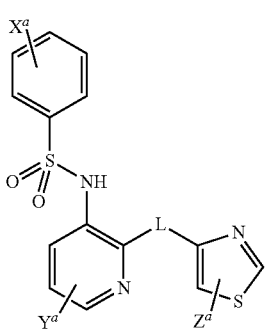 (LII)
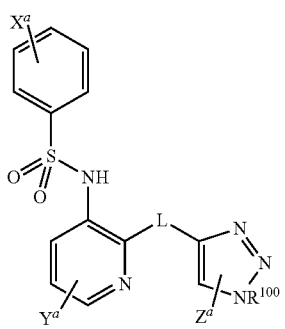 (LIIIa)

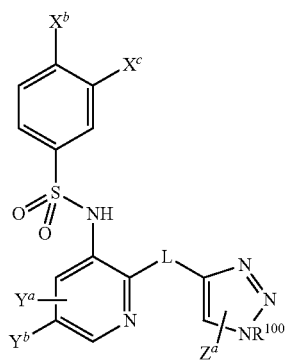
(LIIIb)
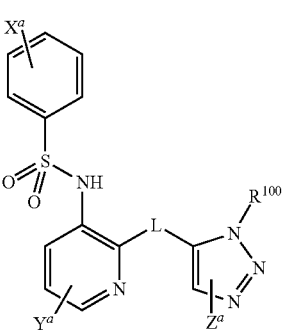
(LIVa)
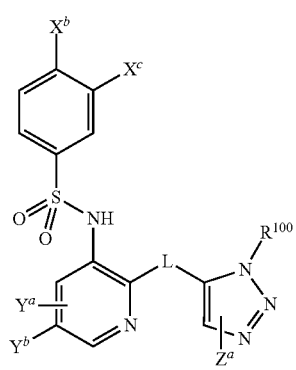
(LIVb)
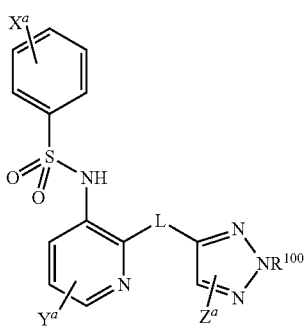
(LVa)
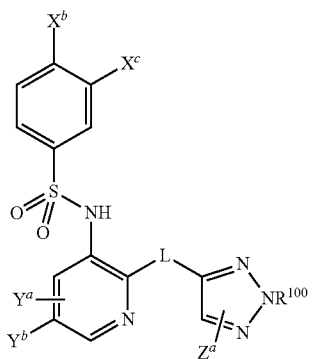
(LVb)
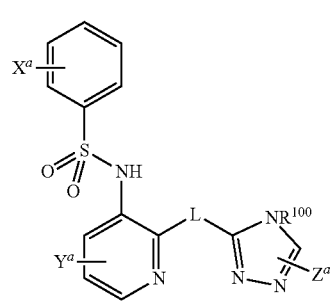
(LVc)
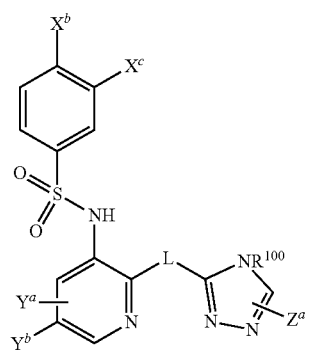
(LVd)
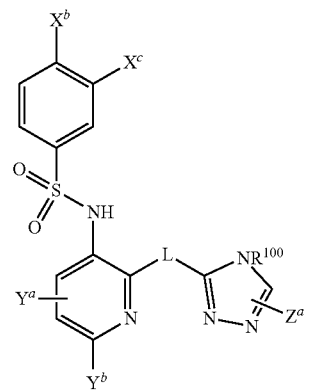
(LVe)

(LVf)
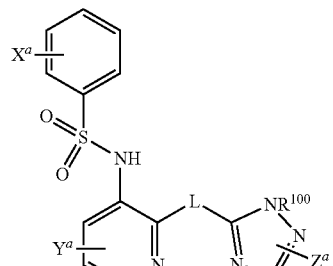
(LVg)
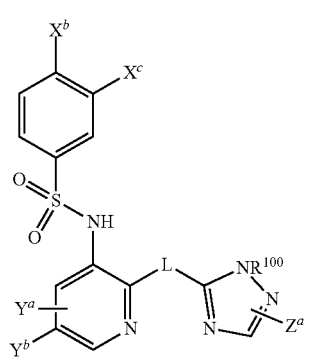
(LVh)
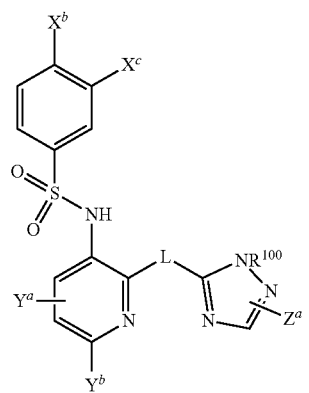
(LVi)
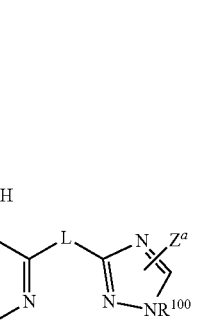
(LVj)
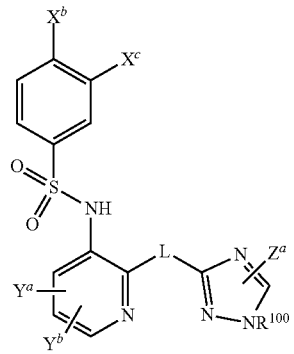
(LVk)
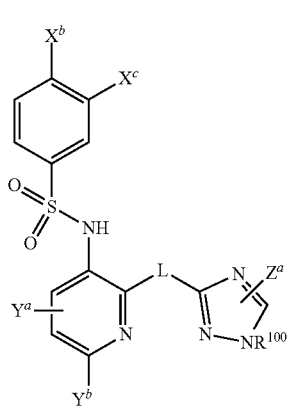
(LVl)
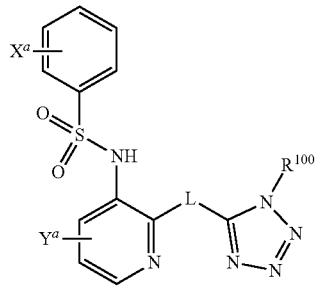
(LVII)
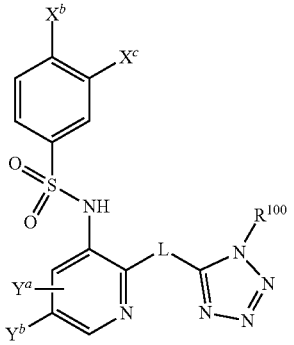

(LVIII)
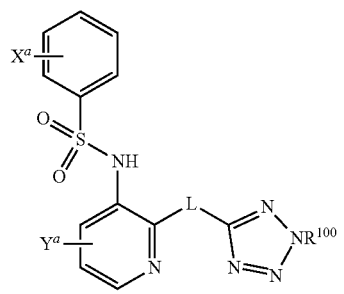
(LIX)
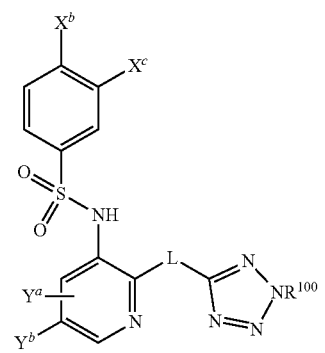
(LXa)
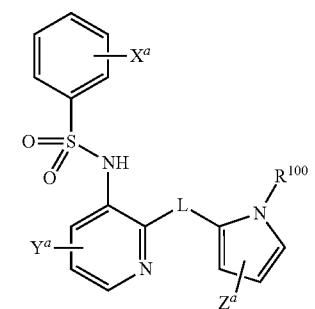
(LXb)
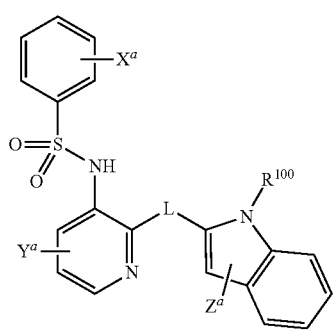
(LXc)
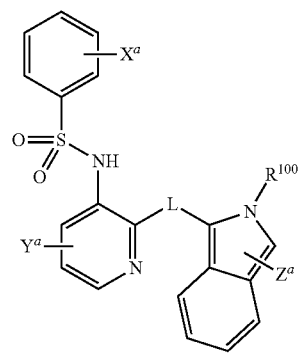
(LXIa)
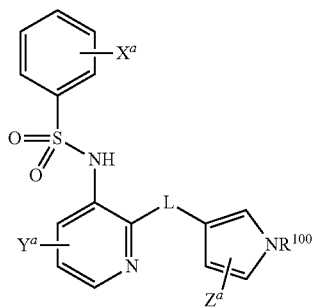
(LXIb)
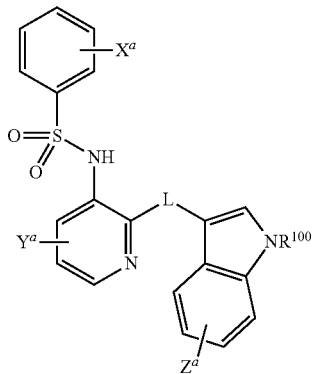
(LXIIa)
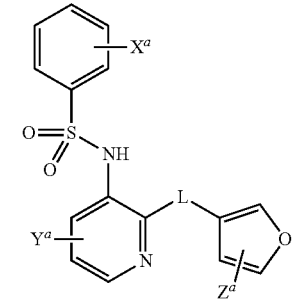
(LXIIb)
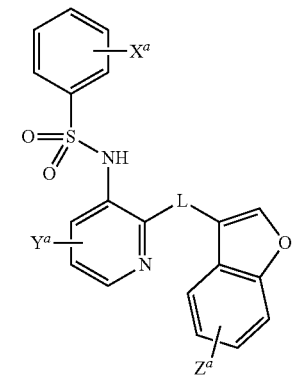

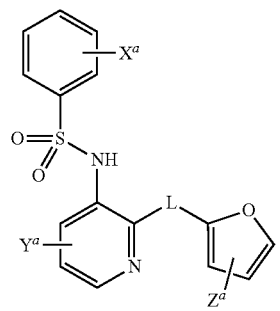
(LXIIIa)
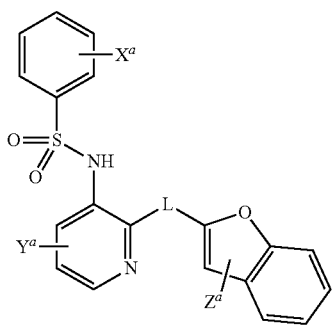
(LXIIIb)
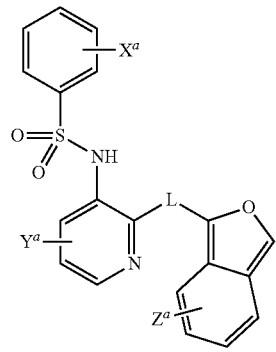
(LXIIIc)
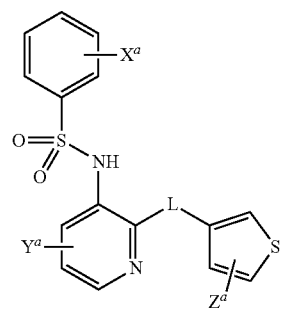
(LXIV)
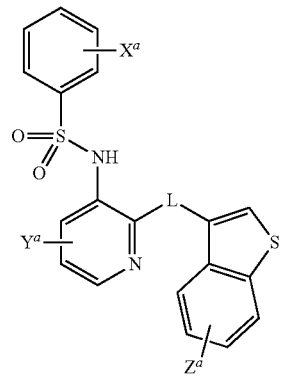
(LXIV)
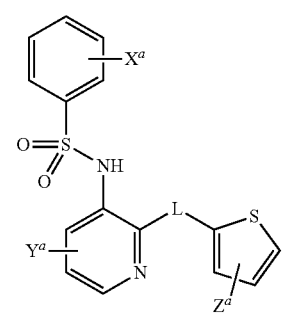
(LXV)
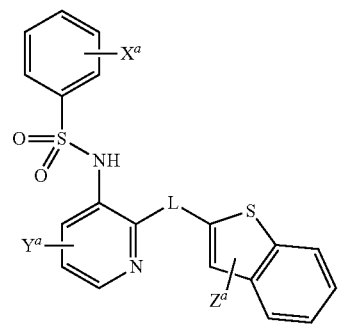
(LXV)
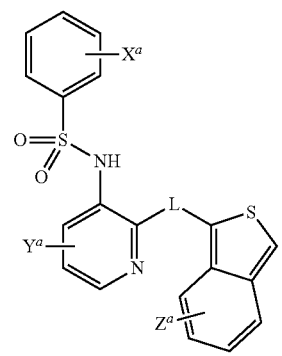
(LXV)

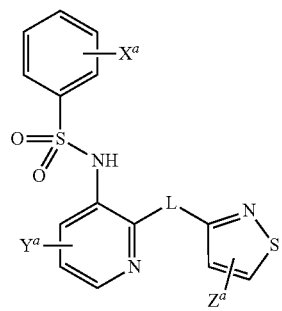
(LXVIa)
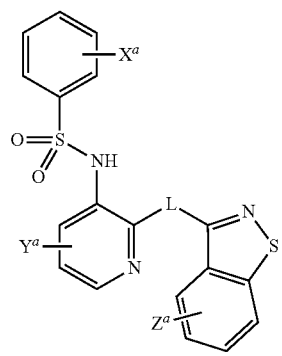
(LXVIb)
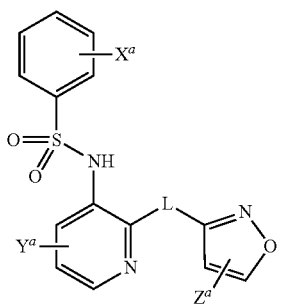
(LXVIIa)
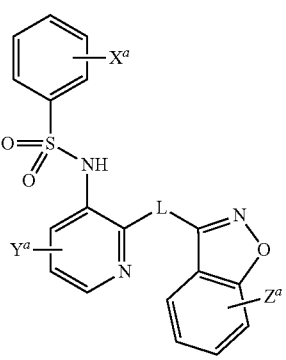
(LXVIIb)
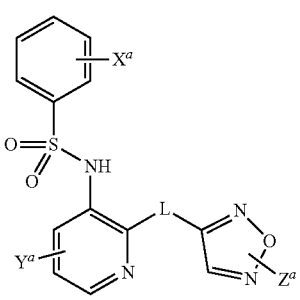
(LXVIII)
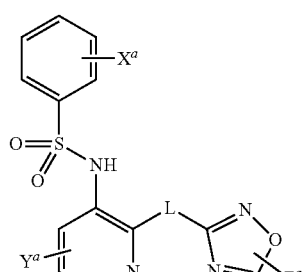
(LXIX)
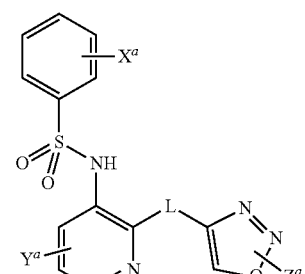
(LXX)
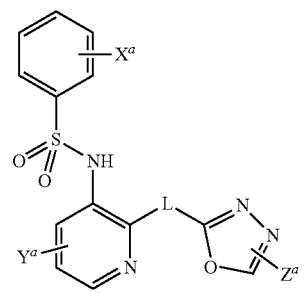
(LXXI)
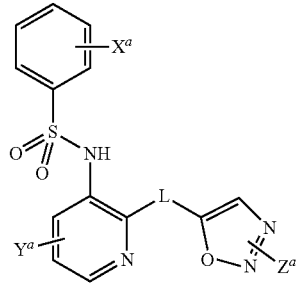
(LXXII)
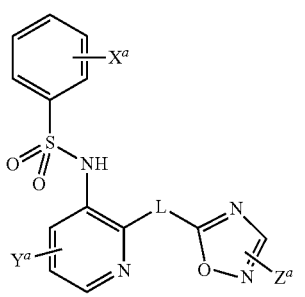
(LXXIII)

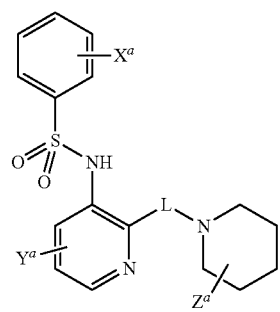 (LXXIV)
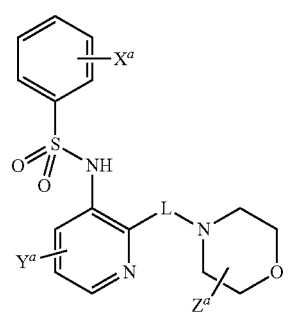 (LXXV)
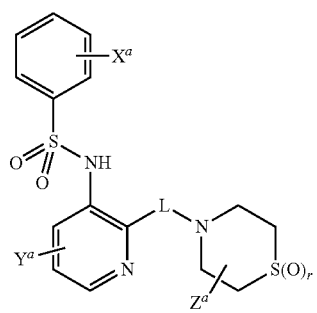 (LXXVI)
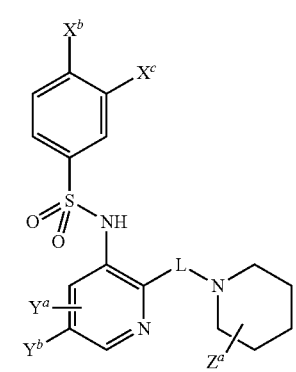 (LXXVII)
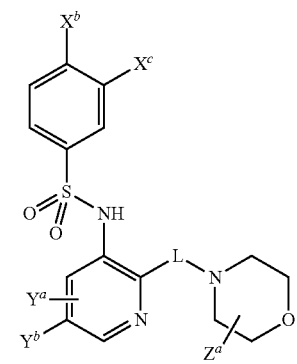 (LXXVIII)
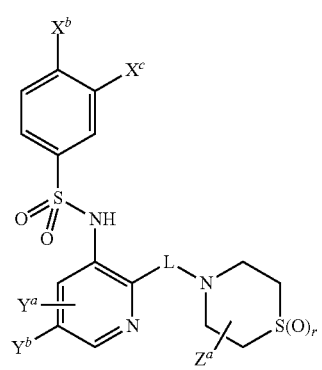 (LXXIX)
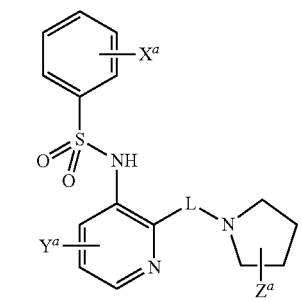 (LXXX)
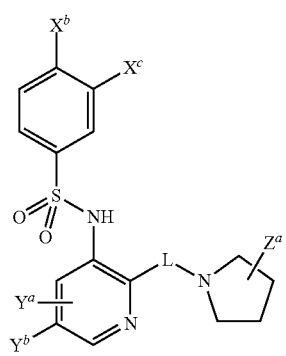 (LXXXI)

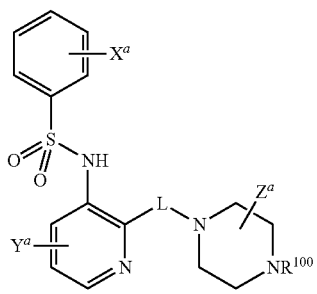
(LXXXII)
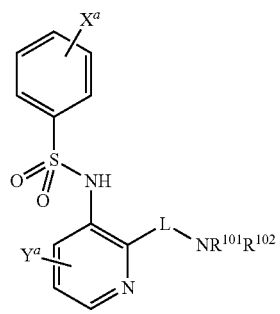
(LXXXIIIa)
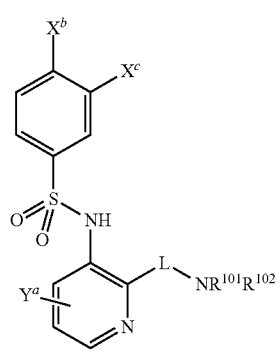
(LXXXIIIb)
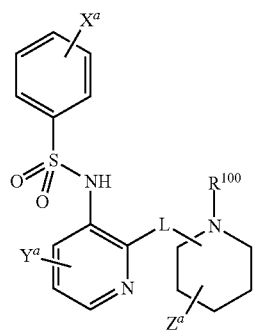
(LXXXIV)
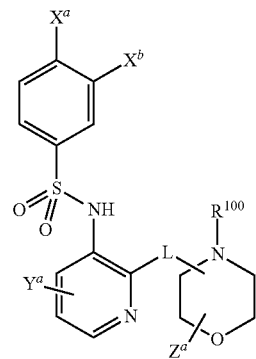
(LXXXV)
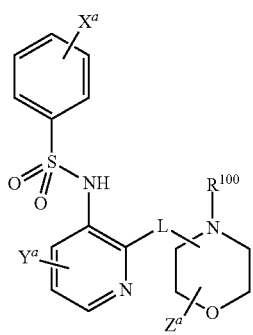
(LXXXVI)
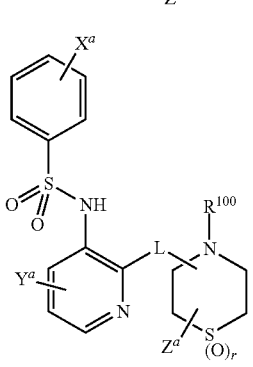
(LXXXVII)
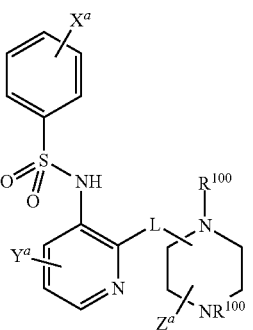
(LXXXVIII)
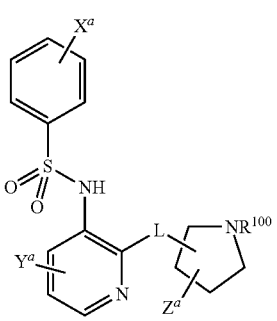
(LXXXX)
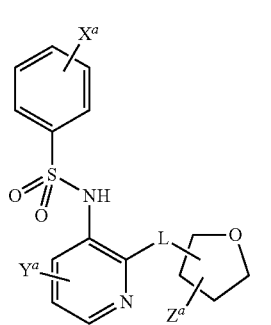
(LXXXXI)

US 11,433,061 B2

57
-continued

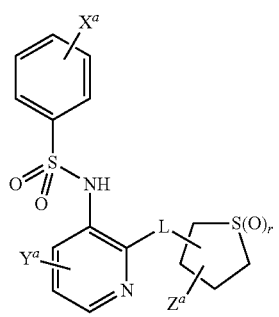
(LXXXXII)

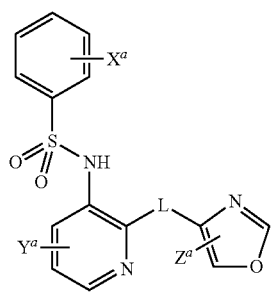
(XCIII)

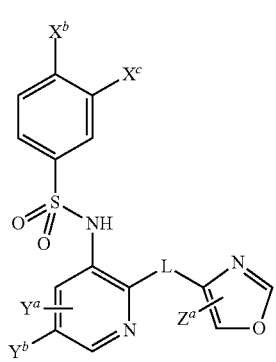
(XCIV)

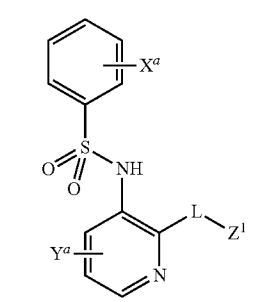
(XCV)

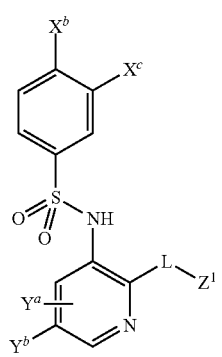
(XCVI)

58
-continued

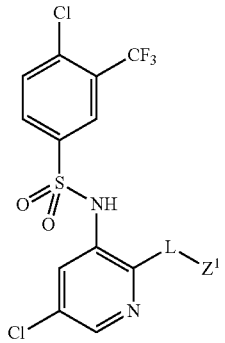
(XCVII)

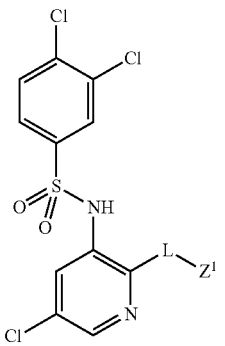
(XCVIII)

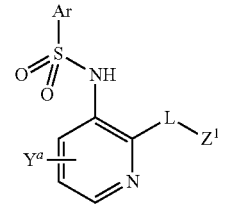
(XCIX)

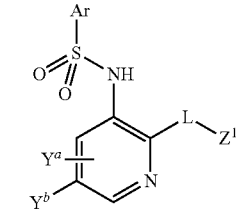
(C)

Formulae IV to C are examples of Formula I.

In the following descriptions and embodiments, references to specific substituents only correspond to formula numbers in which those specific substituents are present or appear.

In each of the formulae (IV to C), Ar, L and $Z^1$ are as defined above.

A is selected from the group consisting of —CH—, —$CZ^{16}$—, —N—, and —$N^+(O)^-$—;

each occurrence of $Z^{16}$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, oxo (=O or —O$^-$), —NO$_2$, —OR$^{42}$, —OC(O)R$^{42}$, —CO$_2$R$^{42}$, —C(O)R$^{42}$, —C(O)NR$^{42}$R$^{43}$, —OC(O)NR$^{42}$R$^{43}$, —NR$^{42}$C(O)R$^{43}$, —NR$^{42}$C(O)NR$^{43}$R$^{44}$, —NR$^{42}$R$^{43}$, —NR$^{42}$CO$_2$R$^{43}$, —SR$^{42}$, —S(O)R$^{42}$, —S(O)$_2$R$^{42}$, —S(O)$_2$NR$^{42}$R$^{43}$, —NR$^{42}$S(O)$_2$R$^{43}$, substituted or unsubstituted $C_{6-10}$ aryl, substituted or unsubstituted 5- to 10-membered heteroaryl, substituted or unsubstituted 3- to 10-membered heterocyclyl, substituted or unsubstituted ($C_{1-4}$ alkyl)-($C_{6-10}$ aryl), and substituted or unsubstituted ($C_{1-4}$ alkyl)-(5- to 10-membered heteroaryl); or where two or more A are $CZ^{16}$, then the $Z^{16}$ substituents together can form a carbocyclic or heterocyclic ring;

$R^{42}$, $R^{43}$ and $R^{44}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl;

$X^a$ represents 0 to 5 substituents each independently selected from the group consisting of halogen, —CN, —C(O)$R^{24}$, —CO$_2$$R^{24}$, —C(O)NR$^{24}$R$^{25}$, —OR$^{24}$, —OC(O)R$^{24}$, —OC(O)NR$^{24}$R$^{25}$, —SR$^{24}$, —S(O)R$^{24}$, —S(O)$_2$R$^{24}$, —S(O)$_2$NR$^{24}$R$^{25}$, —NO$_2$, —NR$^{24}$R$^{25}$, —NR$^{24}$C(O)R$^{25}$, —NR$^{24}$C(O)$_2$R$^{25}$, —NR$^{24}$S(O)$_2$R$^{25}$, —NR$^{24}$C(O)NR$^{25}$R$^{26}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{24}$, $R^{25}$ and $R^{26}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{24}$ and $R^{25}$, $R^{25}$ and $R^{26}$ or $R^{24}$ and $R^{26}$ may, together with the atoms to which they are attached, form a substituted or unsubstituted 5-, 6-, or 7-membered ring.

$X^b$ and $X^c$ are each independently selected from the group consisting of hydrogen, halogen, —CN, —C(O)R$^{24a}$, —CO$_2$R$^{24a}$, —C(O)NR$^{24a}$R$^{25a}$, —OR$^{24a}$, —OC(O)R$^{24a}$, —OC(O)NR$^{24a}$R$^{25a}$, —SR$^{24a}$, —S(O)R$^{24a}$, —S(O)$_2$R$^{24a}$, —S(O)$_2$NR$^{24a}$R$^{25a}$, —NO$_2$, —NR$^{24a}$R$^{25a}$, —NR$^{24a}$C(O)R$^{25a}$, —NR$^{24a}$C(O)$_2$R$^{25a}$, —NR$^{24a}$S(O)$_2$R$^{25a}$, —NR$^{24a}$C(O)NR$^{25a}$R$^{26a}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{24a}$, $R^{25a}$ and $R^{26a}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{24a}$ and $R^{25a}$, $R^{25a}$ and $R^{26a}$ or $R^{24a}$ and $R^{26a}$ may, together with the atoms to which they are attached, form a substituted or unsubstituted 5-, 6-, or 7-membered ring.

$Y^a$ represents 0 to 3 substituents each independently selected from the group consisting of halogen, —CN, —C(O)R$^{27}$, —CO$_2$R$^{27}$, —C(O)NR$^{27}$R$^{28}$, —OR$^{27}$, —OC(O)R$^{27}$, —OC(O)NR$^{27}$R$^{28}$, —SR$^{27}$, —S(O)R$^{27}$, —S(O)$_2$R$^{27}$, —S(O)$_2$NR$^{27}$R$^{28}$, —NO$_2$, —NR$^{27}$R$^{28}$, —NR$^{27}$C(O)R$^{28}$, —NR$^{27}$C(O)$_2$R$^{28}$, —NR$^{27}$S(O)$_2$R$^{28}$, —NR$^{27}$C(O)NR$^{28}$R$^{29}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{27}$, $R^{28}$ and $R^{29}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{27}$ and $R^{28}$, $R^{28}$ and $R^{29}$ or $R^{27}$ and $R^{29}$ may, together with the atoms to which they are attached, form a substituted or unsubstituted 5-, 6-, or 7-membered ring.

$Y^b$ is independently selected from the group consisting of hydrogen, halogen, —CN, —C(O)R$^{27a}$, —CO$_2$R$^{27a}$, —C(O)NR$^{27a}$R$^{28a}$, —OR$^{27a}$, —OC(O)R$^{27a}$, —OC(O)NR$^{27a}$R$^{28a}$, —SR$^{27a}$, —S(O)R$^{27a}$, —S(O)$_2$R$^{27a}$, —S(O)$_2$NR$^{27a}$R$^{28a}$, —NO$_2$, —NR$^{27a}$R$^{28a}$, —NR$^{27a}$C(O)R$^{28a}$, —NR$^{27a}$C(O)$_2$R$^{28a}$, —NR$^{27a}$S(O)$_2$R$^{28a}$, —NR$^{27a}$C(O)NR$^{28a}$R$^{29a}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{27a}$, $R^{28a}$ and $R^{29a}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{27a}$ and $R^{28a}$, $R^{28a}$ and $R^{29a}$ or $R^{27a}$ and $R^{29a}$ may, together with the atoms to which they are attached, form a substituted or unsubstituted 5-, 6-, or 7-membered ring.

$Z^a$ represents 0 to 5 substituents each independently selected from the group consisting of halogen, —CN, —C(O)R$^{30}$, —CO$_2$R$^{30}$, —C(O)NR$^{30}$R$^{31}$, —OR$^{30}$, —OC(O)R$^{30}$, —OC(O)NR$^{30}$R$^{31}$, —SR$^{30}$, —S(O)R$^{30}$, —S(O)$_2$R$^{30}$, —S(O)$_2$NR$^{30}$R$^{31}$, —NO$_2$, —NR$^{30}$R$^{31}$, —NR$^{30}$C(O)R$^{31}$, —NR$^{30}$C(O)$_2$R$^{31}$, —NR$^{30}$S(O)$_2$R$^{31}$, —NR$^{30}$C(O)NR$^{31}$R$^{32}$, oxo (=O or —O$^-$), substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl); or alternatively where two of $Z^a$ together with the atoms which they substitute, form a carbocyclic or heterocyclic ring such that Z is a bi- or tri-cyclic ring;

$R^{30}$, $R^{31}$ and $R^{32}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and $R^{30}$ and $R^{31}$, $R^{31}$ and $R^{32}$ or $R^{30}$ and $R^{32}$ may, together with the atoms to which they are attached, form a substituted or unsubstituted 5-, 6-, or 7-membered ring.

$Z^b$ is selected from the group consisting of hydrogen, halogen, —CN, —C(O)R$^{30a}$, —CO$_2$R$^{30a}$, —C(O)NR$^{30a}$R$^{31a}$, —OR$^{30a}$, —OC(O)R$^{30a}$, —OC(O)NR$^{30a}$R$^{31a}$, —SR$^{30a}$, —S(O)R$^{30a}$, —S(O)$_2$R$^{30a}$, —S(O)$_2$NR$^{30a}$R$^{31a}$, —NO$_2$, —NR$^{30a}$R$^{31a}$, —NR$^{30a}$C(O)R$^{31a}$, —NR$^{30a}$C(O)$_2$R$^{31a}$, —NR$^{30a}$S(O)$_2$R$^{31a}$, —NR$^{30a}$C(O)NR$^{31a}$R$^{32a}$, OXO (=O or —O$^-$), substituted or unsubstituted $C_{1-8}$ alkyl, substituted or unsubstituted $C_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, substituted or unsubstituted 5- to 10-membered heteroaryl, substituted or unsubstituted (C$_{1-4}$ alkyl)-(C$_{6-10}$ aryl), and substituted or unsubstituted (C$_{1-4}$ alkyl)-(5- to 10-membered heteroaryl); or alternatively where two of Z$^a$ and Z$^b$ together with the atoms which they substitute, form a carbocyclic or heterocyclic ring such that Z is a bi- or tri-cyclic ring;

R$^{30a}$, R$^{31a}$ and R$^{32a}$ are each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl; and R$^{30a}$ and R$^{31a}$, R$^{31a}$ and R$^{32a}$ or R$^{30a}$ and R$^{32a}$ may, together with the atoms to which they are attached, form a substituted or unsubstituted 5-, 6-, or 7-membered ring.

R$^{100}$ is selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, —S(O)R$^{33}$, or —S(O)$_2$R$^{33}$; —C(O)R$^{33}$, —C(O)$_2$R$^{33}$;

R$^{33}$ is independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl.

R$^{101}$ and R$^{102}$ are each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl;

R$^{101}$ and R$^{102}$ may, together with the nitrogen, form a substituted or unsubstituted 4-, 5-, 6-, or 7-membered heterocyclyl;

r is 0, 1, or 2.

Preferred Embodiments

In one embodiment, any of formulae (I-CIII) is other than N-(2-benzoyl-pyridin-3-yl)-4-isopropoxy-benzenesulfonamide.

In one embodiment, any of formulae (I-CIII), is other than formula CC:

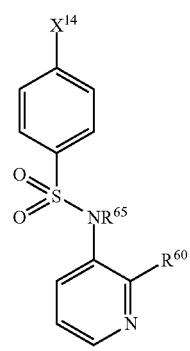

CC where X$^{14}$ is selected from the group consisting of —Cl, —NO$_2$, —OCH$_3$, —CH$_3$, —NHC(O)CH$_3$, and —CH$_2$CH$_2$-(phenyl);

R$^{65}$ is selected from the group consisting of hydrogen, substituted or unsubstituted C$_{1-4}$ alkyl, and substituted or unsubstituted —SO$_2$(phenyl); and R$^{60}$ is selected from the group consisting of —NR$^{61}$CH$_2$CH$_2$OR$^{62}$, —NR$^{61}$CH$_2$CH$_2$NR$^{63}$R$^{64}$, —NR$^{61}$CH$_2$CH$_2$SR$^{62}$,

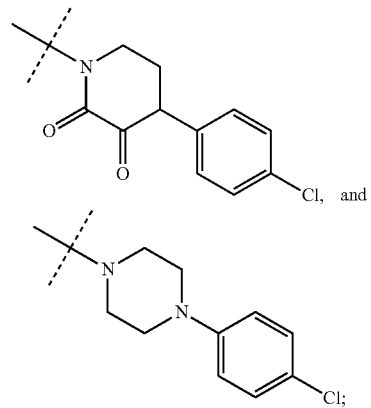

where R$^{61}$ is selected from the group consisting of hydrogen and substituted or unsubstituted phenyl;

R$^{62}$ is selected from the group consisting of substituted or unsubstituted phenyl, and substituted or unsubstituted C$_{1-4}$ alkyl; and R$^{63}$ and R$^{64}$ are each independently selected from the group consisting of hydrogen, substituted or unsubstituted C$_{1-8}$ alkyl, substituted or unsubstituted phenyl, substituted or unsubstituted —SO$_2$(phenyl), —C(O)CH$_3$, —C(O)C(O)OH, and —C(O)$_2$C(CH$_3$)$_3$.

Preferred Ar and X Substituents

In one embodiment of formula (III), at least one of X$^2$, X$^3$, X$^4$, X$^5$ and X$^6$ is other than hydrogen; or at least two of X$^2$, X$^3$, X$^4$, X$^5$ and X$^6$ is other than hydrogen.

In one embodiment of formula (III), X$^3$ is other than hydrogen.

In one embodiment of formula (III), X$^4$ is other than hydrogen.

In one embodiment of formula (III), X$^4$ is other than isopropoxy.

In one embodiment of formula (III), X$^4$ is other than methyl.

In one embodiment of formula (III), X$^3$ and X$^4$ are other than hydrogen.

In one embodiment of formula (III), when X$^4$ is isopropoxy, at least one of X$^2$, X$^3$, X$^5$ and X$^6$ is other than hydrogen.

In one embodiment of formula (III), X$^2$, X$^3$, X$^4$, X$^5$ and X$^6$ are each independently selected from the group consisting of hydrogen, halogen, —CN, —NO$_2$, —OR$^{18}$, —C(O)R$^{18}$, —SO$_2$R$^{18}$, —NR$^{18}$R$^{19}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formula (III), X$^2$, X$^3$, X$^4$, X$^5$ and X$^6$ are each independently selected from the group consisting of hydrogen, halogen, —CN, —NO$_2$, —OR$^{18}$, —C(O)R$^{18}$, —SO$_2$R$^{18}$, —NR$^{18}$R$^{19}$, unsubstituted C$_{2-8}$ alkyl, substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formula (III), $X^2$, $X^3$, $X^4$, $X^5$ and $X^6$ are each independently selected from the group consisting of hydrogen, halogen, —CN, —NO$_2$, —OR$^{18}$ (but not isopropoxy), —C(O)R$^{18}$, —SO$_2$R$^{18}$, —NR$^{18}$R$^{19}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formula (III), $X^2$, $X^3$, $X^4$, $X^5$ and $X^6$ are each independently selected from the group consisting of hydrogen, halogen, —CN, —NO$_2$, —OR$^{18}$ (but not isopropoxy), —C(O)R$^{18}$, —SO$_2$R$^{18}$, —NR$^{18}$R$^{19}$, unsubstituted C$_{2-8}$ alkyl, substituted C$_{1-8}$ alkyl, unsubstituted or substituted phenyl, unsubstituted or substituted 5- or 6-membered heteroaryl, and unsubstituted or substituted 5- or 6-membered heterocyclyl.

In another embodiment of formula (III), $X^2$, $X^3$, $X^4$, $X^5$ and $X^6$ are each independently selected from the group consisting of: hydrogen, halogen, —CN, —NO$_2$, —OR$^{18}$, —C(O)R$^{18}$, —SO$_2$R$^{18}$, —NR$^{18}$R$^{19}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl; with the proviso that at least two of $X^2$, $X^3$, $X^4$, $X^5$ and $X^6$ are other than hydrogen; or with the proviso that at least one of $X^2$, $X^3$, $X^4$, $X^5$ and $X^6$ is other than hydrogen.

In another embodiment of formula (III), $X^2$, $X^3$, $X^4$, $X^5$ and $X^6$ are each independently selected from the group consisting of: hydrogen, halogen, —CN, —NO$_2$, —OR$^{18}$, —C(O)R$^{18}$, —SO$_2$R$^{18}$, —NR$^{18}$R$^{19}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl; with the proviso that at least two of $X^3$, $X^4$ and $X^5$ are other than hydrogen; or with the proviso at least one of $X^3$, $X^4$ and $X^5$ is other than hydrogen.

In a further embodiment of formula (III), $X^2$, $X^3$, $X^4$, $X^5$ and $X^6$ are each independently selected from the group consisting of: hydrogen, halogen, —CN, —NO$_2$, —OR$^{18}$, —C(O)R$^{18}$, —SO$_2$R$^{18}$, and —NR$^{18}$R$^{19}$; with the proviso that at least three of $X^2$, $X^3$, $X^4$, $X^5$ and $X^6$ are other than hydrogen; or with the proviso that at least two of $X^2$, $X^3$, $X^4$, $X^5$ and $X^6$ is other than hydrogen; or with the proviso that at least one of $X^2$, $X^3$, $X^4$, $X^5$ and $X^6$ is other than hydrogen.

In a further embodiment of formula (III), $X^2$, $X^3$, $X^4$, $X^5$ and $X^6$ are each independently selected from the group consisting of: hydrogen, halogen, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl; with the proviso that at least three of $X^2$, $X^3$, $X^4$, $X^5$ and $X^6$ are other than hydrogen; or with the proviso that at least two of $X^2$, $X^3$, $X^4$, $X^5$ and $X^6$ is other than hydrogen; or with the proviso that at least one of $X^2$, $X^3$, $X^4$, $X^5$ and $X^6$ is other than hydrogen.

In one embodiment of formula (III), $X^4$ is selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, —CN, —C(O)R$^{18}$, —COO$_2$R$^{18}$, —C(O)NR$^{18}$R$^{19}$, —OC(O)R$^{19}$, —OC(O)NR$^{18}$R$^{19}$, —NO$_2$, —NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —SR$^{18}$, —S(O)R$^{18}$, —S(O)$_2$R$^{18}$, —S(O)$_2$NR$^{18}$R$^{19}$, substituted or unsubstituted C$_{6-10}$ aryl, substituted or unsubstituted 5- to 10-membered heteroaryl, and substituted or unsubstituted 3- to 10-membered heterocyclyl.

In one embodiment of formula (III), $X^4$ is selected from the group consisting of halogen and —CH$_3$, and $X^3$ is selected from the group consisting of halogen, —CH$_3$, —CF$_3$, —OCH$_3$, and —OCF$_3$.

In one embodiment of formula (III), when $X^2$, $X^3$, $X^5$ and $X^6$ are hydrogen, $X^4$ is other than —Cl, —NO$_2$, —OCH$_3$, —CH$_3$, —NHC(O)CH$_3$, or —CH$_2$CH$_2$-(phenyl).

In one embodiment of formulae (IV-C), $X^a$ represents 1 to 5 substituents each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, —CN, —C(O)R$^{18}$, —CO$_2$R$^{18}$, —C(O)NR$^{18}$R$^{19}$, —OC(O)R$^{19}$, —OC(O)NR$^{18}$R$^{19}$, —NO$_2$, —NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —SR$^{18}$, —S(O)R$^{18}$, —S(O)$_2$R$^{18}$, —S(O)$_2$NR$^{18}$R$^{19}$, substituted or unsubstituted C$_{6-10}$ aryl, substituted or unsubstituted 5- to 10-membered heteroaryl, and substituted or unsubstituted 3- to 10-membered heterocyclyl.

In one embodiment of formulae (IV-C), $X^a$ represents 1 to 5 substituents each independently selected from the group consisting of halogen, —CN, —C(O)R$^{24}$, —CO$_2$R$^{24}$, —C(O)NR$^{24}$R$^{25}$, —OR$^{24}$, —OC(O)R$^{24}$, —OC(O)NR$^{24}$R$^{25}$, —SR$^{24}$, —S(O)R$^{24}$, —S(O)$_2$R$^{24}$, —S(O)$_2$NR$^{24}$R$^{25}$, —NO$_2$, —NR$^{24}$R$^{25}$, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl.

In one embodiment of formulae (IV-C), $X^a$ represents 1 to 5 substituents each independently selected from the group consisting of halogen, —CN, —C(O)R$^{24}$, —CO$_2$R$^{24}$, —C(O)NR$^{24}$R$^{25}$, —OR$^{24}$, —OC(O)R$^{24}$, —OC(O)NR$^{24}$R$^{25}$, —SR$^{24}$, —S(O)R$^{24}$, —S(O)$_2$R$^{24}$, —S(O)$_2$NR$^{24}$R$^{25}$, —NO$_2$, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl.

In one embodiment of formulae (IV-C), when $X^a$ is para alkyl, L is C(O), and $Z^1$ is phenyl, at least one other $X^a$ substituent is present.

In one embodiment of formulae (IV-C), when $X^a$ is para isopropoxy, L is C(O), and $Z^1$ is phenyl, at least one other $X^a$ substituent is present.

In one embodiment of formulae (IV-C), $X^a$ represents 1 to 3 substituents each independently selected from the group consisting of halogen, —CN, —NO$_2$, —OR$^{24}$, —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formulae (IV-C), $X^a$ represents 1 to 3 substituents each independently selected from the group consisting of halogen, —CN, —NO$_2$, —OR$^{24}$ (but not isopropoxy), —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formulae (IV-C), $X^a$ represents two substituents each independently selected from the group consisting of halogen, —CN, —NO$_2$, —OR$^{24}$, —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formulae (IV-C), X$^a$ represents two substituents each independently selected from the group consisting of halogen, methyl, —OCH$_3$, —OCF$_3$, and —CF$_3$.

In one embodiment of formulae (IV-C), X$^a$ represents 1 to 2 substituents each independently selected from the group consisting of halogen, —CN, and —CF$_3$.

In one embodiment of each of the formulae (IV-C), X$^4$, X$^b$, or at least one of X$^a$ or X is a substituted or unsubstituted 5- or 6-membered heterocyclic ring, and the heterocycle is selected from the group consisting of pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene. In one embodiment, X$^c$, X$^2$, X$^3$, X$^5$, and X$^6$ are hydrogen.

In one embodiment of each of the formulae (IV-C), X$^4$, X$^b$, or at least one of X$^a$ or X is substituted or unsubstituted 5- or 6-membered heteroaryl ring selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl. In one embodiment, X$^c$, X$^2$, X$^3$, X$^5$, and X$^6$ are hydrogen.

In one embodiment of each of the formulae (IV-C), X$^4$, X$^b$, or at least one of X$^a$ or X is substituted or unsubstituted heterocyclic group selected from the group consisting of pyrrolidinyl, piperidinyl, piperazinyl, morpholinyl, 1,3-dioxalanyl, thiomorpholinyl, thiomorpholinyl-S,S-dioxide, piperazinyl and pyranyl. In one embodiment, X$^c$, X$^2$, X$^3$, X$^5$, and X$^6$ are hydrogen.

In one embodiment of each of the formulae (IV-C), X$^4$, X$^b$, or at least one of X$^a$ or X is a substituted C$_{1-8}$ alkyl, where suitable substituents are as defined for formula (II). Preferably, the substituent is a substituted or unsubstituted heterocyclic group of the formula (AA) as defined above in "Abbreviations and Definitions". More preferably, the substituent is selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene. In one embodiment, X$^c$, X$^2$, X$^3$, X$^5$, and X$^6$ are hydrogen.

In one embodiment of each of the formulae (IV-C), X$^4$, X$^b$, or at least one of X$^a$ or X is a substituted C$_{1-8}$ alkyl, where suitable substituents are as defined for formula (II). In one preferred embodiment, the substituted C$_{1-8}$ alkyl is substituted with a 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl. More preferably, the substituted C$_{1-8}$ alkyl is substituted with oxazolyl. In one embodiment, X$^c$, X$^2$, X$^3$, X$^5$, and X$^6$ are hydrogen.

In one embodiment of each of the formulae (IV-C), a suitable substituent for substituted C$_{1-8}$ alkyl (as X, X$^1$, X$^2$, X$^3$, X$^4$, X$^5$, X$^a$, X$^b$, or X$^c$) can be selected from the group consisting of —CN, —OR$^{18}$, —C(O)R$^{18}$, —CO$_2$R$^{18}$, —O(CO)R$^{18}$, —SO$_2$R$^{18}$ and halogen. In one embodiment, X$^c$, X$^2$, X$^3$, X$^5$, and X$^6$ are hydrogen.

In one embodiment of each of the formulae (IV-C), at least one of X$^a$, X$^b$, X$^c$, X$^1$, X$^2$, X$^3$, X$^4$, X$^5$ or at least one X is halogen, particularly chlorine.

In one embodiment of each of the formulae (IV-C), at least one of X$^a$, X$^b$, X$^c$, X$^1$, X$^2$, X$^3$, X$^4$, X$^5$ or at least one X is an unsubstituted C$_{1-8}$ alkyl.

In one embodiment of each of the formulae (IV-C), at least one of X$^a$, X$^b$, X$^c$, X$^1$, X$^2$, X$^3$, X$^4$, X$^5$ or at least one X is an unsubstituted C$_{2-8}$ alkyl.

In one embodiment of each of the formulae (IV-C), at least one of X$^a$, X$^b$, X$^c$, X$^1$, X$^2$, X$^3$, X$^4$, X$^5$ or at least one X is t-butyl.

In one embodiment of each of the formulae (IV-C), at least one of X$^a$, X$^b$, X$^c$, X$^1$, X$^2$, X$^3$, X$^4$, X$^5$ or at least one X is oxazolyl.

In one embodiment of each of the formulae (IV-C), at least one of X$^a$, X$^b$, X$^c$, X$^1$, X$^2$, X$^3$, X$^4$, X$^5$ or at least one X is trifluoromethoxy.

In one embodiment of each of the formulae (IV-C), at least one of X$^a$, X$^b$, X$^c$, X$^1$, X$^2$, X$^3$, X$^4$, X$^5$ or at least one X is —SO$_2$R$^{18}$. In one particular embodiment, R$^{18}$ is methyl.

In one embodiment of each of the formulae (IV-C), at least one of X$^a$, X$^b$, X$^c$, X$^1$, X$^2$, X$^3$, X$^4$, X$^5$ or at least one X is —OR$^{18}$. In one particular embodiment, R$^{18}$ is methyl.

In one embodiment of each of the formulae (IV-C), at least one of X$^a$, X$^b$, X$^c$, X$^1$, X$^2$, X$^3$, X$^4$, X$^5$ or at least one X is —SR$^{18}$. In one particular embodiment, R$^{18}$ is methyl.

In one embodiment of each of the formulae (IV-C), at least one of X$^a$, X$^b$, X$^c$, X$^1$, X$^2$, X$^3$, X$^4$, X$^5$ or at least one X is unsubstituted C$_{1-6}$ alkyl (in particular methyl) or C$_{1-6}$ haloalkyl (in particular —CF$_3$).

In one embodiment of each of the formulae (IV-C), at least one of X$^a$, X$^b$, X$^c$, X$^1$, X$^2$, X$^3$, X$^4$, X$^5$ or at least one X is substituted C$_{1-6}$ alkyl (preferably not C$_{1-6}$ haloalkyl).

In one embodiment of each of the formulae (IV-C), at least one of X$^a$, X$^b$, X$^c$, X$^1$, X$^2$, X$^3$, X$^4$, X$^5$ or at least one X is isopropyl.

In one embodiment of each of the formulae (IV-C), at least one of X$^a$, X$^b$, X$^c$, X$^1$, X$^2$, X$^3$, X$^4$, X$^5$ or at least one X is a cyano.

In one embodiment of each of the formulae (IV-C), at least one of X$^a$, X$^b$, X$^c$, X$^1$, X$^2$, X$^3$, X$^4$, X$^5$ or at least one X is a cyano, halogen or trifluoromethyl group.

In one embodiment of each of the formulae (IV-C), at least one of X$^a$, X$^b$, X$^c$, X$^1$, X$^2$, X$^3$, X$^4$, X$^5$ or at least one X is —C(Me)$_2$CH$_2$OH.

In one embodiment of each of the formulae (IV-C), at least one of X$^a$, X$^b$, X$^c$, X$^1$, X$^2$, X$^3$, X$^4$, X$^5$ or at least one X is —C(O)Me.

In one embodiment of each of the formulae (IV-C), at least one of X$^a$, X$^b$, X$^c$, X$^1$, X$^2$, X$^3$, X$^4$, X$^5$ or at least one X is —(CH$_2$)$_2$CO$_2$Me.

In one embodiment of each of the formulae (IV-C), at least one of X$^a$, X$^b$, X$^c$, X$^1$, X$^2$, X$^3$, X$^4$, X$^5$ or at least one X is isoamyl.

In one embodiment of each of the formulae (IV-C), at least one of X$^a$, X$^b$, X$^c$, X$^1$, X$^2$, X$^3$, X$^4$, X$^5$ or at least one X is 1,3-dioxalanyl.

In one embodiment of each of the formulae (IV-C), at least one of X$^a$, X$^b$, X$^c$, X$^1$, X$^2$, X$^3$, X$^4$, X$^5$ or at least one X is furyl.

In one embodiment of each of the formulae (IV-C), at least one of X$^a$, X$^b$, X$^c$, X$^1$, X$^2$, X$^3$, X$^4$, X$^5$ or at least one X is pyrazolyl.

In one embodiment of each of the formulae (IV-C), at least one of $X^a$, $X^b$, $X^c$, $X^1$, $X^2$, $X^3$, $X^4$, $X^5$ or at least one X is thienyl.

In one embodiment of formulae (IV-C), at least one of $X^b$ and $X^c$ is other than hydrogen.

In one embodiment of formulae (IV-C), $X^b$ and $X^c$ are each independently selected from the group consisting of hydrogen, halogen, —CN, —C(O)R$^{24a}$, —CO$_2$R$^{24a}$, —C(O)NR$^{24a}$R$^{25a}$, —OR$^{24a}$, —OC(O)R$^{24a}$, —OC(O)NR$^{24a}$R$^{25a}$, —SR$^{24a}$, —S(O)R$^{24a}$, —S(O)$_2$R$^{24a}$, —S(O)$_2$NR$^{24a}$R$^{25a}$, —NO$_2$, —NR$^{24a}$R$^{25a}$, substituted or unsubstituted C$_{1-8}$ alkyl, substituted or unsubstituted C$_{2-8}$ alkenyl, substituted or unsubstituted C$_{2-8}$ alkynyl, substituted or unsubstituted 3- to 10-membered heterocyclyl, substituted or unsubstituted C$_{6-10}$ aryl, and substituted or unsubstituted 5- to 10-membered heteroaryl.

In one embodiment of formulae (IV-C), at least one of $X^b$ and $X^c$ is selected from the group consisting of halogen, —CN, —NO$_2$, —OR$^{24}$, —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In one embodiment of formulae (IV-C), at least one of $X^b$ and $X^c$ is selected from the group consisting of halogen, —CN, —NO$_2$, —OR$^{24}$ (but not isopropoxy), —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In another embodiment of formulae (IV-C), $X^b$ and $X^c$ are both other than hydrogen.

In another embodiment of formulae (IV-C), when $X^b$ is isopropoxy, $X^c$ is other than hydrogen.

In another embodiment of formulae (IV-C), when $X^b$ is methyl, $X^c$ is other than hydrogen.

In another embodiment of formulae (IV-C), $X^b$ and $X^c$ are both selected from the group consisting of halogen, —CN, —NO$_2$, —OR$^{24}$, —C(O)R$^{24}$, —SO$_2$R$^{24}$, —NR$^{24}$R$^{25}$, unsubstituted or substituted C$_{1-8}$ alkyl, unsubstituted or substituted phenyl, unsubstituted or substituted 5- or 6-membered heteroaryl, and unsubstituted or substituted 5- or 6-membered heterocyclyl.

In another embodiment of formulae (IV-C), $X^b$ and $X^c$, or any two occurrences of $X^a$ that are located adjacently to each other, can be joined to form a substituted 5- or 6-membered substituted or unsubstituted heterocyclyl or substituted or unsubstituted heteroaryl.

In one embodiment of formulae (IV-C), at least one of $X^b$ and $X^c$ is selected from the group consisting of halogen, —CN, and —CF$_3$.

In one embodiment of formulae (IV-C), both $X^b$ and $X^c$ are selected from the group consisting of halogen, —CN, and —CF$_3$.

In an additional embodiment of formulae (IV-C), one of $X^b$, and $X^c$ is halogen and one of $X^b$ and $X^c$ is selected from the group consisting of halogen, —CN, and —CF$_3$.

In an additional embodiment of formulae (IV-C), one of $X^b$, and $X^c$ is halogen and one of $X^b$ and $X^c$ is selected from the group consisting of halogen, —CN, —CH$_3$, and —CF$_3$.

In an additional embodiment of formulae (IV-C), one of $X^b$, and $X^c$ is hydrogen and one of $X^b$ and $X^c$ is selected from the group consisting of halogen, —CN, and —CF$_3$.

In an additional embodiment of formulae (IV-C), one of $X^b$, and $X^c$ is hydrogen and one of $X^b$ and $X^c$ is selected from the group consisting of halogen, —CN, —CH$_3$, and —CF$_3$.

In an additional embodiment of formulae (IV-C), $X^b$ is selected from the group consisting of halogen and —CH$_3$, and $X^c$ is selected from the group consisting of halogen, —CN, —CH$_3$, —OCH$_3$, —OCF$_3$ and —CF$_3$.

In an additional embodiment of formulae (IV-C), when $X^c$ is hydrogen, $X^b$ represents 1 to 5 substituents each independently selected from the group consisting of hydrogen, substituted or unsubstituted C$_{1-8}$ alkyl, substituted or unsubstituted C$_{2-8}$ alkenyl, substituted or unsubstituted C$_{2-8}$ alkynyl, —CN, —C(O)R$^{18}$, —CO$_2$R$^{18}$, —C(O)NR$^{18}$R$^{19}$, —OC(O)R$^{19}$, —OC(O)NR$^{18}$R$^{19}$, —NO$_2$, —NR$^{18}$C(O)NR$^{19}$R$^{20}$, —NR$^{18}$R$^{19}$, —NR$^{18}$CO$_2$R$^{19}$, —NR$^{18}$S(O)$_2$R$^{19}$, —SR$^{18}$, —S(O)R$^{18}$, —S(O)$_2$R$^{18}$, —S(O)$_2$NR$^{18}$R$^{19}$, substituted or unsubstituted C$_{6-10}$ aryl, substituted or unsubstituted 5- to 10-membered heteroaryl, and substituted or unsubstituted 3- to 10-membered heterocyclyl.

In an additional embodiment of formulae (IV-C), when $X^c$ is hydrogen, $X^b$ is other than —Cl, —NO$_2$, —OCH$_3$, —CH$_3$, —NHC(O)CH$_3$, or —CH$_2$CH$_2$-(phenyl).

In an additional embodiment of formulae (IV-C), $X^a$ represents 2 substituents, one of which is halogen and the other of which is selected from the group consisting of halogen, —CN, and —CF$_3$.

In an additional embodiment of formulae (IV-C), $X^a$ represents 2 substituents, where one occurrence of $X^a$ is halogen and one occurrence of $X^a$ is located para to the sulfonamido bond.

In an additional embodiment of formulae (IV-C), at least one of one occurrence of $X^a$ or alternatively one of $X^b$ or $X^c$ is —CN.

In another embodiment of formulae (IV-C), at least one of one occurrence of $X^a$ or alternatively one of $X^b$ or $X^c$ is halogen.

In an additional embodiment of formulae (IV-C), at least one of one occurrence of $X^a$ or alternatively one of $X^b$ or $X^c$ is —CF$_3$.

In an additional embodiment of formulae (IV-C), at least one of one occurrence of $X^a$, or one of $X^b$ and $X^c$, is selected from the group consisting of:

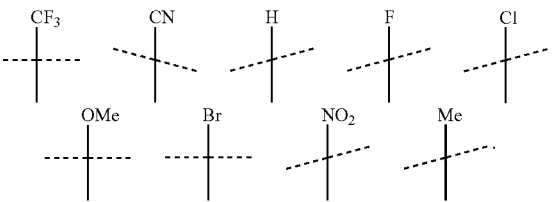

In one embodiment of the formulae (I, II, XCV-C), Ar is selected from the group consisting of substituted or unsubstituted C$_{6-10}$ aryl and substituted or unsubstituted 5- to 10-membered heteroaryl, with the proviso that Ar is other than para-isopropoxy phenyl.

In one embodiment of the formulae (I, II, XCV-C), Ar is selected from the group consisting of:

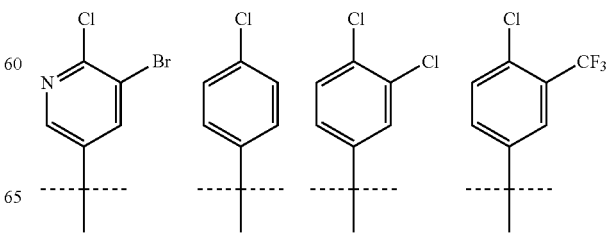

-continued

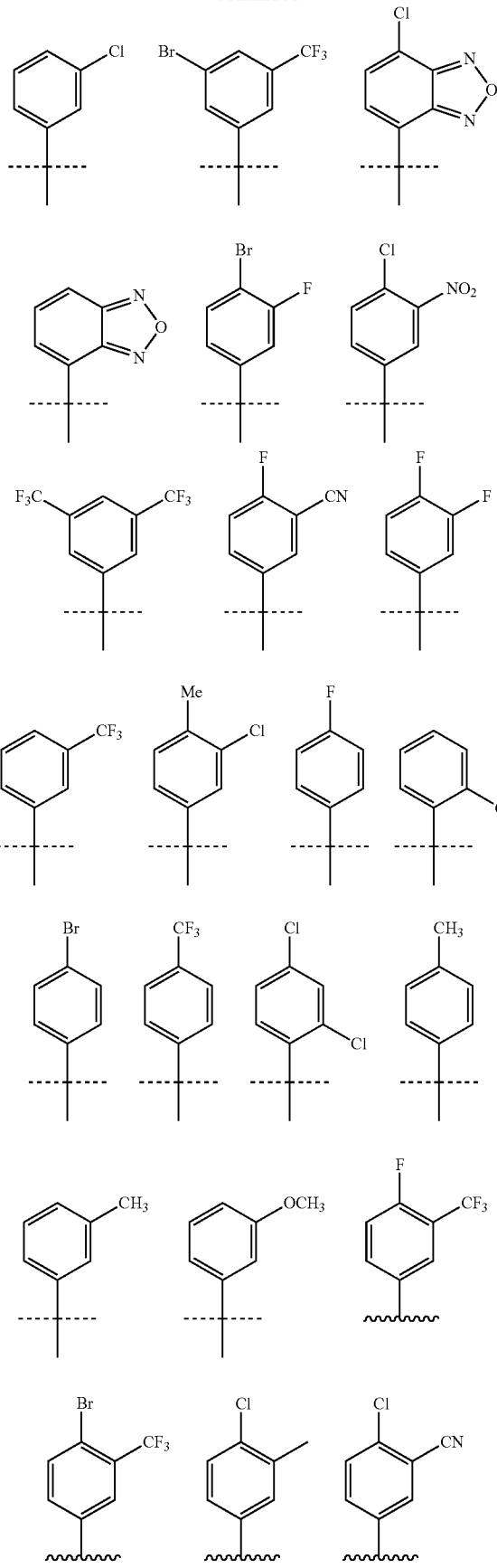

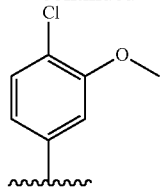

Preferred R¹ Substituents

In one embodiment of formula (I and II), $R^1$ is hydrogen.

In one embodiment of formula (I and II), $R^1$ is methyl.

In one embodiment of formula (I and II), $R^1$ is selected from the group consisting of hydrogen, unsubstituted $C_{2-8}$ alkyl, substituted $C_{1-8}$ alkyl, substituted or unsubstituted $C_{2-6}$ alkenyl, substituted or unsubstituted $C_{2-6}$ alkynyl, and substituted or unsubstituted 3- to 10-membered heterocyclyl.

In one embodiment of formula (I and II), $R^1$ is selected from the group consisting of hydrogen, substituted or unsubstituted $C_{2-6}$ alkenyl, substituted or unsubstituted $C_{2-6}$ alkynyl, and substituted or unsubstituted 3- to 10-membered heterocyclyl.

In one embodiment of formula (I and II), $R^1$ is selected from the group consisting of unsubstituted $C_{2-8}$ alkyl, substituted, $C_{1-8}$ alkyl, substituted or unsubstituted $C_{2-6}$ alkenyl, substituted or unsubstituted $C_{2-6}$ alkynyl.

In one embodiment of formula (I and II), $R^1$ is substituted or unsubstituted 3- to 10-membered heterocyclyl.

In one embodiment of formula (I and II), $R^1$ is selected from the group consisting of substituted or unsubstituted $C_{5-8}$ alkyl, substituted or unsubstituted $C_{2-6}$ alkenyl, substituted or unsubstituted $C_{2-6}$ alkynyl, and substituted or unsubstituted 3- to 10-membered heterocyclyl;

In one embodiment of formula (I and II), $R^1$ is other than hydrogen, and substituted or unsubstituted $C_{1-4}$ alkyl.

Preferred Y and R² Substituents

In one embodiment of formula (I), $Y^1$, $Y^2$ and $Y^3$ are —$CR^{2a}$—, —$CR^{2b}$—, and —$CR^{2c}$— respectively, where $R^{2a}$, $R^{2b}$, and $R^{2c}$ are each hydrogen.

In one embodiment of formula (I), $Y^1$, $Y^2$ and $Y^3$ are —$CR^{2a}$—, —$CR^{2b}$—, and —$CR^{2c}$— respectively, where 1 to 3 of $R^{2a}$, $R^{2b}$, and $R^{2c}$ are other than hydrogen.

In one embodiment of formula (I), $Y^1$, $Y^2$ and $Y^3$ are —$CR^{2a}$—, —$CR^{2b}$—, and —$CR^{2c}$— respectively and $R^{2a}$, $R^{2b}$, and $R^{2c}$ are each independently selected from the group consisting of halogen, —$CO_2R^3$, —$OR^3$, and substituted or unsubstituted $C_{1-8}$ alkyl, where 1 to 3 of $R^{2a}$, $R^{2b}$, and $R^{2c}$ are other than hydrogen.

In one embodiment of formula (I), $Y^1$, $Y^2$ and $Y^3$ are —$CR^{2a}$—, —$CR^{2b}$—, and —$CR^{2c}$— respectively and $R^{2a}$, $R^{2b}$, and $R^{2c}$ are each independently selected from the group consisting of hydrogen, fluorine, chlorine, and bromine, where 1 to 2 of $R^{2a}$, $R^{2b}$, and $R^{2c}$ are other than hydrogen.

In one embodiment of formula (I), at least one of $Y^1$, $Y^2$ and $Y^3$ is —N— or —$N^+(O)^-$—.

In one embodiment of formula (I), only one of $Y^1$, $Y^2$ and $Y^3$ is —N— or —$N^+(O)^-$—.

In one embodiment of formula (II), $Y^5$, $Y^6$, and $Y^7$ are each independently selected from the group consisting of hydrogen, halogen, —$CO_2R^3$, —$OR^3$, and substituted or unsubstituted $C_{1-8}$ alkyl, where 1 to 2 of $Y^5$, $Y^6$, and $Y^7$ are other than hydrogen.

In one embodiment of formula (II), $Y_5$, $Y^6$, and $Y^7$ are each independently selected from the group consisting of hydrogen, fluorine, chlorine, and bromine, where 1 to 2 of $Y^5$, $Y^6$, and $Y^7$ are other than hydrogen.

In another embodiment of formula (II), at least one of $Y^5$, $Y^6$ and $Y^7$ is other than hydrogen; preferably $Y^6$ is halogen.

In another embodiment of formula (II), $Y^5$ and $Y^7$ are hydrogen and $Y^6$ is halogen.

In another embodiment of formula (II), $Y^5$ and $Y^7$ are hydrogen and $Y^6$ is chloro.

In one embodiment of formula (III), $Y^8$, $Y^9$, and $Y^{10}$ are each independently selected from the group consisting of hydrogen, halogen, —$CO_2R^3$, —$OR^3$, and substituted or unsubstituted $C_{1-8}$ alkyl, where 1 to 2 of $Y^8$, $Y^9$, and $Y^{10}$ are other than hydrogen.

In one embodiment of formula (III), $Y^8$, $Y^9$, and $Y^{10}$ are each independently selected from the group consisting of hydrogen, fluorine, chlorine, and bromine, where 1 to 2 of $Y^8$, $Y^9$, and $Y^{10}$ are other than hydrogen.

In one embodiment of formula (III), at least one of $Y^8$, $Y^9$ and $Y^{10}$ is other than hydrogen; preferably $Y^9$ is other than hydrogen.

In another embodiment of formula (III), at least two of $Y^8$, $Y^9$ and $Y^{10}$ are other than hydrogen.

In a further embodiment of formula (III), $Y^8$ and $Y^{10}$ are hydrogen and $Y^9$ is halogen.

In a further embodiment of formula (III), $Y^8$ and $Y^{10}$ are hydrogen and $Y^9$ is chloro.

In one embodiment of formulae (IV-C), $Y^b$ or at least one occurrence of $Y^a$ is other than hydrogen.

In one embodiment of formulae (IV-C), $Y^a$ represents zero substituents and $Y^b$ is hydrogen.

In one embodiment of formulae (IV-C), $Y^a$ represents zero substituents and $Y^b$ is other than hydrogen.

In one embodiment of formulae (IV-C), $Y^b$ and each occurrence of $Y^a$ are selected from the group consisting of halogen, —$C(O)R^{27}$, —$OR^{27}$, and substituted or unsubstituted $C_{1-8}$ alkyl.

In one embodiment of formulae (IV-C), $Y^b$ and each occurrence of $Y^a$ are selected from the group consisting of halogen, fluorine, chlorine and bromine.

In one embodiment of formulae (IV-C), $Y^b$ and each occurrence of $Y^a$ are selected from the group consisting of fluorine, chlorine and bromine.

In one embodiment of formulae (IV-C), $Y^b$ and each occurrence of $Y^a$ are selected from the group consisting of chlorine and hydrogen, where one of $Y^a$ and $Y^b$ is hydrogen and one of $Y^a$ and $Y^b$ is chlorine.

Preferred L Substituents

In one embodiment of formula (I-C), L is a bond.
In one embodiment of formula (I-C), L is —C(O)—.
In one embodiment of formula (I-C), L is —S—.
In one embodiment of formula (I-C), L is —O—.
In one embodiment of formula (I-C), L is —S(O)—.
In one embodiment of formula (I-C), L is —S(O)$_2$—.
In one embodiment of formula (I-C), L is —$CR^6R^7$—.

In one embodiment of any of formulae (I-C) where L is —$CR^6R^7$—, $R^6$ is hydrogen, halogen, —$OR^9$ (where $R^3$ is as defined in formula (I) and preferably is hydrogen or $C_{1-4}$ alkyl), substituted or unsubstituted $C_{2-4}$ alkyl, or substituted or unsubstituted $C_{2-4}$ alkenyl.

In one embodiment of any of formulae (I-C) where L is —$CR^6R^7$—, $R^7$ is hydrogen, halogen, or —$OR^9$ (where $R^9$ is as defined in formula (I) and preferably is hydrogen or $C_{1-4}$ alkyl).

In one embodiment of any of formulae (I-C) where L is —$CR^6R^7$—, one of $R^6$ and $R^7$ is other than hydrogen.

In one embodiment of any of formulae (I-C) where L is —$CR^6R^7$—, $R^6$ and $R^7$ are both halogen, and more preferably, are both fluorine.

In one embodiment of any of formulae (I-C) where L is —$CR^6R^7$—, $R^6$ is hydrogen and $R^7$ is —$OR^9$ (where $R^9$ is as defined in formula (I) and is preferably hydrogen or $C_{1-4}$ alkyl).

In one embodiment of any of formulae (I-C) where L is —$CR^6R^7$—, $R^6$ and $R^7$ are both —$OR^9$ (where $R^9$ is as defined in formula (I)) and where both $R^9$ groups are combined together with the atoms to which they are attached to form a 5-7 membered heterocyclic acetal ring system.

In one embodiment of any of formulae (I-C) where L is —$CR^6R^7$—, $R^6$ is $C_{1-4}$ alkyl or $C_{2-4}$ alkenyl and $R^7$ is —$OR^9$ (where $R^9$ is as defined in formula (I) and is preferably hydrogen or $C_{1-4}$ alkyl).

In one embodiment of formula (I-C), L is —$NR^8$—, $R^8$ is selected from the group consisting of hydrogen, $C(O)R^{12}$, $S(O)_2R^{12}$, $COO_2R^{12}$, substituted or unsubstituted $C_{1-8}$ alkyl, substituted or unsubstituted 3- to 10-membered heterocyclyl, substituted or unsubstituted $C_{2-6}$ alkenyl, and substituted or unsubstituted $C_{2-6}$ alkynyl.

In one embodiment, in each of the formulae I-C where L is —$NR^8$—, $R^8$ is hydrogen or —C(O)Me.

In one embodiment, in each of the formulae I-C where L is —$NR^8$—, $R^8$ is hydrogen or —C(O)Me.

In one preferred embodiment of any of formulae (I-C) where L is —$NR^8$—, $R^8$ is hydrogen, —$S(O)_2R^{12}$ or —$C(O)R^{12}$.

In one embodiment of formula (I-C), L is —$NR^8C(O)$—.
In one embodiment of formula (I-C), L is —$C(O)NR^8$—.

Preferred $Z^1$ Groups and Substituents

In one embodiment of formulae (I-C), $Z^1$ is substituted or unsubstituted aryl.

In one embodiment of formulae (I-C), $Z^1$ is substituted aryl.

In one embodiment of formulae (I-C), $Z^1$ is substituted or unsubstituted heteroaryl.

In one embodiment of formulae (I-C), $Z^1$ is substituted heteroaryl.

In one embodiment of formulae (I-C), $Z^1$ is unsubstituted heteroaryl.

In one embodiment of formulae (I-C), $Z^1$ is substituted or unsubstituted heterocyclyl.

In one embodiment of formulae (I-C), $Z^1$ is —$NR^{35b}R^{36b}$, where:

$R^{35b}$ and $R^{36b}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{35b}$ and $R^{36b}$ may, together with the nitrogen, form a substituted or unsubstituted 4-, 5-, 6-, or 7-membered heterocyclyl.

In one embodiment of formulae (I-C), $Z^1$ is —$NR^{13}R^{14}$, where $R^{13}$ and $R^{14}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{13}$ and $R^{14}$ may, together with the nitrogen, form a substituted or unsubstituted 4-, 5-, 6-, or 7-membered heterocyclyl.

In one embodiment of formulae (I-C), $Z^1$ is other than

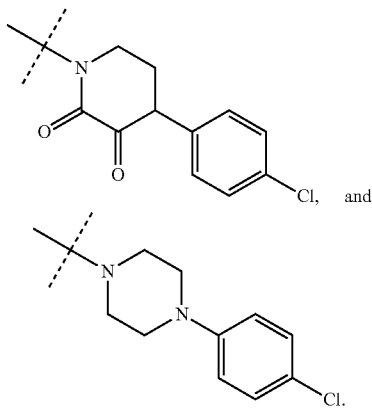

In one embodiment of formulae (I-C), $Z^1$ is one of the following formulae (CI and CII):

CI

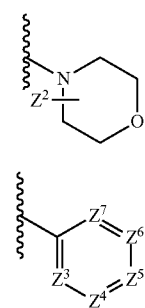

CII where $Z^2$ represents 0 to 5 substituents selected from the group consisting of halogen, —CN, —C(O)$R^{34}$, —CO$_2R^{34}$, —C(O)NR$^{34}$R$^{36}$, —OR$^{34}$, —OC(O)R$^{34}$, —OC(O)NR$^{34}$R$^{36}$, —SR$^{34}$, —S(O)R$^{34}$, —S(O)$_2$R$^{34}$, —S(O)$_2$NR$^{34}$R$^{36}$, —NO$_2$, —NR$^{34}$R$^{35}$, —NR$^{34}$C(O)R$^{35}$, —NR$^{34}$C(O)$_2$R$^{35}$, —NR$^{34}$S(O)$_2$R$^{35}$, —NR$^{34}$C(O)NR$^{35}$R$^{36}$, oxo (=O or —O⁻), substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{34}$, $R^{35}$, and $R^{36}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl;

$Z^3$, $Z^4$, $Z^5$, $Z^6$ and $Z^7$ are each independently selected from the group consisting of —CR$^{2a}$—, —N—, and —N$^+$(O)$^-$—;

each $R^{2a}$ is independently selected from the group consisting of hydrogen, halogen, —CN, —C(O)R$^3$, —CO$_2$R$^3$, —C(O)NR$^3$R$^4$, —OR$^3$, —OC(O)R$^3$, —OC(O)NR$^3$R$^4$, —SR$^3$, —S(O)R$^3$, —S(O)$_2$R$^3$, —S(O)$_2$NR$^3$R$^4$, —NO$_2$, —NR$^3$R$^4$, —NR$^3$C(O)R$^4$, —NR$^3$C(O)OR$^4$, —NR$^3$S(O)$_2$R$^4$, —NR$^3$C(O)NR$^4$R$^5$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^3$, $R^4$, and $R^5$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^3$ and $R^4$, $R^4$ and $R^5$ or $R^3$ and $R^5$ may, together with the atoms to which they are attached, form a substituted or unsubstituted 5-, 6-, or 7-membered ring.

In one embodiment of formulae (CI and CII), $Z^3$, $Z^4$, $Z^5$, $Z^6$ and $Z^7$ are —CH—.

In one embodiment of formulae (CI and CII), at least one of $Z^3$, $Z^4$, $Z^5$, $Z^6$ and $Z^7$ is —N—, or —N$^+$(O)$^-$—.

In one embodiment of formulae (CI and CII), at least one of $Z^3$, $Z^4$, $Z^5$, $Z^6$ and $Z^7$ is —N$^+$(O)$^-$—.

In one embodiment of formulae (CI and CII), at least one of $Z^3$, $Z^4$, $Z^5$, $Z^6$ and $Z^7$ is —N—.

In one embodiment of formulae (CI and CII), Ar is substituted or unsubstituted $C_{6-10}$ aryl and one of $Z^3$, $Z^4$, $Z^5$, $Z^6$ and $Z^7$ is —N—, or In one embodiment of formulae (CI and CII), Ar is substituted or unsubstituted $C_{6-10}$ aryl, L is —O—, —S—, —S(O)— or S(O)$_2$— and one of $Z^3$, $Z^4$, $Z^5$ and $Z^6$ is —N—, or —N$^+$(O)$^-$—.

In one embodiment of formulae (CI and CII), Ar is substituted phenyl, L is —O—, —S—, —S(O)— or S(O)$_2$— and one of $Z^3$, $Z^4$, $Z^5$ and $Z^6$ is —N—, or —N$^+$(O)$^-$—.

In one embodiment of formulae (CI and CII), Ar is substituted or unsubstituted $C_{6-10}$ aryl, L is —CR$^5$R$^6$—, —NR$^7$—, —C(O)— and one of $Z^3$, $Z^4$, $Z^5$ and $Z^6$ is —N—, or —N$^+$(O)$^-$—.

In one embodiment of formulae (CI and CII), Ar is substituted phenyl, L is —CR$^5$R$^6$—, —NR$^7$—, —C(O)— and one of $Z^3$, $Z^4$, $Z^5$ and $Z^6$ is —N—, or —N$^+$(O)$^-$—.

In one embodiment of formulae (I-C), $Z^1$ is one of the following formulae

CIII

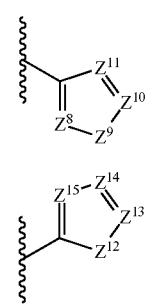

CIV where $Z^8$, $Z^{10}$, $Z^{11}$, $Z^{13}$, $Z^{14}$ and $Z^{15}$ are each independently selected from the group consisting of of —CR$^{37}$—, —N—, and —N$^+$(O)$^-$—;

$R^{37}$ represents 0 to 4 substituents selected from the group consisting of halogen, —CN, —C(O)$R^{38}$, —COO$_2R^{38}$, —C(O)N$R^{38}R^{39}$, —O$R^{38}$, —OC(O)$R^{38}$, —OC(O)N$R^{38}R^{39}$, —S$R^{38}$, —S(O)$R^{39}$, —S(O)$_2R^{38}$, —S(O)$_2$N$R^{38}R^{39}$, —NO$_2$, —N$R^{38}R^{39}$, —N$R^{38}$C(O)$R^{39}$, —N$R^{38}$C(O)$_2R^{39}$, —N$R^{38}$S(O)$_2R^{39}$, —N$R^{38}$C(O)N$R^{39}R^{40}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{38}$, $R^{39}$, and $R^{40}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl;

$Z^9$ and $Z^{12}$ are each independently selected from the group consisting of —O—, —S—, —N$R^{41}$—, and —N$^+$(O)$^-$—;

$R^{41}$ is selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (CIII and CIV), one of $Z^8$, $Z^{10}$ and $Z^{11}$ is —N— or —N$^-$—O$^+$ or one of $Z^{13}$, $Z^{14}$ and $Z^{15}$ is —N— or —N$^-$—O$^+$.

In one embodiment of formulae (CIII and CIV), at least one of $Z^8$, $Z^{10}$ and $Z^{11}$ is —N— or —N$^-$—O$^+$ or one of $Z^{13}$, $Z^{14}$ and $Z^{15}$ is —N— or —N$^-$—O$^+$.

In one embodiment of formulae (I-C), $Z^1$ is selected from the formulae (CV-CXXI):

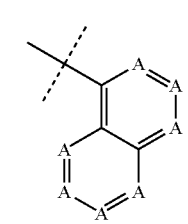

CV

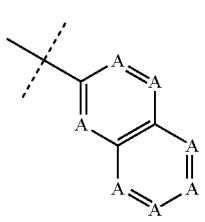

CVI

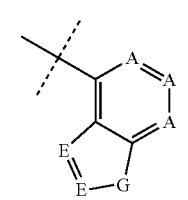

CVII

-continued

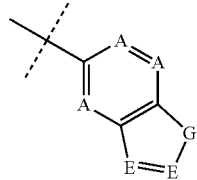

CVIII

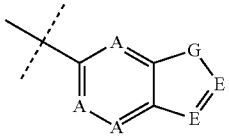

CVIX

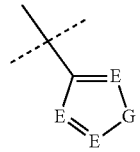

CX

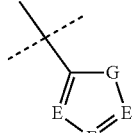

CXI

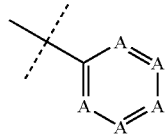

CXII

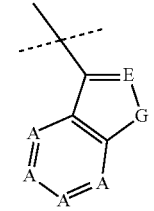

CXIII

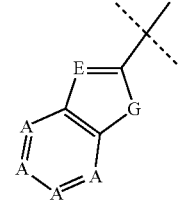

CXIV

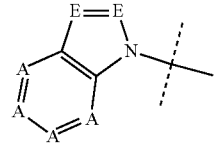

CXV

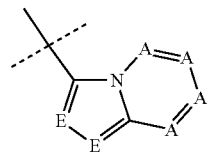

CXVI

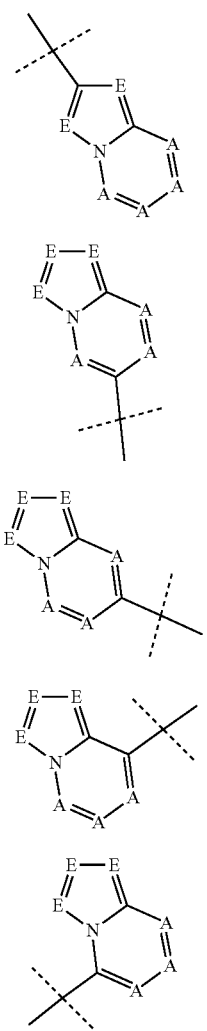

where,

A is selected from the group consisting of —CH—, —CZ$^{16}$—, —N—, and —N$^+$(O)$^-$—;

each occurrence of Z$^{16}$ is independently selected from the group consisting of halogen, substituted or unsubstituted C$_{1-8}$ alkyl, substituted or unsubstituted C$_{2-8}$ alkenyl, substituted or unsubstituted C$_{2-8}$ alkynyl, —CN, oxo (=O or —O$^-$), —NO$_2$, —OR$^{42}$, —OC(O)R$^{42}$, —CO$_2$R$^{42}$, —C(O)R$^{42}$, —C(O)NR$^{42}$R$^{43}$, —OC(O)NR$^{42}$R$^{43}$, —NR$^{42}$C(O)R$^{43}$, —NR$^{42}$C(O)NR$^{43}$R$^{44}$, —NR$^{42}$R$^{43}$, —NR$^{42}$CO$_2$R$^{43}$, —SR$^{42}$, —S(O)R$^{42}$, —S(O)$_2$R$^{42}$, —S(O)$_2$NR$^{42}$R$^{43}$, —NR$^{42}$S(O)$_2$R$^{43}$, substituted or unsubstituted C$_{6-10}$ aryl, substituted or unsubstituted 5- to 10-membered heteroaryl, substituted or unsubstituted 3- to 10-membered heterocyclyl, substituted or unsubstituted (C$_{1-4}$ alkyl)-(C$_{6-10}$ aryl), and substituted or unsubstituted (C$_{1-4}$ alkyl)-(5- to 10-membered heteroaryl); or where two or more A are CZ$^{16}$, then the Z$^{16}$ substituents together can form a carbocyclic or heterocyclic ring;

R$^{42}$, R$^{43}$ and R$^{44}$ are each independently selected from the group consisting of hydrogen, substituted or unsubstituted C$_{1-8}$ alkyl, substituted or unsubstituted 3- to 10-membered heterocyclyl, substituted or unsubstituted C$_{2-6}$ alkenyl, substituted or unsubstituted C$_{2-6}$ alkynyl, substituted or unsubstituted C$_{6-10}$ aryl, and substituted or unsubstituted 5- to 10-membered heteroaryl;

E is selected from the group consisting of —CH—, —CZ$^{17}$—, —N—, and —N$^+$(O)$^-$—;

each occurrence of Z$^{17}$ is independently selected from the group consisting of halogen, substituted or unsubstituted C$_{1-8}$ alkyl, substituted or unsubstituted C$_{2-8}$ alkenyl, substituted or unsubstituted C$_{2-8}$ alkynyl, —CN, oxo (=O or —O$^-$), —NO$_2$, —OR$^{44}$, —OC(O)R$^{44}$, —CO$_2$R$^{44}$, —C(O)R$^{44}$, —C(O)NR$^{44}$R$^{45}$, —OC(O)NR$^{44}$R$^{45}$, —NR$^{44}$C(O)R$^{45}$, —NR$^{44}$C(O)NR$^{45}$R$^{46}$, —NR$^{44}$R$^{45}$, —NR$^{44}$CO$_2$R$^{45}$, —SR$^{44}$, —S(O)R$^{44}$, —S(O)$_2$R$^{44}$, —S(O)$_2$NR$^{44}$R$^{45}$, —NR$^{44}$S(O)$_2$R$^{45}$, substituted or unsubstituted C$_{6-10}$ aryl, substituted or unsubstituted 5- to 10-membered heteroaryl, substituted or unsubstituted 3- to 10-membered heterocyclyl, substituted or unsubstituted (C$_{1-4}$ alkyl)-(C$_{6-10}$ aryl), and substituted or unsubstituted (C$_{1-4}$ alkyl)-(5- to 10-membered heteroaryl); or where two or more E are CZ$^{17}$, then the Z$^{17}$ substituents together can form a carbocyclic or heterocyclic ring;

R$^{44}$, R$^{45}$ and R$^{46}$ are each independently selected from the group consisting of hydrogen, substituted or unsubstituted C$_{1-8}$ alkyl, substituted or unsubstituted 3- to 10-membered heterocyclyl, substituted or unsubstituted C$_{2-6}$ alkenyl, substituted or unsubstituted C$_{2-6}$ alkynyl, substituted or unsubstituted C$_{6-10}$ aryl, and substituted or unsubstituted 5- to 10-membered heteroaryl;

G is selected from the group consisting of —O—, —S—, and —NR$^{47}$—;

R$^{47}$ is selected from the group consisting of hydrogen, substituted or unsubstituted C$_{1-8}$ alkyl, substituted or unsubstituted 3- to 10-membered heterocyclyl, substituted or unsubstituted C$_{2-6}$ alkenyl, substituted or unsubstituted C$_{2-6}$ alkynyl, substituted or unsubstituted C$_{6-10}$ aryl, and substituted or unsubstituted 5- to 10-membered heteroaryl; or where G is —NR$^{47}$—, A is —CZ$^{16}$— and E is —CZ$^{17}$—, two the R$^{47}$, Z$^{16}$, and Z$^{17}$ substituents together can form a carbocyclic or heterocyclic ring.

In one embodiment of formulae (I-C), Z$^1$ is substituted or unsubstituted 5- to 10-membered heteroaryl.

In one embodiment of formulae (I-C), Z$^1$ is substituted 5- or 6-membered heteroaryl.

In one embodiment of formulae (I-C), Z$^1$ is unsubstituted 5- or 6-membered heteroaryl.

In one embodiment of formulae (I-C), Z$^1$ is substituted 9- or 10-membered heteroaryl.

In one embodiment of formulae (I-C), Z$^1$ is unsubstituted 9- or 10-membered heteroaryl.

In one embodiment of formulae (I-C), Z$^1$ is substituted 5- to 10-membered heteroaryl, wherein one substituent is located ortho- to one of the heteroatoms in the ring.

In one embodiment of formulae (I-C), Z$^1$ is selected from the group consisting of substituted or unsubstituted 5- or 6-membered heteroaryl with 1 to 2 nitrogen atoms and with 0 or 2 substituents independently selected from the group consisting of halogen, unsubstituted or substituted C$_{1-8}$ alkyl, oxo (=O or —O$^-$), —CN, —NO$_2$, —OR$^{48}$, —C(O)R$^{48}$, —C(O)NR$^{48}$R$^{49}$, —NR$^{48}$C(O)R$^{49}$, —NR$^{48}$R$^{49}$, —SR$^{48}$, —S(O)R$^{48}$, —S(O)$_2$R$^{48}$, —SO$_2$NR$^{48}$R$^{49}$, —NR$^{48}$SO$_2$R$^{49}$, unsubstituted or substituted 5- to 6-membered heteroaryl, unsubstituted or substituted 3- to 10-membered heterocyclyl, substituted or unsubstituted (C$_{1-4}$ alkyl)-(C$_{6-10}$ aryl), and substituted or unsubstituted (C$_{1-4}$ alkyl)-(5- to 10-membered heteroaryl);

R$^{48}$ and R$^{49}$ are each independently selected from the group consisting of hydrogen, substituted or unsubstituted C$_{1-8}$ alkyl, substituted or unsubstituted 3- to 10-membered heterocyclyl, substituted or unsubstituted C$_{2-8}$ alkenyl, substituted or unsubstituted $C_{2-8}$ alkynyl, substituted or unsubstituted $C_{6-10}$ aryl, and substituted or unsubstituted 5- to 10-membered heteroaryl.

In one embodiment of formulae (I-C), $Z^1$ is selected from the group consisting of substituted or unsubstituted 5- or 6-membered heteroaryl with 1 to 2 nitrogen atoms and with 0 or 2 substituents each independently selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, oxo (=O or —O⁻), —NO$_2$, —OR$^{44}$, —OC(O)R$^{44}$, —CO$_2$R$^{44}$, —C(O)R$^{44}$, —C(O)NR$^{44}$R$^{45}$, —OC(O)NR$^{44}$R$^{45}$, —NR$^{44}$C(O)R$^{45}$, —NR$^{44}$C(O)NR$^{45}$R$^{46}$, —NR$^{44}$R$^{45}$, —NR$^{44}$CO$_2$R$^{45}$, —SR$^{44}$, —S(O)R$^{44}$, —S(O)$_2$R$^{44}$, —S(O)$_2$NR$^{44}$R$^{45}$, —NR$^{44}$S(O)$_2$R$^{45}$, substituted or unsubstituted $C_{6-10}$ aryl, substituted or unsubstituted 5- to 10-membered heteroaryl and substituted or unsubstituted 3- to 10-membered heterocyclyl;

$R^{44}$, $R^{45}$ and $R^{46}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl;

In one embodiment of formulae (I-C), $Z^1$ is selected from the group consisting of substituted or unsubstituted 5- or 6-membered heteroaryl with 1 to 2 nitrogen atoms and with 0 or 2 substituents independently selected from the group consisting of substituted or unsubstituted $C_{2-8}$ alkenyl, substituted or unsubstituted $C_{2-8}$ alkynyl, —CO$_2$R$^{44a}$, —OC(O)NR$^{44a}$R$^{45a}$, —NR$^{44a}$C(O)NR$^{45a}$R$^{46a}$, —NR$^{44a}$CO$_2$R$^{45a}$ and substituted or unsubstituted $C_{6-10}$ aryl;

$R^{44a}$, $R^{45a}$ and $R^{46a}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-8}$ alkenyl, substituted or unsubstituted $C_{2-8}$ alkynyl, substituted or unsubstituted $C_{6-10}$ aryl, and substituted or unsubstituted 5- to 10-membered heteroaryl;

In one embodiment of formulae (I-C), $Z^1$ is selected from the group consisting of substituted or unsubstituted 9- or 10-membered heteroaryl with 1 to 2 nitrogen atoms and with 0 or 2 substituents independently selected from the group consisting of halogen, unsubstituted or substituted $C_{1-8}$ alkyl, oxo (=O or —O⁻), —CN, —NO$_2$, —OR$^{48}$, —C(O)R$^{48}$, —C(O)NR$^{48}$R$^{49}$, —NR$^{48}$C(O)R$^{49}$, —NR$^{48}$R$^{49}$, —SR$^{48}$, —S(O)R$^{48}$, —S(O)$_2$R$^{48}$, —SO$_2$NR$^{48}$R$^{49}$, —NR$^{48}$SO$_2$R$^{49}$, unsubstituted or substituted 5- to 6-membered heteroaryl, unsubstituted or substituted 3- to 10-membered heterocyclyl, and unsubstituted or substituted ($C_{1-4}$ alkyl)-(5- to 10-membered heteroaryl);

$R^{48}$ and $R^{49}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-8}$ alkenyl, substituted or unsubstituted $C_{2-8}$ alkynyl, substituted or unsubstituted $C_{6-10}$ aryl, and substituted or unsubstituted 5- to 10-membered heteroaryl.

In one embodiment of formulae (I-C), $Z^1$ is selected from the group consisting of substituted or unsubstituted 9- or 10-membered heteroaryl with 1 to 2 nitrogen atoms and with 0 or 2 substituents each independently selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, oxo (=O or —O⁻), —NO$_2$, —OR$^{44}$, —OC(O)R$^{44}$, —COO$_2$R$^{44}$, —C(O)R$^{44}$, —C(O)NR$^{44}$R$^{45}$, —OC(O)NR$^{44}$R$^{45}$, —NR$^{44}$C(O)R$^{45}$, —NR$^{44}$C(O)NR$^{45}$R$^{46}$, —NR$^{44}$R$^{45}$, —NR$^{44}$CO$_2$R$^{45}$, —SR$^{44}$, —S(O)R$^{44}$, —S(O)$_2$R$^{44}$, —S(O)$_2$NR$^{44}$R$^{45}$, —NR$^{44}$S(O)$_2$R$^{45}$, substituted or unsubstituted $C_{6-10}$ aryl, substituted or unsubstituted 5- to 10-membered heteroaryl and substituted or unsubstituted 3- to 10-membered heterocyclyl;

$R^{44}$, $R^{45}$ and $R^{46}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl;

In one embodiment of formulae (I-C), $Z^1$ is selected from the group consisting of substituted or unsubstituted 9- or 10-membered heteroaryl with 1 to 2 nitrogen atoms and with 0 or 2 substituents independently selected from the group consisting of substituted or unsubstituted $C_{2-8}$ alkenyl, substituted or unsubstituted $C_{2-8}$ alkynyl, —CO$_2$R$^{44a}$, —OC(O)NR$^{44a}$R$^{45a}$, —NR$^{44a}$C(O)NR$^{45a}$R$^{46a}$, —NR$^{44a}$CO$_2$R$^{45a}$ and substituted or unsubstituted $C_{6-10}$ aryl;

$R^{44a}$, $R^{45a}$ and $R^{46a}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-8}$ alkenyl, substituted or unsubstituted $C_{2-8}$ alkynyl, substituted or unsubstituted $C_{6-10}$ aryl, and substituted or unsubstituted 5- to 10-membered heteroaryl;

In one embodiment of formulae (I-C), $Z^1$ is selected from the group consisting of substituted or unsubstituted pyridyl, substituted or unsubstituted pyrimidinyl, substituted or unsubstituted pyridazinyl, and substituted or unsubstituted pyrazinyl, where the nitrogen atoms may also be —N⁺(O)⁻—.

In one embodiment of formulae (I-C), $Z^1$ is substituted or unsubstituted 5- to 10-membered heteroaryl, where the heteroaryl group contains only one nitrogen.

In one embodiment of formulae (I-C), $Z^1$ is substituted or unsubstituted 5- or 6-membered heteroaryl, where the heteroaryl group contains only one nitrogen.

In one embodiment of formulae (I-C), $Z^1$ is substituted or unsubstituted 9- or 10-membered heteroaryl, where the heteroaryl group contains only one nitrogen.

In one embodiment of formulae (I-C), $Z^1$ is selected from the group consisting of isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl, where each of these groups may be substituted or unsubstituted.

In one embodiments of formulae (I-C), $Z^1$ is substituted pyrazolyl with 0 to 3 substituents, substituted imidazolyl with 0 to 3 substituents, substituted tetrazolyl with 0 to 3 substituents, or substituted oxazolyl with 0 to 3 substituents.

In one embodiment of formulae (I-C), $Z^1$ is selected from the group consisting of pyridyl, pyrrolyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, pyrrolopyirdinyl, imidazopyridinyl, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl and thienyl, where each of these groups may be substituted or unsubstituted.

In one embodiment of formulae (I-C), $Z^1$ is selected from the group consisting of pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzoxazolyl, benzisoxazolyl, isobenzofuryl, isoindolyl, indolizinyl, benzotriazinyl, thienopyridinyl, thienopyrimidinyl, pyrazolopyridyl, imidazopyridyl, oxazolopyridyl, isoxaxolopyridyl, thiazolopyridyl, isothiazolopyridyl, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl and thienyl, where each of these groups may be substituted or unsubstituted.

In one embodiment of formulae (I-C), $Z^1$ is selected from the group consisting of quinolinyl, quinoxalinyl, quinazolinyl, cinnolinyl, phthalazinyl, benzotriazinyl, purinyl, benzimidazolyl, benzopyrazolyl, benzotriazolyl, benzoxazolyl, benzoxazolyl, benzisoxazolyl, isobenzofuryl, isoindolyl, indolizinyl, benzotriazinyl, pyrazolopyridyl, imidazopyridyl, oxazolopyridyl, isoxaxolopyridyl, thiazolopyridyl, isothiazolopyridyl, pyridopyridazinyl, pyridopyrimidinyl, pyridopyrazinyl, benzothiazolyl, benzofuranyl, benzothienyl, indolyl, quinolyl, isoquinolyl, indazolyl, and pteridinyl where each of these groups may be substituted or unsubstituted.

In one embodiment of formulae (I-C), $Z^1$ is selected from the group consisting of pyrazolopyridyl, imidazopyridyl, oxazolopyridyl, isoxaxolopyridyl, thiazolopyridyl, isothiazolopyridyl, pyridopyridazinyl, pyridopyrimidinyl, and pyridopyrazinyl where each of these groups may be substituted or unsubstituted.

In one embodiment of formulae (I-C), $Z^1$ is selected from the group consisting of pyrazolopyridyl, isoxaxolopyridyl, and isothiazolopyridyl, where each of these groups may be substituted or unsubstituted.

In one embodiment of formulae (I-C), $Z^1$ is selected from the group consisting of 4-azaindolyl, 5-azaindolyl, 6-azaindolyl, 6-azaindolyl, 4-azaindazolyl, 5-azaindazolyl, 6-azaindazolyl, 7-azaindazolyl, where each of these groups may be substituted or unsubstituted.

In one embodiment of formulae (I-C), $Z^1$ is a substituted or unsubstituted 3- to 10-membered heterocyclyl.

In one embodiment of formulae (I-C), $Z^1$ is unsubstituted or substituted 4- to 7-membered heterocyclyl.

In one embodiment of formulae (I-C), $Z^1$ is substituted or unsubstituted 3- to 10-membered heterocyclyl, where the 3- to 10-membered heterocyclyl is selected from the group consisting of pyrrolidine, piperidine, imidazolidine, pyrazolidine, butyrolactam, valerolactam, imidazolidinone, hydantoin, phthalimide, piperidine, 1,4-dioxane, morpholine, thiomorpholine, thiomorpholine-S,S-dioxide, piperazine, pyran, pyridone, 3-pyrroline, thiopyran, pyrone, tetrahydrofuran, and tetrahydrothiophene.

In one embodiment of formulae (I-C), $Z^1$ is substituted morpholinyl with from 0 to 3 substituents, substituted pyrrolidinyl with from 0 to 3 substituents, substituted piperidinyl with from 0 to 3 substituents, substituted thiomorpholine-S,S-dioxide with from 0 to 3 substituents, or substituted piperazinyl with from 0 to 3 substituents.

In one embodiment of formulae (I-C), when $Z^1$ is substituted $Z^1$ may be substituted with chlorine, fluorine, unsubstituted or substituted $C_{1-8}$ alkyl, oxo (=O or —O⁻), —CN, —NO₂, —OMe, —C(O)Me, —CONH₂, —CONHMe, —CONMe₂, —NHC(O)Me, —NH₂, —NHMe, —NMe₂, —SMe, —S(O)Me, —S(O)₂Me, —NHSO₂Me, morpholinyl, —CH₂OH, —CH₂OMe, —CH₂NH₂, —CH₂NHMe, or —CH₂NMe₂.

In one embodiment of formulae (I-C), when $Z^1$ is substituted, $Z^1$ may be substituted with substituted or unsubstituted $(C_{1-4}$ alkyl)-$(C_{6-10}$ aryl), substituted or unsubstituted $(C_{1-4}$ alkyl)-(5- to 10-membered heteroaryl).

In one embodiment of formulae (I-C), when $Z^1$ is substituted $Z^1$ may be substituted with chlorine, fluorine, methyl, oxo (=O or —O⁻), —CN, —OMe.

In one embodiment of formulae (I-C), $Z^1$ is substituted or unsubstituted 2-pyridyl.

In one embodiment of formulae (I-C), $Z^1$ is substituted or unsubstituted 2-pyridyl-N-oxide.

In one embodiment of formulae (I-C), $Z^1$ is substituted or unsubstituted 3-pyridyl.

In one embodiment of formulae (I-C), $Z^1$ is substituted or unsubstituted 3-pyridyl-N-oxide.

In one embodiment of formulae (I-C), $Z^1$ is substituted or unsubstituted 4-pyridyl.

In one embodiment of formulae (I-C), $Z^1$ is substituted or unsubstituted 4-pyridyl-N-oxide.

In one embodiment of formulae (I-C), $Z^1$ is substituted or unsubstituted pyrazolyl.

In one embodiment of formulae (I-C), $Z^1$ is substituted or unsubstituted imidazolyl.

In one embodiment of formulae (I-C), $Z^1$ is substituted or unsubstituted tetrazolyl.

In one embodiment of formulae (I-C), $Z^1$ is substituted or unsubstituted oxazolyl.

In one embodiment of formulae (I-C), $Z^1$ is substituted or unsubstituted morpholinyl.

In one embodiment of formulae (I-C), $Z^1$ is substituted or unsubstituted pyrrolidinyl.

In one embodiment of formulae (I-C), $Z^1$ is substituted or unsubstituted piperidinyl.

In one embodiment of formulae (I-C), $Z^1$ is substituted or unsubstituted thiomorpholinyl-S,S-dioxide.

In one embodiment of formulae (I-C), $Z^1$ is substituted or unsubstituted pyridopyridazinyl.

In one embodiment of formulae (I-C), $Z^1$ is substituted or unsubstituted phthalazinyl.

In one embodiment of formulae (I-C), $Z^1$ is substituted or unsubstituted pyrazolopyridyl.

In one embodiment of formulae (I-C), $Z^1$ is not substituted.

In one embodiment of formula (I-C), $Z^1$ is substituted by —CH₃ or oxo (=O or —O⁻).

In one embodiment of formula (I-C), $Z^1$ is substituted by —CH₃ and oxo (=O or —O⁻).

In one embodiment of formulae (I-C), $Z^1$ is selected from the group consisting of:

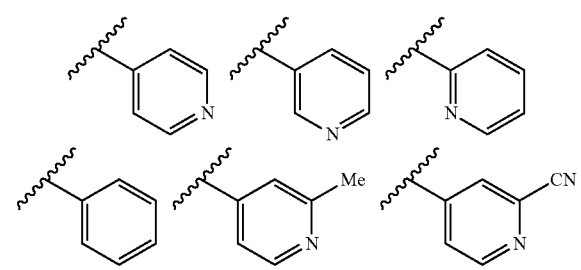

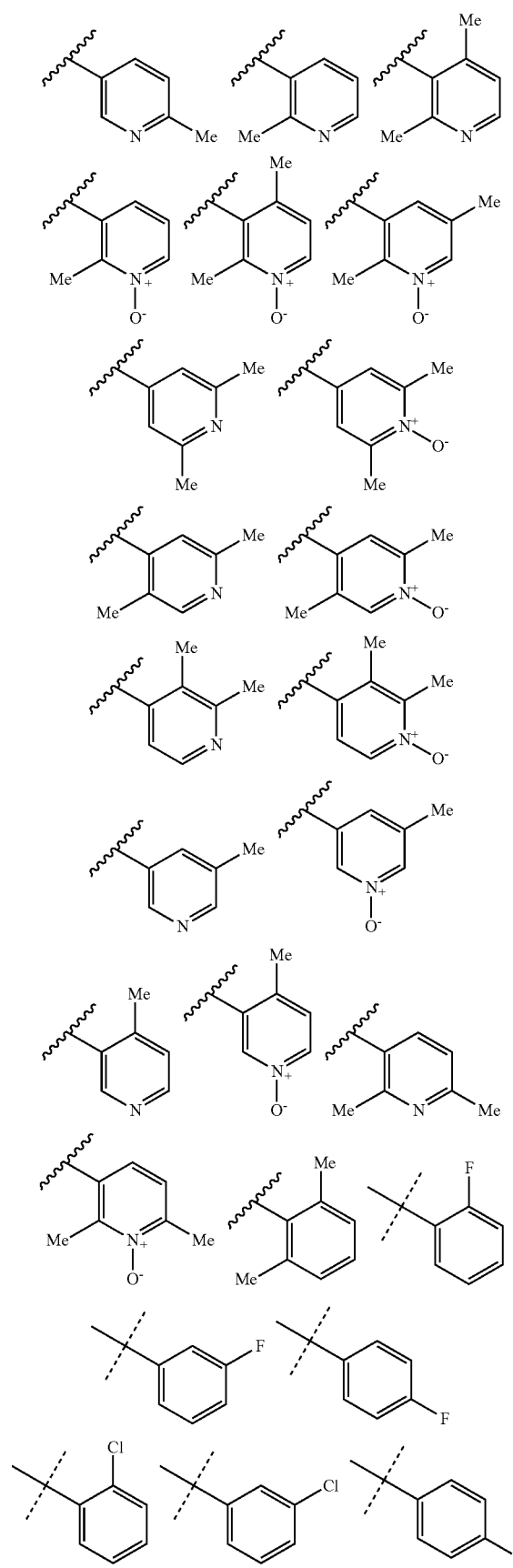
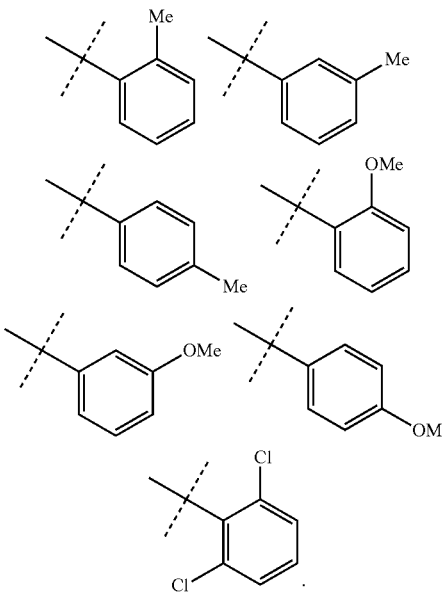
In one embodiment of formulae (I-C), $Z^1$ is selected from the group consisting of:
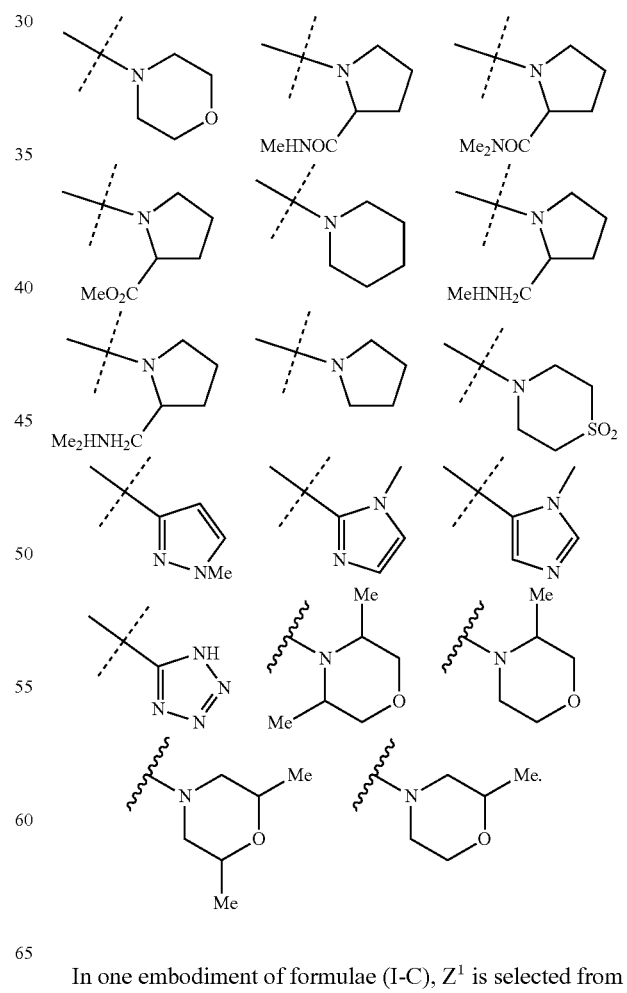
In one embodiment of formulae (I-C), $Z^1$ is selected from the group consisting of:

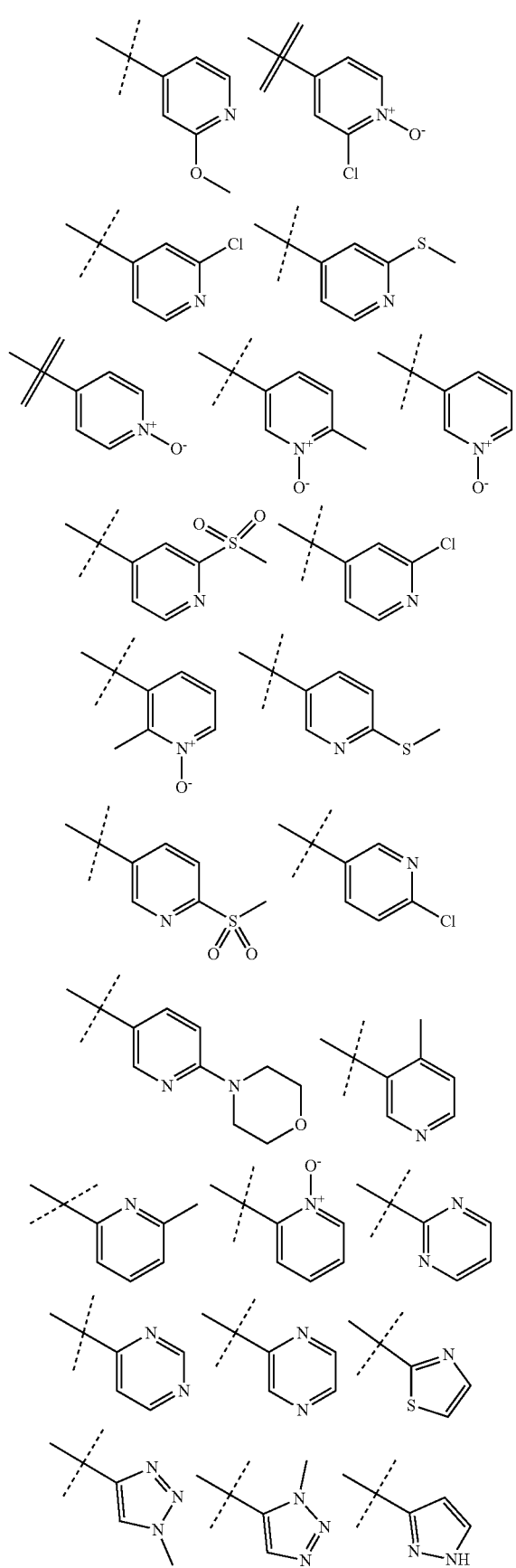
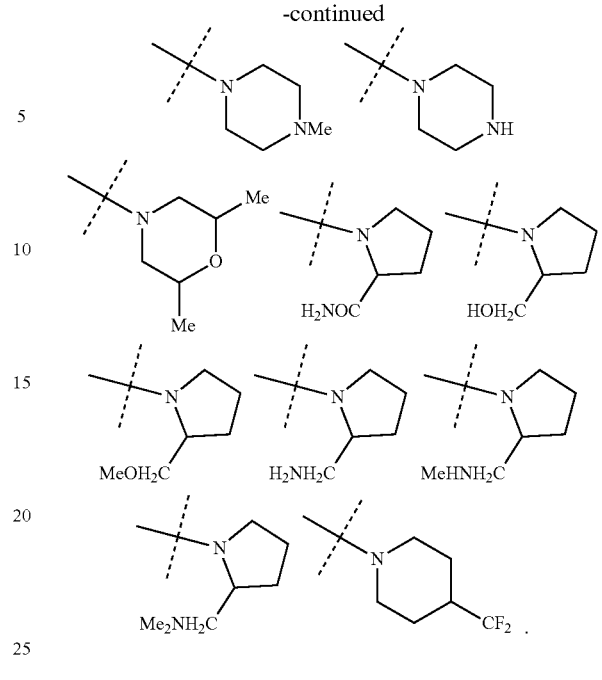
In one embodiment of formulae (I-C), $Z^1$ is selected from the group consisting of:
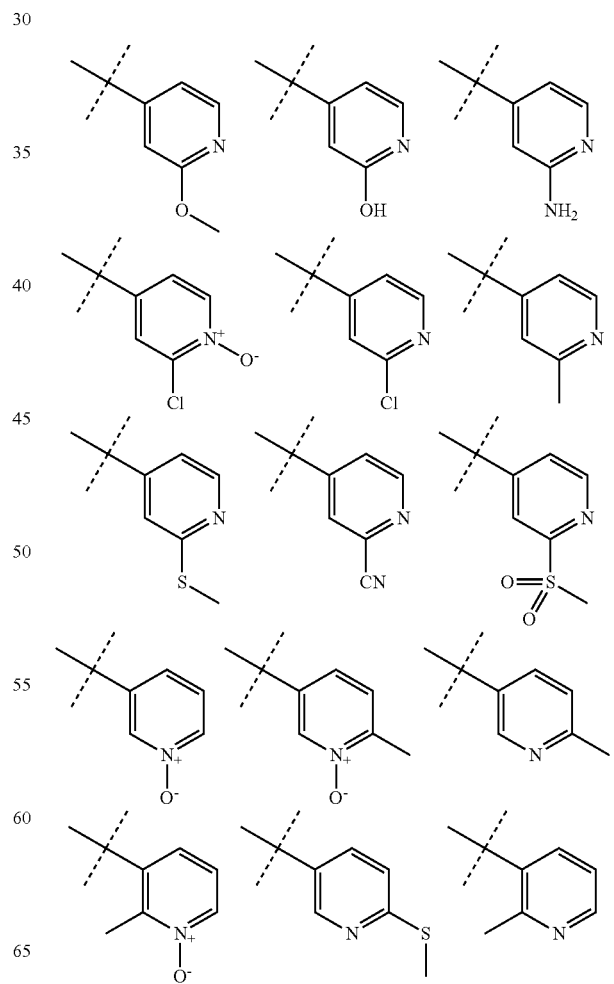

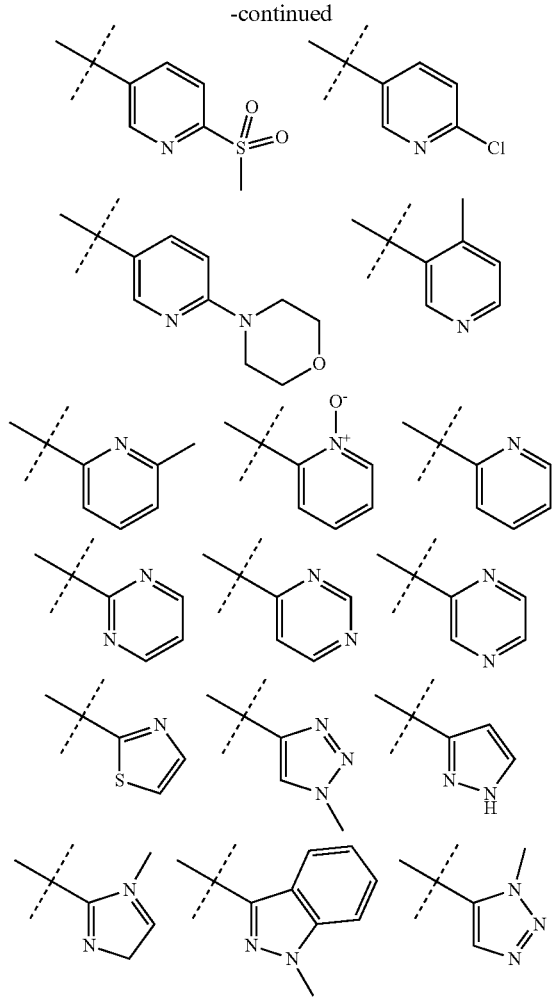
In one embodiment of formulae (I-C), $Z^1$ is selected from the group consisting of:
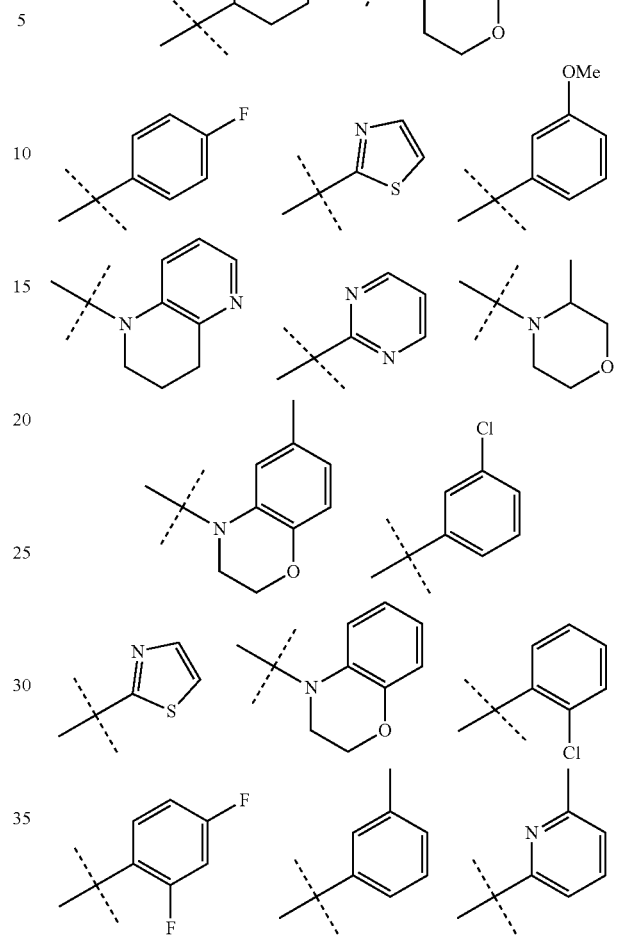
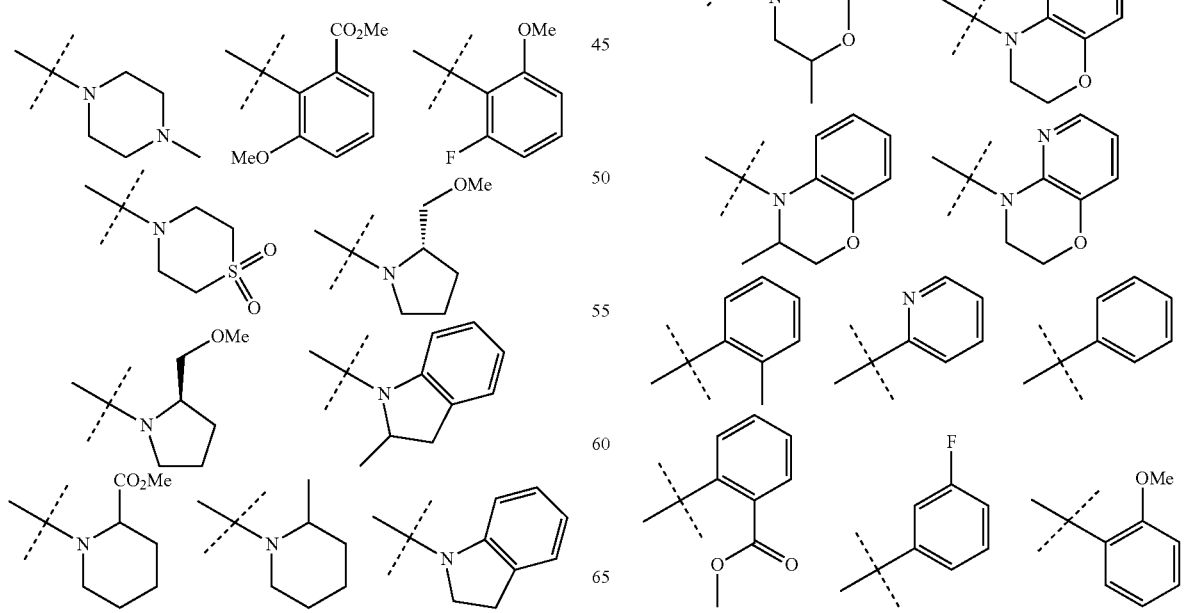

-continued

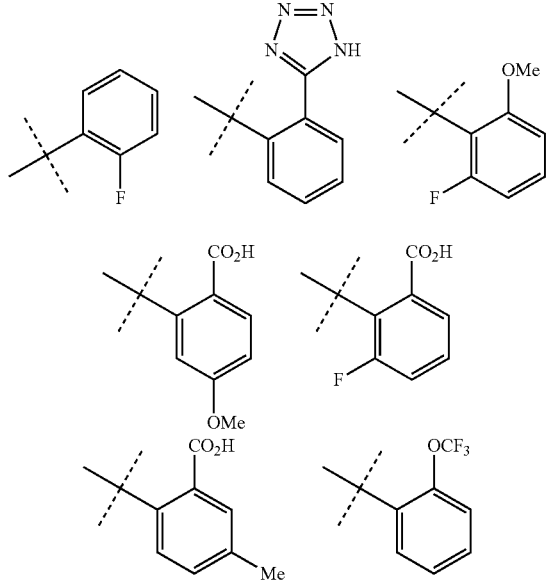

-continued

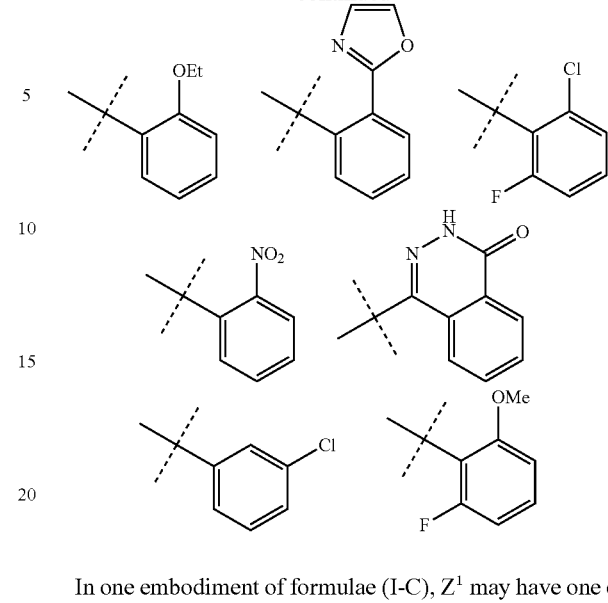

In one embodiment of formulae (I-C), $Z^1$ may have one or more substituents selected from the group consisting of:

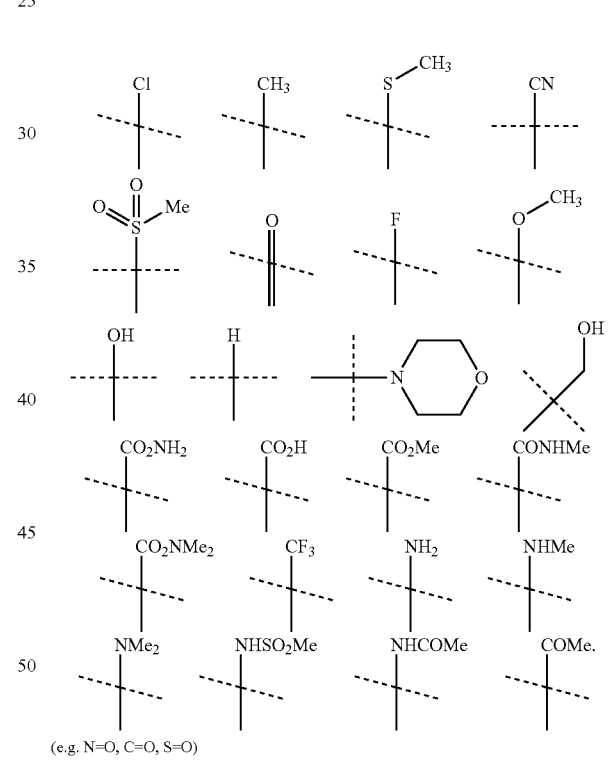

(e.g. N=O, C=O, S=O)

In one embodiment of formula (I-C), $Z^1$ has 0 to 3 substituents, each of which are independently selected from the group consisting of —CH$_3$ and oxo (=O or —O$^-$).

In one embodiment of formulae (I-C), $Z^a$ and/or $Z^b$ is located ortho- to one of the heteroatoms in the ring.

In one embodiment of formulae (I-C), $Z^a$ and $Z^b$ are each independently selected from the group consisting of halogen, unsubstituted or substituted C$_{1-8}$ alkyl, oxo (=O or —O$^-$), —CN, —NO$_2$, —OR$^{50}$, —C(O)R$^{50}$, —CONR$^{50}$R$^{51}$, —NR$^{50}$C(o)R$^{51}$, —NR$^{50}$R$^{51}$, —SR$^{50}$, —S(O)R$^{50}$, —S(O)$_2$R$^{50}$, —SO$_2$NR$^{50}$R$^{51}$, —NR$^{50}$SO$_2$R$^{51}$, unsubstituted or substituted 5- to 6-membered heteroaryl, unsubstituted or sub-

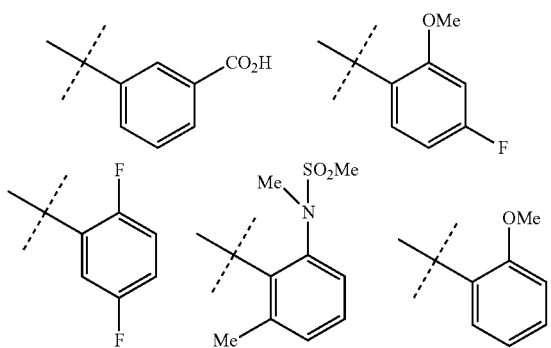

stituted 4- to 7-membered heterocyclyl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{50}$ and $R^{51}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (I-C), $Z^a$ and $Z^b$ are each independently selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, oxo (=O or —O⁻), —NO₂, —OR$^{50a}$, —OC(O)R$^{50a}$, —CO₂R$^{50a}$, —C(O)R$^{50a}$, —C(O)NR$^{50a}$R$^{51a}$, —OC(O)NR$^{50a}$R$^{51a}$, —NR$^{50a}$C(O)R$^{51a}$, NR$^{50a}$C(O)NR$^{51a}$R$^{51b}$, —NR$^{50a}$R$^{51a}$, —NR$^{50a}$CO₂R$^{51a}$, —SR$^{50a}$, —S(O)R$^{50a}$, —S(O)₂R$^{50a}$, —S(O)₂NR$^{50a}$R$^{51a}$, —NR$^{50a}$S(O)₂R$^{51a}$, substituted or unsubstituted $C_{6-10}$ aryl, substituted or unsubstituted 5- to 10-membered heteroaryl, substituted or unsubstituted 3- to 10-membered heterocyclyl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{50a}$, $R^{51a}$ and $R^{51b}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (I-C), $Z^a$ and $Z^b$ are each independently selected from the group consisting of substituted or unsubstituted $C_{2-8}$ alkenyl, substituted or unsubstituted $C_{2-8}$ alkynyl, —CO₂R$^{50a}$, —OC(O)NR$^{50a}$R$^{51a}$, —NR$^{50a}$C(O)NR$^{51a}$R$^{51b}$, —NR$^{50a}$CO₂R$^{51a}$, substituted or unsubstituted $C_{6-10}$ aryl and substituted or unsubstituted 3- to 10-membered heterocyclyl;

$R^{50a}$, $R^{51a}$ and $R^{51b}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (I-C), $Z^a$ and $Z^b$ are each independently selected from the group consisting of substituted $C_{1-8}$ alkyl, substituted $C_{2-8}$ alkenyl or substituted $C_{2-8}$ alkynyl, the substituted $C_{1-8}$ alkyl, substituted $C_{2-8}$ alkenyl or substituted $C_{2-8}$ alkynyl may have 1 to 3 substituents each independently selected from the group consisting of halogen, oxo (=O or —O⁻), —OR$^{52}$, —CO₂R$^{52}$, —C(O)R$^{52}$, —CONR$^{52}$R$^{53}$, —NR$^{52}$C(O)R$^{53}$, —NR$^{52}$R$^{53}$, —SR$^{52}$, —S(O)R$^{52}$, —S(O)₂R$^{52}$, —SO₂NR$^{52}$R$^{53}$, —NR$^{52}$SO₂R$^{53}$, unsubstituted or substituted phenyl, unsubstituted or substituted 5- to 6-membered heteroaryl, unsubstituted or substituted 4- to 7-membered heterocyclyl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{52}$ and $R^{53}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (I-C), $Z^a$ and $Z^b$ are each independently selected from the group consisting of substituted phenyl, substituted 5- or 6-membered heteroaryl or substituted 4- to 7-membered heterocyclyl, the substituted phenyl, substituted 5- or 6-membered heteroaryl and substituted 4- to 7-membered heterocyclyl may have 1 to 3 substituents independently selected from the group consisting of halogen, —OR$^{56}$, —CN, —NO₂, OXO (=O or —O⁻), —OC(O)R$^{56}$, —CO₂R$^{56}$, —C(O)R$^{56}$, —CONR$^{56}$R$^{57}$, —NR$^{56}$C(O)R$^{57}$, —NR$^{56}$R$^{57}$, —SR$^{56}$, —S(O)R$^{56}$, —S(O)₂R$^{56}$, —NR$^{56}$SO₂R$^{57}$, unsubstituted 4- to 7-membered heterocyclyl and unsubstituted $C_{1-8}$ alkyl, with the proviso that if the substituent on the $Z^1$ group is heterocyclic, then the substituents on this heterocycle do not include another heterocycle;

$R^{56}$ and $R^{57}$ are each independently selected from the group consisting of hydrogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, substituted or unsubstituted $C_{6-10}$ aryl, and substituted or unsubstituted 5- to 10-membered heteroaryl.

In one embodiment of formulae (I-C), $Z^a$ and $Z^b$ are each independently selected from the group consisting of chlorine, fluorine, unsubstituted or substituted $C_{1-8}$ alkyl (particularly methyl and trifluoromethyl), oxo (=O or —O⁻), —CN, —NO₂, —OMe, —C(O)Me, —CONH₂, —CONHMe, —CONMe₂, —NHC(O)Me, —NH₂, —NHMe, —NMe₂, —SMe, —S(O)Me, —S(O)₂Me, —NHSO₂Me, morpholinyl, —CH₂OH, —CH₂OMe, —CH₂NH₂, —CH₂NHMe, and —CH₂NMe₂.

In one embodiment of formulae (I-C), $Z^a$ and $Z^b$ are selected from the group consisting of chlorine, fluorine, methyl, oxo (=O or —O⁻), —CN, and —OMe.

In one embodiment of formulae (I-C), $Z^a$ and $Z^b$ are selected from the group consisting of chlorine, fluorine, methyl, isopropyl, oxo (=O or —O⁻), —CN, and —OMe.

In one embodiment of formulae (I-C), one of $Z^a$ and $Z^b$ is hydrogen and one of $Z^a$ and $Z^b$ is selected from the group consisting of chlorine, fluorine, methyl, isopropyl, oxo (=O or —O⁻), —CN, and —OMe.

In one embodiment of formulae (I-C), $Z^a$ and $Z^b$ are selected from the group consisting of chlorine, fluorine, methyl, isopropyl, oxo (=O or —O⁻), —CN, —OMe, —S(O)Me, —SO₂Me, —CO₂H, and —CO₂Me.

In one embodiment of any of formulae (I-C) $Z^a$ and $Z^b$ are selected from the group consisting of:

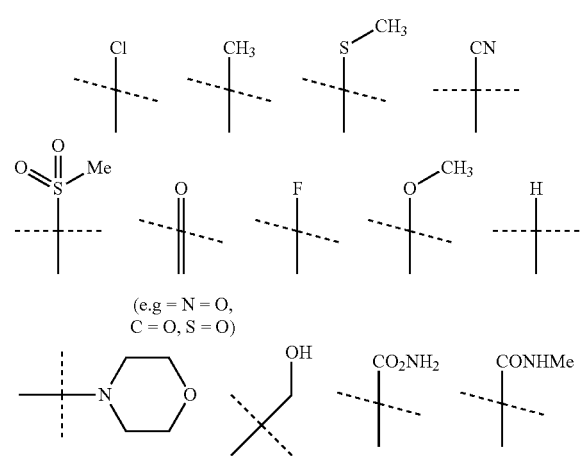

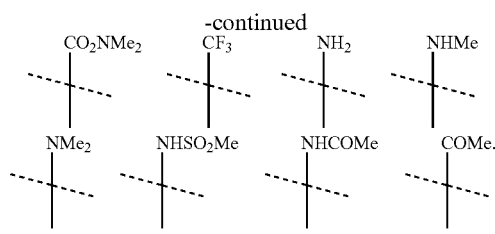

In a further embodiment, the compounds are represented by formula (CLI), or salts thereof:

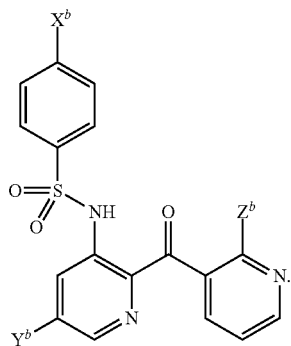

CLI

Formula CLI is an example of Formula I.

$X^b$, $Y^b$ and $Z^b$ are as defined above.

In one embodiment of formula (CLI), $Y^b$ is halogen.

In one embodiment of formula (CLI), $Y^b$ is Cl.

In one embodiment of formula (CLI), $X^b$ is selected from the group consisting of —$OR^{24a}$, and substituted or unsubstituted $C_{1-8}$ alkyl; and $Z^b$ is selected from the group consisting of substituted or unsubstituted $C_{1-8}$ alkyl.

In a further embodiment, the compounds are represented by formula (CLII), or salts thereof:

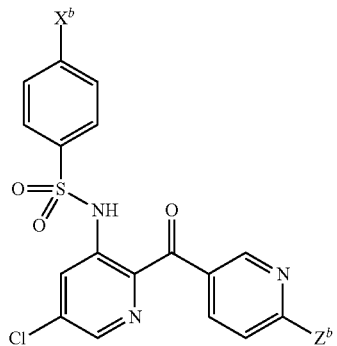

CLII

Formula CLII is an example of Formula I.

$X^b$ and $Z^b$ are as defined above.

In one embodiment of formula (CLII), $X^b$ is selected from the group consisting of —$OR^{24a}$, and substituted or unsubstituted $C_{1-8}$ alkyl; and $Z^b$ is —$OR^{30a}$ where $R^{30a}$ is selected from the group consisting of hydrogen and substituted or unsubstituted $C_{1-8}$ alkyl.

In a further embodiment, the compounds are represented by formula (CLIII), or salts thereof:

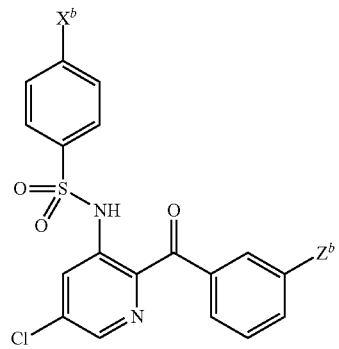

CLIII

Formula CLIII is an example of Formula I.

$X^b$ and $Z^b$ are as defined above.

In one embodiment of formula (CLIII), $X^b$ is selected from the group consisting of —$OR^{24a}$, and substituted or unsubstituted $C_{1-8}$ alkyl; and $Z^b$ is halogen. Preferably $Z^b$ is fluorine.

In one embodiment of formulae (CLI-CLIII), $X^b$ is —$OR^{24a}$.

In one embodiment of formulae (CLI-CLIII), $X^b$ is —$OR^{24a}$; and $R^{24a}$ is substituted or unsubstituted $C_{1-8}$ alkyl.

In one embodiment of formulae (CLI-CLIII), $X^b$ is —$OR^{24a}$; and $R^{24a}$ is substituted $C_{1-8}$ alkyl.

In one embodiment of formulae (CLI-CLIII), $X^b$ is iso-propoxy.

In one embodiment of formulae (CLI-CLIII), $X^b$ is substituted or unsubstituted $C_{1-8}$ alkyl.

In one embodiment of formulae (CLI-CLIII), $X^b$ is substituted $C_{1-8}$ alkyl or unsubstituted $C_{2-8}$ alkyl.

In one embodiment of formulae (CLI-CLIII), $X^b$ is substituted $C_{1-8}$ alkyl.

In one embodiment of formulae (CLI-CLIII), $X^b$ is unsubstituted $C_{2-8}$ alkyl.

In one embodiment of formulae (CLI-CLIII), $X^b$ is tert-butyl.

In one embodiment of formulae (CLI), $Z^b$ is unsubstituted $C_{1-8}$ alkyl.

In one embodiment of formulae (CLI), $Z^b$ is methyl.

In one embodiment of formulae (CII), $Z^b$ is —$OR^{30a}$, where $R^{30a}$ is unsubstituted $C_{1-8}$ alkyl.

In one embodiment of formulae (CLII), $Z^b$ is —$OR^{30a}$, where $R^{30a}$ is substituted $C_{1-8}$ alkyl.

In one embodiment of formulae (CLII), $Z^b$ is hydroxy.

In one embodiment of formulae (CLII), $Z^b$ is methoxy.

In one embodiment of formulae (CLIII), $Z^b$ is fluorine.

In one embodiment of formulae (CLIII), $Z^b$ is chlorine.

In one embodiment of formulae (CLIII), $Z^b$ is bromine.

In one embodiment of formulae (CLIII), $Z^b$ is iodine.

Compositions that Modulate Chemokine Activity

In another aspect, the present invention provides compositions that modulate chemokine activity, specifically CCR2 activity or CCR9 activity. Generally, the compositions for modulating chemokine receptor activity in humans and animals will comprise a pharmaceutically acceptable excipient or diluent and a compound having the formula provided above as formula (I).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

In one embodiment, the present invention provides a composition consisting of a pharmaceutically acceptable carrier and a compound of the invention.

Methods of Treatment

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, wherein a compound or composition of the invention is administered either alone or in combination with a second therapeutic agent, wherein said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present invention may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudoephedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a β2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating or Preventing CCR2-Mediated Conditions or Diseases

In yet another aspect, the present invention provides methods of treating or preventing a CCR2-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR2-mediated condition or disease" and related phrases and terms refer to a condition or disease characterized by inappropriate, i.e., less than or greater than normal, CCR2 functional activity. Inappropriate CCR2 functional activity might arise as the result of CCR2 expression in cells which normally do not express CCR2, increased CCR2 expression (leading to, e.g., inflammatory and immunoregulatory disorders and diseases) or decreased CCR2 expression. Inappropriate CCR2 functional activity might also arise as the result of MCP-1 secretion by cells which normally do not secrete MCP-1, increased MCP-1 expression (leading to, e.g., inflammatory and immunoregulatory disorders and diseases) or decreased MCP-1 expression. A CCR2-mediated condition or disease may be completely or partially mediated by inappropriate CCR2 functional activity. However, a CCR2-mediated condition or disease is one in which modulation of CCR2 results in some effect on the underlying condition or disease (e.g., a CCR2 antagonist results in some improvement in patient well being in at least some patients). Furthermore, MCP-2, 3 and 4 are also CCR2 ligands.

In one embodiment, the present invention provides a method of treating a CCR2-mediated condition or disease involving administering to a subject a safe and effective amount of the compound or composition of the invention.

In one embodiment, the present invention provides a method of treating a CCR2-mediated condition or disease involving administering to a subject a safe and effective amount of the compound or composition of the invention, where the CCR2-mediated condition or disease is atherosclerosis.

In one embodiment, the present invention provides a method of treating a CCR2-mediated condition or disease involving administering to a subject a safe and effective amount of the compound or composition of the invention, where the CCR2-mediated condition or disease is restenosis.

In one embodiment, the present invention provides a method of treating a CCR2-mediated condition or disease involving administering to a subject a safe and effective amount of the compound or composition of the invention, where the CCR2-mediated condition or disease is multiple sclerosis.

In one embodiment, the present invention provides a method of treating a CCR2-mediated condition or disease involving administering to a subject a safe and effective amount of the compound or composition of the invention, where the CCR2-mediated condition or disease is selected from the group consisting of inflammatory bowel disease, renal fibrosis, rheumatoid arthritis, obesity and non-insulin-dependent diabetes.

In one embodiment, the present invention provides a method of treating a CCR2-mediated condition or disease involving administering to a subject a safe and effective amount of the compound or composition of the invention, where the CCR2-mediated condition or disease is type 2 diabetes.

In one embodiment, the present invention provides a method of treating a CCR2-mediated condition or disease involving administering to a subject a safe and effective amount of the compound or composition of the invention, where the CCR2-mediated condition or disease is selected from the group consisting of chronic obstructive pulmonary disease, idiopathic pulmonary fibrosis and idiopathic pneumonia syndrome.

In one embodiment, the present invention provides a method of treating a CCR2-mediated condition or disease involving administering to a subject a safe and effective amount of the compound or composition of the invention, where the administering is oral, parenteral, rectal, transdermal, sublingual, nasal or topical.

In one embodiment, the present invention provides a method of treating a CCR2-mediated condition or disease involving administering to a subject a safe and effective amount of the compound or composition of the invention, where the compound is administered in combination with an anti-inflammatory or analgesic agent.

In one embodiment, the present invention provides a method of treating a CCR2-mediated condition or disease involving administering to a subject a safe and effective amount of the compound or composition of the invention, where an anti-inflammatory or analgesic agent is also administered.

In one embodiment, the present invention provides a method of modulating CCR2 function in a cell, where the CCR2 function in the cell is modulated by contacting the cell with a CCR2 modulating amount of the compound of the present invention.

In one embodiment, the present invention provides a method of treating a CCR2-mediated condition or disease involving administering to a subject a safe and effective amount of the compound or composition of the invention, where the disease is selected from the group consisting of pulmonary fibrosis, transplantation rejection, graft-versus-host disease and cancer.

In yet other embodiments, the present methods are directed to the treatment of psoriasis wherein a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Methods of Treating or Preventing CCR9-Mediated Conditions or Diseases

In yet another aspect, the present invention provides methods of treating or preventing a CCR9-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, and (15) irritable bowel syndrome.

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

In yet other embodiments, the present methods are directed to the treatment of psoriasis where a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Preparation of Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

Preparation of CCR2 and CCR9 Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nuclephilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

EXAMPLES

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations have the following meanings:

BOP: (Benzotriazol-1-yloxy)tris(dimethylamino)phosphonium hexafluorophosphate

DCM: dichloromethane

DIEA: diisopropylethyl amine

DMF: dimethylformamide

HATU: N,N,N',N'-Tetramethyl-O-(7-azabenzotriazol-1-yl)uronium hexafluorophosphate LAH: lithium aluminum hydride NMP: N-methylpyrrolidinone PMB: para methoxybenzyl TEA: triethylamine TFA: trifluoroacetic acid T$_3$P: 1-propane phosphonic acid cyclic anhydride This compound was prepared according to the following literature procedure: Zhou et al.; *Bioorganic & Med. Chem.*, 9, 2061-2071 (2001).

Example 1: 2-Bromo-5-chloro-3-nitro-pyridine

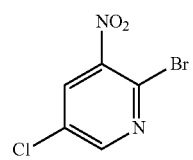 [SMILES: O=[N+]([O-])c1cc(Cl)cnc1Br]

This compound was prepared according to the following literature procedure: Zhou et al.; *Bioorganic & Med. Chem.*, 9, 2061-2071 (2001).

Example 2: 2-Bromo-5-chloro-pyridin-3-ylamine

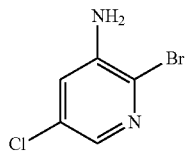

2-Bromo-5-chloro-3-nitro-pyridine (11.87 g, 50 mmol) was dissolved in 100 mL ether. Tin(II) chloride dihydrate (56.4 g, 0.5 mol) was dissolved in 100 mL of concentrated hydrochloric acid and added drop wise over 15 minutes to the stirring ethereal solution of the nitro compound. The exothermic reaction brought the ether to boiling and it was allowed to evaporate off. After the addition was complete the reaction mixture was placed on a 50° C. oil bath and stirred for 30 minutes to boil of the remaining ether. The flask was then cooled on in an ice bath. The precipitate formed was collected and by filtration and dissolved in 100 mL of water. The pH was adjusted to 9-10 by the addition of concentrated ammonium hydroxide solution and the product was extracted with ethyl acetate (2×100 mL). The organic layer was washed with diluted ammonium hydroxide, water and brine and dried over $Na_2SO_4$ and the solvent was evaporated to afford 7.4 g of tan crystalline solid. MS m/z: 208.9 (M+H).

Example 3: General Procedure A: Synthesis of 5-chloro-3-nitro-2-aryloxy-pyridines and 5-chloro-3-nitro-2-arylsulfanyl-pyridines

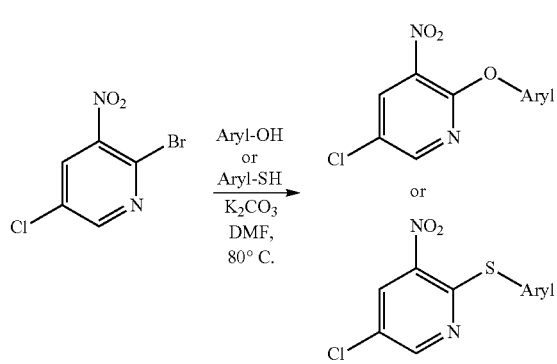

A mixture of the appropriate hydroxyaryl or thioaryl (1.3 equiv), 2-bromo-5-chloro-3-nitro-pyridine (1 equiv) and $K_2CO_3$ (1.5 equiv) in DMF was heated at 80° C. overnight. The resulting mixture was cooled to room temperature, and diluted with water and $CH_2Cl_2$. The biphasic mixture was separated and the aqueous portion was extracted with $CH_2Cl_2$. The combined extracts were washed with saturated aqueous $NaHCO_3$, brine and dried ($Na_2SO_4$). It was then filtered and filtrate was concentrated under reduced pressure and the product was purified by flash column chromatography on silica gel to provide desired product.

Example 4: 5-Chloro-3-nitro-2-phenoxy-pyridine

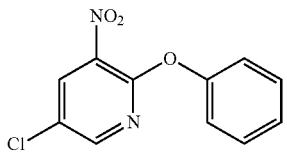

This compound was prepared according to the general procedure A described above using 2-bromo-5-chloro-3-nitro-pyridine (500 mg, 2.11 mmol), phenol (258 mg, 2.75 mmol), $K_2CO_3$ (437 mg, 3.16 mmol) and DMF (2 mL). MS m/z: 250.4 (M+H).

Example 5: 5-Chloro-3-nitro-2-(pyridin-4-ylsulfanyl)-pyridine

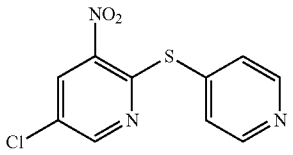 [SMILES: O=[N+]([O-])c1cc(Cl)cnc1Sc1ccncc1]

The title compound was prepared according to general procedure A using 2-bromo-5-chloro-3-nitro-pyridine (500 mg, 2.11 mmol), 4-mercaptopyridinel (306 mg, 2.75 mmol), $K_2CO_3$ (437 mg, 3.16 mmol) and DMF (2 mL). MS m/z: 267.5 (M+H).

Example 6: 5-Chloro-2-(2-fluoro-phenoxy)-3-nitro-pyridine

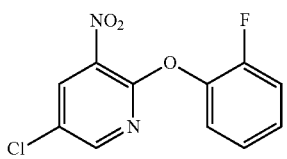

This compound was prepared according to general procedure A using 2-bromo-5-chloro-3-nitro-pyridine (750 mg, 3.17 mmol), 2-fluorophenol (463 mmol, 4.13 mmol), $K_2CO_3$ (437 mg, 4.75 mmol) and DMF (5 mL). MS m/z: 269.0 (M+H).

Example 7: 5-Chloro-2-(4-fluoro-phenoxy)-3-nitro-pyridine

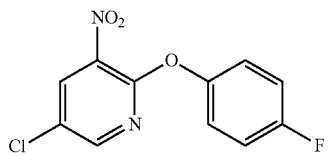 [SMILES: O=[N+]([O-])c1cc(Cl)cnc1Oc1ccc(F)cc1]

The title compound was prepared according to general procedure A using 2-bromo-5-chloro-3-nitro-pyridine (750 mg, 3.17 mmol), 4-fluorophenol (463 mmol, 4.13 mmol), K$_2$CO$_3$ (437 mg, 4.75 mmol) and DMF (5 mL). MS m/z: 269.0 (M+H).

Example 8: 5-Chloro-3-nitro-pyridine-2-carboxylic acid

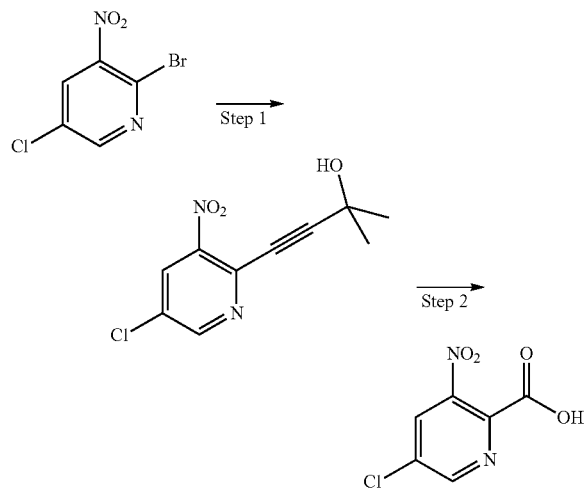

Step 1: To a mixture of 2-bromo-5-chloro-3-nitro-pyridine (2.5 g, 10.6 mmol), CuI (141 mg, 0.74 mmol), Pd(PPh$_3$)$_4$, (367 mg, 0.32 mmol) and 2-Methyl-3-butyn-2-ol (1.5 mL, 15.8 mmol) was added 1-methyl-2-pyrrolidone (20 mL) followed by Et$_3$N (6 mL, 22 mmol). After stirring for 4 h 30 min at room temperature, the reaction mixture was poured into water (20 mL) and extracted with EtOAc (3×30 mL). The combined organic extracts were washed with brine (20 mL), dried (Na$_2$SO$_4$), filtered and concentrated under reduced pressure, and the residue was purified by flash column chromatography over silica gel (EtOAc/Hexanes, 2:98, then 5:95) to provide 4-(5-chloro-3-nitro-pyridin-2-yl)-2-methyl-but-3-yn-2-ol. MS m/z: 241.0 (M+H).

Step 2: A suspension of the alkyne from step 1 (1.96 g, 8.2 mmol) in water (20 mL) was heated at 75-80° C. KMnO$_4$ (4.27 g, 27.1 mmol) was added portion wise over 30 min. After complete addition, heating was continued for 45 min. The reaction mixture was then cooled to room temperature and the pH adjusted to 9 by the addition of 1.0 M aqueous NaOH and filtered through filter paper. The filter cake was thoroughly washed with 0.3 M aqueous NaOH. The filtrate was extracted with EtOAc and discarded. The aqueous part was acidified to pH 3-4 with 1 M HCl and saturated with solid NaCl. This solution was extracted with EtOAc (4×30 mL). The combined extract was dried (Na$_2$SO$_4$) and concentrated under reduced pressure to provide the crude acid (500 mg). MS m/z: 200.8 (M–H).

Example 9: (5-Chloro-3-nitro-pyridin-2-yl)-phenyl-methanone

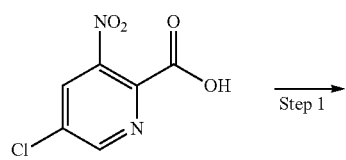

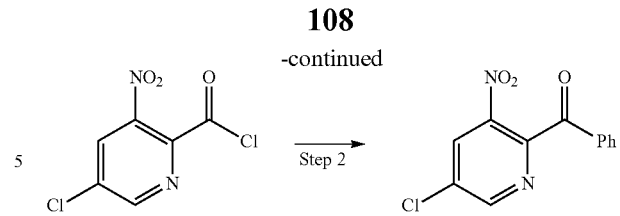

Step 1: To a stirred solution of the carboxylic acid (250 mg, 1.3 mmol) in CH$_2$Cl$_2$, at room temperature, was added oxalyl chloride (216 µL, 2.5 mmol) followed by a drop of DMF. After stirring for 1-2 h, the reaction mixture the solvent was removed under reduced pressure to provide the chloride which was used in the next step without further purification.

Step 2: The above acid chloride was dissolved in benzene (30 mL) and AlCl$_3$ (246 mg, 1.85 mmol) was added. The resulting mixture was heated at 80° C. for 3.5 h. The reaction mixture was quenched with aqueous NaHCO$_3$. The organic phases then separated and the aqueous portion was extracted with EtOAc and the combined organic extracts washed with brine, dried (Na$_2$SO$_4$) and filtered. The filtrate was concentrated under reduced pressure and residue was purified by flash chromatography to on silica gel to provide the title compound. Mass spectrum m/z: 262.5 (M+H).

Example 10: (3-Amino-5-chloro-pyridin-2-yl)-phenyl-methanone

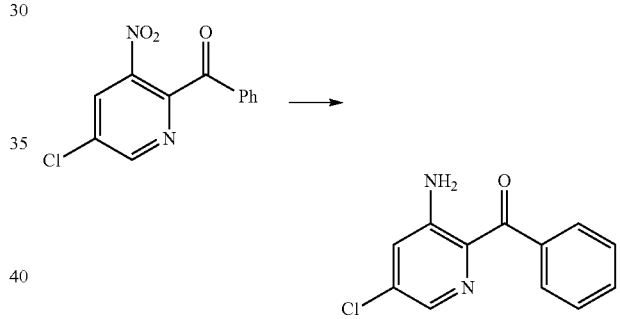

A mixture of (5-chloro-3-nitro-pyridin-2-yl)-phenyl-methanone (159 mg, 0.61) and SnCl$_2$ (771 mg, 3.42 mmol) in EtOH (10 mL) was heated at 80° C. in an oil bath for several days. The progress of the reaction was followed by LCMS and upon completion the solvent was removed and treated with aqueous NaOH to adjust the pH 10-11. This cloudy mixture was extracted with EtOAc and washed with water and brine. The combined extracts were dried over anhydrous Na$_2$SO$_4$, filtered and concentrated under reduced pressure and the residue was purified by flash column chromatography to provide the aniline. Mass spectrum m/z: 232.6 (M+H).

Example 11: General Procedure B: Reduction of Nitropyridines

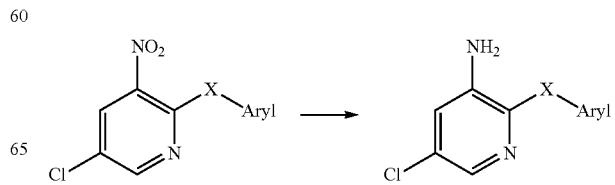

A mixture of the nitropyridine (1 equiv) and SnCl$_2$ (3-5 equiv) in EtOH was heated at 80° C. in an oil bath for several hour. The progress of the reaction was followed by LCMS and upon completion the solvent was removed and treated with aqueous NaOH. This cloudy mixture was extracted with EtOAc and washed with water and brine. The combined extracts were dried over anhydrous Na$_2$SO$_4$, filtered and concentrated under reduced pressure and the residue was purified by flash column chromatography to provide the appropriate aminopyridine.

Example 12: 5-Chloro-2-phenoxy-pyridin-3-ylamine

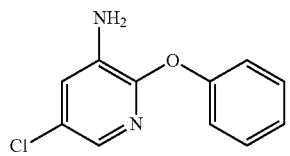 [SMILES: Nc1cc(Cl)cnc1Oc1ccccc1]

This compound was prepared according to general procedure B using the corresponding nitropyridine (500 mg, 2.11 mmol), SnCl$_2$ (1.77 mmol, 5.4 mmol), and EtOH (10 mL). MS m/z: 220.5 (M+H).

Example 13: 5-Chloro-2-(2-fluoro-phenoxy)-pyridin-3-ylamine

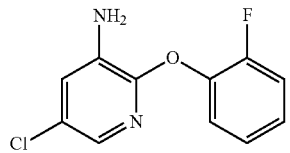

The title compound was prepared according to general procedure B using the appropriate nitropyridine (450 mg, 1.67 mmol), SnCl$_2$ (1.50 mmol, 6.68 mmol), and EtOH (10 mL). MS m/z: 239.0 (M+H).

Example 14: 5-Chloro-2-(4-fluoro-phenoxy)-pyridin-3-ylamine

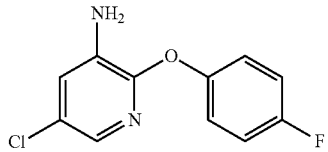 [SMILES: Nc1cc(Cl)cnc1Oc1ccc(F)cc1]

The title compound was prepared according to general procedure B using the corresponding nitro compound (450 mg, 1.67 mmol), SnCl$_2$ (1.50 mmol, 6.68 mmol) and EtOH (10 mL). Mass spectrum m/z: 239.0 (M+H).

Example 15: 5-Chloro-2-(pyridin-4-ylsulfanyl)-pyridin-3-ylamine

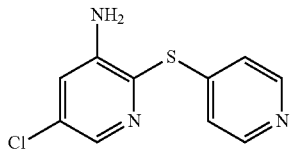 [SMILES: Nc1cc(Cl)cnc1Sc1ccncc1]

The title compound was prepared according to general procedure B using the corresponding nitro compound (296 mg, 1.11 mmol), SnCl$_2$ (1.00 gm mmol, 4.40 mmol), EtOH (10 mL) Reaction mixture was extracted with a mixture of EtOAc and THF (1:1). MS m/z: 237.3 (M+H).

Example 16: (3-Amino-5-chloro-pyridin-2-yl)-pyridin-3-yl-methanone

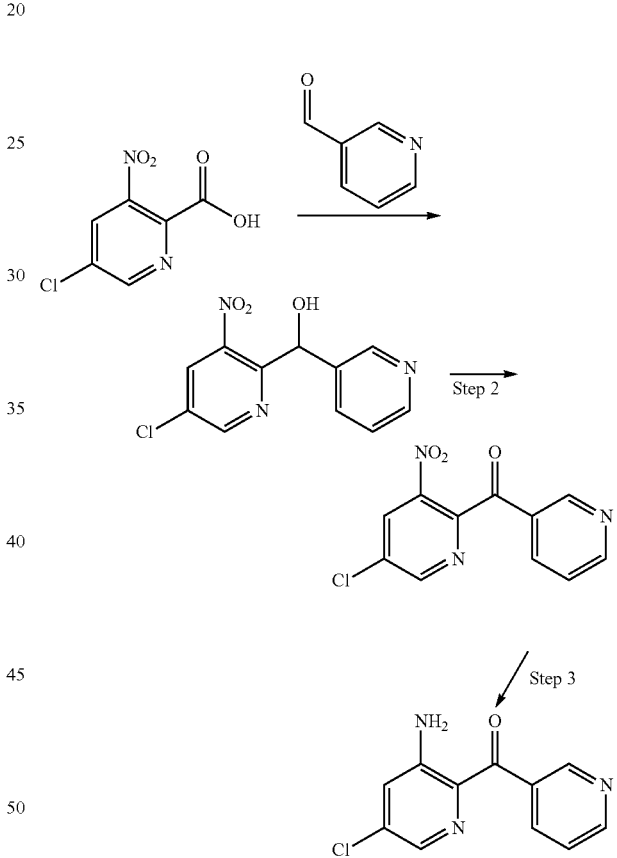

Step 1: A mixture of pyridine-3-carboxaldehyde (0.5 mL) and 5-Chloro-3-nitro-pyridine-2-carboxylic acid (200 mg) was heated at 190° C. for 4 minutes in a sealed tube using a microwave apparatus. The reaction mixture was diluted with CH$_2$Cl$_2$ and concentrated under reduced pressure. This residue was washed with aqueous NaHCO$_3$ and extracted with EtOAc. The combined organic extracts washed with brine, dried (Na$_2$SO$_4$) and filtered. The residue which contained the desired alcohol was utilized in the following oxidation without further purification. MS m/z: 266.0 (M+H).

Step 2: A mixture of the alcohol obtained from the above reaction and PCC (426 mg) was stirred at room temperature for 2 h. It was then treated with small amount of silica gel and filtered. The filtrate was concentrated under reduced pressure and the residue was purified by flash column chromatography on silica gel to provide the ketone. MS m/z: 264.0 (M+H).

Step 3: A mixture of the (5-Chloro-3-nitro-pyridin-2-yl)-pyridin-3-yl-methanone from Step 2 above (30 mg, 0.11 mmol) and SnCl₂ (200 mg, 0.88 mmol) in EtOH (3 mL) was heated at 80° C. in an oil bath for 3 days. The progress of the reaction was followed by LCMS and upon completion the solvent was removed and treated with aqueous NaOH to adjust the pH to 10-11. This cloudy mixture was extracted with EtOAc and washed with water and brine. The combined extracts were dried over anhydrous Na₂SO₄, filtered and concentrated under reduced pressure and the residue separated by preparative HPLC (20→80% gradient of ACN-water) and pure product fractions were treated with NaHCO₃ and extracted with EtOAc to provide (3-amino-5-chloro-pyridin-2-yl)-pyridin-3-yl-methanone. MS m/z: 234.1 (M+H).

Example 17: 4-Chloro-N-(5-chloro-2-phenoxy-phenyl)-3-trifluoromethyl-benzenesulfonamide

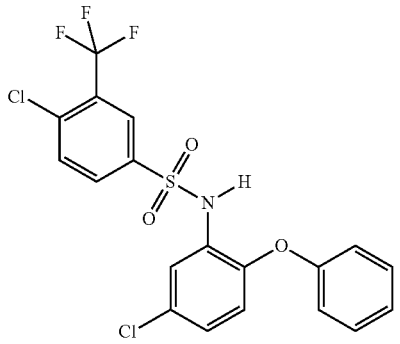 [SMILES: O=S(=O)(Nc1cc(Cl)ccc1Oc1ccccc1)c1ccc(Cl)c(C(F)(F)F)c1]

To a solution of 5-chloro-2-phenoxy-phenylamine (75 mg, 0.34 mmol) in anhydrous pyridine (0.5 mL) was added drop wise a solution of 4-chloro-3-trifluoromethyl-benzenesulfonyl chloride (95 mg, 0.341 mmol) in pyridine (0.5 mL). The resulting mixture was stirred at room temperature for 2 h. The reaction mixture was separated by preparative HPLC using acetonitrile-water solvent mixture and pure product fractions were lyophilized to provide pure product as a solid. ¹H NMR (400 MHz, CDCl₃) δ 8.04 (d, J=2.0 Hz, 1H), 7.80 (dd, J=8.4, 2.0 Hz, 1H), 7.70 (d, J=2.4 Hz, 1H), 7.51 (d, J=8.4 Hz, 1H), 7.27-7.23 (m, 2H), 7.14-7.10 (m, 1H), 7.05-7.02 (m, 2H), 6.66 (d, J=8.4 Hz, 1H), 6.60-6.56 (m, 2H). MS m/z: 484.0 (M+Na).

Example 18: 4-Chloro-N-(5-chloro-2-phenoxy-pyridin-3-yl)-3-trifluoromethyl-benzene Sulfonamide

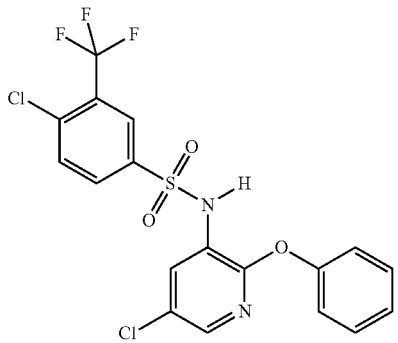 [SMILES: O=S(=O)(Nc1cc(Cl)cnc1Oc1ccccc1)c1ccc(Cl)c(C(F)(F)F)c1]

To a solution of 5-chloro-2-phenoxy-pyridin-3-ylamine (60 mg, 0.27 mmol) in anhydrous pyridine (0.5 mL) was added drop wise a solution of 4-chloro-3-trifluoromethyl-benzenesulfonyl chloride (76 mg, 0.27 mmol) in pyridine (0.5 mL). The resulting mixture was stirred at room temperature for 5 h. The reaction mixture was separated by preparative HPLC using acetonitrile-water solvent mixture and pure product fractions were lyophilized to provide pure product as a solid. ¹H NMR (400 MHz, CDCl₃) δ 8.14 (s, 1H), 7.89-7.87 (m, 2H), 7.81 (m, 1H), 7.59 (d, J=8.0 Hz, 1H), 7.35 (t, J=8.4 Hz, 1H), 7.25-7.19 (m, 2H), 6.76 (d, J=8.0 Hz, 2H). MS m/z: 463.0 (M+H).

Example 19: 4-Chloro-N-[5-chloro-2-(pyridin-4-ylsulfanyl)-pyridin-3-yl]-3-trifluoromethyl-benzenesulfonamide

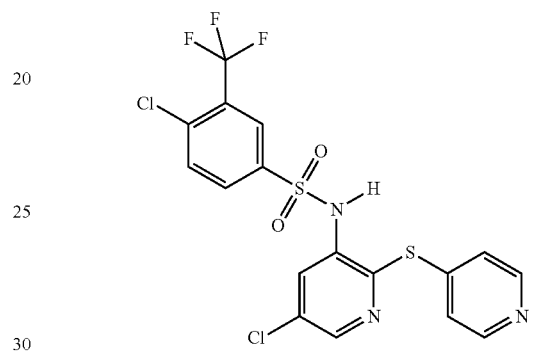

To a solution of 5-chloro-2-(pyridin-4-ylsulfanyl)-pyridin-3-ylamine (100 mg, 0.42 mmol) in anhydrous pyridine (0.5 mL) was added drop wise a solution of 4-chloro-3-trifluoromethyl-benzenesulfonyl chloride (117 mg, 0.42 mmol) in pyridine (0.25 mL). The resulting mixture was stirred at room temperature for 2 days. The reaction mixture was concentrated under reduced pressure and diluted with EtOAc and brine. The aqueous portion was separated and extracted with EtOAc. The combined extracts were dried (Na₂SO₄) filtered and concentrated under reduced pressure. The residue was treated with 0.3 M aqueous NaOH and washed with CH₂Cl₂. The aqueous portion was acidified with conc HCl to pH 3 and extracted with EtOAc. The combined extracts were dried (Na₂SO₄) filtered and concentrated under reduced pressure. The residue was separated by preparative HPLC (20→80% gradient of ACN-water) and pure product fractions were lyophilized to provide pure product as a solid. Mass spectrum m/z: 480.0 (M+H).

Example 20: 4-Chloro-N-[5-chloro-2-(2-fluoro-phenoxy)-pyridin-3-yl]-3-trifluoromethyl-benzenesulfonamide

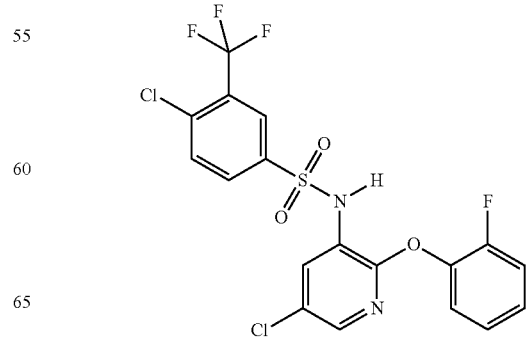

A solution of 5-chloro-2-(2-fluoro-phenoxy)-pyridin-3-ylamine (75 mg, 0.31 mmol), 4-chloro-3-trifluoromethyl-benzenesulfonyl chloride (103 mg, 0.36 mmol), DMAP (20 mg, 0.16 mmol) in anhydrous pyridine (1 mL) was stirred at room temperature for 2 days. The reaction product was separated by preparative HPLC using acetonitrile-water solvent mixture and pure product fractions were lyophilized to provide pure product as a solid. $^1$H NMR (400 MHz, CDCl$_3$) δ 8.16 (s, 1H), 7.96 (s, 1H), 7.89 (d, J=8.0 Hz, 1H), 7.79 (s, 1H), 7.62 (d, J=8.0 Hz, 1H), 7.15-7.13 (m, 3H), 7.00-6.96 (m, 1H). MS m/z: 481.0 (M+H).

Example 21: 4-Chloro-N-[5-chloro-2-(2-fluoro-phenoxy)-pyridin-3-yl]-3-trifluoromethyl-benzenesulfonamide

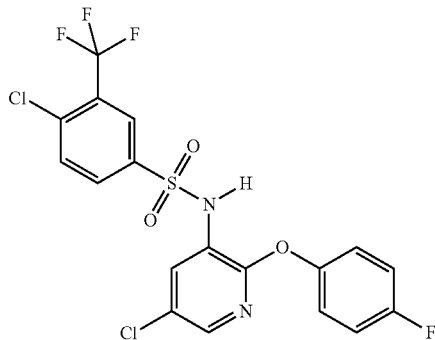 [SMILES: O=S(=O)(Nc1cc(Cl)cnc1Oc1ccc(F)cc1)c1ccc(Cl)c(C(F)(F)F)c1]

A solution of 5-chloro-2-(4-fluoro-phenoxy)-pyridin-3-ylamine (75 mg, 0.31 mmol), 4-chloro-3-trifluoromethyl-benzenesulfonyl chloride (103 mg, 0.36 mmol), DMAP (20 mg, 0.16 mmol) in anhydrous pyridine (1 mL) was stirred at room temperature for 2 days. The reaction mixture was separated by preparative HPLC and pure product fractions were lyophilized to provide pure product as a solid. $^1$H NMR (400 MHz, CDCl$_3$) δ 8.16 (s, 1H), 7.92-7.90 (m, 2H), 7.81 (s, 1H), 7.64 (d, J=7.6 Hz, 1H), 7.11 (s, 1H), 7.06-7.03 (m, 2H), 6.76-6.74 (m, 2H). Mass spectrum m/z: 481.0 (M+H).

Example 22: N-(2-Benzoyl-5-chloro-pyridin-3-yl)-4-chloro-3-trifluoromethyl-benzene Sulfonamide

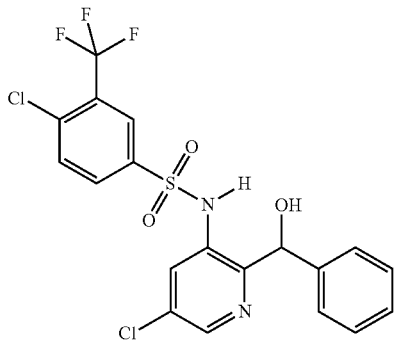 [SMILES: O=S(=O)(Nc1cc(Cl)cnc1C(O)c1ccccc1)c1ccc(Cl)c(C(F)(F)F)c1]

A solution of (3-amino-5-chloro-pyridin-2-yl)-phenyl-methanone (40 mg, 0.17 mmol), 4-chloro-3-trifluoromethyl-benzenesulfonyl chloride (72 mg, 0.26 mmol), and DMAP (11 mg, 0.09 mmol) in anhydrous pyridine (0.5 mL) was heated at 60° C. for 4 days. The product was separated by preparative HPLC and pure product fractions were lyophilized to provide pure product as a solid. $^1$H NMR (400 MHz, CDCl$_3$) δ 10.56 (s, 1H), 8.39 (s, 1H), 8.17 (s, 1H), 8.07 (s, 1H), 7.87 (d, J=8.0 Hz, 1H), 7.54 (d, J=7.6 Hz, 2H), 7.61-7.58 (m, 1H), 7.50 (d, J=8.4 Hz, 1H), 7.45-7.42 (m, 2H); MS m/z: 475.0 (M+H).

Example 23: 4-Chloro-N-[5-chloro-2-(pyridine-3-carbonyl)-pyridin-3-yl]-3-trifluoromethyl-benzene-sulfonamide

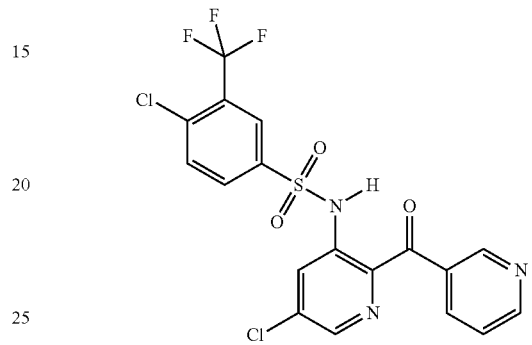

A solution of (3-amino-5-chloro-pyridin-2-yl)-pyridin-3-yl-methanone (26 mg, 0.11 mmol), 4-chloro-3-trifluoromethyl-benzenesulfonyl chloride (28 mg, 0.10 mmol), DMAP (7.3 mg, 0.06 mmol) in anhydrous pyridine (0.5 mL) was heated at 60° C. for 2 days. The reaction mixture was separated by preparative HPLC and pure product fractions were lyophilized to provide pure product as a solid. $^1$H NMR (400 MHz, CDCl$_3$) δ 11.03 (s, 1H), 9.15 (s, 1H), 8.81-8.80 (m, 1H), 8.37 (d, J=2.0 Hz, 1H), 8.29-8.26 (m, 1H), 8.20-8.18 (m, 2H), 7.98 (dd, J=8.4, 2.8 Hz, 1H), 7.63 (d, J=8.4 Hz, 1H), 7.51-7.48 (m, 1H). Mass spectrum m/z: 476.0 (M+H).

Example 24: N-(2-Bromo-5-chloro-pyridin-3-yl)-4-chloro-3-trifluoromethyl-benzenesulfonamide

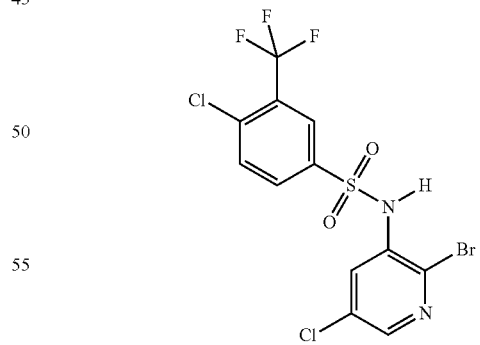

A mixture of 4-chloro-3-trifluoromethyl-benzenesulfonyl chloride (1.5 g, 5.3 mmol) and 2-bromo-5-chloro-pyridin-3-ylamine (500 mg, 2.4 mmol) dissolved in pyridine (20 mL) was heated at 60° C. for 16 h. The solvent was evaporated and the residue suspended in a 1:1 mixture of 2 M NaOH and methanol (20 mL) and heated at 70° C. for 30 min. The methanol was evaporated under reduced pressure and the residue diluted with 15 mL water. The solution was cooled on ice bath and the pH was adjusted to 3 by drop wise addition of concentrated HCl. The solid formed was collected by filtration and the product was purified by flash chromatography on silica gel column to afford the desired product. MS m/z: 450.8 (M+H).

Example 25: N-(2-Bromo-5-chloro-pyridin-3-yl)-4-chloro-N-methoxymethyl-3-trifluoromethyl-benzenesulfonamide

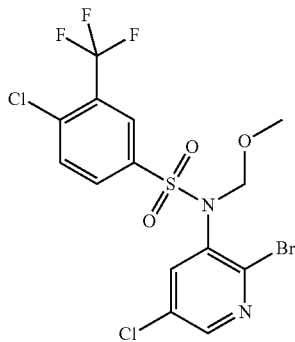 [SMILES: COCN(c1cc(Cl)cnc1Br)S(=O)(=O)c1ccc(Cl)c(C(F)(F)F)c1]

To a stirred solution of N-(2-bromo-5-chloro-pyridin-3-yl)-4-chloro-3-trifluoromethyl-benzenesulfonamide (100 mg, 0.22 mmol) and $K_2CO_3$ (91 mg, 0.66 mmol) in THF (5 mL) was added chloromethyl methyl ether (0.054 mL, 0.66 mmol) at room temperature. The resulting mixture was stirred for 3 h at room temperature then filtered. The filter cake was washed with THF and the combined filtrate was concentrated under reduced pressure. The resulting residue was purified by flash column chromatography to provide desired product. Mass spectrum m/z: 494.9 (M+H).

Example 26: 4-Chloro-N-[5-chloro-2-(hydroxy-pyridin-4-yl-methyl)-pyridin-3-yl]-N-methoxymethyl-3-trifluoromethyl-benzenesulfonamide

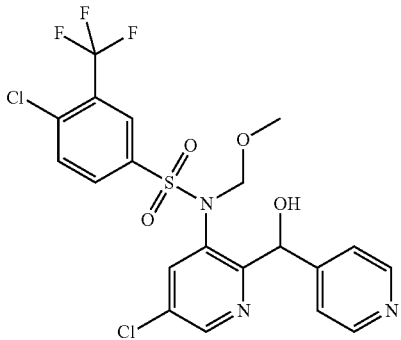 [SMILES: COCN(c1cc(Cl)cnc1C(O)c1ccncc1)S(=O)(=O)c1ccc(Cl)c(C(F)(F)F)c1]

To a stirred solution N-(2-bromo-5-chloro-pyridin-3-yl)-4-chloro-N-methoxymethyl-3-trifluoromethyl-benzenesulfonamide (105 mg, 0.21 mmol) in anhydrous THF (3 mL) was added 2 M isopropylmagnesiumbromide (0.15 mL, 0.3 mmol) at −60° C. The solution was then slowly warmed to room temperature over 1 h and stirred at room temperature for 20 minutes. At this point the reaction mixture turns brownish and additional 0.05 mL of isopropylmagnesiumbromide solution was added and stirring continued for 10 minutes. It was then cooled to −40° C. and pyridine-4-carboxaldehyde (0.05 mL, 0.52 mmol) was added. After 1.5 h the reaction mixture was quenched with brine and extracted with $Et_2O$. The combined extract was dried ($Na_2SO_4$), filtered and concentrated under reduced pressure. The residue was purified by flash column chromatography on silica gel to provide alcohol. Mass spectrum m/z: 522.0 (M+H).

Example 27: 4-Chloro-N-[5-chloro-2-(hydroxy-pyridin-4-yl-methyl)-pyridin-3-yl]-3-trifluoromethyl-benzenesulfonamide

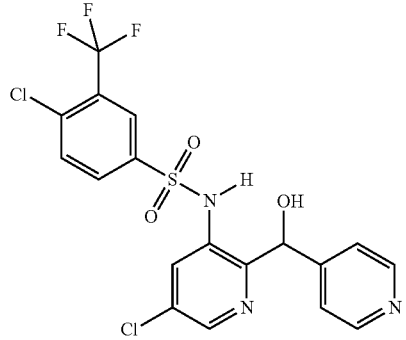 [SMILES: O=S(=O)(Nc1cc(Cl)cnc1C(O)c1ccncc1)c1ccc(Cl)c(C(F)(F)F)c1]

4-Chloro-N-[5-chloro-2-(hydroxy-pyridin-4-yl-methyl)-pyridin-3-yl]-N-methoxymethyl-3-trifluoromethyl-benzenesulfonamide (30 mg, 0.06 mmol) in 50% aqueous of MeOH (10 mL) was treated with 5-10 drops of conc. HCl and heated at 80° C. for 3 days. The resulting mixture was cooled to room temperature, concentrated under reduced pressure and neutralized with aqueous $NaHCO_3$ to pH 7. It was then extracted with EtOAc to provide crude 4-chloro-N-[5-chloro-2-(hydroxy-pyridin-4-yl-methyl)-pyridin-3-yl]-3-trifluoromethyl-benzenesulfonamide which was purified by preparative HPLC. $^1$H NMR (400 MHz, $CDCl_3$) δ 8.34 (br, 2H), 8.29 (d, J=2.0 Hz, 1H), 7.97 (s, 1H), 7.91 (s, 1H), 7.44 (d, J=8.4 Hz, 1H), 7.38 (d, J=8.4 Hz, 1H), 7.11 (d, J=5.6 Hz, 2H), 5.98 (s, 1H); MS m/z: 478.0 (M+H).

Example 28: 4-Chloro-N-[5-chloro-2-(pyridine-4-carbonyl)-pyridin-3-yl]-3-trifluoromethyl-benzenesulfonamide

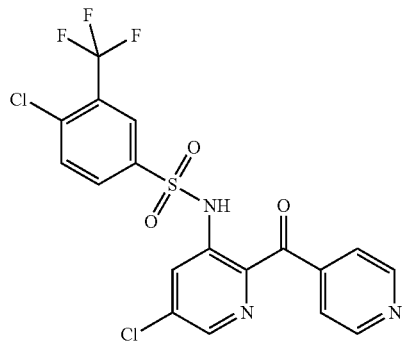 [SMILES: O=C(c1ccncc1)c1ncc(Cl)cc1NS(=O)(=O)c1ccc(Cl)c(C(F)(F)F)c1]

A mixture of 4-chloro-N-[5-chloro-2-(hydroxy-pyridin-4-yl-methyl)-pyridin-3-yl]-3-trifluoromethyl-benzenesulfonamide (15 mg, 0.03 mmol) and PCC (15 mg) was stirred at room temperature for 2 h. It was then treated with small amount of silica gel and filtered. The filtrate was concentrated under reduced pressure to provide the crude ketone. $^1$H NMR (400 MHz, CDCl$_3$) δ 10.90 (br s, 1H), 8.78 (dd, J=4.4, 1.6 Hz, 2H), 8.35 (d, J=2.0 Hz, 1H), 8.19-8.17 (m, 2H), 7.98 (dd, J=8.4, 2.0 Hz, 1H), 7.65-7.61 (m, 3H). MS m/z: 476.0 (M+H).

Example 29: 4-Chloro-N-[5-chloro-2-(6-methyl-pyridine-3-carbonyl)-pyridin-3-yl]-3-trifluoromethyl-benzenesulfonamide

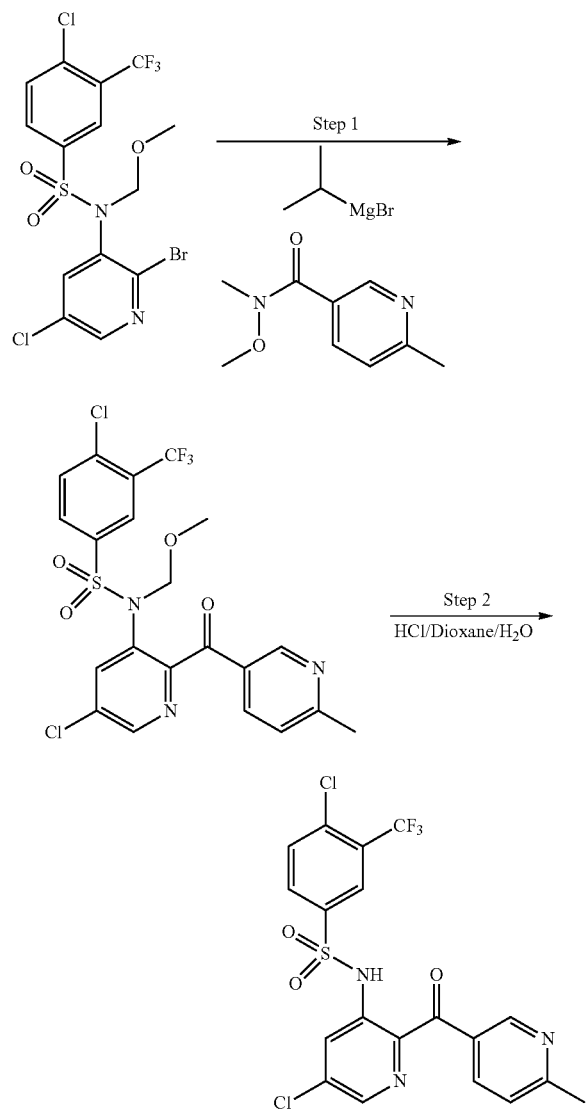

Step 1: To a solution of N-(2-bromo-5-chloro-pyridin-3-yl)-4-chloro-N-methoxymethyl-3-trifluoromethyl-benzenesulfonamide (90 mg, 0.2 mmol) in 2.0 mL of THF under nitrogen atmosphere at −78° C. was added drop-wise 0.3 mL (0.6 mmol) of isopropylmagnesium chloride. The mixture was then stirred for 10 min at −78° C. followed by warming to room temperature and stirred at that temperature for 30 min. The mixture was cooled to 0° C. (ice water) and a solution of N-methoxy-6,N-dimethyl-nicotinamide (72 mg, 0.4 mmol) in 1 mL of THF was added. The mixture was stirred at room temperature for 3 hours, quenched with 1 M HCl and neutralized with 1 M NaOH until pH was 9. The mixture was extracted with ethyl acetate, dried and concentrated. The residue was purified by flash column (silica gel, 50% ethyl acetate in hexane) to afford 36 mg of 4-chloro-N-[5-chloro-2-(6-methyl-pyridine-3-carbonyl)-pyridin-3-yl]-N-methoxymethyl-3-trifluoromethyl-benzenesulfonamideas an off white solid. MS: (M+H)/z=534.0.

Step 2: A mixture of 4-Chloro-N-[5-chloro-2-(6-methyl-pyridine-3-carbonyl)-pyridin-3-yl]-N-methoxymethyl-3-trifluoromethyl-benzenesulfonamide (30 mg) in 3 mL of 4M HCl in dioxane and 1 mL of water was refluxed for 3 hours. After cooling to rt the mixture was diluted with water and sodium bicarbonate was added until pH was 9. The mixture was extracted with ethyl acetate, dried and concentrated. The residue was further purified via flash column (70% ethyl acetate in hexane) to afford 9.1 mg of title compound as an off white solid. $^1$H NMR: (400 MHZ, CDCl3) δ 8.97 (m, 1H), 8.35 (m, 1H), 8.16-8.13 (m, 2H), 8.08-8.05 (m, 1H), 7.93-7.91 (m, 1H), 7.59-7.57 (m, 1H), 7.25-7.23 (1H), 2.63 (s, 3H). MS: (M+H)/z=490.0.

Example 30: 4-Chloro-N-[5-chloro-2-(2-methyl-pyridine-3-carbonyl)-pyridin-3-yl]-3-trifluoromethyl-benzenesulfonamide

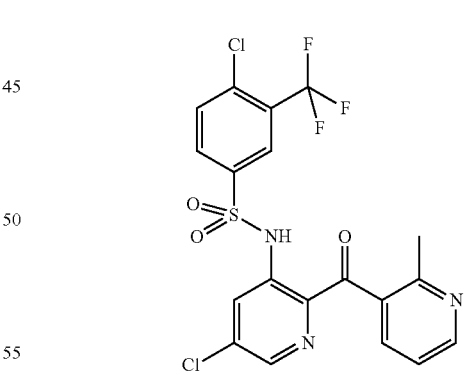

The title compound was prepared by procedure analogous to that described in Example 29 using N-(2-bromo-5-chloro-pyridin-3-yl)-4-chloro-N-methoxymethyl-3-trifluoromethyl-benzenesulfonamide and N-methoxy-2,N-dimethyl-nicotinamide. $^1$H NMR: (400 MHZ, CDCl3) δ 8.61 (m, 1H), 8.26 (m, 1H), 8.20 (m, 1H), 8.17 (m, 1H), 8.04-8.01 (m, 1H), 7.67 (d, 1H), 7.50 (m, 1H), 7.18 (m, 1H), 2.41 (s, 3H). MS: (M+H)/z=490.0.

Example 31: 4-Chloro-N-[5-chloro-2-(2,4-dimethyl-pyridine-3-carbonyl)-pyridin-3-yl]-3-trifluoromethyl-benzenesulfonamide

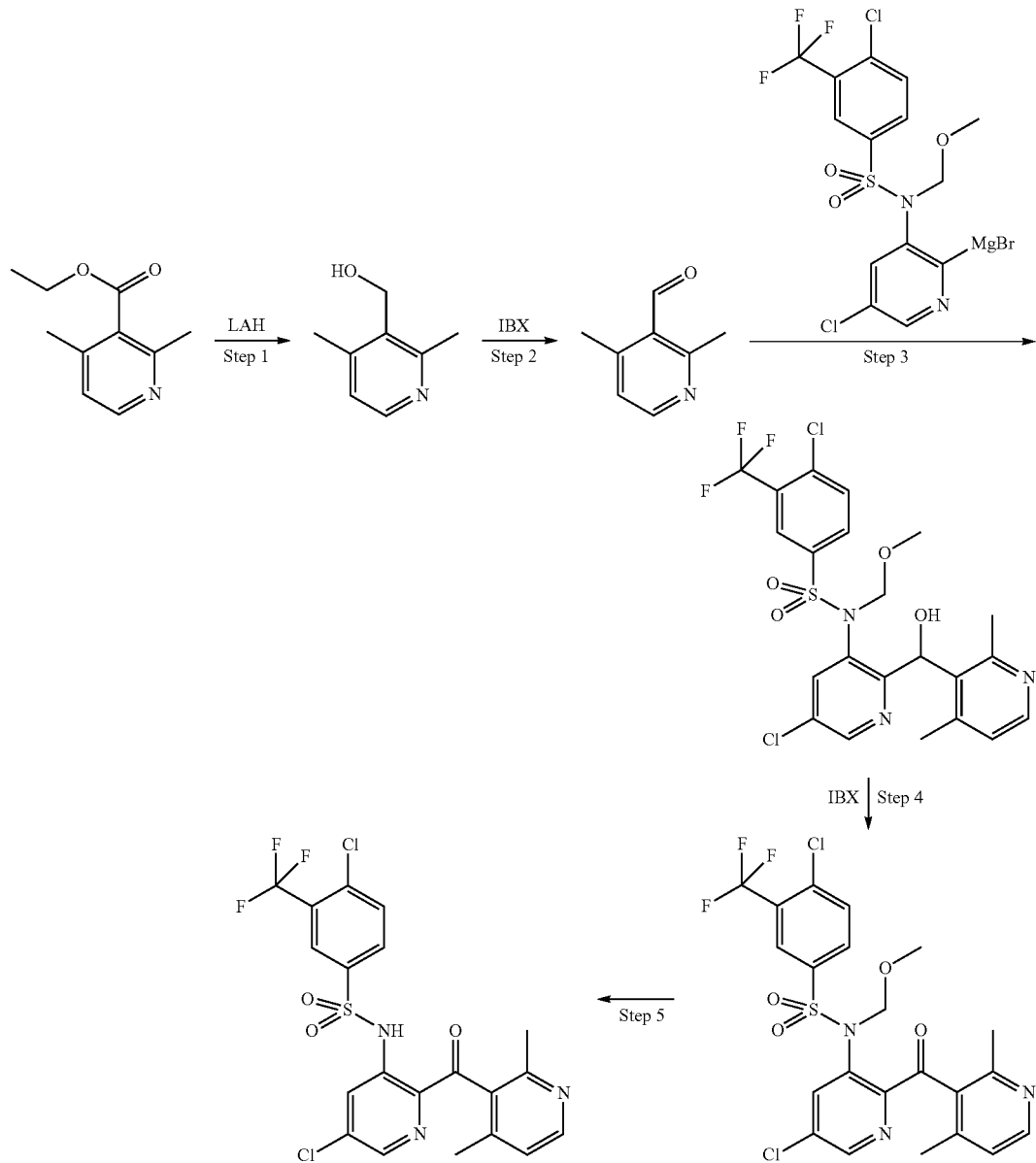

Step 1: A solution of lithium aluminum hydride in THF (1.0 M, 40 mL, 40 mmol) placed in a 100-mL round bottom flask equipped with a magnetic stirring bar was cooled in an ice bath and cautiously treated with a solution of 2,4-dimethyl-nicotinic acid ethyl ester (5.4 g, 30 mmol) in anhydrous THF (10 mL) over 5 min period. After the addition was complete the cold bath was removed and the mixture was allowed to stir at room temperature for 2 h. The reaction mixture was then cooled in an ice bath and the excess LAH was quenched by drop wise addition of water until gas evolution stopped. The reaction mixture was then basified with 2M NaOH to pH 9-10. Ether (100 mL) was added the mixture was washed with 1 M NaOH, water and brine. The organic layer was dried over MgSO₄ and the solvent was evaporated to yield (2,4-dimethyl-pyridin-3-yl)-methanol as a white solid. MS: (M+H)/z=138.

Step 2: A magnetically stirred mixture of (2,4-dimethyl-pyridin-3-yl)-methanol (0.342 g, 2.5 mmol) and IBX (1.40 g, 5 mmol) in acetonitrile (5 mL) placed in a round bottom flask was heated at 80° C. in an oil bath for 1 h. The mixture was cooled to room temperature and filtered. The solid was washed with acetonitrile. The filtrate was concentrated and applied to a short silica gel column and chromatographed using hexane/ethyl acetate solvent mixture (30-60% ethyl acetate). Product containing fractions were combined and the solvent was evaporated to afford 0.283 g of 2,4-dimethyl-pyridine-3-carbaldehyde as a white solid. MS: (M+H)/z=136.

Step 3: N-(2-Bromo-5-chloro-pyridin-3-yl)-4-chloro-N-methoxymethyl-3-trifluoromethyl-benzenesulfonamide (0.494 g, 1 mmol) placed in a 10 mL round bottom flask under nitrogen atmosphere was dissolved in anhydrous THF (5 mL). The solution was cooled to −20° C. The magentically stirring solution was treated with solution of 2.0 M isopropylmagnesium bromide in THF (1.05 mL, 2.1 mmol) drop wise and after the addition was complete the reaction mixture was allowed to warm to 0° C. and maintained at this temperature for 1 h. The resulting deep purple solution was cooled to −20° C. and treated with a solution of 2,4-dimethyl-pyridine-3-carbaldehyde (0.28 g, 2.1 mmol) in THF (2 mL). The mixture was allowed to warm to room temperature and stirred at room temperature over night. After diluting with saturated ammonium chloride solution (10 mL) the product was extracted with ethyl acetate (3×25 mL). The combined organic extract was concentrated and product purified by flash chromatography on silica gel column (10-30% ethyl acetate in hexanes). Product containing fractions were combined and the solvent evaporated to afford 0.33 g of 4-chloro-N-{5-chloro-2-[(2,4-dimethyl-pyridin-3-yl)-hydroxy-methyl]-pyridin-3-yl}-N-methoxymethyl-3-trifluoromethyl-benzenesulfonamide as an off white solid. MS: (M+H)/z=550.

Step 4: The product obtained from Step 3 above was oxidized with IBX according to the procedure described in Step 2 and the product was purified by flash chromatography on silica gel column (30-50% ethyl acetate in hexanes) to afford 4-chloro-N-[5-chloro-2-(2,4-dimethyl-pyridine-3-carbonyl)-pyridin-3-yl]-N-methoxymethyl-3-trifluoromethyl-benzenesulfonamide as a light yellow solid. MS: (M+H)/z=548.

Step 5: The product from Step 4 above (60 mg, 0.1 mmol) was dissolved in 4 M HCl in dioxane (4 mL). Water (1 mL) was added and the mixture was refluxed for 2 h. The solvent was evaporated and the residue was dissolved 20% aqueous acetonitrile and lyophylization yielded 4-chloro-N-[5-chloro-2-(2,4-dimethyl-pyridine-3-carbonyl)-pyridin-3-yl]-3-trifluoromethyl-benzenesulfonamide as the hydrochloride salt. $^1$H NMR: (400 MHZ, DMSO-$d_6$) δ 8.55 (d, J=6 Hz, 1H), 8.45 (d, J=2 Hz, 1H), 8.32 (d, J=2 Hz, 1H), 8.18-8.15 (m, 1H), 8.05 (d, J=2 Hz, 1H), 7.95 (d, J=8.4 Hz, 1H), 7.53 (m, 1H), 2.20 (s, 3H), 2.03 (s, 3H). MS: (M+H)/z=504.

Example 32: 2-Methyl-pyridine-4-carbaldehyde

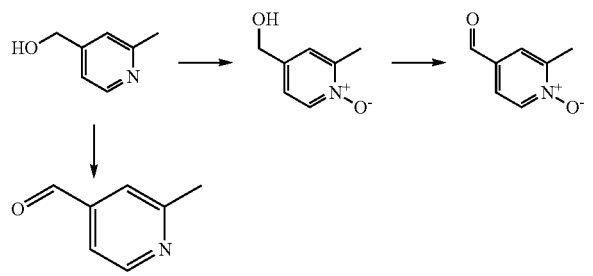

(2-Methyl-pyridin-4-yl)-methanol (1.3 g, 10.6 mmol) (prepared according to the literature procedure, see Ragan, J. A. et al. *Synthesis*, 2002, 4, 483-486) and MnO$_2$ (5.0 g, 57.5 mmol) in CHCl$_3$ (50 mL) was refluxed for 18 h. The reaction mixture was cooled to room temperature and filtered. The filter cake was washed with CHCl$_3$ (2×100 mL). The combined filtrates were concentrated under reduced pressure and the resulting residue was purified by flash column chromatography on silica gel (EtOAc/Hexanes, 3:7) to provide desired aldehyde. Mass spectrum m/z: 122.1 (M+H).

Example 33:
(2-Methyl-1-oxy-pyridin-4-yl)-methanol

A mixture of (2-methyl-pyridin-4-yl)-methanol (1.1 g, 8.9 mmol) and m-CPBA (2.5 g, 10.7 mmol, 75% pure) in CH$_2$Cl$_2$ (50 mL) was stirred at room temperature for 18 h. The reaction mixture was concentrated to 10 mL under reduced pressure and the resulting residue was purified by flash column chromatography on silica gel (MeOH/CH$_2$Cl$_2$, 1:99, then 1:19, then, 2:23) to provide desired the title compound. Mass spectrum m/z: 140.1 (M+H).

Example 34:
2-Methyl-1-oxy-pyridine-4-carbaldehyde

A mixture of alcohol (1.3 g, 5.04 mmol) and MnO$_2$ (3.0 g, 34.5 mmol) in CHCl$_3$ (50 mL) was refluxed for 18 h. The reaction mixture was cooled to room temperature and filtered. The filter cake was washed with CHCl$_3$ (2×100 mL). The combined filtrates were concentrated under reduced pressure to provide desired aldehyde. Mass spectrum m/z: 138.0 (M+H).

Example 35: 4-Chloro-N-{5-chloro-2-[hydroxy-(2-methyl-1-oxy-pyridin-4-yl)-methyl]-pyridin-3-yl}-N-methoxymethyl-3-trifluoromethyl-benzenesulfonamide

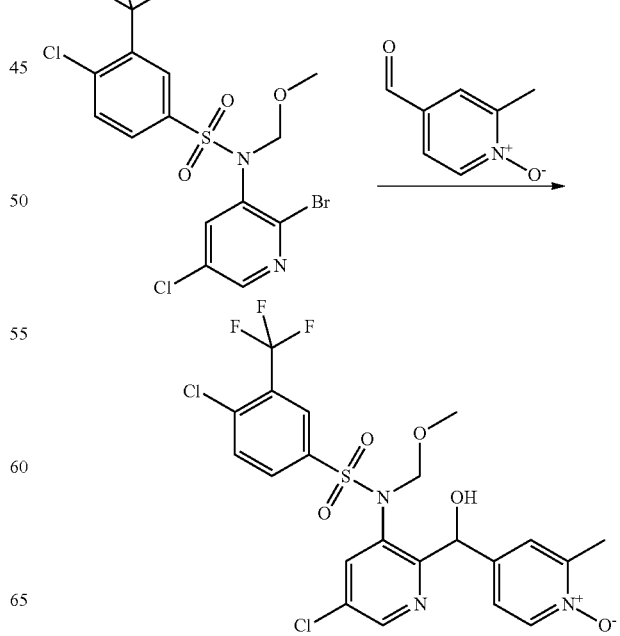

To a stirred solution of N-(2-bromo-5-chloro-pyridin-3-yl)-4-chloro-N-methoxymethyl-3-trifluoromethyl-benzenesulfonamide (494 mg, 1.0 mmol) in anhydrous THF (10 mL) was added 2 M isopropylmagnesiumchloride in THF (1.20 mL, 2.4 mmol) at −40° C. After 5 minutes dry ice-acetone bath was replaced with a ice water bath and stirred at 0° C. for 1 h. Solid 2-methyl-1-oxy-pyridine-4-carbaldehyde (382 mg, 2.7 mmol) was added in one portion and the progress of the reaction was followed by LCMS. The reaction mixture was warmed to room temperature and stirred for 6 h and stirred overnight. It was then quenched with saturated aqueous NH$_4$Cl (2 mL), and extracted with EtOAc. The combined extracts were dried (Na$_2$SO$_4$), filtered and concentrated under reduced pressure to provide the desired product which was utilized in the following step without further purification. MS m/z: 552.0 (M+H).

Example 36: 4-Chloro-N-[5-chloro-2-(2-methyl-1-oxy-pyridine-4-carbonyl)-pyridin-3-yl]-N-methoxymethyl-3-trifluoromethyl-benzenesulfonamide

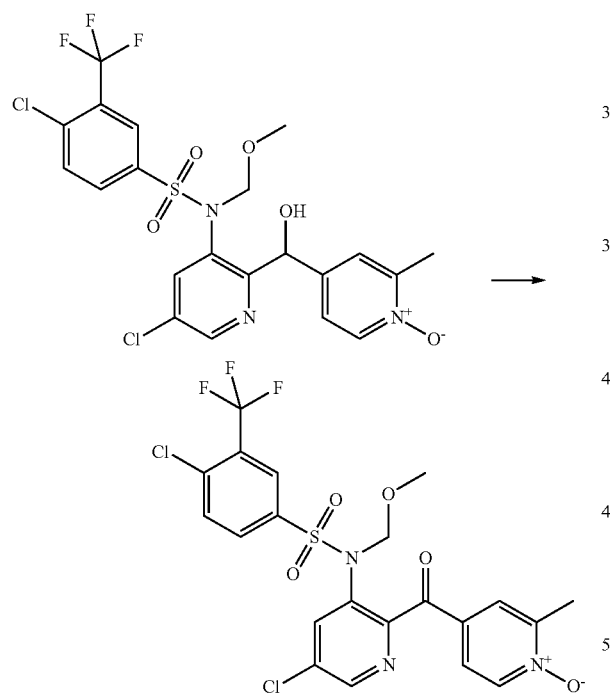

To a stirred solution of the alcohol from Example 35 (500 mg) in anhydrous CHCl$_3$ (50 mL) was added MnO$_2$ (2.00 g, 23 mmol). The resulting mixture was heated at reflux for 2 days. The reaction mixture was cooled to room temperature and filtered through a filter paper and the filter cake was washed with EtOAc. The filtrate was partitioned between EtOAc and brine. The organic portion was separated and aqueous part was extracted with EtOAc. The combined extracts were dried (Na$_2$SO$_4$), filtered and concentrated under reduced pressure. The residue was purified by flash column chromatography on silica gel to provide the desired ketone (EtOAc/Hexanes, 2:3 then MeOH/CH$_2$Cl$_2$, 3:97). Mass spectrum m/z: 550.0 (M+H).

Example 37: 4-Chloro-N-[5-chloro-2-(2-methyl-1-oxy-pyridine-4-carbonyl)-pyridin-3-yl]-3-trifluoromethyl-benzenesulfonamide

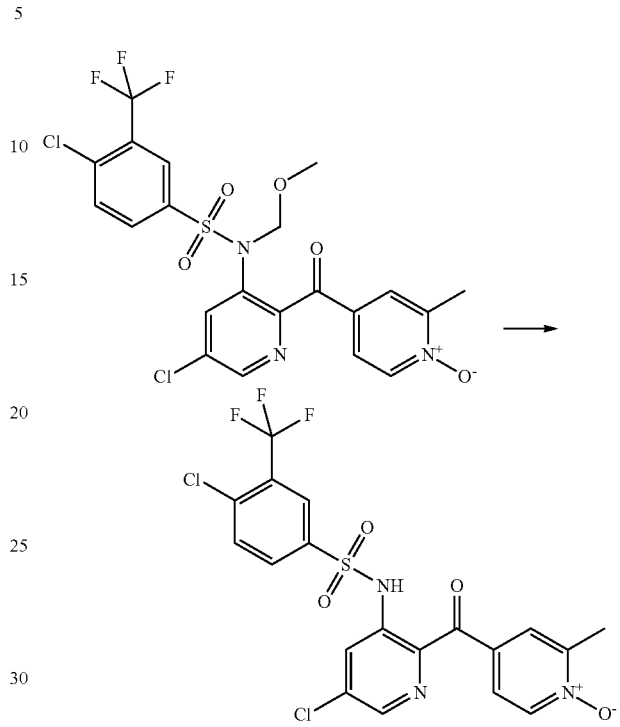

A mixture of mom-protected sulfonamide (150 mg, 0.27 mmol) in 4 M HCl in dioxane (10 mL), and water (4 mL) was heated at 100° C. for 3 h. The reaction mixture was concentrated to dryness under reduced pressure and it was treated with aqueous NaHCO$_3$ to adjust pH to 5-6 and extracted with EtOAc. The combined extracts were dried (Na$_2$SO$_4$), filtered and concentrated under reduced pressure. The residue was purified by flash column chromatography on silica gel (MeOH: CH$_2$Cl$_2$: 1:99, then 2:98) to provide the desired product. $^1$H NMR (400 MHz, CDCl$_3$) δ 10.86 (s, 1H), 8.39 (s, 1H), 8.24 (d, J=6.8 Hz, 1H), 8.18-8.14 (m, 2H), 7.95 (d, J=9.2 Hz, 1H), 7.90 (s, 1H), 7.82 (d, J=6.8 Hz, 1H), 7.61 (d, J=8.8 Hz, 1H), 2.54 (s, 3H); MS m/z: 506.0 (M+H).

Example 38: 4-Chloro-N-{5-chloro-2-[hydroxy-(2-methyl-pyridin-4-yl)-methyl]-pyridin-3-yl}-N-methoxymethyl-3-trifluoromethyl Benzenesulfonamide

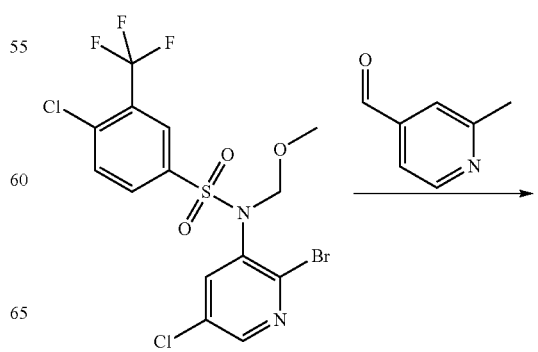

-continued

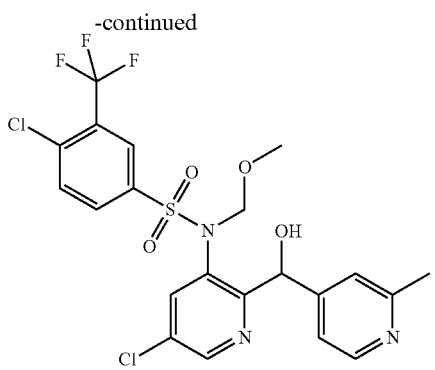

To a stirred solution of N-(2-bromo-5-chloro-pyridin-3-yl)-4-chloro-N-methoxymethyl-3-trifluoromethyl-benzenesulfonamide (494 mg, 1.0 mmol) in anhydrous THF (10 mL) was added 2 M isopropylmagnesiumchloride in THF (1.20 mL, 2.4 mmol) at −40° C. After 5 minutes dry ice-acetone bath was replaced with a ice water bath and stirred at 0° C. for 1 h. Solid 2-methyl-pyridine-4-carbaldehyde (327 mg, 2.7 mmol) was added in one portion and the progress of the reaction was followed by LCMS. The reaction mixture was warmed to room temperature and stirred overnight. It was then quenched with saturated aqueous NH$_4$Cl (2 mL), and extracted with EtOAc. The combined extracts were dried (Na$_2$SO$_4$), filtered and concentrated under reduced pressure to provide the desired product which was utilized in the following step without further purification. MS m/z: 536.0 (M+H).

Example 39: 4-Chloro-N-[5-chloro-2-(2-methyl-pyridine-4-carbonyl)-pyridin-3-yl]-N-methoxymethyl-3-trifluoromethyl-benzenesulfonamide

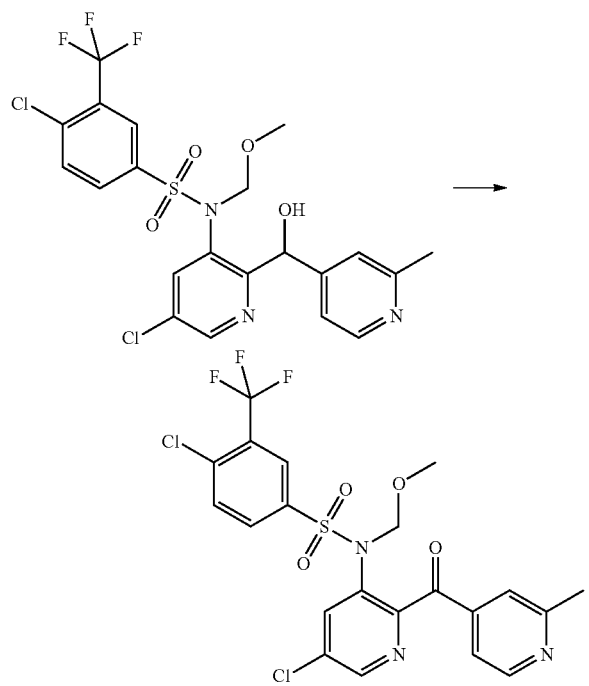

To a stirred solution of 4-chloro-N-[5-chloro-2-(2-methyl-pyridine-4-carbonyl)-pyridin-3-yl]-N-methoxymethyl-3-trifluoromethyl-benzenesulfonamide (~500 mg) in anhydrous CHCl$_3$ (50 mL) was added MnO$_2$ (2.00 g, 23 mmol). The resulting mixture was heated at reflux for 4 days. The reaction mixture was cooled to room temperature and filtered through a filter paper and the filter cake was washed with EtOAc. The filtrate was partitioned between EtOAc and brine. The organic portion was separated and aqueous part was extracted with EtOAc. The combined extracts were dried (Na$_2$SO$_4$), filtered and concentrated under reduced pressure. The residue was purified by flash column chromatography on silica gel to provide the desired ketone (EtOAc/Hexanes, 2:3 then 4:1). MS m/z: 534.0 (M+H).

Example 40: 4-Chloro-N-[5-chloro-2-(2-methyl-pyridine-4-carbonyl)-pyridin-3-yl]-3-trifluoromethyl-benzenesulfonamide

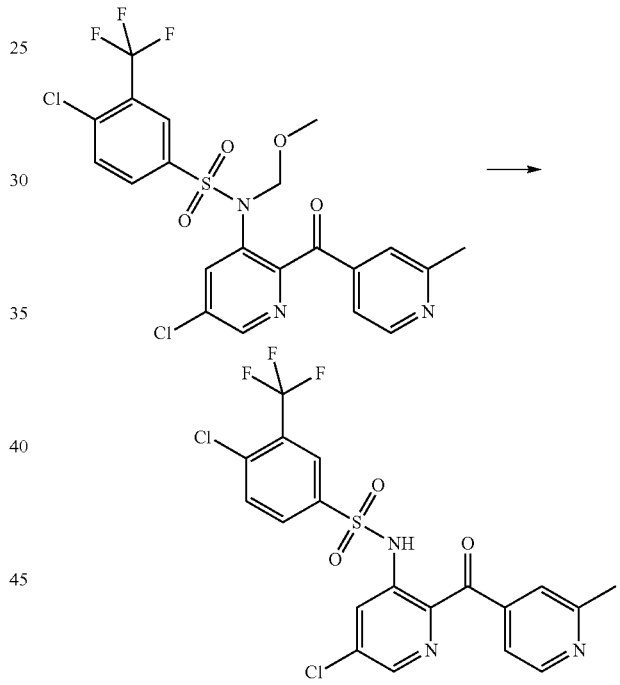

A mixture of 4-Chloro-N-[5-chloro-2-(2-methyl-pyridine-4-carbonyl)-pyridin-3-yl]-N-methoxymethyl-3-trifluoromethyl-benzenesulfonamide (150 mg, 0.27 mmol) from Example 39 dissolved in 4 M HCl in dioxane (10 mL), and water (4 mL) was heated at 100° C. for 3 h. The reaction mixture was concentrated to dryness under reduced pressure and it was treated with aqueous NaHCO$_3$ to adjust pH to 5-6 and extracted with EtOAc. The combined extracts were dried (Na$_2$SO$_4$), filtered and concentrated under reduced pressure. The residue was purified by flash column chromatography on silica gel (MeOH: CH$_2$Cl$_2$: 1:99, then 2:98) to provide the desired product. $^1$H NMR (400 MHz, CDCl$_3$) δ 10.9 (s, 1H), 8.64 (d, J=5.2 Hz, 1H), 8.36 (s, 1H), 8.18-8.16 (m, 2H), 7.96 (d, J=8.4 Hz, 1H), 7.62 (d, J=8.4 Hz, 1H), 7.41-7.38 (m, 2H), 2.64 (s, 3H); MS m/z: 490.0 (M+H).

Example 41: 4-Chloro-N-[5-chloro-2-(4-chloro-benzoyl)-pyridin-3-yl]-3-trifluoromethyl-benzenesulfonamide

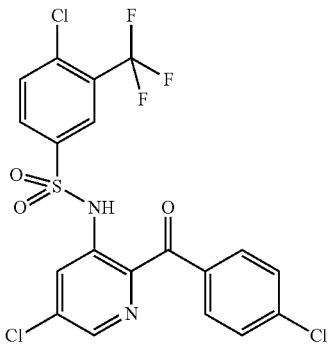 [SMILES: O=C(c1ccc(Cl)cc1)c1ncc(Cl)cc1NS(=O)(=O)c1ccc(Cl)c(C(F)(F)F)c1]

The title compound was prepared by procedure analogous to that described in Example 29 using N-(2-bromo-5-chloro-pyridin-3-yl)-4-chloro-N-methoxymethyl-3-trifluoromethyl-benzenesulfonamide and 4-chloro-N-methoxy-N-methyl-benzamide $^1$H NMR (400 MHz, CDCl$_3$) δ☐10.61 (s, 1H), 8.37 (m, 1H), 8.16 (m, 1H), 8.09 (m, 1H), 7.84 (m, 1H), 7.77-7.75 (m, 2H), 7.53 (m, 1H), 7.42-7.40 (m, 2H), 7.23 (m, 1H) MS: (M+H)/z=509.0.

Example 42: 4-Chloro-N-[3-(morpholine-4-carbonyl)-pyrazin-2-yl]-3-trifluoromethyl-benzenesulfonamide

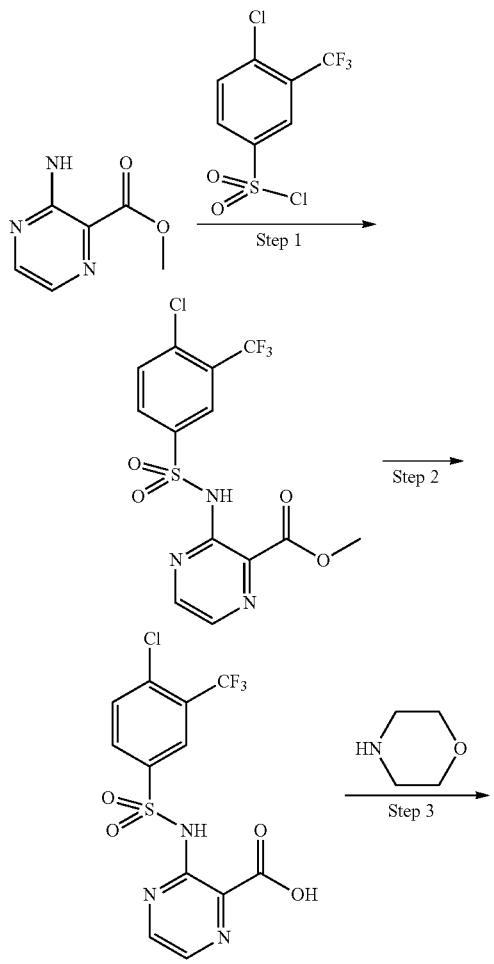

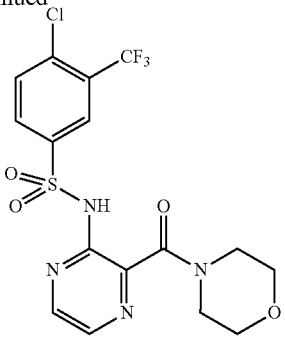

Step 1: To a solution of 3-amino-pyrazine-2-carboxylic acid methyl ester (153 mg, 1.0 mmol) in 2.0 mL of pyridine was added 4-chloro-3-trifluoromethyl-benzenesulfonyl chloride (279 mg, 1.0 mmol) in 1.0 mL of pyridine. The mixture was stirred at room temperature for 16 h, diluted with 15 mL of ethyl acetate, washed twice with 1M HCl (15 mL), dried on MgSO$_4$ and the solvent was evaporated. The product was purified on silica gel column (15% ethyl acetate in hexane) to afford 185 mg of 3-(4-chloro-3-trifluoromethyl-benzenesulfonylamino)-pyrazine-2-carboxylic acid methyl ester as white powder. MS: (M+H)/z=396.0.

Step 2: A mixture of 3-(4-chloro-3-trifluoromethyl-benzenesulfonylamino)-pyrazine-2-carboxylic acid methyl ester (60 mg), 3 mL of 2N NaOH and 3 mL of methanol was stirred at room temperature overnight. To the reaction mixture was added slowly 2M HCl until white solid precipitated. Filtration followed by vacuum drying afforded 3-(4-chloro-3-trifluoromethyl-benzenesulfonylamino)-pyrazine-2-carboxylic acid as a white solid. MS: (M+H)/z=382.0.

Step 3: To a mixture of 20 mg of 3-(4-chloro-3-trifluoromethyl-benzenesulfonylamino)-pyrazine-2-carboxylic acid, 10 mg of morpholine and 20 µl of DIEA in 1.5 mL of CH$_2$Cl$_2$ was added 32 µL of 1-propanephosphonic acid cyclic anhydride (50% in ethyl acetate). After 3-4 hours the reaction mixture was directly purified via flash column (65% ethyl acetate in hexane) to afford 14 mg of 4-chloro-N-[3-(morpholine-4-carbonyl)-pyrazin-2-yl]-3-trifluoromethyl-benzenesulfonamide as a white powder. MS: (M+H)/z=451.0.

Example 43: 3-(3,4-Dichloro-benzenesulfonylamino)-pyrazine-2-carboxylic Acid

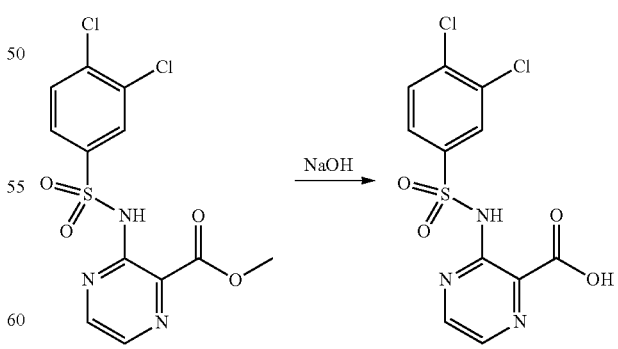

This title compound was prepared following procedure described in example 42 step 2 wherein 3-(3,4-dichloro-benzenesulfonylamino)-pyrazine-2-carboxylic acid methyl ester was treated with 2M NaOH and methanol. Usual work up afforded the above title product as a white powder. MS: (M+Na)/z=382.0.

Example 44: 3,4-Dichloro-N-[3-(morpholine-4-carbonyl)-pyrazin-2-yl]benzenesulfonamide

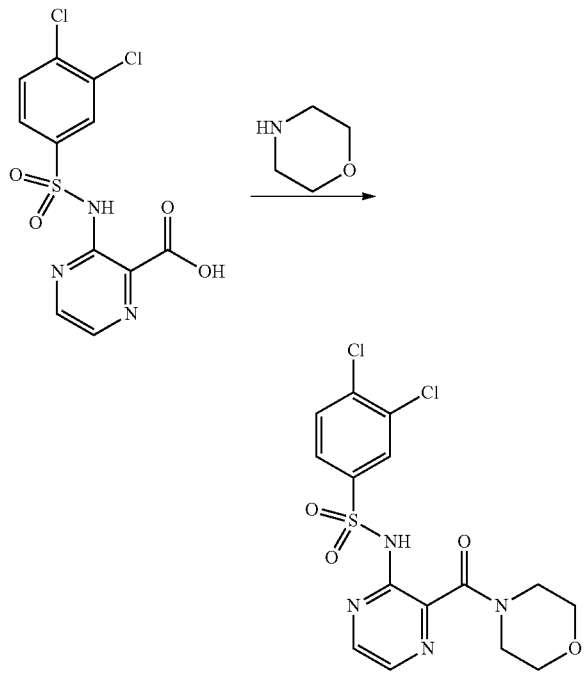

This title compound was prepared following procedure described in example 42 step 3 wherein 3-(3,4-dichloro-benzenesulfonylamino)-pyrazine-2-carboxylic acid was coupled with morpholine. The crude was purified by flash column (65% ethyl acetate in hexane) to afford the above title product as a white powder. MS: (M+Na)/z=451.0.

Example 45: N-(2-Bromo-5-chloro-pyridin-3-yl)-4-tert-butyl-N-methoxymethyl-benzenesulfonamide

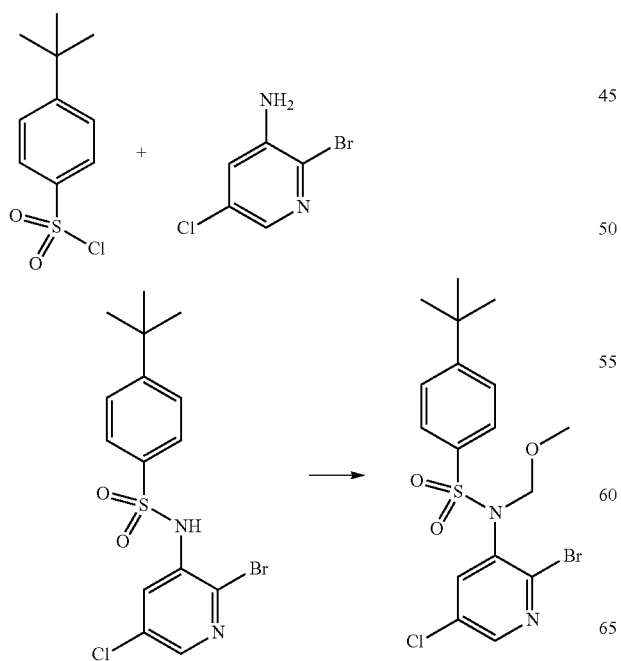

A 200 mL round-bottom flask was charged with 2-bromo-5-chloro-pyridin-3-ylamine (10.4 g, 50.0 mmol), 4-tert-butyl-benzenesulfonyl chloride (20.0 g, 85.0 mmol), and pyridine (38 mL). The resultant solution was heated to 70° C. and stirred overnight. The following day, the pyridine was removed in vacuo and THF (30 mL) and 4.0 N NaOH (100 mL) were added and the reaction was stirred at 60° C. overnight. The organics were subsequently removed in vacuo and the residues were diluted with water (400 mL). The small quantity of insoluble solid was removed by filtration and the pH was adjusted to 6-7 with concentrated HCl. The resultant aqueous solution was extracted with EtOAc, washed with brine, dried over $MgSO_4$, and concentrated under reduced pressure to afford the diarylsulfonamide (13.4 g) in 66% yield. To a solution of the crude sulfonamide (12.0 g, 35.0 mmol) and $K_2CO_3$ (24.0 g, 170 mmol) in anhydrous THF (80 mL) was added chloromethyl methyl ether (4.0 mL, 52.7 mmol). The resultant heterogeneous solution was stirred for 60 min at ambient temperature and the solids were subsequently removed via filtration. The filtrate was then removed in vacuo and the residue was dissolved in EtOAc. The organics were washed with saturated $Na_2CO_3$, dried over $MgSO_4$, and evaporated in vacuo to generate a brownish oil. The oil was triturated with hexanes and the resultant solid filtered to produce the desired product as a light yellowish solid (11.5 g, 86% yield).

Example 46: 4-tert-Butyl-N-[5-chloro-2-(2-methyl-pyridin-3-yloxy)-pyridin-3-yl]-benzenesulfonamide

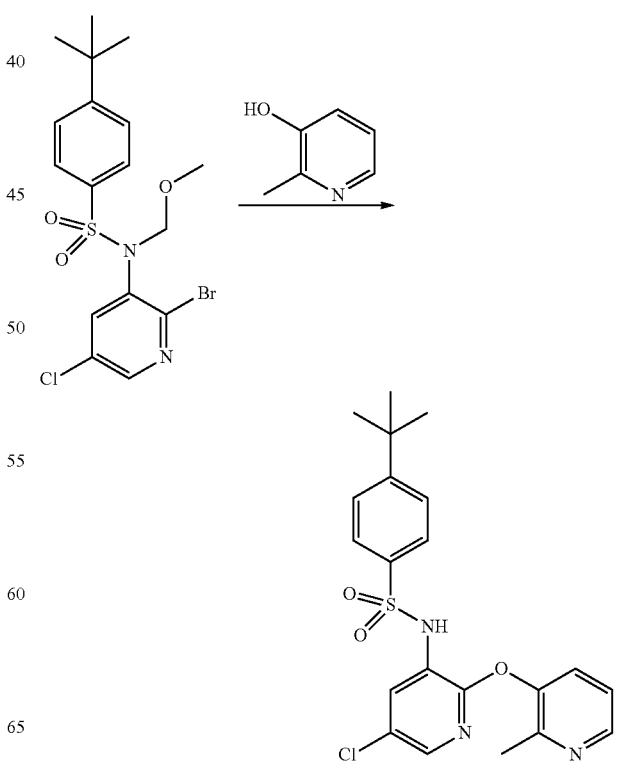

A 5 mL pear-shaped flask was charged with N-(2-bromo-5-chloro-pyridin-3-yl)-4-tert-butyl-N-methoxymethyl-benzenesulfonamide (134 mg, 0.30 mmol), 4-methyl-pyridin-3-ol (100 mg, 0.90 mmol), potassium carbonate (250 mg, 18.0 mmol), and DMA (0.9 mL). The heterogeneous mixture was heated to 150° C. and stirred overnight. The crude reaction mixture was subsequently purified via reverse phase HPLC (Column: Varian Dynamax 250×21.4 mm Microsorb100-8 C18, 0.1% TFA/H$_2$O (Eluent A): 0.1% TFA/MeCN (Eluent B)): $^1$H NMR (400 MHz, CDCl$_3$) δ 8.06 (d, 1H), 7.95 (d, 1H), 7.76 (d, 2H), 7.73 (d, 1H), 7.50 (d, 2H), 7.12 (d, 1H), 7.04 (dd, 1H), 2.55 (s, 3H), 1.34 (s, 9H); MS (ES) M+H expect 432.1, found 432.5.

Example 47: 4-tert-Butyl-N-(5-chloro-2-phenoxy-pyridin-3-yl)-benzenesulfonamide

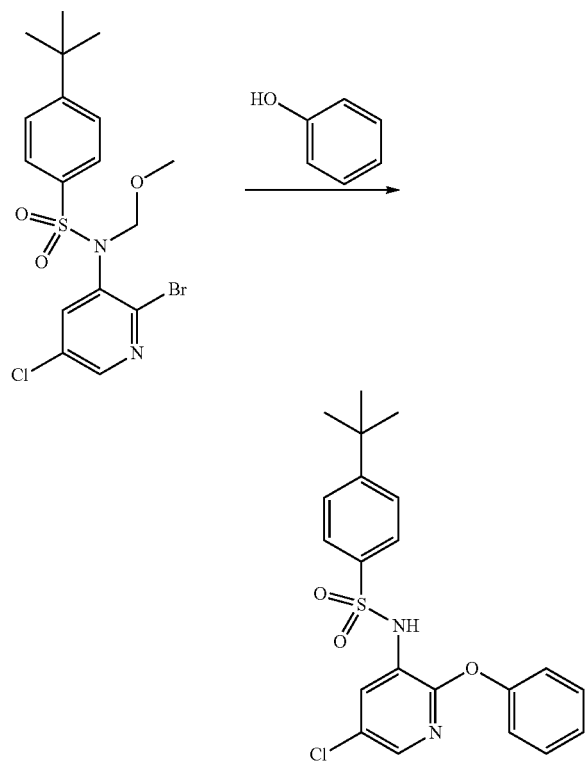

A 5 mL pear-shaped flask was charged with N-(2-bromo-5-chloro-pyridin-3-yl)-4-tert-butyl-N-methoxymethyl-benzenesulfonamide (134 mg, 0.30 mmol), phenol (85 mg, 0.90 mmol), potassium carbonate (250 mg, 18.0 mmol), and DMA (0.9 mL). The heterogeneous solution was heated to 150° C. and stirred overnight. The crude reaction mixture was subsequently purified via reverse phase HPLC (Column: Varian Dynamax 250×21.4 mm Microsorb100-8 C18, 0.1% TFA/H$_2$O (Eluent A): 0.1% TFA/MeCN (Eluent B)): $^1$H NMR (400 MHz, CDCl$_3$) δ 7.95 (d, 1H), 7.75 (d, 1H), 7.72 (d, 2H), 7.48 (d, 2H), 7.28-7.34 (m, 2H), 7.17-7.21 (m, 1H), 7.05 (bs, 1H), 6.71-6.76 (m, 2H), 1.34 (s, 9H); MS (ES) M+H expect 417.1, found 417.4.

Example 48: 4-tert-Butyl-N-[5-chloro-2-(2-fluoro-benzoyl)-pyridin-3-yl]-benzenesulfonamide

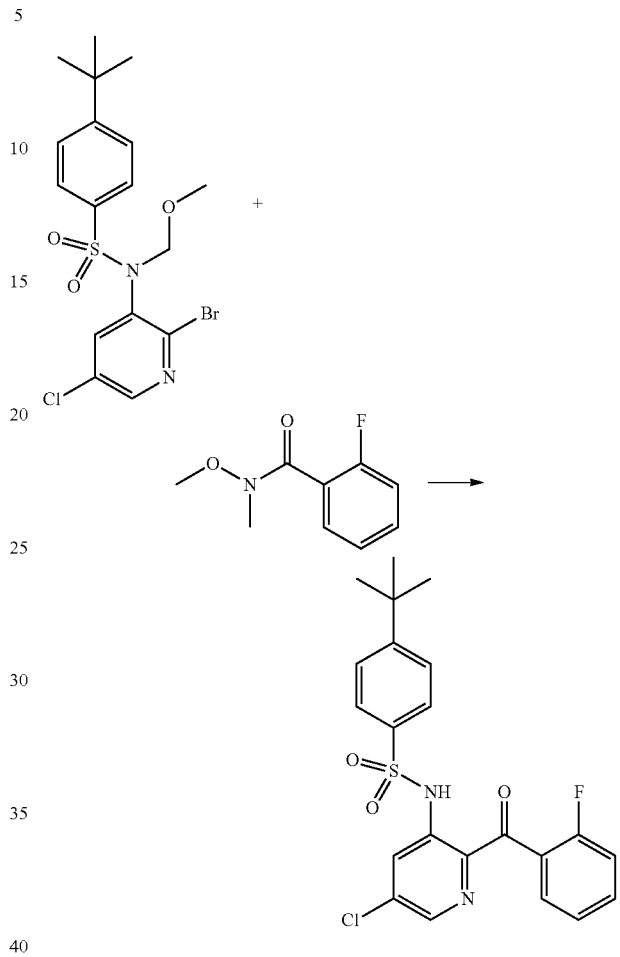

N-(2-Bromo-5-chloro-pyridin-3-yl)-4-tert-butyl-N-methoxymethyl-benzenesulfonamide (140 mg, 300 mmol) was placed in a dry 2-neck 10 mL round-bottom flask. The flask was evacuated and purged with nitrogen, followed by the addition of THF (1 mL). The homogeneous mixture was lowered to −5° C. and iPrMgCl (0.33 mL, 2.0 M) was added dropwise. Upon completion of the addition, the reaction was stirred 90 minutes, followed by the slow addition of 2-fluoro-N-methoxy-N-methyl-benzamide (140 mg, 750 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl (in dioxane) (1 mL, 4.0 mmol) and H$_2$O (0.33 mL), and then stirred at 80° C. for two hours. The resultant solution was diluted with EtOAc, washed with water, saturated sodium bicarbonate, and brine; dried with MgSO$_4$, and evaporated employing reduced pressure. The crude sulfonamide was finally purified via preparatory TLC (20% EtOAc/hexanes) and recrystallization from MeCN/H$_2$O to afford 98 mg of the title compound: $^1$H NMR (400 MHz, CDCl$_3$) δ 10.6 (s, 1H), 8.3 (d, 1H), 8.2 (d, 1H), 7.74 (d, 2H), 7.6 (d, 1H), 7.5 (d, 1H), 7.43 (d, 2H), 7.42-7.37 (m, 2H), 1.26 (s, 9H); MS (ES) M+H expect 447.1, found 447.5.

Example 49: 4-tert-Butyl-N-[5-chloro-2-(4-fluoro-benzoyl)-pyridin-3-yl]-benzenesulfonamide

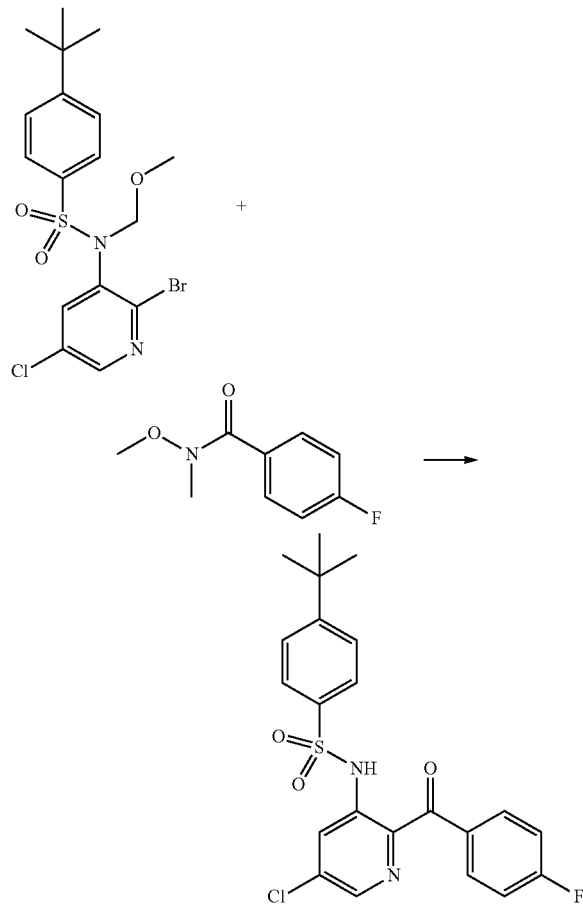

N-(2-Bromo-5-chloro-pyridin-3-yl)-4-tert-butyl-N-methoxymethyl-benzenesulfonamide (140 mg, 300 mmol) was placed in a dry 2-neck 10 mL round-bottom flask. The flask was evacuated and purged with nitrogen, followed by the addition of THF (1 mL). The homogeneous mixture was lowered to −5° C. and iPrMgCl (0.33 mL, 2.0 M) was added dropwise. Upon completion of the addition, the reaction was stirred 90 minutes, followed by the slow addition of 4-fluoro-N-methoxy-N-methyl-benzamide (137 mg, 750 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (1 mL, 4.0 mmol) and H$_2$O (0.33 mL), and then stirred at 80° C. for two hours. The resultant solution was diluted with EtOAc, washed with water, saturated sodium bicarbonate, and brine; dried with MgSO$_4$, and evaporated employing reduced pressure. The crude residue was subsequently purified via reverse phase HPLC (Column: Varian Dynamax 250×21.4 mm Microsorb100-8 C18, 0.1% TFA/H$_2$O (Eluent A): 0.1% TFA/MeCN (Eluent B)): $^1$H NMR (400 MHz, CDCl$_3$) δ 10.63 (bs, 1H), 8.29 (d, 1H), 8.20 (d, 1H), 7.85-7.91 (m, 2H), 7.74 (d, 2H), 7.42 (d, 2H), 7.09 (t, 2H), 1.25 (s, 9H); MS (ES) M+Na expect 469.1, found 469.4.

Example 50: 4-tert-Butyl-N-[5-chloro-2-(3-methoxy-benzoyl)-pyridin-3-yl]-benzenesulfonamide

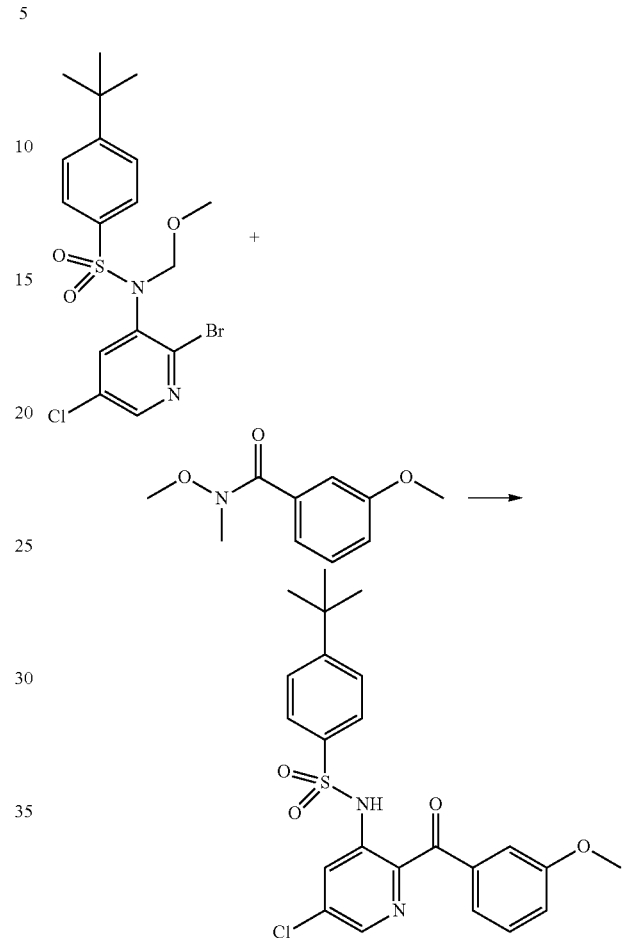

N-(2-Bromo-5-chloro-pyridin-3-yl)-4-tert-butyl-N-methoxymethyl-benzenesulfonamide (140 mg, 300 mmol) was placed in a dry 2-neck 10 mL round-bottom flask. The flask was evacuated and purged with nitrogen, followed by the addition of THF (1 mL). The homogeneous mixture was lowered to −5° C. and iPrMgCl (0.33 mL, 2.0 M) was added dropwise. Upon completion of the addition, the reaction was stirred 90 minutes, followed by the slow addition of 3,N-dimethoxy-N-methyl-benzamide (146 mg, 750 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (1 mL, 4.0 mmol) and H$_2$O (0.33 mL), and then stirred at 80° C. for two hours. The resultant solution was diluted with EtOAc, washed with water, saturated sodium bicarbonate, and brine; dried with MgSO$_4$, and evaporated employing reduced pressure. The crude residue was subsequently purified via reverse phase HPLC (Column: Varian Dynamax 250×21.4 mm Microsorb100-8 C18, 0.1% TFA/H$_2$O (Eluent A): 0.1% TFA/MeCN (Eluent B)): $^1$H NMR (400 MHz, CDCl$_3$) δ 10.61 (s, 1H), 8.29 (d, 1H), 8.20 (d, 1H), 7.74 (d, 2H), 7.58 (s, 1H), 7.50 (d, 1H), 7.42 (d, 2H), 7.37 (d, 1H), 7.29 (t, 1H), 2.40 (s, 3H), 1.25 (s, 9H); MS (ES) M+H expect 459.1, found 459.5.

Example 51: 4-tert-Butyl-N-[5-chloro-2-(3-methanesulfonyl-benzoyl)-pyridin-3-yl]-benzenesulfonamide

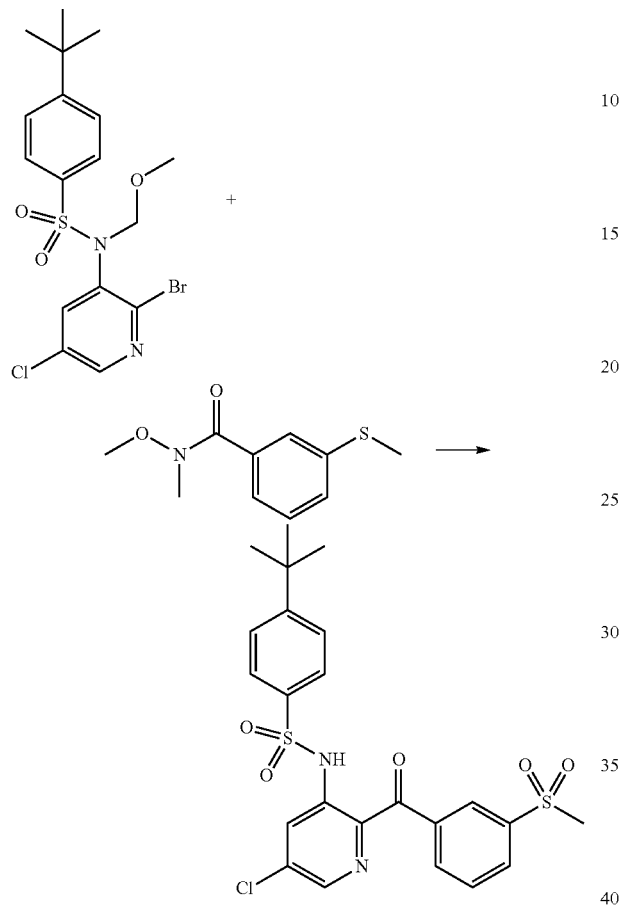

N-(2-Bromo-5-chloro-pyridin-3-yl)-4-tert-butyl-N-methoxymethyl-benzenesulfonamide (500 mg, 1.12 mmol) was placed in a dry 2-neck 50 mL round-bottom flask. The flask was evacuated and purged with nitrogen, followed by the addition of THF (5.6 mL). The homogeneous mixture was lowered to −5° C. and iPrMgCl (1.28 mL, 2.0 M) was added dropwise. Upon completion of the addition, the reaction was stirred 90 minutes, followed by the slow addition of N-methoxy-N-methyl-3-methylsulfanyl-benzamide (471 mg, 2.23 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (4.76 mL, 19.0 mmol) and H$_2$O (1.59 mL), and then stirred at 80° C. overnight. The following day, the organics were removed in vacuo and the residue was diluted with EtOAc. The resultant organics were washed with water, saturated sodium bicarbonate, and brine; dried with MgSO$_4$, and evaporated employing reduced pressure. The crude residue was subsequently purified via automated flash chromatography to afford the desired arylthioether. To a stirring solution of the thioether (100 mg, 0.211 mmol) in methylene chloride (0.8 mL) was added mCPBA (77% maximum) (141 mg, 0.632 mmol), during which the exothermic reaction caused slight boiling of the methylene chloride. Upon stirring 30 min, the reaction was quenched with aqueous sodium metabisulfite and then stirred a further 15 min. The solution was diluted with EtOAc and the combined organics were washed with sodium metabisulfite and saturated sodium bicarbonate. The organic layer was then dried with MgSO$_4$ and concentrated in vacuo to generate the desired arylmethylsulfone: $^1$H NMR (400 MHz, CDCl$_3$) δ 10.86 (s, 1H), 8.43 (dd, 1H), 8.27 (d, 1H), 8.22 (d, 1H), 8.11 (dd, 2H), 7.80 (d, 2H), 7.65 (t, 1H), 7.48 (d, 2H), 3.18 (s, 3H), 1.27 (s, 9H); MS (ES) M+H expect 507.1, found 507.5.

Example 52: N-[2-(3-Amino-benzoyl)-5-chloro-pyridin-3-yl]-4-tert-butyl-benzenesulfonamide

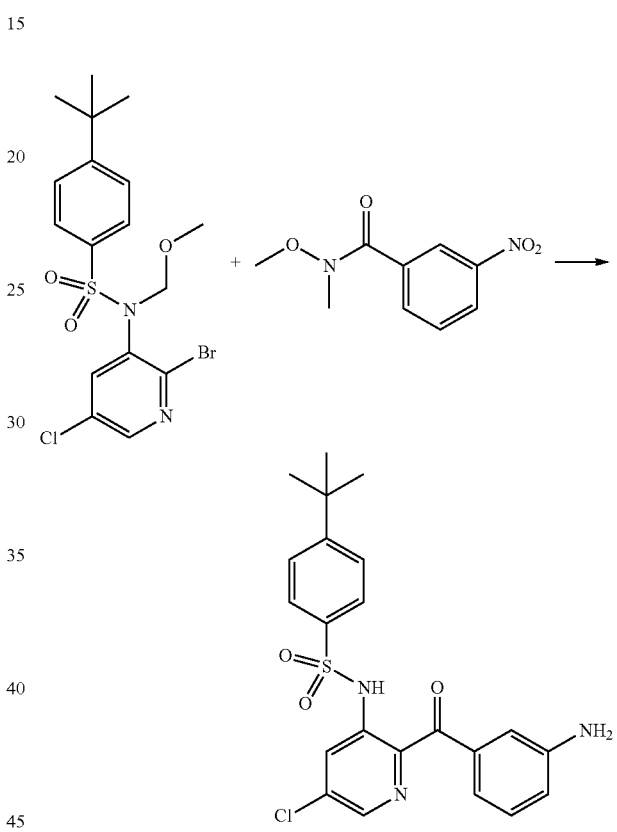

N-(2-Bromo-5-chloro-pyridin-3-yl)-4-tert-butyl-N-methoxymethyl-benzenesulfonamide (3.84 g, 8.57 mmol) was placed in a dry 2-neck 250 mL round-bottom flask. The flask was evacuated and purged with nitrogen, followed by the addition of THF (43 mL). The homogeneous mixture was lowered to −5° C. and iPrMgCl (9.86 mL, 2.0 M) was added dropwise. Upon completion of the addition, the reaction was stirred 90 minutes, followed by the slow addition of N-methoxy-N-methyl-3-nitro-benzamide (4.50 g, 21.43 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (36 mL, 146 mmol) and H$_2$O (12 mL), and then stirred at 80° C. overnight. The following day, the organics were removed in vacuo and the residue was diluted with EtOAc. The resultant organics were washed with water, saturated sodium bicarbonate, and brine; dried with MgSO$_4$, and evaporated employing reduced pressure. The crude residue was subsequently purified via automated flash chromatography to afford the desired nitroarene. To a rapidly stirring solution of iron (274 mg, 5.07 mmol) in acetic acid (5 mL) at 80° C. was added dropwise a homogeneous solution of the nitroarene (685 mg, 1.45 mmol) in AcOH/CH$_2$Cl$_2$ (8 mL/2 mL). The reaction was stirred 60 min, cooled to ambient temperature, diluted with EtOAc (12 mL), and filtered through celite. The filtrate was washed thoroughly with EtOAc and concentrated in vacuo. The resultant residue was dissolved in EtOAc, washed two times with saturated NaHCO$_3$, dried with sodium sulfate, and concentrated at reduced pressure to afford the crude aniline: $^1$H NMR (400 MHz, CDCl$_3$) δ 10.54 (s, 1H), 8.28 (d, 1H), 8.19 (d, 1H), 7.72 (d, 2H), 7.40 (d, 2H), 7.16 (t, 1H), 7.08 (ddd, 1H), 7.04 (ddd, 1H), 6.85 (ddd, 1H), 3.78 (bs, 2H), 1.25 (s, 9H); MS (ES) M+H expect 444.1, found 444.1.

Example 53: 4-tert-Butyl-N-[5-chloro-2-(3-methanesulfonylamino-benzoyl)-pyridin-3-yl]-benzenesulfonamide To a stirring solution of N-[2-(3-amino-benzoyl)-5-chloro-pyridin-3-yl]-4-tert-butyl-benzenesulfonamide (60 mg, 0.135 mmol) in pyridine (0.2 mL) was added methanesulfonyl chloride (0.012 mL, 0.163 mmol). The homogeneous reaction was stirred overnight to generate a mixture of mono- and bis-sulfonamide. The resultant solution was partitioned with EtOAc/10% HCl, and the organics were washed with 10% HCl and saturated sodium bicarbonate. The organic layer was then dried with sodium sulfate and concentrated in vacuo to produce the crude sulfonamide mixture that co-eluted via both reverse-phase and normal-phase chromatography. A 5 mL flask was charged with the resultant sulfonamide mixture, tetrabutylammonium fluoride (0.405 mL, 1.0 M), and THF (1.3 mL). The reaction was stirred 90 min and then partitioned with EtOAc/10% HCl. The organics were washed with 10% HCl and saturated sodium bicarbonate, dried with sodium sulfate, and concentrated in vacuo to produce the desired mono-sulfonamide which was further purified through automated normal-phase chromatography: $^1$H NMR (400 MHz, CDCl$_3$) δ 10.71 (bs, 1H), 8.27 (d, 1H), 8.20 (d, 1H), 7.79 (d, 2H), 7.69-7.71 (m, 1H), 7.60-7.62 (m, 1H), 7.42-7.49 (m, 4H), 6.48 (bs, 1H), 3.06 (s, 3H), 1.28 (s, 9H); MS (ES) M+H expect 522.1, found 522.1.

Example 54: N-{3-[3-(4-tert-Butyl-benzenesulfonylamino)-5-chloro-pyridine-2-carbonyl]-phenyl}-acetamide

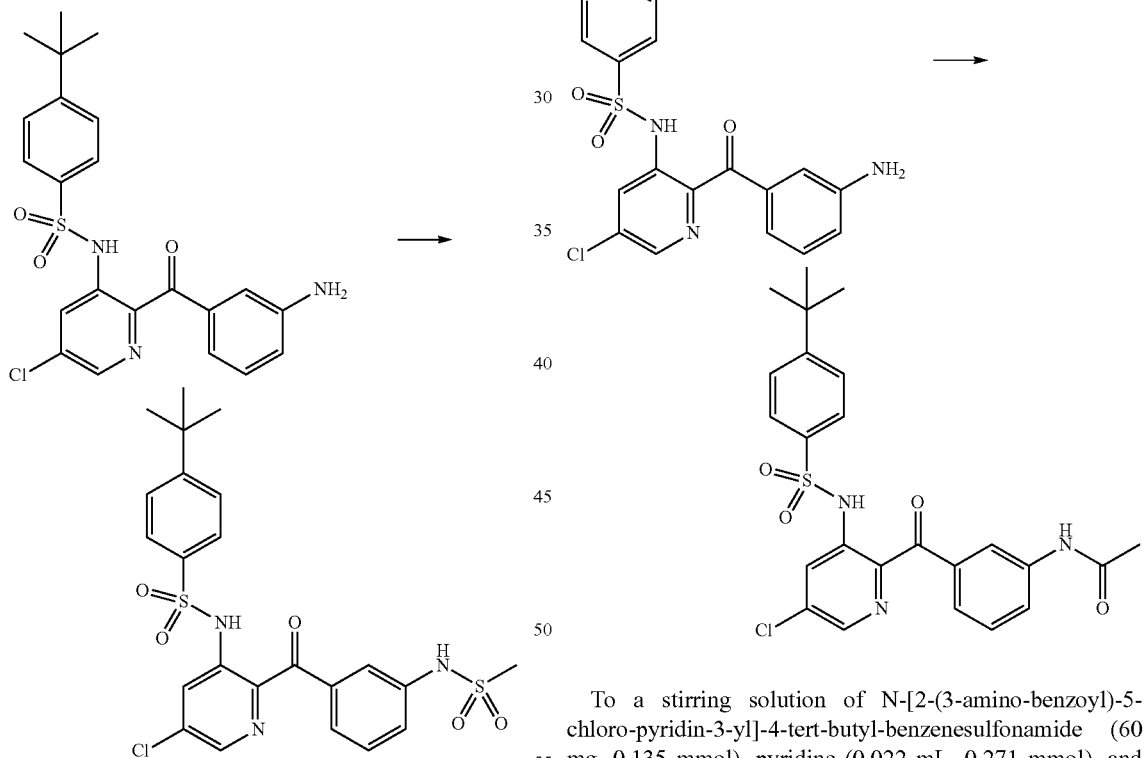

To a stirring solution of N-[2-(3-amino-benzoyl)-5-chloro-pyridin-3-yl]-4-tert-butyl-benzenesulfonamide (60 mg, 0.135 mmol), pyridine (0.022 mL, 0.271 mmol), and methylene chloride (0.68 mL) at 0° C. was added acetyl chloride (0.011 mL, 0.149 mmol). The homogeneous reaction was stirred 90 min, diluted with EtOAc, and then quenched with 10% HCl. The organics were washed with 10% HCl and saturated sodium bicarbonate, dried with sodium sulfate, and concentrated in vacuo to produce the target aryl acetamide: $^1$H NMR (400 MHz, CDCl$_3$) δ 10.71 (bs, 1H), 8.28 (d, 1H), 8.18 (d, 1H), 7.88-7.91 (m, 1H), 7.79 (d, 1H), 7.74 (d, 2H), 7.50 (d, 1H), 7.43 (d, 2H), 7.36 (t, 1H), 7.22 (bs, 1H), 2.18 (s, 3H), 1.25 (s, 9H); MS (ES) M+H expect 486.1, found 486.5.

Example 55: 4-tert-Butyl-N-[5-chloro-2-(6-hydroxy-pyridine-3-carbonyl)-pyridin-3-yl]-benzenesulfonamide

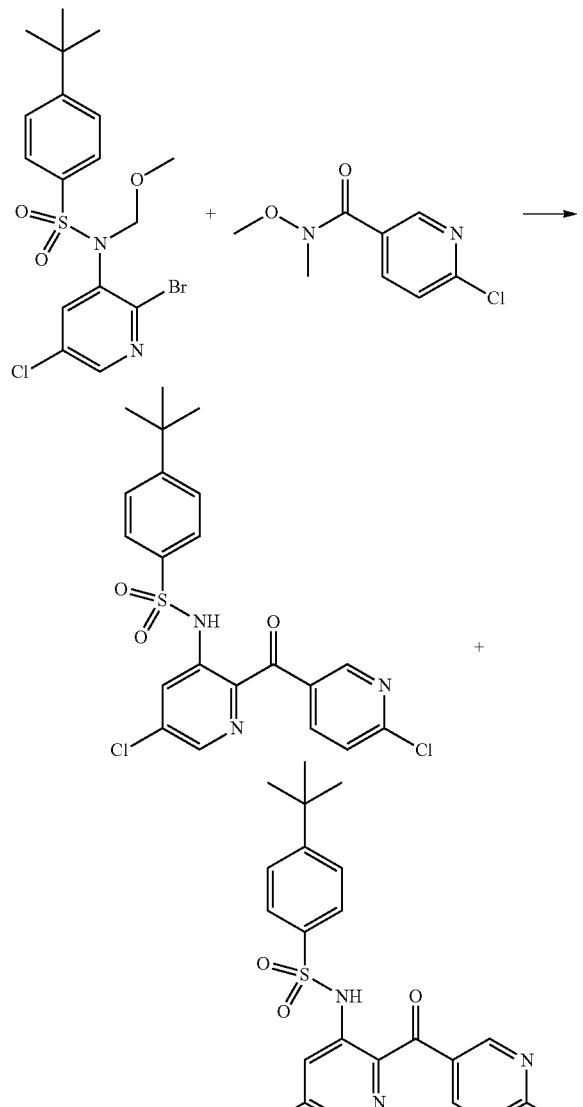

N-(2-Bromo-5-chloro-pyridin-3-yl)-4-tert-butyl-N-methoxymethyl-benzenesulfonamide (2.00 g, 4.46 mmol) was placed in a dry 2-neck 50 mL round-bottom flask. The flask was evacuated and purged with nitrogen, followed by the addition of THF (15 mL). The homogeneous mixture was lowered to −5° C. and iPrMgCl (5.13 mL, 2.0 M) was added dropwise. Upon completion of the addition, the reaction was stirred 90 minutes, followed by the slow addition of 6-chloro-N-methoxy-N-methyl-nicotinamide (1.44 g, 7.14 mmol). The reaction was stirred overnight, during which the ice-bath warmed to room temperature. The resultant solution was quenched with 10% HCl and diluted with EtOAc. The organics were washed with 10% HCl and saturated sodium bicarbonate, dried with sodium sulfate, concentrated in vacuo, and purified via automated silica gel chromatography to afford the diaryl ketone (1.049 g) in 46% yield. A microwave flask was charged with the diaryl ketone (40 mg, 0.078 mmol), HCl in dioxane (0.335 mL, 4.0 M), and water (0.12 mL). The reaction vessel was subjected to a microwave reaction at 90° C. for 10 min. The reaction was incomplete, thus the vessel was reacted a further 10 min at 120° C., during which the starting materials were consumed. The crude mixture was diluted with EtOAc and neutralized to pH 7-8 with saturated sodium bicarbonate. The organics were washed with saturated sodium bicarbonate, dried with sodium sulfate, concentrated in vacuo, and purified via automated column chromatography to generate a mixture of the desired 4-tert-butyl-N-[5-chloro-2-(6-hydroxy-pyridine-3-carbonyl)-pyridin-3-yl]-benzenesulfonamide and 4-tert-butyl-N-[5-chloro-2-(6-chloro-pyridine-3-carbonyl)-pyridin-3-yl]-benzenesulfonamide: $^1$H NMR (400 MHz, CDCl$_3$) δ 10.98 (bs, 1H), 8.70 (d, 1H), 8.29 (d, 1H), 8.16-8.20 (m, 2H), 7.76 (d, 2H), 7.45 (d, 2H), 6.59 (d, 1H), 1.27 (s, 9H); MS (ES) M+H expect 446.1, found 446.3.

Example 56: 4-tert-Butyl-N-[5-chloro-2-(6-methoxy-pyridine-3-carbonyl)-pyridin-3-yl]-benzenesulfonamide

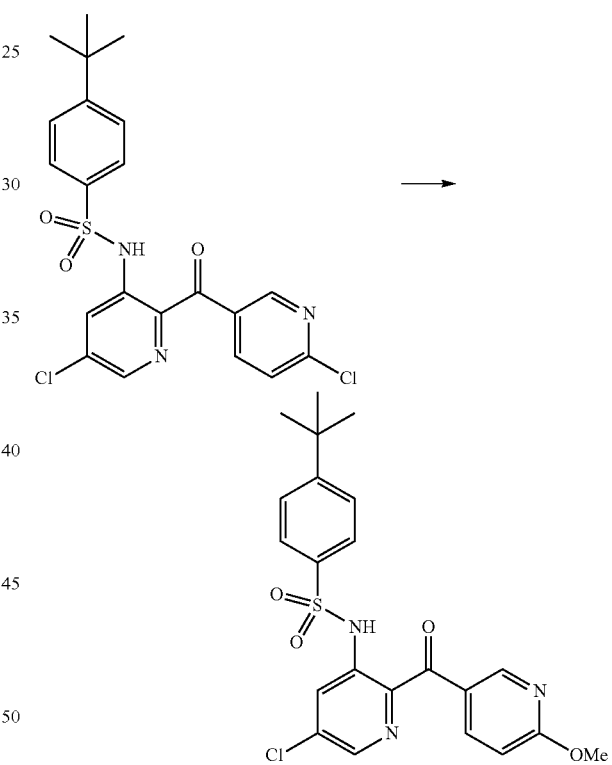

To a stirring solution of 4-tert-butyl-N-[5-chloro-2-(6-chloro-pyridine-3-carbonyl)-pyridin-3-yl]-benzenesulfonamide (30 mg, 0.065 mmol) in MeOH (0.65 mL) was added NaOMe (18 mg, 0.324 mmol). The resultant solution was heated to 80° C. and stirred 4 h. The reaction was quenched with 10% HCl (to pH 6-7), diluted with EtOAc, and the pH adjusted to 7-8 with saturated sodium bicarbonate. The organics were washed with saturated sodium bicarbonate, dried with sodium sulfate, concentrated in vacuo, and purified via automated flash chromatography to produce the target methoxy pyridine: $^1$H NMR (400 MHz, CDCl$_3$) δ 10.71 (bs, 1H), 8.72 (d, 1H), 8.26 (d, 1H), 8.08-8.20 (m, 2H), 7.72 (d, 2H), 7.37 (d, 2H), 6.75 (d, 1H), 4.00 (s, 3H), 1.23 (s, 9H); MS (ES) M+H expect 460.1, found 460.2.

Example 57: N-[2-(6-Amino-pyridine-3-carbonyl)-5-chloro-pyridin-3-yl]-4-tert-butyl-benzenesulfonamide

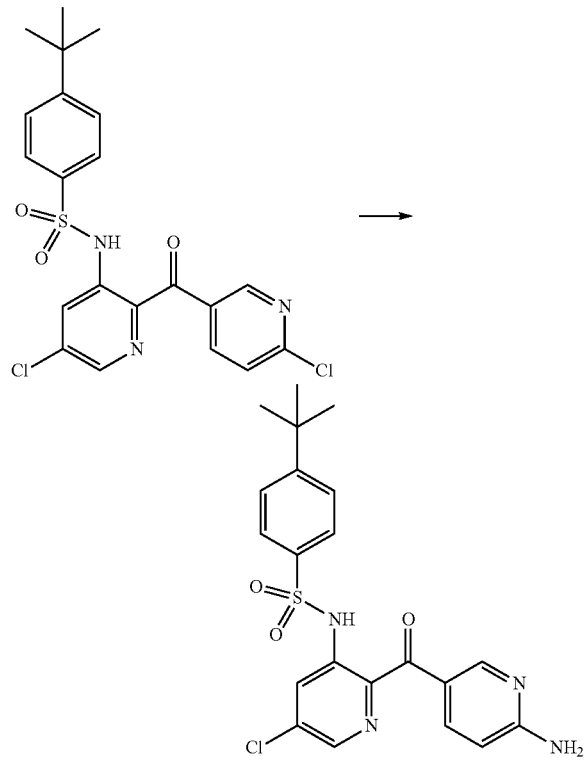

A sealed tube was charged with 4-tert-butyl-N-[5-chloro-2-(6-chloro-pyridine-3-carbonyl)-pyridin-3-yl]-benzenesulfonamide (320 mg, 0.631 mmol), concentrated ammonium hydroxide (3.2 mL), and THF (3.2 mL). The tube was sealed and stirred for 3 days at 100° C. The solvents were subsequently removed in vacuo and the residue purified by automated flash chromatography to provide the desired aminopyridine: $^1$H NMR (400 MHz, CDCl$_3$) δ 10.72 (bs, 1H), 8.69 (d, 1H), 8.28 (dd, 1H), 8.16 (dd, 1H), 8.02 (dd, 1H), 7.71 (d, 2H), 7.40 (d, 2H), 6.46 (d, 1H), 5.00 (bs, 2H), 1.24 (s, 9H); MS (ES) M+H expect 445.1, found 445.1.

Example 58: 4-tert-Butyl-N-[5-chloro-2-(2-methylpyridine-3-carbonyl)-pyridin-3-yl]-benzenesulfonamide

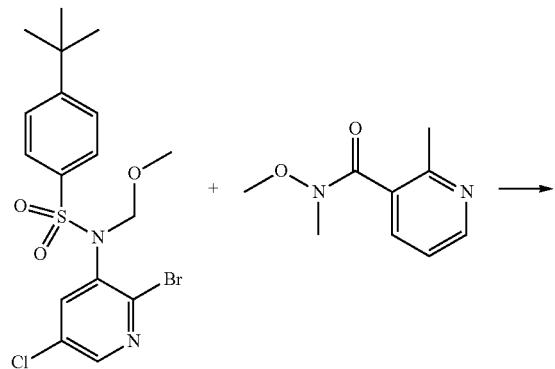

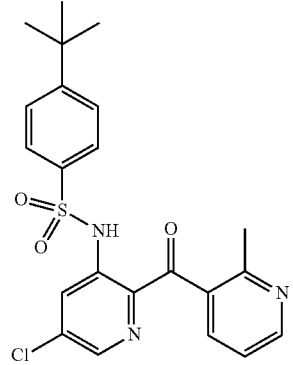

N-(2-Bromo-5-chloro-pyridin-3-yl)-4-tert-butyl-N-methoxymethyl-benzenesulfonamide (140 mg, 300 mmol) was placed in a dry 2-neck 10 mL round-bottom flask. The flask was evacuated and purged with nitrogen, followed by the addition of THF (1 mL). The homogeneous mixture was lowered to −5° C. and iPrMgCl (0.33 mL, 2.0 M) was added dropwise. Upon completion of the addition, the reaction was stirred 90 minutes, followed by the slow addition of N-methoxy-2,N-dimethyl-nicotinamide (135 mg, 750 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (1 mL, 4.0 mmol) and H$_2$O (0.33 mL), and then stirred at 80° C. for two hours. The resultant solution was diluted with EtOAc, washed with water, saturated sodium bicarbonate, and brine; dried with MgSO$_4$, and evaporated employing reduced pressure. The crude residue was subsequently purified via automated flash chromatography to afford the desired sulfonamide: $^1$H NMR (400 MHz, CDCl$_3$) δ 10.9 (s, 1H), 8.58 (d, 1H), 8.22 (d, 2H), 7.81 (d, 2H), 7.53-7.46 (m, 3H), 7.20-7.14 (m, 1H), 2.30 (s, 3H), 1.31 (s, 9H); MS (ES) M+H expect 444.1, found 444.5.

Example 59: (3-Amino-5-chloropyridin-2-yl)(3-fluorophenyl)methanone

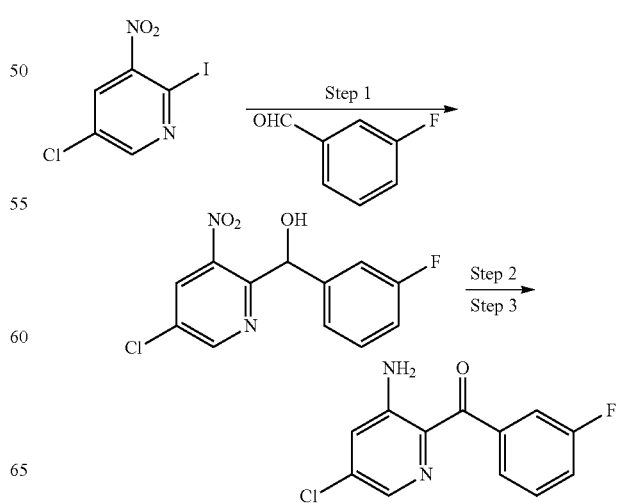

Step 1: A freshly oven dried 250 mL round-bottom flask was charged with 2-iodo-3-nitro-5-chloro-pyridine (1.41 g, 5.0 mmol). The resultant solution was cooled to −78° C. under $N_2$ and PhMgCl (2 M, 3 mL, 6.0 mmol) added and then stirred at the same temperature for 30 min. 3-Fluorobenzaldehyde (1.24 g, 10 mmol) was added and the resulting mixture stirred at −78° C. for two hours and then at room temperature for 24 h. The reaction was quenched with $NH_4Cl$ (sat), extracted with EtOAc, washed with brine, dried over $MgSO_4$, and concentrated under reduced pressure. The residue was further purified through automated normal-phase chromatography to afford 5-chloro-3-nitropyridin-2-yl)(3-fluorophenyl)methanol (560 mg, 40%) which was used directly for the next step: $^1$H NMR (400 MHz, $CDCl_3$) δ 8.85 (d, 1H), 8.37 (d, 1H), 7.23 (m, 1H), 7.06 (dd, 1H), 6.95 (dd, 1H), 6.43 (d, 2H), 4.99 (d, 1H); MS (ES) ($M^+$—OH) expect 265.0, found 265.1.

Step 2: A 50 mL round-bottom flask was charged with the above alcohol (500 mg, 1.78 mmol) and dichloromethane (10 mL). To the resultant solution was added Dess-Martin periodinane (900 mg, 2.13 mmol) and stirred at the room temperature for 30 min. The reaction was quenched with $NaS_2O_3$, filtered through celite, and extracted with EtOAc, washed with brine, dried over $MgSO_4$, and concentrated under reduced pressure to afford the crude nitro ketone (500 mg, quantitative) which was used directly for the next step: $^1$H NMR (400 MHz, $CDCl_3$) δ 8.87 (d, 1H), 8.50 (s, 1H), 7.53 (m, 2H), 7.44 (m, 1H), 7.33 (m, 1H); MS (ES) ($M^+$+H) expect 281.0, found 281.1.

Step 3: A 50 mL round-bottom flask was charged with the iron powder (336 mg, 6.0 mmol) in acetic acid (10 mL) and heated to 80° C. (oil bath) under $N_2$. To this mixture was added slowly the nitroketone (500 mg, 1.78 mmol) in acetic acid (5 mL) via dropping funnel and stirred at 80° C. for another 30 min after the addition. After cooling the reaction mixture, it was diluted with EtOAc, filtered through celite and the solvent evaporated in vacuo. The residue was dissolved in EtOAc and washed with saturated $NaHCO_3$, brine, dried over $MgSO_4$, and concentrated under reduced pressure. The residue was purified through automated normal-phase chromatography to afford 3-amino-5-chloropyridin-2-yl)(3-fluorophenyl)methanone (430 mg, 97%) which was used directly for the next step: $^1$H NMR (400 MHz, $CDCl_3$) δ 7.93 (d, 1H), 7.70-7.62 (m, 1H), 7.40 (m, 1H), 7.20 (m, 1H), 7.09 (d, 1H), 6.26 (br s, 2H); MS (ES) ($M^+$+H) expect 251.0, found 251.0.

Example 60: 6-isopropoxypyridine-3-sulfonyl Chloride

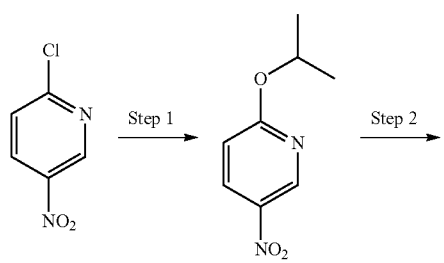

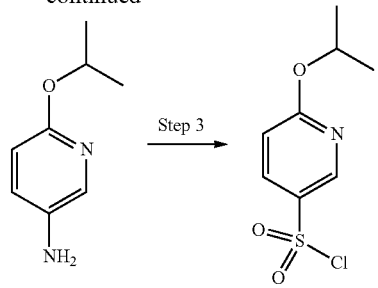

Step 1: A freshly oven dried 500 mL round-bottom flask was charged with 2-chloro-5-nitropyridine (5.0 g, 31.6 mmol) and anhydrous iPrOH (50 mL). The resultant solution was cooled in an ice bath and iPrONa (50 mmol) in iPrOH (250 mL) added slowly, followed by stirring at the same temperature for 30 min and then at room temperature for 14 h. The reaction was quenched with $H_2O$ (5 mL), filtered through celite, and concentrated under reduced pressure. The residue was diluted with EtOAc and washed with brine, dried over $MgSO_4$, and concentrated under reduced pressure. The residue was purified through automated normal-phase chromatography to afford 2-isopropoxyl-5-nitropyridine (4.6 g, 79%) which was used directly for the next step: $^1$H NMR (400 MHz, $CDCl_3$) δ 9.02 (d, 1H), 8.30 (dt, 1H), 6.75 (d, 1H), 5.40 (sep, 1H), 1.38 (d, 6H); MS (ES) ($M^+$+H) expect 183.1, found 183.1.

Step 2: A 100 mL round-bottom flask was charged with the iron powder (5.6 g, 10 mmol) in acetic acid (30 mL) and heated to 80° C. (oil bath) under $N_2$. To this mixture was added slowly the above 2-isopropoxyl-5-nitropyridine (4.6 g, 25.2 mmol) in acetic acid (30 mL) via dropping funnel and the reaction stirred at 80° C. for another 30 min after the addition. After cooling the reaction mixture, it was diluted with EtOAc, filtered through celite, and the solvent evaporated in vacuo. The residue was dissolved in EtOAc and washed with $NaHCO_3$ (sat.), brine, dried over $MgSO_4$, and concentrated under reduced pressure. The residue was purified through automated normal-phase chromatography to afford 2-isopropoxyl-5-aminopyridine (3.8 g, 99%) which was used directly for the next step: $^1$H NMR (400 MHz, $CDCl_3$) δ 7.64 (d, 1H), 7.00 (dt, 1H), 6.52 (d, 1H), 5.10 (sep, 1H), 1.30 (d, 6H); MS (ES) ($M^+$+H) expect 153.1, found 153.1.

Step 3: A 50 mL round-bottom flask was charged with 2-isopropoxyl-5-aminopyridine (1.6 g, 10.5 mmol), hydrochloric acid (conc.) (10 mL) and glacial acetic acid (8 mL) and cooled to −10° C. To this mixture was added slowly a solution of $NaNO_2$ (828 mg, 12 mmol) in $H_2O$ (2 mL) and the reaction stirred at −10° C. for another 30 min after the addition. In a second flask, sulfur dioxide was bubbled into a magnetically stirred acetic acid (16 mL) to saturation. Cuprous chloride (250 mg) was added and the introduction of sulfur dioxide was continued until the yellow-green suspension became blue-green. The mixture was then cooled to −10° C. The diazonium salt mixture was added in portions (gas evolution) and the temperature was kept under −5° C. The dark mixture was kept at −10° C. for 30 min and then at −5° C. for 1 h. The mixture was poured to ice water and extracted with ether, washed with $NaHCO_3$ (sat.) until the washings were neutral, then with cold water, dried over $MgSO_4$, and concentrated under reduced pressure to afford 6-isopropoxypyridine-3-sulfonyl chloride (1.5 g, 64%) which was used directly for the next step: $^1$H NMR (400

MHz, CDCl$_3$) δ 8.80 (d, 1H), 8.06 (dt, 1H), 6.80 (d, 1H), 5.42 (sep, 1H), 1.38 (d, 6H); MS (ES) (M$^+$+H) expect 235.0, found 235.1.

Example 61: N-(5-chloro-2-(3-fluorobenzoyl)pyridin-3-yl)-4-isopropoxybenzenesulfonamide

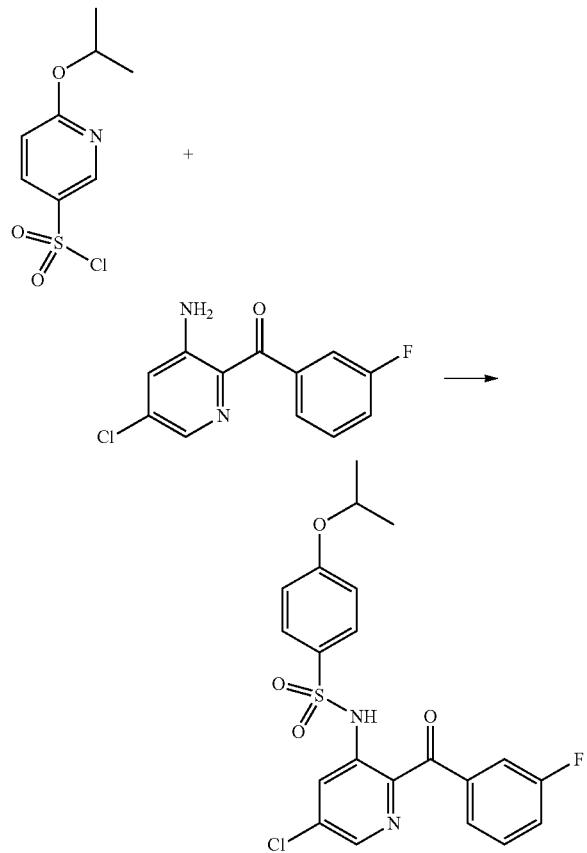

A 25 mL round-bottom flask was charged with (3-amino-5-chloropyridin-2-yl)(3-fluorophenyl)methanone (130 mg, 0.52 mmol), 6-isopropoxypyridine-3-sulfonyl chloride (130 mg, 0.55 mmol), pyridine (2 mL) and dichloromethane (2 mL). The resultant solution was heated to 70° C. and stirred for 15 h. The pyridine was removed in vacuo and THF (5 mL) and 4.0 N NaOH (2 mL) were added. The mixture was stirred at 60° C. for 24 h. The solvent was subsequently removed in vacuo and the residue was diluted with water (5 mL) and the pH was adjusted to 6-7 with 10% HCl. The resultant aqueous solution was extracted with EtOAc, washed with brine, dried over MgSO$_4$, and concentrated under reduced pressure. The residue was purified through automated normal-phase chromatography to afford N-(5-chloro-2-(3-fluorobenzoyl)pyridin-3-yl)-4-isopropoxybenzenesulfonamide (60 mg, 26%): $^1$H NMR (400 MHz, CDCl$_3$) δ 10.62 (s, 1H), 8.58 (d, 1H), 8.32 (d, 1H), 8.18 (d, 1H), 7.86 (dd, 1H), 7.60 (dd, 1H), 7.52 (dt, 1H), 7.40 (m, 1H), 7.30 (dd, 1H), 6.60 (d, 1H), 5.30 (sep, 1H), 1.30 (d, 1H); MS (ES) (M++2H) expect 250.0, found 250.1.

Example 62: N-(2-Benzoyl)-5-chloro-pyridin-3-yl)-4-isopropoxybenzenesulfonamide

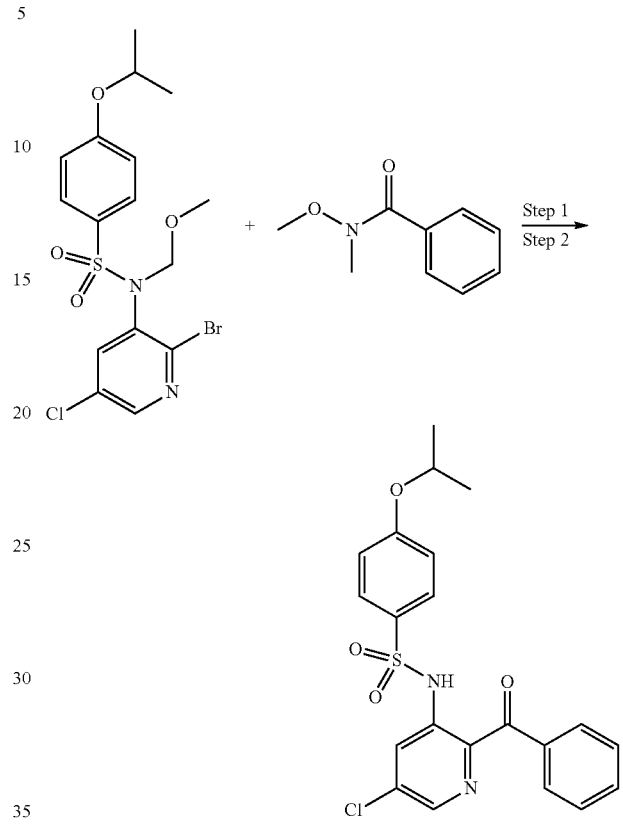

Step 1: N-(2-Bromo-5-chloro-pyridin-3-yl)-4-isopropoxyl-N-methoxymethyl-benzenesulfonamide (450 mg, 1.0 mmol) was placed in a dry 100 mL round-bottom flask sealed with septa. The flask was evacuated and purged with nitrogen, followed by the addition of dry THF (30 mL). The homogeneous solution was cooled to 0° C. and iPrMgCl (1.5 mL, 2.0 M) was added dropwise. Upon completion of the addition, the mixture was stirred at 0° C. for 90 min, followed by the slow addition of N-methoxy-N-methyl-benzamide (660 mg, 4.0 mmol). The reaction mixture was stirred at 0° C. for 2 h and then at room temperature overnight. The reaction was quenched with NH$_4$Cl (sat.) and extracted with EtOAc, washed with brine, dried over MgSO$_4$, and concentrated under reduced pressure. The residue was purified through automated normal-phase chromatography to afford MOM-protected sulfonamide (360 mg, 76%) which was used directly for the next step: $^1$H NMR (400 MHz, CDCl$_3$) δ 8.55 (d, 1H), 7.78 (m, 3H), 7.58 (d, 2H), 7.52 (t, 1H), 7.42 (d, 2H), 7.33 (t, 2H), 6.55 (d, 2H), 5.20 (s, 2H), 4.33 (sep, 1H), 3.47 (s, 3H), 1.27 (d, 6H); MS (ES) (M++Na) expect 497.1, found 497.1.

Step 2: The above MOM-protected sulfonamide (400 mg, 0.84 mmol) was treated with 4.0 M HCl in dioxane (4 mL, 16 mmol) and H$_2$O (2 mL), and then stirred at 80° C. for 1.5 h. The mixture was diluted with EtOAc. The resultant organics were washed with NaHCO$_3$ (sat.), and brine; dried (MgSO$_4$), and concentrated under reduced pressure and was purified through automated normal-phase chromatography to afford N-(2-benzoyl)-5-chloro-pyridin-3-yl)-4-iso-propoxybenzenesulfonamide: $^1$H NMR (400 MHz, CDCl$_3$) δ 10.54 (s, 1H), 8.29 (s, 1H), 8.16 (s, 1H), 7.73 (m, 4H), 7.55 (t, 1H), 7.40 (t, 2H), 6.80 (d, 2H), 4.33 (sep, 1H), 1.27 (d, 6H); MS (ES) (M$^+$+H) expect 431.1, found 431.1.

Step 63: N-(2-Benzoyl)-5-chloro-pyridin-3-yl)-4-tert-butyl-benzenesulfonamide

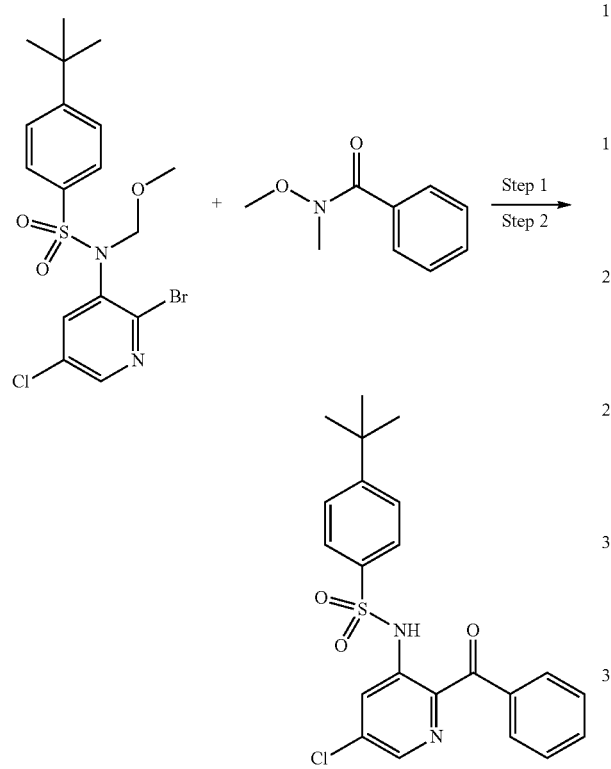

Step 1: N-(2-Bromo-5-chloro-pyridin-3-yl)-4-tert-butyl-N-methoxymethyl-benzenesulfonamide (450 mg, 1.0 mmol) was placed in a dry 100 mL round-bottom flask sealed with septa. The flask was evacuated and purged with nitrogen, followed by the addition of dry THF (30 mL). The homogeneous solution was cooled to 0° C. and iPrMgCl (1.5 mL, 2.0 M) was added dropwise. Upon completion of the addition, the mixture was stirred at 0° C. for 90 min, followed by the slow addition of N-methoxy-N-methyl-benzamide (660 mg, 4.0 mmol). The reaction mixture was stirred at 0° C. for 2 h and then at room temperature overnight. The reaction was quenched with NH$_4$Cl (sat.) and extracted with EtOAc, washed with brine, dried over MgSO$_4$, and concentrated under reduced pressure. The residue was purified through automated normal-phase chromatography to afford MOM-protected sulfonamide (360 mg, 76%) which was used directly for the next step: $^1$H NMR (400 MHz, CDCl$_3$) δ 8.55 (d, 1H), 7.65 (m, 3H), 7.50 (m, 3H), 7.37 (t, 2H), 7.24 (d, 2H), 5.20 (s, 2H), 3.45 (s, 3H), 1.19 (s, 9H); MS (ES) (M++Na) expect 495.1, found 495.1.

Step 2: The above MOM-protected sulfonamide (340 mg, 0.72 mmol) was treated with 4.0 M HCl in dioxane (4 mL, 16 mmol) and H$_2$O (2 mL), and then stirred at 80° C. for 1.5 h. The mixture was diluted with EtOAc. The resultant organics were washed with NaHCO$_3$ (sat.), and brine; dried (MgSO$_4$), concentrated under reduced pressure, and purified through automated normal-phase chromatography to afford N-(2-benzoyl)-5-chloro-pyridin-3-yl)-4-tert-butyl-benzenesulfonamide: $^1$H NMR (400 MHz, CDCl$_3$) δ 10.64 (s, 1H), 8.29 (d, 1H), 8.19 (d, 1H), 7.73 (t, 3H), 7.55 (t, 1H), 7.40 (t, 3H), 7.25 (d, 1H), 1.24 (s, 9H); MS (ES) (M$^+$+H) expect 429.1, found 429.1.

Example 64: N-(2-bromo-5-chloro-pyridin-3-yl)-4-isopropoxy-N-methoxymethyl-benzenesulfonamide

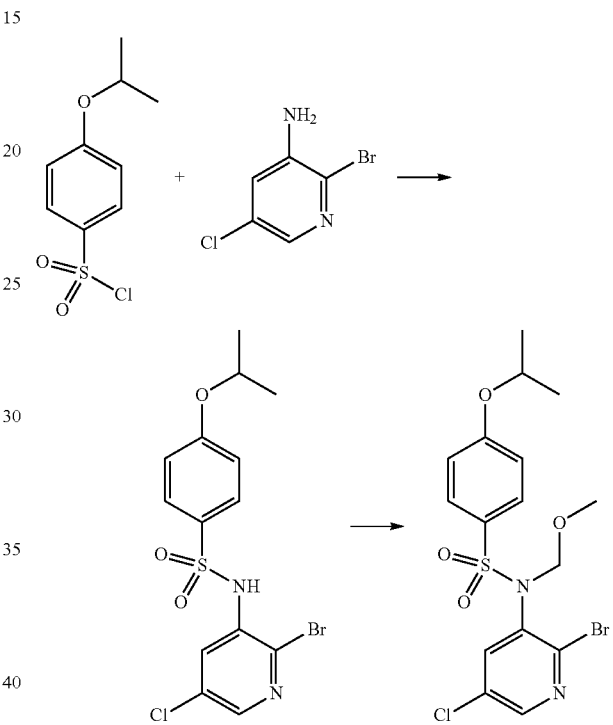

A 200 mL round-bottom flask was charged with 2-bromo-5-chloro-pyridin-3-ylamine (2.06 g, 9.94 mmol), 4-isopropoxysulfonyl chloride (3.5 g, 14.91 mmol), and pyridine (10 mL). The resultant solution was heated to 80° C. and stirred overnight. The following day, the pyridine was removed in vacuo and THF (20 mL) and 4.0 N NaOH (30 mL) were added and the reaction was stirred at 60° C. for 72 hours. The organics were subsequently removed in vacuo and the residues were diluted with water (100 mL). The small quantity of insoluble solid was removed by filtration and the pH was adjusted to 6-7 with concentrated HCl. The resultant precipitate was filtered and washed with water to afford the diarylsulfonamide (3.44 g) in 85% yield. To a solution of the crude sulfonamide (3.41 g, 8.41 mmol) and K$_2$CO$_3$ (4.65 g, 33.64 mmol) in anhydrous THF (21 mL) was added chloromethyl methyl ether (1.3 mL, 16.81 mmol). The resultant heterogeneous solution was stirred overnight at ambient temperature and the solids were subsequently removed via filtration. The filtrate was then removed in vacuo to produce the desired product as a light yellowish solid (3.54 g, 94% yield).

Example 65: N-[5-chloro-2-(2-methyl-pyridine-3-carbonyl)-pyridin-3-yl]-4-isopropoxy-benzenesulfonamide

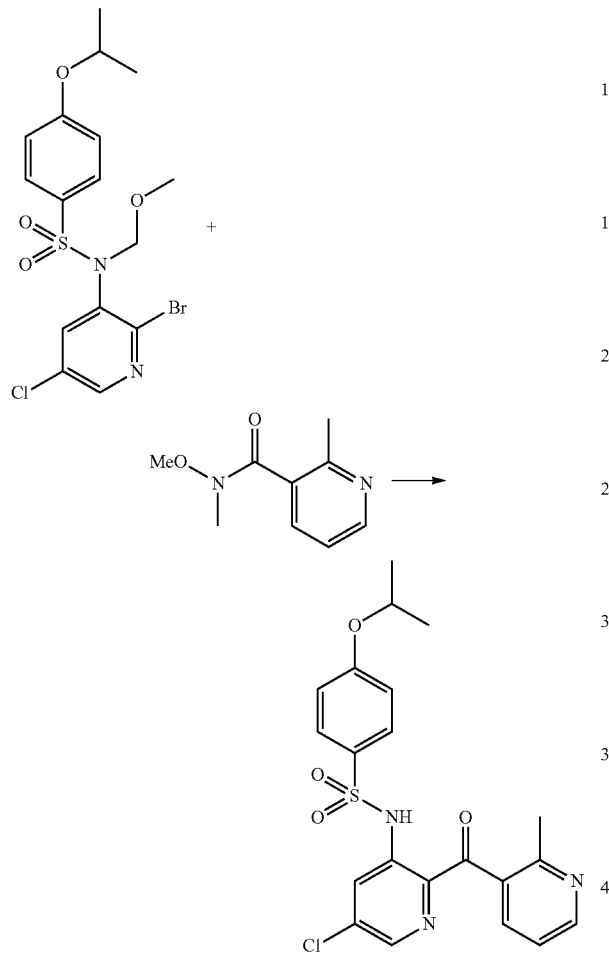

N-(2-bromo-5-chloro-pyridin-3-yl)-4-isopropoxy-N-methoxymethyl-benzenesulfonamide (592 mg, 1.32 mmol) was placed in a dry 25 mL round-bottom flask. The flask was evacuated and purged with nitrogen, followed by the addition of THF (5 mL). The homogeneous mixture was lowered to −5° C. and iPrMgCl (1.72 mL, 2.0 M) was added dropwise. Upon completion of the addition, the reaction was stirred 60 minutes, followed by the addition of N-methoxy-2,N-dimethyl-nicotinamide (379 mg, 2.11 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (6 mL, 24.0 mmol) and H$_2$O (6.0 mL), and then stirred at 80° C. for two hours. The resultant solution was concentrated in vacuo and saturated sodium bicarbonate was added to adjust to neutral pH. The solution was extracted with ethyl acetate, dried over magnesium sulfate, filtered and concentrated in vacuo. The crude sulfonamide was finally purified via automated flash chromatography to afford the title compound: $^1$H NMR (400 MHz, CDCl$_3$) δ 10.90 (s, 1H), 8.58 (d, 1H), 8.17 (m, 2H), 7.80 (d, 2H), 7.49 (d, 1H), 7.16 (m, 1H), 6.89 (d, 2H), 4.57 (sep, 1H), 2.34 (s, 3H), 1.33 (d, 6H); MS (ES) M+H expect 445.9, found 446.1.

Example 66: N-[5-Chloro-2-(3-fluoro-benzoyl)-pyridin-3-yl]-4-isopropoxy-benzenesulfonamide

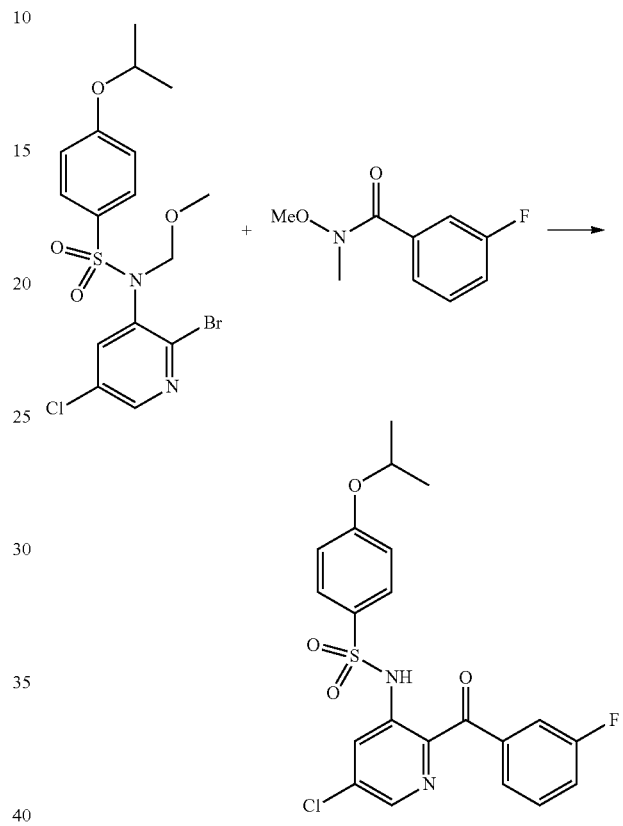

N-(2-Bromo-5-chloro-phenyl)-4-isopropoxy-N-methoxymethyl-benzenesulfonamide (300 mg, 0.67 mmol) was placed in a dry 25 mL round-bottom flask. The flask was evacuated and purged with nitrogen, followed by the addition of THF (3 mL). The homogeneous mixture was lowered to −5° C. and iPrMgCl (0.87 mL, 2.0 M) was added dropwise. Upon completion of the addition, the reaction was stirred 60 minutes, followed by the addition of 3-fluoro-N-methoxy-N-methyl-benzamide (196 mg, 1.1 mmol). The reaction was stirred overnight, during which the ice-bath warmed to room temperature. The following day, the reaction was quenched with a small quantity of MeOH and the solvents evaporated in vacuo. The residue was subsequently treated with 4.0 M HCl in dioxane (3 mL, 12.0 mmol) and H$_2$O (1 mL), and then stirred at 80° C. overnight. The resultant solution was concentrated in vacuo and saturated sodium bicarbonate was added to adjust to neutral pH. The solution was extracted with ethyl acetate, dried over magnesium sulfate, filtered and concentrated in vacuo. The crude sulfonamide was finally purified via automated flash chromatography to afford the title compound: $^1$H NMR (400 MHz, CDCl$_3$) δ 10.50 (s, 1H), 8.28 (d, 1H), 8.17 (d, 1H), 7.20 (d, 2H), 7.59 (d, 1H), 7.47 (m, 1H), 7.39 (m, 1H), 7.26 (m, 1H), 6.83 (d, 2H), 4.53 (sep, 1H), 1.32 (d, 6H); MS (ES) M+H expect 449.9, found 449.2.

151

Example 67: 4-Chloro-3-methylsulfonylchloride

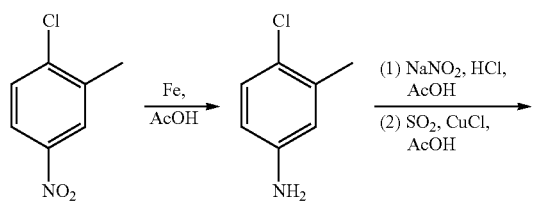

Iron powder (150 g, 2.68 mol) and AcOH (600 mL) were charged into a 2 L round bottom flask equipped with a mechanical stirrer and thermometer. The mixture as warmed to 80° C. 4-Chloro-3-methylnitrobenzene (150 g, 0.87 mol) in AcOH (200 mL) was added slowly to the flask over 4 h, keeping the reaction temperature below 90° C. Upon consumption of the reactants, the mixture was filtered through a pad of Celite and the filter cake was washed with methanol (200 mL). The filtrate was concentrated and the residue was poured into 1.5 L of ice water (1:1) and the resulting precipitate was filtered. The crude product was dissolved in 300 mL 6N HCl in water/dioxane (1:1) and stirred at 100° C. for 3 h. It was then cooled to room temperature and the precipitate was filtered and dried to provide 130 g of 4-chloro-3-methyl-phenylamine hydrochloride as a colorless powder.

4-Chloro-3-methylaniline hydrochloride (75 g, 0.54 mol) was dissolved in 200 mL concentrated hydrochloride acid (200 mL) and acetic acid (60 mL). The mixture was cooled to −5° C. and NaNO₂ (40.9 g, 0.59 mmol) was added. The mixture was stirred between −10° C. to −5° C. for 1 h. While the diazotization was in progress, glacial AcOH (600 mL) was placed in a 4000-mL beaker and stirred magnetically. Sulfur dioxide was introduced by a bubbler tube with a fritted end immersed below the surface of the AcOH until saturation was evident. Cuprous chloride (15 g) was added to the solution. The introduction of sulfur dioxide was continued until the yellow-green suspension becomes blue-green. The mixture was then placed in an ice bath and cooled to 10° C. The diazotization reaction mixture was subsequently added in portions over a 30 min period to the sulfur dioxide solution, ensuring the temperature of the solution did not exceed 30° C. After all the diazonium salt mixture was added, the mixture was poured into ice water (2 L). The resulting precipitate was filtered and re-dissolved in hexane (500 mL). The mixture was filtered through a pad of silica gel (100 g) and the filter pad was washed with hexane (300

152 mL). The combined filtrate was concentrated to yield 50 g of 4-chloro-3-methylbenzenesulfonyl chloride as slightly yellow solid.

Example 68: N-(2-Bromo-5-chloro-pyridin-3-yl)-N-methoxymethyl-3-trifluoromethyl-benzenesulfonamide

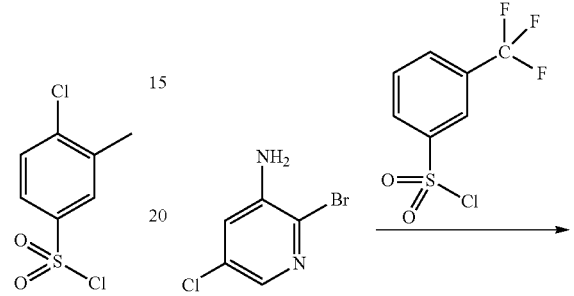

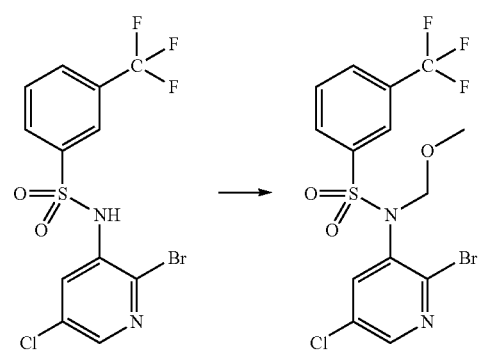

To a stirred solution of 2-bromo-5-chloro-pyridin-3-ylamine (2.07 g, 10.0 mmol) in anhydrous pyridine (20 mL) was added 3-(trifluoromethyl)benzenesulfonyl chloride (4.90 g, 20.0 mmol) and the progress of the reaction was followed by LCMS. The reaction mixture was stirred overnight (18 h), then concentrated to dryness. The residue was dissolved in THF (20 mL) and stirred 18 h with 1M TBAF (20 mL) in THF to cleave the bis-sulfonamide. The THF was subsequently evaporated and the residue was dissolved in ethyl acetate. The organic phase was then washed with water (2×100 mL), brine, and then dried (MgSO₄), filtered, and concentrated under reduced pressure. The residue was purified by chromatography on silica gel using ethyl acetate-hexane to provide N-(2-Bromo-5-chloro-pyridin-3-yl)-3-trifluoromethyl-benzenesulfonamide as a white crystalline solid. MS m/z 417.1 (M+H).

Methoxymethyl chloride (720 mg, 8.94 mmol) was added dropwise to a mixture of N-(2-bromo-5-chloro-pyridin-3-yl)-3-trifluoromethyl-benzenesulfonamide (2.51 g, 6.04 mmol) and potassium carbonate (5.1 g) in THF (60 mL) at room temperature. After 5 h, the potassium salts removed by vacuum filtration, and the filtrate was concentrated under reduced pressure. The residual light yellow solid was chromatographed on silica gel using ethyl acetate-hexane to provide N-(2-bromo-5-chloro-pyridin-3-yl)-N-methoxymethyl-3-trifluoromethyl-benzenesulfonamide as white crystals. MS m/z 461.2 (M+H).

Example 69: N-(2-Bromo-5-chloro-pyridin-3-yl)-4-chloro-N-methoxymethyl-3-methyl-benzenesulfonamide

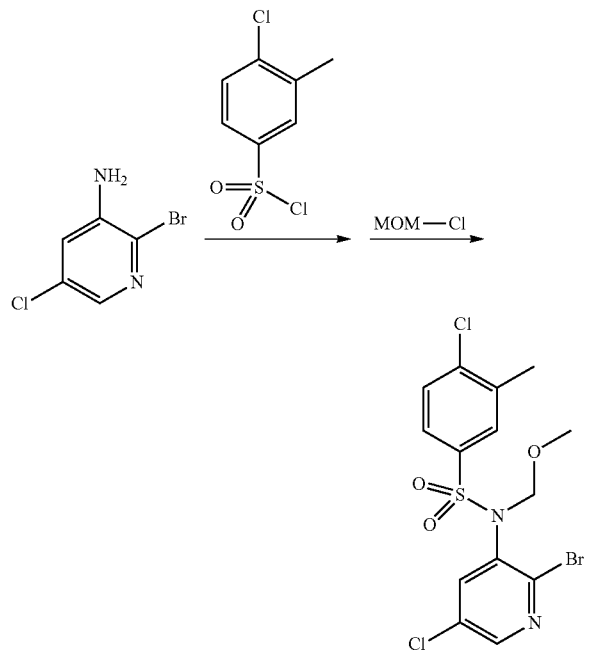

To a stirred solution of 2-bromo-5-chloro-pyridin-3-ylamine (4.12 g, 20 mmol) in anhydrous pyridine (100 mL) was added 3-methyl-4-chlorobenzenesulfonyl chloride (6.35 g, 26 mmol) and the progress of the reaction was followed by LCMS. The reaction mixture was stirred overnight (18 h), then concentrated to remove as much of the pyridine as possible. The residue was dissolved in THF and was stirred 18 h with aqueous sodium hydroxide (20 mL) in THF to cleave the bis-sulfonamide. The reaction mixture was subsequently neutralized with aqueous HCl and extracted with EtOAc; the organic phase was washed with water (2×100 mL), brine, and then dried (MgSO$_4$), filtered, and concentrated under reduced pressure. The residue was purified by chromatography on silica gel using EtOAc-hexane to provide N-(2-bromo-5-chloro-pyridin-3-yl)-4-chloro-3-methyl-benzenesulfonamide as a white crystalline solid. MS m/z 397.1 (M+H).

Methoxymethyl chloride (1.2 g, 14.3 mmol) was added dropwise to a mixture of N-(2-bromo-5-chloro-pyridin-3-yl)-4-chloro-3-methyl-benzenesulfonamide (5.0 g, 12.7 mmol) and potassium carbonate (3.2 g, 23.2 mmol) in THF (30 mL) at room temperature. After 5 h, the potassium salts were removed by vacuum filtration and the filtrate was concentrated under reduced pressure. The residual light yellow solid was chromatographed on silica gel using ethyl acetate-hexane to provide the N-(2-bromo-5-chloro-pyridin-3-yl)-4-chloro-N-methoxymethyl-3-methyl-benzenesulfonamide as white crystals. MS m/z 441.2 (M+H).

Example 70: 4-Chloro-N-[5-chloro-2-(2-ethoxy-benzoyl)-pyridin-3-yl]-N-methoxymethyl-3-trifluoromethyl-benzenesulfonamide

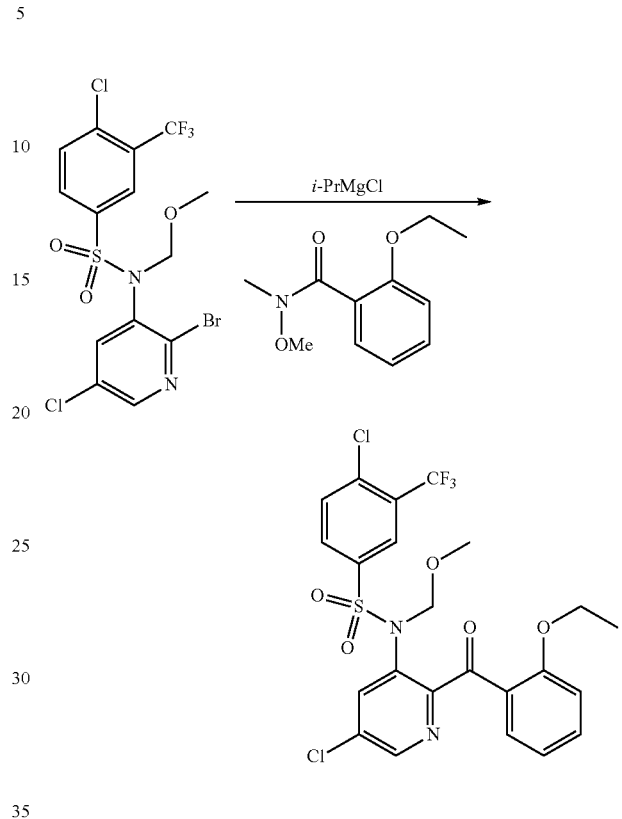

4-Chloro-N-[5-chloro-2-(2-ethoxy-benzoyl)-pyridin-3-yl]-N-methoxymethyl-3-trifluoromethyl-benzenesulfonamide was prepared from 2-ethoxy-N-methoxy-N-methyl-benzamide and N-(2-bromo-5-chloro-pyridin-3-yl)-4-chloro-N-methoxymethyl-3-trifluoromethyl-benzenesulfonamide according to previously described procedure in example 29. The product was purified by flash column chromatography on silica gel using ethyl acetate-hexane. MS m/z: 562.4 (M+H).

Example 71: 4-Chloro-N-[5-chloro-2-(2-ethoxy-benzoyl)-pyridin-3-yl]-3-trifluoromethyl-benzenesulfonamide

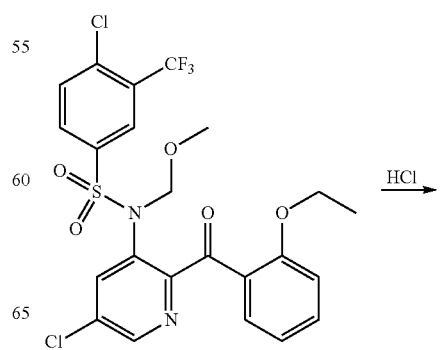

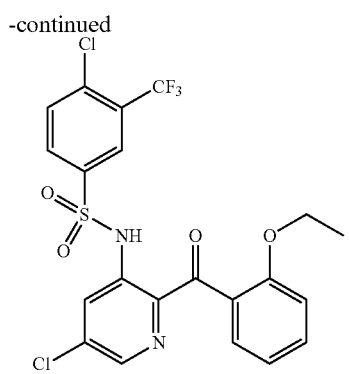

4-Chloro-N-[5-chloro-2-(2-ethoxy-benzoyl)-pyridin-3-yl]-N-methoxymethyl-3-trifluoromethyl-benzenesulfonamide was hydrolyzed using 4 M HCl in dioxane (12 mL) and water (4 mL) at 100° C. to provide 4-chloro-N-[5-chloro-2-(2-ethoxy-benzoyl)-pyridin-3-yl]-3-trifluoromethyl-benzenesulfonamide. Product was purified by HPLC. MS m/z 519.1 (M+H).

Example 72: 4-Chloro-N-[5-chloro-2-(2-methoxy-6-methyl-benzoyl)-pyridin-3-yl]-N-methoxymethyl-3-methyl-benzenesulfonamide

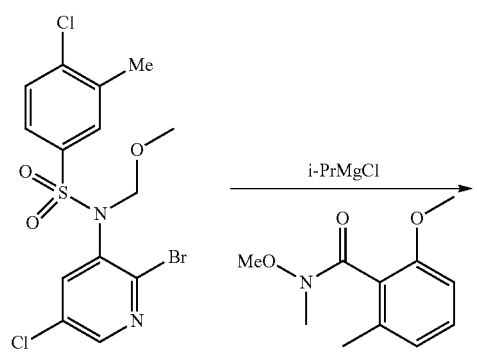

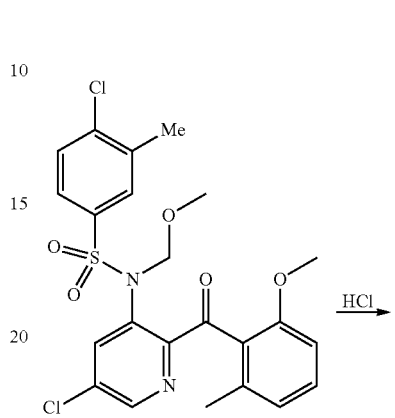

4-Chloro-N-[5-chloro-2-(2-methoxy-6-methyl-benzoyl)-pyridin-3-yl]-N-methoxymethyl-3-methyl-benzenesulfonamide was prepared from N-(2-Bromo-5-chloro-pyridin-3-yl)-4-chloro-N-methoxymethyl-3-methyl-benzenesulfonamide and 2,N-Dimethoxy-6,N-dimethyl-benzamide according to previously described procedure example 29. The product was purified by chromatography on silica gel using ethyl acetate-hexane. MS m/z: 509.4 (M+H).

Example 73: 4-Chloro-N-[5-chloro-2-(2-methoxy-6-methyl-benzoyl)-pyridin-3-yl]-3-methyl-benzenesulfonamide

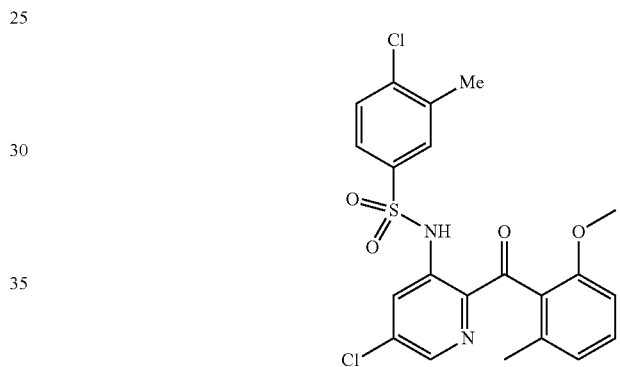

4-Chloro-N-[5-chloro-2-(2-methoxy-6-methyl-benzoyl)-pyridin-3-yl]-N-methoxymethyl-3-methyl-benzenesulfonamide was hydrolyzed using 4 M HCl in dioxane (12 mL), and water (4 mL) at 100° C. to provide 4-chloro-N-[5-chloro-2-(2-methoxy-6-methyl-benzoyl)-pyridin-3-yl]-3-methyl-benzenesulfonamide. The product was purified by HPLC. MS m/z: 465.4 (M+H).

Example 74: N-[5-Chloro-2-(2-fluoro-6-methoxy-benzoyl)-pyridin-3-yl]-N-methoxymethyl-3-trifluoromethyl-benzenesulfonamide

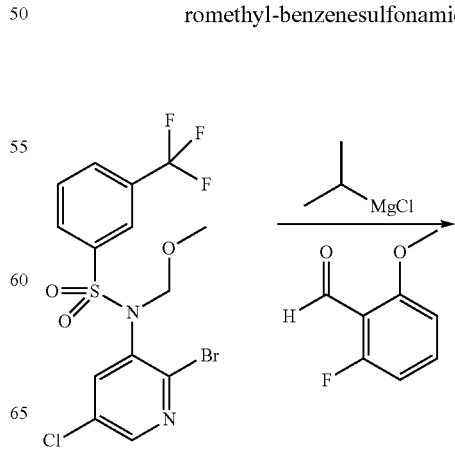

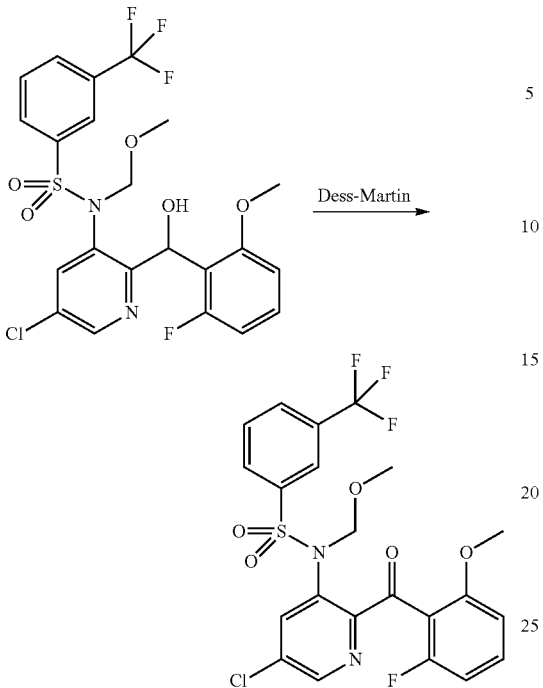

To a stirred solution of N-(2-Bromo-5-chloro-pyridin-3-yl)-N-methoxymethyl-3-trifluoromethyl-benzenesulfonamide (459 mg, 1.00 mmol) in anhydrous THF (5 mL) at −10° C. was added 2 M isopropylmagnesium chloride in THF (1.1 mL, 2.2 mmol) and stirred at the same temperature for 30 min. 2-Fluoro-6-methoxy-benzaldehyde (308 mg, 2.00 mmol) was subsequently added in one portion, and the reaction mixture was warmed to room temperature and stirred overnight (18 h). It was then quenched with saturated aqueous NH₄Cl (10 mL), and extracted with EtOAc (3×75 mL). The combined extracts were washed with aqueous NaHCO₃ and brine, dried (Na₂SO₄), filtered, and concentrated under reduced pressure. The residue was purified by chromatography on silica gel using ethyl acetate-hexane to provide N-{5-chloro-2-[(2-fluoro-6-methoxy-phenyl)-hydroxy-methyl]-pyridin-3-yl}-N-methoxymethyl-3-trifluoromethyl-benzenesulfonamide. MS m/z 535.4 (M+H).

A mixture of N-{5-chloro-2-[(2-fluoro-6-methoxy-phenyl)-hydroxy-methyl]-pyridin-3-yl}-N-methoxymethyl-3-trifluoromethyl-benzenesulfonamide (0.38 g) and Dess-Martin reagent (0.90 g, 2.1 mmol) in CH₂Cl₂ (15 mL) at room temperature was stirred for 5 h. A mixture of 10% aqueous Na₂S₂O₃ (10 mL) and saturated aqueous NaHCO₃ (10 mL) was then added and the biphasic mixture vigorously stirred for 30 min. The organic phase was then separated and the aqueous portion was extracted with CH₂Cl₂. The combined organic extracts were washed with saturated aqueous NaHCO₃ and brine, dried (Na₂SO₄), and filtered. The filtrate was concentrated under reduced pressure and the residue purified by chromatography on silica gel using ethyl acetate-hexane to provide N-[5-chloro-2-(2-fluoro-6-methoxy-benzoyl)-pyridin-3-yl]-N-methoxymethyl-3-trifluoromethyl-benzenesulfonamide. MS m/z 555.1 (M+Na).

Example 75: N-[5-Chloro-2-(2-fluoro-6-methoxy-benzoyl)-pyridin-3-yl]-3-trifluoromethyl-benzenesulfonamide

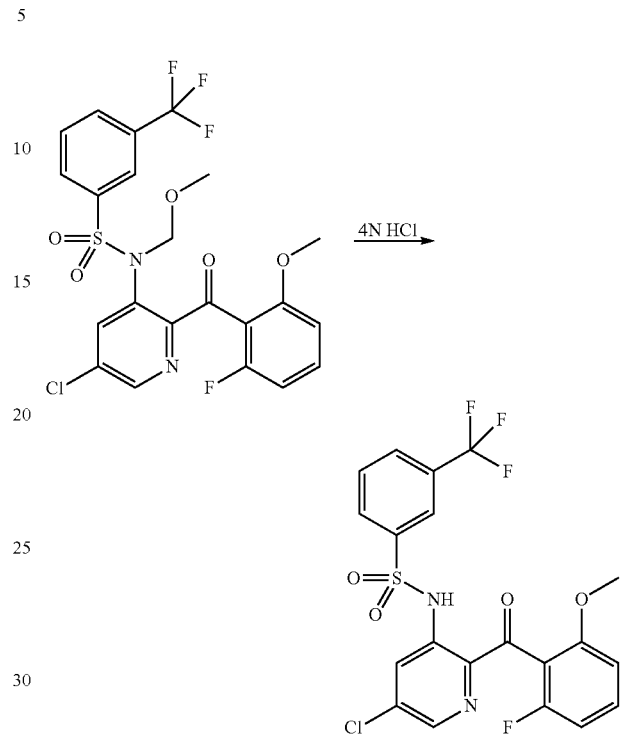

N-[5-Chloro-2-(2-fluoro-6-methoxy-benzoyl)-pyridin-3-yl]-N-methoxymethyl-3-trifluoromethyl-benzenesulfonamide (180 mg, 0.313 mmol) was magnetically stirred in water (1.0 mL) and 4N HCl in dioxane (2.5 mL) and heated at 85° C. for 7 h. The reaction was subsequently concentrated and the residue was neutralized (pH 7) with aqueous sodium bicarbonate and extracted with EtOAc (3×80 mL). The extracts were dried (MgSO₄), filtered, and chromatographed on silica gel using EtOAc-hexane (gradient, 0:100 to 50:50) to provide N-[5-chloro-2-(2-fluoro-6-methoxy-benzoyl)-pyridin-3-yl]-3-trifluoromethyl-benzenesulfonamide: MS m/z 489.1 (M+H); 511.0 (M+Na).

Example 76: 4-Chloro-N-{2-[(2-fluoro-6-methoxy-phenyl)-hydroxy-methyl]-5-methyl-pyridin-3-yl}-N-methoxymethyl-3-trifluoromethyl-benzene sulfonamide

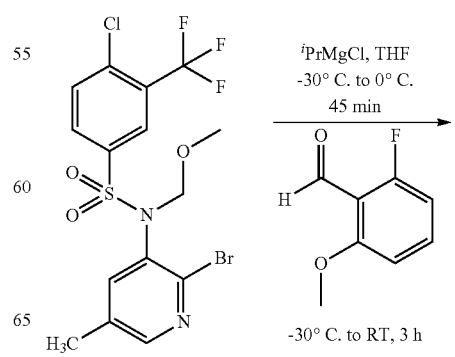

-continued

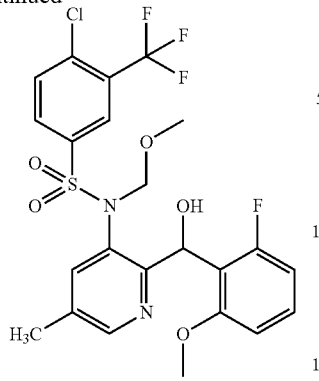

To a solution of N-(2-bromo-5-methyl-pyridin-3-yl)-4-chloro-N-methoxymethyl-3-trifluoromethyl-benzenesulfonamide (158 mg, 0.33 mmol) in THF (3 mL) under nitrogen atmosphere at −30° C. was added isopropylmagnesium chloride (2 M solution in THF, 0.4 mL, 0.8 mmol) via dropwise addition. The mixture was then stirred for 30 min at 0° C. followed by the addition of a solution of 2-fluoro-6-methoxy-benzaldehyde (96.6 mg, 0.63 mmol) at −30° C. The mixture was stirred at room temperature for 3 h, quenched with saturated aqueous NH$_4$Cl solution (5 mL), and extracted with EtOAc (2×25 mL). The combined organic extracts were washed with saturated aqueous NH$_4$Cl solution (25 mL) and brine (25 mL), dried (Na$_2$SO$_4$), and concentrated under reduced pressure. The obtained residue was purified by flash column chromatography on silica gel (30% EtOAc-hexanes) to obtain 4-chloro-N-{2-[(2-fluoro-6-methoxyphenyl)-hydroxy-methyl]-5-methyl-pyridin-3-yl}-N-methoxymethyl-3-trifluoromethyl-benzenesulfonamide (110 mg) as yellow syrup in 60% yield. ESMS m/z: 549 (M+H).

-continued

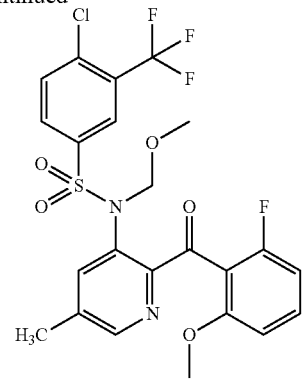

To a solution of 4-chloro-N-{2-[(2-fluoro-6-methoxyphenyl)-hydroxy-methyl]-5-methyl-pyridin-3-yl}-N-methoxymethyl-3-trifluoromethyl-benzenesulfonamide (110 mg, 0.2 mmol) in CH$_2$Cl$_2$ (5 mL) was added Dess-Martin periodinane (170 mg, 0.4 mmol) and stirred for 3 h at room temperature. 10% aqueous Na$_2$S$_2$O$_3$ (5 mL) and saturated aqueous NaHCO$_3$ solution (5 mL) were added and stirred for 30 min. The aqueous layer was then extracted with EtOAc (2×25 mL). The combined organic extracts were subsequently washed with saturated aqueous NaHCO$_3$ solution (20 mL) and brine (20 mL), dried (Na$_2$SO$_4$), concentrated to obtain 4-chloro-N-[2-(2-fluoro-6-methoxy-benzoyl)-5-methyl-pyridin-3-yl]-N-methoxymethyl-3-trifluoro-methyl-benzenesulfonamide (85.4 mg) in 78% yield which was used without further purification. MS m/z: 515 (M+H-MeOH), 569 (M+Na).

Example 77: 4-Chloro-N-[2-(2-fluoro-6-methoxy-benzoyl)-5-methyl-pyridin-3-yl]-N-methoxymethyl-3-trifluoromethyl-benzenesulfonamide Example 78: 4-Chloro-N-[2-(2-fluoro-6-methoxy-benzoyl)-5-methyl-pyridin-3-yl]-3-trifluoromethyl-benzenesulfonamide

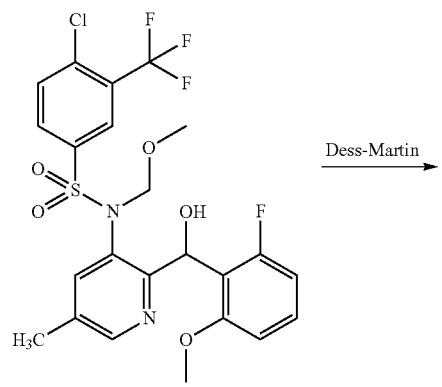

Dess-Martin →

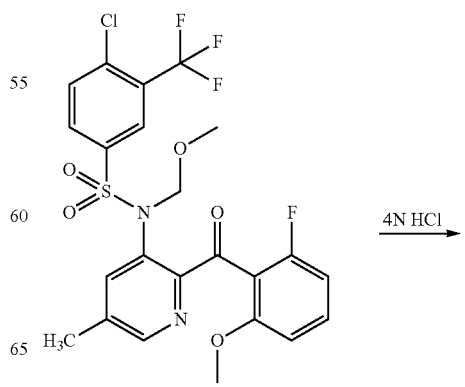

4N HCl →

-continued

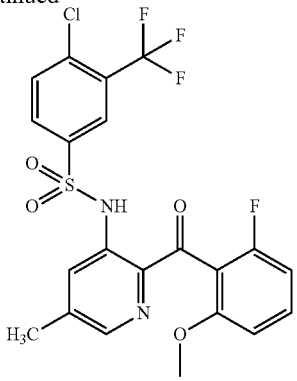

A mixture of 4-chloro-N-[2-(2-fluoro-6-methoxy-benzoyl)-5-methyl-pyridin-3-yl]-N-methoxymethyl-3-trifluoromethyl-benzenesulfonamide (85 mg, 0.15 mmol) in 4 M HCl in dioxane (5 mL) and water (1 mL) was refluxed for 3 h. The reaction mixture was cooled to room temperature, evaporated to dryness, and neutralized with saturated aqueous NaHCO$_3$ solution to pH 7-8. The mixture was extracted with EtOAc (2×25 mL), dried (Na$_2$SO$_4$), filtered and concentrated. The obtained residue was purified by flash column chromatography on silica gel (70% EtOAc-hexanes) to afford 4-chloro-N-[2-(2-fluoro-6-methoxy-benzoyl)-5-methyl-pyridin-3-yl]-3-trifluoromethyl-benzenesulfonamide (55 mg) as an off white solid in 70% yield. MS m/z 503 (M+H).

Example 79: 4-Chloro-N-{5-chloro-2-[(2-chloro-6-fluoro-phenyl)-hydroxy-methyl]-pyridin-3-yl}-N-methoxymethyl-3-trifluoromethyl-benzenesulfonamide

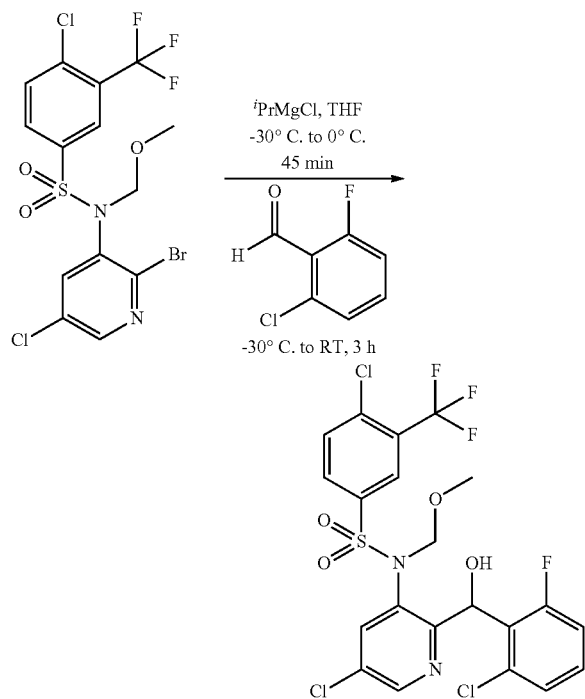

To a solution of N-(2-bromo-5-methyl-pyridin-3-yl)-4-chloro-N-methoxymethyl-3-trifluoromethyl-benzenesulfonamide (246 mg, 0.5 mmol) in THF (3 mL) under nitrogen atmosphere at −30° C. was added isopropylmagnesium chloride (2 M solution in THF, 0.6 mL, 1.2 mmol) via dropwise addition. The mixture was then stirred for 30 min at 0° C. followed by the addition of a solution of 2-chloro-6-fluoro-benzaldehyde (150.6 mg, 0.95 mmol) at −30° C. The mixture was stirred at room temperature for 3 h, quenched with saturated aqueous NH$_4$Cl solution (5 mL) and extracted with EtOAc (2×25 mL). The combined organic layers were washed with saturated aqueous NH$_4$Cl solution (25 mL) and brine (25 mL), dried (Na$_2$SO$_4$), and concentrated under reduced pressure. The obtained residue was purified by flash column chromatography on silica gel (30% EtOAc-hexanes) to obtain 4-chloro-N-{5-chloro-2-[(2-chloro-6-fluoro-phenyl)-hydroxy-methyl]-pyridin-3-yl}-N-methoxymethyl-3-trifluoromethyl-benzenesulfonamide (144 mg) as yellow syrup in 51% yield. MS m/z 573 (M+H).

Example 80: 4-Chloro-N-[5-chloro-2-(2-chloro-6-fluoro-benzoyl)-pyridin-3-yl]-N-methoxymethyl-3-trifluoromethyl-benzenesulfonamide

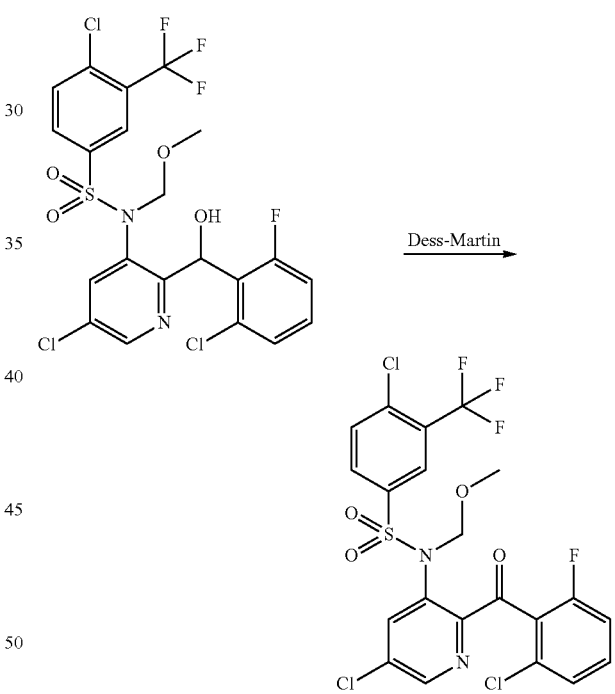

To a solution of 4-chloro-N-{5-chloro-2-[(2-chloro-6-fluoro-phenyl)-hydroxy-methyl]-pyridin-3-yl}-N-methoxymethyl-3-trifluoromethyl-benzenesulfonamide (144 mg, 0.252 mmol) in CH$_2$Cl$_2$ (5 mL) was added Dess-Martin periodinane (213.5 mg, 0.5 mmol) and stirred for 3 h at room temperature. 10% aqueous Na$_2$S$_2$O$_3$ (5 mL) and saturated aqueous NaHCO$_3$ solution (5 mL) were added to the reaction mixture and stirred for 30 min. The aqueous layer was then extracted with EtOAc (2×25 mL). The combined organic extracts were subsequently washed with saturated aqueous NaHCO$_3$ solution (20 mL) and brine (20 mL), dried (Na$_2$SO$_4$), and concentrated to obtain 4-chloro-N-[5-chloro-2-(2-chloro-6-fluoro-benzoyl)-pyridin-3-yl]-N-methoxymethyl-3-trifluoromethyl-benzenesulfonamide (107 mg) in 75% yield which was used without further purification. MS m/z: 539 (M-MeOH+H), 593 (M+Na).

Example 81: 4-chloro-N-[5-chloro-2-(2-chloro-6-fluoro-benzoyl)-pyridin-3-yl]-3-trifluoromethyl-benzenesulfonamide

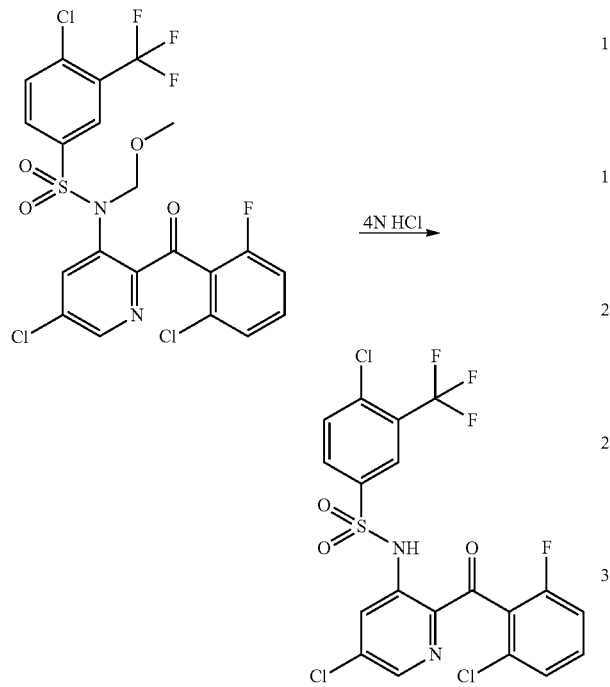

A mixture of 4-chloro-N-[5-chloro-2-(2-chloro-6-fluoro-benzoyl)-pyridin-3-yl]-N-methoxymethyl-3-trifluoromethyl-benzenesulfonamide (100 mg, 0.17 mmol) in 4 M HCl in dioxane (5 mL) and water (1 mL) was heated at reflux for 3 h. The reaction mixture was cooled to room temperature, evaporated to dryness, and neutralized with saturated aqueous NaHCO₃ solution to pH 7-8. The mixture was extracted with EtOAc (2×25 mL), dried (Na₂SO₄), filtered and concentrated. The residual solid was purified by flash column chromatography (70% EtOAc-hexanes) on silica gel to afford 4-chloro-N-[5-chloro-2-(2-chloro-6-fluoro-benzoyl)-pyridin-3-yl]-3-trifluoromethyl-benzenesulfonamide (62 mg) as an off white solid in 67% yield. MS m/z: 527 (M+H), 549 (M+Na).

Example 82: 4-Chloro-N-[5-chloro-2-(7-chloro-3-oxo-1,3-dihydro-isobenzofuran-1-yl)-pyridin-3-yl]-N-methoxymethyl-3-trifluoromethyl-benzenesulfonamide

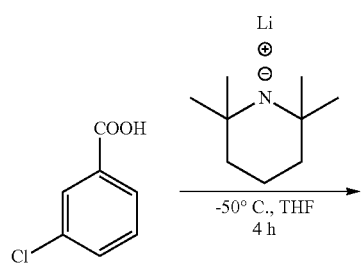

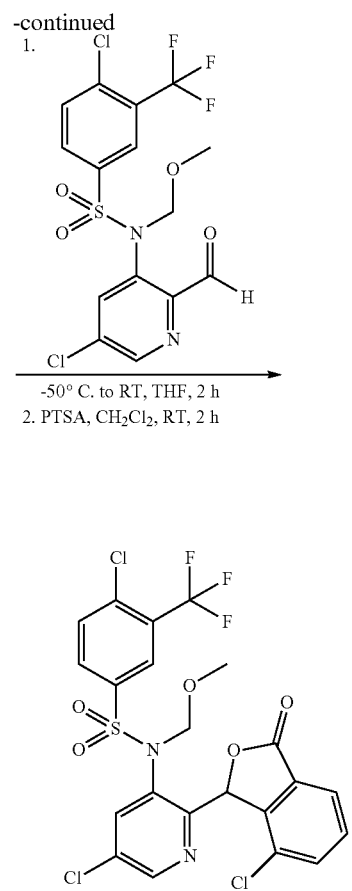

To a solution of n-BuLi in hexane (0.69 mL, 1.1 mmol, 1.6 M solution in hexane) under N₂ atm at −20° C. was added a solution of 2,2,6,6-tetramethyl piperidine (TMP, 187 µL) in THF (1 mL). The mixture cooled to −50° C. and a solution of 3-chlorobenzoic acid (78.3 mg, 0.5 mmol) in THF (0.5 mL) was added. The resulting reaction mixture was stirred at −50° C. for 4 h and treated slowly with 4-chloro—N-(5-chloro-2-formyl-pyridin-3-yl)-N-methoxymethyl-3-trifluoromethyl-benzenesulfonamide (884 mg, 2.0 mmol) in THF (1 mL), warmed to room temperature and stirred for 2 h. The reaction mixture was slowly poured in ice cold water (10 mL), and ether was added. The bilayer was separated and the aqueous portion was washed with diethyl ether (2×25 mL) and separated. The aqueous layer was acidified with 4 N HCl solutions to pH 2 and extracted with diethyl ether (2×25 mL). The combined organic extracts were dried (Na₂SO₄), filtered and evaporated. The residual solid was dissolved in CH₂Cl₂ (5 mL), treated with p-toluenesulfonic acid monohydrate (100 mg), and stirred at room temperature for 2 h. The reaction mixture was concentrated and purified by flash chromatography (25% EtOAc in hexanes) to obtain 4-chloro-N-[5-chloro-2-(7-chloro-3-oxo-1,3-dihydro-isobenzofuran-1-yl)-pyridin-3-yl]-N-methoxymethyl-3-trifluoromethyl-benzenesulfonamide (77 mg) in 26.6% yield. MS m/z: 581 (M+H).

Example 83: 4-Chloro-N-[5-chloro-2-(7-chloro-3-oxo-1,3-dihydro-isobenzofuran-1-yl)-pyridin-3-yl]-3-trifluoromethyl-benzenesulfonamide

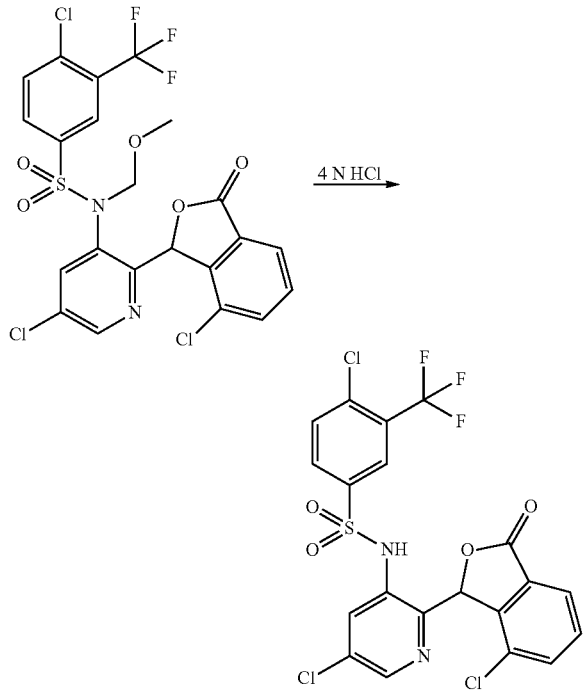

A mixture of 4-chloro-N-[5-chloro-2-(7-chloro-3, 3-dihydro-isobenzofuran-1-yl)-pyridin-3-yl]-N-methoxymethyl-3-trifluoromethyl-benzene-sulfonamide (77 mg, 0.13 mmol) in 4M HCl in dioxane (3 mL) and water (1 mL) was heated at reflux for 3 h. The reaction mixture was then cooled to room temperature, evaporated to dryness and neutralized with saturated aqueous NaHCO₃ solution to pH 2-3. The aqueous layer was extracted with EtOAc (2×25 mL), dried (Na₂SO₄), and concentrated. The obtained residue was purified by flash chromatography on silica gel (50% EtOAc-hexanes) to afford 4-chloro-N-[5-chloro-2-(7-chloro-3-oxo-1,3-dihydro-isobenzofuran-1-yl)-pyridin-3-yl]-3-trifluoromethyl-benzenesulfonamide (40 mg) as a white solid in 56% yield. MS m/z: 537 (M+H), 559 (M+Na).

Example 84: 4-Chloro-N-[5-chloro-2-(3-oxo-1,3-dihydro-isobenzofuran-1-yl)-pyridin-3-yl]-N-methoxymethyl-3-trifluoromethyl-benzenesulfonamide

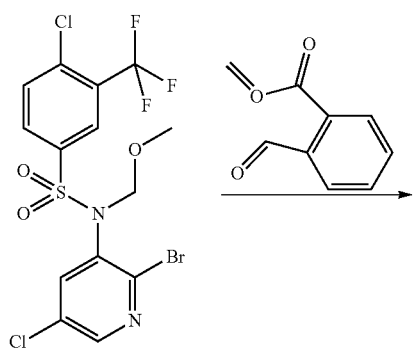

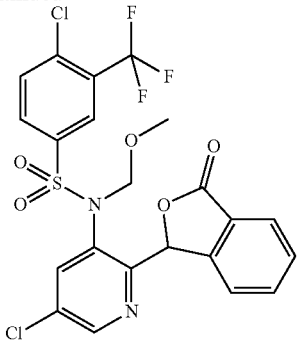

To a solution of N-(2-bromo-5-chloro-pyridin-3-yl)-4-chloro-N-methoxymethyl-3-trifluoromethyl-benzenesulfonamide (250 mg, 0.50 mmol) in THF (3.0 mL) under nitrogen atmosphere at 0° C. was added isopropylmagnesium chloride (0.60 mL, 1.2 mmol, 2 M in THF). The mixture was then stirred for 30 min at 0° C. and 2-formylbenzoic acid methyl ester (164 mg, 1.0 mmol) was added. The aqueous layer was stirred at room temperature overnight, quenched with saturated aqueous ammonium chloride, and followed by sodium bicarbonate to pH 6. The mixture was extracted with ethyl acetate, dried, and concentrated to provide 4-chloro-N-[5-chloro-2-(3-oxo-1,3-dihydro-isobenzofuran-1-yl)-pyridin-3-yl]-N-methoxymethyl-3-trifluoromethyl-benzenesulfonamide. The crude residue was used directly in the next step.

Example 85: 4-Chloro-N-[5-chloro-2-(3-oxo-1,3-dihydro-isobenzofuran-1-yl)-pyridin-3-yl]-3-trifluoromethyl-benzenesulfonamide

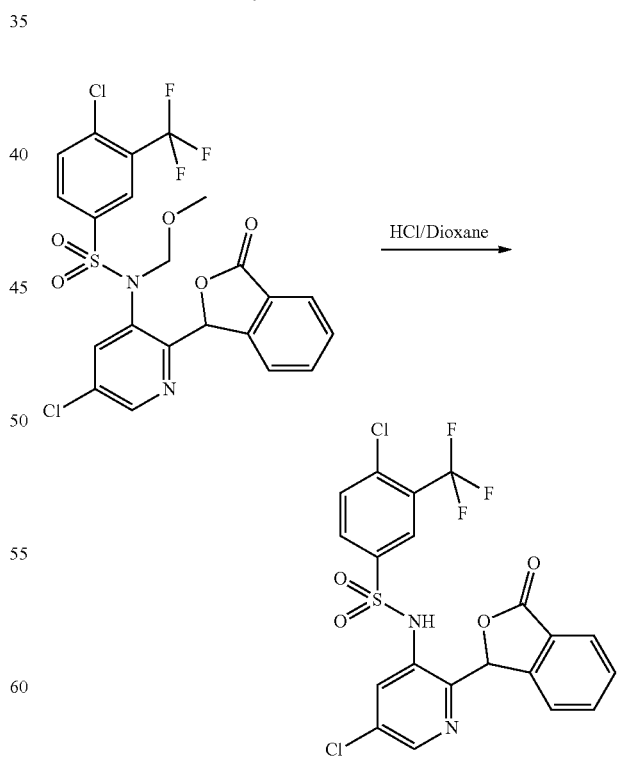

A solution of 4-chloro-N-[5-chloro-2-(3-oxo-1,3-dihydro-isobenzofuran-1-yl)-pyridin-3-yl]-N-methoxymethyl-3-trifluoromethyl-benzenesulfonamide in 3 mL HCl (4

M in dioxane) and 1 mL water was refluxed for 2 h. After cooling to room temperature, the mixture was concentrated and the residue was purified via preparative TLC (50% EtOAc in hexane) to provide 11 mg of 4-chloro-N-[5-chloro-2-(3-oxo-1,3-dihydro-isobenzofuran-1-yl)-pyridin-3-yl]-3-trifluoromethyl-benzenesulfonamide as an off white solid. MS m/z 503.3 (M+H).

Example 86: N-[2-(2-Amino-benzoyl)-5-chloro-pyridin-3-yl]-4-chloro-N-methoxymethyl-3-trifluoromethyl-benzenesulfonamide

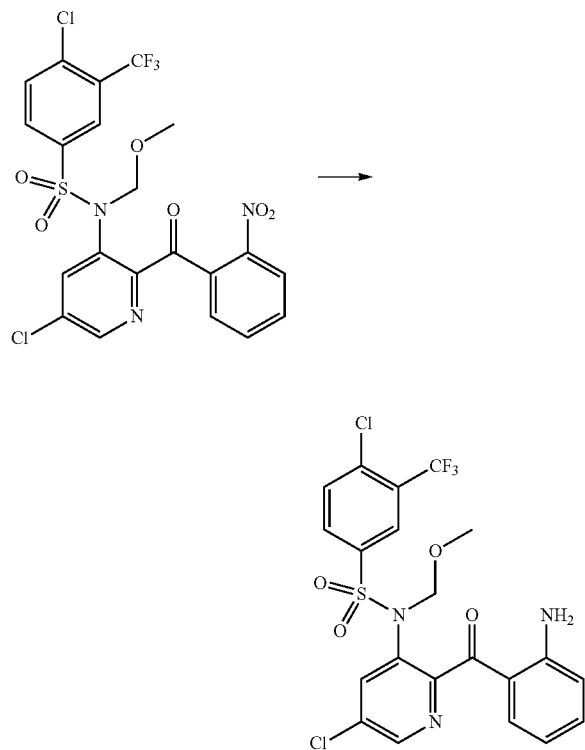

To a stirred suspension of Fe (376 mg, 6.73 mmol) in glacial AcOH (10 mL) at 80° C. was added a solution 4-chloro-N-[5-chloro-2-(2-nitro-benzoyl)-pyridin-3-yl]-N-methoxymethyl-3-trifluoromethyl-benzenesulfonamide (700 mg, 1.34 mmol) in AcOH (5 mL) over 15 min. After complete addition, the mixture was stirred for 2 h and the progress of the reaction was followed by LCMS. Upon consumption of reactants, the reaction mixture was cooled to room temperature, diluted with EtOAc, and filtered through a pad of Celite. The filtrate was concentrated under reduced pressure and residue was partitioned with aqueous NaHCO₃ and EtOAc. The organic portion was separated and the aqueous portion was extracted with EtOAc. The combined extracts were dried (Na₂SO₄), filtered, and concentrated under reduced pressure. The residue was purified by flash column chromatography on silica gel to provide N-[2-(2-amino-benzoyl)-5-chloro-pyridin-3-yl]-4-chloro-N-methoxymethyl-3-trifluoromethyl-benzenesulfonamide. MS m/z: 556.0 (M+Na).

Example 87: 4-Chloro-N-{5-chloro-2-[2-(methanesulfonyl-methyl-amino)-benzoyl]-pyridin-3-yl}-N-methoxymethyl-3-trifluoromethyl-benzenesulfonamide

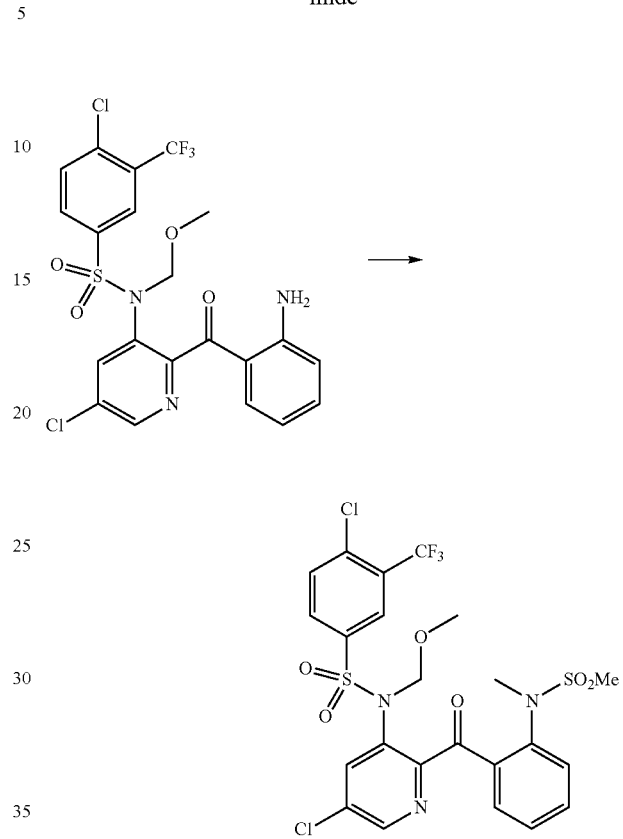

To a stirred suspension of N-[2-(2-amino-benzoyl)-5-chloro-pyridin-3-yl]-4-chloro-N-methoxymethyl-3-trifluoromethyl-benzenesulfonamide in pyridine (1 mL) was added methanesulfonyl chloride (26 mg, 0.226 mmol). After 2 h the reaction mixture was poured into 1 M HCl and the aqueous portions were subsequently extracted with EtOAc. The combined extracts were dried and concentrated under reduced pressure. The resulting residue was dissolved in THF (5 mL), treated with TBAF (1 M in THF, 200 FL, 0.200 mmol), and then stirred at room temperature for 3-4 h. The reaction mixture was subsequently poured into 1 M HCl and the aqueous layer was extracted with EtOAc. The combined organic extracts were dried (Na₂SO₄), filtered, and concentrated under reduced pressure to provide 4-chloro-N-[5-chloro-2-(2-methanesulfonylamino-benzoyl)-pyridin-3-yl]-N-methoxymethyl-3-trifluoromethyl-benzenesulfonamide. MS m/z: 634.0 (M+Na).

A mixture of this crude product, K₂CO₃ (31 mg, 0.226 mmol), and iodomethane (15 FL, 0.226 mmol) in anhydrous DMF (1 mL) were stirred at 50° C. overnight. The resulting mixture was poured into water and extracted with EtOAc. The extracts were concentrated to dryness under reduced pressure to provide 4-chloro-N-{5-chloro-2-[2-(methanesulfonyl-methyl-amino)-benzoyl]-pyridin-3-yl}-N-methoxymethyl-3-trifluoromethyl-benzenesulfonamide. MS m/z: 648.3 (M+Na).

Example 88: 4-Chloro-N-{5-chloro-2-[2-(methanesulfonyl-methyl-amino)-benzoyl]-pyridin-3-yl}-3-trifluoromethyl-benzenesulfonamide

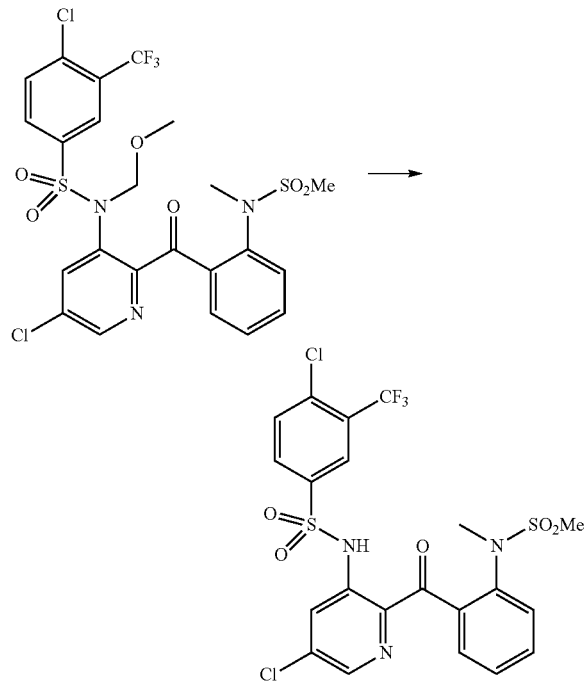

A mixture 4-chloro-N-{5-chloro-2-[2-(methanesulfonyl-methyl-amino)-benzoyl]-pyridin-3-yl}-N-methoxymethyl-3-trifluoromethyl-benzenesulfonamide (30 mg crude) in 4 M HCl in dioxane (12 mL) and water (4 mL) were heated at 100° C. for 18 h. The reaction mixture was concentrated to dryness under reduced pressure and subsequently neutralized aqueous NaHCO₃ to pH to 5-6. The aqueous layer was extracted with EtOAc, the combined extracts were dried (Na₂SO₄), filtered, and concentrated under reduced pressure. The residue was purified by preparative HPLC (20→80% gradient of MeCN-water) to provide 4-chloro-N-{5-chloro-2-[2-(methanesulfonyl-methyl-amino)-benzoyl]-pyridin-3-yl}-3-trifluoromethyl-benzenesulfonamide as a solid. MS m/z: 582.0 (M+H).

Example 89: 5-Chloro-2-(2-fluoro-6-methoxy-phenoxy)-pyridin-3-ylamine

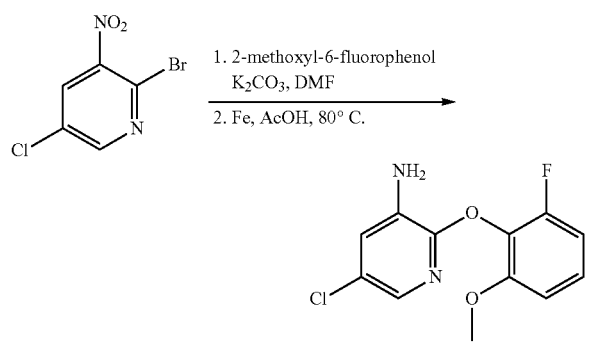

To a stirred solution of 2-bromo-5-chloro-3-nitropyridine (2.37 g, 10 mmol) was dissolved in 40 mL DMF was added of 2-methoxyl-6-fluorophenol (1.7 g 11.9 mmol) was added into the solution followed by potassium carbonate (2.76, 20 mmol). The mixture was stirred at room temperature for 5 h, then poured into ice water (200 mL). The precipitate was filtered and dried under high vacuum to provide 5-chloro-2-(2-fluoro-6-methoxy-phenoxy)-3-nitro-pyridine.

AcOH (30 mL) and iron powder (5 g) were charged into a round bottom flask equipped with a magnetic stirring bar and warmed to 80° C. A solution of crude 5-chloro-2-(2-fluoro-6-methoxy-phenoxy)-3-nitro-pyridine in AcOH was added slowly into the mixture, keeping the temperature under 85° C. The reaction mixture was then cooled to room temperature, diluted with EtOAc, and filtered through a pad of Celite. The filtrate was concentrated under reduced pressure and the residue was partitioned between NaHCO₃ and EtOAc. The organic portion was separated and the aqueous portion was extracted with EtOAc. The combined extracts were dried (Na₂SO₄), filtered, and concentrated under reduced pressure. The residue was purified by flash column chromatography on silica gel to provide 5-chloro-2-(2-fluoro-6-methoxy-phenoxy)-pyridin-3-ylamine (3.56 g) as a colorless powder.

Example 90: General Procedure C: Synthesis of 3-Amino-5-chloro-pyridin-2-yl Aryl Ketones

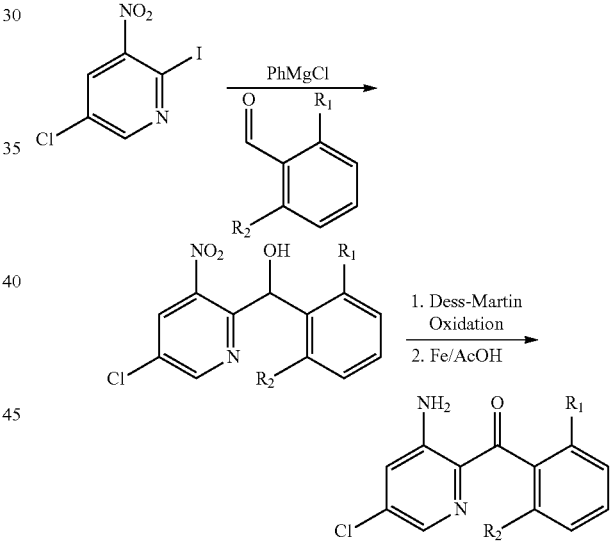

Step 1: To a stirred solution of 5-chloro-2-iodo-3-nitropyridine (2.85 g, 10.01 mmol) in anhydrous THF (20 mL) at −78° C. was added 2 M phenylmagnesiumchloride in THF (5.22 mL, 10.5 mmol). The reaction mixture stirred at the same temperature for 30 min and the appropriate aldehyde (15 mmol) was added in one portion (either via syringe if liquid or as solid). and the progress of the reaction was followed by LCMS. The reaction mixture was warmed to room temperature and stirred several hours (5-18 h). It was then quenched with saturated aqueous NH₄Cl (10 mL), and the aqueous layer was extracted with EtOAc. The combined extracts were washed with aqueous NaHCO₃ and brine, dried (Na₂SO₄), filtered, and concentrated under reduced pressure to afford the desired benzylic alcohol which was directly in the following reaction without further purification.

Step 2: A mixture of crude secondary alcohol and Dess-Martin periodinane (6.4 g, 15 mmol) in CH$_2$Cl$_2$ (30 mL) at room temperature was stirred for 5-10 h. A mixture of 10% aqueous Na$_2$S$_2$O$_3$ (20 mL) and saturated aqueous NaHCO$_3$ (20 mL) was then added and the biphasic mixture vigorously stirred for 30 min. The phases were then separated and the aqueous portion extracted with CH$_2$Cl$_2$. The combined organic extracts were washed with saturated aqueous NaHCO$_3$ and brine, dried (Na$_2$SO$_4$), and filtered. The filtrate was concentrated under reduced pressure and the residue purified by flash column chromatography over silica gel to provide the corresponding nitro ketone.

Step 3: To a stirred suspension of Fe (4-5 equiv.) in glacial AcOH at 80° C. was added a solution of nitropyridyl ketone (1 equiv.) in AcOH (5 mL) over 15 minutes. After complete addition, the mixture was stirred at the same temperature for 1-2 h. The reaction mixture was cooled to room temperature, and diluted with EtOAc and filtered through a pad of Celite. The filtrate was concentrated under reduced pressure and residue was partitioned between NaHCO$_3$ and EtOAc. The organic layer was separated and the aqueous portion was extracted with EtOAc. The combined extracts were dried (Na$_2$SO$_4$), filtered, and concentrated under reduced pressure. The residue was purified by flash column chromatography on silica gel to provide the corresponding aniline.

Example 91: (3-Amino-5-chloro-pyridin-2-yl)-(2-chloro-phenyl)-methanone

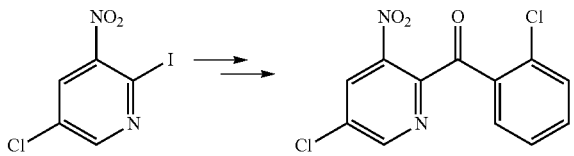 [SMILES: O=[N+]([O-])c1cc(Cl)cnc1I ; O=C(c1ccccc1Cl)c1ncc(Cl)cc1[N+](=O)[O-]]

(3-Amino-5-chloro-pyridin-2-yl)-(2-chloro-phenyl)-methanone was prepared from 2-chlorobenzaldehyde and 5-chloro-2-iodo-3-nitro-pyridine in three steps according to the general procedure for synthesis of 3-Amino-5-chloro-pyridin-2-yl aryl ketones. MS m/z: 267.0 (M+H).

Example 92: (3-Amino-5-chloro-pyridin-2-yl)-(2-methoxy-phenyl)-methanone

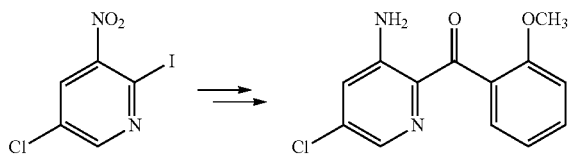 [SMILES: O=[N+]([O-])c1cc(Cl)cnc1I ; COc1ccccc1C(=O)c1ncc(Cl)cc1N]

(3-Amino-5-chloro-pyridin-2-yl)-(2-methoxy-phenyl)-methanone was prepared from 2-methoxybenzaldehyde and 5-chloro-2-iodo-3-nitro-pyridine in three steps according to the General Procedure C. MS m/z: 263.1 (M+H).

Example 93: (3-Amino-5-chloro-pyridin-2-yl)-(2-fluoro-6-methoxy-phenyl)-methanone

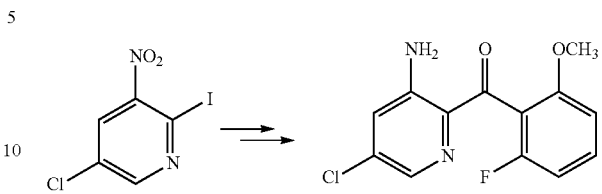

(3-Amino-5-chloro-pyridin-2-yl)-(2-fluoro-6-methoxy-phenyl)-methanone was prepared from 2-fluoro-6-methoxy-benzaldehyde and 5-chloro-2-iodo-3-nitro-pyridine in three steps according to the General Procedure C. MS m/z: 281.0 (M+Na).

Example 94: 3,4-Dichloro-N-[5-chloro-2-(2-chloro-benzoyl)-pyridin-3-yl]-benzenesulfonamide

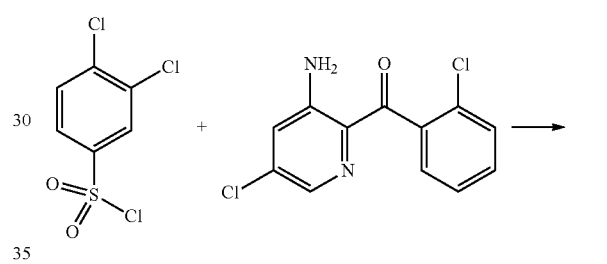

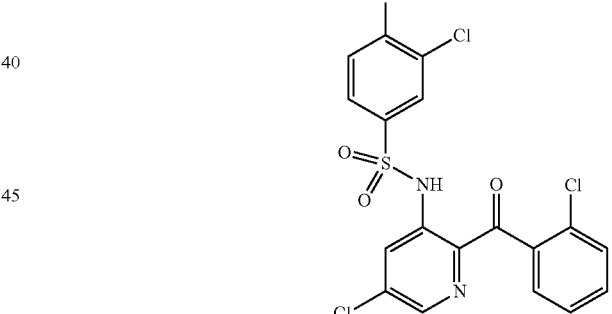

A mixture of (3-amino-5-chloro-pyridin-2-yl)-(2-chloro-phenyl)-methanone (26.8 mg, 0.10 mmol) and 3,4-dichloro-benzenesulfonyl chloride (24.5 mg, 0.10 mmol) in anhydrous pyridine (1 mL) were stirred overnight at 60° C. Reaction mixture was concentrated and the residue was treated with 1 M NaOH (5 mL) and THF(5 mL) to hydrolyze bis-sulfonamide. The resultant solution was neutralized to pH 6 and the aqueous layer was extracted with EtOAc. The combined organic extracts were washed with brine, dried (Na$_2$SO$_4$) and concentrated. The was purified by preparative HPLC (20→90% gradient of MeCN-water) and pure product fractions were lyophilized to provide 3,4-dichloro-N-[5-chloro-2-(2-chloro-benzoyl)-pyridin-3-yl]-benzenesulfonamide as a solid. MS m/z: 498.0 (M+Na).

Example 95: 3,4-Dichloro-N-[5-chloro-2-(2-methoxy-benzoyl)-pyridin-3-yl]-benzenesulfonamide

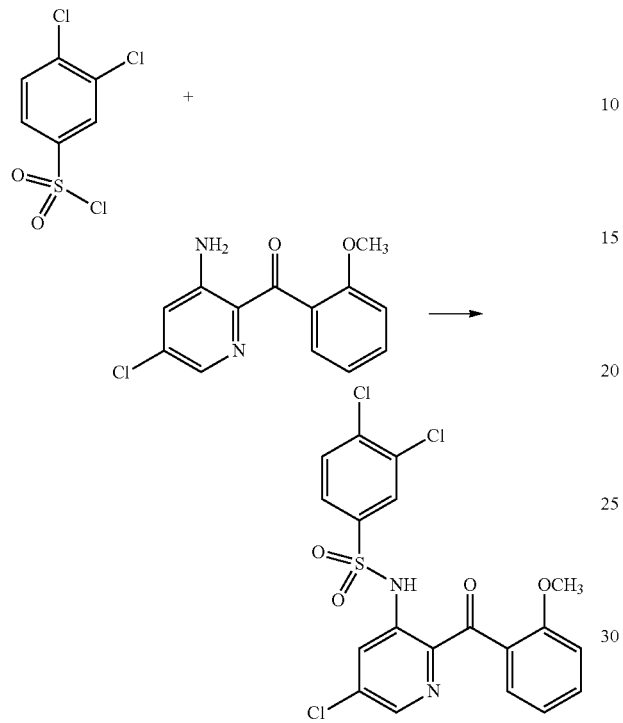

Following the procedure in example 94, 3,4-dichloro-N-[5-chloro-2-(2-methoxy-benzoyl)-pyridin-3-yl]-benzenesulfonamide was synthesized from (3-amino-5-chloro-pyridin-2-yl)-(2-methoxy-phenyl)-methanone (54 mg, 0.206 mmol) and 3,4-dichloro-benzenesulfonyl chloride (101 mg, 0.412 mmol). MS m/z: 471.0 (M+H).

Example 96: 3,4-Dichloro-N-[5-chloro-2-(2-fluoro-6-methoxy-benzoyl)-pyridin-3-yl]-benzenesulfonamide

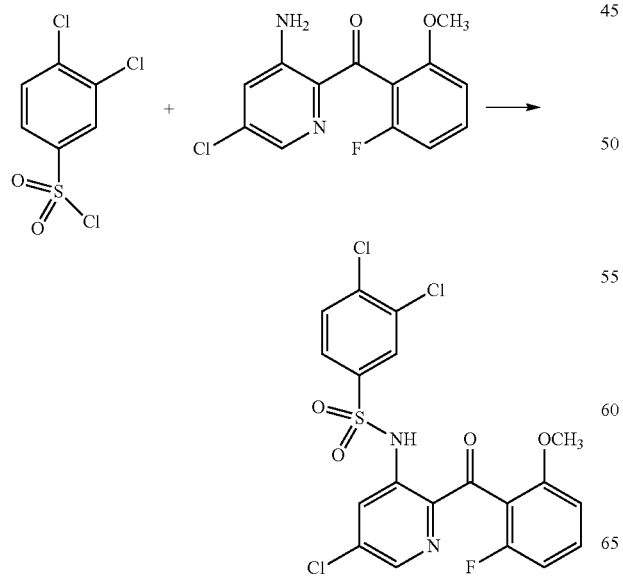

Following the procedure in example 94, 3,4-dichloro-N-[5-chloro-2-(2-fluoro-6-methoxy-benzoyl)-pyridin-3-yl]-benzenesulfonamide was synthesized from (3-amino-5-chloro-pyridin-2-yl)-(2-fluoro-6-methoxy-phenyl)-methanone (54 mg, 0.192 mmol) and 3,4-dichloro-benzenesulfonyl chloride (87 mg, 0.368 mmol). MS m/z: 510.9 (M+Na).

Example 97: 4-Chloro-N-[5-chloro-2-(2-fluoro-6-methoxy-benzoyl)-pyridin-3-yl]-3-methyl-benzenesulfonamide

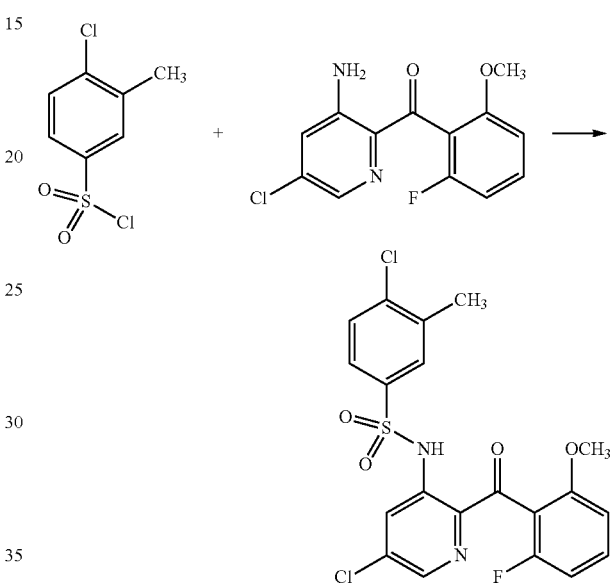

Following the procedure in example 94, 4-chloro-N-[5-chloro-2-(2-fluoro-6-methoxy-benzoyl)-pyridin-3-yl]-3-methyl-benzenesulfonamide was synthesized from (3-amino-5-chloro-pyridin-2-yl)-(2-fluoro-6-methoxy-phenyl)-methanone (56 mg, 0.20 mmol) and 4-Chloro-3-methyl-benzenesulfonyl chloride (87 mg, 0.368 mmol). MS m/z: 491.0 (M+Na).

Example 98: 4-Chloro-N-[5-chloro-2-(2-fluoro-6-methoxy-benzoyl)-pyridin-3-yl]-3-methyl-benzenesulfonamide

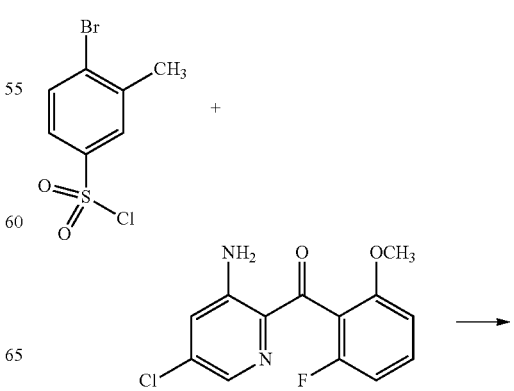

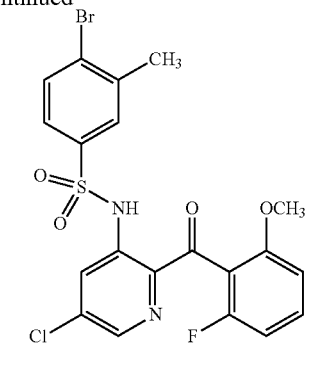

Following the procedure in example 94, 4-chloro-N-[5-chloro-2-(2-fluoro-6-methoxy-benzoyl)-pyridin-3-yl]-3-methyl-benzenesulfonamide was synthesized from (3-amino-5-chloro-pyridin-2-yl)-(2-fluoro-6-methoxy-phenyl)-methanone (66 mg, 0.20 mmol) and 4-bromo-3-methyl-benzenesulfonyl chloride (120 mg, 0.448 mmol). MS m/z: 491.0 (M+Na).

Example 99: 2-Chloro-N-[5-chloro-2-(2-fluoro-6-methoxy-benzoyl)-pyridin-3-yl]-benzenesulfonamide

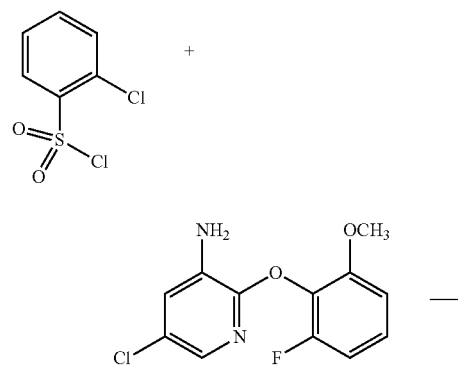

Following the procedure in example 94, 2-chloro-N-[5-chloro-2-(2-fluoro-6-methoxy-benzoyl)-pyridin-3-yl]-benzenesulfonamide was synthesized from (3-amino-5-chloro-pyridin-2-yl)-(2-fluoro-6-methoxy-phenyl)-methanone (50 mg, 0.178 mmol) and 2-chloro-benzenesulfonyl chloride (83 mg, 0.392 mmol). MS m/z: 455.0 (M+H).

Example 100: 4-Chloro-N-[5-chloro-2-(2-fluoro-6-methoxy-phenoxy)-pyridin-3-yl]-3-trifluoromethyl-benzenesulfonamide

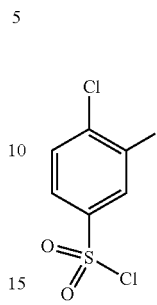

Following the procedure in example 94, 4-chloro-N-[5-chloro-2-(2-fluoro-6-methoxy-phenoxy)-pyridin-3-yl]-3-trifluoromethyl-benzenesulfonamide was synthesized from 5-chloro-2-(2-fluoro-6-methoxy-phenoxy)-pyridin-3-ylamine (100 mg), 4-chloro-3-trifluoromethyl-benzenesulfonyl chloride (100 mg). MS m/z: 511.1 (M+H).

Example 101: 5-Chloro-3-[(4-chloro-3-trifluoromethyl-benzenesulfonyl)-methoxymethyl-amino]-pyridine-2-carboxylic Acid

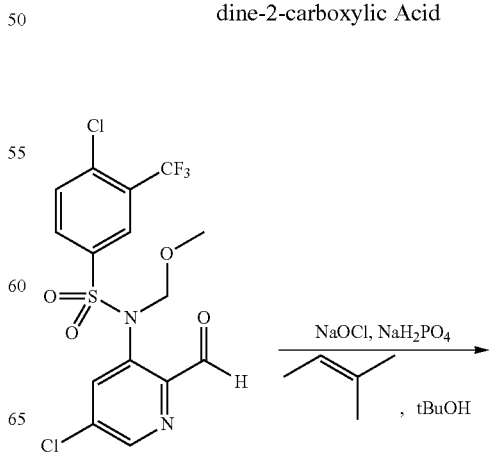

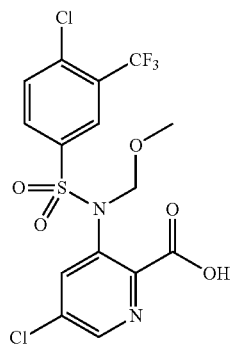

To a solution of 4-chloro-N-(5-chloro-2-formyl-pyridin-3-yl)-N-methoxymethyl-3-trifluoromethyl-benzenesulfonamide (590 mg, 1.33 mmol) in tert-butanol (26 mL) was added isobutylene (5 mL), sodium chlorite (751 mg, 6.66 mmol) sodium dihydrogen phosphate (919 mg, 6.66 mmol) and water (26 mL). After the solution was stirred at room temperature for 3 h, EtOAc(10 mL) was added and the layers were separated. The organic layer was washed with saturated sodium bicarbonate (2×10 mL) and brine (1×10 mL), dried over magnesium sulfate, filtered, and concentrated in vacuo to yield 5-chloro-3-[(4-chloro-3-trifluoromethyl-benzenesulfonyl)-methoxymethyl-amino]-pyridine-2-carboxylic acid as a white solid.

Example 102: 5-Chloro-3-(4-chloro-3-trifluoromethyl-benzenesulfonylamino)-pyridine-2-carboxylic acid isopropyl-phenyl-amide

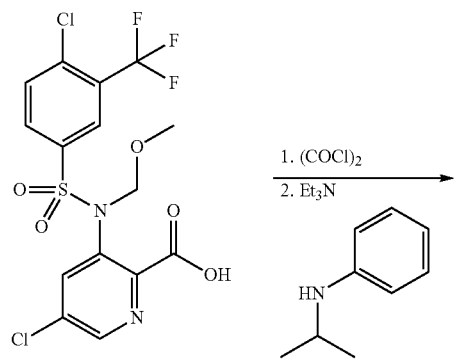

To a magnetically stirred solution of 5-chloro-3-[(4-chloro-3-trifluoromethyl-benzenesulfonyl)-methoxymethyl-amino]-pyridine-2-carboxylic acid (229 mg, 0.50 mmol) in anhydrous methylene chloride (5 mL) was added oxalyl chloride (1.0 mL) at room temperature. The reaction was heated at reflux for 2 h, then concentrated to dryness. The residue was dissolved in methylene chloride (4 mL) and this solution was added dropwise to a magnetically stirred solution of triethylamine (1.0 mL) and N-isopropylaniline (135 mg, 1.00 mmol) in methylene chloride (2 mL). The reaction mixture was stirred 1 h (the reaction was monitored by LCMS), then quenched with saturated aqueous NH$_4$Cl (50 mL), and the aqueous layer extracted with EtOAc (3×75 mL). The combined extracts were washed with 0.5 M HCl (50 mL), washed with water (50 mL), dried (MgSO$_4$), filtered, and concentrated. The residue was purified by chromatography on silica gel using a gradient of ethyl acetate-hexane (0:100 to 100:0) to afford pure 5-chloro-3-[(4-chloro-3-trifluoromethyl-benzenesulfonyl)-methoxymethyl-amino]-pyridine-2-carboxylic acid N-isopropyl-N-phenylamide. MS m/z 576.0 (M+H); 544.0 (M+H−MeOH).

The intermediate MOM derivative (180 mg, 0.313 mmol) was magnetically stirred in water (1.0 mL) and 4N HCl in dioxane (2.5 mL) at 85° C. (oil bath) for 7 h. Upon consumption of the reactant, the reaction mixture was concentrated, the residue neutralized (pH 7) with aqueous sodium bicarbonate, and the aqueous layer extracted with EtOAc (3×80 mL). The combined organic extracts were dried (MgSO$_4$), filtered, and chromatographed on silica gel using ethyl acetate-hexane gradient (0:100 to 50:50) to provide 5-chloro-3-(4-chloro-3-trifluoromethyl-benzenesulfonylamino)-pyridine-2-carboxylic acid isopropyl-phenyl-amide. MS m/z 532.0 (M+H).

Example 103: 5-Chloro-3-(4-chloro-3-trifluoromethyl-benzenesulfinylamino)-pyridine-2-carboxylic Acid Phenylamide

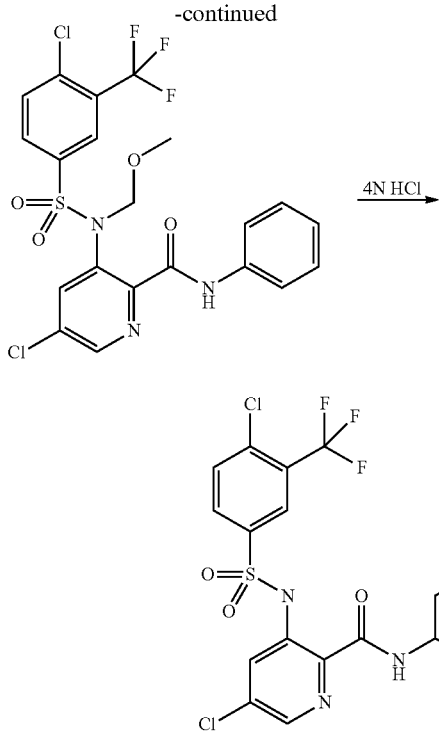

To a magnetically stirred solution of 5-chloro-3-[(4-chloro-3-trifluoromethyl-benzenesulfonyl)-methoxymethyl-amino]-pyridine-2-carboxylic acid (229 mg, 0.50 mmol) in anhydrous methylene chloride (5 mL) was added oxalyl chloride (0.5 mL) at room temperature. The reaction was heated at reflux for 1 h, then concentrated to dryness. The residue was dissolved in methylene chloride (4 mL) and this solution was added dropwise to a magnetically stirred solution of triethylamine (1.0 mL) and aniline (93 mg, 1.00 mmol) in methylene chloride (2 mL). The reaction mixture was stirred 1 h (the reaction was monitored by LCMS), quenched with saturated aqueous $NH_4Cl$ (50 mL), and the aqueous layer was extracted with EtOAc (3×75 mL). The combined extracts were washed with 0.5 M HCl (50 mL) and water (50 mL), dried ($MgSO_4$), filtered, and concentrated. The residue was purified by chromatography on silica gel using a gradient of ethyl acetate-hexane (0:100 to 100:0) to afford pure 5-chloro-3-[(4-chloro-3-trifluoromethyl-benzenesulfonyl)-methoxymethyl-amino]-pyridine-2-carboxylic acid phenylamide. MS m/z 556.1 (M+Na); 502.1 (M+H-MeOH).

5-Chloro-3-[(4-chloro-3-trifluoromethyl-benzenesulfonyl)-methoxymethyl-amino]-pyridine-2-carboxylic acid phenylamide (120 mg, 0.224 mmol) was magnetically stirred in water (1.0 mL) and 4N HCl in dioxane (2.5 mL) at 85° C. (oil bath) for 4 h. Upon consumption of the reactant, the reaction mixture was concentrated, the residue neutralized (pH 7) with aqueous sodium bicarbonate, and the aqueous layer was extracted with EtOAc (3×80 mL). The combined organic extracts were dried ($MgSO_4$), filtered, and chromatographed on silica gel using ethyl acetate-hexane gradient (0:100 to 50:50) to provide pure final product. MS m/z 490.0 (M+H).

Example 104: 5-Chloro-3-(4-chloro-3-trifluoromethyl-benzenesulfonylamino)-pyridine-2-carboxylic Acid N-methyl-N-phenylamide

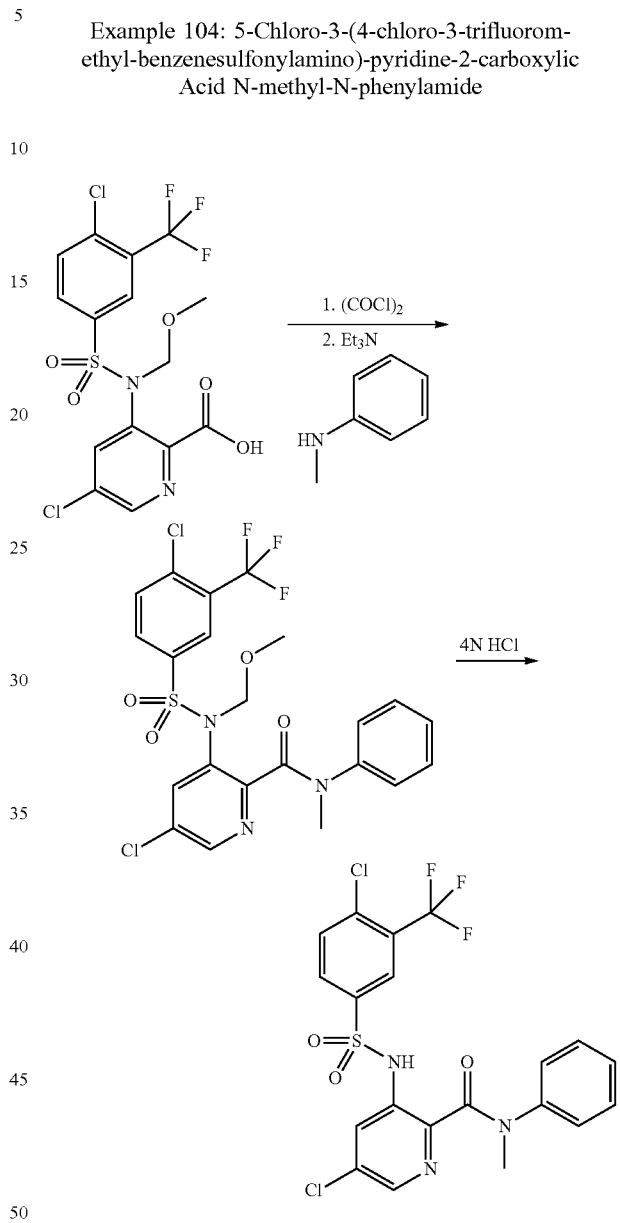

To a magnetically stirred solution of 5-chloro-3-[(4-chloro-3-trifluoromethyl-benzenesulfonyl)-methoxymethyl-amino]-pyridine-2-carboxylic acid (458 mg, 1.00 mmol) in anhydrous methylene chloride (5 mL) was added oxalyl chloride (1.0 mL) at room temperature. The reaction was heated at reflux for 2 h, then concentrated to dryness. The residue was dissolved in methylene chloride (4 mL) and this solution was added dropwise to a magnetically stirred solution of triethylamine (1.0 mL) and N-methylaniline (108 mg, 1.00 mmol) in methylene chloride (2 mL). The reaction mixture was stirred 1 h (the reaction was monitored by LCMS), quenched with saturated aqueous $NH_4Cl$ (50 mL), and the aqueous layer was extracted with EtOAc (3×75 mL). The combined extracts were washed with 0.5 M HCl (50 mL), washed with water (50 mL), dried ($MgSO_4$), filtered and concentrated. The residue was purified by chromatography on silica gel using a gradient of ethyl acetate-hexane (0:100 to 100:0) to afford pure 5-chloro-3-[(4-chloro-3-trifluoromethyl-benzenesulfonyl)-methoxymethyl-amino]-pyridine-2-carboxylic acid N-methyl-N-phenylamide. MS m/z: 548.2 (M+H), 526.0 (M+H-MeOH).

5-Chloro-3-[(4-chloro-3-trifluoromethyl-benzenesulfonyl)-methoxymethyl-amino]-pyridine-2-carboxylic acid N-methyl-N-phenylamide (132 mg, 0.24 mmol) was magnetically stirred in water (1.0 mL) and 4N HCl in dioxane (2.5 mL) and heated at 85° C. (oil bath) for 7 h. LCMS indicated complete reaction; the reaction was concentrated and the residue was neutralized (pH 7) with aqueous sodium bicarbonate and the aqueous layer was extracted with EtOAc (3×80 mL). The extracts were dried (MgSO$_4$), filtered, and chromatographed on silica gel using ethyl acetate-hexane gradient (0:100 to 50:50) to provide 5-chloro-3-(4-chloro-3-trifluoromethyl-benzenesulfonylamino)-pyridine-2-carboxylic acid N-methyl-N-phenylamide. MS m/z: 504.1 (M+H).

Example 105: 5-Chloro-3-(4-chloro-3-trifluoromethyl-benzenesulfonylamino)-pyridine-2-carboxylic Acid N-methyl —N-(4-fluorophenyl)amide

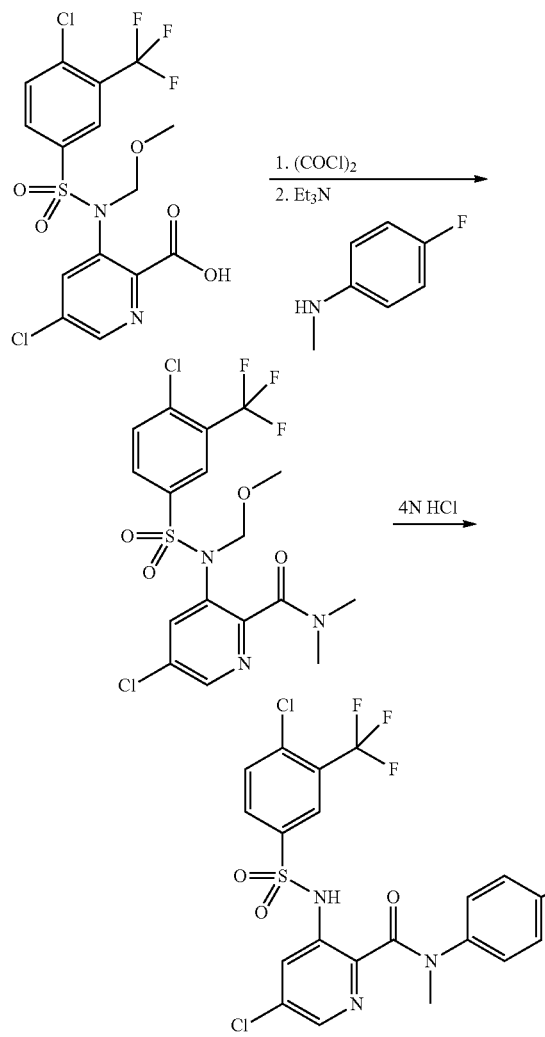

To a magnetically stirred solution of 5-chloro-3-[(4-chloro-3-trifluoromethyl-benzenesulfonyl)-methoxymethyl-amino]-pyridine-2-carboxylic acid (458 mg, 1.00 mmol) in anhydrous methylene chloride (5 mL) was added oxalyl chloride (1.0 mL) at room temperature. The reaction was heated at reflux for 1 h then was concentrated to dryness. The residue was dissolved in methylene chloride (4 mL) and this solution was added dropwise to a magnetically stirred solution of triethylamine (1.0 mL) and N-methyl-N-(4-fluorophenyl)aniline (0.50 mL, 3.5 mmol) in methylene chloride (2 mL). The reaction mixture was stirred 1 h (the reaction was monitored by LCMS) then quenched with saturated aqueous NH$_4$Cl (50 mL), and extracted with EtOAc (3×75 mL). The combined extracts were washed with 0.5M HCl (50 mL), washed with water (50 mL), dried (MgSO$_4$), filtered and concentrated. The residue was purified by chromatography on silica gel using a gradient of ethyl acetate-hexane (0:100 to 100:0) to afford pure 5-chloro-3-[(4-chloro-3-trifluoromethyl-benzenesulfonyl)-methoxymethyl-amino]-pyridine-2-carboxylic acid N-methyl-N-(4-fluorophenyl)amide. MS m/z 570.1 (M+Na); 526.0 (M+H-MeOH).

5-Chloro-3-[(4-chloro-3-trifluoromethyl-benzenesulfonyl)-methoxymethyl-amino]-pyridine-2-carboxylic acid N-methyl-N-(4-fluorophenyl)amide (141 mg, 0.258 mmol) was magnetically stirred in water (1.0 mL) and 4N HCl in dioxane (2.5 mL) and heated at 85° C. (oil bath) for 7 h. LCMS indicated complete reaction; the reaction was concentrated and the residue was neutralized (pH 7) with aqueous sodium bicarbonate and extracted with EtOAc (3×80 mL). The extracts were dried (MgSO$_4$), filtered, and chromatographed on silica gel using ethyl acetate-hexane gradient (0:100 to 50:50) to provide 5-chloro-3-(4-chloro-3-trifluoromethyl-benzenesulfonylamino)-pyridine-2-carboxylic acid N-methyl-N-(4-fluorophenyl)amide. MS m/z 522.1 (M+H).

Example 106: 5-Chloro-3-(4-chloro-3-trifluoromethyl-benzenesulfonylamino)-pyridine-2-carboxylic Acid 2-isopropylaminopyridin-2-yl Amide

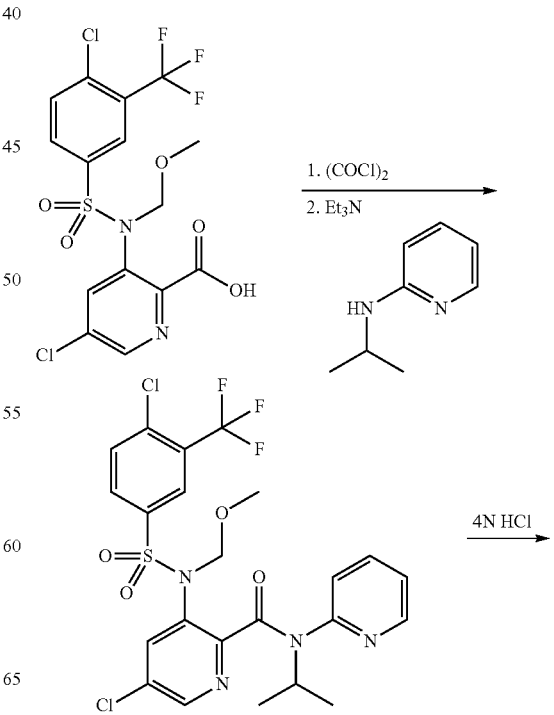

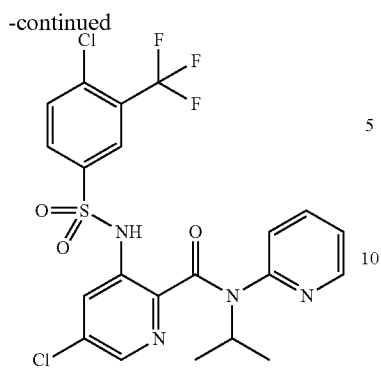

To a magnetically stirred solution of 5-chloro-3-[(4-chloro-3-trifluoromethyl-benzenesulfonyl)-methoxymethyl-amino]-pyridine-2-carboxylic acid (229 mg, 0.50 mmol) in anhydrous methylene chloride (5 mL) was added oxalyl chloride (0.5 mL) at room temperature. The reaction was heated at reflux for 1 h then was concentrated to dryness. The residue was dissolved in methylene chloride (4 mL) and this solution was added dropwise to a magnetically stirred solution of triethylamine (1.0 mL) and 2-(isopropylamino) pyridine (136 mg, 1.00 mmol) in methylene chloride (2 mL). The reaction mixture was stirred 1 h (the reaction was monitored by LCMS) then quenched with saturated aqueous NH$_4$Cl (50 mL), and extracted with EtOAc (3×75 mL). The combined extracts were washed with 0.5M HCl (50 mL), washed with water (50 mL), dried (MgSO$_4$), filtered and concentrated. The residue was purified by chromatography on silica gel using a gradient of ethyl acetate-hexane (0:100 to 100:0) to afford pure 5-chloro-3-[(4-chloro-3-trifluoromethyl-benzenesulfonyl)-methoxymethyl-amino]-pyridine-2-carboxylic acid 2-(isopropylamino)pyridylamide. MS m/z 577.1 (M+H).

5-Chloro-3-[(4-chloro-3-trifluoromethyl-benzenesulfonyl)-methoxymethyl-amino]-pyridine-2-carboxylic acid 2-(isopropylamino)pyridylamide (120 mg, 0.208 mmol) was magnetically stirred in water (1.0 mL) and 4N HCl in dioxane (2.5 mL) and heated at 85° C. (oil bath) for 9 h. LCMS indicated complete reaction; the reaction was concentrated and the residue was neutralized (pH 7) with aqueous sodium bicarbonate and extracted with EtOAc (3×80 mL). The extracts were dried (MgSO$_4$), filtered, and chromatographed on silica gel using ethyl acetate-hexane gradient (0:100 to 50:50) to provide 5-chloro-3-(4-chloro-3-trifluoromethyl-benzenesulfonylamino)-pyridine-2-carboxylic acid 2-isopropylaminopyridin-2-yl amide. MS m/z: 533.1 (M+H).

Example 107: 4-Chloro-N-[5-chloro-2-(2,3-dihydro-benzo[1,4]oxazine-4-carbonyl)-pyridin-3-yl]-N-methoxymethyl-3-trifluoromethyl-benzenesulfonamide

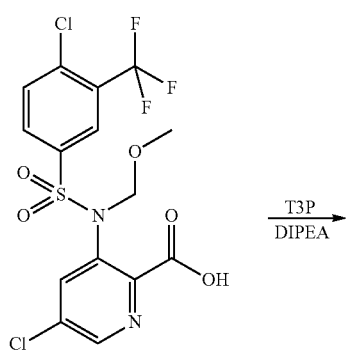

To a mixture of 5-chloro-3-[(4-chloro-3-trifluoromethyl-benzenesulfonyl)-methoxymethyl-amino]-pyridine-2-carboxylic acid (112 mg, 0.244 mmol), 100 mg (0.70 mmol) of 3,4-dihydro-2H-benzo[1,4]oxazine, and 0.174 mL (1.0 mmol) of DIEA in CH$_2$Cl$_2$ (2.5 mL) was added 0.19 mL 1-propanephosphonic acid cyclic anhydride (50% in ethyl acetate). After 3 h the reaction mixture was directly purified via flash column (50% EtOAc in hexane) to afford 79 mg of 4-chloro-N-[5-chloro-2-(2,3-dihydro-benzo[1,4]oxazine-4-carbonyl)-pyridin-3-yl]-N-methoxymethyl-3-trifluoromethyl-benzenesulfonamide as a white powder. MS m/z: 576.38 (M+H).

Example 108: 4-Chloro-N-[5-chloro-2-(2,3-dihydro-benzo[1,4]oxazine-4-carbonyl)-pyridin-3-yl]-3-trifluoromethyl-benzenesulfonamide

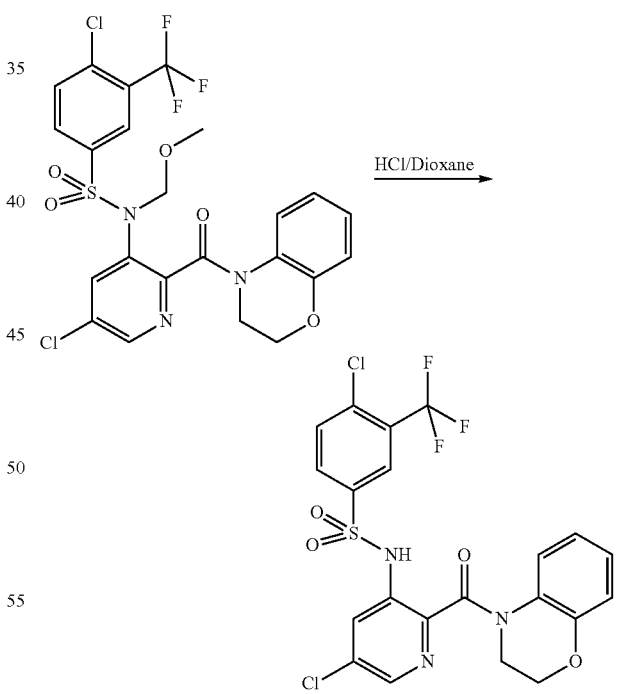

A solution of 4-chloro-N-[5-chloro-2-(2,3-dihydro-benzo[1,4]oxazine-4-carbonyl)-pyridin-3-yl]-N-methoxymethyl-3-trifluoromethyl-benzenesulfonamide (50 mg) in 3 mL HCl (4 M in dioxane) and water (1 mL) was refluxed for 2 h. Upon cooling to room temperature, the mixture was concentrated and the residue was purified via preparative TLC (50% EtOAc in hexane) to afford 4-chloro-N-[5-chloro-2-(2,3-dihydro-benzo[1,4]oxazine-4-carbonyl)-pyridin-3-yl]-

Example 109: 4-Chloro-N-[5-chloro-2-(3-methyl-morpholine-4-carbonyl)-pyridin-3-yl]-N-methoxymethyl-3-trifluoromethyl-benzenesulfonamide

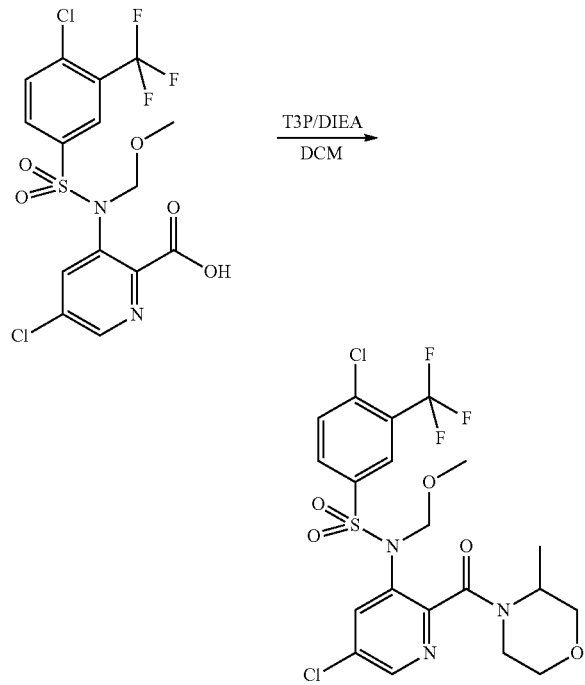

To a mixture of 112 mg (0.244 mmol) of 5-chloro-3-[(4-chloro-3-trifluoromethyl-benzenesulfonyl)-methoxymethyl-amino]-pyridine-2-carboxylic acid, 70 mg (0.70 mmol) of 2-methylmorpholine and 0.174 mL (1.0 mmol) of DIEA in CH$_2$Cl$_2$ (2.5 mL) was added 0.19 mL 1-propanephosphonic acid cyclic anhydride (50% in ethyl acetate). After 3 h the reaction mixture was directly purified via flash column (50% EtOAc in hexane) to afford 67 mg of 4-chloro-N-[5-chloro-2-(3-methyl-morpholine-4-carbonyl)-pyridin-3-yl]-N-methoxymethyl-3-trifluoromethyl-benzenesulfonamide as a white powder. MS m/z: 542.36 (M+H).

Example 110: 4-Chloro-N-[5-chloro-2-(3-methyl-morpholine-4-carbonyl)-pyridin-3-yl]-3-trifluoromethyl-benzenesulfonamide

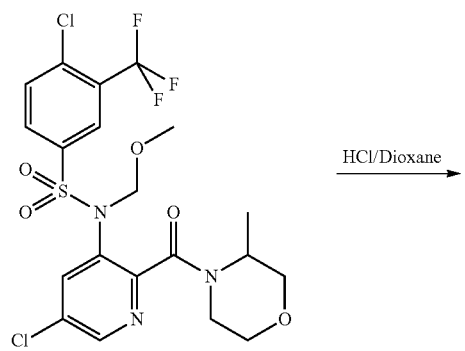

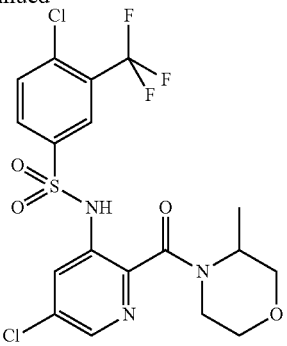

A solution of 4-chloro-N-[5-chloro-2-(3-methyl-morpholine-4-carbonyl)-pyridin-3-yl]-N-methoxymethyl-3-trifluoromethyl-benzenesulfonamide (40 mg) in 3 mL HCl (4M in dioxane) and water (1 mL) was refluxed for 2 h. Upon Cooling to room temperature, the mixture was concentrated and the residue was purified via preparative TLC (50% EtOAc in hexane) to afford 21 mg of 4-chloro-N-[5-chloro-2-(3-methyl-morpholine-4-carbonyl)-pyridin-3-yl]-3-trifluoromethyl-benzenesulfonamide as an off white solid. MS m/z: 498.0 (M+H).

Example 111: 5-Chloro-3-[(4-chloro-3-trifluoromethyl-benzenesulfonyl)-methoxymethyl-amino]-pyridine-2-carbonyl chloride

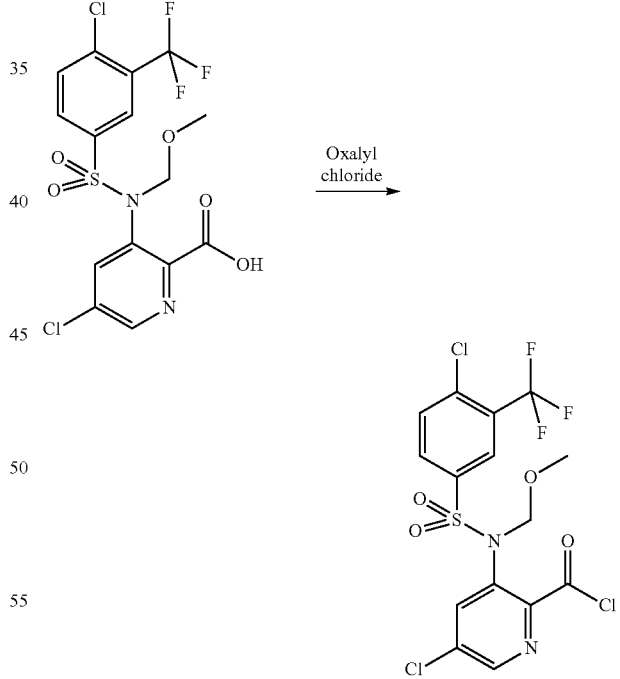

To a solution of 5-chloro-3-[(4-chloro-3-trifluoromethyl-benzenesulfonyl)-methoxymethyl-amino]-pyridine-2-carboxylic acid (450 mg, 1.0 mmol) in 3.0 mL CH$_2$Cl$_2$ and DMF (0.02 mL) was added oxalyl chloride (0.110 mL). The mixture was stirred for 2 h and concentrated to dryness to provide 5-chloro-3-[(4-chloro-3-trifluoromethyl-benzenesulfonyl)-methoxymethyl-amino]-pyridine-2-carbonyl chloride.

Example 112: 4-Chloro-N-[5-chloro-2-(3-methyl-2,3-dihydro-benzo[1,4]oxazine-4-carbonyl)-pyridin-3-yl]-N-methoxymethyl-3-trifluoromethyl-benzenesulfonamide

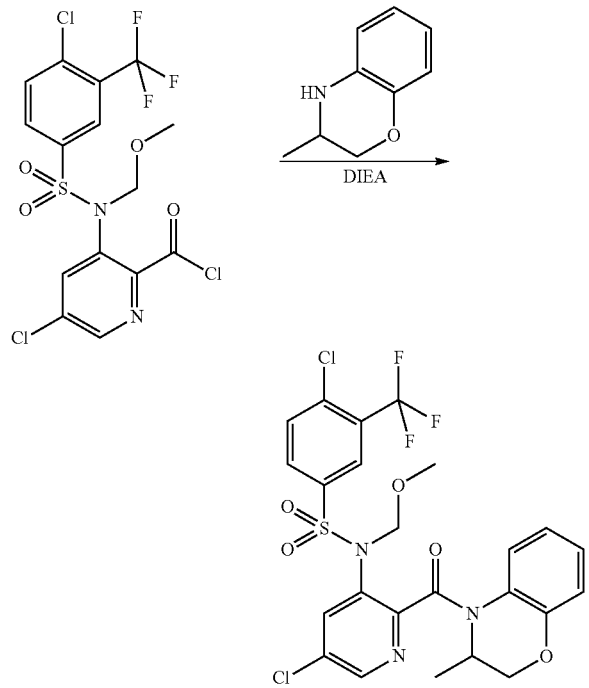

A mixture of 5-chloro-3-[(4-chloro-3-trifluoromethyl-benzenesulfonyl)-methoxymethyl-amino]-pyridine-2-carbonyl chloride (50 mg, 0.11 mmol), 3-sethyl-3,4-dihydro-2H-benzo[1,4]oxazine (60 mg, 0.40 mmol) and di-isopropylethylamine (DIEA, 0.07 mL, 0.40 mmol) in CH₂CL₂ (1.5 mL) was stirred at room temperature overnight. The mixture was concentrated to provide 4-chloro-N-[5-chloro-2-(3-methyl-2,3-dihydro-benzo[1,4]oxazine-4-carbonyl)-pyridin-3-yl]-N-methoxymethyl-3-trifluoromethyl-benzenesulfonamide, which was directly used in the next step without any purification.

Example 113: 4-Chloro-N-[5-chloro-2-(2,6-dimethyl-morpholine-4-carbonyl)-pyridin-3-yl]-N-methoxymethyl-3-trifluoromethyl-benzenesulfonamide

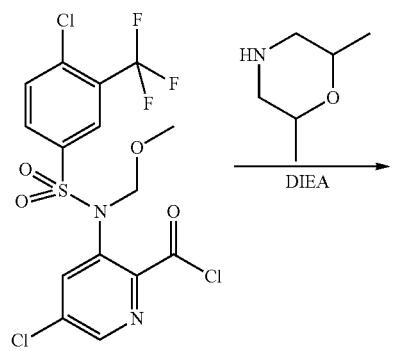

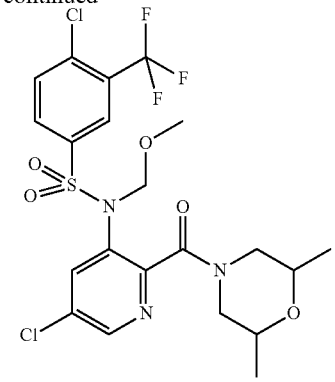

A mixture of 5-chloro-3-[(4-chloro-3-trifluoromethyl-benzenesulfonyl)-methoxymethyl-amino]-pyridine-2-carbonyl chloride (50 mg, 0.11 mmol), cis-2,6-dimethylmorpholine (50 mg, 0.40 mmol) and di-isopropylethylamine (DIEA, 0.07 mL, 0.40 mmol) in CH₂Cl₂ (1.5 mL) was stirred at room temperature overnight. The mixture was concentrated to provide 4-chloro-N-[5-chloro-2-(cis-2,6-dimethyl-morpholine-4-carbonyl)-pyridin-3-yl]-N-methoxymethyl-3-trifluoromethyl-benzenesulfonamide, which was directly used in the next step without any purification.

Example 114: 4-Chloro-N-[5-chloro-2-(3-methyl-2,3-dihydro-benzo[1,4]oxazine-4-carbonyl)-pyridin-3-yl]-3-trifluoromethyl-benzenesulfonamide

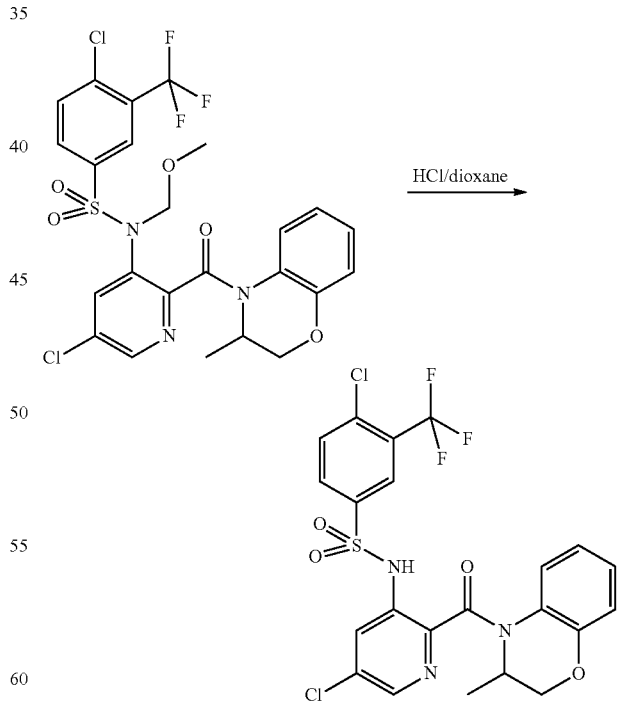

A solution of crude 4-chloro-N-[5-chloro-2-(3-methyl-2,3-dihydro-benzo[1,4]oxazine-4-carbonyl)-pyridin-3-yl]-N-methoxymethyl-3-trifluoromethyl-benzenesulfonamide in 3 mL HCl (4M in dioxane) and water (1 mL) was refluxed for 2 h. Upon cooling to room temperature, the mixture was concentrated and the residue was purified via preparative TLC (50% EtOAc in hexane) to afford 11 mg of 4-chloro-N-[5-chloro-2-(3-methyl-2,3-dihydro-benzo[1,4]oxazine-4-carbonyl)-pyridin-3-yl]-3-trifluoromethyl-benzenesulfonamide as an off white solid. MS m/z: 546.1 (M+H).

Example 115: 4-Chloro-N-[5-chloro-2-(2,6-dimethyl-morpholine-4-carbonyl)-pyridin-3-yl]-3-trifluoromethyl-benzenesulfonamide

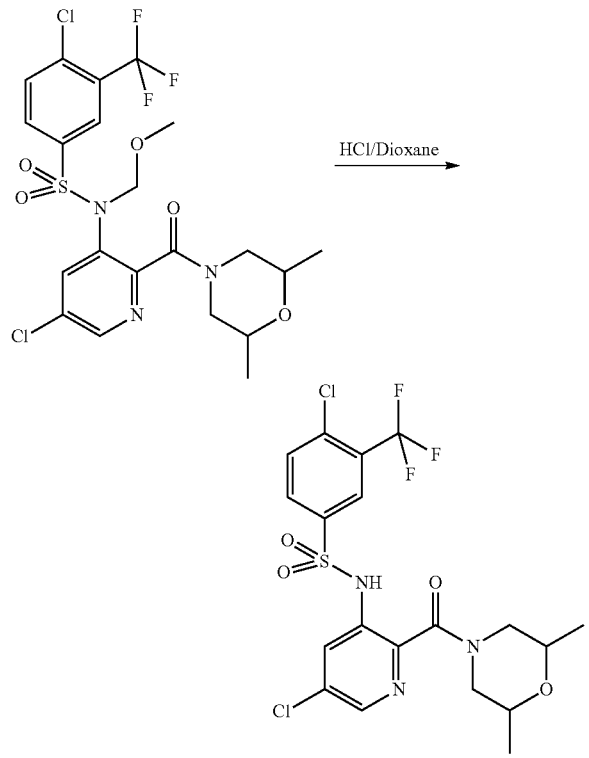

A solution of crude 4-chloro-N-[5-chloro-2-(2,6-dimethyl-morpholine-4-carbonyl)-pyridin-3-yl]-N-methoxymethyl-3-trifluoromethyl-benzenesulfonamide in 3 mL HCl (4M in dioxane) and water (1 mL) was refluxed for 2 h. Upon cooling to room temperature, the mixture was concentrated and the residue was purified via preparative TLC (50% EtOAc in hexane) to afford 28 mg of 4-chloro-N-[5-chloro-2-(2,6-dimethyl-morpholine-4-carbonyl)-pyridin-3-yl]-3-trifluoromethyl-benzenesulfonamide as an off white solid. MS m/z: 512.0 (M+H).

Example 116: 5-Chloro-3-(4-chloro-3-trifluoromethyl)phenylsulfonamido)picolinic Acid

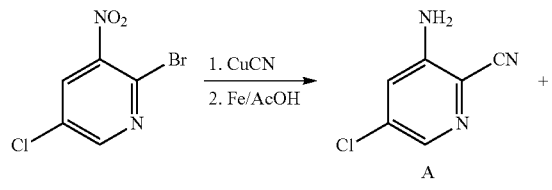

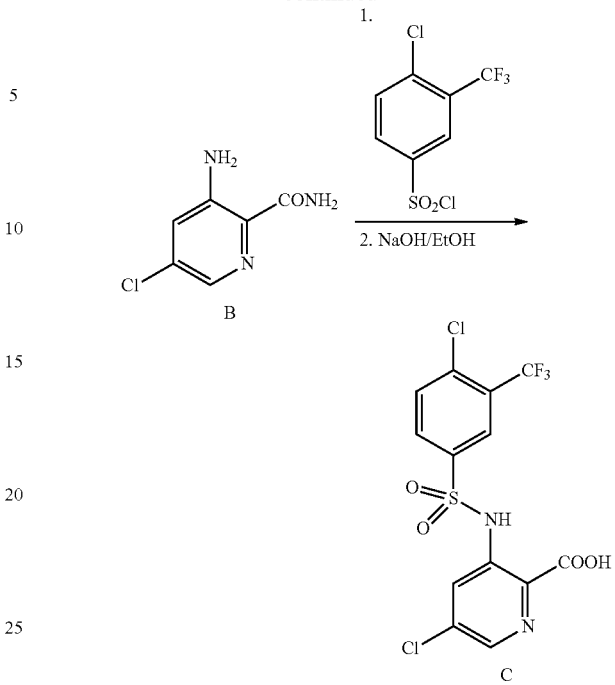

Step 1: A dry 250 mL flask was charged with 2-bromo-5-chloro-3-nitropyridine (24 g, 10 mmol), CuCN (19 g, 20 mmol) and DMF (100 mL). The resultant mixture was stirred at 110° C. for 2 h and then concentrated under reduced pressure. Water (100 mL) was added and the aqueous layer was extracted with EtOAc (250 mL×3). The combined organic layer was washed with brine, dried (MgSO$_4$), and evaporated in vacuo to afford a light yellow solid (15 g) which was used directly for the next step.

Step 2: A 250 mL round-bottom flask was charged with the iron powder (15.6 g, 0.3 mol), AcOH (80 mL) and heated to 80° C. (oil bath) under N$_2$. To this mixture, was added a solution of nitrocyanopyridine (10 g, 0.055 mmol) in AcOH (80 mL) via addition funnel and stirred at 80° C. for an additional 30 min after the addition. The reaction was subsequently cooled to room temperature, diluted with EtOAc, filtered through a pad of Celite and concentrated under reduced pressure. The residue was dissolved in EtOAc and washed with 3 N NaOH and brine, dried over MgSO$_4$, and concentrated under reduced pressure and to afford the crude 3-amino-2-cyano-5-chloropyridine along with the 2-amide (7.7 g) which was used directly for the next step: MS 154.0 (M+H).

Step 3: A 500 mL round-bottom flask was charged with the above 3-amino-2-cyano-5-chloropyridine (7.7 g, 50 mmol), 4-Cl-3-trifluoromethyl-benzenesulfonyl chloride (28 g, 100 mmol), and pyridine (50 mL). The resultant solution was heated to 70° C. and stirred for 5 h. The pyridine was removed in vacuo and EtOH (80%, 260 mL) was added, followed by NaOH (30 g, 0.75 mol). The mixture was heated at reflux for 12 h. The solvent was subsequently removed in vacuo and ice (100 g) was added and the pH adjusted to 2-3 with conc HCl. The resultant aqueous solution was extracted with EtOAc, washed with brine, dried over MgSO$_4$, and concentrated under reduced pressure. The resultant light yellow solid was further crystallized from EtOAc/hexane (1:1) to afford 5-chloro-3-(4-chloro-3-(trifluoromethyl)phenylsulfonamido)picolinic acid as white needles (10 g, 44% overall): $^1$H NMR (400 MHz, CDCl$_3$) δ 10.80 (s, 1H), 8.23 (m, 3H), 8.00 (d, 1H), 7.63 (d, 1H); MS (ES) 415.0 (M+H).

Example 117: General Procedure D: Synthesis of 5-chloro-3-(4-chloro-3-(trifluoromethyl)phenylsulfonamido)picolinic Amides

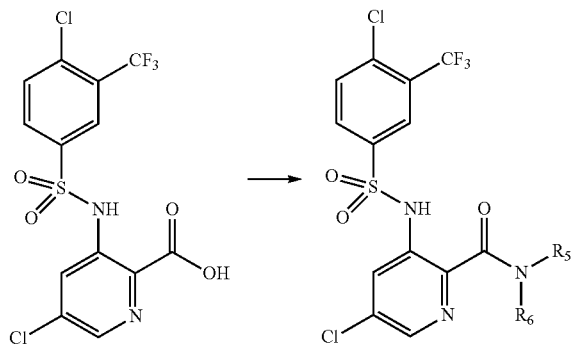

A 10 mL scintillation vial was charged with 5-chloro-3-(4-chloro-3-(trifluoromethyl)phenylsulfonamido)picolinic acid (1 equiv), amine (2-3 equiv.), coupling agent [HATU, BOP or T3P, 1.1-1.3 equiv), and base [DIEA (3-5 equiv.) or Et₃N (1-3 equiv.)] in anhydrous DMF (or CH₂Cl₂). The resultant solution was stirred at room temperature (or 70° C.) for several hours until the starting material was consumed. The reaction mixture was diluted with MeCN (1-2 mL) and purified by preparative HPLC (20→90% gradient of MeCN-water) and pure product fractions were lyophilized to provide pure product as a solid. Non-commercial amines were prepared according to procedures available in literature.

Example 118: 4-chloro-N-(5-chloro-2-(1,2,3-4-tetrahydro-1,5-napthyridine-1-carbonyl-pyridine-3-yl)-3-(trifluoromethyl)benzenefulfonamide

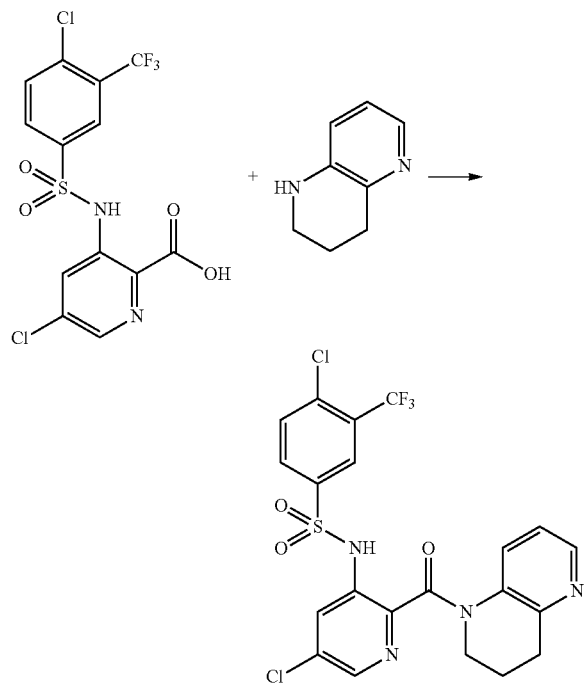

5-Chloro-3-(4-chloro-3-(trifluoromethyl)phenylsulfonamido)picolinic acid (164 mg, 0.4 mmol), 1,2,3,4-tetrahydro-1,5-napthyridine [(70 mg, 0.56 mmol), 1,2,3,4-tetrahydro-1,5-napthyridine prepared freshly from 1,5-napthyridine via hydrogenation over Pt₂O], HATU (200 mg, 0.5 mmol), DIEA (260 mg, 2 mmol) were reacted according to the procedure D to provide the title compound. HPLC purification (20→90% gradient of MeCN-water) provided 4-chloro-N-(5-chloro-2-(1,2,3-4-tetrahydro-1,5-napthyridine-1-carbonyl-pyridine-3-yl)-3-(trifluoromethyl)benzenefulfonamide: $^1$H NMR (400 MHz, CDCl₃) δ 8.52 (d, 1H), 8.18 (m, 2H), 8.09 (d, 1H), 8.00 (m, 2H), 7.69 (d, 1H), 7.52 (m, 1H), 3.92 (m, 2H), 3.35 (t, 2H), 2.11 (m, 2H); MS m/z: 531.0 (M+H).

Example 119: 5-Chloro-3(4-chloro-3-(trifluoromethyl)phenylsulfonamido)-N-ethyl-(thiazol-2-yl)picolinamide

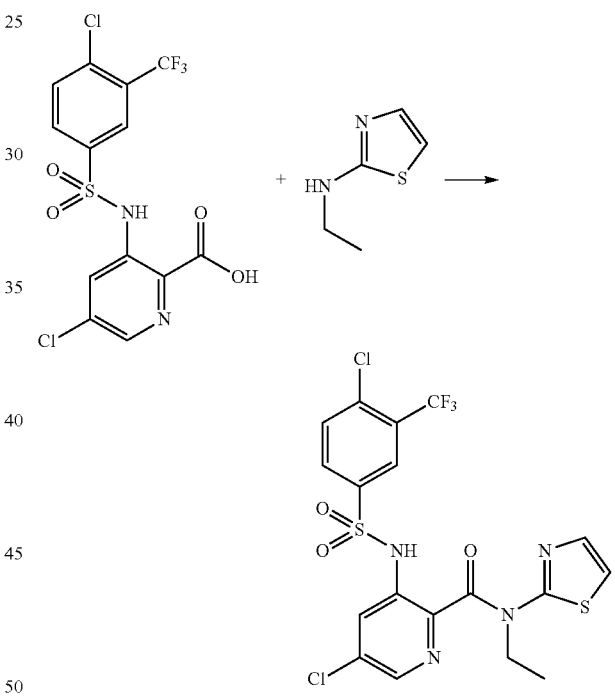

5-Chloro-3-(4-chloro-3-(trifluoromethyl)phenylsulfonamido)picolinic acid (120 mg, 0.3 mmol), 2-ethylaminothiazole [(50 mg, 0.4 mmol) 2-Ethylaminothiazole was prepared freshly from 2-aminothiazole and acetylaldehyde via standard reductive amination condition using NaCNBH₃ as the reducing agent], HATU (190 mg, 0.5 mmol), DIEA (130 mg, 1 mmol) were reacted according to the procedure D to provide the title compound. HPLC purification (20→90% gradient of MeCN-water) provided 5-Chloro-3(4-chloro-3-(trifluoromethyl)phenylsulfonamido)-N-ethyl-(thiazol-2-yl)picolinamide: $^1$H NMR (400 MHz, CDCl₃) δ 9.20 (s, 1H), 8.23 (s, 1H), 8.07 (s, 1H), 7.82 (d, 1H), 7.61 (s, 1H), 7.46 (d, 1H), 7.20 (s, 1H), 6.0 (s, 2H), 4.02 (q, 2H), 1.25 (t, 3H); MS m/z 525.0 (M+H).

193

Example 120: 4-Chloro-N-[5-chloro-2-(3,4-dihydro-2H-[1,8]naphthyridine-1-carbonyl)-pyridin-3-yl]-3-trifluoromethyl-benzenesulfonamide

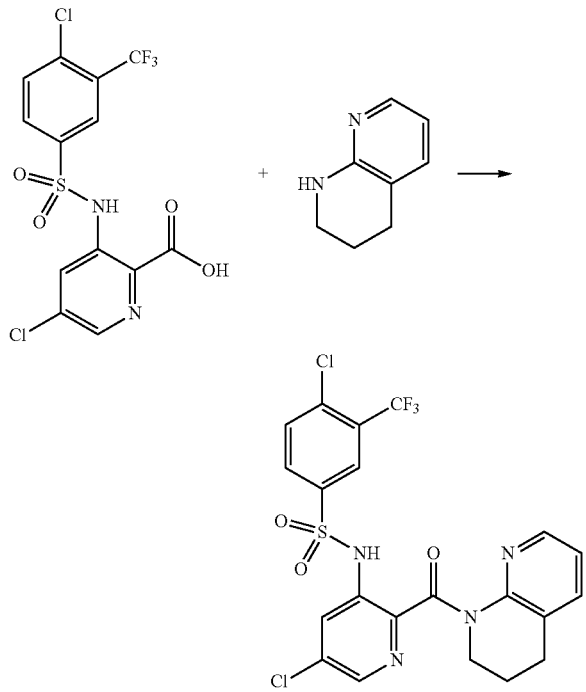

5-Chloro-3-(4-chloro-3-(trifluoromethyl)phenylsulfonamido)picolinic acid (208 mg, 0.50 mmol), 1,2,3,4-tetrahydro-[1,8]naphthyridine [(135 mg, 1.0 mmol) 1,2,3,4-tetrahydro-[1,8]naphthyridine was prepared freshly from 1,8-napthyridine via hydrogenation over $Pt_2O$], BOP (486 mg, 1.1 mmol), DIEA (185 mg, 1.4 mmol) were reacted according to the procedure D to provide the title compound. HPLC purification (20→90% gradient of MeCN-water) provided 4-chloro-N-[5-chloro-2-(3,4-dihydro-2H-[1,8]naphthyridine-1-carbonyl)-pyridin-3-yl]-3-trifluoromethyl-benzenesulfonamide: MS m/z: 531.0 (M+H).

Example 121: 5-Chloro-3-(4-chloro-3-trifluoromethyl-benzenesulfonylamino)-pyridine-2-carboxylic Acid methyl-m-tolyl-amide

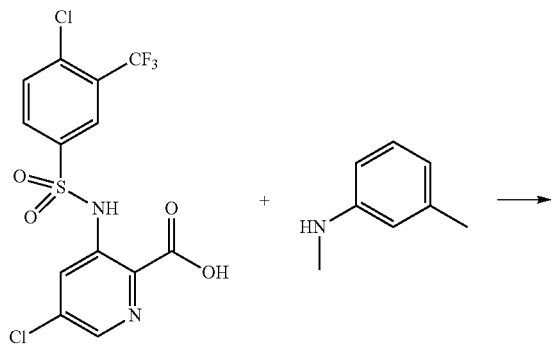

194

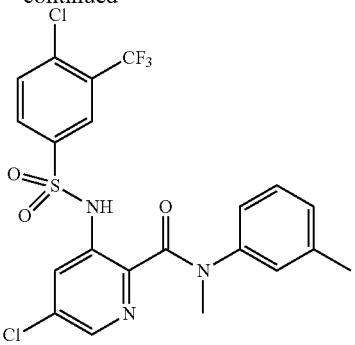

5-Chloro-3-(4-chloro-3-(trifluoromethyl)phenylsulfonamido)picolinic acid (50 mg, 0.12 mmol), methyl-m-tolyl-amine (44 mg, 0.36 mmol), BOP (69 mg, 0.36 mmol), DIEA (130 FL, 0.72 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid methyl-m-tolyl-amide: MS m/z: (M+H) 518.1.

Example 122: 5-Chloro-3-(4-chloro-3-trifluoromethyl-benzenesulfonylamino)-pyridine-2-carboxylic acid (3-chloro-phenyl)-methyl-amide

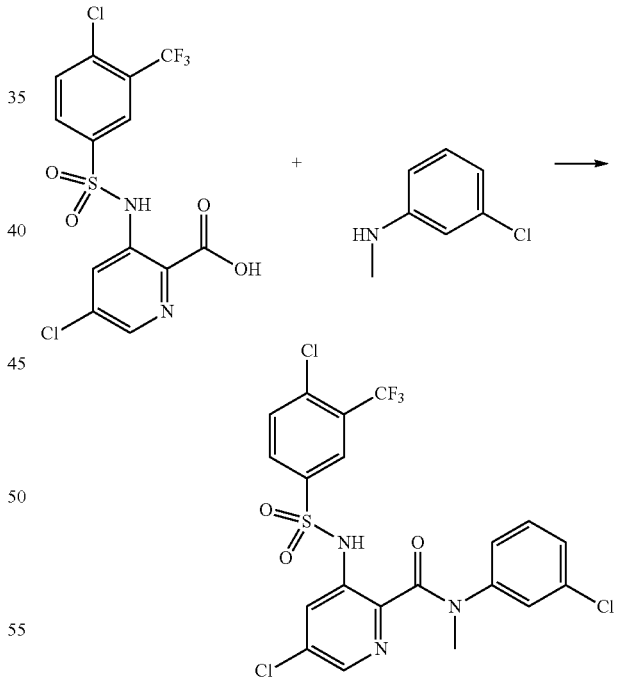

5-Chloro-3-(4-chloro-3-(trifluoromethyl)phenylsulfonamido)picolinic acid (50 mg, 0.12 mmol), (3-chloro-phenyl)-methyl-amine (50 mg, 0.36 mmol), BOP (69 mg, 0.36 mmol), DIEA (130 FL, 0.72 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid (3-chloro-phenyl)-methyl-amide: MS m/z: (M+H) 537.9.

Example 123: 5-Chloro-3-(4-chloro-3-trifluoromethyl-benzenesulfonylamino)-pyridine-2-carboxylic acid (3-fluoro-phenyl)-methyl-amide

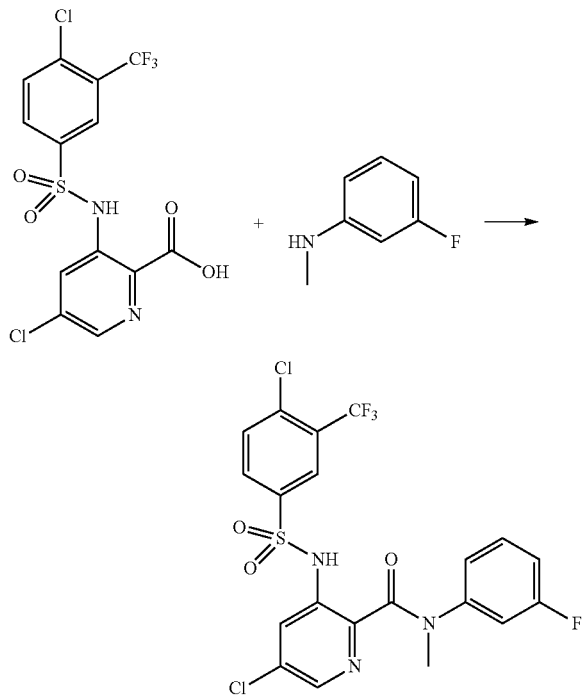

5-Chloro-3-(4-chloro-3-(trifluoromethyl)phenylsulfonamido)picolinic acid (50 mg, 0.12 mmol), (3-fluoro-phenyl)-methyl-amine (45 mg, 0.36 mmol), BOP (69 mg, 0.36 mmol), DIEA (130 FL, 0.72 mmol) were were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid (3-fluoro-phenyl)-methyl-amide: MS m/z: (M+H) 521.9.

Example 124: 5-Chloro-3-(4-chloro-3-trifluoromethyl-benzenesulfonylamino)-pyridine-2-carboxylic Acid methyl-pyridin-2-yl-amide

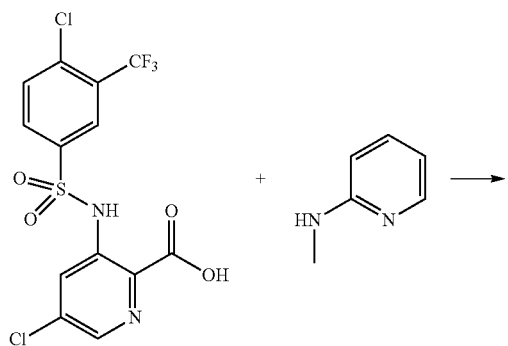

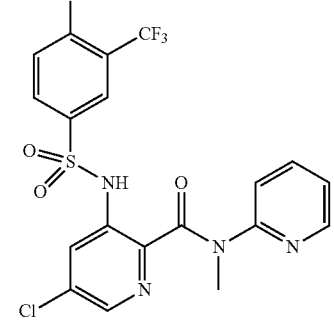

5-Chloro-3-(4-chloro-3-(trifluoromethyl)phenylsulfonamido)picolinic acid (75 mg, 0.18 mmol), methyl-pyridin-2-yl-amine (60 mg, 0.54 mmol), BOP (103 mg, 0.234 mmol), DIEA (193 FL, 1.08 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid methyl-pyridin-2-yl-amide: MS m/z: (M+H) 505.1.

Example 125: 5-Chloro-3-(4-chloro-3-trifluoromethyl-benzenesulfonylamino)-pyridine-2-carboxylic Acid (2,4-difluoro-phenyl)-methyl-amide

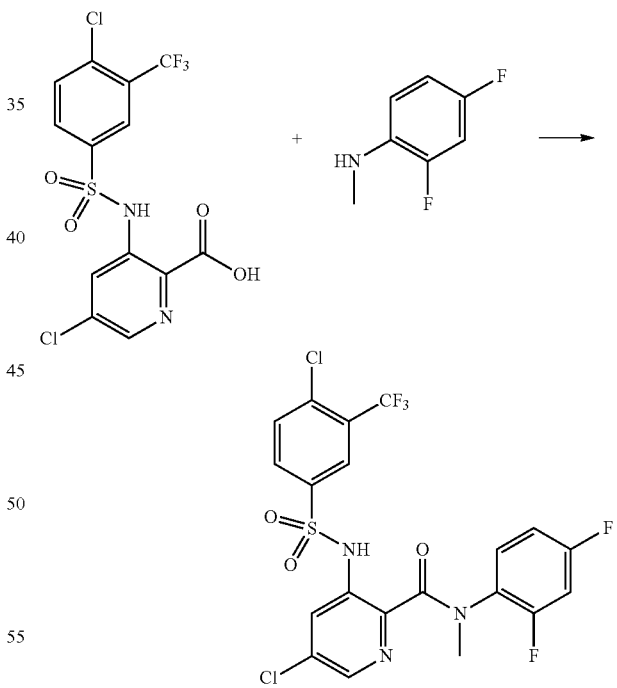

5-Chloro-3-(4-chloro-3-(trifluoromethyl)phenylsulfonamido)picolinic acid (100 mg, 0.24 mmol), (2,4-difluoro-phenyl)-methyl-amine (103 mg, 0.72 mmol), BOP (137 mg, 0.31 mmol), DIEA (265 FL, 1.44 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid (2,4-difluoro-phenyl)-methyl-amide: MS m/z: (M+H) 541.0.

Example 126: 2-{[5-Chloro-3-(4-chloro-3-trifluoromethyl-benzenesulfonylamino)-pyridine-2-carbonyl]-methyl-amino}-benzoic Acid Methyl Ester

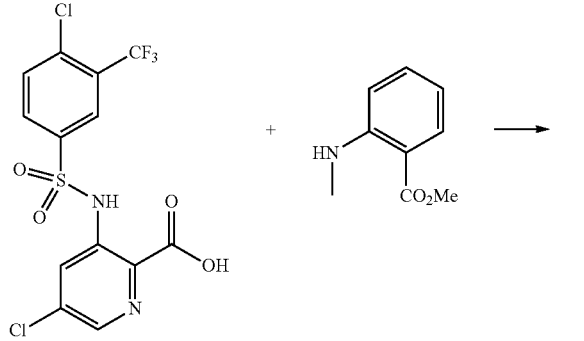

5-Chloro-3-(4-chloro-3-(trifluoromethyl)phenylsulfonamido)picolinic acid (100 mg, 0.24 mmol), 2-methylaminobenzoic acid methyl ester (119 mg, 0.722 mmol), BOP (137 mg, 0.312 mmol), DIEA (265 FL, 1.08 mmol) were reacted according to the procedure D to provide the title compound. HPLC purification (20→90% gradient of MeCN-water) provided 2-{[5-chloro-3-(4-chloro-3-trifluoromethyl-benzenesulfonylamino)-pyridine-2-carbonyl]-methyl-amino}-benzoic acid methyl ester: MS m/z: (M+H) 562.1.

Example 127: 5-Chloro-3-(4-chloro-3-trifluoromethyl-benzenesulfonylamino)-pyridine-2-carboxylic acid methyl-o-tolyl-amide

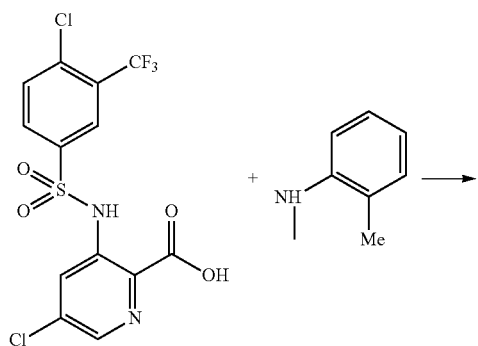

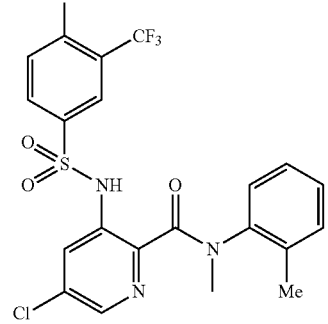

5-Chloro-3-(4-chloro-3-(trifluoromethyl)phenylsulfonamido)picolinic acid (50 mg, 0.12 mmol), methyl-o-tolyl-amine (44 mg, 0.36 mmol), BOP (69 mg, 0.36 mmol), DIEA (130 FL, 0.72 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid methyl-o-tolyl-amide: MS m/z: (M+H) 518.0.

Example 128: 5-Chloro-3-(4-chloro-3-trifluoromethyl-benzenesulfonylamino)-pyridine-2-carboxylic Acid (2-fluoro-phenyl)-methyl-amide

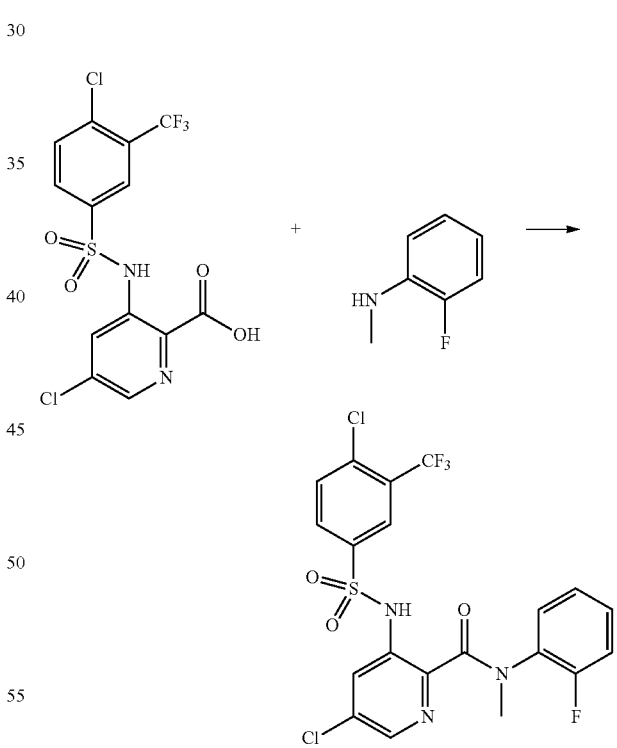

5-Chloro-3-(4-chloro-3-(trifluoromethyl)phenylsulfonamido)picolinic acid (50 mg, 0.12 mmol), (2-fluoro-phenyl)-methyl-amine (45 mg, 0.36 mmol), BOP (69 mg, 0.36 mmol), DIEA (130 ⌈L, 0.72 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid (2-fluoro-phenyl)-methyl-amide: MS m/z: (M+H) 522.1.

Example 129: 5-Chloro-3-(4-chloro-3-trifluoromethyl-benzenesulfonylamino)-pyridine-2-carboxylic Acid (2-chloro-phenyl)-methyl-amide

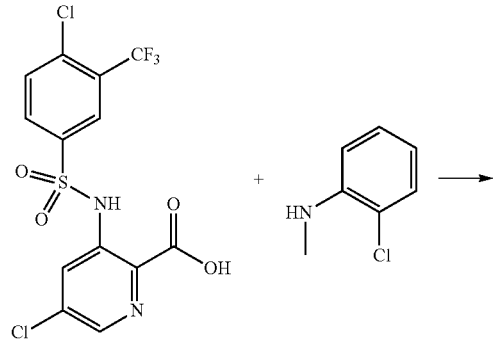

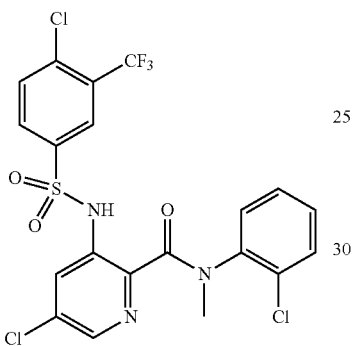

5-Chloro-3-(4-chloro-3-(trifluoromethyl)phenylsulfonamido)picolinic acid (50 mg, 0.12 mmol), (2-chloro-phenyl)-methyl-amine (50 mg, 0.36 mmol), BOP (69 mg, 0.36 mmol), DIEA (130 ⌈L, 0.72 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid (2-chloro-phenyl)-methyl-amide: MS m/z: (M+H) 537.4.

Example 130: 5-Chloro-3-(4-chloro-3-trifluoromethyl-benzenesulfonylamino)-pyridine-2-carboxylic Acid ethyl-pyridin-2-yl-amide

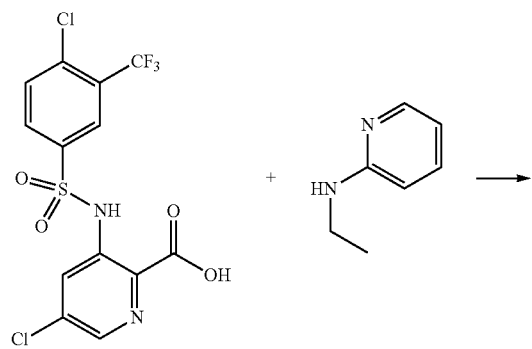

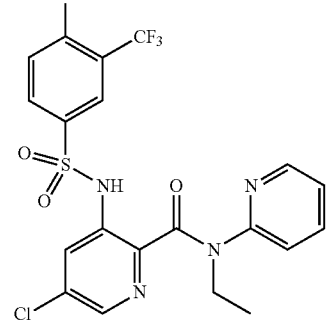

5-Chloro-3-(4-chloro-3-(trifluoromethyl)phenylsulfonamido)picolinic acid (150 mg, 0.36 mmol), ethyl-pyridin-2-yl-amine (131 mg, 1.08 mmol), BOP (207 mg, 0.47 mmol), DIEA (400 ⌈L, 2.16 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid ethyl-pyridin-2-yl-amide: MS m/z: (M+H) 519.0.

Example 131: 5-Chloro-3-(4-chloro-3-trifluoromethyl-benzenesulfonylamino)-pyridine-2-carboxylic Acid methyl-(6-methyl-pyridin-2-yl)-amide

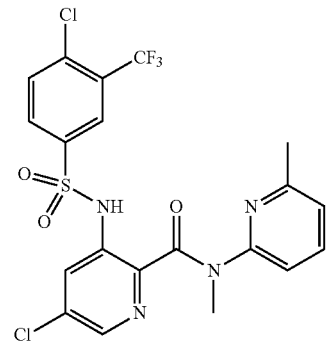

5-Chloro-3-(4-chloro-3-(trifluoromethyl)phenylsulfonamido)picolinic acid (100 mg, 0.24 mmol), methyl-(6-methyl-pyridin-2-yl)-amine (88 mg, 0.72 mmol), BOP (137 mg, 0.31 mmol), DIEA (265 ⌈L, 1.44 mmol) were reacted according to the procedure D to provide the title compound. HPLC purification (20→90% gradient of MeCN-water) provided 5-Chloro-3-(4-chloro-3-trifluoromethyl-benzenesulfonylamino)-pyridine-2-carboxylic acid methyl-(6-methyl-pyridin-2-yl)-amide: MS m/z: 519.0 (M+H).

Example 132: 5-Chloro-3-(4-chloro-3-trifluoromethyl-benzenesulfonylamino)-pyridine-2-carboxylic Acid methyl-(4-methyl-pyridin-2-yl)-amide

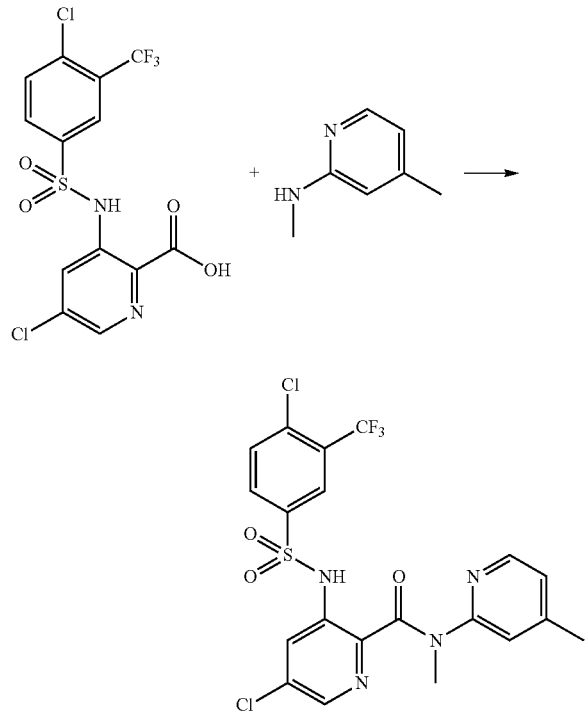

5-Chloro-3-(4-chloro-3-(trifluoromethyl)phenylsulfonamido)picolinic acid (100 mg, 0.24 mmol), methyl-(4-methyl-pyridin-2-yl)-amine (88 mg, 0.72 mmol), BOP (137 mg, 0.31 mmol) and DIEA (265 FL, 1.44 mmol) were reacted according to the procedure D to provide the title compound. HPLC purification (20→90% gradient of MeCN-water) provided 5-chloro-3-(4-chloro-3-trifluoromethyl-benzenesulfonylamino)-pyridine-2-carboxylic acid methyl-(4-methyl-pyridin-2-yl)-amide: MS m/z: 519.0 (M+H).

Example 133: 4-Chloro-N-[5-chloro-2-(8-fluoro-2,3-dihydro-benzo[1,4]oxazine-4-carbonyl)-pyridin-3-yl]-3-trifluoromethyl-benzenesulfonamide

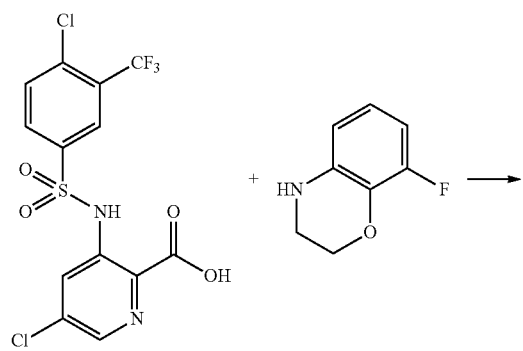

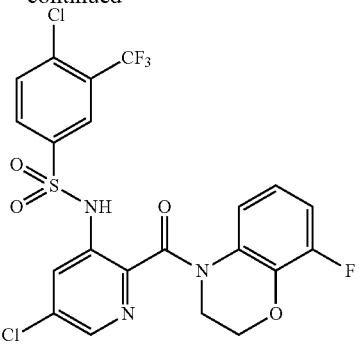

8-Fluoro-3,4-dihydro-2H-benzo[1,4]oxazine, 5-chloro-3-(4-chloro-3-(trifluoromethyl)phenylsulfonamido)picolinic acid, T3P, and Et₃N were reacted according to the procedure D to provide the title compound. HPLC purification provided 4-chloro-N-[5-chloro-2-(8-fluoro-2,3-dihydro-benzo[1,4]oxazine-4-carbonyl)-pyridin-3-yl]-3-trifluoromethyl-benzenesulfonamide. Reverse phase HPLC gradient acetonitrile 0.1% TFA 20-95% in 4 min: 2.986 min. MS m/z 550.1 (M+H).

Example 134: 4-Chloro-N-[5-chloro-2-(6-chloro-2,3-dihydro-benzo[1,4]oxazine-4-carbonyl)-pyridin-3-yl]-3-trifluoromethyl-benzenesulfonamide

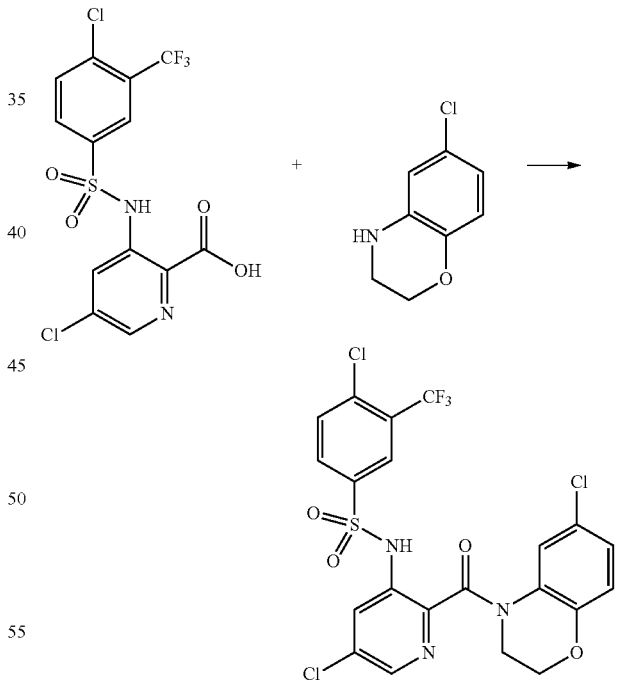

6-Chloro-3,4-dihydro-2H-benzo[1,4]oxazine 5-chloro-3-(4-chloro-3-(trifluoromethyl)phenylsulfonamido)picolinic acid, T3P, and Et₃N were reacted according to the procedure D to provide the title compound. HPLC purification provided 4-chloro-N-[5-chloro-2-(6-chloro-2,3-dihydro-benzo[1,4]oxazine-4-carbonyl)-pyridin-3-yl]-3-trifluoromethyl-benzenesulfonamide. Reverse phase HPLC gradient acetonitrile 0.1% TFA 20-95% in 4 min: 3.180 min MS m/z: 567.1 (M+H).

Example 135: 4-Chloro-N-[5-chloro-2-(2,3-dihydro-pyrido[3,2-b][1,4]oxazine-4-carbonyl)-pyridin-3-yl]-3-trifluoromethyl-benzenesulfonamide

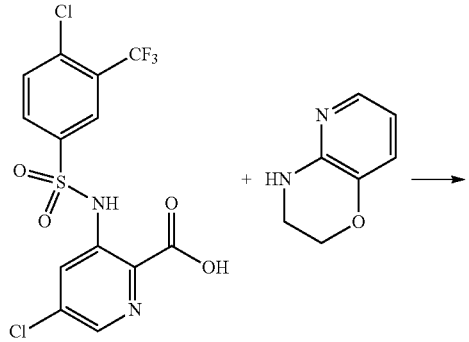

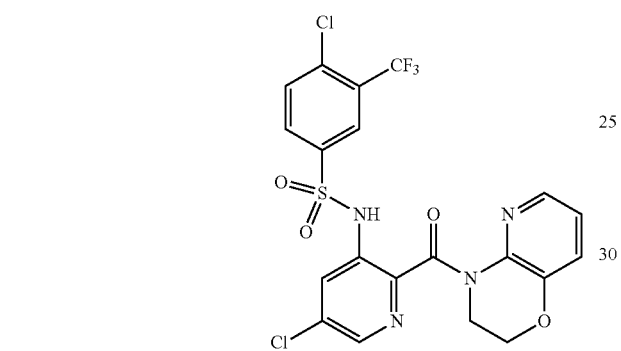

3,4-Dihydro-2H-pyrido[3,2-b][1,4]oxazine 5-chloro-3-(4-chloro-3-(trifluoromethyl)phenylsulfonamido)picolinic acid, T3P, and Et₃N were reacted according to the procedure D to provide the title compound. HPLC purification provided 4-chloro-N-[5-chloro-2-(2,3-dihydro-pyrido[3,2-b][1,4]oxazine-4-carbonyl)-pyridin-3-yl]-3-trifluoromethyl-benzenesulfonamide; Reverse phase HPLC gradient acetonitrile 0.1% TFA 20-95% in 4 min: 2.871 min; MS m/z 533.1 (M+H).

Example 136: 4-Chloro-N-[5-chloro-2-(6-fluoro-2,3-dihydro-benzo[1,4]oxazine-4-carbonyl)-pyridin-3-yl]-3-trifluoromethyl-benzenesulfonamide

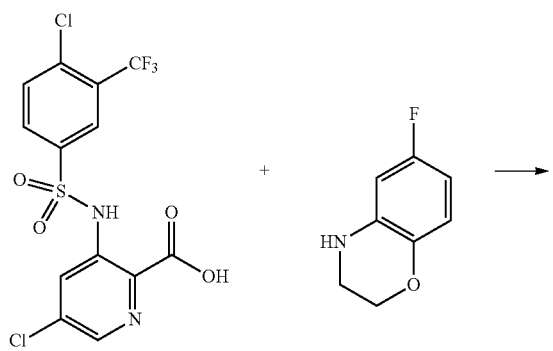

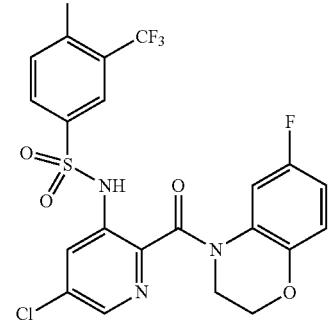

6-Fluoro-3,4-dihydro-2H-benzo[1,4]oxazine 5-chloro-3-(4-chloro-3-(trifluoromethyl)phenylsulfonamido)picolinic acid, T3P, and Et₃N were reacted according to the procedure D to provide the title compound. HPLC purification provided 4-chloro-N-[5-chloro-2-(6-fluoro-2, 3-dihydro-benzo[1,4]oxazine-4-carbonyl)-pyridin-3-yl]-3-trifluoromethyl-benzenesulfonamide: Reverse phase HPLC gradient acetonitrile 0.1% TFA 20-95% in 4 min: 3.041 min MS m/z: 550.1 (M+H).

Example 137: 4-Chloro-N-[5-chloro-2-(6-methyl-2,3-dihydro-benzo[1,4]oxazine-4-carbonyl)-pyridin-3-yl]-3-trifluoromethyl-benzenesulfonamide

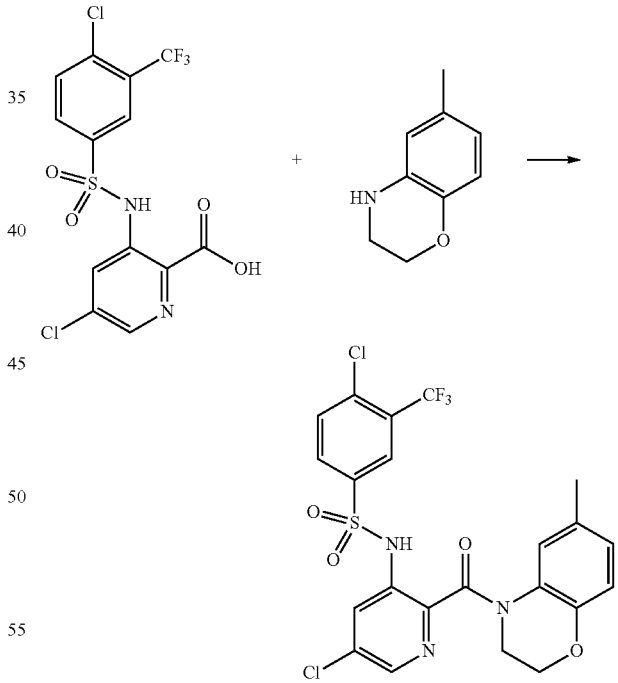

6-Methyl-3,4-dihydro-2H-benzo[1,4]oxazine 5-chloro-3-(4-chloro-3-(trifluoromethyl)phenylsulfonamido)picolinic acid, T3P, and Et₃N were reacted according to the procedure D to provide the title compound. HPLC purification provided 4-chloro-N-[5-chloro-2-(6-methyl-2,3-dihydro-benzo[1,4]oxazine-4-carbonyl)-pyridin-3-yl]-3-trifluoromethyl-benzenesulfonamide: Reverse phase HPLC gradient acetonitrile 0.1% TFA 20-95% in 4 min: 3.099 min; MS m/z: 546.1 (M+H).

Example 138: General Procedure E: Synthesis of 4-chlorobenzooxazin

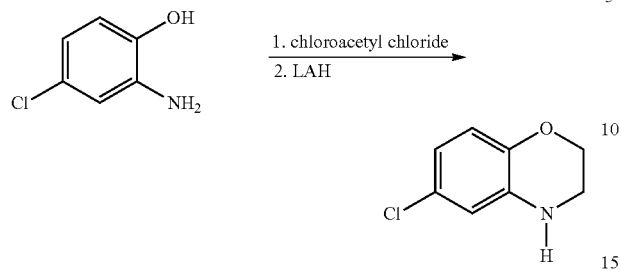

3-Chlorophenol (2.87 g, 20 mmol) was added into a magnetically stirred mixture of 50 mL saturated aqueous solution of sodium bicarbonate and 30 mL tetrahydrofuran. Chloroacetylchloride (2.82 g, 25 mmol) was added and the reaction mixture was stirred at room temperature for 2 h. The reaction was heated to 80° C. and stirred an additional 18 h. The mixture was poured into water (200 mL) and the aqueous layer was extracted with ethyl acetate (200 mL). The combined organic extracts were concentrated and dried under high vacuum.

The crude product was dissolved in tetrahydrofuran (30 mL) and stirred under nitrogen. 10 mL lithium aluminum hydride solution in THF (2.4 M, 24 mmol) was slowly added to the solution. The resultant mixture was stirred at room temperature for 2 h, quenched by adding saturated aqueous solution of sodium bicarbonate (20 mL). The aqueous layer was extracted with 50 mL chloroform twice and the combined organic extracts were concentrated under reduced pressure. The crude product was purified by flash chromatograph to yield 3.13 g of product as a colorless solid.

Example 139: 5-Chloro-thiophene-2-sulfonic acid [5-chloro-2-(2-fluoro-6-methoxy-benzoyl)-pyridin-3-yl]-amide

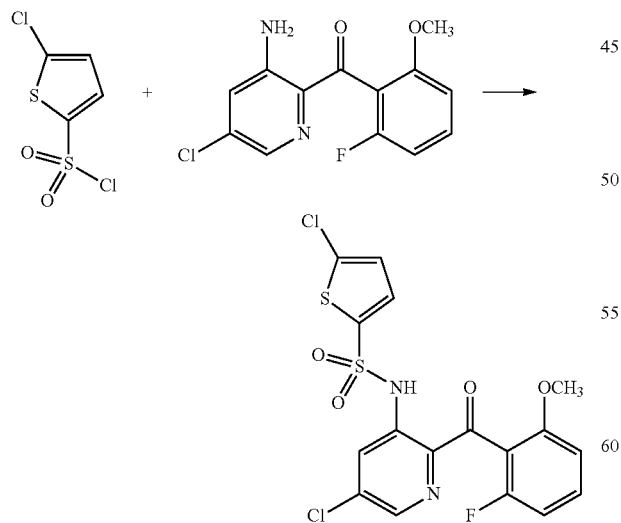

(3-Amino-5-chloro-pyridin-2-yl)-(2-fluoro-6-methoxyphenyl)-methanone (50 mg, 0.178 mmol) and 5-chlorothiophene-2-sulfonyl chloride (85 mg, 0.392 mmol) were reacted according to the procedure described in example 94. The crude product was purified by flash chromatography on silica gel using Combi-flash and pure product fractions were dried under reduced pressure to provide 5-chloro-thiophene-2-sulfonic acid [5-chloro-2-(2-fluoro-6-methoxy-benzoyl)-pyridin-3-yl]-amide. MS m/z: 460.9 (M+H).

Example 140: 4-Chloro-N-(5-chloro-2-formyl-pyridin-3-yl)-N-methoxymethyl-3-trifluoromethyl-benzenesulfonamide

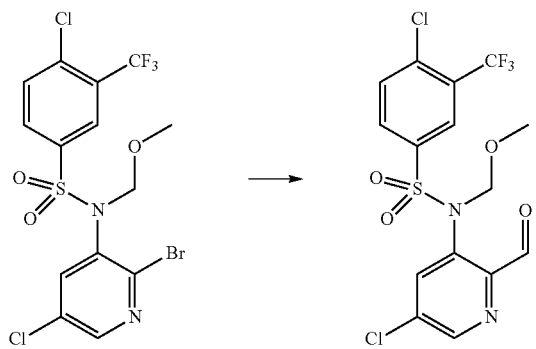 [SMILES: COCN(c1cc(Cl)cnc1Br)S(=O)(=O)c1ccc(Cl)c(C(F)(F)F)c1 ; COCN(c1cc(Cl)cnc1C=O)S(=O)(=O)c1ccc(Cl)c(C(F)(F)F)c1]

To a stirred solution of N-(2-bromo-5-chloro-pyridin-3-yl)-4-chloro-N-methoxymethyl-3-trifluoromethyl-benzenesulfonamide (280 mg, 0.566 mmol) in anhydrous THF (3 mL) was added 2 M isopropylmagnesiumchloride in THF (700 FL, 1.36 mmol) at 0° C. It was stirred at the same temperature for 20 minutes and then DMF (174 FL, 1.36 mmol) was added in dropwise and the progress of the reaction was followed by LCMS. The reaction mixture was warmed to room temperature and stirred for 6 h. It was then quenched with saturated aqueous NH$_4$Cl (2 mL), and extracted with EtOAc. The combined extracts were dried (Na$_2$SO$_4$), filtered and concentrated under reduced pressure. The residue was purified by flash column chromatography to provide 4-Chloro-N-(5-chloro-2-formyl-pyridin-3-yl)-N-methoxymethyl-3-trifluoromethyl-benzenesulfonamide Mass spectrum m/z: 443.0 (M+H).

Example 141: 4-Chloro-N-{5-chloro-2-[hydroxy-(2-nitro-phenyl)-methyl]-pyridin-3-yl}-N-methoxymethyl-3-trifluoromethyl-benzenesulfonamide

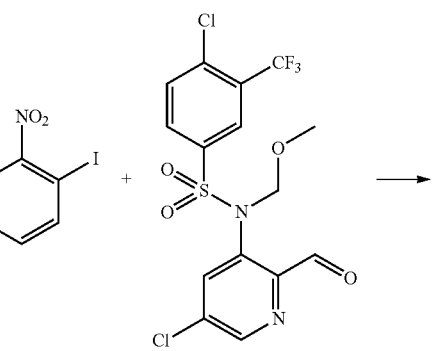

-continued

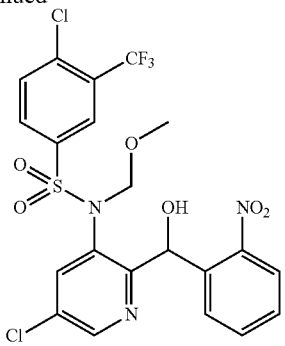

To a stirred solution of 1-iodo-2-nitro-benzene (769 mg, 3.08 mmol) in anhydrous THF (3 mL) was added 2 M phenylmagnesiumchloride in THF (1.62 mL, 3.24 mmol) at −40° C. under an atmosphere of nitrogen. It was stirred at the same temperature for 15 minutes and then 4-chloro-N-(5-chloro-2-formyl-pyridin-3-yl)-N-methoxymethyl-3-trifluoromethyl-benzenesulfonamide (1.04 g, 2.36 mmol) was added in one portion and the progress of the reaction was followed by LCMS. The reaction mixture was warmed to room temperature and stirred for 3 h. It was then quenched with saturated aqueous NH$_4$Cl (2 mL), and extracted with EtOAc. The combined extracts were dried (Na$_2$SO$_4$), filtered and concentrated under reduced pressure to provide crude 4-chloro-N-{5-chloro-2-[hydroxy-(2-nitro-phenyl)-methyl]-pyridin-3-yl}-N-methoxymethyl-3-trifluoromethyl-benzenesulfonamide, which was used in the following step without any purification. Mass spectrum m/z: 566.3 (M+H).

Example 142: 4-Chloro-N-[5-chloro-2-(2-nitro-benzoyl)-pyridin-3-yl]-N-methoxymethyl-3-trifluoromethyl-benzenesulfonamide

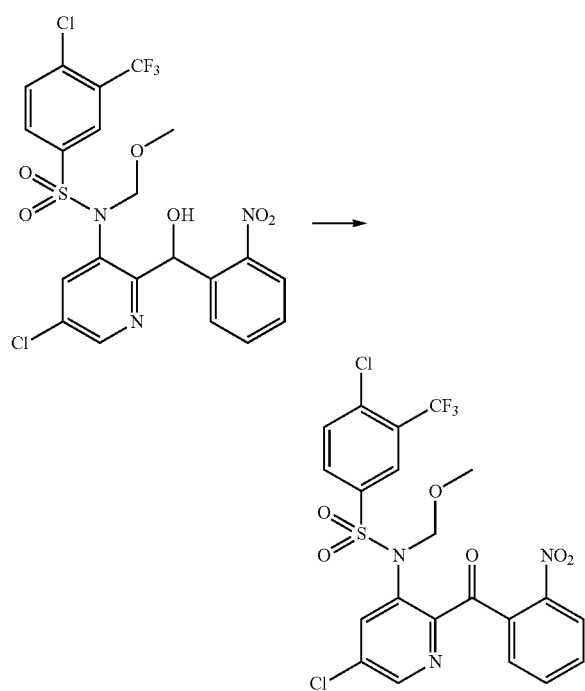

A mixture of 4-chloro-N-{5-chloro-2-[hydroxy-(2-nitrophenyl)-methyl]-pyridin-3-yl}-N-methoxymethyl-3-trifluoromethyl-benzenesulfonamide (1.0 g) and Dess-Martin periodinane (1.50 g, 3.54 mmol) in CH$_2$Cl$_2$ (20 mL) at room temperature was stirred for 2-4 h. A mixture of 10% aqueous Na$_2$S$_2$O$_3$ (10 mL) and saturated aqueous NaHCO$_3$ (10 mL) was then added and the biphasic mixture vigorously stirred for 30 min. The phases were then separated and the aqueous portion extracted with CH$_2$Cl$_2$. The combined organic extracts were washed with saturated aqueous NaHCO$_3$, then brine, dried (Na$_2$SO$_4$) and filtered. The filtrate was concentrated under reduced pressure and the residue purified by flash column chromatography over silica gel (EtOAc/hexanes, 1:4, then 2:3) to provide 4-Chloro-N-[5-chloro-2-(2-nitro-benzoyl)-pyridin-3-yl]-N-methoxymethyl-3-trifluoromethyl-benzenesulfonamide. Mass spectrum m/z: 586.3 (M+Na).

Example 143: 4-Chloro-N-[5-chloro-2-(2-nitro-benzoyl)-pyridin-3-yl]-3-trifluoromethyl-benzenesulfonamide

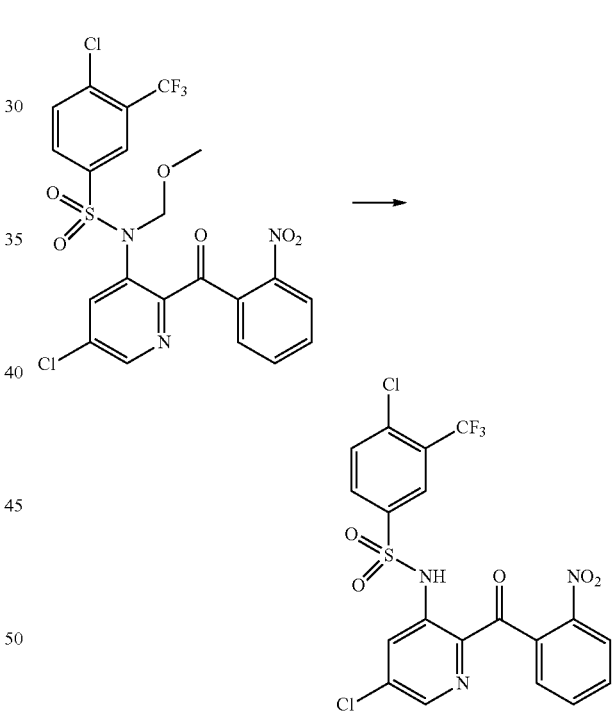

A mixture 4-chloro-N-[5-chloro-2-(2-nitro-benzoyl)-pyridin-3-yl]-N-methoxymethyl-3-trifluoromethyl-benzenesulfonamide (580 g, 1.02 mmol) in 4 M HCl in dioxane (15 mL), and water (5 mL) was heated at 100° C. for 8 h and then at room temperature for 10 h. The reaction mixture was concentrated to dryness under reduced pressure and it was treated with aqueous NaHCO$_3$ to adjust pH to 5-6 and extracted with EtOAc. The combined extracts were dried (Na$_2$SO$_4$), filtered and concentrated under reduced pressure. The residue was purified by flash column chromatography on silica gel to provide the desired product 4-Chloro-N-[5-chloro-2-(2-nitro-benzoyl)-pyridin-3-yl]-3-trifluoromethylbenzenesulfonamide. $^1$H NMR (400 MHz, CDCl$_3$) δ 11.06 (s, 1H), 8.23 (d, J=2.4 Hz, 1H), 8.18 (d, J=2.4 Hz, 1H), 8.14 (dd, J=8.0, 1.4 Hz, 1H), 8.07 (d, J=2.4 Hz, 1H), 8.00 (dd, J=8.4, 2.0 Hz, 1H), 7.80-7.77 (m, 1H), 7.70-7.66 (m, 2H), 7.45 (dd, J=8.0, 1.6 Hz, 1H); Mass spectrum m/z: 520.2 (M+H).

Example 144: N-[2-(2-Amino-benzoyl)-5-chloro-pyridin-3-yl]-4-chloro-3-trifluoromethyl-benzene-sulfonamide

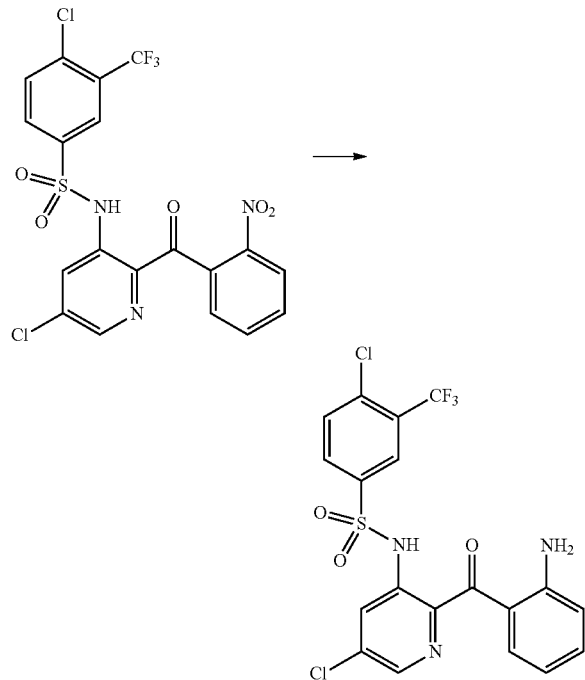

To a stirred suspension of Fe (176 mg, 3.15 mmol) in glacial acetic acid (5 mL) was added a solution 4-chloro-N-[5-chloro-2-(2-nitro-benzoyl)-pyridin-3-yl]-3-trifluoromethyl-benzenesulfonamide (410 mg, 0.788 mmol) in AcOH (5 mL) at 80° C. for 15 minutes. After complete addition the mixture was stirred at the same temperature for 30 minutes and the progress of the reaction was followed by LCMS. The reaction mixture was then cooled to room temperature and it was then diluted with EtOAc and filtered through a pad of Celite. The filtrate was concentrated under reduced pressure and residue was portioned between NaHCO$_3$ and EtOAc. The organic portion was separated and the aqueous portion was extracted with EtOAc. The combined extracts were dried (Na$_2$SO$_4$), filtered and concentrated under reduced pressure. The residue was purified by flash column chromatography on silica gel to provide N-[2-(2-amino-benzoyl)-5-chloro-pyridin-3-yl]-4-chloro-3-trifluoromethyl-benzene-sulfonamide. $^1$H NMR (400 MHz, CDCl$_3$) δ 8.98 (s, 1H), 8.42 (d, J=2.4 Hz, 1H), 8.12 (d, J=2.0 Hz, 1H), 7.93 (d, J=2.4 Hz, 1H), 7.64-7.61 (m, 1H), 7.30-7.26 (m, 2H), 7.03-7.00 (m, 1H), 6.64 (d, J=8.4 Hz, 1H), 6.47-6.43 (m, 1H), 6.26 (s, 2H); Mass spectrum m/z: 490.0 (M+H).

Example 145: 4-Chloro-N-[5-chloro-2-(2-oxo-1,2-dihydro-quinazolin-4-yl)-pyridin-3-yl]-3-trifluoromethyl-benzenesulfonamide

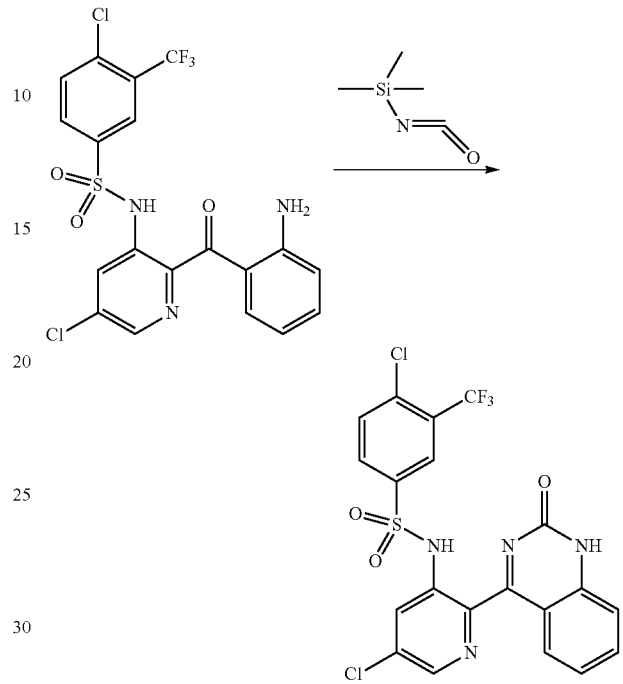

To a stirred solution of N-[2-(2-amino-benzoyl)-5-chloro-pyridin-3-yl]-4-chloro-3-trifluoromethyl-benzenesulfonamide (48 mg, 0.097 mmol) in anhydrous THF (2 mL) and AcOH (400 ⌈L) was added TMSisocyanate (32 ⌈L, 0.22 mmol) and the resulting mixture was heated at 65° C. overnight. The crude reaction mixture was directly purified by HPLC to provide 4-Chloro-N-[5-chloro-2-(2-oxo-1,2-dihydro-quinazolin-4-yl)-pyridin-3-yl]-3-trifluoromethyl-benzenesulfonamide. $^1$H NMR (400 MHz, CDCl$_3$) δ 10.50 (br s, 1H), 8.58 (d, J=2.4 Hz, 1H), 8.19 (d, J=2.4 Hz, 1H), 8.06 (d, J=7.6 Hz, 1H), 7.92 (d, J=2.4 Hz, 1H), 7.80-7.76 (m, 1H), 7.65 (dd, J=8.4, 2.4 Hz, 1H), 7.41 (d, J=8.0 Hz, 1H), 7.23-7.22 (m, 2H); Mass spectrum m/z: 515.0 (M+H).

Example 146: 4-Chloro-N-[5-chloro-2-(2-methane-sulfonylamino-benzoyl)-pyridin-3-yl]-3-trifluoromethyl-benzenesulfonamide

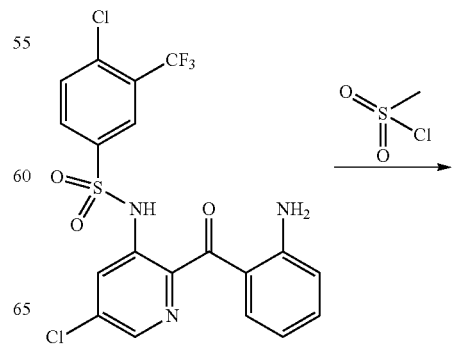

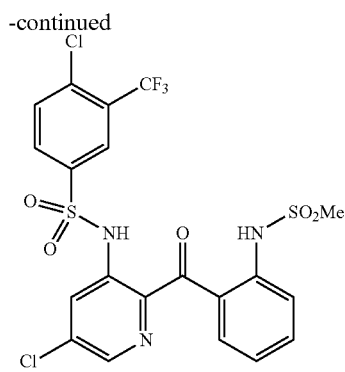

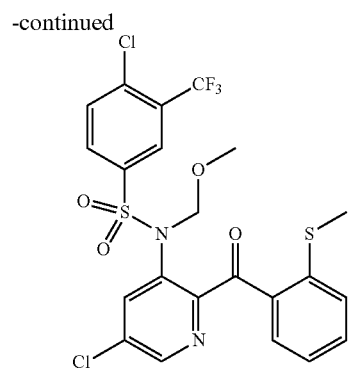

To a solution of N-[2-(2-amino-benzoyl)-5-chloro-pyridin-3-yl]-4-chloro-3-trifluoromethyl-benzenesulfonamide (24 mg, 0.048 mmol) in anhydrous pyridine (1 mL) was added methane sulfonyl chloride (9 mg, 0.075 mmol). The resulting mixture was stirred at room temperature for 2 h was poured into 1 M HCl and extracted with EtOAc. The extracts were concentrated under reduced pressure and the residues was purified by flash column chromatography to trisulfonamide Mass spectrum m/z: 515.0 (M+H). To this trisulfonamide (14 mg, 0.021 mmol) in THF was added TBAF (1 M in THF, 40 FL, 0.04 mmol) and the resulting mixture was stirred overnight. The reaction mixture was quenched with 1 M HCl and extracted with EtOAc. The combined extracts were dried ($Na_2SO_4$), filtered and concentrated under reduced pressure. The residue was purified by flash column chromatography on silica gel (combi-flash) to provide 4-Chloro-N-[5-chloro-2-(2-methanesulfonylamino-benzoyl)-pyridin-3-yl]-3-trifluoromethyl-benzenesulfonamide. $^1$H NMR (400 MHz, $CDCl_3$) δ 9.60 (br, 2H), 8.38 (d, J=2.0 Hz, 1H), 8.16 (d, J=2.0 Hz, 1H), 8.04 (d, J=2.0 Hz, 1H), 7.87 (dd, J=8.4, 2.4 Hz, 1H), 7.72-7.70 (m, 1H), 7.62-7.57 (m, 1H), 7.53 (d, J=8.4 Hz, 1H), 7.29 (dd, J=8.0, 2.4 Hz, 1H), 7.08-7.05 (m, 1H), 3.07 (s, 3H); Mass spectrum m/z: 515.0 (M+H).

Example 147: 4-Chloro-N-[5-chloro-2-(2-methylsulfanyl-benzoyl)-pyridin-3-yl]-N-methoxymethyl-3-trifluoromethyl-benzenesulfonamide

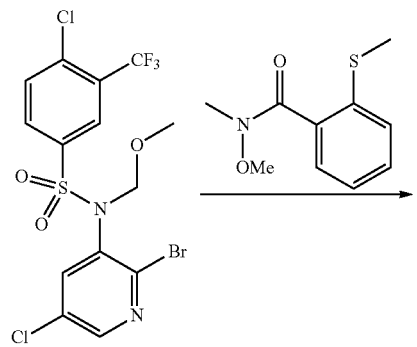

To a stirred solution of N-(2-bromo-5-chloro-pyridin-3-yl)-4-chloro-N-methoxymethyl-3-trifluoromethyl-benzenesulfonamide (8.26 g, 16.6 mmol) in anhydrous THF (50 mL) was added 2 M isopropylmagnesiumchloride in THF (18.4 mL, 36.8 mmol) at −40° C. It was then warmed to 0° C. and stirred at the same temperature for 30 minutes and then N-Methoxy-N-methyl-2-methylsulfanyl-benzamide (10.5 g, 49.8 mmol) was added in and the progress of the reaction was followed by LCMS. The reaction mixture was warmed to room temperature and stirred overnight (18 h). It was then quenched with saturated aqueous $NH_4Cl$ (2 mL), and extracted with EtOAc. The combined extracts were dried ($Na_2SO_4$), filtered and concentrated under reduced pressure. The residue was purified by flash column chromatography to provide 4-chloro-N-[5-chloro-2-(2-methylsulfanyl-benzoyl)-pyridin-3-yl]-N-methoxymethyl-3-trifluoromethyl-benzenesulfonamide. Mass spectrum m/z: 486.9 (M+Na).

Example 148: 4-Chloro-N-[5-chloro-2-(2-methanesulfonyl-benzoyl)-pyridin-3-yl]-N-methoxymethyl-3-trifluoromethyl-benzenesulfonamide

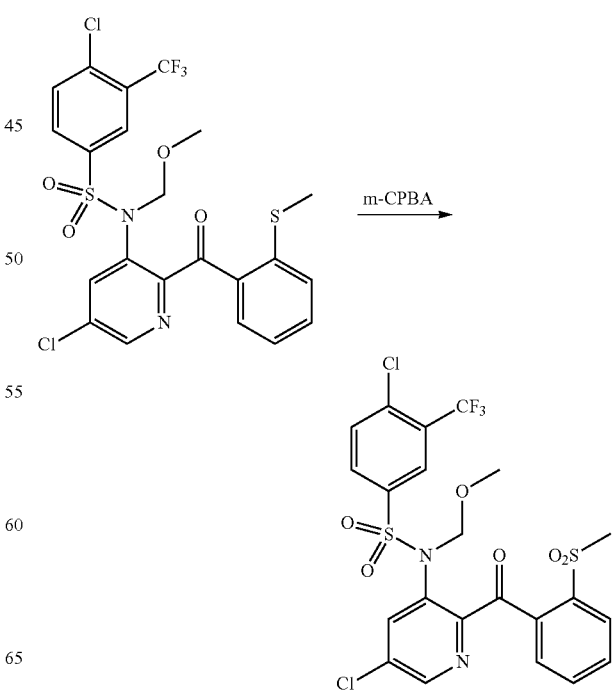

To a stirred solution of 4-chloro-N-[5-chloro-2-(2-methylsulfanyl-benzoyl)-pyridin-3-yl]-N-methoxymethyl-3-trifluoromethyl-benzenesulfonamide (10.0 g, 17.7 mmol) in CH$_2$Cl$_2$ (100 mL) was added m-CPBA (8.9 g, 75% by wt, 38.9 mmol) in one portion and the progress of the reaction was monitored by LCMS. After overnight stirring at room temperature, the reaction mixture was quenched with pyridine (10 mL) and reaction mixture was stirred for 30 minutes. Then portioned between diethyl ether and water, the aqueous portion was separated and the organic portion was washed with NH$_4$Cl and NaHCO$_3$ respectively. The combined extracts were dried (Na$_2$SO$_4$), filtered and concentrated under reduced pressure. The residue was purified by flash column chromatography to provide 4-chloro-N-[5-chloro-2-(2-methanesulfonyl-benzoyl)-pyridin-3-yl]-N-methoxymethyl-3-trifluoromethyl-benzenesulfonamide. Mass spectrum m/z: 497.4 (M+H).

Example 149: 4-Chloro-N-[5-chloro-2-(2-methanesulfonyl-benzoyl)-pyridin-3-yl]-3-trifluoromethyl-benzenesulfonamide

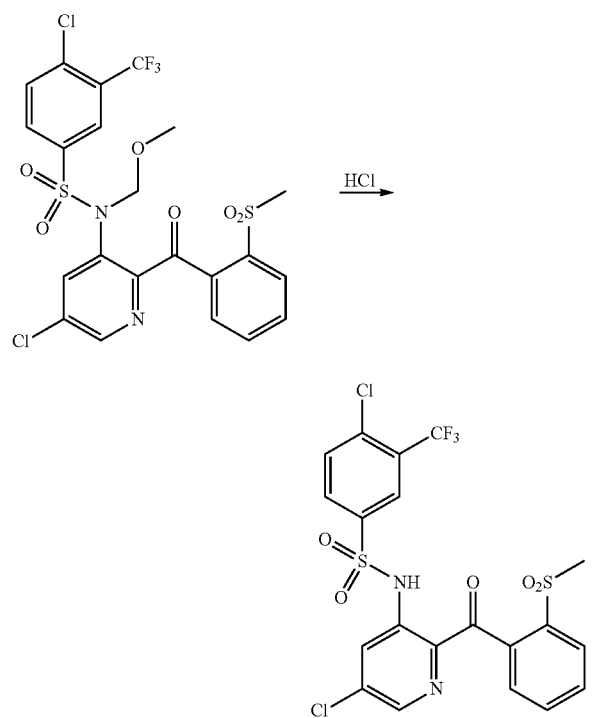

A mixture 4-chloro-N-[5-chloro-2-(2-methanesulfonyl-benzoyl)-pyridin-3-yl]-N-methoxymethyl-3-trifluoromethyl-benzenesulfonamide (9.6 g, 16.1 mmol) in 4 M HCl in dioxane (60 mL), and water (15 mL) was heated at 100° C. for 20 h. The reaction mixture was concentrated to dryness under reduced pressure and it was treated with aqueous NaHCO$_3$ to adjust pH to 5-6 and extracted with EtOAc. The combined extracts were dried (Na$_2$SO$_4$), filtered and concentrated under reduced pressure. The residue was purified by flash column chromatography on silica gel to provide the desired product. $^1$H NMR (400 MHz, CDCl$_3$)) 11.1 (s, 1H), 8.22-8.14 (m, 2H), 8.00-7.97 (m, 1H), 7.72-7.65 (m, 3H), 7.33 (d, J=7.2 Hz, 1H), 3.04 (s, 3H); Mass spectrum m/z: 553.40 (M+H).

Example 150: 4-Chloro-N-[5-chloro-6-methyl-2-(2-methylsulfanyl-benzoyl)-pyridin-3-yl]-N-methoxymethyl-3-trifluoromethyl-benzenesulfonamide

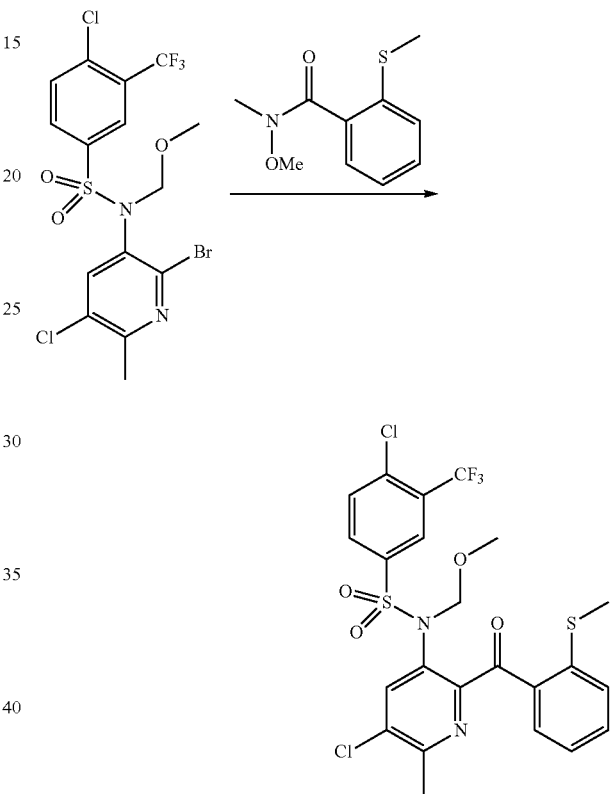

To a stirred solution of N-(2-bromo-5-chloro-6-methyl-pyridin-3-yl)-4-chloro-N-methoxymethyl-3-trifluoromethyl-benzenesulfonamide (255 mg, 0.5 mmol) in anhydrous THF (3 mL) was added 2 M isopropylmagnesiumchloride in THF (600 FL, 1.2 mmol) at −40° C. It was then warmed to 0° C. and stirred at the same temperature for 1 h and then N-Methoxy-N-methyl-2-methylsulfanyl-benzamide (422 mg, 1.00 mmol) was added in and the progress of the reaction was followed by LCMS. The reaction mixture was warmed to room temperature and stirred overnight (18 h). It was then quenched with saturated aqueous NH$_4$Cl (2 mL), and extracted with EtOAc. The combined extracts were dried (Na$_2$SO$_4$), filtered and concentrated under reduced pressure. The residue was purified by flash column chromatography (ISCO) to provide 4-chloro-N-[5-chloro-6-methyl-2-(2-methylsulfanyl-benzoyl)-pyridin-3-yl]-N-methoxymethyl-3-trifluoromethyl-benzenesulfonamide. Mass spectrum m/z: 601.4 (M+Na).

Example 151: 4-Chloro-N-[5-chloro-2-(2-methane-sulfonyl-benzoyl)-6-methyl-pyridin-3-yl]-N-methoxymethyl-3-trifluoromethyl-benzenesulfonamide

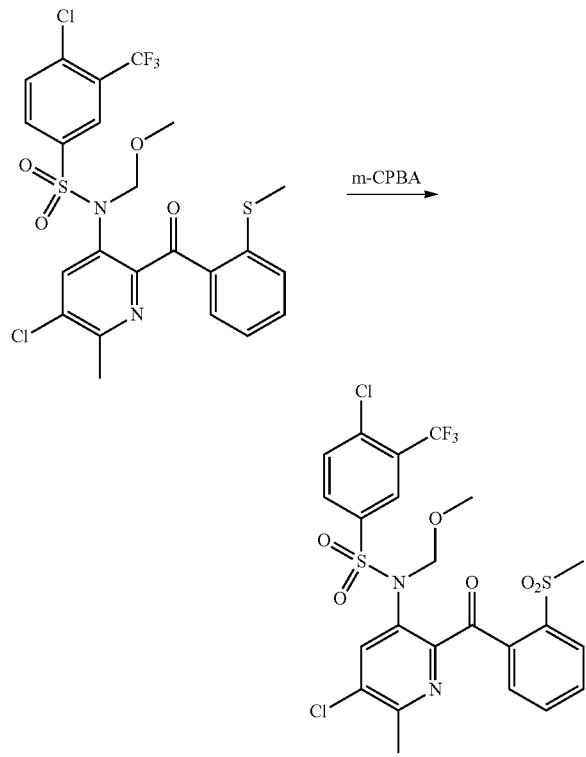

To a stirred solution of 4-chloro-N-[5-chloro-6-methyl-2-(2-methylsulfanyl-benzoyl)-pyridin-3-yl]-N-methoxymethyl-3-trifluoromethyl-benzenesulfonamide (100 mg, 0.17) in CH$_2$Cl$_2$ (5 mL) was added m-CPBA (125 g, 75% by wt, 0.54 mmol) in one portion and the progress of the reaction was monitored by LCMS. After overnight stirring at room temperature, the reaction mixture was quenched with pyridine (200 FL) and reaction mixture was purified by reverse phase HPLC to provide 4-chloro-N-[5-chloro-2-(2-methanesulfonyl-benzoyl)-6-methyl-pyridin-3-yl]-N-methoxymethyl-3-trifluoromethyl-benzenesulfonamide. Mass spectrum m/z: 633.4 (M+Na).

Example 152: 4-Chloro-N-[5-chloro-2-(2-methane-sulfonyl-benzoyl)-6-methyl-pyridin-3-]3-trifluoromethyl-benzenesulfonamide

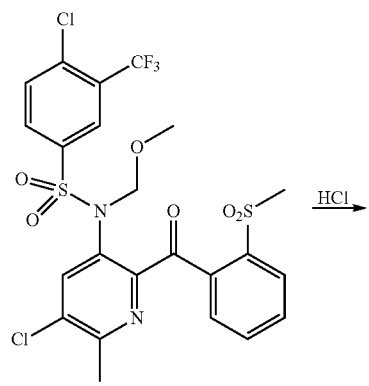

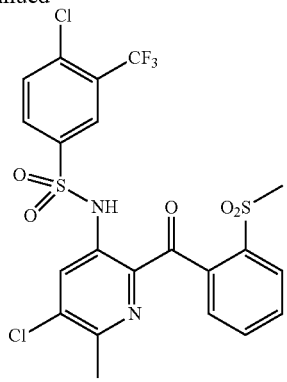

A mixture 4-chloro-N-[5-chloro-2-(2-methanesulfonyl-benzoyl)-6-methyl-pyridin-3-yl]-N-methoxymethyl-3-trifluoromethyl-benzenesulfonamide (40 mg, 0.07 mmol) in 4 M HCl in dioxane (2 mL), and water (1 mL) was heated at 100° C. for 4 h and then it was stirred at room temperature overnight. The reaction mixture was concentrated to dryness under reduced pressure and it was treated with aqueous NaHCO$_3$ to adjust pH to 5-6 and extracted with EtOAc. The combined extracts were dried (Na$_2$SO$_4$), filtered and concentrated under reduced pressure. The residue was purified by flash column chromatography on silica gel to provide the desired product. $^1$H NMR (400 MHz, CDCl$_3$) δ 10.93 (s, 1H), 8.21 (s, 1H), 8.15 (s, 1H), 7.98-7.96 (m, 2H), 7.70-7.62 (m, 3H), 7.33-7.31 (m, 1H); Mass spectrum m/z: 567.4.0 (M+H).

Example 153: 4-Chloro-N-[5-chloro-2-(2-methoxy-benzoyl)-pyridin-3-yl]-N-methoxymethyl-3-trifluoromethyl-benzenesulfonamide

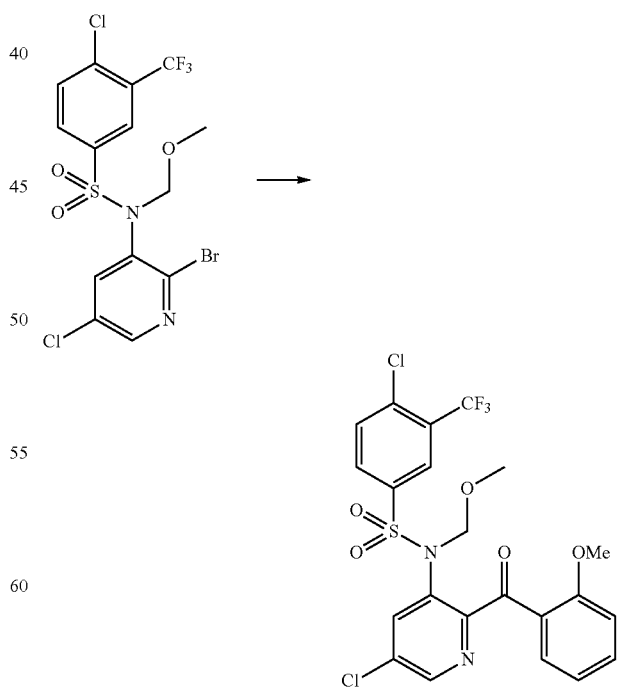

4-Chloro-N-[5-chloro-2-(2-methoxy-benzoyl)-pyridin-3-yl]-N-methoxymethyl-3-trifluoromethyl-benzenesulfonamide was prepared according to procedure described in example 29 from 2,N-dimethoxy-N-methyl-benzamide. Mass spectrum m/z: 571.0 (M+Na).

Example 154: 4-Chloro-N-[5-chloro-2-(5-fluoro-2-methoxy-benzoyl)-pyridin-3-yl]-N-methoxymethyl-3-trifluoromethyl-benzenesulfonamide

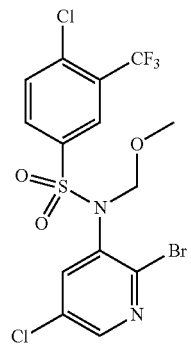  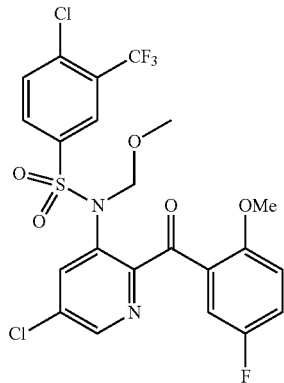

4-Chloro-N-[5-chloro-2-(5-fluoro-2-methoxy-benzoyl)-pyridin-3-yl]-N-methoxymethyl-3-trifluoromethyl-benzenesulfonamide was prepared according to procedure described in example 29. Mass spectrum m/z: 589.3 (M+Na).

Example 155: 4-Chloro-N-[5-chloro-2-(2-fluoro-6-methoxy-benzoyl)-pyridin-3-yl]-N-methoxymethyl-3-trifluoromethyl-benzenesulfonamide

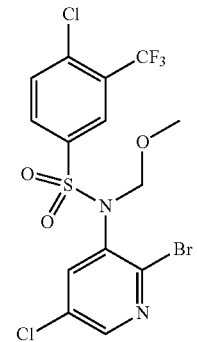  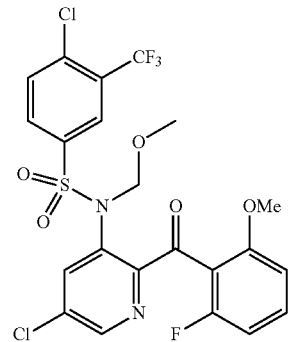

4-Chloro-N-[5-chloro-2-(2-fluoro-6-methoxy-benzoyl)-pyridin-3-yl]-N-methoxymethyl-3-trifluoromethyl-benzenesulfonamide was prepared according to procedure described in example 29. Mass spectrum m/z: 589.0 (M+H).

Example 156: 4-Chloro-N-[5-chloro-2-(2-methoxy-6-methyl-benzoyl)-pyridin-3-yl]-N-methoxymethyl-3-trifluoromethyl-benzenesulfonamide

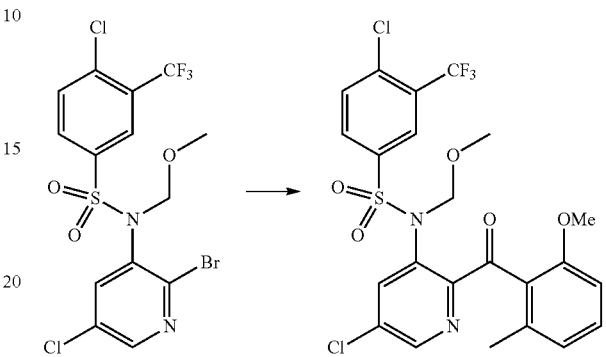

4-Chloro-N-[5-chloro-2-(2-methoxy-6-methyl-benzoyl)-pyridin-3-yl]-N-methoxymethyl-3-trifluoromethyl-benzenesulfonamide. was prepared according to procedure described in example 29. Mass spectrum m/z: 585.0 (M+H).

Example 157: 4-Chloro-N-[5-chloro-2-(2-methoxy-benzoyl)-pyridin-3-yl]-3-trifluoromethyl-benzenesulfonamide

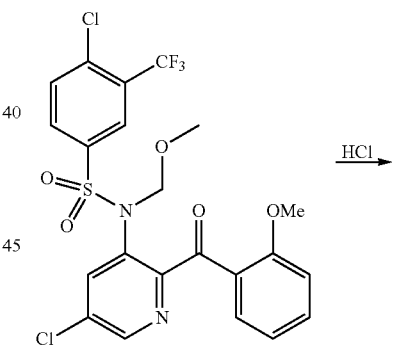

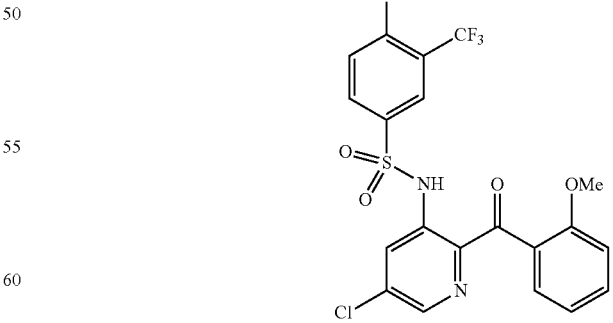

The title compound was prepared according to the procedure described in Example 149. $^1$H NMR (400 MHz, CDCl$_3$) δ 10.81 (s, 1H), 8.24 (d, J=2.0 Hz, 1H), 8.15-8.14 (m, 2H), 7.95 (dd, J=8.4, 2.0 Hz, 1H), 7.60 (d, J=8.4 Hz, 1H), 7.51-7.47 (m, 1H), 7.32-7.30 (m, 1H), 7.05-7.01 (m, 1H), 6.90 (d, J=8.4 Hz, 1H), 3.52 (s, 3H); Mass spectrum m/z: 505.2 (M+H).

Example 158: 4-Chloro-N-[5-chloro-2-(5-fluoro-2-methoxy-benzoyl)-pyridin-3-yl]-3-trifluoromethyl-benzenesulfonamide

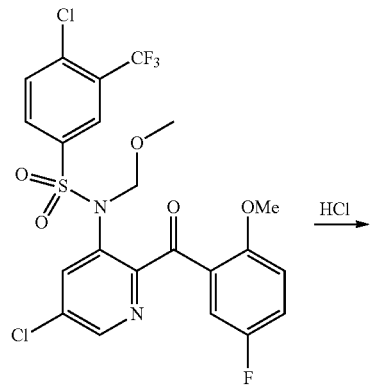

The title compound was prepared according to the procedure described in Example 149. $^1$H NMR (400 MHz, CDCl$_3$) δ 10.76 (s, 1H), 8.24 (d, J=2.0 Hz, 1H), 8.15-8.14 (m, 2H), 7.96 (dd, J=8.0, 2.0 Hz, 1H), 7.62 (d, J=8.4 Hz, 1H), 7.25-7.16 (m, 1H), 7.05-7.03 (m, 1H), 6.87-6.84 (m, 1H), 3.51 (s, 3H); Mass spectrum m/z: 505.2 (M+H).

Example 159: 4-Chloro-N-[5-chloro-2-(2-fluoro-6-methoxy-benzoyl)-pyridin-3-yl]-3-trifluoromethyl-benzenesulfonamide

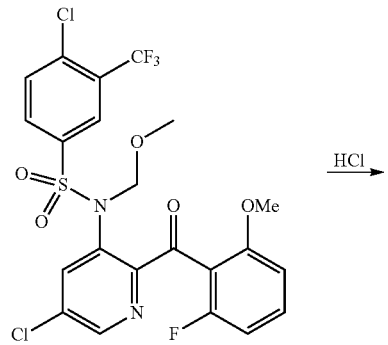

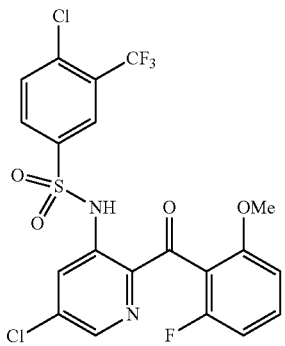

The title compound was prepared according to the procedure described in Example 149. $^1$H NMR (400 MHz, CDCl$_3$) δ 11.10 (s, 1H), 8.23 (d, J=2.4 Hz, 1H), 8.18 (d, J=2.0 Hz, 1H), 8.15 (d, J=2.0 Hz, 1H), 8.00 (dd, J=8.4, 2.4 Hz, 1H), 7.65 (d, J=8.4 Hz, 1H), 7.35-7.41 (m, 1H), 6.70-6.75 (m, 2H), 3.68 (s, 3H); Mass spectrum m/z: 523.0 (M+H).

Example 160: 4-Chloro-N-[5-chloro-2-(2-methoxy-6-methyl-benzoyl)-pyridin-3-yl]-N-methoxymethyl-3-trifluoromethyl-benzenesulfonamide

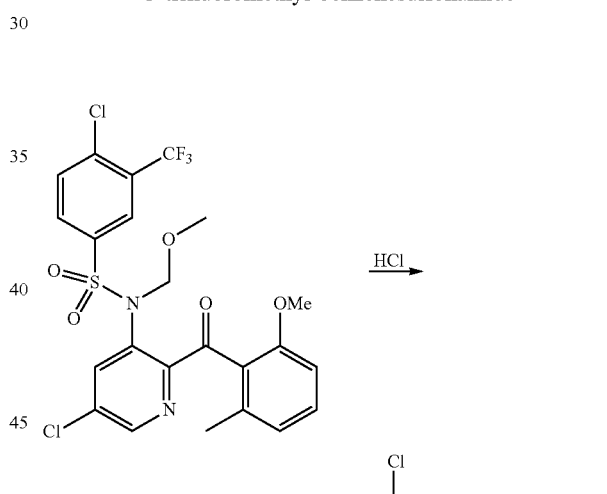

The title compound was prepared according to the procedure described in Example 149. $^1$H NMR (400 MHz, CDCl$_3$) δ 11.32 (s, 1H), 8.17-8.22 (m, 3H), 8.13 (dd, J=8.0, 2.0 Hz, 1H), 7.65 (d, J=8.0 Hz, 1H), 7.25-7.32 (m, 1H), 6.84 (d, J=8.0 Hz, 1H), 6.73 (d, J=8.0 Hz, 1H), 3.50 (s, 3H), 2.06 (s, 3H); Mass spectrum m/z: 519.0 (M+H).

Example 161: 5-Chloro-2-iodo-3-nitro-pyridine

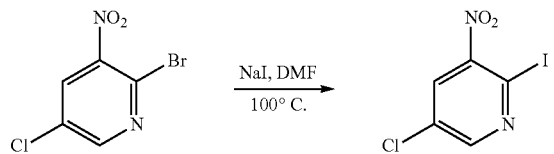 [SMILES: O=[N+]([O-])c1cc(Cl)cnc1Br ; O=[N+]([O-])c1cc(Cl)cnc1I]

To a stirred mixture of 2-bromo-5-chloro-3-nitro-pyridine (2.5 g, 10.5 mmol) in anhydrous DMF (20 mL) was added NaI (12.0 g, 80 mmol) was added in one portion and the resulting mixture was heated at 95-100° C. for 2 days. The reaction mixture was cooled to roomtempearture and poured into water. It was then extracted with EtOAc and the combined extracts were washed with aqueous 10% Na$_2$S$_2$O$_3$. The combined extracts were dried (Na$_2$SO$_4$), filtered and concentrated under reduced pressure. The residue was purified by flash column chromatography on silica gel to provide 5-Chloro-2-iodo-3-nitro-pyridine. Mass spectrum m/z: 285.2 (M+H).

Example 162: (5-Chloro-3-nitro-pyridin-2-yl)-(2,4-dimethyl-pyridin-3-yl)-methanol

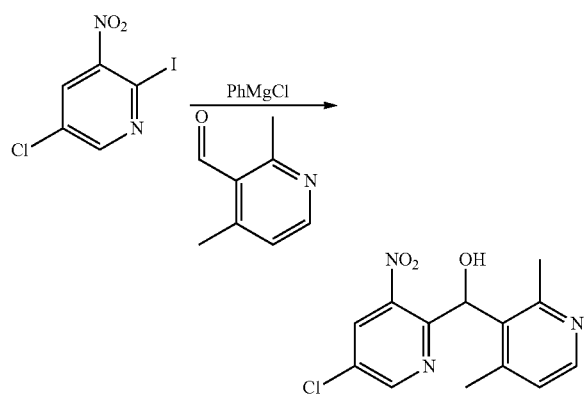

To a stirred solution of 5-Chloro-2-iodo-3-nitro-pyridine (2.5 g, 8.77 mmol) in anhydrous THF (20 mL) at −78° C. was added 2 M phenylmagnesiumchloride in THF (4.8 mL, 9.6 mmol) and stirred at the same temperature for 30 minutes and then 2,4-Dimethyl-pyridine-3-carbaldehyde (1.82 g, 13.15 mmol) was added in one portion and the progress of the reaction was followed by LCMS. The reaction mixture was warmed to room temperature and stirred overnight (18 h). It was then quenched with saturated aqueous NH$_4$Cl (10 mL), and extracted with EtOAc. The combined extracts were washed with aqueous NaHCO$_3$, brine, and then dried (Na$_2$SO$_4$), filtered and concentrated under reduced pressure. The residue was purified by flash column chromatography to (5-Chloro-3-nitro-pyridin-2-yl)-(2,4-dimethyl-pyridin-3-yl)-methanol. Mass spectrum m/z: 294.4 (M+H).

Example 163: (5-Chloro-3-nitro-pyridin-2-yl)-(2,4-dimethyl-pyridin-3-yl)-methanone

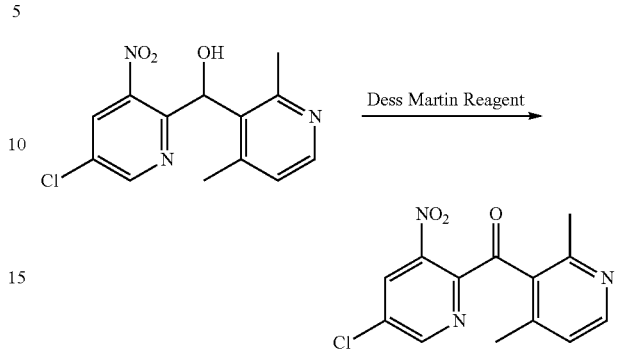

A mixture of (5-chloro-3-nitro-pyridin-2-yl)-(2,4-dimethyl-pyridin-3-yl)-methanol (1.46 g) and Dess-Martin periodinane (2.52 g, 5.91 mmol) in CH$_2$Cl$_2$ (15 mL) at room temperature was stirred for 5 h. A mixture of 10% aqueous Na$_2$S$_2$O$_3$ (10 mL) and saturated aqueous NaHCO$_3$ (10 mL) was then added and the biphasic mixture vigorously stirred for 30 min. The phases were then separated and the aqueous portion extracted with CH$_2$Cl$_2$. The combined organic extracts were washed with saturated aqueous NaHCO$_3$, then brine, dried (Na$_2$SO$_4$) and filtered. The filtrate was concentrated under reduced pressure and the residue purified by flash column chromatography over silica gel to provide (5-chloro-3-nitro-pyridin-2-yl)-(2,4-dimethyl-pyridin-3-yl)-methanone. Mass spectrum m/z: 292.3 (M+Na).

Example 1648: (3-Amino-5-chloro-pyridin-2-yl)-(2,4-dimethyl-pyridin-3-yl)-methanone

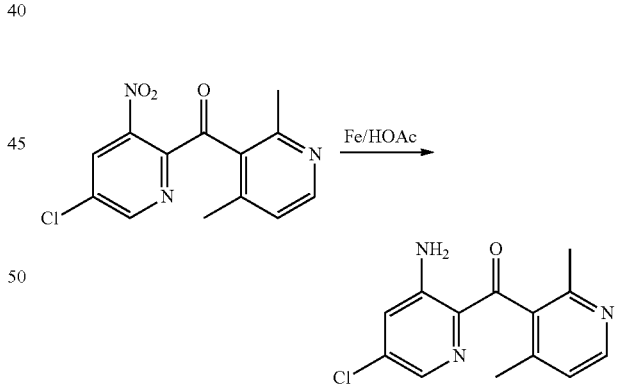

To a mixture of iron powder (220 mg, 4.0 mmol) in 4 ml of acetic acid at 80° C. was slowly added a solution of (3-Nitro-5-chloro-pyridin-2-yl)-(2,4-dimethyl-pyridin-3-yl)-methanone (260 mg, 0.89 mmol) in 2 ml of acetic acid. After the completion of addition the mixture was stirred at 80° C. for half an hour and then cooled. The mixture was diluted with ethyl acetate, filtered through celite and the filtrate was concentrated. The residue was purified by flash column (50% ethyl acetate in hexane) to afford 140 mg of title compound as off-white solid. MS: (M+H)/z=262.0.

Example 165: 3,4-Dichloro-N-[5-chloro-2-(2,4-dimethyl-pyridine-3-carbonyl)-pyridin-3-yl]-benzenesulfonamide

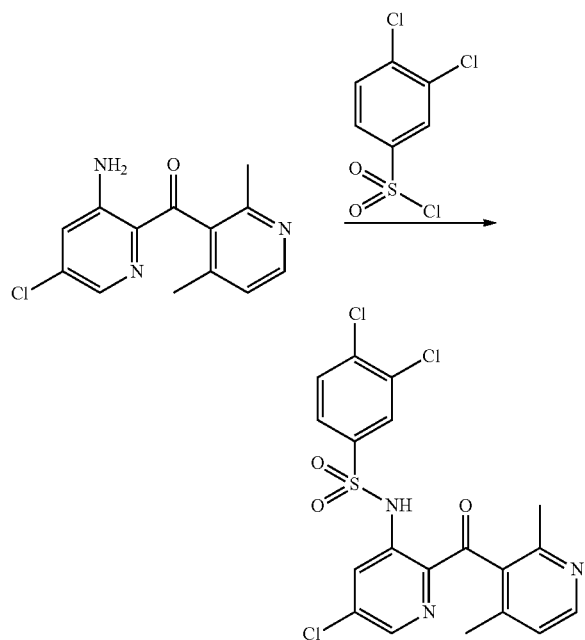

To a solution of (3-Amino-5-chloro-pyridin-2-yl)-(2,4-dimethyl-pyridin-3-yl)-methanone (43 mg, 0.16 mmol) and 10 mg of dimethylaminopyridine in 1.0 ml of pyridine was added 3,4-dichlorobenzenesulfonylchloride (70 mg, 0.28 mmol). The mixture was stirred at 80° C. for 3 hours, cooled to room temperature and concentrated. The residue was directly purified by flash column (50% ethyl acetate in hexane) or preparative HPLC (20-80% acetonitrile in water) to afford 18 mg of title compound as an off-white solid. MS: (M+H)/z=470.4.

Example 166: 5-methyl-3-nitro-pyridin-2-ylamine

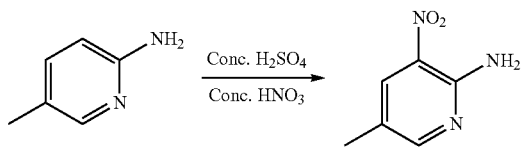

Sulfuric acid (97%, 100 mL) was placed in a −10° C. bath and when the internal temperature reached to 5° C., 2-amino-picoline (25 g, 231.2 mmol) was added in small portions with stirring (in 1 h). The suspension was stirred at ambient temperature to dissolve rest of the solid. The resulting solution was heated to 55° C. and 70% conc. $HNO_3$ (15.6 mL) was added dropwise while maintaining the internal temperature between 55-60° C. The mixture was stirred further 30 min after the addition, poured into crushed ice (800 g), stirred to get solution and treated with 40% aqueous NaOH solution at 0° C. to reach pH 9 and extracted with $CHCl_3$ (3×250 mL). Combined organic layers were washed with brine (2×200 mL), dried (anhydrous $Na_2SO_4$) and concentrated under reduced pressure to afford 5-methyl-3-nitro-pyridin-2-ylamine (9.49 g) as yellow solid in 27% yield. ESMS m/z (relative intensity): 154 $(M+H)^+$ (100).

Example 167: 2-Bromo-5-methyl-3-nitro-pyridine

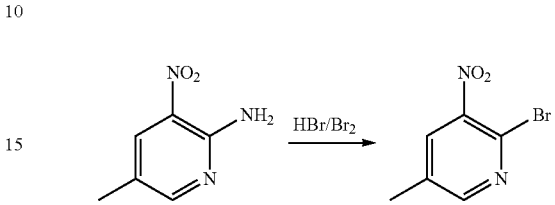

To concentrated HBr (48%, 28.6 mL) was added 5-methyl-3-nitro-pyridin-2-ylamine (5 g, 32.6 mmol) in portions at 0° C. temperature with stirring. The mixture was stirred until the internal temperature reached to −10° C., then bromine was added drop wise. A solution of $NaNO_2$ (7.6 g, 110.84 mmol) in water (11 mL) was added slowly to maintain the reaction mixture temperature below 0° C. The dark mixture (gas evolution was observed) was stirred for 1 h at 0° C. then was carefully treated (slow addition) with a solution of NaOH (12 g, 300 mmol) in water (17 mL) while maintaining the internal temperature below 20° C. The mixture was stirred for an additional 1 h, then was filtered, dried under vacuum for 6 h and purified by recrystallization using 95% EtOH to get pure 2-bromo-5-methyl-3-nitro-pyridine (1.96 g) as yellow solid in 28% first crop yield. ESMS m/z (relative intensity): 217 $(M+H)^+$ (100).

Example 168: 2-Bromo-5-methyl-pyridin-3-ylamine

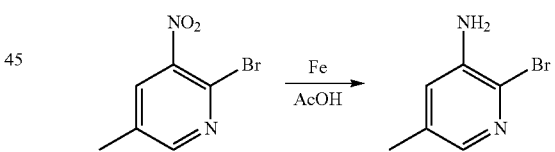

To Fe power (2.18 g, 39.0 mmol), AcOH (10 mL) was added drop wise and heated to 80° C. To it, a solution of 2-bromo-5-methyl-3-nitro-pyridine (1.96 g, 9.07 mmol) in AcOH (10 mL) was added slowly. After 30 min, reaction mixture was allowed to cool to room temperature and diluted with EtOAc (25 mL), filtered through a pad of celite. The filter cake was washed with EtOAc (25 mL) and filterate was concentrated. The residual liquid was slowly treated with saturated aqueous $NaHCO_3$ solution (70 mL), followed by small portions of solid $NaHCO_3$ to neutralize the AcOH, extracted with EtOAc (2×50 mL) and the extracts were dried (anhydrous $Na_2SO_4$) and concentrated under reduced pressure to get 2-bromo-5-methyl-pyridin-3-ylamine (1.45 g) as a brown solid in 86.3% yield. ESMS m/z (relative intensity): 187 $(M+H)^+$ (100).

Example 169: N-(2-Bromo-5-methyl-pyridin-3-yl)-4-chloro-3-trifluoromethyl benzenesulfonamide

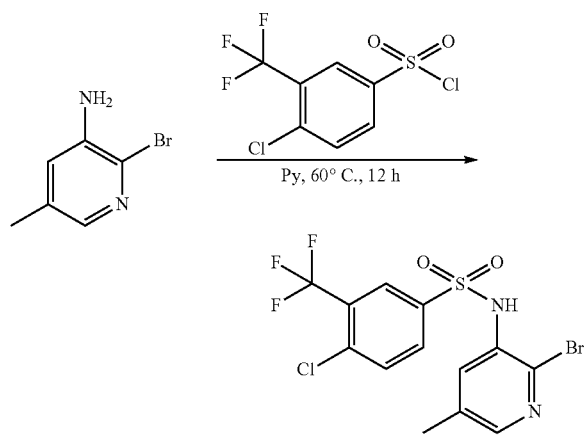

A solution of 2-bromo-5-methyl-pyridin-3-ylamine (1 g, 5.38 mmol) and 4-chloro-3-trifluoromethylbenzenesulfonylchloride (1.8 g, 6.46 mmol) in pyridine (5 mL) was stirred at 60° C. for 12 h. The mixture was concentrated under reduced pressure and to it, was added 1:1 EtOAc-10% aqueous HCl (50 mL). Aqueous layer was separated and extracted with EtOAc (2×50 mL). Combined EtOAc layers were washed with 10% aqueous HCl (50 mL), dried (anhydrous Na$_2$SO$_4$), concentrated and column purified (SiO$_2$, 50% EtOAc-hexanes) to obtain N-(2-bromo-5-methyl-pyridin-3-yl)-4-chloro-3-trifluoromethyl-benzenesulfonamide (1.42 g) in 84% yield as a half white solid. ESMS m/z (relative intensity): 429 (M+H)$^+$ (100).

Example 170: N-(2-bromo-5-methyl-pyridin-3-yl)-4-chloro-N methoxy methyl-3-trifluoromethyl-benzenesulfonamide

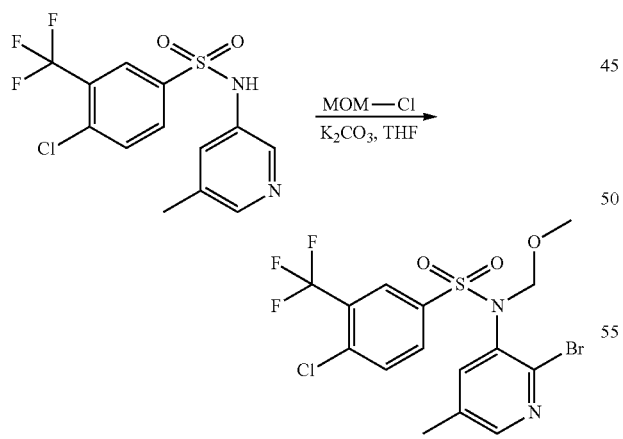

A mixture of N-(2-bromo-5-methyl-pyridin-3-yl)-4-chloro-3-trifluoromethyl-benzenesulfonamide (1.4 g, 3.27 mmol), chloromethyl methyl ether (0.4 mL, 5.23 mmol) and K$_2$CO$_3$ (1.35 g, 9.81 mmol) in THF (20 mL) was stirred at room temperature for 3 h. The mixture was filtered and the filtrate was concentrated and purified by flash chromatography (SiO$_2$, 20% EtOAc-hexanes) to afford N-(2-bromo-5-methyl-pyridin-3-yl)-4-chloro-N-methoxymethyl-3-trifluoromethyl-benzenesulfonamide (1.3 g) as a white solid in 84% yield. ESMS m/z (relative intensity): 473 (M+H)$^+$ (100).

Example 171: 4-Chloro-N-{2-[(2,4-dimethyl-pyridin-3-yl)-hydroxy-methyl]-5-methyl]-5-methyl-pyridin-3-yl}-N-methoxymethyl-3-trifluoromethyl-benzenesulfonamide

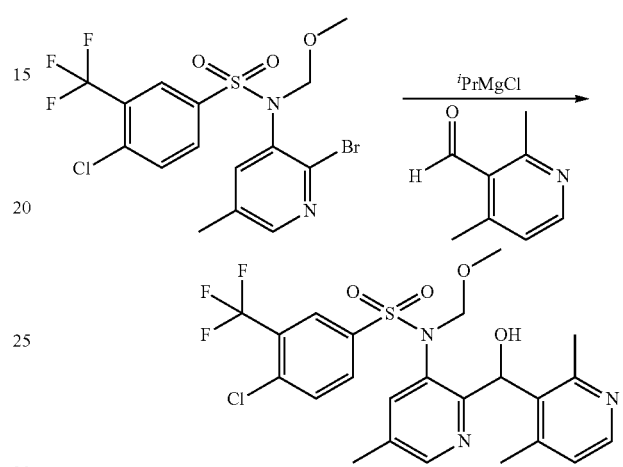

To a solution of N-(2-bromo-5-methyl-pyridin-3-yl)-4-chloro-N-methoxymethyl-3-trifluoromethyl-benzenesulfonamide (500 mg, 1.06 mmol) in THF (3 mL) under nitrogen atmosphere at −30° C. was added drop wise isopropylmagnesium chloride (2 M solution in THF, 1.27 mL, 2.54 mmol). The mixture was then stirred for 30 min at 0° C. followed by the addition of a solution of 2,4-dimethyl-pyridine-3-carbaldehyde (271 mg, 2.01 mmol) at −30° C. The mixture was stirred at room temperature for 3 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 50% EtOAc-hexanes) to obtain 4-chloro-N-{2-[(2,4-dimethyl-pyridin-3-yl)-hydroxy-methyl]-5-methyl]-5-methyl-pyridin-3-yl}-N-methoxymethyl-3-trifluoromethyl-benzene sulfonamide (288 mg) as yellow foam in 51% yield. ESMS m/z (relative intensity): 530 (M+H)$^+$ (100).

Example 172: 4-Chloro-N-[2-(2,4-dimethyl-pyridine-3-carbonyl)-5-methyl-pyridin-3-yl]-N-methoxymethyl-3-trifluoromethyl-benzenesulfonamide

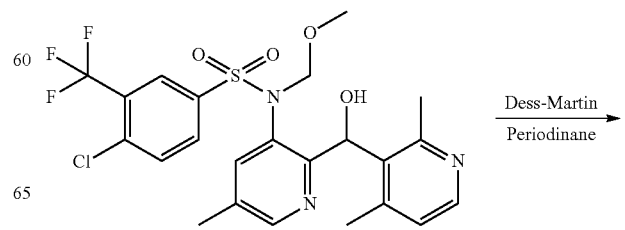

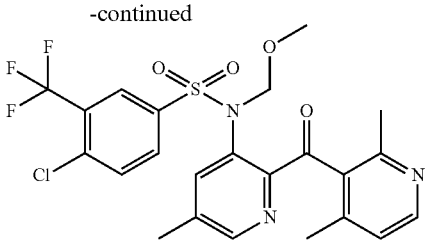

To a solution of 4-chloro-N-{2-[(2,4-dimethyl-pyridin-3-yl)-hydroxy-methyl]-5-methyl]-5-methyl-pyridin-3-yl}-N-methoxymethyl-3-trifluoromethyl-benzene sulfonamide (280 mg, 0.53 mmol) in CH$_2$CH$_2$ (5 mL) was added Dess-Martin periodinane (403 mg, 0.95 mmol) and stirred for 3 h at room temperature. 10% Na$_2$S$_2$O$_3$ (5 mL) and saturated aqueous NaHCO$_3$ solution (5 mL) was added and stirred for 30 min. Aqueous layer was separated and extracted with EtOAc (2×25 mL). Combined organic layers were washed with saturated aqueous NaHCO$_3$ solution (20 mL), brine (20 mL), dried (anhydrous Na$_2$SO$_4$), concentrated to obtain 4-chloro-N-[2-(2,4-dimethyl-pyridine-3-carbonyl)-5-methyl-pyridin-3-yl]-N-methoxymethyl-3-trifluoromethyl-benzenesulfonamide (277 mg) as thick yellow syrup in quantitative crude yield which was used for further transformation without purification. ESMS m/z (relative intensity): 528 (M+H)$^+$ (100).

Example 173: 4-Chloro-N-[2-(2,4-dimethyl-pyridine-3-carbonyl)-5-methyl-pyridin-3-yl]-3-trifluoromethyl-benzenesulfonamide

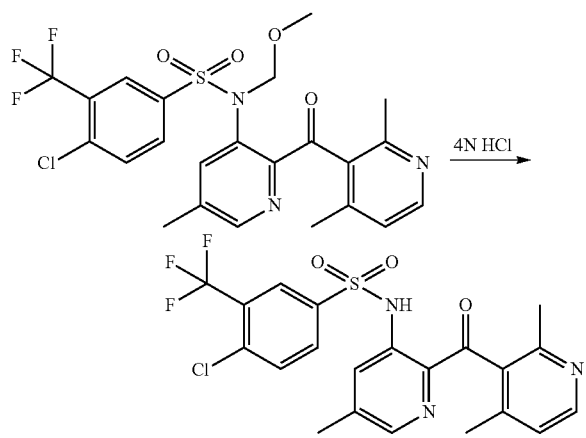

A mixture of 4-chloro-N-[2-(2,4-dimethyl-pyridine-3-carbonyl)-5-methyl-pyridin-3-yl]-N-methoxymethyl-3-trifluoromethyl-benzenesulfonamide (260 mg, 0.49 mmol) in 4M HCl in dioxane (5 mL) and water (1 mL) was refluxed for 3 h. Reaction mixture was cooled to room temperature, evaporated to dryness and treated with saturated aqueous NaHCO$_3$ solution till pH 7-8. The mixture was extracted with EtOAc (2×25 mL), dried (anhydrous Na$_2$SO$_4$) and concentrated. The obtained residue was purified by flash chromatography (SiO2, 70% EtOAc-hexanes) to afford 4-chloro-N-[2-(2,4-dimethyl-pyridine-3-carbonyl)-5-methyl-pyridin-3-yl]-3-trifluoromethyl-benzenesulfonamide (78 mg) as an off white solid (after lyophilization) in 33% yield. ESMS m/z (relative intensity): 484 (M+H)$^+$ (100).

Example 174: 4-Chloro-N-{2-[(2-chlorophenyl)-hydroxy-methyl]-5-methyl]-5-methyl-pyridin-3-yl}-N-methoxymethyl-3-trifluoromethyl-benzenesulfonamide

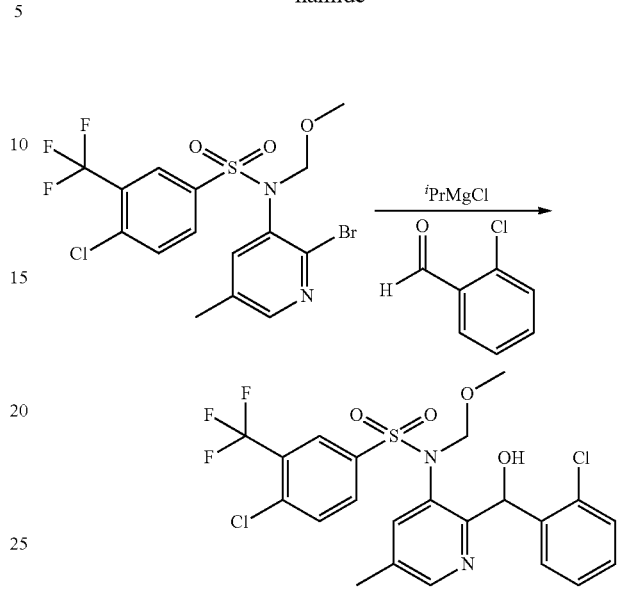

To a solution of N-(2-bromo-5-methyl-pyridin-3-yl)-4-chloro-N-methoxymethyl-3-trifluoromethyl-benzenesulfonamide (500 mg, 1.06 mmol) in THF (3 mL) under nitrogen atmosphere at −30° C. was added drop wise isopropylmagnesium chloride (2 M solution in THF, 1.27 mL, 2.54 mmol). The mixture was then stirred for 30 min at 0° C. followed by the addition of a solution of 2-chlorobenzaldehyde (271 µL, 2.01 mmol) at −30° C. The mixture was stirred at room temperature for 3 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 50% EtOAc-hexanes) to obtain 4-chloro-N-{2-[(2-chlorophenyl)-hydroxy-methyl]-5-methyl]-5-methyl-pyridin-3-yl}-N-methoxymethyl-3-trifluoromethyl-benzenesulfonamide (274 mg) as yellow foam in 48% yield. ESMS m/z (relative intensity): 535 (M+H)$^+$ (100).

Example 175: 4-Chloro-N-[2-(2-chloro-benzoyl)-5-methyl-pyridin-3-yl]-N-methoxymethyl-3-trifluoromethyl-benzenesulfonamide

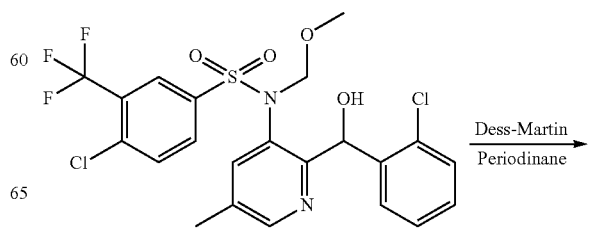

-continued

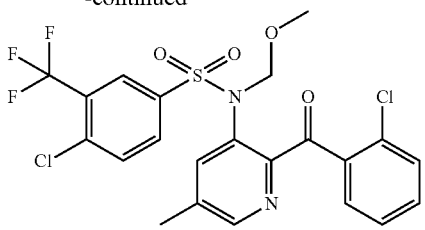

To a solution of 4-chloro-N-{2-[(2-chlorophenyl)-hydroxy-methyl]-5-methyl]-5-methyl-pyridin-3-yl}-N-methoxymethyl-3-trifluoromethyl-benzene sulfonamide (260 mg, 0.49 mmol) in CH₂Cl₂ (5 mL) was added Dess-Martin periodinane (373 mg, 0.88 mmol) and stirred for 3 h at room temperature. 10% Na₂S₂O₃ (5 mL) and saturated aqueous NaHCO₃ solution (5 mL) was added and stirred for 30 min. Aqueous layer was separated and extracted with EtOAc (2×25 mL). Combined organic layers were washed with saturated aqueous NaHCO₃ solution (20 mL), brine (20 mL), dried (anhydrous Na₂SO₄), concentrated to obtain 4-chloro-N-[2-(2-chloro-benzoyl)-5-methyl-pyridin-3-yl]-N-methoxymethyl-3-trifluoromethyl-benzenesulfonamide (260 mg) as thick yellow syrup in quantitative crude yield which was used for further transformation without purification. ESMS m/z (relative intensity): 501 (M-MeOH)⁺ (100).

Example 176: 4-Chloro-N-[2-(2-chloro-benzoyl)-5-methyl-pyridin-3-yl]-3-trifluoromethyl Benzenesulfonamide

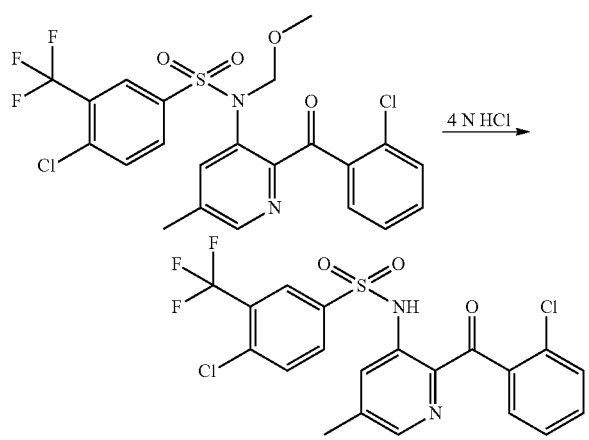

A mixture of 4-chloro-N-[2-(2-chloro-benzoyl)-5-methyl-pyridin-3-yl]-N-methoxymethyl-3-trifluoromethyl-benzenesulfonamide (260 mg, 0.49 mmol) in 4M HCl in dioxane (5 mL) and water (1 mL) was refluxed for 3 h. Reaction mixture was cooled to room temperature, evaporated to dryness and treated with saturated aqueous NaHCO₃ solution till pH 7-8. The mixture was extracted with EtOAc (2×25 mL), dried (anhydrous Na₂SO₄) and concentrated. The obtained residue was purified by flash chromatography (SiO2, 70% EtOAc-hexanes) to afford 4-chloro-N-[2-(2-chloro-benzoyl)-5-methyl-pyridin-3-yl]-3-trifluoromethyl-benzenesulfonamide (106 mg) as a white solid (after lyophilization) in 45% yield. ESMS m/z (relative intensity): 489 (M+H)⁺ (100).

Example 177: 2-{5-Chloro-3-[(4-chloro-3-trifluoromethyl-benzenesulfonyl)-methoxymethyl-amino]-pyridine-2-carbonyl}-benzoic Acid

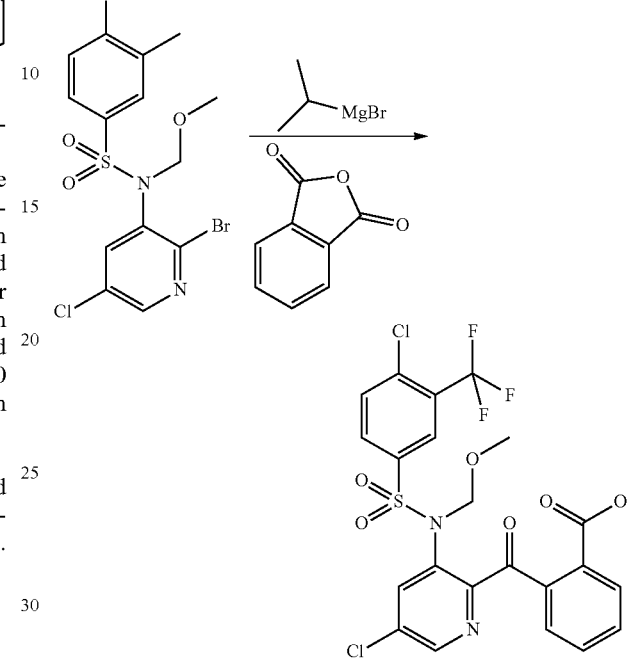

To a solution of N-(2-Bromo-5-chloro-pyridin-3-yl)-4-chloro-N-methoxymethyl-3-trifluoromethyl-benzenesulfonamide (250 mg, 0.50 mmol) in 4.0 ml of THF under nitrogen atmosphere at 0° C. was added drop-wise 0.6 ml (1.2 mmol) of isopropylmagnesium chloride. The mixture was then stirred for 20 min at 0° C. followed by addition of a solution of phthalic anhydride (148 mg, 1.0 mmol) in 1 ml of DCM. The mixture was stirred at room temperature overnight, quenched with saturated ammonium chloride and extracted with ethyl acetate. After concentration the residue was purified by flash chromatograph (70% ethyl acetate in hexane) to afford 80 mg of title compound as an off white solid. MS: (M+H)/z=564.0, (M−32)/z=532.0.

Example 178: 2-[5-Chloro-3-(4-chloro-3-trifluoromethyl-benzenesulfonylamino)-pyridine-2-carbonyl]-benzoic Acid

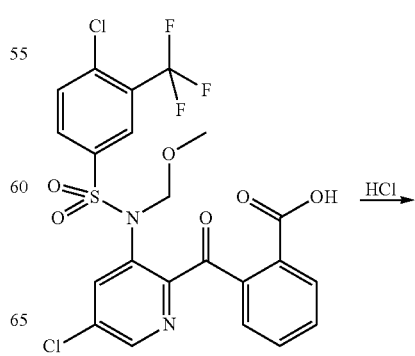

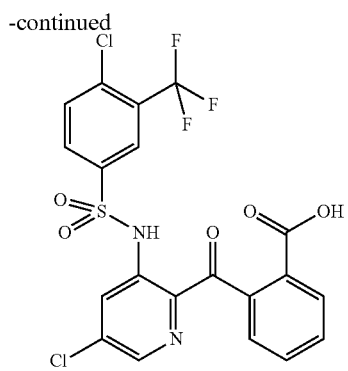

A mixture of 2-{5-Chloro-3-[(4-chloro-3-trifluoromethyl-benzenesulfonyl)-methoxymethyl-amino]-pyridine-2-carbonyl}-benzoic acid (150 mg, 0.27 mmol) in 3 ml of 4M HCl in dioxane and 1 mL of water was refluxed for 2 hours. After cooling to room temperature the mixture was concentrated and then diluted with water. Sodium bicarbonate was added until pH was 6. The mixture was extracted with ethyl acetate, dried and concentrated. The residue was further purified via flash column (70% ethyl acetate in hexane) to afford 60 mg of title compound as an off white solid. MS: (M+H)/z=519.4.

Example 179: 4-Chloro-N-[5-chloro-2-(4-oxo-3,4-dihydro-phthalazin-1-yl)-pyridin-3-yl]-3-trifluoromethyl-benzenesulfonamide

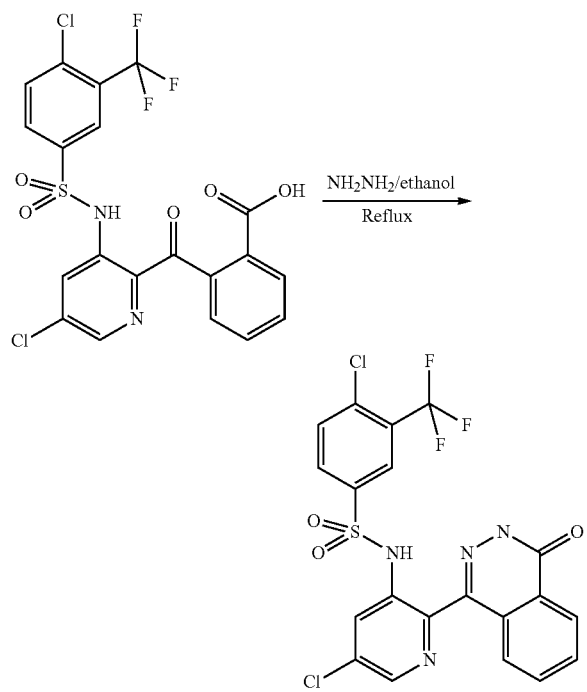

A mixture of 2-[5-Chloro-3-(4-chloro-3-trifluoromethyl-benzenesulfonylamino)-pyridine-2-carbonyl]-benzoic acid (18 mg, 0.0347 mmol) and 2.3 mg of hydrazine hydrate in 1.0 ml of ethanol was refluxed for 4 hours. After cooled to room temperature the mixture was concentrated and the residue was purified via preparative TLC to afford 12 mg of title compound as a white powder. MS: (M+H)/z=515.2.

Example 180: 2-Oxazol-2-yl-benzoic Acid Methyl Ester

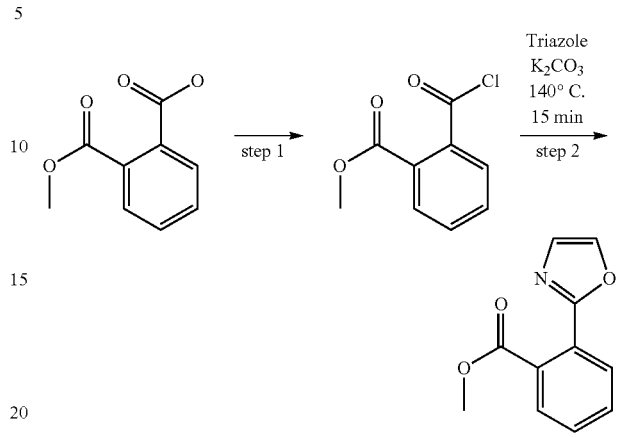

Step 1: To a solution of phthalic acid monomethyl ester (1.8 g, 10 mmol) and 0.020 ml of DMF in 10 ml of DCM was added oxalyl chloride (1.52 g, 12 mmol). The mixture was stirred at room temperature for 2 hours and then concentrated. The residue was used directly for the step 2.

Step 2: A mixture of 2-Chlorocarbonyl-benzoic acid methyl ester (1.3 gram, 6.56 mmol), 1H-triazole (0.42 ml, 7.22 mmol) and potassium carbonate (2.78 g, 20 mmol) in 12 ml of tetramethylene sulfone was heated at 140° C. for half an hour. The mixture was cooled, diluted with ethyl acetate, washed with water 5 times, and dried. After concentration the crude was purified by flash column (50% ethyl acetate in hexane) to afford 250 mg of 2-Oxazol-2-yl-benzoic acid methyl ester as a light yellow liquid. MS: (M+H)/z=204.1.

Example 181: N-Methoxy-N-methyl-2-oxazol-2-yl-benzamide

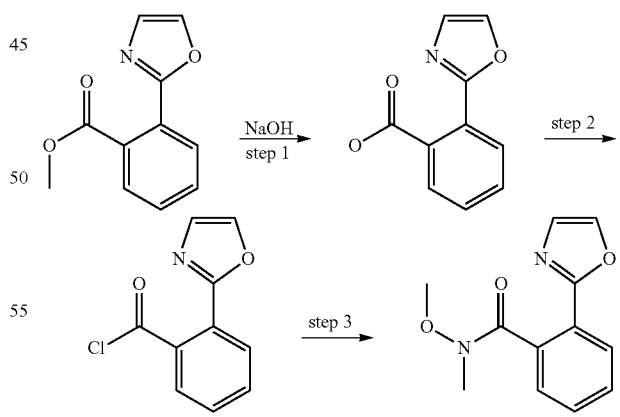

Step 1: A mixture of 2-Oxazol-2-yl-benzoic acid methyl ester (200 mg) in a mixture of 5 mL of methanol and 10 ml of 1 M NaOH was stirred for 3 hours at room temperature. The mixture was neutralized with 2N HCl until pH was 4. The mixture was concentrated and 30 ml of ethyl acetate was added and the resulting mixture was filtrated, the filtrate was concentrated and the residue was used directly at step 2.

Step 2: 2-Oxazol-2-yl-benzoyl chloride was made by according to the previously described procedure.

Step 3: To a mixture of 2-Oxazol-2-yl-benzoyl chloride (104 mg, 0.5 mmol), DIEA (0.26 mL, 1.5 mmol) in 2 ml of DCM was added N,O-dimethylhydroxylamine hydrochloride (59 mg, 0.6 mmol). The mixture was stirred at room temperature for 2 hours, washed with dilute HCl solution followed by brine. Concentration of the organic layer afforded 100 mg of N-Methoxy-N-methyl-2-oxazol-2-yl-benzamide as a sticky light yellow liquid. MS: (M+H)/z=233.1.

Example 182: 4-Chloro-N-[5-chloro-2-(2-oxazol-2-yl-benzoyl)-pyridin-3-yl]-N-methoxymethyl-3-trifluoromethyl-benzenesulfonamide

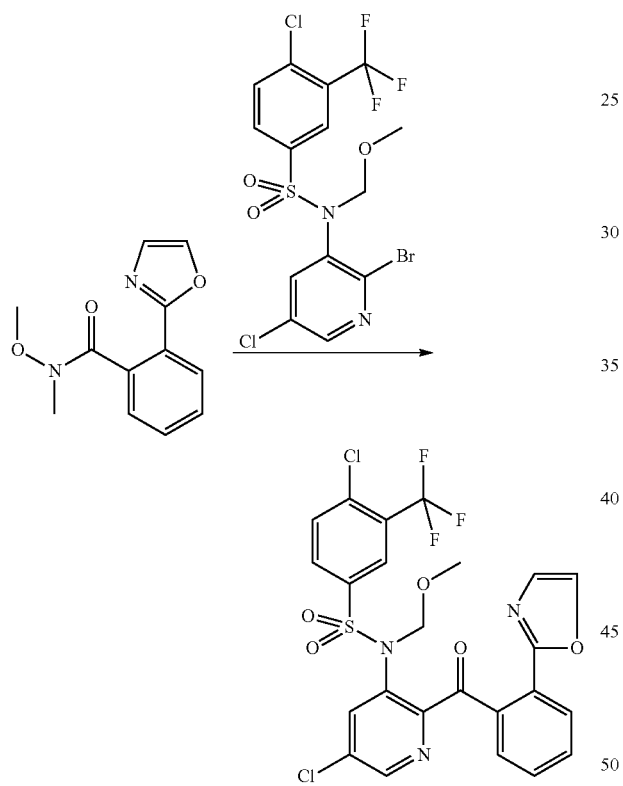

To a solution of N-(2-Bromo-5-chloro-pyridin-3-yl)-4-chloro-N-methoxymethyl-3-trifluoromethyl-benzenesulfonamide (125 mg, 0.25 mmol) in 2.0 mL of THF under nitrogen atmosphere at 0° C. was added drop-wise 0.3 ml (0.6 mmol) of isopropylmagnesium chloride. The mixture was then stirred for 20 min at 0° C. followed by addition of N-Methoxy-N-methyl-2-oxazol-2-yl-benzamide (100 mg, 0.43 mmol). The mixture was stirred at room temperature overnight, quenched with saturated ammonium chloride and extracted with ethyl acetate. After concentration the residue was purified by flash chromatograph (30% ethyl acetate in hexane) to afford 30 mg of title compound as an off white solid. MS: (M+H)/z=586.1.

Example 183: 4-Chloro-N-[5-chloro-2-(2-oxazol-2-yl-benzoyl)-pyridin-3-yl]-3-trifluoromethyl-benzenesulfonamide

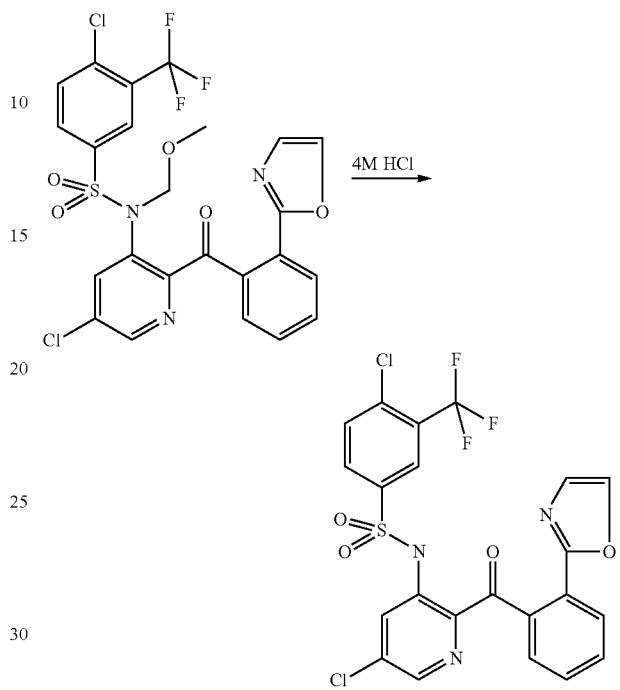

A mixture of 4-Chloro-N-[5-chloro-2-(2-oxazol-2-yl-benzoyl)-pyridin-3-yl]-N-methoxymethyl-3-trifluoromethyl-benzenesulfonamide(15 mg) in 2 mL of 4M HCl in dioxane and 1 mL of water was refluxed for 2 hours. After cooling to rt the mixture was concentrated, diluted with water and then sodium bicarbonate was added until pH was 6. The mixture was extracted with ethyl acetate, dried and concentrated. The residue was purified via flash column (35% ethyl acetate in hexane) to afford 8.0 mg of title compound as an off white solid. MS: (M+H)/z=542.3.

Example 184: N-[2-(2-Bromo-benzoyl)-5-chloro-pyridin-3-yl]-4-chloro-N-methoxymethyl-3-trifluoromethyl-benzenesulfonamide

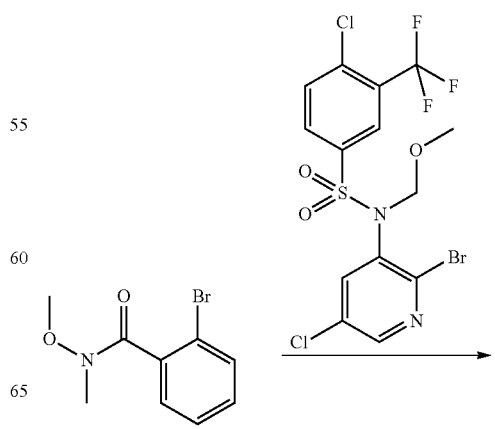

-continued

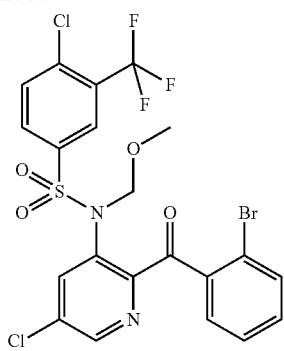

To a solution of N-(2-Bromo-5-chloro-pyridin-3-yl)-4-chloro-N-methoxymethyl-3-trifluoromethyl-benzenesulfonamide (250 mg, 0.50 mmol) in 4.0 ml of THF under nitrogen atmosphere at 0° C. was added drop-wise 0.6 mLI (1.2 mmol) of isopropylmagnesium chloride. The mixture was then stirred for 20 min at 0° C. followed by addition of a solution of 2-Bromo-N-methoxy-N-methyl-benzamide (244 mg, 1.0 mmol) in 1 mL of THF. The mixture was stirred at room temperature overnight, quenched with saturated ammonium chloride and extracted with ethyl acetate. After concentration of the solvent the residue was purified by flash chromatograph (20% ethyl acetate in hexane) to afford 180 mg of title compound as an off white solid. MS: (M+Na)/z=621.2, (M−32)/z=567.0.

Example 185: N-[2-(2-Bromo-benzoyl)-5-chloro-pyridin-3-yl]-4-chloro-3-trifluoromethyl-benzenesulfonamide

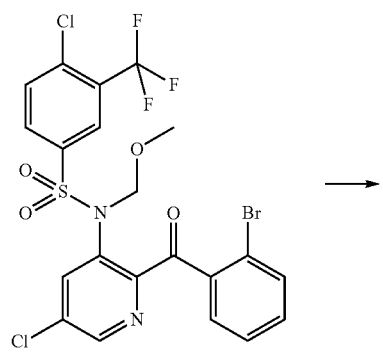

→

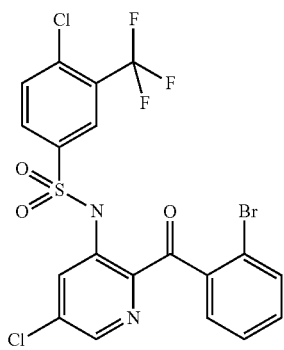

A mixture of N-[2-(2-Bromo-benzoyl)-5-chloro-pyridin-3-yl]-4-chloro-N-methoxymethyl-3-trifluoromethyl-benzenesulfonamide (100 mg, 0.167 mmol) in 3 ml of 4M HCl in dioxane and 1 mL of water was refluxed for 3 hours. After cooling to rt the mixture was concentrated, diluted with water and then sodium bicarbonate was added until pH was 6. The mixture was extracted with ethyl acetate, dried and concentrated. The residue was further purified via flash column (30% ethyl acetate in hexane) to afford 50 mg of title compound as an off white solid. MS: (M+H)/z=555.3, (M+Na)/z=575.3.

Example 186: 4-Chloro-N-[5-chloro-2-(1-hydroxy-2,4-dimethyl-pyridine-3-carbonyl)-pyridin-3-yl]-N-methoxymethyl-3-trifluoromethyl-benzenesulfonamide

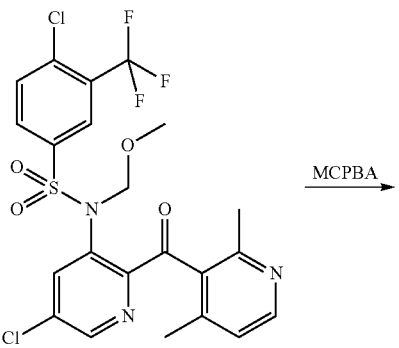

MCPBA

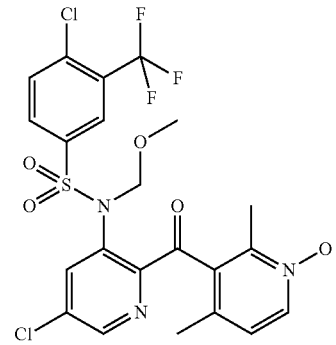

To a solution of 4-Chloro-N-[5-chloro-2-(2,4-dimethyl-pyridine-3-carbonyl)-pyridin-3-yl]-N-methoxymethyl-3-trifluoromethyl-benzenesulfonamide (100 mg, 0.182 mmol) in 3.5 mL of DCM was added meta-chloroperoxybenzoic acid (77%, 95 mg, 0.424 mmol). After thirty hours the crude mixture was added 1.0 ml of pyridine and the mixture was concentrated. The mixture was diluted with ethyl acetate, washed with water, dried over sodium sulfate and concentrated. The crude was used at next step without any further purification. MS: (M+H)/z=564.0.

Example 187: 4-Chloro-N-[5-chloro-2-(1-hydroxy-2,4-dimethyl-pyridine-3-carbonyl)-pyridin-3-yl]-3-trifluoromethyl-benzenesulfonamide

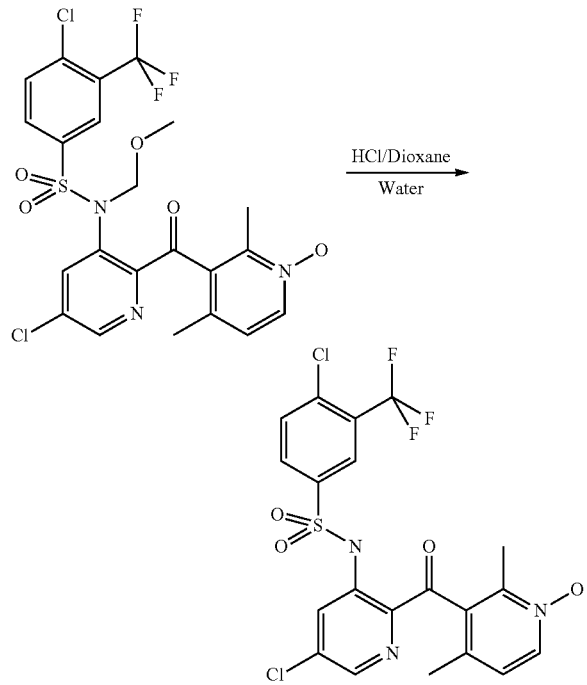

A solution of 4-Chloro-N-[5-chloro-2-(1-hydroxy-2,4-dimethyl-pyridine-3-carbonyl)-pyridin-3-yl]-N-methoxymethyl-3-trifluoromethyl-benzenesulfonamide (21 mg) in 6 ml of HCl (4M in dioxane) and 2 mL of water was refluxed for 2 hours. After cooling to rt the mixture was concentrated and was added 3 mL of water. Sodium bicarbonate was added until the final pH was 6. The mixture was extracted with ethyl acetate, dried and concentrated. The residue was further purified via short flash column (8% methanol in DCM) to afford 7.9 mg of title compound as an off white solid. MS: (M+H)/z=520.0.

Example 188: 4-Chloro-N-[5-chloro-2-(2-chloro-benzoyl)-pyridin-3-yl]-3-trifluoromethyl-benzenesulfonamide

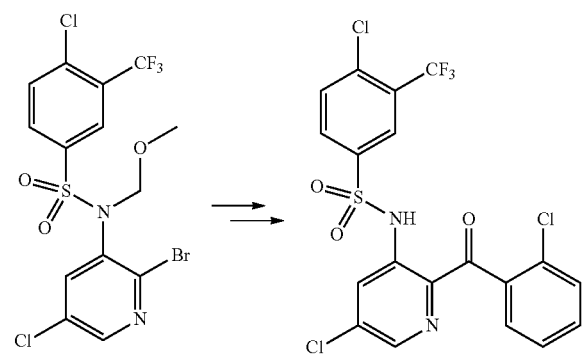 [SMILES: COCN(c1cc(Cl)cnc1Br)S(=O)(=O)c1ccc(Cl)c(C(F)(F)F)c1 ; O=C(c1ccccc1Cl)c1ncc(Cl)cc1NS(=O)(=O)c1ccc(Cl)c(C(F)(F)F)c1]

To a magnetically stirred solution of N-(2-bromo-5-chloro-pyridin-3-yl)-4-chloro-N-methoxymethyl-3-(trifluoromethyl)-benzenesulfonamide (1.5 g, 3.03 mmol) in anhydrous THF (15 mL) was added 2 M isopropylmagnesium chloride in THF (3.3 mL, 6.6 mmol) at −20° C. The temperature was allowed to slowly rise to 10° and then 2-chloro-N-methoxy-N-methylbenzamide (1.2 g, 6.0 mmol) was added and the progress of the reaction was followed by LCMS. The reaction mixture was warmed to room temperature and stirred for 16 h. It was then quenched with saturated aqueous NH$_4$Cl (50 mL), and extracted with ethyl acetate (3×100 mL). The combined extracts were dried (MgSO$_4$), filtered and concentrated. The residue was purified by chromatography on silica gel using ethyl acetate-hexane mixtures (2:98, 5:95) to provide 4-chloro-N-[5-chloro-2-(2-chloro-benzoyl)-pyridin-3-yl]-N-methoxymethyl-3-trifluoromethyl-benzenesulfonamide mass spectrum m/z 574.8 (M+Na); 521.0 (M−31).

The intermediate MOM derivative (1.1 g, 1.99 mmol) was stirred in water (2.5 mL) and 4N HCl in dioxane (12 mL) and heated at 100° C. (oil bath) for 2.5 h. LCMS indicated complete reaction; the reaction was concentrated and the residue was neutralized with saturated aqueous sodium bicarbonate and extracted with ethyl acetate (3×80 mL). The extracts were dried (MgSO$_4$), filtered, and chromatographed on silica gel using EtOAc-hexane mixtures (2:98, 5:95) to provide pure product. mass spectrum m/z 510.9 (M+H); 532.9 (M+Na).

Example 189: 5-Chloro-2-(2,6-dimethyl-phenoxy)-pyridin-3-ylamine

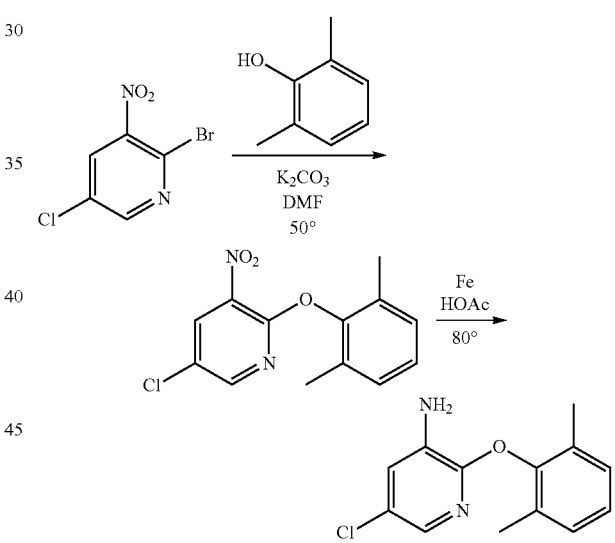

2-Bromo-3-nitro-5-chloropyridine (4.8 g, 20 mmol) and 2,6-dimethylphenol (5.0 g, 41 mmol) were magnetically stirred in dry DMF (65 mL) and potassium carbonate (11.0 g, 80 mmol) was added. The mixture was heated at 50° C. for 4 days, allowed to cool to room temperature and added to ice; the product was extracted with ethyl acetate (3×100 mL). The extracts were washed with saturated aqueous NaHCO$_3$ and dried (MgSO$_4$), filtered and concentrated to provide the desired product.

The nitro compound (4.5 g, 16 mmol) was dissolved in glacial acetic acid (80 mL) and this solution was added dropwise to a well-stirred suspension of iron powder (4.5 g, 80 mmol) in glacial acetic acid (40 mL) heated in an oil bath at 80° C. under nitrogen. The progress of the reaction was checked by LCMS. After 20 min, the reaction was allowed to cool and was diluted with ethyl acetate (120 mL). The resulting mixture was vacuum filtered through a pad of Celite, the filter cake was washed with ethyl acetate (100 mL) and the filtrate was concentrated. The residue was slowly treated with saturated aqueous sodium bicarbonate, followed by the addition of small portions of solid sodium bicarbonate to neutralize the acetic acid. The mixture was extracted using ethyl acetate (3×150 mL) and the extracts were dried (MgSO$_4$), filtered and concentrated (rotovap). The product was isolated as a crystalline solid after drying (vacuum). mass spectrum m/z 251.3 (M+H).

Example 190: 4-Chloro-N-[5-chloro-2-(2,6-dimethyl-phenoxy)-pyridin-3-yl]-3-trifluoromethyl-benzenesulfonamide

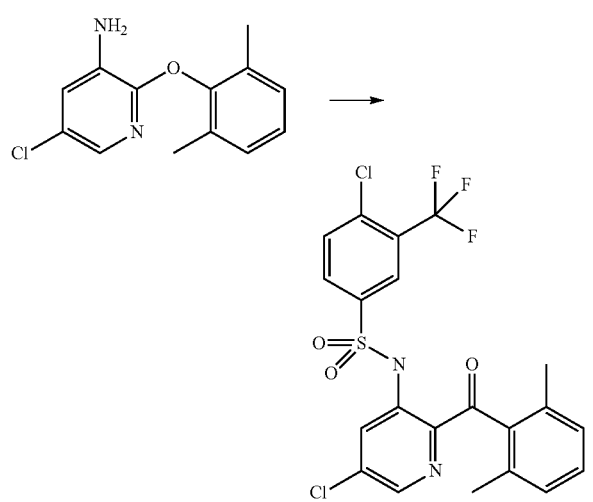

The starting aniline was magnetically stirred in pyridine and reacted with 4-chloro-3-(trifluoromethyl)benzenesulfonyl chloride according to the procedure described in Example 94 to provide the desired product. mass spectrum m/z 491.4 (M+1).

Example 191: 2-Chloro-N-[5-chloro-2-(2,6-dimethyl-phenoxy)-pyridin-3-yl]-5-trifluoromethyl-benzenesulfonamide

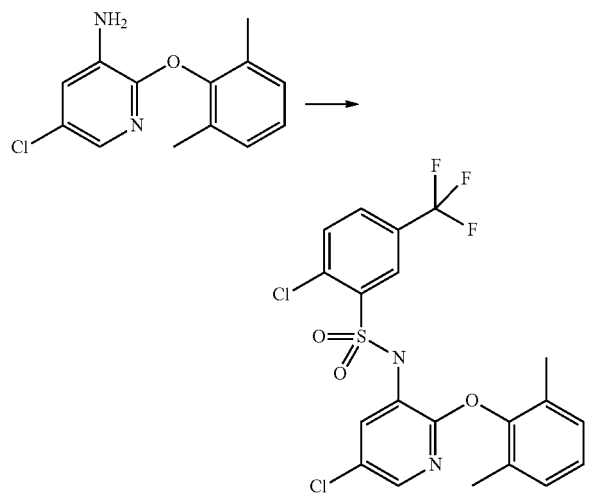

The starting aniline was magnetically stirred in pyridine and reacted with 2-chloro-5-(trifluoromethyl)benzenesulfonyl chloride according to the procedure described in Example 94 to provide the desired product. mass spectrum m/z 491.4 (M+H).

Example 192: 4-Chloro-N-[5-chloro-2-(2-hydroxymethyl-4-methyl-pyridine-3-carbonyl)-pyridin-3-yl]-3-trifluoromethyl-benzenesulfonamide and 4-Chloro-N-[5-chloro-2-(4-hydroxymethyl-2-methyl-pyridine-3-carbonyl)-pyridin-3-yl]-3-trifluoromethyl-benzenesulfonamide

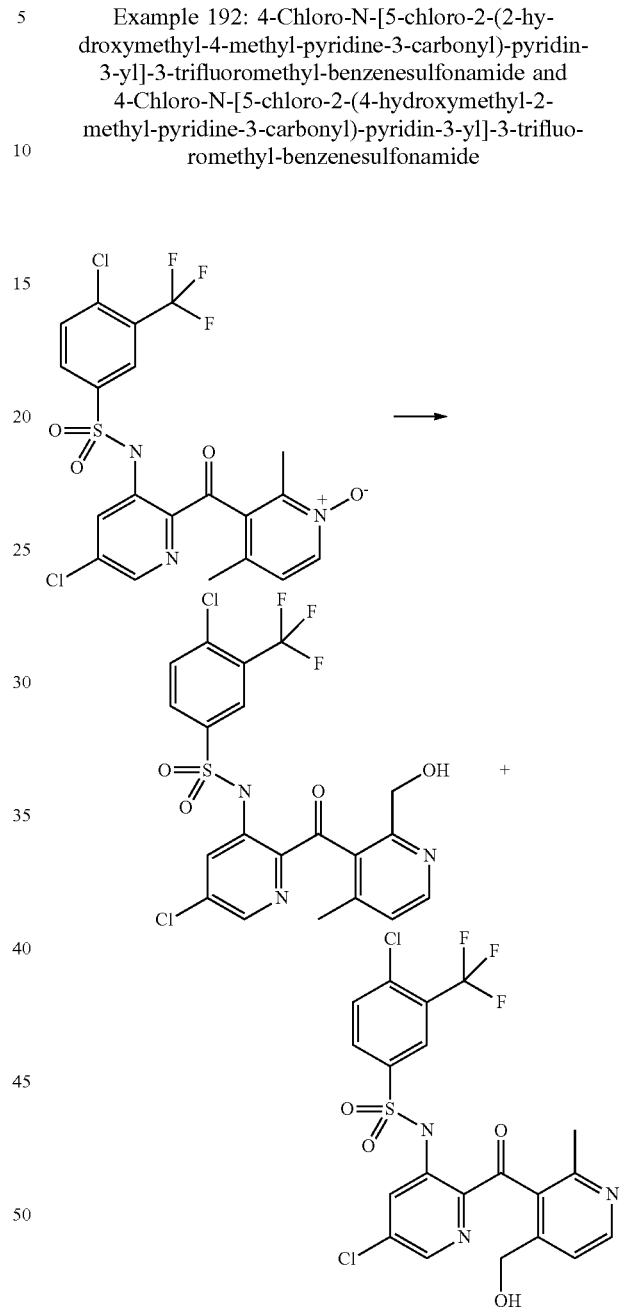

The starting N-oxide (1.0 g, 1.92 mmol) was dissolved in methylene chloride (35 mL) and cooled in an ice bath. Trifluoroacetic anhydride (0.7 mL, 1.05 g) was added dropwise to the magnetically stirred solution, and more (0.7 mL) was added after 5 min. The deep red reaction mixture was stirred 16 h at room temperature; no starting material was detected by LCMS. The reaction was cooled to 0° C. and water (20 mL) was added dropwise, then the mixture was allowed to come to room temperature. The layers were separated and the water layer was extracted with methylene chloride (2×25 mL). The combined organic layer was dried (MgSO$_4$), filtered and concentrated to give a red oil. Chromatography on silica gel (ethyl acetate-hexane) using a 5:95 to 95:5 gradient gave several mixed fractions and a few fractions each of the two products. Major Isomer: 4-chloro-N-[5-chloro-2-(2-hydroxymethyl-4-methyl-pyridine-3-carbonyl)-pyridin-3-yl]-3-trifluoromethyl-benzenesulfonamide mass spectrum m/z 520.4 (M+1). Minor Isomer: 4-chloro-N-[5-chloro-2-(4-hydroxymethyl-2-methyl-pyridine-3-carbonyl)-pyridin-3-yl]-3-trifluoromethyl-benzenesulfonamide. mass spectrum m/z 520.4 (M+1).

Example 193: 5-Chloro-3-(4-methyl-3-trifluoromethyl-benzenesulfonylamino)-pyridine-2-carboxylic Acid

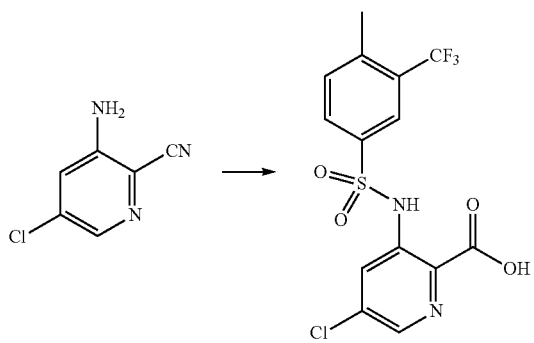 [SMILES: N#Cc1ncc(Cl)cc1N ; Cc1ccc(S(=O)(=O)Nc2cc(Cl)cnc2C(=O)O)cc1C(F)(F)F]

A 100 mL round-bottom flask was charged with the above 3-amino-2-cyano-5-chloropyridine (8.95 g, 61.54 mmol), 4-chloro-3-trifluoromethyl-benzenesulfonyl chloride (19.6 g, 80 mmol), and pyridine (50 mL). The resultant solution was heated to 60° C. and stirred for overnight. The pyridine was removed in vacuo and dioxane (200 mL) was added, followed by NaOH (28 g, 0.70 mol). The mixture was stirred under reflux for two days. The solvent was subsequently removed in vacuo and ice (100 g) was added and the pH adjusted to 2-3 with conc HCl. The resultant solid was filtered and washed with water twice and was dried in vacuo to afford the light yellow solid. This solid was dissolved in EtOAc and any insoluble solid was filtered off. The filtrate was washed with brine, dried (Na$_2$SO$_4$), filtered and the filtrate was concentrated under reduced pressure to afford 5-chloro-3-(4-methyl-3-trifluoromethyl-benzenesulfonylamino)-pyridine-2-carboxylic acid (16.5 g): (M+H)$^+$ expect 395.0, found 395.0.

Example 194: 5-Chloro-3-(4-chloro-3-methyl-benzenesulfonylamino)-pyridine-2-carboxylic Acid

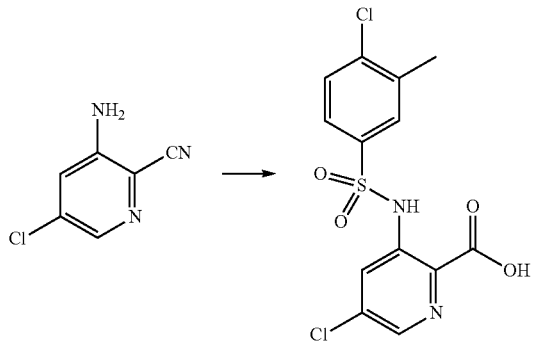 [SMILES: N#Cc1ncc(Cl)cc1N ; Cc1cc(S(=O)(=O)Nc2cc(Cl)cnc2C(=O)O)ccc1Cl]

5-Chloro-3-(4-chloro-3-methyl-benzenesulfonylamino)-pyridine-2-carboxylic acid was prepared from 3-amino-2-cyano-5-chloropyridine and 4-chloro-3-methyl-benzenesulfonyl chloride following a procedure as described in example 116, step 3. MS m/z: 361.0 (M+H)$^+$.

Example 195: 3-(4-tert-Butyl-benzenesulfonylamino)-5-chloro-pyridine-2-carboxylic Acid

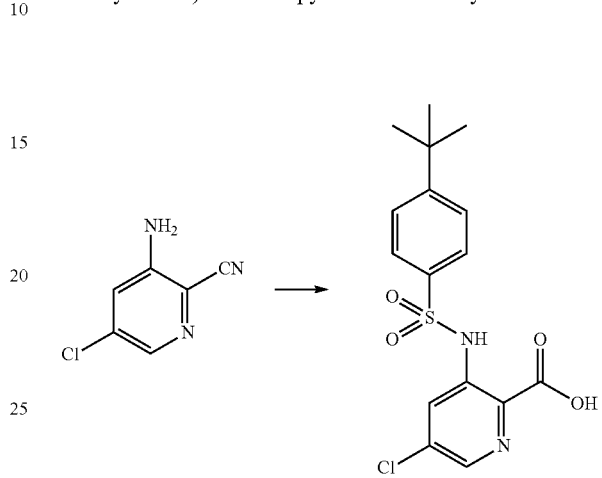

A 25 mL round-bottom flask was charged with the above 3-amino-2-cyano-5-chloropyridine (1.04 g, 6.8 mmol), 4-tert-butyl-benzenesulfonyl chloride (2.09 g, 8.8 mmol), and pyridine (6 mL). The resultant solution was heated to 70° C. and stirred for 5 h. The pyridine was removed in vacuo and EtOH (70%, 20 mL) was added, followed by NaOH (3.20 g, 0.8 mol). The mixture was stirred under refluxed for 12 h. The solvent was subsequently removed in vacuo and ice (10 g) was added and the pH adjusted to 2-3 with conc HCl. The resultant aqueous solution was extracted with EtOAc, washed with brine, dried over MgSO$_4$, and concentrated under reduced pressure. The light yellow solid was further crystallized from EtOAc/hexane (1:1) to afford the desired acid as white needles (734.8 mg): MS (ES) (M+H)$^+$ expected 369.1, found 369.0.

Example 196: 4-Chloro-N-(5-chloro-2-formyl-pyridin-3-yl)-3-trifluoromethyl-benzenesulfonamide

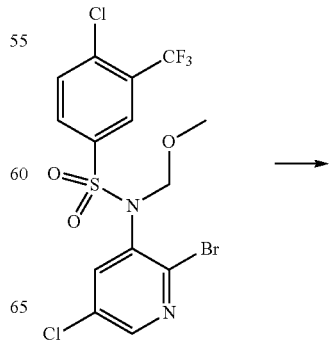

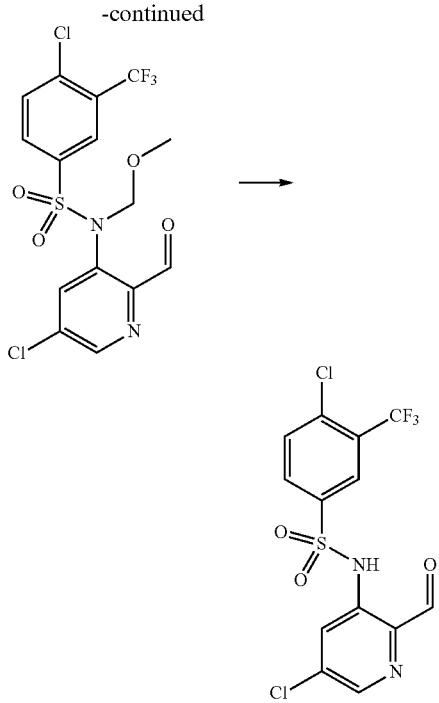

To a solution of N-(2-bromo-5-chloro-pyridin-3-yl)-4-chloro-N-methoxymethyl-3-trifluoromethyl-benzenesulfonamide (10.6 mg, 21.4 mmol) in THF (80 mL) under nitrogen atmosphere at −40° C. was added isopropylmagnesium chloride (25 mL, 50 mmol, 2 M in THF). The mixture was then warmed to 0° C. over 30 min and DMF (4 mL, 51 mmol) was added. The reaction mixture was stirred at room temperature overnight, quenched with saturated aqueous ammonium chloride, and followed by HCl (1 M) to pH ~3. The mixture was extracted with ethyl acetate, dried, and concentrated to provide 4-chloro-N-(5-chloro-2-formyl-pyridin-3-yl)-N-methoxymethyl-3-trifluoromethyl-benzenesulfonamide. MS: (M+H)/z=442.9.

The unpurified aldehyde from the previous reaction was magnetically stirred in dioxane (20 mL), water (20 mL), and 4N HCl in dioxane (40 mL); and heated at 80° C. (oil bath) overnight. LCMS indicated complete reaction; the reaction was concentrated and the residue was neutralized (pH 6) with aqueous sodium bicarbonate and extracted with ethyl acetate (3×80 mL). The extracts were dried (Na$_2$SO$_4$), filtered, and purified by flash column chromatography on silica gel using ethyl acetate-hexane to provide 4-chloro-N-(5-chloro-2-formyl-pyridin-3-yl)-3-trifluoromethyl-benzenesulfonamide. MS: (M+H)/z=398.9.

Example 197: 5-Chloro-3-(4-chloro-3-trifluoromethyl-benzenesulfonylamino)-pyridine-2-carboxylic Acid methoxy-methyl-amide

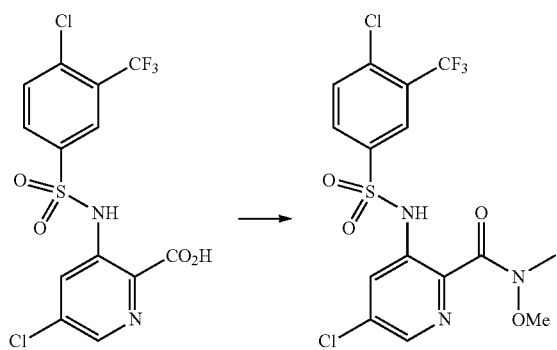 [SMILES: O=C(O)c1ncc(Cl)cc1NS(=O)(=O)c1ccc(Cl)c(C(F)(F)F)c1 ; CON(C)C(=O)c1ncc(Cl)cc1NS(=O)(=O)c1ccc(Cl)c(C(F)(F)F)c1]

5-Chloro-3-(4-chloro-3-trifluoromethyl-benzenesulfonylamino)-pyridine-2-carboxylic acid (15.8, 38 mmol), N,O-dimethyl hydroxylamine hydrochloride (11.1 mg, 114 mmol), DIEA (41 mL, 228 mmol) methyl-m-tolyl-amine (44 mg, 0.36 mmol), and BOP (69 mg, 49 mmol), were reacted according to the procedure D for the synthesis of 5-chloro-3-(4-chloro-3-(trifluoromethyl)phenylsulfonamido)-picolinic amides at 50° C. The reaction mixture was quenched with 1 (M) HCl, extracted with EtOAc, and the organic portions were washed with 1 (M) aqueous HCl, NaHCO$_3$ and brine. The combined organic extracts were dried (Na$_2$SO$_4$), filtered and concentrated under reduced pressure. The resulting residue was purified by flash column chromatography to afford 5-chloro-3-(4-chloro-3-trifluoromethyl-benzenesulfonylamino)-pyridine-2-carboxylic acid methoxy-methyl-amide: MS m/z: (M+H) 458.0.

Example 198: 5-Chloro-3-(4-methyl-3-trifluoromethyl-benzenesulfonylamino)-pyridine-2-carboxylic Acid methoxy-methyl-amide

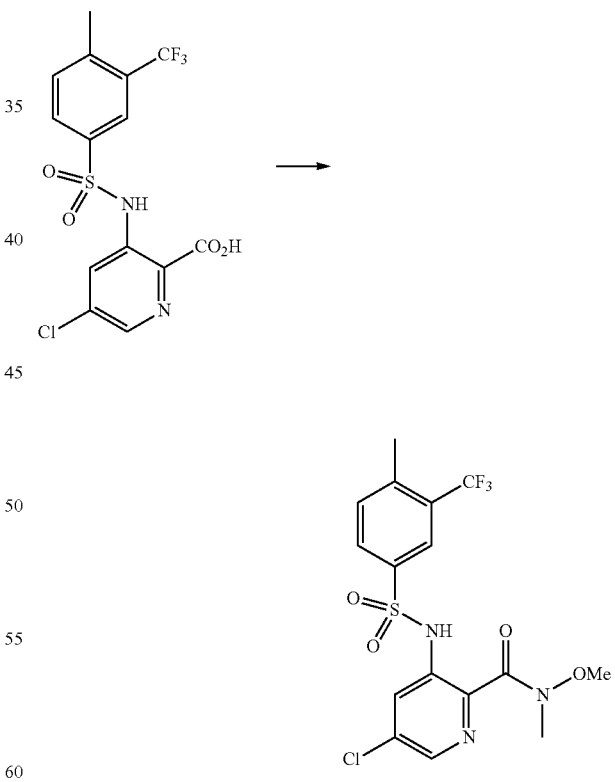

5-Chloro-3-(4-methyl-3-trifluoromethyl-benzenesulfonylamino)-pyridine-2-carboxylic acid methoxy-methyl-amide was prepared from 5-Chloro-3-(4-methyl-3-trifluoromethyl-benzenesulfonylamino)-pyridine-2-carboxylic acid as described in example 144.

Example 199: 5-Chloro-3-[methoxymethyl-(4-methyl-3-trifluoromethyl-benzenesulfonyl)-amino]-pyridine-2-carboxylic Acid methoxy-methyl-amide

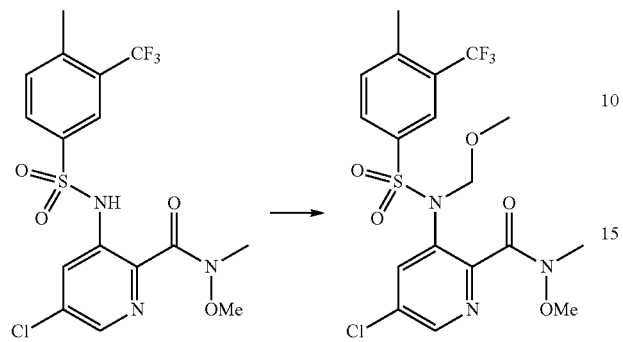

To a mixture of sodium hydride (164 mg, 4.10 mmol) in 5 mL of THF was added a mixture of 5-chloro-3-(4-methyl-3-trifluoromethyl-benzenesulfonylamino)-pyridine-2-carboxylic acid methoxy-methyl-amide (1.50 g, 3.42 mmol) and chloromethyl methyl ether (0.388 mL, 5.13 mmol) in 5 mL of THF. The mixture was stirred at room temperature overnight. After the removal of the solvents the residue was purified by flash column (20% ethyl acetate in hexane) to afford 1.50 grams of the title compound as a white solid: (M$^+$+H) expect 482.0, found 482.0.

Example 200: 5-Chloro-3-[methoxymethyl-(4-chloro-3-trifluoromethyl-benzenesulfonyl)-amino]-pyridine-2-carboxylic Acid methoxy-methyl-amide

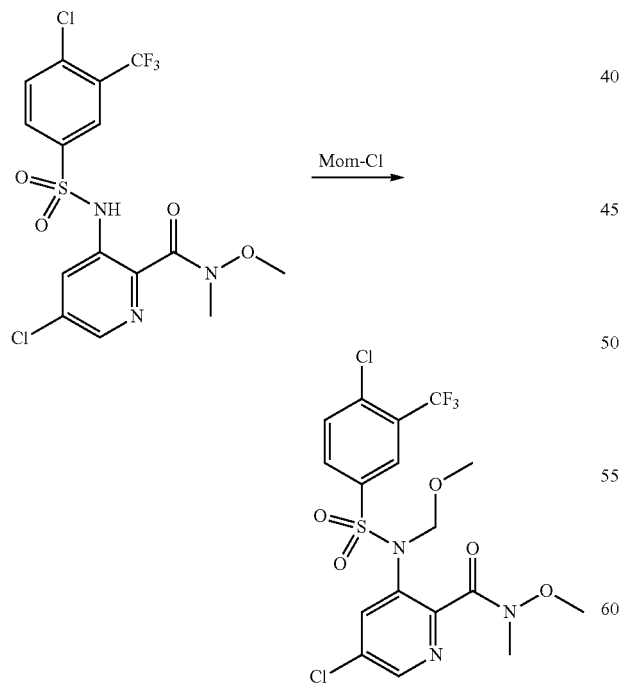

To a suspension of sodium hydride (314 mg, 7.86 mmol) in 8 mL of THF was added a mixture of 5-chloro-3-(4-chloro-3-trifluoromethyl-benzenesulfonylamino)-pyridine-2-carboxylic acid methoxy-methyl-amide (3.0 g, 6.55 mmol) and chloromethyl methyl ether (0.741 mL, 9.825 mmol) in 8 mL of THF. The mixture was stirred at room temperature overnight. After the removal of the solvents the residue was purified by flash column (20% ethyl acetate in hexane) to afford 2.70 grams of the title compound as a white solid. (M+H)$^+$ expect 502.0, found 502.0.

Example 201: 4-Chloro-N-[5-chloro-2-(2-chloro-pyridine-3-carbonyl)-pyridin-3-yl]-3-trifluoromethyl-benzenesulfonamide

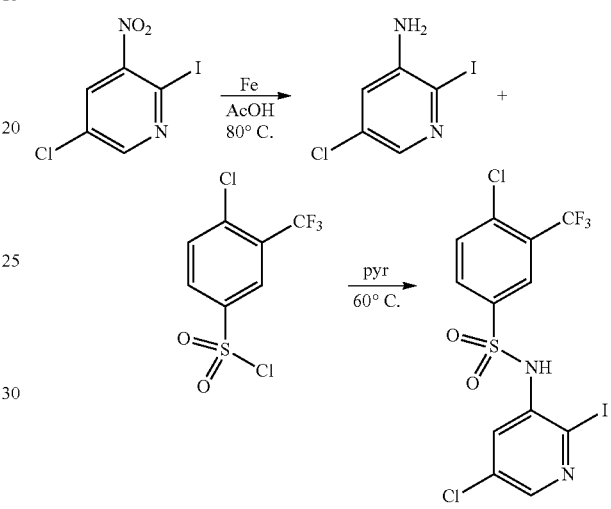

Following the procedure for example 116, step 2; 5-chloro-2-iodo-3-nitro-pyridine was converted to 5-chloro-2-iodo-pyridin-3-ylamine.

Following the procedure for example 24, 4-chloro-N-(5-chloro-2-iodo-pyridin-3-yl)-3-trifluoromethyl-benzenesulfonamide was synthesized from 5-chloro-2-iodo-pyridin-3-ylamine and 4-chloro-3-trifluoromethyl-benzenesulfonyl chloride.

Example 202: N-(2-bromo-5-methyl-pyridin-3-yl)-4-chloro-N-methoxy methyl-3-trifluoromethyl-benzenesulfonamide

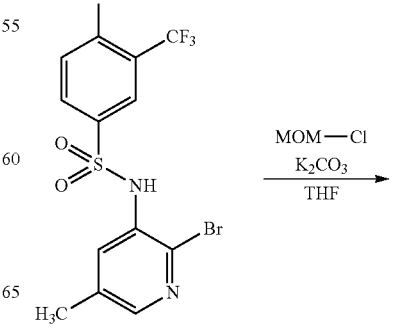

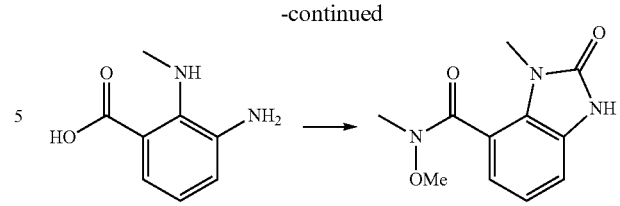

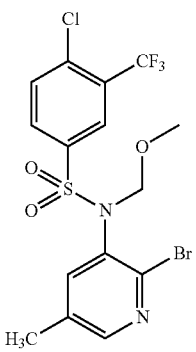

A mixture of N-(2-bromo-5-methyl-pyridin-3-yl)-4-chloro-3-trifluoromethyl-benzenesulfonamide (1.4 g, 3.27 mmol), chloromethyl methyl ether (0.4 mL, 5.23 mmol) and K₂CO₃ (1.35 g, 9.81 mmol) in THF (20 mL) was stirred at room temperature for 3 h. The mixture was filtered and the filtrate was concentrated and purified by flash chromatography (SiO₂, 20% EtOAc-hexanes) to afford N-(2-bromo-5-methyl-pyridin-3-yl)-4-chloro-N-methoxymethyl-3-trifluoromethyl-benzenesulfonamide (1.3 g) as a white solid in 84% yield. ESMS m/z (relative intensity): 473 (M+H)⁺ (100).

Example 203: N-(2-Bromo-5-chloro-pyridin-3-yl)-N-methoxymethyl-4-methyl-3-trifluoromethyl-benzenesulfonamide

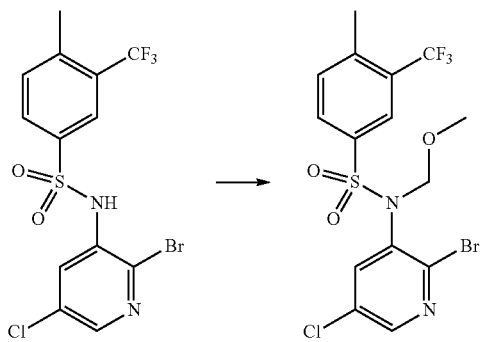 [SMILES: Cc1ccc(S(=O)(=O)Nc2cc(Cl)cnc2Br)cc1C(F)(F)F ; COCN(c1cc(Cl)cnc1Br)S(=O)(=O)c1ccc(C)c(C(F)(F)F)c1]

N-(2-Bromo-5-chloro-pyridin-3-yl)-N-methoxymethyl-4-methyl-3-trifluoromethyl-benzenesulfonamide was prepared from N-(2-bromo-5-chloro-pyridin-3-yl)-4-methyl-3-trifluoromethyl-benzenesulfonamide according to the procedure described in example 149.

Example 204: 3-Methyl-2-oxo-2,3-dihydro-1H-benzoimidazole-4-carboxylic Acid methoxy-methyl-amide

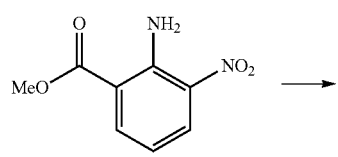

To a stirred solution of 2-amino-3-nitro-benzoic acid methyl ester (2.0 g, 10.2 mmol) in THF (10 mL) at 0° C. was added Et₃N (4.76 mL, 33 mmol) was added followed by a solution of trifluoroacetic anhydride (3.3 g, 1.6 mmol) in THF (5 mL) dropwise. The resulting mixture was warmed to room temperature and stirred at room temperature overnight. It was quenched with water (2 mL) and resulting mixture was concentrated under reduced pressure. Cold water was added to the residue to cause white which filtered and washed water to provide 3-nitro-2-(2,2,2-trifluoro-acetylamino)-benzoic acid methyl ester as a white solid. MS m/z: 260.9 (M+H).

To a stirred suspension of NaH (112 mg, 2.80 mmol, 60% dispersion in mineral oil) in DMF (5 mL) at 0° C. was added 3-nitro-2-(2,2,2-trifluoro-acetylamino)-benzoic acid methyl ester (750 mg, 2.55 mmol) portion wise. The resulting mixture was stirred for 1 h, then MeI (175 mL, 2.80 mmol) was added and the progress of the reaction was followed by LCMS. Upon consumption of 3-nitro-2-(2,2,2-trifluoro-acetylamino)-benzoic acid methyl ester, the reaction mixture was quenched with aqueous NH₄Cl, and extracted with EtOAc. The combined extracts were washed with brine, dried (Na₂SO₄), filtered, and concentrated under reduced pressure. The residue was purified by chromatography on silica gel using ethyl acetate-hexane to provide 2-[methyl-(2,2,2-trifluoro-acetyl)-amino]-3-nitro-benzoic acid methyl ester. MS m/z: 275.0 (M+H)⁺.

A mixture of 2-[methyl-(2,2,2-trifluoro-acetyl)-amino]-3-nitro-benzoic acid methyl ester (1.7 g, 5.5 mmol) and 5 M aqueous NaOH (5 mL) in THF (10 mL) was stirred at 50° C. for several hours. The mixture was acidified with 4 M HCl and extracted with EtOAc to provide 2-methylamino-3-nitro-benzoic acid. MS m/z: 197.0 (M+H)⁺.

A mixture of 2-methylamino-3-nitro-benzoic acid and 10% Pd/C (300 mg) in EtOAc (5 mL) and EtOH (5 mL) was stirred in an atmosphere of hydrogen over night. The mixture was filtered though a pad of Celite and the filter cake was washed with EtOAc. The filtrate was concentrated under reduced pressure to provide 3-amino-2-methylamino-benzoic acid.

To a mixture of 3-amino-2-methylamino-benzoic acid (50 mg, 0.30 mmol) and DIEA (138 FL, 0.75 mmol) in THF was added triphosgene (106 mg, 0.41 mmol). The resulting mixture was stirred at room temperature for 6 h, then N,O-dimethyl hydroxylamine hydrochloride (88 mg, 0.9 mmol) and DIEA (276 FL, 1.5 mmol) was added. The resulting mixture was stirred at room temperature overnight, then quenched with saturated aqueous NH₄Cl (10 mL), and extracted with EtOAc (3×15 mL). The combined extracts were washed with brine, dried (Na₂SO₄), filtered, and concentrated under reduced pressure. The residue was purified by chromatography on silica gel using MeOH/CH₂Cl₂ to provide 2-amino-N-methoxy-N-methyl-3-(3-N,O-dimethyl-ureido)-benzamide. MS m/z: 297.0 (M+H)⁺.

A mixture of 2-amino-N-methoxy-N-methyl-3-(3-N,O-dimethyl-ureido)-benzamide and K₂CO₃ was heated at reflux for 48 h. The resulting mixture was neutralized with saturated aqueous NH₄Cl (10 mL), and extracted with EtOAc (3×15 mL). The combined extracts were washed with brine, dried (Na₂SO₄), filtered, and concentrated under reduced pressure. The residue was purified by chromatography on silica gel using MeOH/CH$_2$Cl$_2$ to provide 3-methyl-2-oxo-2,3-dihydro-1H-benzoimidazole-4-carboxylic acid methoxy-methyl-amide. MS m/z: 237.0 (M+H)$^+$.

Example 205: N-[5-Chloro-2-(3-methyl-2-oxo-2,3-dihydro-1H-benzoimidazole-4-carbonyl)-pyridin-3-yl]-N-methoxymethyl-4-methyl-3-trifluoromethyl-benzenesulfonamide

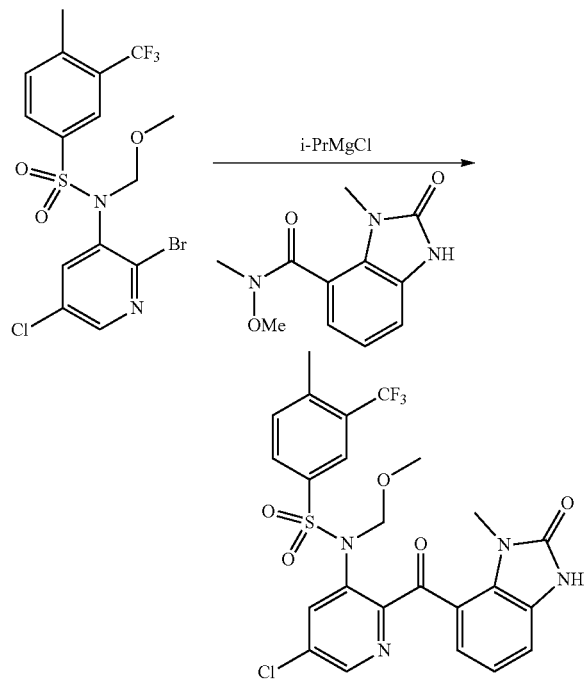

N-[5-Chloro-2-(3-methyl-2-oxo-2,3-dihydro-1H-benzoimidazole-4-carbonyl)-pyridin-3-yl]-N-methoxymethyl-4-methyl-3-trifluoromethyl-benzenesulfonamide was prepared from 3-methyl-2-oxo-2,3-dihydro-1H-benzoimidazole-4-carboxylic acid methoxy-methyl-amide and N-(2-bromo-5-chloro-pyridin-3-yl)-N-methoxymethyl-4-methyl-3-trifluoromethyl-benzenesulfonamide according to previously described procedure in example 29, step 1. The product was purified by flash column chromatography on silica gel using ethyl acetate-hexane. MS m/z: 569.0 (M+H)$^+$.

Example 206: N-[5-Chloro-2-(3-methyl-2-oxo-2,3-dihydro-1H-benzoimidazole-4-carbonyl)-pyridin-3-yl]-4-methyl-3-trifluoromethyl-benzenesulfonamide

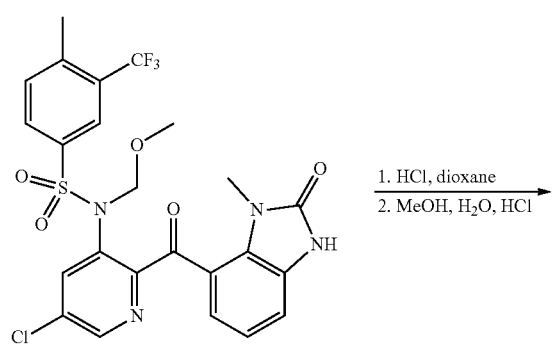

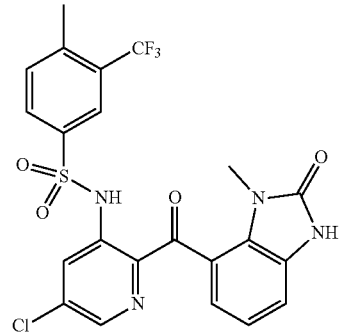

A solution of N-[5-Chloro-2-(3-methyl-2-oxo-2,3-dihydro-1H-benzoimidazole-4-carbonyl)-pyridin-3-yl]-N-methoxymethyl-4-methyl-3-trifluoromethyl-benzenesulfonamide in 4 M HCl in dioxane (2 mL) and water (1 mL) was heated at 95° C. for 7 h, then MeOH (1 mL) and water (2 mL) was added and heating was continued overnight. The resulting mixture was purified by HPLC to provide N-[5-chloro-2-(3-methyl-2-oxo-2,3-dihydro-1H-benzoimidazole-4-carbonyl)-pyridin-3-yl]-4-methyl-3-trifluoromethyl-benzenesulfonamide. $^1$H NMR (400 MHz, CDCl$_3$) δ 10.94 (s, 1H), 8.28 (d, J=2.0 Hz, 1H), 8.21 (d, J=1.6 Hz, 1H), 8.08 (s, 1H), 7.95 (d, J=7.6 Hz, 1H), 7.42 (d, J=8.0 Hz, 1H), 7.19-7.17 (m, 1H), 7.01 (t, J=7.6 Hz, 1H), 6.82 (d, J=7.6 Hz, 1H), 3.10 (s, 3H), 2.53 (s, 3H); MS m/z 524.9 (M+H)$^+$.

Example 207: N-[5-Chloro-2-(2-methylamino-pyridine-4-carbonyl)-pyridin-3-yl]-4-methyl-3-trifluoromethyl-benzenesulfonamide

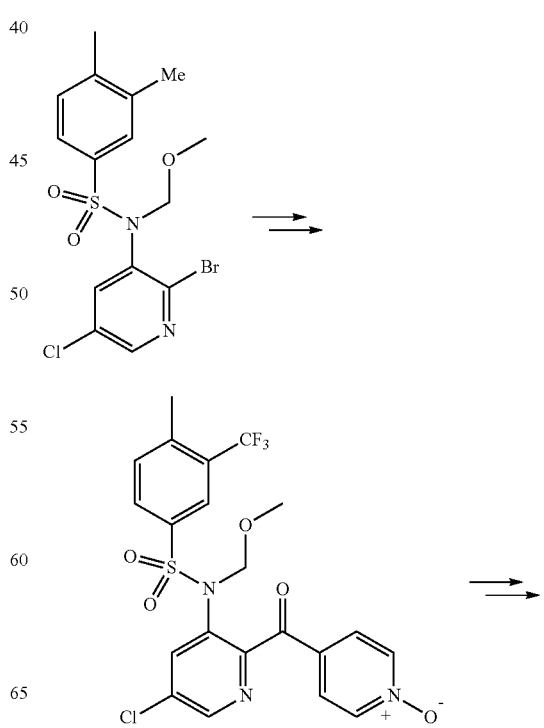

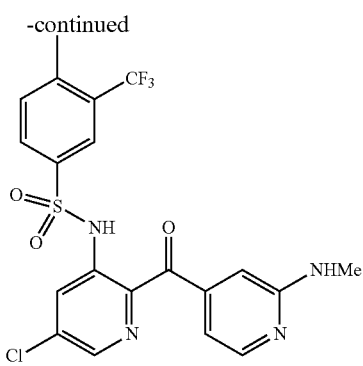

To a stirred solution of N-(2-bromo-5-chloro-pyridin-3-yl)-N-methoxymethyl-3,4-dimethyl-benzenesulfonamide (4.71 mg, 10 mmol) in anhydrous THF (40 mL) under nitrogen was added 2 M isopropylmagnesium chloride in THF (11 mL, 22 mmol) at −20° C. It was then warmed to 0° C. over 45 minutes the exchange of bromo-functional group with magnesium reagent was followed by LCMS. Weinreb amide (1.99 g, 12 mmol) was added with a syringe in one portion and the reaction mixture was slowly warmed to room temperature over 5 h. The progress of the reaction was followed by LCMS. After 2 h stirring at room temperature, the resulting mixture was neutralized with saturated aqueous NH$_4$Cl (10 mL), and extracted with EtOAc (3×15 mL). The combined extracts were washed with aqueous NaHCO$_3$, brine, dried (Na$_2$SO$_4$), filtered, and concentrated under reduced pressure. The residue was purified by chromatography on silica gel using MeOH/CH$_2$Cl$_2$ to provide N-[5-chloro-2-(pyridine-4-carbonyl)-pyridin-3-yl]-N-methoxymethyl-4-methyl-3-trifluoromethyl-benzenesulfonamide. Mass spectrum m/z: 500.0 (M+H)$^+$.

To a stirred solution of N-[5-chloro-2-(pyridine-4-carbonyl)-pyridin-3-yl]-N-methoxymethyl-4-methyl-3-trifluoromethyl-benzenesulfonamide (3.0 g, 6.0 mmol) in CH$_2$Cl$_2$ (20 mL) was added peracetic acid (2.1 mL, 9.0 mmol) at room temperature. The reaction mixture was stirred at room temperature for 20 h. At this time, saturated aqueous NaHSO$_3$ (5 mL) and the biphasic mixture was stirred for 5 minutes. The resulting mixture was extracted with EtOAc and washed with aqueous NaHCO$_3$ and brine. The combined organic extract was dried, filtered and then concentrated under reduced pressure. The residue was purified by flash column chromatography to provide N-[5-chloro-2-(1-oxy-pyridine-4-carbonyl)-pyridin-3-yl]-N-methoxymethyl-4-methyl-3-trifluoromethyl-benzenesulfonamide. Mass spectrum m/z: 516.0 (M+H)$^+$.

To a stirred solution of acetamide (412 mg, 5.64 mmol) and 2,6-lutidine (1.3 mL, 11.28 mmol) in CH$_2$Cl$_2$ at 0° C. was added oxalyl chloride (505 FL, 5.64 mmol) drop-wise. After 15 minutes, stirring at the same temperature N-[5-chloro-2-(1-oxy-pyridine-4-carbonyl)-pyridin-3-yl]-N-methoxymethyl-4-methyl-3-trifluoromethyl-benzenesulfonamide (971 mg, 1.88 mmol) was added stirred overnight at room temperature. The reaction mixture was poured into an aqueous solution of NaHCO$_3$ and extracted with EtOAc (2×30 mL). The combined organic extract was dried, filtered and then concentrated under reduced pressure. The residue was purified by flash column chromatography to provide N-(4-{5-chloro-3-[methoxymethyl-(4-methyl-3-trifluoromethyl-benzenesulfonyl)-amino]-pyridine-2-carbonyl}-pyridin-2-yl)-N-methyl-acetamide. Mass spectrum m/z: 571.0 (M+H)$^+$.

A solution of N-(4-{5-chloro-3-[methoxymethyl-(4-methyl-3-trifluoromethyl-benzenesulfonyl)-amino]-pyridine-2-carbonyl}-pyridin-2-yl)-N-methyl-acetamide in 4 M HCl in dioxane (4 mL) and water (2 mL) was heated at 95° C. for 4 h, then MeOH (2 mL) and 2 M aqueous HCl (5 mL) was added and heating was continued overnight. Upon cooling of the reaction mixture N-[5-chloro-2-(2-methyl-amino-pyridine-4-carbonyl)-pyridin-3-yl]-4-methyl-3-trifluoromethyl-benzenesulfonamide was obtained was obtained as pale yellow solid. Mass spectrum m/z: 485.0 (M+H)$^+$. $^1$H NMR (400 MHz, CDCl$_3$) δ 10.94 (s, 1H), 8.03 (d, J=5.2 Hz, 1H), 7.87 (s, 1H), 7.79-7.75 (m, 2H), 7.51 (d, J=8.0 Hz, 1H), 6.95 (bs, 1H), 6.56-6.52 (m, 2H), 2.78 (s, 3H), 2.42 (s, 3H); MS m/z 485.0 (M+H)$^+$.

Example 208: N-{2-[5-chloro-3-(4-chloro-3-trifluoromethyl-benzenesulfonylamino)-pyridine-2-carbonyl]-3-methoxy-phenyl}-2,2-dimethyl-propionamide

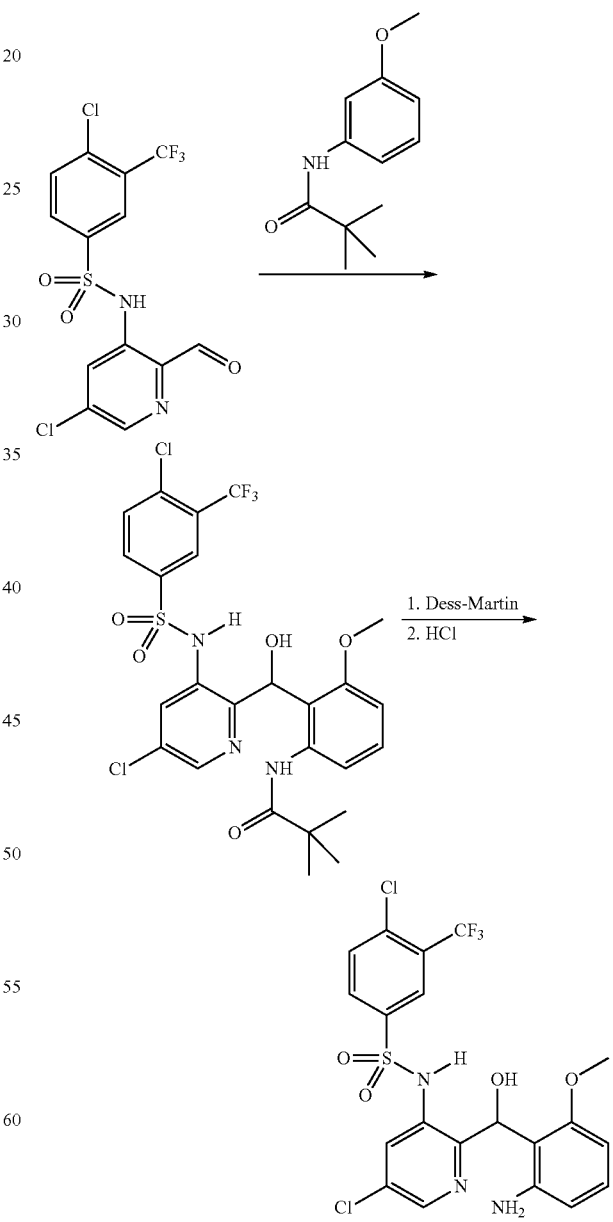

To a stirred solution of N-(3-methoxy-phenyl)-2,2-dimethyl-propionamide (1.11 g, 4.8 mmol) in anhydrous THF at 0° C. was added a solution of n-BuLi (3.65 mL, 9.1 mmol) in hexanes. After 45 minutes, anhydrous MgBr$_2$-Et$_2$O (1.23 g, 4.8 mmol) was added in one portion and stirring was continued at the same temperature for 1 h. The mixture was then cooled to −78° C. and solid 4-chloro-N-(5-chloro-2-formyl-pyridin-3-yl)-3-trifluoromethyl-benzenesulfonamide (300 mg, 0.75 mmol) was added in one portion and slowly warmed to room temperature over 4 h. The mixture was then quenched with saturated aqueous NH$_4$Cl (10 mL), and extracted with EtOAc (3×75 mL). The combined extracts were washed with brine, dried (Na$_2$SO$_4$), filtered, and concentrated under reduced pressure. The residue was purified by chromatography on silica gel using ethyl acetate-hexane to provide N-(2-{[5-chloro-3-(4-chloro-3-trifluoromethyl-benzenesulfonylamino)-pyridin-2-yl]-hydroxy-methyl}-3-methoxy-phenyl)-2,2-dimethyl-propionamide: MS m/z 606.0 (M+H)$^+$.

A mixture of N-(2-{[5-chloro-3-(4-chloro-3-trifluoromethyl-benzenesulfonylamino)-pyridin-2-yl]-hydroxy-methyl}-3-methoxy-phenyl)-2,2-dimethyl-propionamide (0.17 g, 0.33 mmol) and Dess-Martin reagent (0.185 g, 0.44 mmol) in CH$_2$Cl$_2$ (10 mL) at room temperature was stirred for 5 h. A mixture of 10% aqueous Na$_2$S$_2$O$_3$ (10 mL) and saturated aqueous NaHCO$_3$ (10 mL) was then added and the biphasic mixture vigorously stirred for 30 min. The organic phase was then separated and the aqueous portion was extracted with CH$_2$Cl$_2$. The combined organic extracts were washed with saturated aqueous NaHCO$_3$ and brine, dried (Na$_2$SO$_4$), and filtered. The filtrate was concentrated under reduced pressure and the residue purified by chromatography on silica gel using ethyl acetate-hexane to provide N-{2-[5-chloro-3-(4-chloro-3-trifluoromethyl-benzenesulfonylamino)-pyridine-2-carbonyl]-3-methoxy-phenyl}-2,2-dimethyl-propionamide: MS m/z 604.0 (M+H)$^+$.

A solution of N-{2-[5-chloro-3-(4-chloro-3-trifluoromethyl-benzenesulfonylamino)-pyridine-2-carbonyl]-3-methoxy-phenyl}-2,2-dimethyl-propionamide (105 mg, 0.17 mmol) in AcOH (6 mL) and 2 M aqueous HCl (1 mL) was heated at 60° C. for 4 days. The reaction mixture was neutralized with aqueous NaHCO$_3$, extracted with EtOAc. The combined organic extracts were washed with saturated aqueous NaHCO$_3$ and brine, dried (Na$_2$SO$_4$), and filtered. The filtrate was concentrated under reduced pressure and the residue purified by HPLC to provide N-[2-(2-amino-6-methoxy-benzoyl)-5-chloro-pyridin-3-yl]-4-chloro-3-trifluoromethyl-benzenesulfonamide: MS m/z 520.0 (M+H)$^+$.

Example 209: 2-(2-Dimethylamino-vinylamino)-N-methoxy-N-methyl-isonicotinamide

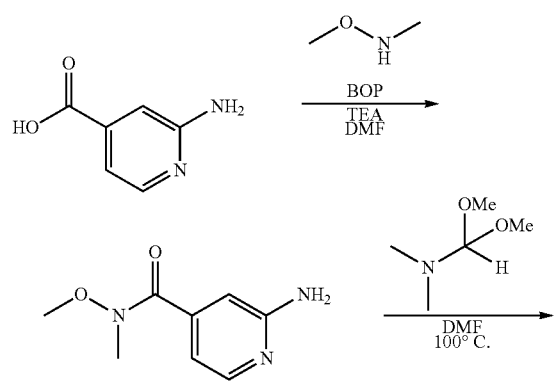

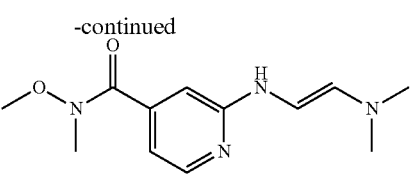

A 250 mL round-bottom flask was charged with 2-amino-isonicotinic acid (3.98 g, 28.6 mmol), N,O-dimethyl hydroxylamine hydrochloride (4.21 g, 42.9 mmol), triethylamine (11.6 g, 114.5 mmol), and dimethylformamide (57 mL). The mixture was cooled to 0° C., and then BOP (14.0 g, 31.5 mmol) was added slowly. The resultant heterogeneous solution was allowed to stir overnight, during which the reaction warmed to ambient temperature as the ice-bath melted. The following day, the reaction was diluted with EtOAc, the organics were washed with saturated sodium bicarbonate, dried with sodium sulfate, concentrated in vacuo, and purified via automated silica gel chromatography to afford the Weinreb amide.

To a solution of 2-amino-N-methoxy-N-methyl-isonicotinamide (2.80 g) in DMF (15 mL) was added DMF dimethylacetal (6.14 mL, 46.2 mmol). The solution was warmed to 100° C. and stirred overnight. The following day, the organics were removed in vacuo and the oily residue was partitioned with EtOAc/saturated sodium bicarbonate. The aqueous layer was extracted with EtOAc, dried with sodium sulfate, concentrated in vacuo, and purified via automated silica gel chromatography to produce 3.21 g (88%) of 2-(2-dimethylamino-vinylamino)-N-methoxy-N-methyl-isonicotinamide contaminated with a small quantity of HMPA.

Example 210: 2-Chloro-N-methoxy-N-methyl-nicotinamide

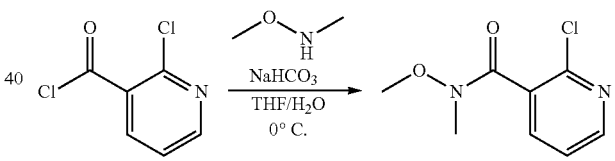

To a solution of 2-chloro-nicotinoyl chloride (7.00 g, 39.8 mmol) and sodium bicarbonate (10.0 g, 119 mmol) in 1:1 THF/H$_2$O (110 mL) at 0° C. was added N,O-dimethyl hydroxylamine hydrochloride (4.68 g, 47.7 mmol). The resultant solution was stirred 2 h at 0° C., neutralized with 10% HCl to pH ~7, and the aqueous layer was extracted two times with EtOAc. The combined organics were dried with sodium sulfate and concentrated in vacuo to produce 6.96 g (87%) of the crude nicotinamide, which was used without further purification.

Example 211: Pyridine-2-carboxylic acid methoxy-methyl-amide

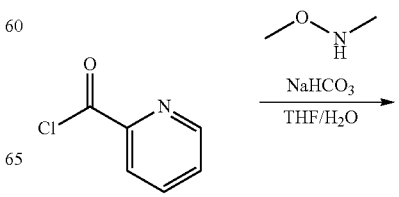

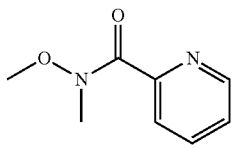

Following the procedure for example 157, picolinoyl chloride hydrochloride (3.0 g, 16.9 mmol) was converted to pyridine-2-carboxylic acid methoxy-methyl-amide.

Example 212: 2-Chloro-N-methoxy-N-methyl-isonicotinamide

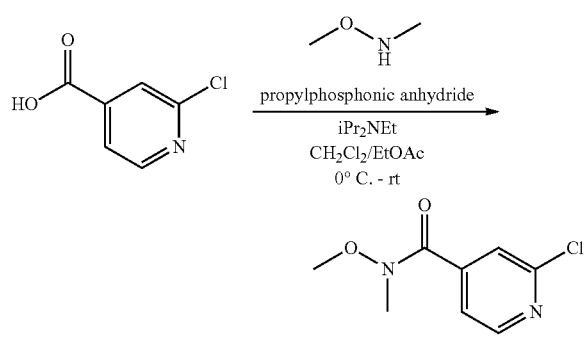

A 500 mL round-bottom flask was charged with 2-chloro isonicotinic acid (4.19 g, 26.5 mmol), N,O-dimethyl hydroxylamine hydrochloride (3.12 g, 31.8 mmol), diisopropylethylamine (12.0 g, 92.7 mmol), and methylene chloride (130 mL). The mixture was cooled to 0° C., and then propylphosphonic anhydride (16.6 mL, 50% solution in EtOAc) was added slowly. The resultant heterogeneous solution was allowed to stir overnight, during which the reaction warmed to ambient temperature as the ice-bath melted. The following day, the reaction was diluted with EtOAc, the organics were washed with saturated sodium bicarbonate, dried with sodium sulfate, concentrated in vacuo, and purified via automated silica gel chromatography to afford the Weinreb amide.

Example 213: 2-[Bis-(4-methoxy-benzyl)-amino]-N-methoxy-N-methyl-isonicotinamide

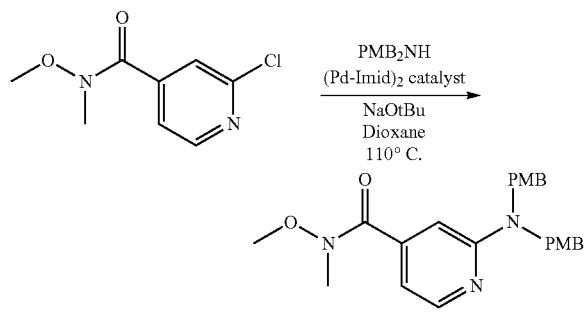

A 40 mL vial was charged with 2-chloro-N-methoxy-N-methyl-isonicotinamide (800 mg, 3.86 mmol), bis-(4-methoxy-benzyl)-amine (1.49 g, 5.80 mmol), 1,3-bis(2,6-diisopropylphenyl)imidazol-2-ylidene-(1,4-naphthoquinone)palladium (0) dimer (126 mg, 0.097 mmol), sodium tert-butoxide (519 mg, 5.41 mmol), and dioxane (12 mL). The vial was sealed, warmed to 110° C., and stirred overnight. The next day, the reaction was filtered through Celite, dry loaded onto silica gel, and purified via automated silica gel chromatography to generate 795 mg (47%) of the protected aminopyridine.

Example 214: 6-Chloro-pyridine-2-carboxylic acid methoxy-methyl-amide

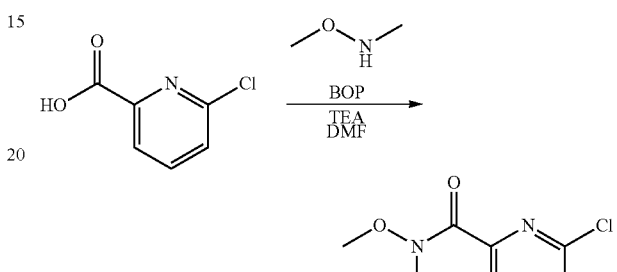

A 250 mL round-bottom flask was charged with 6-chloro picolinic acid (4.00 g, 25.3 mmol), N,O-dimethyl hydroxylamine hydrochloride (2.73 g, 27.8 mmol), triethylamine (8.44 g, 83.5 mmol), and dimethylformamide (50 mL). The mixture was cooled to 0° C., and then BOP (11.8 g, 26.6 mmol) was added slowly. The resultant heterogenous solution was allowed to stir overnight, during which the reaction warmed to ambient temperature as the ice-bath melted. The following day, the reaction was diluted with EtOAc, the organics were washed with saturated sodium bicarbonate, dried with sodium sulfate, concentrated in vacuo, and purified via automated silica gel chromatography to afford the Weinreb amide.

Example 215: 2-Methanesulfonylamino-N-methoxy-N-methyl-isonicotinamide

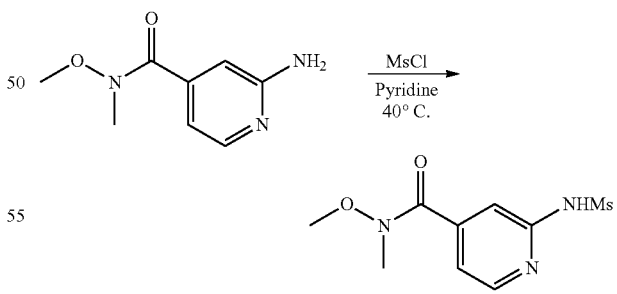

2-Amino-N-methoxy-N-methyl-isonicotinamide (575 mg, 3.16 mmol) was dissolved in pyridine (4 mL), followed by the addition of methanesulfonyl chloride (0.73 mL, 9.48 mmol). The reaction was subsequently warmed to 40° C. and stirred 5 h. The resultant mixture was quenched with 10% HCl, diluted with EtOAc, and the organic layer washed with 10% HCl and saturated sodium bicarbonate. The combined organics were dried with sodium sulfate, concentrated

Example 216: 2-chloro-N-methoxy-3,N-dimethyl-benzamide

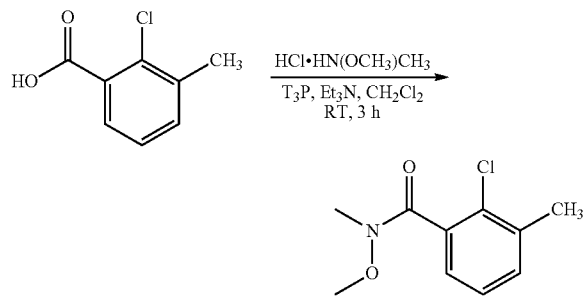

To a cooled mixture of 2-chloro-3-methyl-benzoic acid (1 g, 5.88 mmol), N,O-dimethylhydroxyl amine (860 mg, 8.82 mmol) and Et$_3$N (3.27 mL, 23.52 mmol) in CH$_2$Cl$_2$ (10 mL) was added 1-propane phosphonic acid cyclic anhydride (4.49 mL, 7.05 mmol; 50 wt % solution in EtOAc) dropwise and stirred at room temperature for 3 h. The reaction mixture was filtered, washed with CH$_2$Cl$_2$ (2×10 mL), evaporated to dryness and subjected to column chromatography (SiO$_2$, 40% EtOAc-hexanes) to obtain 2-chloro-N-methoxy-3,N-dimethyl-benzamide (1.19 g) in 95% yield. ESMS m/z (relative intensity): 214 (M+H)$^+$ (100).

Example 217: 2-chloro-N-methoxy-5,N-dimethyl-benzamide

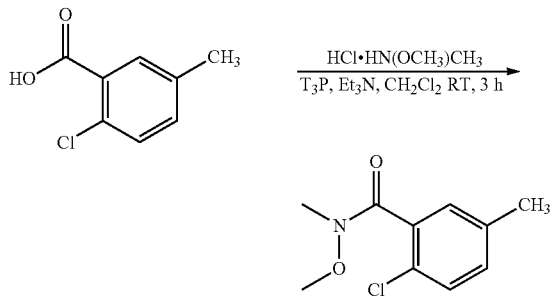

To a cooled mixture of 2-chloro-5-methyl-benzoic acid (1 g, mmol), N,O-dimethylhydroxyl amine (860 mg, 8.82 mmol) and Et$_3$N (3.27 mL) in CH$_2$Cl$_2$ (10 mL) was added 1-propane phosphonic acid cyclic anhydride (4.49 mL, 7.05 mmol; 50 wt % solution in EtOAc) dropwise and stirred at room temperature for 3 h. The reaction mixture was filtered, washed with CH$_2$Cl$_2$ (mL), evaporated to dryness and subjected to column chromatography (SiO$_2$, 40% EtOAc-hexanes) to obtain 2-chloro-N-methoxy-5,N-dimethyl-benzamide (1.19 g) as white crystalline solid in 95% yield. ESMS m/z (relative intensity): 214.1 (M+H)$^+$ (100).

in vacuo, and purified via automated silica gel chromatography to produce the desired sulfonamide.

Example 218: 2,N-dimethoxy-N-methyl-nicotinamide

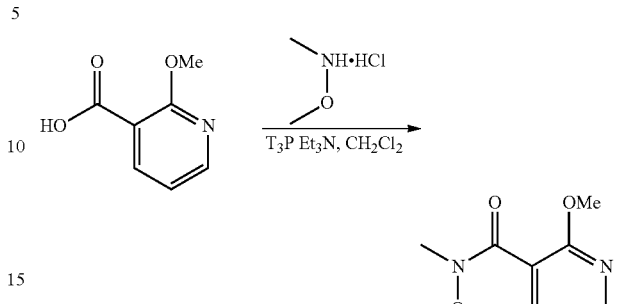

To a cooled mixture of 2-methoxy-nicotinic acid (2 g, 13.05 mmol), N,O-dimethylhydroxyl amine (1.91 g, 19.59 mmol) in CH$_2$Cl$_2$ (20 mL) and Et$_3$N (7.26 mL, 15.66 mmol) was added 1-propane phosphonic acid cyclic anhydride (9.96 mL, 15.66 mmol; 50 wt % solution in EtOAc) dropwise and stirred at room temperature for 2 h. The reaction mixture was filtered, washed with CH$_2$Cl$_2$ (10 mL), evaporated to dryness and subjected to column chromatography (SiO$_2$, 50% EtOAc-hexanes) to obtain 2,N-dimethoxy-N-methyl-nicotinamide (2.33 g) in 91% yield.

Example 219: 4-Chloro-N-[5-chloro-2-(2-chloro-pyridine-3-carbonyl)-pyridin-3-yl]-3-trifluoromethyl-benzenesulfonamide

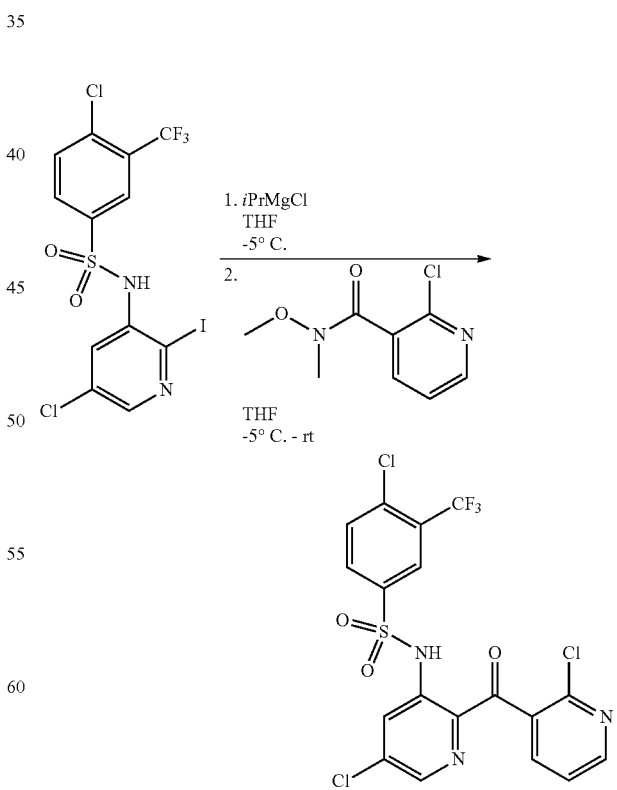

4-Chloro-N-(5-chloro-2-iodo-pyridin-3-yl)-3-trifluoromethyl-benzenesulfonamide (250 mg, 0.503 mmol) was placed in a dry 2-neck 10 mL round-bottom flask. The flask was evacuated and purged with nitrogen, followed by the addition of THF (1.7 mL). The homogeneous mixture was lowered to −5° C. and i-PrMgCl (0.60 mL, 2.0 M) was added dropwise. Upon completion of the addition, the reaction was stirred 45 minutes, followed by the addition of 2-chloro-N-methoxy-N-methyl-nicotinamide (201 mg, 1.01 mmol). The homogeneous mixture was stirred 70 min at −5° C., then overnight at ambient temperature. The resultant solution was quenched with 10% HCl and diluted with EtOAc. The organics were washed with 10% HCl and saturated sodium bicarbonate, dried with sodium sulfate, concentrated in vacuo, and purified via automated silica gel chromatography to afford the diaryl ketone: MS (ES) (M+H)+ expected 509.9, found 509.8.

Example 220: 4-Chloro-N-[5-chloro-2-(2,3-dichloro-pyridine-4-carbonyl)-pyridin-3-yl]-3-trifluoromethyl-benzenesulfonamide

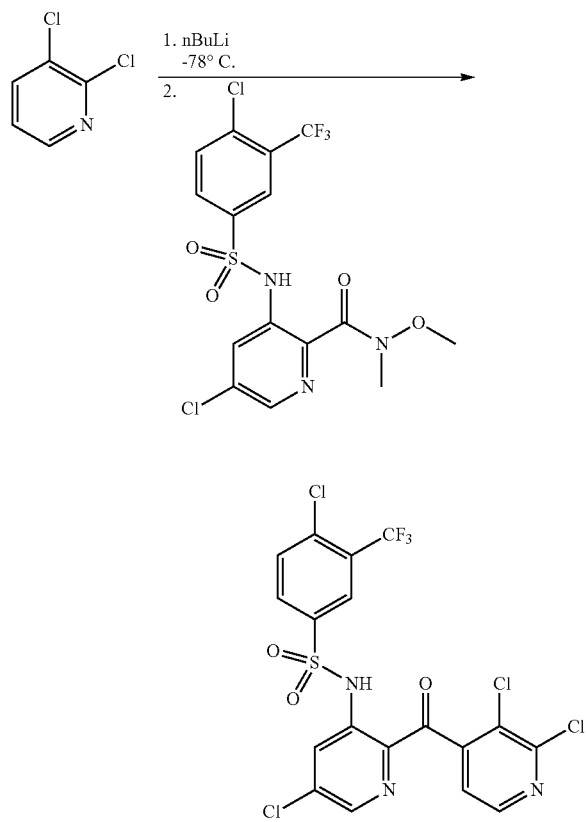 [SMILES: Clc1cccnc1Cl ; CON(C)C(=O)c1ncc(Cl)cc1NS(=O)(=O)c1ccc(Cl)c(C(F)(F)F)c1 ; O=C(c1ccnc(Cl)c1Cl)c1ncc(Cl)cc1NS(=O)(=O)c1ccc(Cl)c(C(F)(F)F)c1]

2,3-Dichloropyridine (129 mg, 0.873 mmol) was placed in a dry 2-neck 10 mL round-bottom flask. The flask was evacuated and purged with nitrogen, followed by the addition of THF (1.75 mL). The homogeneous mixture was lowered to −78° C. and nBuLi (0.35 mL, 2.5 M) was added dropwise. Upon completion of the addition, the reaction was stirred for 90 minutes, followed by the addition of 5-chloro-3-(4-chloro-3-trifluoromethyl-benzenesulfonylamino)-pyridine-2-carboxylic acid methoxy-methyl-amide (50 mg, 0.109 mmol). The homogeneous mixture was stirred 60 min at −78° C., then warmed to room temperature and stirred an additional 6 h. The resultant solution was quenched with 10% HCl and diluted with EtOAc. The organics were washed with 10% HCl and saturated sodium bicarbonate, dried with sodium sulfate, concentrated in vacuo, and purified via automated silica gel chromatography to afford the desired diaryl ketone: $^1$H NMR (400 MHz, CDCl$_3$) δ 10.88 (bs, 1H), 8.41 (d, 1H), 8.16-8.28 (m, 3H), 8.04 (d, 1H), 7.71 (d, 1H), 7.12 (d, 1H); MS (ES) (M+H)+ expected 543.9, found 543.8.

Example 221: 4-Chloro-N-[5-chloro-2-(3-chloro-2-hydroxy-pyridine-4-carbonyl)-pyridin-3-yl]-3-trifluoromethyl-benzenesulfonamide

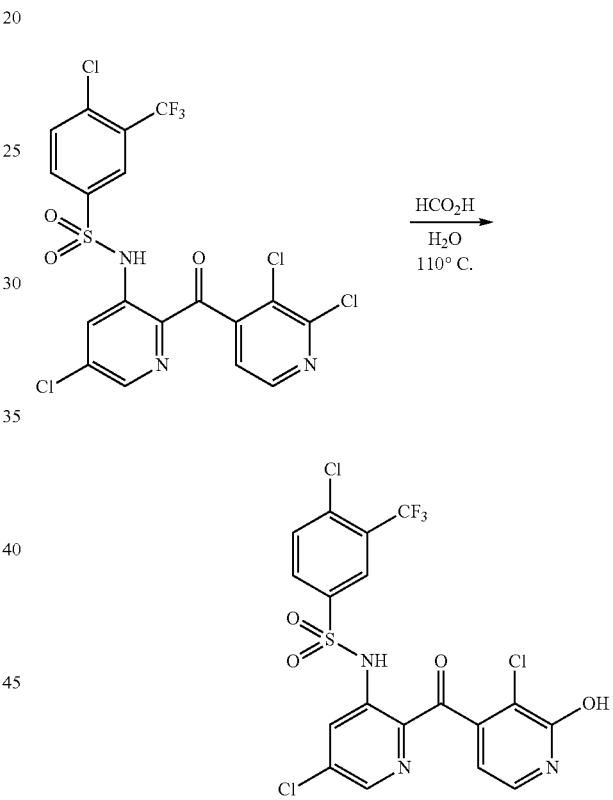

A 1 dram vial was charged with 4-chloro-N-[5-chloro-2-(2,3-dichloro-pyridine-4-carbonyl)-pyridin-3-yl]-3-trifluoromethyl-benzenesulfonamide (15 mg, 0.028 mmol), formic acid (0.39 mL) and water (0.13 mL). The heterogeneous solution was warmed to 100° C. and stirred overnight. The following day, starting material remained; therefore, an additional 0.26 mL of formic acid was added. The reaction was subsequently warmed to 110° C. and stirred overnight. The resultant mixture was neutralized with saturated aqueous sodium bicarbonate, diluted with EtOAc, and the organic layer washed with saturated sodium bicarbonate. The combined organics were dried with sodium sulfate, concentrated in vacuo, and purified via automated silica gel chromatography to afford the desired hydroxypyridine: $^1$H NMR (400 MHz, CD$_3$OD) δ 8.26-8.38 (m, 1H), 8.17-8.20 (m, 2H), 8.02-8.07 (m, 1H), 7.72-7.76 (m, 1H), 7.34-7.37 (m, 1H), 6.17-6.20 (m, 1H); MS (ES) (M+H)$^+$ expected 525.9, found 525.9.

Example 222: 4-chloro-N-[5-chloro-2-(2-chloro-3-methyl-benzoyl)-pyridin-3-yl]-N-methoxymethyl-3-trifluoromethyl-benzenesulfonamide

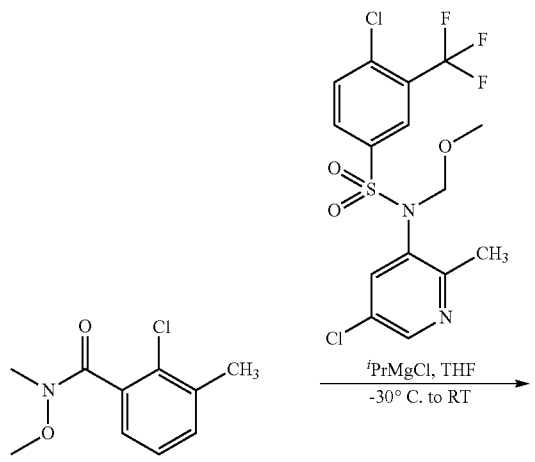

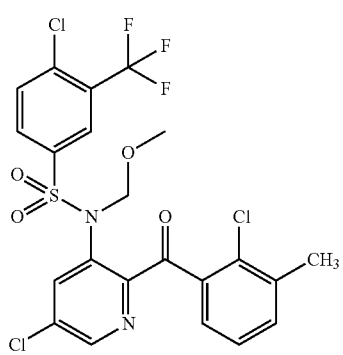

To a solution of N-(2-bromo-5-chloro-pyridin-3-yl)-4-chloro-N-methoxymethyl-3-trifluoromethyl-benzenesulfonamide (984 mg, 2.0 mmol) in THF (10 mL) under nitrogen atmosphere at 0° C. was added dropwise isopropylmagnesium chloride (2 M solution in THF, 2.5 mL, 5.0 mmol). The mixture was then stirred for 30 min at 0° C. followed by the addition of 2-chloro-N-methoxy-3,N-dimethyl-benzamide (852 mg, 4.0 mmol) at 0° C. The mixture was stirred at room temperature for 3 h, quenched with saturated aqueous NH$_4$Cl solution (5 mL), and extracted with EtOAc (2×25 mL). The combined organic layers were washed with saturated aqueous NH$_4$Cl solution (25 mL), brine (25 mL), dried (anhydrous Na$_2$SO$_4$) and concentrated under reduced pressure. The residue was column purified (SiO$_2$, 50% EtOAc-hexanes) to obtain 4-chloro-N-[5-chloro-2-(2-chloro-3-methyl-benzoyl)-pyridin-3-yl]-N-methoxymethyl-3-trifluoromethyl-benzenesulfonamide (586 mg) in 52% yield. ESMS m/z (relative intensity): 534.9 [(M−32+H)]+(70), 588.9 (M+Na)$^+$.

Example 223: 4-Chloro-N-[5-chloro-2-(2-chloro-3-methyl-benzoyl)-pyridin-3-yl]-3-trifluoromethyl-benzenesulfonamide


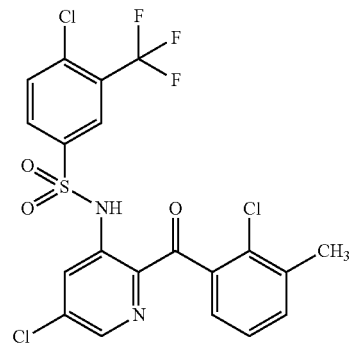

A mixture of 4-chloro-N-[5-chloro-2-(2-chloro-3-methyl-benzoyl)-pyridin-3-yl]-N-methoxymethyl-3-trifluoromethyl-benzenesulfonamide (58.6 mg, 1.03 mmol) in 4 N HCl in dioxane (4 mL) and water (1 mL) was stirred at 100° C. for overnight. The reaction mixture was cooled to room temperature, evaporated to dryness and treated with saturated aqueous NaHCO$_3$ solution till pH 7-8. The mixture was extracted with EtOAc (2×25 mL), dried (anhydrous Na$_2$SO$_4$) and concentrated. The obtained residue was purified via column chromatography (SiO$_2$, 70% EtOAc in hexanes) to afford 4-chloro-N-[5-chloro-2-(2-chloro-3-methyl-benzoyl)-pyridin-3-yl]-3-trifluoromethyl-benzenesulfonamide (34.5 mg) in 64% yield. $^1$H NMR (400 MHz, CDCl$_3$) δ11.00 (s, 1H), 8.24 (d, 1H), 8.18 (m, 1H), 8.17 (d, 1H), 7.98 (dd, 1H), 7.63 (d, 1H), 7.35 (d, 1H), 7.24 (t, 1H), 7.1 (d, 1H), 2.37 (s, 3H); ESMS m/z (relative intensity): 522.9 (M+H)⁺ (100), 544.9 (M+Na)⁺ (100).

Example 224: 4-chloro-N-[5-chloro-2-(2-chloro-5-methyl-benzoyl)-pyridin-3-yl]-N-methoxymethyl-3-trifluoromethyl-benzenesulfonamide To a solution of N-(2-bromo-5-chloro-pyridin-3-yl)-4-chloro-N-methoxymethyl-3-trifluoromethyl-benzenesulfonamide (984 mg, 2.0 mmol) in THF (10 mL) under nitrogen atmosphere at 0° C. was added dropwise isopropylmagnesium chloride (2 M solution in THF, 2.5 mL, 5.0 mmol). The mixture was then stirred for 30 min at 0° C. followed by the addition of 2-chloro-N-methoxy-5,N-dimethyl-benzamide (852 mg, 4.0 mmol) at 0° C. The mixture was stirred at room temperature for 3 hours, quenched with saturated aqueous NH₄Cl solution (5 mL) and extracted with EtOAc (2×25 mL). The combined organic layers were washed with saturated aqueous NH₄Cl solution (25 mL), brine (25 mL), dried (anhydrous Na₂SO₄), and concentrated under reduced pressure. The obtained residue was purified via column chromatography (SiO₂, 50% EtOAc-hexanes) to obtain 4-chloro-N-[5-chloro-2-(2-chloro-5-methyl-benzoyl)-pyridin-3-yl]-N-methoxymethyl-3-trifluoromethyl-benzenesulfonamide (543 mg) in 48% yield. ESMS m/z (relative intensity): 534.9 [(M−32+H)]+(35), 588.9 (M+Na)⁺ (100).

Example 225: 4-chloro-N-[5-chloro-2-(2-chloro-5-methyl-benzoyl)-pyridin-3-yl]-3-trifluoromethyl-benzenesulfonamide


A mixture of 4-chloro-N-[5-chloro-2-(2-chloro-5-methyl-benzoyl)-pyridin-3-yl]-N-methoxymethyl-3-trifluoromethyl-benzenesulfonamide (50 mg, 0.088 mmol) in 4N HCl in dioxane (4 mL) and water (1 mL) was stirred at 100° C. for overnight. The reaction mixture was cooled to room temperature, evaporated to dryness and treated with saturated aqueous NaHCO₃ solution till pH 7-8. The mixture was extracted with EtOAc (2×25 mL), dried (anhydrous Na₂SO₄) and concentrated. The obtained residue was purified via column chromatography to afford 4-chloro-N-[5-chloro-2-(2-chloro-5-methyl-benzoyl)-pyridin-3-yl]-3-trifluoromethyl-benzene sulfonamide (29.5 mg) in 64% yield. ESMS m/z (relative intensity): 522.9 (M+H)⁺ (30), 544.9 (M+Na)+(50).

Example 226: 4-chloro-N-[5-chloro-2-(2-methoxy-pyridine-3-carbonyl)-pyridin-3-yl]-N-methoxymethyl-3-trifluoromethyl-benzenesulfonamide


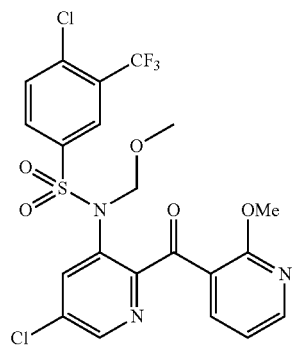

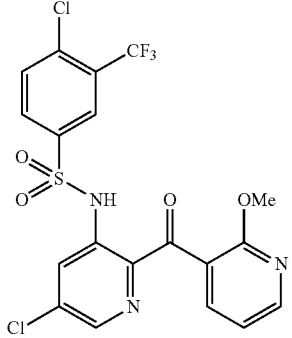

To a solution of N-(2-bromo-5-chloro-pyridin-3-yl)-4-chloro-N-methoxymethyl-3-trifluoromethyl-benzenesulfonamide (612 mg, 1.24 mmol) in THF (5 mL) under nitrogen atmosphere at 0° C. was added dropwise isopropylmagnesium chloride (2 M solution in THF, 1.55 mL, 3.1 mmol). The mixture was then stirred for 30 min at 0° C. followed by the addition of a solution of 2,N-dimethoxy-N-methyl-nicotinamide (487 mg, 2.48 mmol) in THF (2 mL) at 0° C. The mixture was stirred at room temperature for 6 hours, quenched with saturated aqueous NH$_4$Cl solution (5 mL) and extracted with EtOAc (2×25 mL). The combined organic layers were washed with saturated aqueous NH$_4$Cl solution (25 mL), brine (25 mL), dried (anhydrous Na$_2$SO$_4$) and concentrated under reduced pressure. The obtained residue was purified via column chromatography (SiO$_2$, 50% EtOAc-hexanes) to obtain 4-chloro-N-[5-chloro-2-(2-methoxy-pyridine-3-carbonyl)-pyridin-3-yl]-N-methoxymethyl-3-trifluoromethyl-benzenesulfonamide (200 mg) in 29.2% yield. ESMS m/z (relative intensity): 550 (M+H)$^+$ (100), 571.9 (M+Na)$^+$ (80).

A mixture of 4-chloro-N-[5-chloro-2-(2-methoxy-pyridine-3-carbonyl)-pyridin-3-yl]-N-methoxymethyl-3-trifluoromethyl-benzenesulfonamide (330.06 mg, mmol) in 5% H$_2$SO$_4$ in TFA (2 mL) and water (1 mL) was stirred at 50° C. for overnight. The reaction mixture was cooled to room temperature, diluted with water (5 mL) and treated slowly with saturated aqueous NaHCO$_3$ solution till pH 7-8. The mixture was extracted with EtOAc (2×25 mL), dried (anhydrous Na$_2$SO$_4$) and concentrated. The obtained residue was purified via column chromatography (SiO$_2$, 5% MeOH in EtOAc) to afford 4-chloro-N-[5-chloro-2-(2-methoxy-pyridine-3-carbonyl)-pyridin-3-yl]-3-trifluoromethyl-benzene sulfonamide (15 mg) in 50% yield. ESMS m/z (relative intensity): 505.9 (M+H)$^+$ (100), 527.9 (M+Na)$^+$ (20).

Example 228: 4-chloro-N-[5-chloro-2-(2-hydroxy-pyridine-3-carbonyl)-pyridin-3-yl]-3-trifluoromethyl-benzenesulfonamide

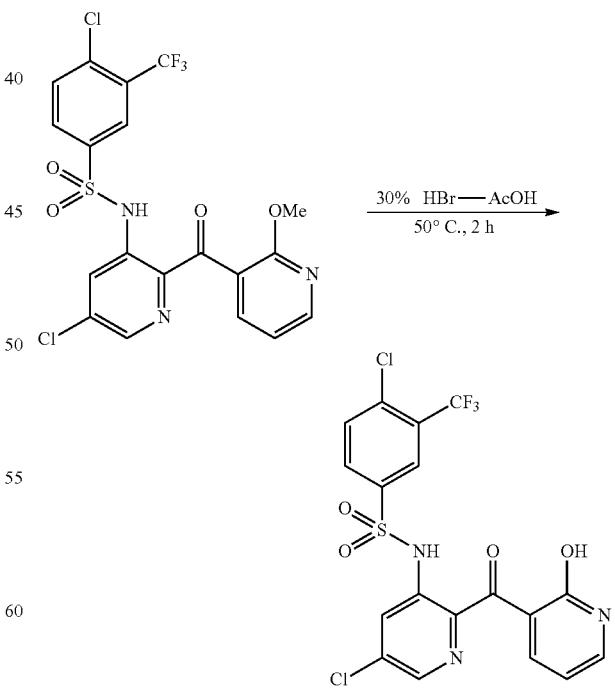

Example 227: 4-chloro-N-[5-chloro-2-(2-methoxy-pyridine-3-carbonyl)-pyridin-3-yl]-3-trifluoromethyl-benzenesulfonamide

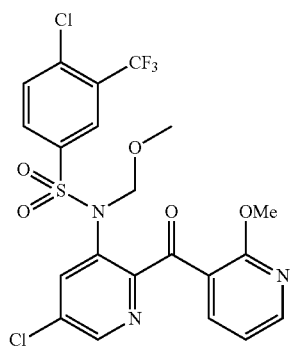

A mixture of 4-chloro-N-[5-chloro-2-(2-methoxy-pyridine-3-carbonyl)-pyridin-3-yl]-3-trifluoromethyl-benzene sulfonamide (10 mg, mmol) in 30% HBr in AcOH (1 mL)

was stirred at 50° C. for 2 h. The reaction mixture was cooled to room temperature, diluted with water (1 mL) and treated with saturated aqueous NaHCO₃ solution slowly till pH 5-6. The mixture was extracted with EtOAc (2×25 mL), dried (anhydrous Na₂SO₄) and concentrated. The obtained residue was column purified (SiO₂, 10% MeOH in CH₂Cl₂) to afford 4-chloro-N-[5-chloro-2-(2-hydroxy-pyridine-3-carbonyl)-pyridin-3-yl]-3-trifluoromethyl-benzenesulfonamide (6 mg) in 61.8% yield. ¹H NMR (400 MHz, CDCl₃) δ 8.24 (d, 1H), 8.17 (d, 1H), 8.15 (d, 1H), 7.97 (dd, 1H), 7.72 (dd, 1H), 7.63 (d, 1H), 7.43 (dd, 1H), 6.37 (t, 1H); ESMS m/z (relative intensity): 491.9 (M+H)⁺ (100).

Example 229: 2-[2-(tert-Butyl-dimethyl-silanyloxy)-ethoxy]-4-iodo-pyridine

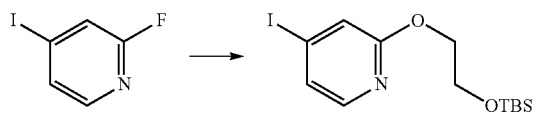 [SMILES: Fc1cc(I)ccn1 ; CC(C)(C)[Si](C)(C)OCCOc1cc(I)ccn1]

2-Fluoro-4-iodo-pyridine (607 mg, 2.72 mmol), ethylene glycol (760 uL, 13.6 mmol) and 60% sodium hydride (120 mg, 2.99 mmol) were sequentially added to 2 mL of anhydrous DMF at room temperature. The solution was then brought to 60° C. and stirred for 2 hours, then cooled down and diluted with 20 mL of water. The mixture was extracted 2 times with 30 mL of diethyl ether. The combined organic layers were washed with 10 mL of water, then 10 mL of brine and dried over anhydrous magnesium sulfate. After concentrating the mixture under reduced pressure, the residue was dissolved in 2 mL of anhydrous acetonitrile. To this solution tert-butylchlorodimethylsilane (453 mg, 3.00 mmol) and triethylamine (459 FL, 3.30 mmol) were added and the mixture was stirred at r.t. for 3 days following evaporation under reduced pressure. The residue was taken up in 40 mL of a 1:1 mixture of diethyl ether and water. The organic layer was concentrated under reduced pressure and the residue purified on a 40 g silica column eluted with a gradient of 0-15% ethyl acetate in hexanes to yield 630 mg of the product as colorless oil. MS: (M+H)/z=380.0.

Example 230: 4-Chloro-N-{5-chloro-2-[2-(2-hydroxy-ethoxy)-pyridine-4-carbonyl]-pyridin-3-yl}-3-trifluoromethyl-benzenesulfonamide

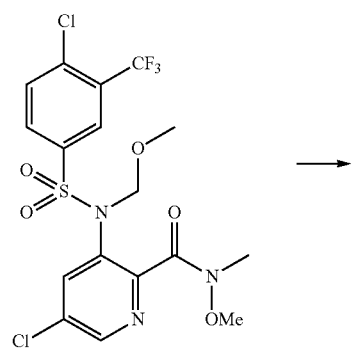

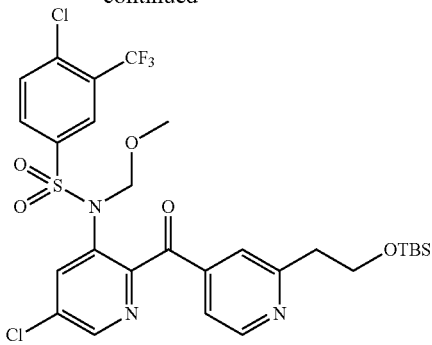

2-[2-(tert-Butyl-dimethyl-silanyloxy)-ethoxy]-4-iodo-pyridine (305 mg, 0.805 mmol) was dissolved in 1 mL of dry THF. To this solution isopropylmagnesium chloride solution (2 M in THF, 0.44 mL, 0.88 mmol) was added at room temperature. After 30 minutes this solution was added to a solution of 5-chloro-3-[(4-chloro-3-trifluoromethyl-benzenesulfonyl)-methoxymethyl-amino]-pyridine-2-carboxylic acid methoxy-methyl-amide (283 mg, 0.564 mmol) in 1 mL dry THF at −78° C. The mixture was allowed to warm up to room temperature and stirred overnight followed by addition of 5 mL of aqueous saturated ammonium chloride and extraction with 15 mL DCM. The organic solution was evaporated under reduced pressure and purified on a 4 g silica column eluted with a gradient of 10-40% ethyl acetate in hexanes to yield 205 mg of N-(2-{2-[2-(tert-butyl-dimethyl-silanyloxy)-ethyl]-pyridine-4-carbonyl}-5-chloro-pyridin-3-yl)-4-chloro-N-methoxymethyl-3-trifluoromethyl-benzenesulfonamide as a colorless oil.

A solution of N-(2-{2-[2-(tert-butyl-dimethyl-silanyloxy)-ethyl]-pyridine-4-carbonyl}-5-chloro-pyridin-3-yl)-4-chloro-N-methoxymethyl-3-trifluoromethyl-benzenesulfonamide in 4N HCl in dioxane (4 mL) and water (1 mL) was stirred at 100° C. for overnight. The reaction mixture was cooled to room temperature, evaporated to dryness and treated with saturated aqueous NaHCO₃ solution till pH 7-8. The mixture was extracted with EtOAc (2×25 mL), dried (anhydrous Na₂SO₄) and concentrated. The crude product was purified by HPLC. ¹H NMR (400 MHz, CDCl3) δ 10.82 (s, 1H), 8.35 (m, 1H), 8.24 (m, 1H), 8.15-8.18 (m, 2H), 7.96 (m, 1H), 7.63 (m, 1H), 7.17 (m, 1H), 7.09 (m, 1H), 4.51 (m, 2H), 3.97 (m, 2H), 3.09 (m, 1H); MS: (M+H)/z=535.9.

Example 231: (S)-4-Chloro-N-(5-chloro-2-(4-hydroxy-3,3-dimethylpiperidine-1-carbonyl)pyridine-3-yl)-3-(trifluoromethyl)benzenesulfonamide

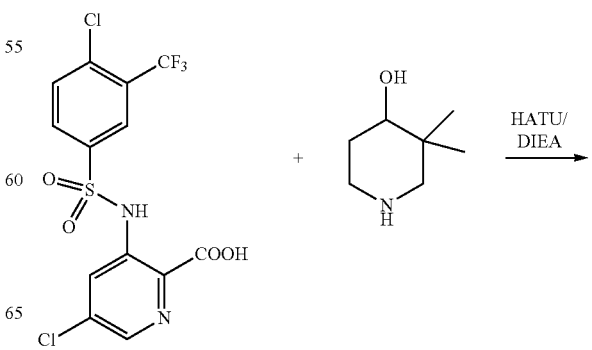

-continued

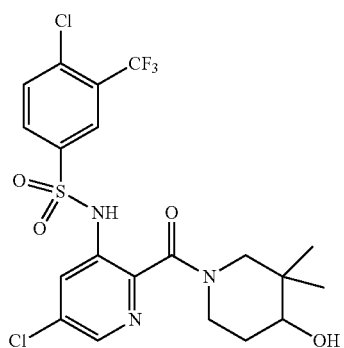

General Synthesis of Amides

A 10 mL scintillation vial was charged with 5-chloro-3-(4-chloro-3-(trifluoromethyl)phenyl-sulfonamido)picolinic acid (164 mg, 0.4 mmol), freshly prepared 3,3-dimethylpiperidin-4-ol (0.56 mmol) ((M+H)+, 130.1), HATU (192 mg, 0.5 mmol), DIEA (260 mg, 2 mmol) and anhydrous DMF (1.5 mL). The resultant solution was heated to 70° C. and stirred for 2 h. After cooled to room temperature, the mixture was purified via preparative HPLC and dried (lyophilizer) to afford the title compound (1:2 mixture of rotamers): $^1$H NMR (400 MHz, CDCl$_3$) (major rotamer) δ 9.54 (s, 1H), 8.26 (d, 1H), 8.12 (d, 1H), 8.00 (d, 1H), 7.88 (dd, 1H), 7.62 (d, 1H), 4.05 (m, 1H), 3.70 (d, 1H), 3.50 (m, 2H), 3.40 (m, 1H), 3.10 (d, 1H), 1.82 (m, 2H), 1.00 (s, 3H), 0.92 (s, 3H); MS (ES) (M+H)+ expected 526.0, found 526.0.

Example 232: 5-Chloro-3-(4-chloro-3-(trifluoromethyl)phenylsulfonamido)-N-methyl-N-(pyridin-3-yl)picolinamide

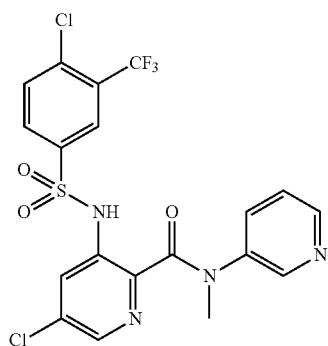 [SMILES: CN(C(=O)c1ncc(Cl)cc1NS(=O)(=O)c1ccc(Cl)c(C(F)(F)F)c1)c1cccnc1]

The title compound was prepared according to above method for example 179: $^1$H NMR (400 MHz, CDCl$_3$) δ 8.62 (dd, 1H), 8.52 (s, 1H), 8.22 (d, 1H), 8.02 (dd, 1H), 7.96 (d, 1H), 7.80 (s, 1H), 7.68 (m, 3H), 3.50 (s, 3H); MS (ES) (M+H)+ expected 505.0, found 505.0.

Example 233: 4-Chloro-N-(5-chloro-2-(2-chloro-6-nitrobenzoyl)pyridin-3-yl)-3-(trifluoromethyl)benzenesulfonamide

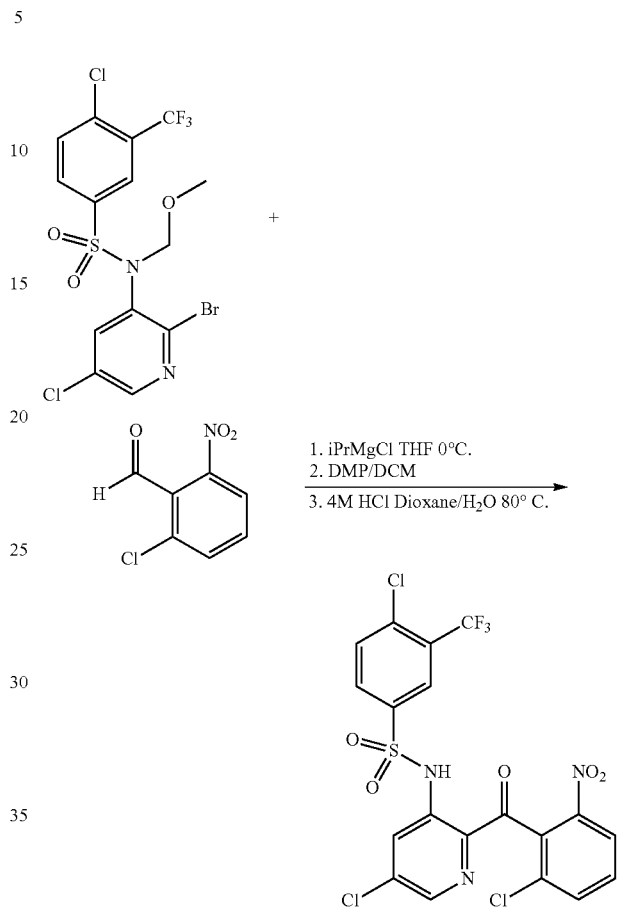

Step 1: N-(2-Bromo-5-chloro-pyridin-3-yl)-4-chloro-N-methoxymethyl-3-(trifluoromethyl)benzenesulfonamide (1.0 g, 2.0 mmol) was placed in a dry 100 mL round-bottom flask sealed with septa. The flask was evacuated and purged with nitrogen, followed by the addition of dry THF (30 mL). The homogeneous solution was cooled to 0° C. and i-PrMgCl (3.0 mL, 2.0 M) was added dropwise. Upon completion of the addition, the mixture was stirred at 0° C. for 60 min, followed by the slow addition of 2-chloro-6-nitrobenzaldehyde (930 mg, 5 mmol). The reaction mixture was stirred at 0° C. for 3 h. The reaction was quenched with NH$_4$Cl (sat) and extracted with EtOAc, washed with brine, dried over MgSO$_4$, and concentrated under reduced pressure. The residue was further purified through automated normal-phase chromatography to afford 4-chloro-N-(5-chloro-2((2-chloro-6-nitrophenyl)(hydroxymethyl)pyridin-3-yl)-N-methoxymethyl-3-(trifluoromethyl)benzenesulfonamide (600 mg, 49%) (which was used directly for the next step).

Step 2: The above 4-chloro-N-(5-chloro-2((2-chloro-6-nitrophenyl)-(hydroxymethyl)pyridin-3-yl)-N-methoxymethyl-3-(trifluoromethyl)-benzenesulfonamide was dissolved in DCM (30 mL) and treated with Dess-Martin periodinane (2.4 g, 5 mmol) at room temperature for 3 h. After evaporation of solvent, the residue was treated with (4.0 M HCl in dioxane) (10 mL, 40 mmol) and H$_2$O (4 mL), and then stirred at 110° C. for 6 h. The mixture was diluted with EtOAc. The resultant organics were washed with NaHCO$_3$ (sat), and brine; dried (MgSO$_4$), and concentrated under reduced pressure and purified through automated normal-phase chromatography to afford the title compound: $^1$H NMR (400 MHz, CDCl$_3$) δ 10.90 (s, 1H), 8.23 (m, 2H), 8.16 (d, 1H), 8.08 (d, 1H), 7.96 (dd, 1H), 7.73 (d, 1H), 7.64 (d, 1H), 7.56 (t, 1H); MS (ES) (M+Na)$^+$ expected 575.9, found 575.9.

Example 234: N-(2-(2-Amino-6-chlorobenzoyl)5-chloro-pyridin-3-yl)-4-chloro-3-(trifluoromethyl)benzenesulfonamide

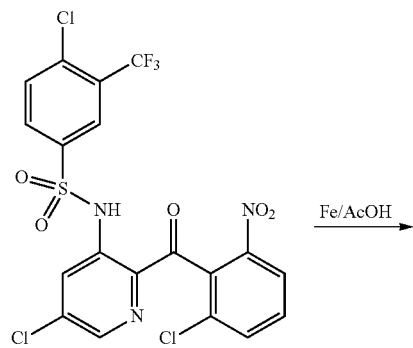

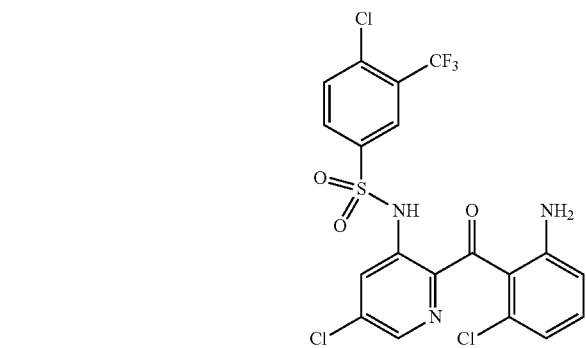

A 50 mL round-bottom flask was charged with 4-chloro-N-(5-chloro-2-(2-chloro-6-nitrobenzoyl)pyridin-3-yl)-3-(trifluoromethyl) benzenesulfonamide (350 mg, 0.63 mmol), iron powder (560 mg, 10 mmol) in acetic acid (30 mL) and stirred at room temperature for 2 h and then at 50° C. for 30 min. After cooling, the reaction mixture was diluted with EtOAc, filtered through Celite and evaporated the solvent in vacuo. The residue was dissolved in EtOAc and washed with NaHCO$_3$ (sat), brine, dried over MgSO$_4$, and concentrated under reduced pressure and was further purified through automated normal-phase chromatography to afford the title compound: $^1$H NMR (400 MHz, CDCl$_3$) δ 10.60 (s, 1H), 8.28 (d, 1H), 8.20 (d, 1H), 8.16 (d, 1H), 7.96 (dd, 1H), 7.60 (d, 1H), 7.09 (t, 1H), 6.64 (dd, 2H), 4.40 (bs, 2H); MS (ES) (M+H)$^+$ expected 523.9, found 523.9.

Example 235: 4-Chloro-N-(5-chloro-2-(5-chloro-6-(methylsulfonamido) benzoyl)pyridin-3-yl)-3-(trifluoromethyl) benzenesulfonamide

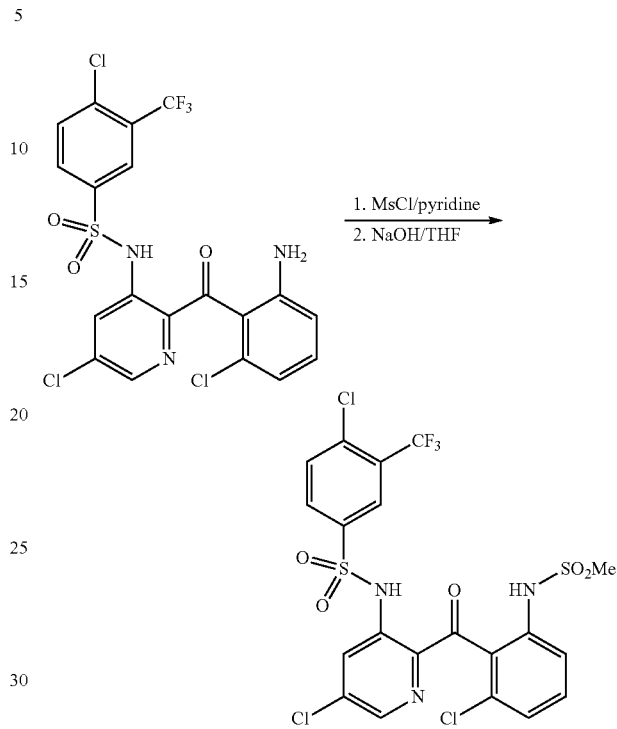

N-(2-(2-Amino-6-chlorobenzoyl)5-chloro-pyridin-3-yl)-4-chloro-3-(trifluoromethyl)benzenesulfonamide (52 mg, 0.1 mmol) in pyridine/1,4-dioxane (1:1, 4 mL) was treated with methanesulfonyl chloride (100 mg) and then stirred at 60° C. for 2 h. After evaporation of solvent under reduced pressure, to the mixture was added THF (5 mL), followed by NaOH (2 N, 2 mL) and stirred at room temperature for another 2 h. The mixture was taken up in EtOAc, washed with 1 N HCl, NaHCO$_3$ (sat), brine, dried over MgSO$_4$, and concentrated under reduced pressure and was further purified through automated normal-phase chromatography to afford the title compound: $^1$H NMR (400 MHz, CDCl$_3$) δ 10.70 (s, 1H), 8.25 (m, 3H), 8.01 (d, 1H), 7.68 (d, 1H), 7.60 (d, 1H), 7.50 (t, 1H), 7.42 (t, 1H), 7.23 (m, 1H), 6.52 (s, 1H), 2.88 (s, 3H); MS (ES) (M+H)$^+$ expected 603.9, found 603.9.

Example 236: 4-Chloro-N-(5-chloro-2-(5-chloro-2-oxo-1,2,3,4-tetrahydroquinazolin-4-yl)pyridine-3-yl)-3-(trifluoromethyl)benzenesulfonamide

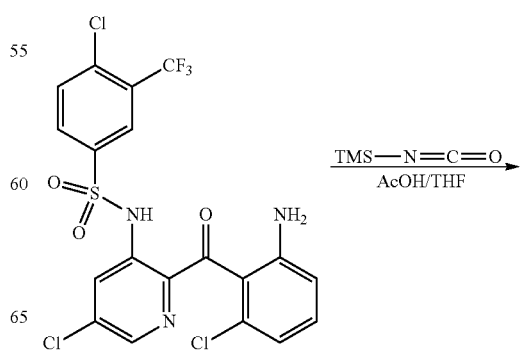

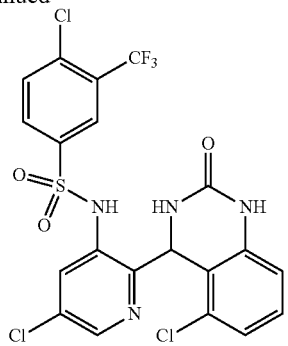

N-(2-(2-Amino-6-chlorobenzoyl)-5-chloro-pyridin-3-yl)-4-chloro-3-(trifluoromethyl)benzenesulfonamide (26 mg, 0.05 mmol) in THF (2 mL) was treated with TMS-isocyanate (100 mg) and AcOH (0.5 mL) and then stirred at 75° C. for 12 h. To the mixture was added MeOH (0.5 mL), followed by NaOH (5 N, 1 mL), and the resultant mixture stirred at 75° C. for another 2 h. To the mixture was added AcOH (0.5 mL), and the mixture was purified through HPLC and dried (lyophilizer) to afford the title compound: $^1$H NMR (400 MHz, CDCl$_3$) δ 8.82 (s, 2H), 8.34 (d, 1H), 8.14 (d, 1H), 7.90 (dd, 1H), 7.66 (d, 1H), 7.46 (s, 1H), 7.16 (t, 1H), 6.90 (d, 2H), 6.81 (d, 1H), 6.14 (d, 1H); MS (ES) (M+H)$^+$ expected 550.9, found 550.9.

Example 237: N-(2-(2-Amino-6-chlorobenzoyl) 5-chloro-pyridin-3-yl)-4-chloro-3-(trifluoromethyl)benzenesulfonamide

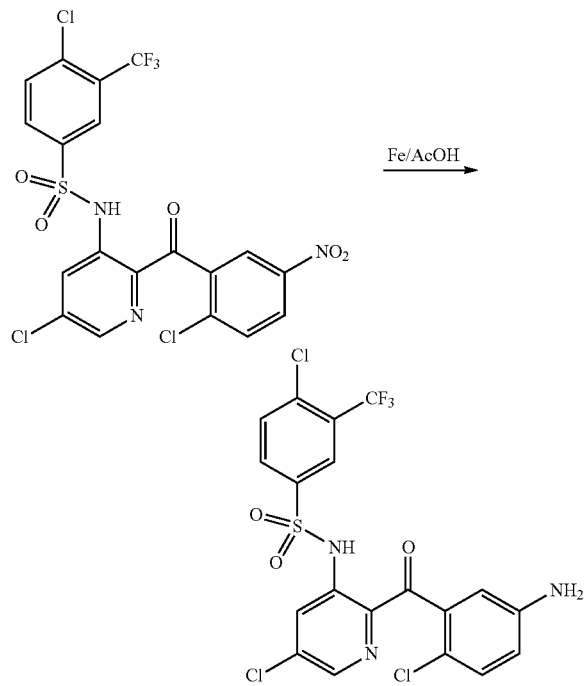

According to the procedure for example 234, 4-chloro-N-(5-chloro-2-(2-chloro-5-nitrobenzoyl)pyridin-3-yl)-3-(trifluoromethyl) benzenesulfonamide (MS 575.9, (M+Na)+) afforded the title compound: $^1$H NMR (400 MHz, CDCl$_3$) δ 10.84 (s, 1H), 8.28 (d, 1H), 8.20 (d, 1H), 8.16 (d, 1H), 7.98 (dd, 1H), 7.62 (d, 1H), 7.09 (t, 1H), 6.70 (d, 1H), 6.58 (d, 1H), 3.80 (s, 2H); MS (ES) (M+H)$^+$ expected 523.9, found 523.9.

Example 238: 4-Chloro-N-(5-chloro-2-(2-chloro-5-ureidobenzoyl)pyridine-3-yl)-3-(trifluoromethyl)benzenesulfonamide

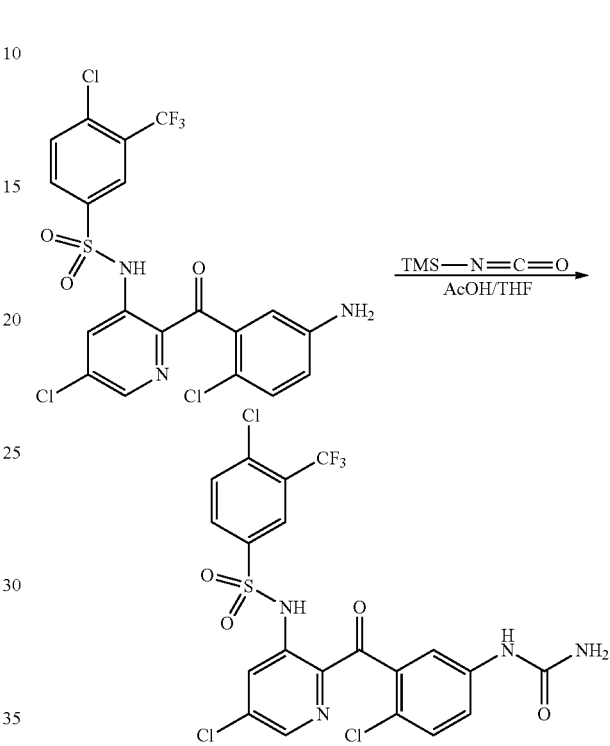

N-(2-(2-Amino-5-chlorobenzoyl) 5-chloro-pyridin-3-yl)-4-chloro-3-(trifluoromethyl)benzenesulfonamide (26 mg, 0.05 mmol) in THF (2 mL) was treated with TMS-isocyanate (100 mg) and AcOH (0.5 mL) and then stirred at room temperature for 2 h. MeOH (1 mL) was added to the mixture which was then purified through HPLC and dried (lyophilizer) to afford the title compound: $^1$H NMR (400 MHz, CDCl$_3$) δ 10.96 (s, 1H), 8.23 (m, 3H), 8.00 (dd, 1H), 7.64 (dd, 1H), 7.36 (m, 3H), 6.80 (d, 1H), 5.00 (br, 2H); MS (ES) (M+H)$^+$ expected 568.9, found 568.9.

Example 239: 4-Chloro-N-(5-chloro-2-(2-chloro-5-(3-methylureido) benzoyl)pyridine-3-yl)-3-(trifluoromethyl)benzenesulfonamide

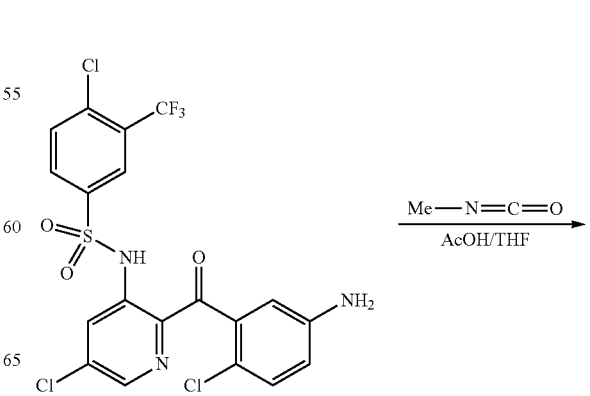

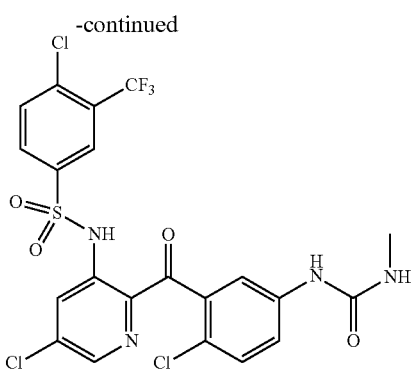

N-(2-(2-Amino-5-chlorobenzoyl)-5-chloro-pyridin-3-yl)-4-chloro-3-(trifluoromethyl)benzenesulfonamide (26 mg, 0.05 mmol) in THF (2 mL) was treated with methyl isocyanate (75 mg) and AcOH (0.5 mL) and then stirred at room temperature for 2 h. MeOH (1 mL) was added to the mixture which was purified through HPLC and dried (lyophilizer) to afford the title compound: $^1$H NMR (400 MHz, CDCl$_3$) δ 10.90 (s, 1H), 8.22 (m, 3H), 8.01 (dd, 1H), 7.64 (d, 1H), 7.23-7.38 (m, 3H), 6.58 (s, 1H), 2.82 (s, 3H); MS (ES) (M+H)$^+$ expected 582.9, found 582.9.

Example 240: 4-Chloro-N-(5-chloro-2-(2-chloro-5-(3-isopropylureido)benzoyl)pyridin-3-yl)-3-(trifluoromethyl)benzenesulfonamide

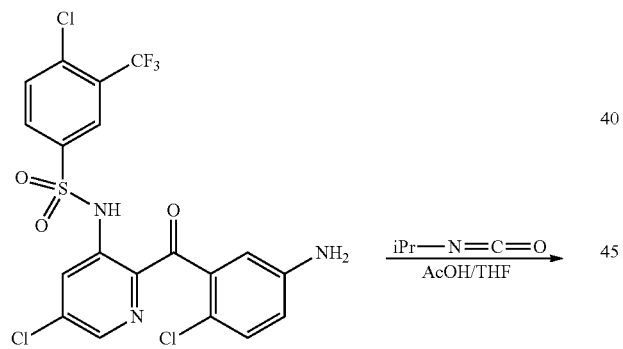

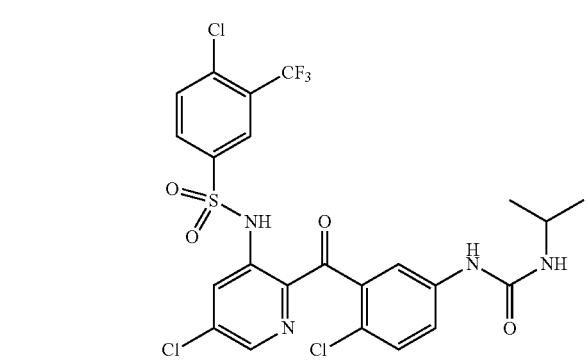

N-(2-(2-Amino-5-chlorobenzoyl)-5-chloro-pyridin-3-yl)-4-chloro-3-(trifluoromethyl)benzenesulfonamide (25 mg, 0.05 mmol) in THF (2 mL) was treated with isopropyl isocyanate (85 mg) and AcOH (0.5 mL) and then stirred at room temperature for 2 h. MeOH (1 mL) was added to the mixture which was purified through HPLC and dried (lyophilizer) to afford the title compound: $^1$H NMR (400 MHz, CDCl$_3$) δ 10.92 (s, 1H), 8.20 (m, 3H), 7.99 (dd, 1H), 7.64 (d, 1H), 7.23-7.38 (m, 3H), 6.90 (s, 1H), 3.92 (m, 1H), 1.09 (d, 6H); MS (ES) (M$^+$+H) expected 611.0, found 611.0.

Example 241: 4-Chloro-N-(5-chloro-2-(2-chloro-5-(33,-dimethylureido)benzoyl)pyridin-3-yl)-3-(trifluoromethyl)benzenesulfonamide

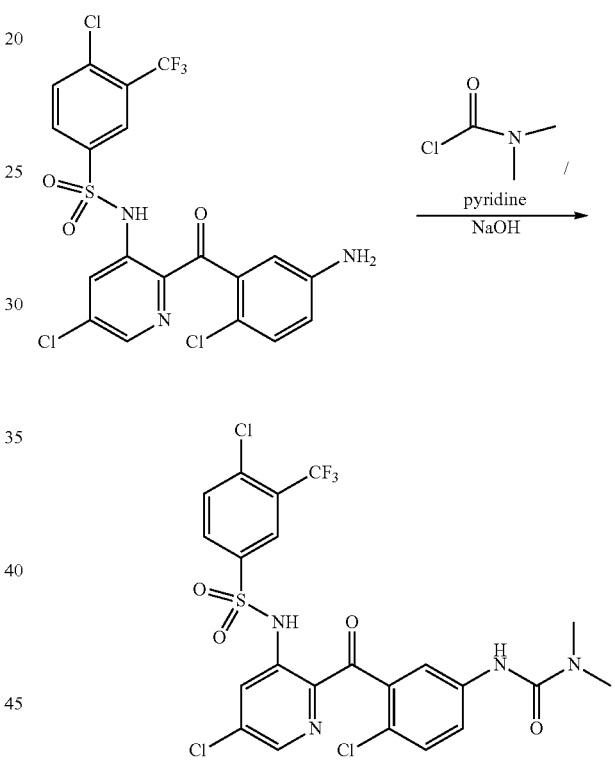

N-(2-(2-Amino-5-chlorobenzoyl)-5-chloro-pyridin-3-yl)-4-chloro-3-(trifluoromethyl)benzenesulfonamide (26 mg, 0.05 mmol) in THF/pyridine (1:1, 4 mL) was treated with dimethyl carbamic chloride (75 mg) and then stirred at 60° C. for 2 h. After evaporation of solvent under reduced pressure, the mixture was added THF (5 mL), followed by NaOH (2 N, 2 mL) and stirred at room temperature for another 2 h. The mixture was in EtOAc and washed with 1N HCl, NaHCO$_3$ (sat), brine, dried over MgSO$_4$, and concentrated under reduced pressure. The residue was purified through HPLC and dried (lyophilizer) to afford the title compound: $^1$H NMR (400 MHz, CDCl$_3$) δ 10.90 (s, 1H), 8.22 (m, 3H), 8.01 (dd, 1H), 7.64 (d, 1H), 7.23-7.38 (m, 3H), 6.58 (s, 1H), 3.10 (s, 3H), 2.80 (s, 3H); MS (ES) (M+H)$^+$ expected 596.9, found 596.9.

Example 242: 4-Chloro-N-(5-chloro-2-(2-chloro-5-(methylsulfonamido) benzoyl)pyridin-3-yl)-3-(trifluoromethyl)benzenesulfonamide

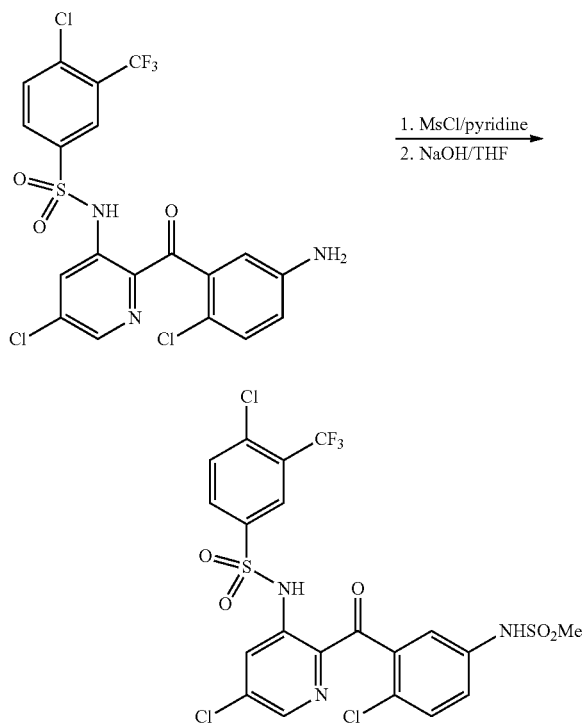

According to the procedure for example 235, N-(2-(2-Amino-5-chlorobenzoyl) 5-chloro-pyridin-3-yl)-4-chloro-3-(trifluoromethyl)-benzenesulfonamide afforded the title compound: $^1$H NMR (400 MHz, CDCl$_3$) δ 10.90 (s, 1H), 8.23 (m, 3H), 8.01 (dd, 1H), 7.64 (d, 2H), 7.38 (d, 1H), 7.23 (m, 1H), 7.16 (d, 1H), 6.50 (s, 1H), 3.02 (s, 3H); MS (ES) (M+H)$^+$ expected 603.9, found 603.9.

Example 243: 4-Chloro-N-(5-chloro-2-(2-methoxy-5-(3-methylureido)benzoyl)pyridine-3-yl)-3-(trifluoromethyl)benzenesulfonamide

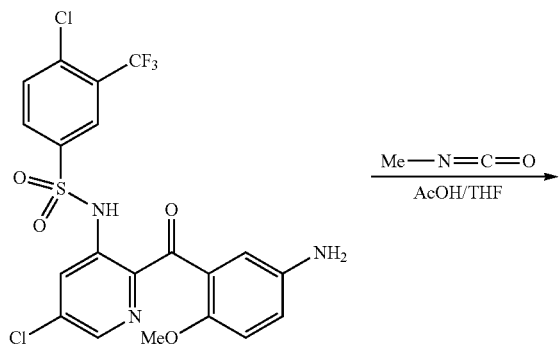

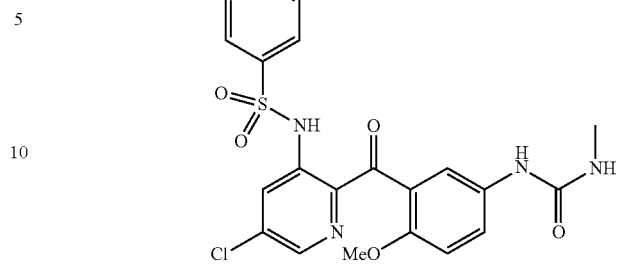

According to the procedure for example 239, N-(2-(2-methoxy-5-aminobenzoyl)-5-chloro-pyridin-3-yl)-4-chloro-3-(trifluoromethyl)-benzenesulfonamide (MS, 520.0, (M+H)$^+$) afforded the title compound: $^1$H NMR (400 MHz, CDCl$_3$) δ 10.82 (s, 1H), 8.23 (d, 1H), 8.16 (m, 2H), 7.96 (dd, 1H), 7.63 (d, 1H), 7.38 (dd, 1H), 7.17 (d, 1H), 6.92 (d, 1H), 3.58 (s, 3H), 2.82 (s, 3H); MS (ES) (M+H)$^+$ expected 577.0, found 577.0.

Example 244: 4-Chloro-N-(5-chloro-2-(5-(3-isopropylureido)-2-methoxybenzoyl)pyridine-3-yl)-3-(trifluoromethyl)benzenesulfonamide

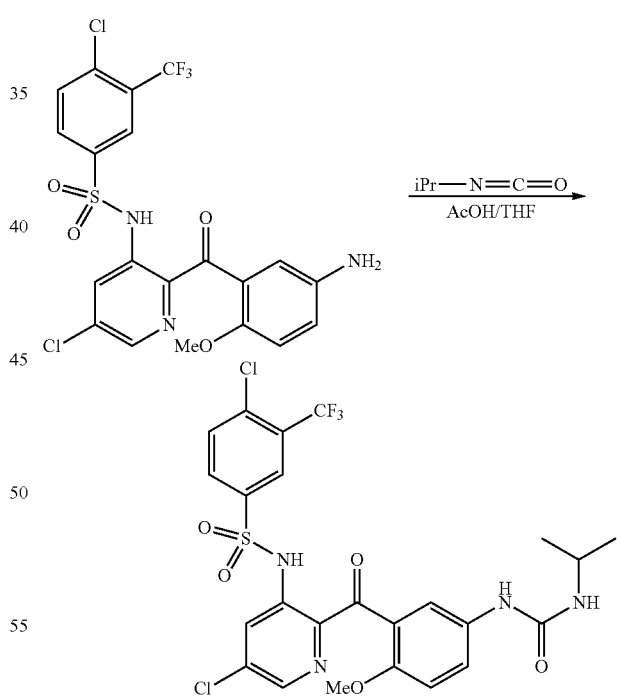

According to the procedure for example 240, N-(2-(2-methoxy-5-aminobenzoyl)-5-chloro-pyridin-3-yl)-4-chloro-3-(trifluoromethyl)-benzenesulfonamide (MS, 520.0, (M+H)$^+$) afforded the title compound: $^1$H NMR (400 MHz, CDCl$_3$) δ 10.82 (s, 1H), 8.23 (d, 1H), 8.16 (m, 2H), 7.96 (dd, 1H), 7.63 (d, 1H), 7.38 (dd, 1H), 7.10 (d, 1H), 6.92 (d, 1H), 3.95 (hep, 1H), 3.58 (s, 3H), 1.18 (d, 6H); MS (ES) (M$^+$+H) expected 605.0, found 605.0.

Example 245: 4-Chloro-N-(5-chloro-2-(2-methoxy-5-(methylsulfonamido) benzoyl)pyridin-3-yl)-3-(trifluoromethyl)benzenesulfonamide

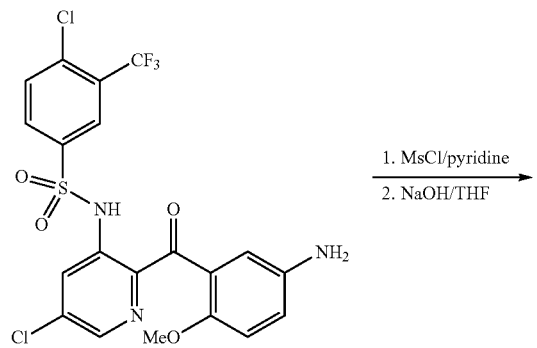

According to the procedure for example 235, N-(2-(2-methoxy-5-aminobenzoyl)-5-chloro-pyridin-3-yl)-4-chloro-3-(trifluoromethyl)-benzenesulfonamide (MS, 520.0, (M+H)$^+$) afforded the title compound: $^1$H NMR (400 MHz, CDCl$_3$) δ 10.82 (s, 1H), 8.23 (d, 1H), 8.16 (m, 2H), 7.96 (dd, 1H), 7.63 (d, 1H), 7.42 (dd, 1H), 7.18 (d, 1H), 6.92 (d, 1H), 6.25 (s, 1H), 3.58 (s, 3H), 3.00 (s, 3H); MS (ES) (M+H)$^+$ expected 597.9, found 597.9.

Example 246: N-(2-(3-Aminobenzoyl)-5-chloro-pyridin-3-yl)-4-chloro-3-(trifluoromethyl)benzenesulfonamide

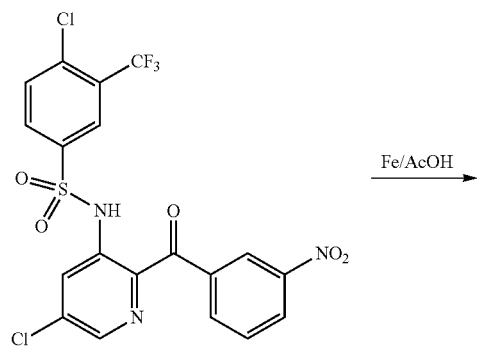

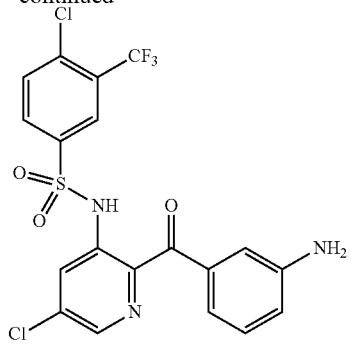

According to the procedure for example 234, N-(2-(3-nitrobenzoyl)-5-chloro-pyridin-3-yl)-4-chloro-3-(trifluoromethyl)benzene-sulfonamide afforded the title compound: $^1$H NMR (400 MHz, CDCl$_3$) δ 10.40 (s, 1H), 8.40 (d, 1H), 8.18 (d, 1H), 8.04 (d, 1H), 7.82 (dd, 1H), 7.50 (dd, 1H), 7.20 (m, 1H), 7.02 (m, 2H), 6.88 (m, 1H), 3.80 (s, 2H); MS (ES) (M+H)$^+$ expected 489.9, found 489.9.

Example 247: 4-Chloro-N-(5-chloro-2-(3-(methylsulfonamido)benzoyl) pyridine-3-yl)-3-(trifluoromethyl)benzenesulfonamide

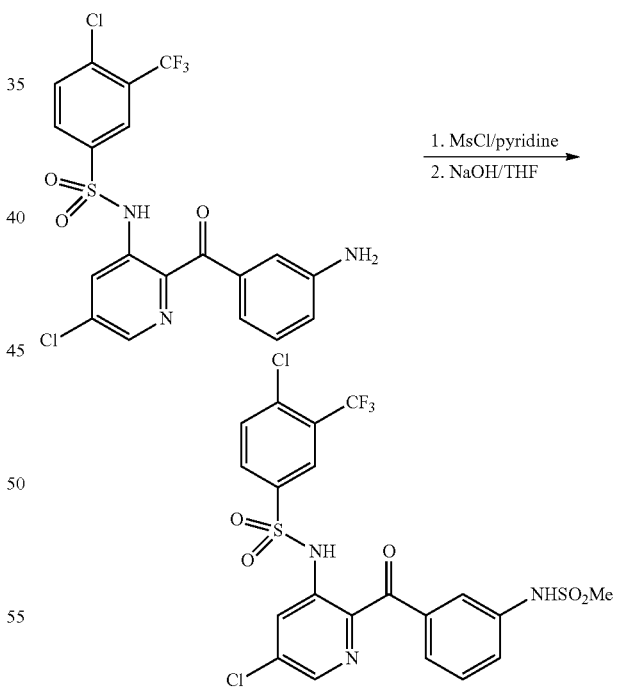

According to the procedure for example 235, N-(2-(3-aminobenzoyl)-5-chloro-pyridin-3-yl)-4-chloro-3-(trifluoromethyl) benzenesulfonamide afforded the title compound: $^1$H NMR (400 MHz, CDCl$_3$) δ 10.70 (s, 1H), 8.38 (d, 1H), 8.18 (d, 1H), 8.12 (d, 1H), 7.90 (dd, 1H), 7.66 (d, 1H), 7.58 (m, 2H), 7.44 (m, 2H), 6.45 (s, 1H), 3.04 (s, 3H); MS (ES) (M+H)$^+$ expected 567.9, found 567.9.

Example 248: 4-Chloro-N-(5-chloro-2-(3-(3-methylureido)benzoyl)pyridine-3-yl)-3-(trifluoromethyl)benzenesulfonamide

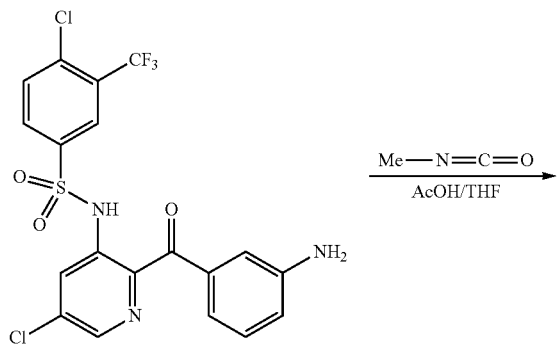

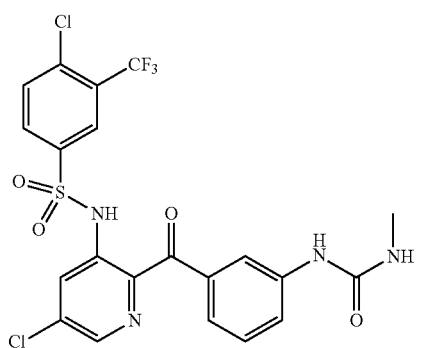

According to the procedure for example 239, N-(2-(3-Aminobenzoyl)-5-chloro-pyridin-3-yl)-4-chloro-3-(trifluoromethyl) benzenesulfonamide afforded the title compound: $^1$H NMR (400 MHz, CDCl$_3$) δ 10.90 (s, 1H), 8.20 (d, 2H), 8.12 (d, 1H), 7.96 (dd, 1H), 7.44 (dd, 1H), 7.32 (d, 1H), 7.23 (d, 1H), 7.14 (d, 1H), 6.45 (s, 1H), 2.58 (s, 3H); MS (ES) (M+H)$^+$ expected 547.0, found 547.0.

Example 249: N-(5-Chloro-2-(3-(3-methylureido)benzoyl)pyridine-3-yl)-4-methyl-3-(trifluoromethyl)benzenesulfonamide

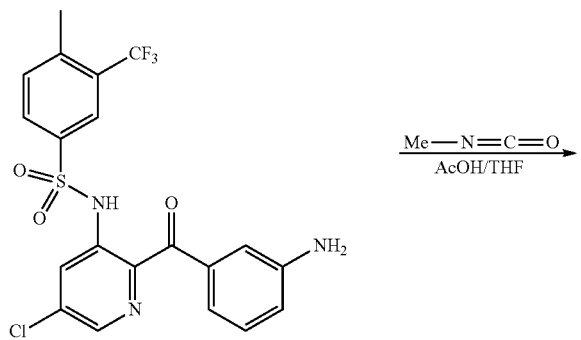

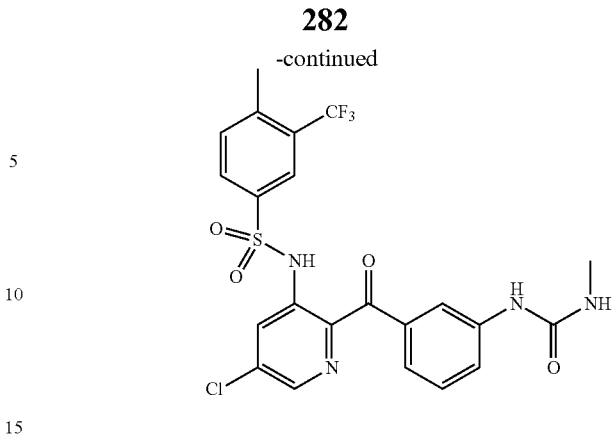

According to the procedure for example 239, N-(2-(3-aminobenzoyl)-5-chloro-pyridin-3-yl)-4-methyl-3-(trifluoromethyl) benzenesulfonamide (MS, 470.0, (M+H)$^+$) afforded the title compound: $^1$H NMR (400 MHz, CDCl$_3$) δ 10.61 (s, 1H), 8.32 (d, 1H), 8.18 (d, 1H), 8.02 (s, 1H), 7.82 (dd, 2H), 7.67 (d, 1H), 7.58 (d, 1H), 7.45 (d, 1H), 7.35 (m, 2H), 6.70 (s, 1H), 2.85 (s, 3H), 2.48 (s, 3H); MS (ES) (M+H)$^+$ expected 527.0, found 527.0.

Example 250: N-(5-Chloro-2-(2-chloro-5-(3-methylureido)benzoyl)pyridine-3-yl)-4-methyl-3-(trifluoromethyl)benzenesulfonamide

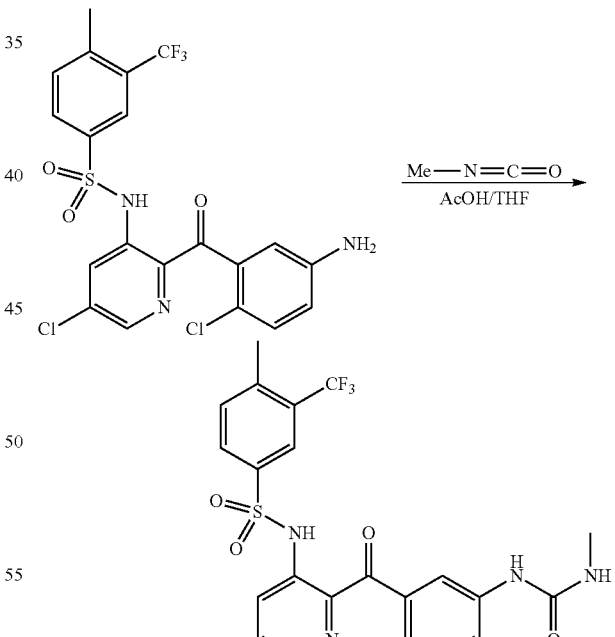

According to the procedure for example 239, N-(2-(2-chloro-5-aminobenzoyl)-5-chloro-pyridin-3-yl)-4-methyl-3-(trifluoromethyl)benzene-sulfonamide (MS, 504.0, (M+H)$^+$) afforded the title compound: $^1$H NMR (400 MHz, CDCl$_3$) δ 10.90 (s, 1H), 8.20 (d, 2H), 8.12 (d, 1H), 7.96 (dd, 1H), 7.40 (m, 3H), 6.40 (s, 1H), 2.83 (s, 3H), 2.58 (s, 3H); MS (ES) (M$^+$+H) expected 561.0, found 561.0.

Example 251: N-(5-chloro-2-(2-chloro-5-(methyl-sulfonamido)benzoyl)pyridin-3-yl)-4-chloro-3-(trifluoromethyl)benzenesulfonamide

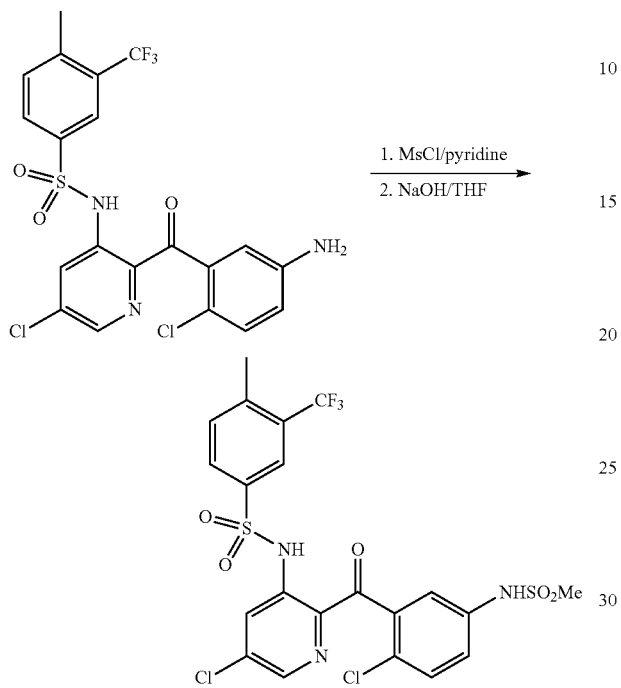

According to the procedure for example 239, N-(2-(2-chloro-5-aminobenzoyl)-5-chloro-pyridin-3-yl)-4-methyl-3-(trifluoromethyl) benzenesulfonamide (MS, 504.0, (M+H)$^+$) afforded the title compound: $^1$H NMR (400 MHz, CDCl$_3$) δ 10.90 (s, 1H), 8.20 (d, 2H), 8.12 (d, 1H), 7.96 (dd, 1H), 7.44 (dd, 1H), 7.32 (d, 1H), 7.23 (d, 1H), 7.14 (d, 1H), 6.45 (s, 1H), 3.04 (s, 3H), 2.58 (s, 3H); MS (ES) (M+H)$^+$ expected 582.0, found 582.0.

Example 252: N-(5-Chloro-2-(2-fluoro-5-(3-methylureido)benzoyl)pyridine-3-yl)-4-methyl-3-(trifluoromethyl)benzenesulfonamide

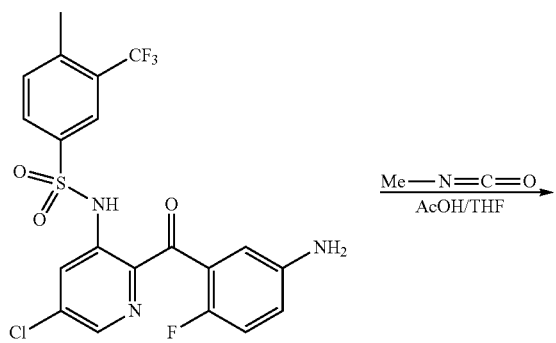

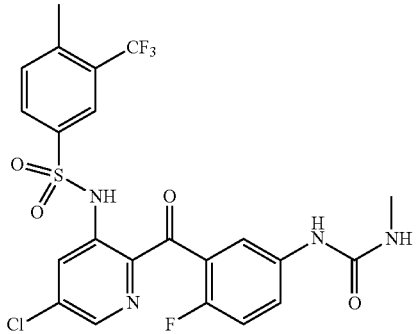

According to the procedure for example 239, N-(2-(2-fluoro-5-aminobenzoyl)-5-chloro-pyridin-3-yl)-4-methyl-3-(trifluoromethyl)benzene-sulfonamide (MS, 488.0, (M+H)$^+$) afforded the title compound: $^1$H NMR (400 MHz, CDCl$_3$) δ 10.70 (s, 1H), 8.24 (d, 1H), 8.18 (d, 1H), 8.08 (d, 1H), 7.90 (dd, 1H), 7.52 (m, 1H), 7.40 (m, 2H), 7.00 (dd, 1H), 6.38 (s, 1H), 2.82 (s, 3H) 2.50 (s, 3H); MS (ES) (M+H)$^+$ expected 545.0, found 545.0.

Example 253: N-(5-Chloro-2-(2-fluoro-5-(3-isopropylureido)benzoyl)pyridine-3-yl)-4-methyl-3-(trifluoromethyl)benzenesulfonamide

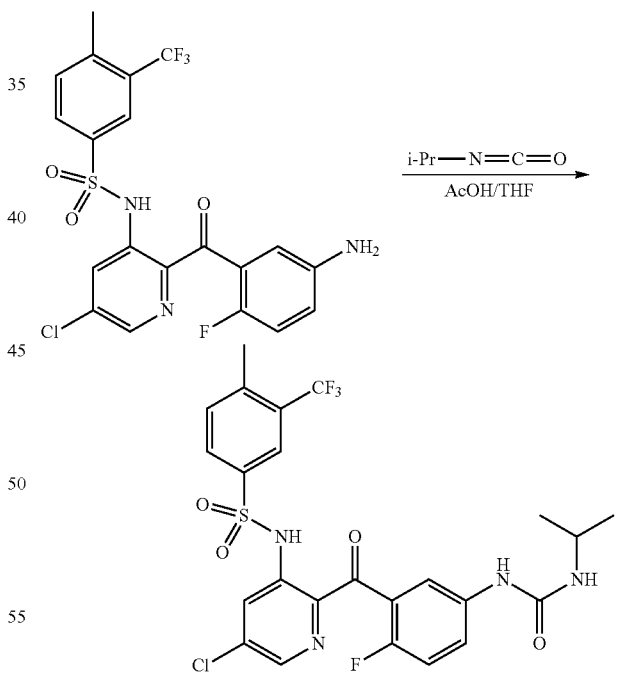

According to the procedure for example 240, N-(2-(2-fluoro-5-aminobenzoyl)-5-chloro-pyridin-3-yl)-4-methyl-3-(trifluoromethyl)benzene-sulfonamide: (MS, 488.0, (M+H)$^+$) afforded the title compound: $^1$H NMR (400 MHz, CDCl$_3$) δ 10.70 (s, 1H), 8.24 (d, 1H), 8.18 (d, 1H), 8.08 (d, 1H), 7.90 (dd, 1H), 7.52 (m, 1H), 7.40 (m, 2H), 7.00 (dd, 1H), 6.24 (s, 1H), 3.95 (hep, 1H), 2.50 (s, 3H), 1.20 (d, 6H); MS (ES) (M+H)$^+$ expected 573.0, found 573.0.

Example 254: N-(5-Chloro-2-(2-methoxy-5-(3-methylureido)benzoyl)pyridine-3-yl)-4-methyl-3-(trifluoromethyl)benzenesulfonamide

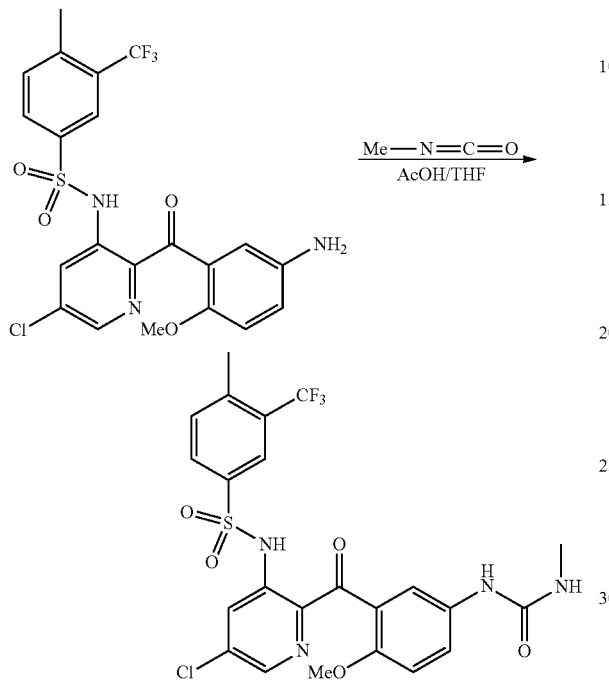

According to the procedure for example 239, N-(2-(2-methoxy-5-aminobenzoyl)-5-chloro-pyridin-3-yl)-4-methyl-3-(trifluoromethyl)benzene-sulfonamide (MS, 500.0, (M+H)$^+$) afforded the title compound: $^1$H NMR (400 MHz, CDCl$_3$) δ 10.90 (s, 1H), 8.18 (d, 1H), 8.16 (d, 1H), 8.10 (d, 1H), 7.96 (dd, 1H), 7.42 (d, 1H), 7.38 (dd, 1H), 7.17 (d, 1H), 6.90 (d, 1H), 3.58 (s, 3H), 2.82 (s, 3H), 2.56 (s, 3H); MS (ES) (M+H)$^+$ expected 557.0, found 557.0.

Example 255: N-(5-Chloro-2-(5-(3-isopropylureido)-2-methoxybenzoyl) pyridine-3-yl)-4-methyl-3-(trifluoromethyl)benzenesulfonamide

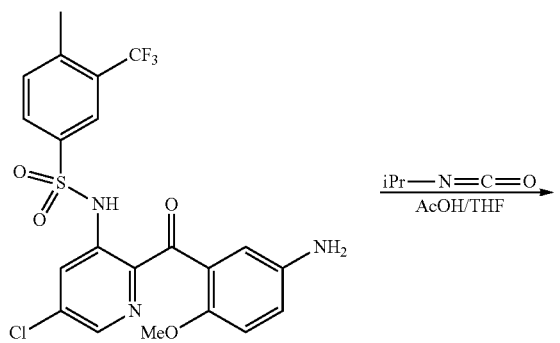

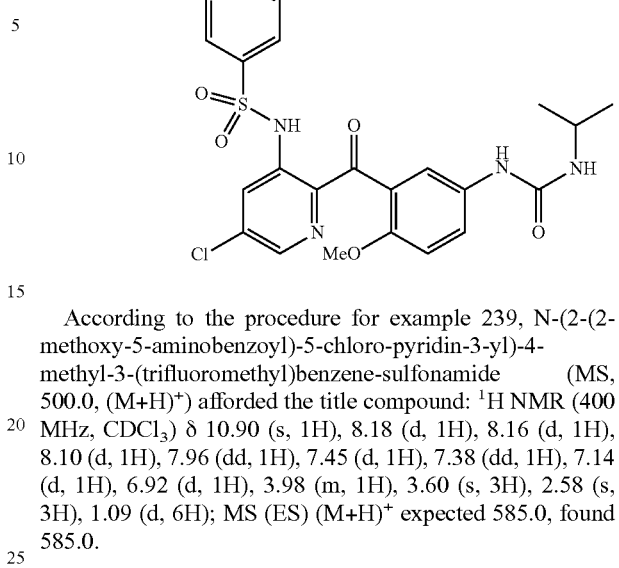

According to the procedure for example 239, N-(2-(2-methoxy-5-aminobenzoyl)-5-chloro-pyridin-3-yl)-4-methyl-3-(trifluoromethyl)benzene-sulfonamide (MS, 500.0, (M+H)$^+$) afforded the title compound: $^1$H NMR (400 MHz, CDCl$_3$) δ 10.90 (s, 1H), 8.18 (d, 1H), 8.16 (d, 1H), 8.10 (d, 1H), 7.96 (dd, 1H), 7.45 (d, 1H), 7.38 (dd, 1H), 7.14 (d, 1H), 6.92 (d, 1H), 3.98 (m, 1H), 3.60 (s, 3H), 2.58 (s, 3H), 1.09 (d, 6H); MS (ES) (M+H)$^+$ expected 585.0, found 585.0.

Example 256: N-(5-chloro-2-(2-methoxy-5-(methylsulfonamido)benzoyl) pyridin-3-yl)-4-methyl-3-(trifluoromethyl)benzenesulfonamide

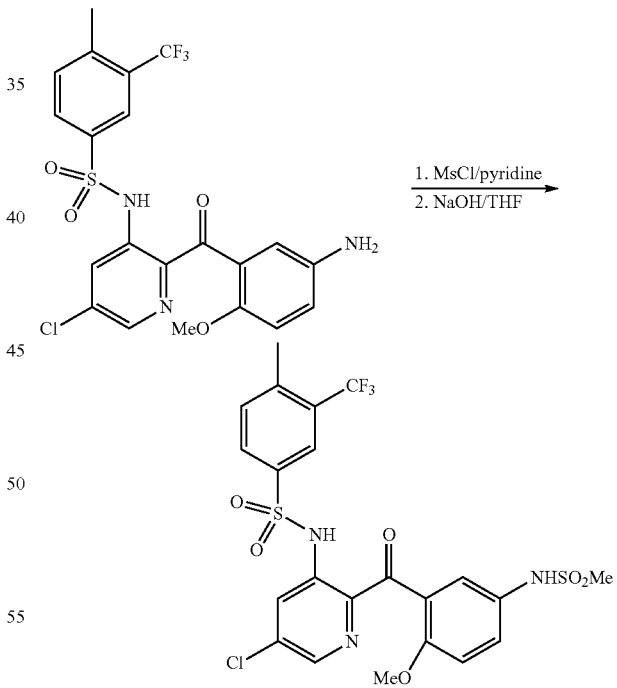

According to the procedure for example 235, N-(2-(2-methoxy-5-aminobenzoyl)-5-chloro-pyridin-3-yl)-4-methyl-3-(trifluoromethyl) benzenesulfonamide (MS, 500.0, (M+H)$^+$) afforded the title compound: $^1$H NMR (400 MHz, CDCl$_3$) (10.90 (s, 1H), 8.18 (d, 1H), 8.16 (d, 1H), 8.10 (d, 1H), 7.96 (dd, 1H), 7.40 (m, 2H), 7.17 (d, 1H), 6.90 (d, 1H), 3.58 (s, 3H), 3.00 (s, 3H), 2.56 (s, 3H); MS (ES) (M+H)$^+$ expected 578.0, found 578.0.

Example 257: N-(5-Chloro-2-(2-methoxy-3-(3-methylureido)benzoyl)pyridine-3-yl)-4-methyl-3-(trifluoromethyl)benzenesulfonamide

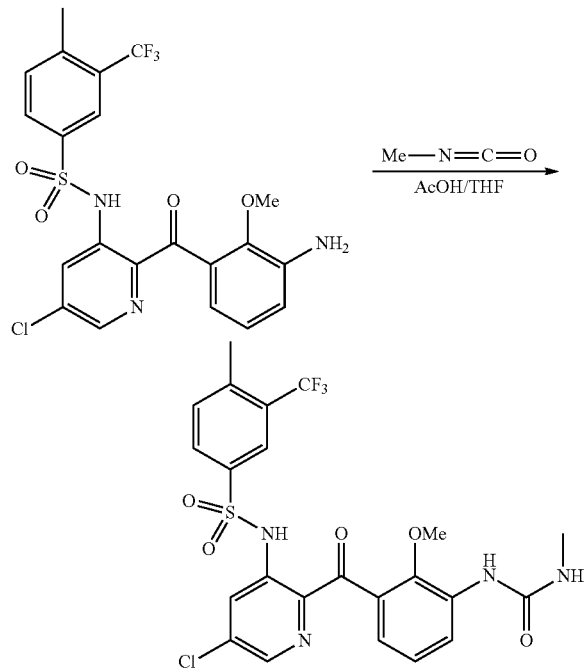

According to the procedure for example 239, N-(2-(2-methoxy-3-aminobenzoyl)-5-chloro-pyridin-3-yl)-4-methyl-3-(trifluoromethyl)benzene-sulfonamide (MS, 500.0, (M$^+$+H)) afforded the title compound: $^1$H NMR (400 MHz, CDCl$_3$) δ 11.00 (s, 1H), 8.22 (d, 1H), 8.15 (d, 1H), 8.10 (m, 1H), 7.96 (dd, 1H), 7.44 (d, 1H), 7.10 (t, 1H), 6.80 (m, 2H), 3.56 (s, 3H), 2.84 (s, 3H), 2.56 (s, 3H); MS (ES) (M+H)$^+$ expected 557.0, found 557.0.

Example 258: 4-Chloro-N-(5-chloro-2-(3-oxo-3,4-dihydro-2H-benzoyl[b][1,4]oxazine-8-carbonyl)pyridin-3-yl)-3-(trifluoromethyl)benzenesulfonamide

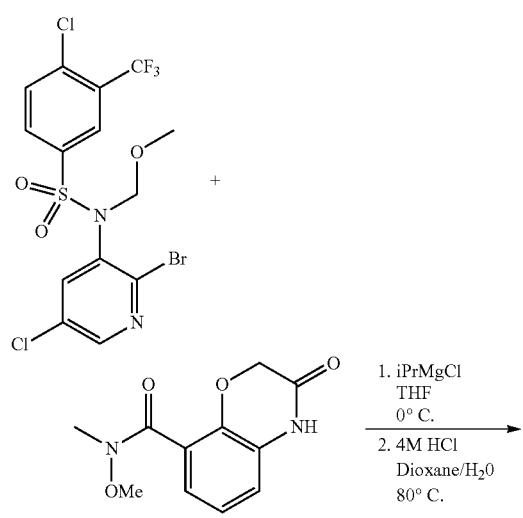

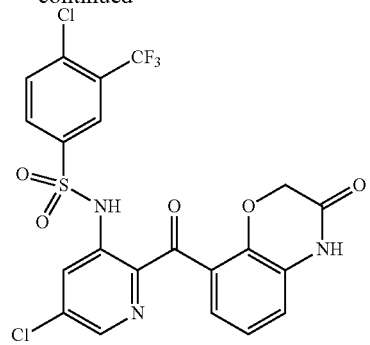

Step 1: N-(2-Bromo-5-chloro-pyridin-3-yl)-4-chloro-N-methoxymethyl-3-(trifluoromethyl)benzenesulfonamide (0.5 g, 1.0 mmol) was placed in a dry 100 mL round-bottom flask sealed with septa. The flask was evacuated and purged with nitrogen, followed by the addition of dry THF (30 mL). The homogeneous solution was cooled to 0° C. and iPrMgCl (1.25 mL, 2.0 M) was added dropwisely. Upon completion of the addition, the mixture was stirred at 0° C. for 60 min, followed by the slow addition of benzo[b][1,4]oxazin-3 (4H)-one Weinreb amide (208 mg, 1 mmol). The reaction mixture was stirred at 0° C. for 3 h. The reaction was quenched with NH$_4$Cl (sat) and extracted with EtOAc, washed with brine, dried over MgSO$_4$, and concentrated under reduced pressure. The residue was further purified through automated normal-phase chromatography to afford 4-xhloro-N-(5-chloro-2-(3-oxo-3,4-dihydro-2H-benzoyl[b][1,4]oxazine-8-carbonyl)pyridin-3-yl)-N-(methoxylmethyl)-3-(trifluoromethyl)benzenesulfonamide (0.5 g, 85%) (which was used directly for the next step).

Step 2: The above 4-chloro-N-(5-chloro-2-(3-oxo-3,4-dihydro-2H-benzoyl[b][1,4]oxazine-8-carbonyl)pyridin-3-yl)-N-(methoxylmethyl)-3-(trifluoromethyl)benzenesulfonamide was treated with (4.0 M HCl in dioxane) (10 mL, 40 mmol) and H$_2$O (4 mL), and then stirred at 110° C. for 6 h. The mixture was diluted with EtOAc. The resultant organics were washed with NaHCO$_3$ (sat), and brine; dried (MgSO$_4$), and concentrated under reduced pressure and was purified through automated normal-phase chromatography to afford the title compound: $^1$H NMR (400 MHz, CDCl$_3$) (10.90 (s, 1H), 8.25 (d, 1H), 8.16 (d, 2H), 7.96 (m, 2H), 7.63 (d, 1H), 7.08 (m, 1H), 6.92 (m, 2H), 4.38 (s, 2H); MS (ES) (M+H)$^+$ expected 546.0, found 546.0.

Example 259: 4-Chloro-N-[5-chloro-2-(6-fluoro-2-oxo-2,3-dihydro-benzooxazole-7-carbonyl)-pyridin-3-yl]-3-trifluoromethyl-benzenesulfonamide

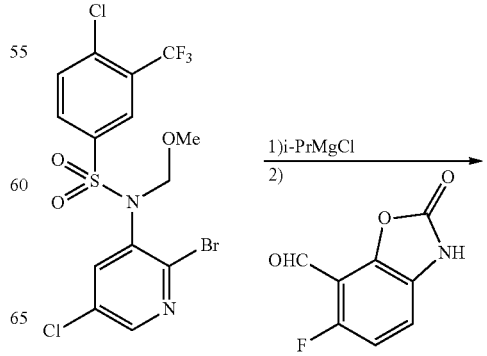

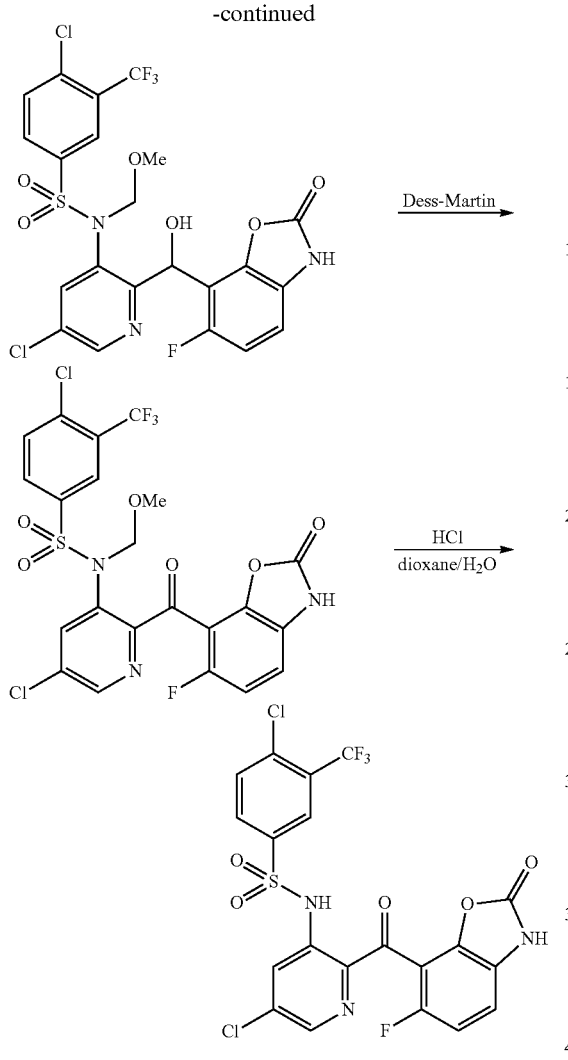

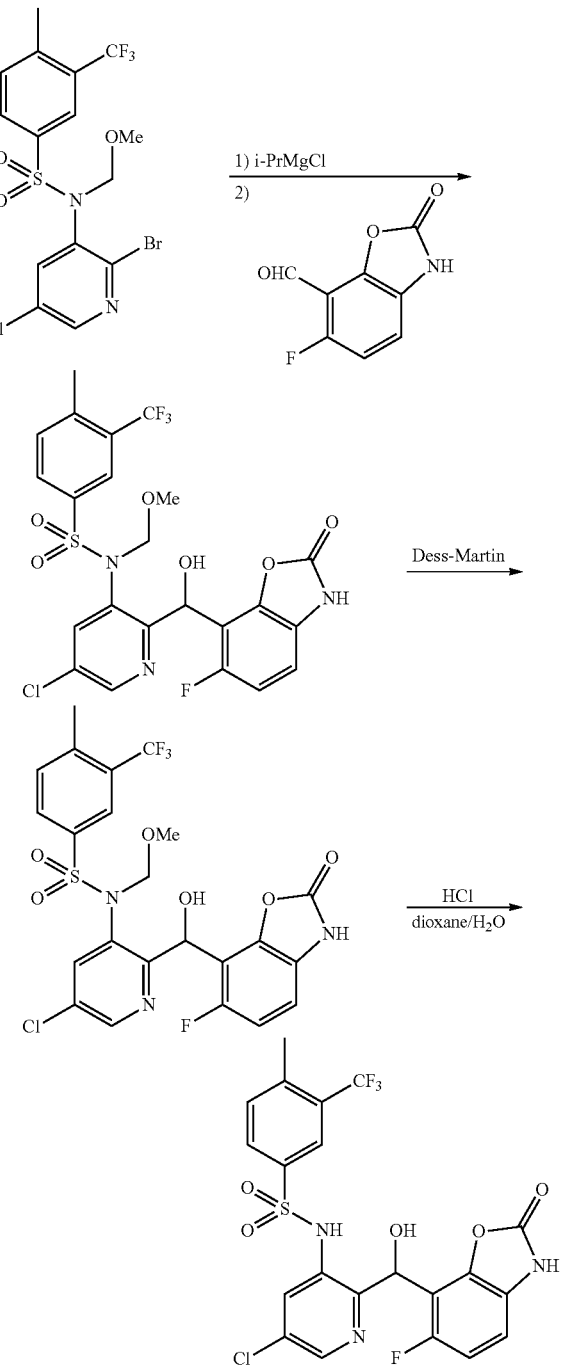

Step 1: To a solution of N-(2-bromo-5-chloro-pyridin-3-yl)-4-chloro-N-methoxymethyl-3-trifluoromethyl-benzene-sulfonamide (198 mg) in THF (0.6 mL) stirring at 0° C. was added isopropylmagnesium chloride (2 M solution in THF, 0.44 mL) via dropwise addition. The mixture was then stirred for 30 min at 0° C. followed by the addition of 6-fluoro-2-oxo-2,3-dihydro-benzooxazole-7-carbaldehyde (Javier et. al., Heterocycles, 1999, 1563.) (35 mg). The mixture was warmed to room temperature, stirred an additional 30 min and quenched by saturated aqueous $NH_4Cl$ solution (1 mL). The organic layer was separated and the aqueous layer was extracted by EtOAc (2×1 mL). The combined organic layers were dried ($Na_2SO_4$), filtered and evaporated in vacuo. The residue was used directly in the next step.

Step 2: The residue from the last step was dissolved in $CH_2Cl_2$ (1 mL) and Dess-Martin periodinane (127 mg) was added. The mixture was stirred at room temperature for 12 h and was concentrated in vacuo. The residue was purified by flash chromatography (silica) to afford 4-chloro-N-{5-chloro-2-[(6-fluoro-2-oxo-2,3-dihydro-benzooxazol-7-yl)-hydroxy-methyl]-pyridin-3-yl}-N-methoxymethyl-3-trifluoromethyl-benzenesulfonamide as a pale yellow solid.

Step 3: The yellow solid from last step was dissolved in a mixture of $H_2O$ (6 mL) and HCl in dioxane (4 M, 3 mL) and heated to 100° C. for 12 h. The mixture was cooled to room temperature and concentrated in vacuo. The residue was dissolved in EtOAc (10 mL) and washed by saturated aqueous $NaHCO_3$ solution (2 mL). The organic layer was separated and evaporated in vacuo. The residue was purified by flash chromatography (silica) to afford the title compound as a white powder. MS $(M+H)^+$: 549.9.

Example 260: N-[5-Chloro-2-(6-fluoro-2-oxo-2,3-dihydro-benzooxazole-7-carbonyl)-pyridin-3-yl]-4-methyl-3-trifluoromethyl-benzenesulfonamide The title compound was synthesized in a manner similar to example 259. MS $(M+H)^+$: 530.0.

Example 261: 4-Chloro-N-[5-chloro-2-(6-fluoro-2-oxo-2,3-dihydro-benzooxazole-7-carbonyl)-pyridin-3-yl]-3-methyl-benzenesulfonamide Example 262: 4-Chloro-N-[5-chloro-2-(6-chloro-2-oxo-2,3-dihydro-benzooxazole-7-carbonyl)-pyridin-3-yl]-3-trifluoromethyl-benzenesulfonamide

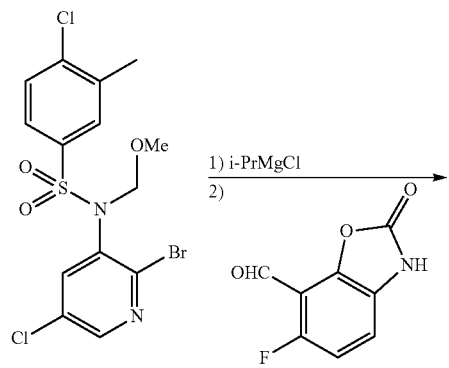
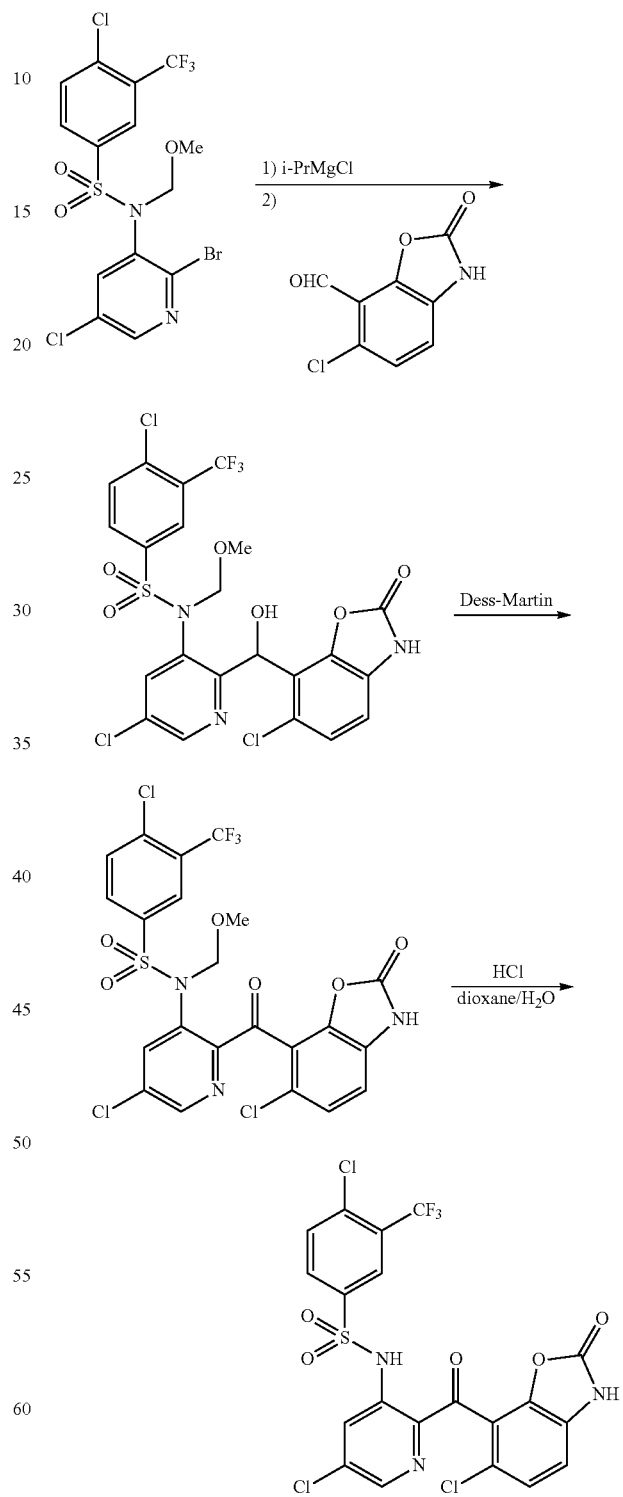

The title compound was synthesized in a manner similar to example 259. MS (M+H)+: 495.9.

The title compound was synthesized in a manner similar to example 259. MS (M+H)+: 565.9.

Example 263: N-[5-Chloro-2-(6-chloro-2-oxo-2,3-dihydro-benzooxazole-7-carbonyl)-pyridin-3-yl]-4-methyl-3-trifluoromethyl-benzenesulfonamide

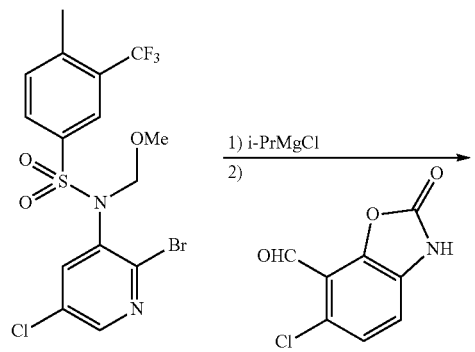

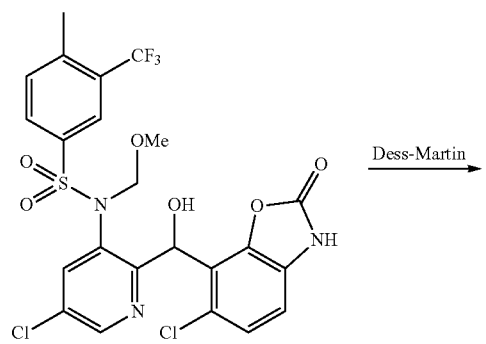

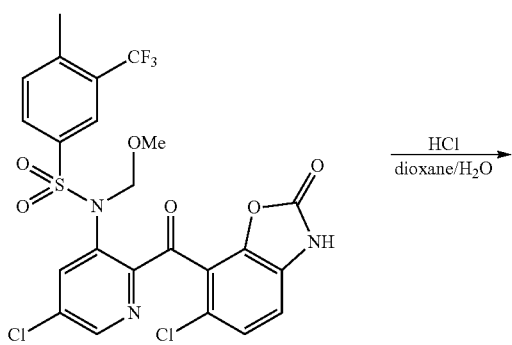

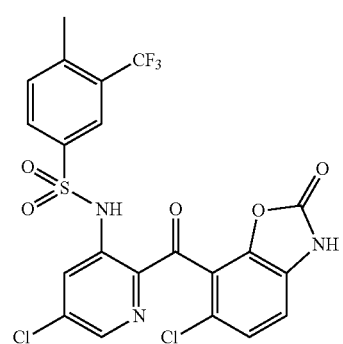

The title compound was synthesized in a manner similar to example 259. MS (M+H)$^+$: 546.0

Example 264: N-[5-Chloro-2-(6-fluoro-2-oxo-2,3-dihydro-benzooxazole-7-carbonyl)-pyridin-3-yl]-3-trifluoromethyl-benzenesulfonamide

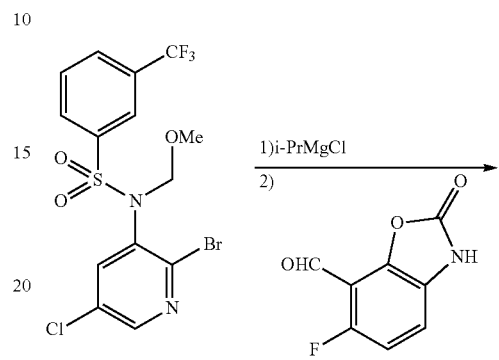

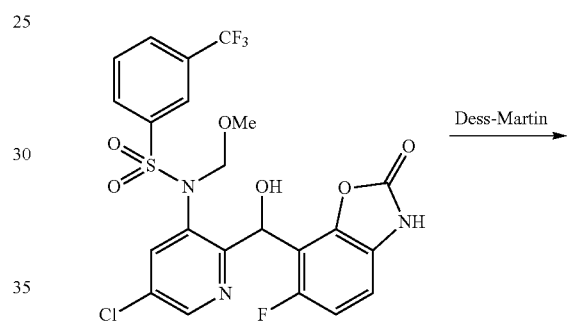

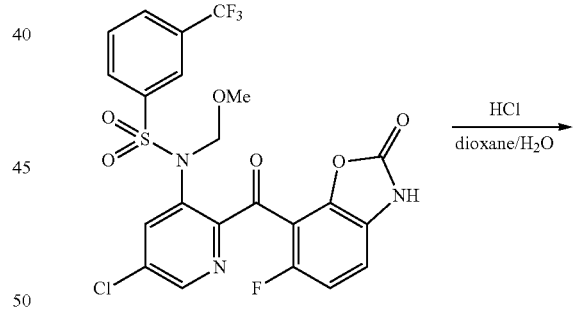

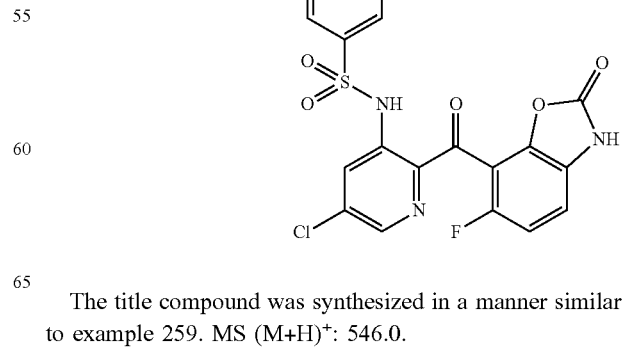

The title compound was synthesized in a manner similar to example 259. MS (M+H)$^+$: 546.0.

295
Example 265: 4-Chloro-N-[5-chloro-2-(2-oxo-2,3-dihydro-benzooxazole-7-carbonyl)-pyridin-3-yl]-3-trifluoromethyl-benzenesulfonamide
296
The title compound was synthesized in a manner similar to example 259. MS (M+H)$^+$: 531.9.
Example 266: N-[5-Chloro-2-(2-oxo-2,3-dihydro-benzooxazole-7-carbonyl)-pyridin-3-yl]-4-methyl-3-trifluoromethyl-benzenesulfonamide
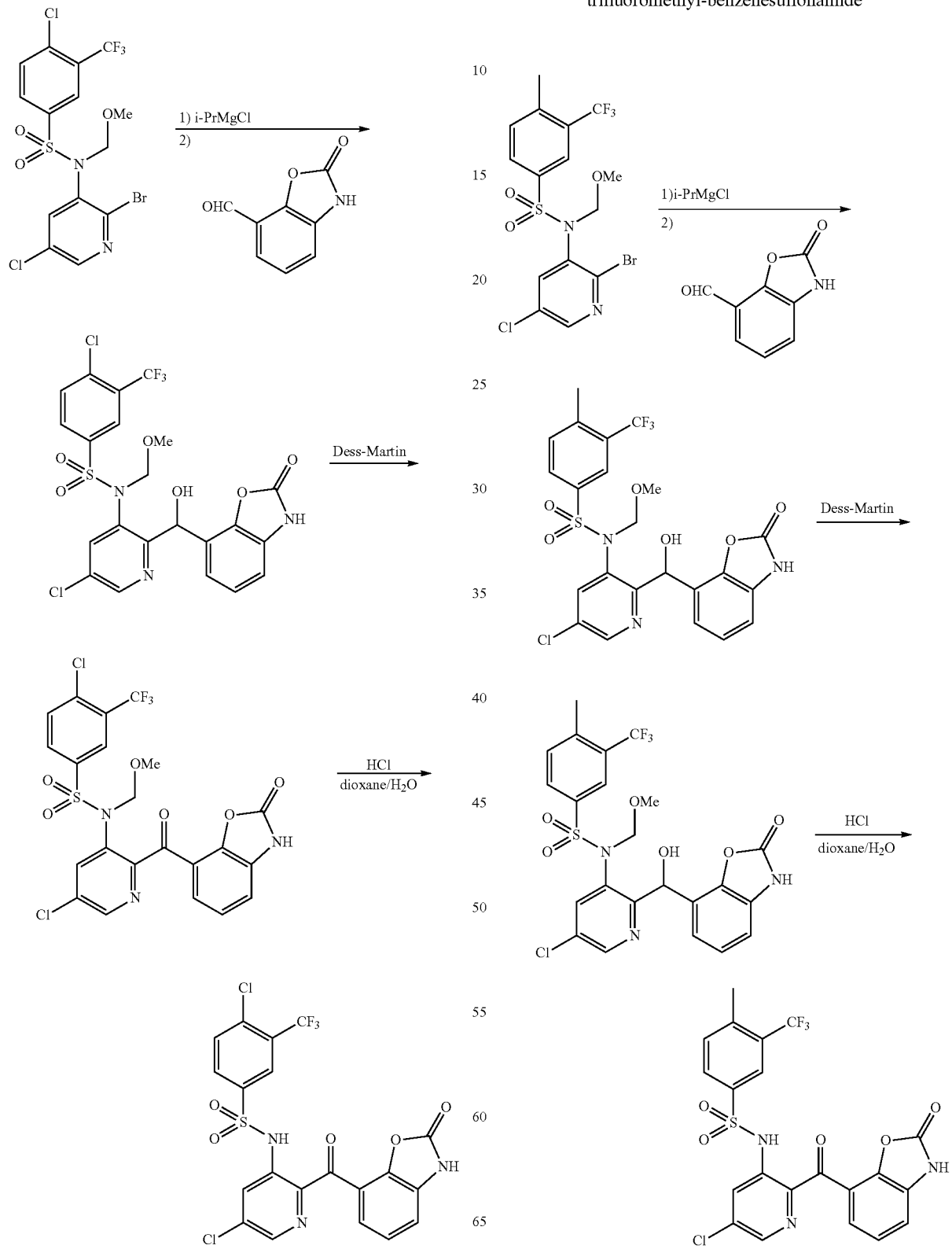

The title compound was synthesized in a manner similar to example 259. MS (M+H)+: 512.0.

Example 267: N-{5-Chloro-2-[hydroxy-(2-oxo-2,3-dihydro-benzooxazol-7-yl)-methyl]-pyridin-3-yl}-4-methyl-3-trifluoromethyl-benzenesulfonamide

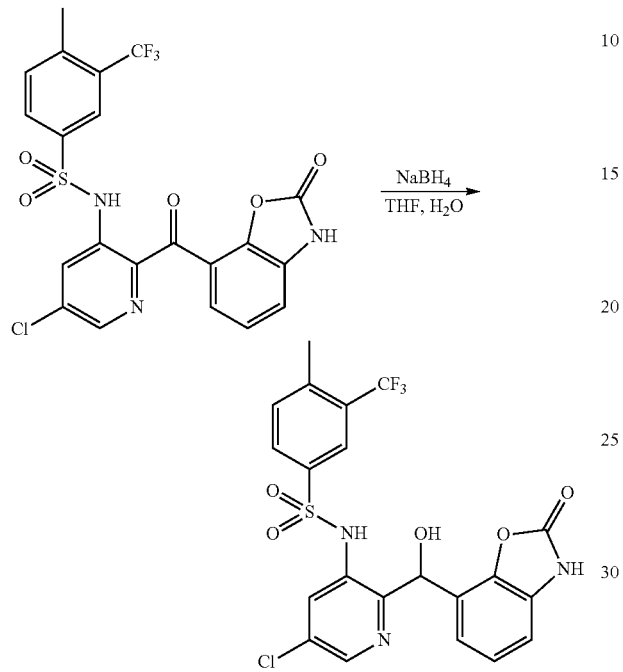

To a solution of N-[5-chloro-2-(2-oxo-2,3-dihydro-benzooxazole-7-carbonyl)-pyridin-3-yl]-4-methyl-3-trifluoromethyl-benzenesulfonamide (41 mg) in THF (1 mL) and H₂O (0.1 mL) was added NaBH₄ (10 mg). The mixture was stirred at room temperature for 1 h, diluted by EtOAc (3 mL) and quenched by saturated aqueous NH₄Cl solution (1 mL). The organic layer was separated, dried (Na₂SO₄), filtered and evaporated in vacuo. The residue was purified by flash chromatography (silica) to afford the title compound as a white powder. MS (M+H)+: 514.0.

Example 268: 4-Chloro-N-[5-chloro-2-(1H-pyrazolo[3,4-b]pyridine-4-carbonyl)-pyridin-3-yl]-3-trifluoromethyl-benzenesulfonamide

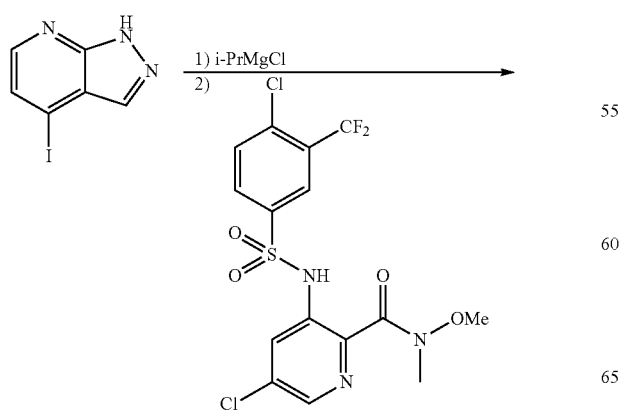

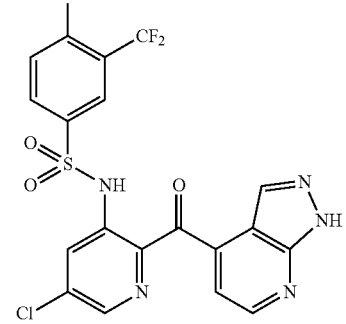

To a solution of 4-iodo-7-azaindazole (Potashman et. al., WO2005070891) (123 mg) in THF (2 mL) at 0° C. was added isopropylmagnesium chloride (2 M solution in THF, 0.5 mL). The mixture was stirred at 0° C. for 30 min and 5-chloro-3-(4-chloro-3-trifluoromethyl-benzenesulfonylamino)-pyridine-2-carboxylic acid methoxy-methyl-amide (114 mg) was added. The reaction mixture was warmed to room temperature, stirred for 2 h and quench by saturated aqueous NH₄Cl solution (2 mL). The organic layer was separated and the aqueous layer was extracted with EtOAc (5 mL). The combined organic layers were dried (Na₂SO₄), filtered and evaporated in vacuo. The residue was purified by flash chromatography (silica) to afford the title compound as a white powder. MS (M+H)+: 515.9.

Example 269: N-[5-Chloro-2-(1H-pyrazolo[3,4-b]pyridine-4-carbonyl)-pyridin-3-yl]-4-methyl-3-trifluoromethyl-benzenesulfonamide

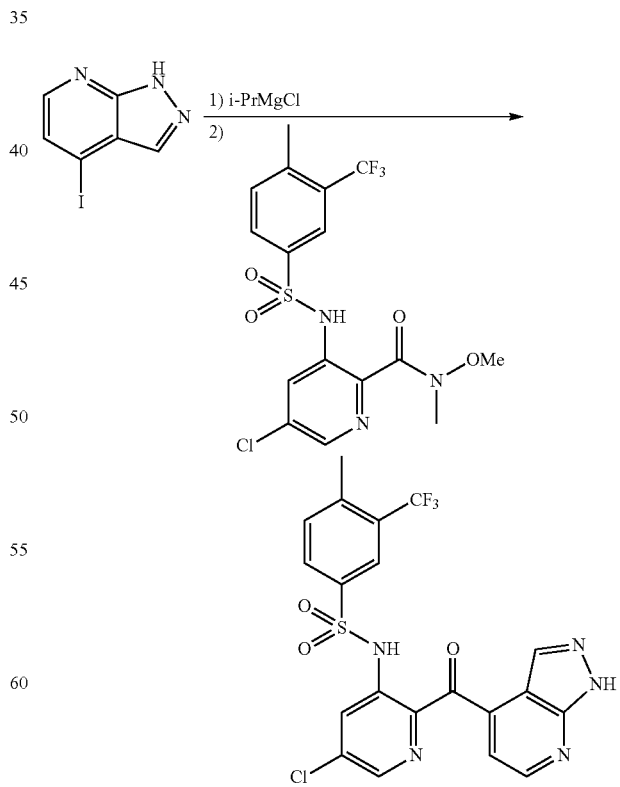

The title compound was synthesized in a manner similar to example 268. MS (M+H)+: 496.0.

Example 270: 4-Chloro-N-[5-chloro-2-(1H-pyrrolo[2,3-b]pyridine-4-carbonyl)-pyridin-3-yl]-3-trifluoromethyl-benzenesulfonamide

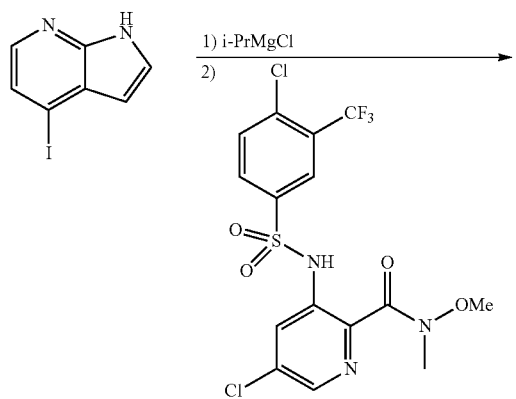

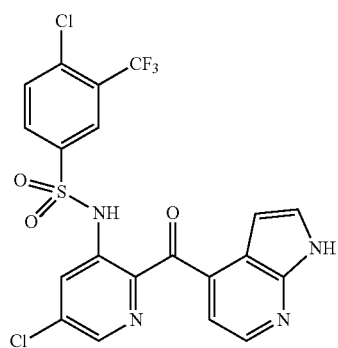

The title compound was synthesized in a manner similar to example 268 using 4-iodo-7-azaindole (Kania et. al, WO2001002369) MS (M+H)+: 496.0.

Example 271: N-[5-Chloro-2-(1H-pyrrolo[2,3-b]pyridine-4-carbonyl)-pyridin-3-yl]-4-methyl-3-trifluoromethyl-benzenesulfonamide

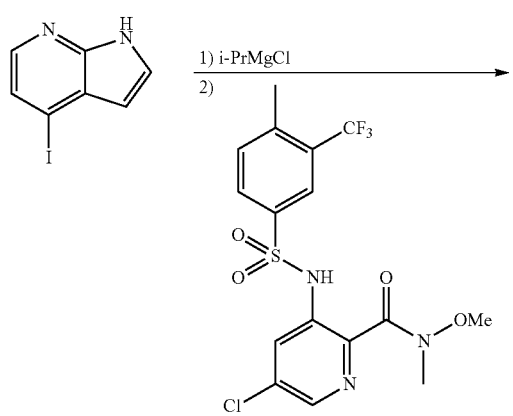

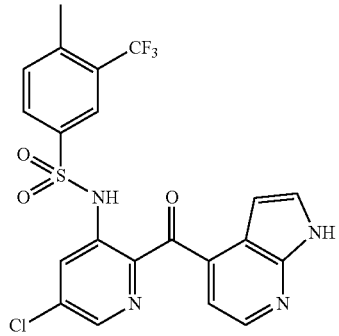

The title compound was synthesized in a manner similar to example 271. MS (M+H)+: 495.0.

Example 272: 4-Chloro-N-[5-chloro-2-(1H-indazole-4-carbonyl)-pyridin-3-yl]-3-trifluoromethyl-benzenesulfonamide

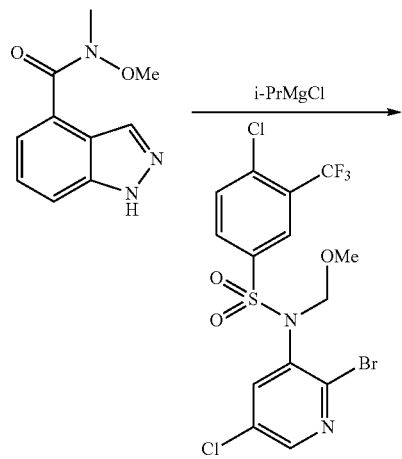

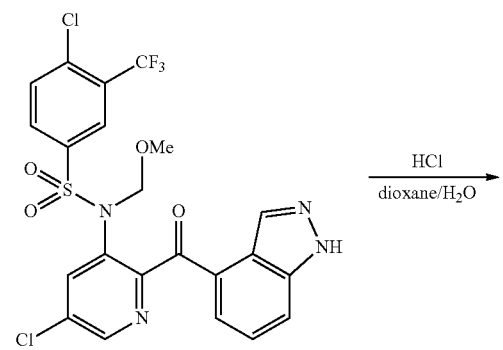

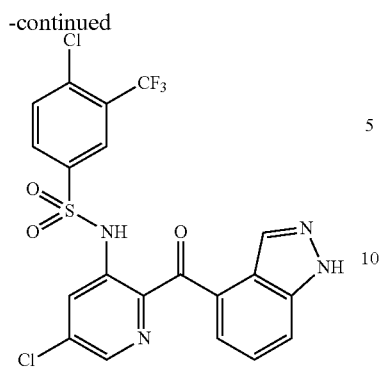

-continued

Step 1: To a solution of 1H-Indazole-4-carboxylic acid (Fletcher et.al., WO2005028445) (480 mg), N,O-dimethylhydroxyamine hydrochloride salt (585 mg) and Et₃N (6 mL) in THF (15 mL) stirring at 0° C. was added T₃P (50% in EtOAc, 3 mL). The mixture was stirred at 0° C. for 1 h, diluted by EtOAc (40 mL) and quenched by saturated aqueous NaHCO₃ solution (15 mL). The organic layer was separated, dried (Na₂SO₄), filtered and evaporated in the vacuo to give a yellow liquid which was used as it was.

Step 2: To a solution of N-(2-bromo-5-chloro-pyridin-3-yl)-4-chloro-N-methoxymethyl-3-trifluoromethyl-benzenesulfonamide (247 mg) in THF (1 mL) stirring at 0° C. was added isopropylmagnesium chloride (2 M solution in THF, 0.55 mL) via dropwise addition. The mixture was then stirred for 30 min at 0° C. followed by the addition of 1H-indazole-4-carboxylic acid methoxy-methyl-amide (50 mg in 1 mL THF) obtained from step 1. The mixture was stirred at room temperature for 1 h and quenched by saturated aqueous NH₄Cl solution (2 mL). The organic layer was separated and the aqueous layer was extracted by EtOAc (2×3 mL). The combined organic layer was dried (Na₂SO₄), filtered and evaporated in vacuo. The residue was purified by flash chromatography to give a yellow solid.

Step 3: The yellow solid obtained from step 2 was dissolved in a solution of HCl in dioxane (4M, 4 mL) and H₂O (4 mL) and heated to 80° C. for 12 h. The mixture was cooled to room temperature and evaporated in vacuo. The residue was dissolved in EtOAc (10 mL) and washed by saturated aqueous NaHCO₃ solution (2 mL). The organic layer was separated and evaporated in vacuo. The residue was was purified by flash chromatography (silica) to afford the title compound as a white powder. MS (M+H)⁺: 515.0.

Example 273: 4-Chloro-N-{5-chloro-2-[methoxy-imino-(1H-pyrrolo[2,3-b]pyridin-4-yl)-methyl]-pyridin-3-yl}-3-trifluoromethyl-benzenesulfonamide

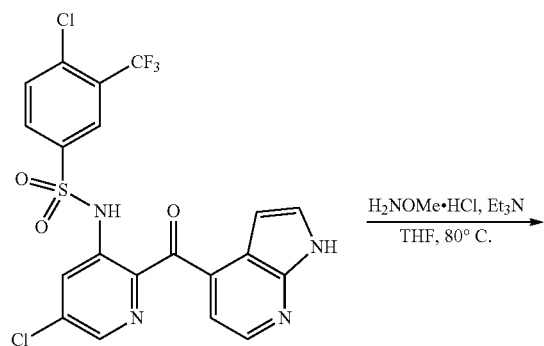

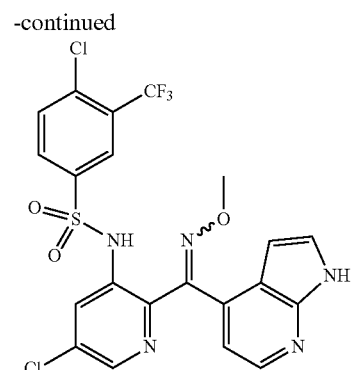

-continued

A solution of 4-chloro-N-[5-chloro-2-(1H-pyrrolo[2,3-b]pyridine-4-carbonyl)-pyridin-3-yl]-3-trifluoromethyl-benzenesulfonamide (41 mg), methoxylamine hydrochloride salt (67 mg) and Et₃N (0.14 mL) in THF (1 mL) was heated to 80° C. for 12 h. The mixture was cooled to room temperature, diluted with EtOAc (5 mL), filtered and evaporated in vacuo. The residue was purified by flash chromatography (silica) to afford the title compound as a white powder. MS (M+H)⁺: 544.0.

Example 274: N-{5-Chloro-2-[methoxyimino-(1H-pyrrolo[2,3-b]pyridin-4-yl)-methyl]-pyridin-3-yl}-4-methyl-3-trifluoromethyl-benzenesulfonamide

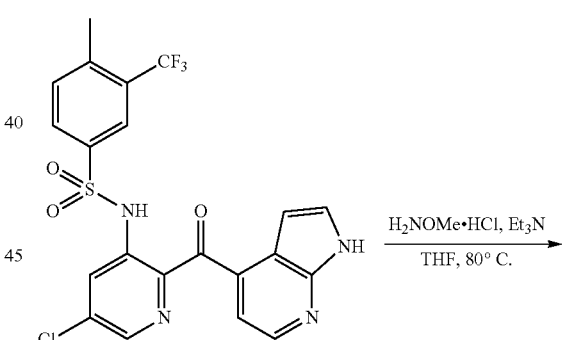

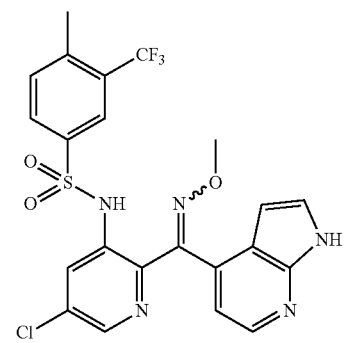

The title compound was synthesized in a manner similar to example 273. MS (M+H)⁺: 524.0.

Example 275: N-{5-Chloro-2-[hydroxyimino-(1H-pyrrolo[2,3-b]pyridin-4-yl)-methyl]-pyridin-3-yl}-4-methyl-3-trifluoromethyl-benzenesulfonamide

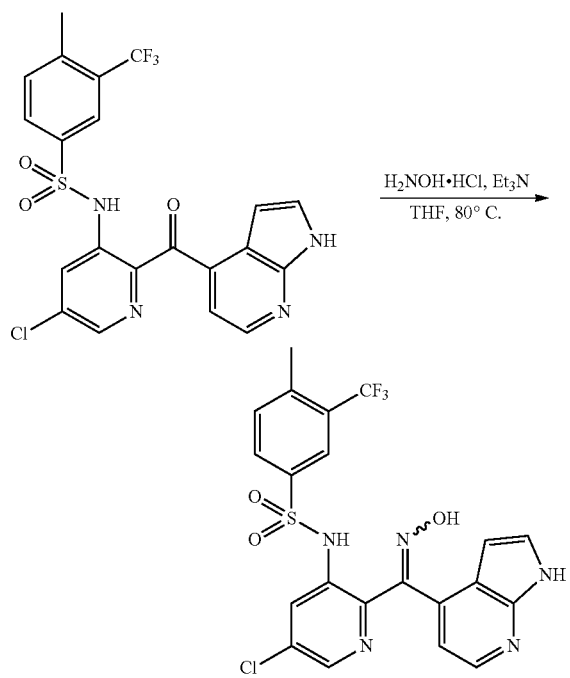

The title compound was synthesized in a manner similar to example 273. MS (M+H)⁺: 524.0.

Example 276: N-{5-Chloro-2-[ethoxyimino-(1H-pyrrolo[2,3-b]pyridin-4-yl)-methyl]-pyridin-3-yl}-4-methyl-3-trifluoromethyl-benzenesulfonamide

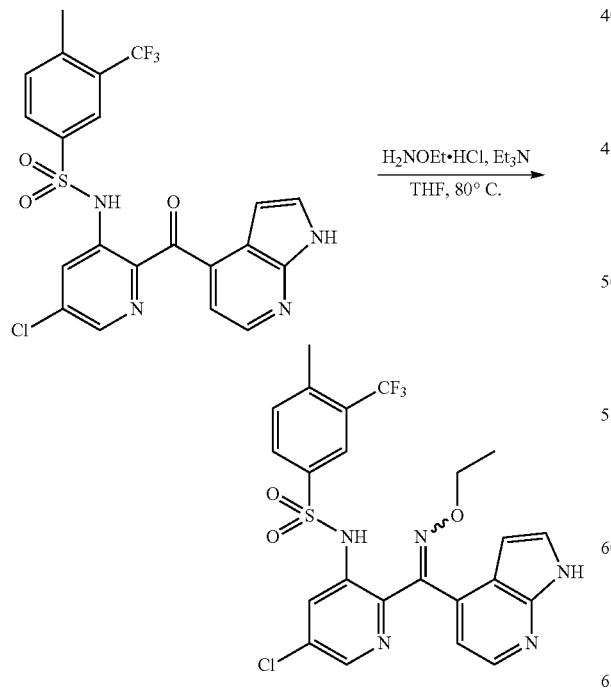

The title compound was synthesized in a manner similar to example 273. MS (M+H)⁺: 538.0.

Example 277: N-{5-Chloro-2-[isopropoxyimino-(1H-pyrrolo[2,3-b]pyridin-4-yl)-methyl]-pyridin-3-yl}-4-methyl-3-trifluoromethyl-benzenesulfonamide

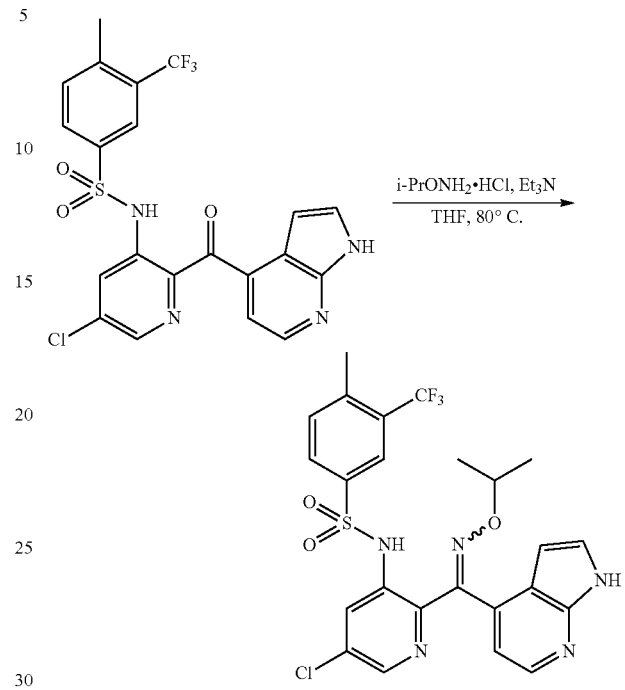

The title compound was synthesized in a manner similar to example 273. MS (M+H)⁺: 552.0.

Example 278: [[5-Chloro-3-(4-methyl-3-trifluoromethyl-benzenesulfonylamino)-pyridin-2-yl]-(1H-pyrrolo[2,3-b]pyridin-4-yl)-methyleneaminooxy]-acetic Acid

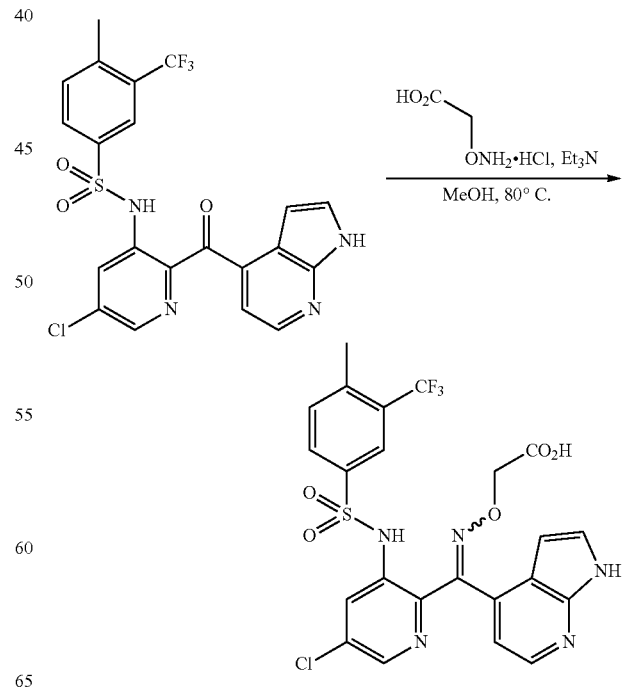

The title compound was synthesized in a manner similar to example 273. MS (M+H)⁺: 568.0.

305

Example 279: N-{2-[(2-Amino-pyridin-4-yl)-methoxyimino-methyl]-5-chloro-pyridin-3-yl}-4-chloro-3-trifluoromethyl-benzenesulfonamide

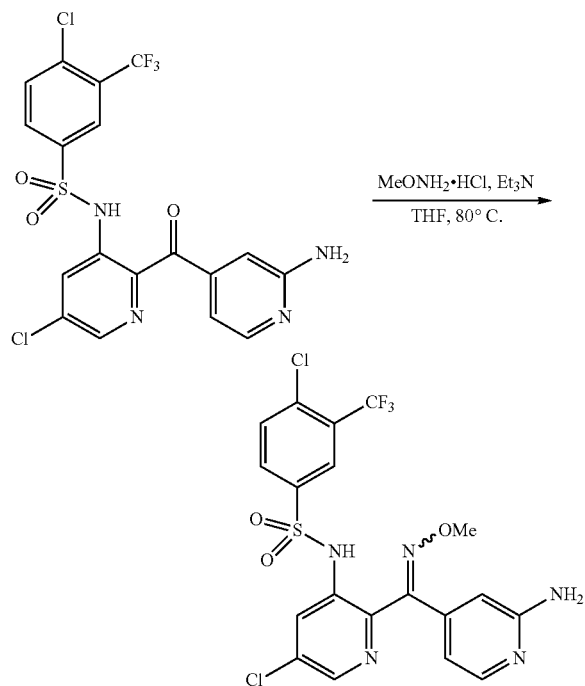

The title compound was synthesized in a manner similar to example 273. MS (M+H)$^+$: 519.9.

Example 280: N-{2-[(2-Amino-pyridin-4-yl)-methoxyimino-methyl]-5-chloro-pyridin-3-yl}-4-methyl-3-trifluoromethyl-benzenesulfonamide

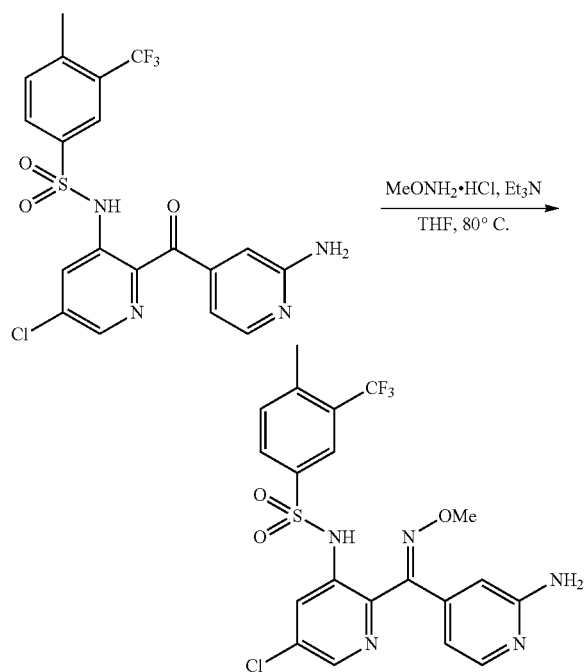

306

The title compound was synthesized in a manner similar to example 273. MS (M+H)$^+$: 500.0.

Example 281: 4-Chloro-N-[5-chloro-2-(7-oxy-1H-pyrrolo[2,3-b]pyridine-4-carbonyl)-pyridin-3-yl]-3-trifluoromethyl-benzenesulfonamide

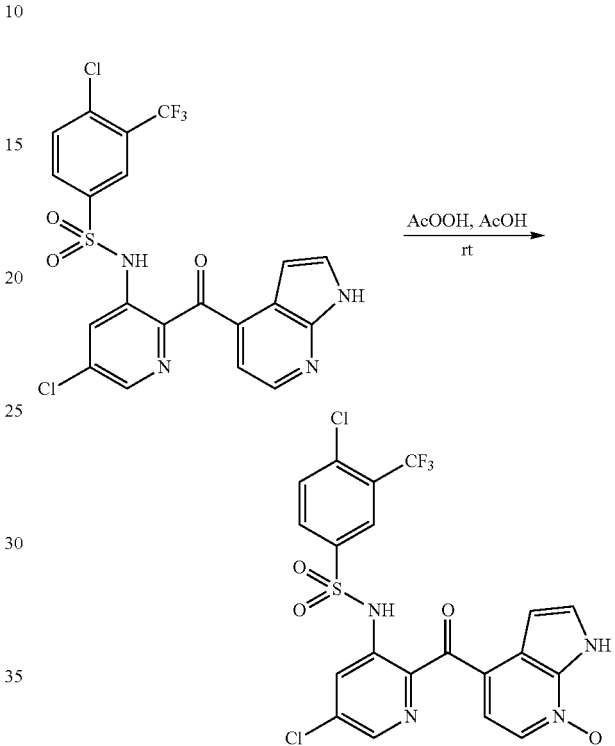

A mixture of 4-chloro-N-[5-chloro-2-(1H-pyrrolo[2,3-b]pyridine-4-carbonyl)-pyridin-3-yl]-3-trifluoromethyl-benzenesulfonamide (26 mg) and peracetic acid (32% wt in HOAc, 0.2 mL) was stirred at room temperature for 12 h. The mixture was loaded on reverse phase HPLC to afford the title compound as a pale yellow powder. MS (M+H)$^+$: 530.9.

Example 282: 4-Chloro-N-{5-chloro-2-[(2-hydroxy-pyridin-4-yl)-methoxyimino-methyl]-pyridin-3-yl}-3-trifluoromethyl-benzenesulfonamide

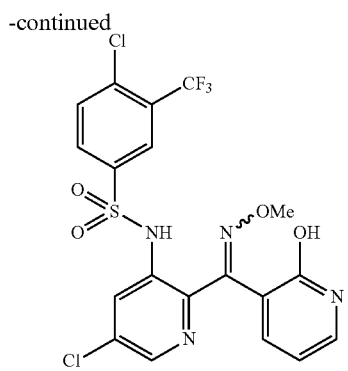

The title compound was prepared by procedure analogous to that described in Example 273 using 4-chloro-N-[5-chloro-2-(2-hydroxy-pyridine-4-carbonyl)-pyridin-3-yl]-3-trifluoromethyl-benzenesulfonamide. Purification on prep-HPLC (20-95% acetonitrile, 75 min) gave two isomers, the minor being the one eluting first: Major isomer: $^1$H NMR (400 MHz, CDCl$_3$) δ 10.82 (s, 1H), 8.20 (m, 1H), 8.17 (m, 1H), 8.01 (m, 1H), 7.93 (m, 1H), 7.67 (m, 1H), 7.33 (m, 1H), 6.26 (s, 1H), 5.84 (m, 1H), 4.14 (s, 3H) MS: (M+H)/z=521.0. Minor isomer: $^1$H NMR (400 MHz, CDCl$_3$) δ 8.50 (m, 1H), 8.10 (m, 1H), 7.97 (m, 1H), 7.60 (m, 1H), 7.47 (m, 1H), 7.16 (m, 1H), 6.50 (m, 1H), 5.48 (s, 1H), 4.10 (s, 3H) MS: (M+H)/z=521.0.

Example 283: 2-Chloro-3-[5-chloro-3-(4-chloro-3-trifluoromethyl benzenesulfonylamino)-pyridine-2-carbonyl] benzoic Acid

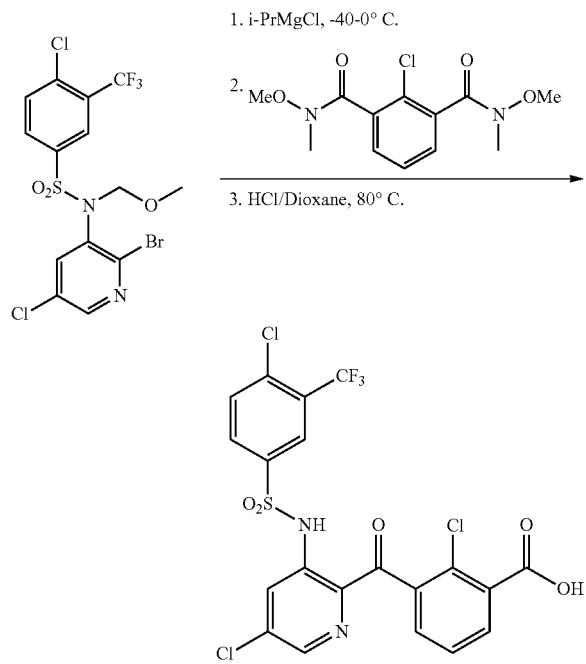

To an oven-dried vial containing N-(2-bromo-5-chloro-pyridin-3-yl)-4-chloro-N-methoxymethyl-3-trifluoromethyl benzenesulfonamide (316 mg, 0.64 mmol) was added anhydrous THF (2 mL) under positive nitrogen pressure. The vial was cooled to −40° C. (dry ice-MeCN) and a 2.0 M solution of i-PrMgCl in THF (0.80 mL, 1.6 mmol) was added. After 5 min, the solution was warmed to 0° C. After a further 30 min, 2-chloro-N,N'-dimethoxy-N,N'-dimethyl-isophthalamide (320 mg, 1.11 mmol) was added, and the reaction mixture was warmed to room temperature over 1 h. The solution was maintained at room temperature for 24 h, after which time it was treated with saturated aqueous NH$_4$Cl (10 mL), and poured into EtOAc (50 mL). The organic phase was washed with saturated aqueous NaCl (2×25 mL) and dried over MgSO$_4$. The volatiles were removed in vacuo, and the residue purified by flash chromatography on 15 g of silica gel (0-75% EtOAc-Hexanes). To the resulting product were added a 4.0 N solution of HCl in dioxane (2.0 mL, 8.0 mmol) and H$_2$O (0.5 mL). The reaction mixture was heated to 80° C. for 2 h, then cooled to room temperature. The volatiles were removed in vacuo. The product was purified by preparative HPLC (20→95% gradient of MeCN-H$_2$O with 0.1% TFA) and the pure fractions lyophilized to afford the title compound (44 mg, 12% yield): HPLC retention time=2.76 minutes. MS (ES) [M−H]$^-$ expected 551.0, found 550.9. $^1$H NMR (400 MHz, CDCl$_3$) δ 11.00 (s, 1H), 8.18-8.21 (m, 3H), 8.08 (dd, J=2.0, 7.6 Hz, 1H), 8.01 (dd, J=2.4, 8.4 Hz, 1H), 7.67 (d, J=8.4 Hz, 1H), 7.40-7.48 (m, 2H).

Example 284: 2-Chloro-3-[5-chloro-3-(4-chloro-3-trifluoromethyl benzenesulfonylamino)-pyridine-2-carbonyl]-N,N-dimethyl-benzamide

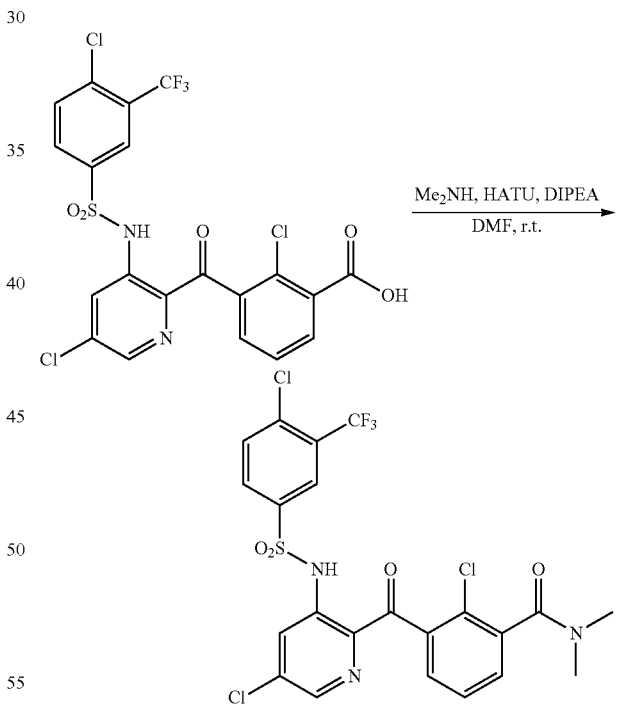

To a vial containing 2-chloro-3-[5-chloro-3-(4-chloro-3-trifluoromethylbenzenesulfonyl amino)-pyridine-2-carbonyl] benzoic acid (24 mg, 0.04 mmol) were added HATU (19 mg, 0.05 mmol), DMF (0.5 mL), a 2.0 M solution of Me$_2$NH in THF (40 μL, 0.08 mmol), and (i-Pr)$_2$NEt (10 μL, 0.06 mmol). The solution was maintained at room temperature for 5 h. EtOAc (10 mL) was added, and the organic phase washed with saturated aqueous NaCl (1×5 mL), 0.1 N acetic acid in water (1×5 mL), and dried over MgSO$_4$. The volatiles were removed in vacuo, and the resulting residue was purified by preparative HPLC (20→95% gradient of MeCN-H$_2$O with 0.1% TFA) and the pure fractions lyophilized to afford the title compound (5 mg, 22% yield): HPLC retention time=2.90 minutes. MS (ES) [M+H]$^+$ expected 580.0, found 579.9. $^1$H NMR (400 MHz, CDCl$_3$) δ 10.94 (s, 1H), 8.17-8.20 (m, 3H), 7.98 (dd, J=2.4, 8.4 Hz, 1H), 7.64 (d, J=8.8 Hz, 1H), 7.41 (d, J=4.4 Hz, 1H), 7.28-7.30 (m, 2H), 3.12 (s, 3H), 2.86 (s, 3H).

Example 285: 4-Chloro-N-[5-chloro-2-(8-chloro-4-oxo-3,4-dihydrophthalazin-1-yl)-pyridin-3-yl]-3-trifluoromethylbenzenesulfonamide. and 4-chloro-N-[5-chloro-2-(5-chloro-4-oxo-3,4-dihydro-phthalazin-1-yl)-pyridin-3-yl]-3-trifluoromethylbenzenesulfonamide

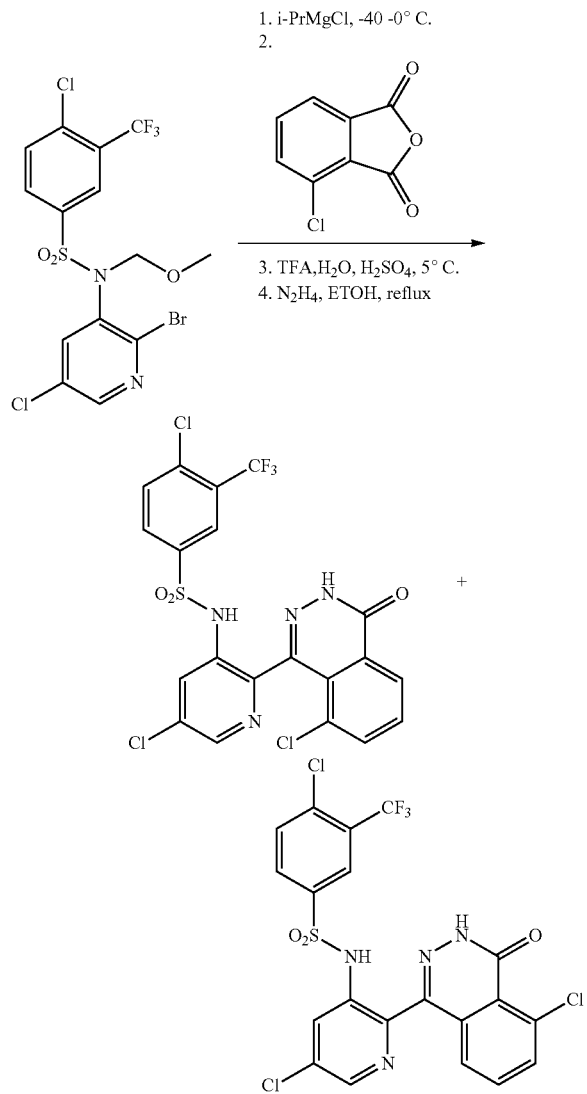

To an oven-dried vial containing N-(2-bromo-5-chloro-pyridin-3-yl)-4-chloro-N-methoxymethyl-3-trifluoromethylbenzene-sulfonamide (500 mg, 1.02 mmol) was added anhydrous THF (2 mL) under positive nitrogen pressure. The vial was cooled to −40° C. (dry ice-MeCN) and a 2.0 M solution of i-PrMgCl in THF (1.07 mL, 2.14 mmol) was added. After 5 min, the solution was warmed to 0° C. After a further 30 min, 3-chlorophthalic anhydride (173 mg, 0.95 mmol) was added, and the reaction mixture was warmed to room temperature over 1 h. The solution was maintained at room temperature for 24 h, after which time it was treated with 1.0 N NaHSO$_4$ (1 mL), and poured into EtOAc (100 mL). The organic phase was washed with saturated aqueous NaCl (2×25 mL) and dried over MgSO$_4$. The volatiles were removed in vacuo, and the resulting residue purified by flash chromatography on 15 g of silica gel (0-20% MeOH—CHCl$_3$ with 0.5% formic acid) to give a 1:1 mixture of 3-chloro-2-{5-chloro-3-[(4-chloro-3-trifluoromethyl benzenesulfonyl)methoxymethyl-amino]pyridine-2-carbonyl}benzoic acid and 2-chloro-6-{5-chloro-3-[(4-chloro-3-trifluoromethylbenzenesulfonyl)methoxymethylamino]pyridine-2-carbonyl}benzoic acid (292 mg, 52% yield).

To the preceding mixture of carboxylic acids was added TFA (3 mL), H$_2$O, (0.6 mL), and conc. H$_2$SO$_4$ (20 µL) at 5° C. After 24 h at this temperature, the reaction mixture was diluted with EtOAc (50 mL), washed with water (1×25 mL), and dried over MgSO$_4$. The volatiles were removed in vacuo to afford a brown oil. EtOH (2 mL) and anhydrous hydrazine (0.1 mL, 3.2 mmol) were added, and the solution heated to reflux. After 1 h, the reaction mixture was cooled to room temperature and diluted with EtOAc (50 mL). The organic phase was washed with 0.1 N aqueous HOAc (3×10 mL), dried over MgSO$_4$, and concentrated in vacuo to afford a brown oil. Purification by flash chromatography on 12 g of silica gel (0→75% EtOAc-Hexanes) afforded 4-chloro-N-[5-chloro-2-(8-chloro-4-oxo-3,4-dihydrophthalazin-1-yl)-pyridin-3-yl]-3-trifluoromethylbenzenesulfonamide (15 mg, 6% yield): HPLC retention time=2.71 minutes. MS (ES) [M+H]$^+$ expected 549.0, found 548.9. $^1$H NMR (400 MHz, CDCl$_3$) δ 11.03 (s, 1H), 8.40-8.41 (m, 1H), 8.32-8.34 (m, 1H), 8.12-8.13 (m, 1H), 7.96 (bs, 1H), 7.42-7.63 (m, 1H), 7.63-7.70 (m, 3H), 7.33-7.36 (m, 1H); and 4-chloro-N-[5-chloro-2-(5-chloro-4-oxo-3,4-dihydrophthalazin-1-yl)pyridin-3-yl]-3-trifluoromethylbenzenesulfonamide (12 mg, 4% yield): HPLC retention time=2.74 minutes. MS (ES) [M+H]$^+$ expected 549.0, found 548.9. $^1$H NMR (400 MHz, CDCl$_3$) δ 10.74 (s, 1H), 8.55 (d, J=2.4 Hz, 1H), 8.14 (d, J=2.4 Hz, 1H), 7.77 (dd, J=1.2, 8.0 Hz, 1H), 7.71 (d, J=2 Hz, 1H), 7.76-7.59 (m, 1H), 7.53 (d, J=8 Hz, 1H), 7.45 (dd, J=1.2, 8.0 Hz, 1H), 7.19-7.24 (m, 2H).

Example 286: 2-Chloro-3-[5-chloro-3-(4-chloro-3-trifluoromethyl-benzenesulfonylamino)-pyridine-2-carbonyl]-N-methyl-benzamide

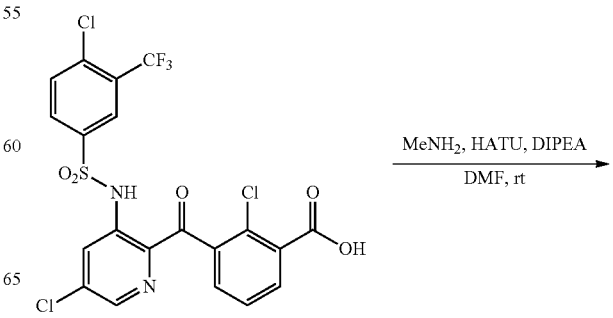

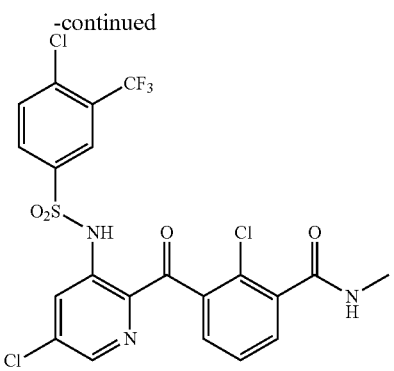

To a vial containing 2-chloro-3-[5-chloro-3-(4-chloro-3-trifluoromethylbenzene-sulfonylamino)-pyridine-2-carbonyl]benzoic acid (24 mg, 0.04 mmol) were added HATU (75 mg, 0.2 mmol), DMF (1 mL), a 2.0 M solution of MeNH₂ in THF (0.3 mL, 0.6 mmol), and (i-Pr)₂NEt (35 [L, 0.2 mmol). The solution was maintained at room temperature for 15 h. EtOAc (20 mL) was added, and the organic phase washed with saturated aqueous NaCl (2×10 mL) and dried over MgSO₄. The volatiles were removed in vacuo, and the resulting residue was purified by preparative HPLC (20→95% gradient of MeCN-H₂O with 0.1% TFA). The pure fractions were lyophilized to afford the title compound (5 mg, 5% yield): HPLC retention time=2.69 minutes. MS (ES) [M+H]⁺ expected 566.0, found 565.9. ¹H NMR (400 MHz, CDCl₃) δ 10.98 (s, 1H), 8.17-8.21 (m, 3H), 8.00 (dd, J=2.4, 8.8 Hz, 1H), 7.65-7.69 (m, 2H), 7.41 (t, J=7.2 Hz, 1H), 7.30 (dd, J=1.6, 7.2 Hz, 1H), 6.01 (bs, 1H), 3.01 (d, J=5.2 Hz, 3H).

Example 287: 4-Chloro-N-[5-chloro-2-(3-(±)-hydroxypyrrolidine-1-carbonyl)pyridin-3-yl]-3-trifluoromethylbenzenesulfonamide

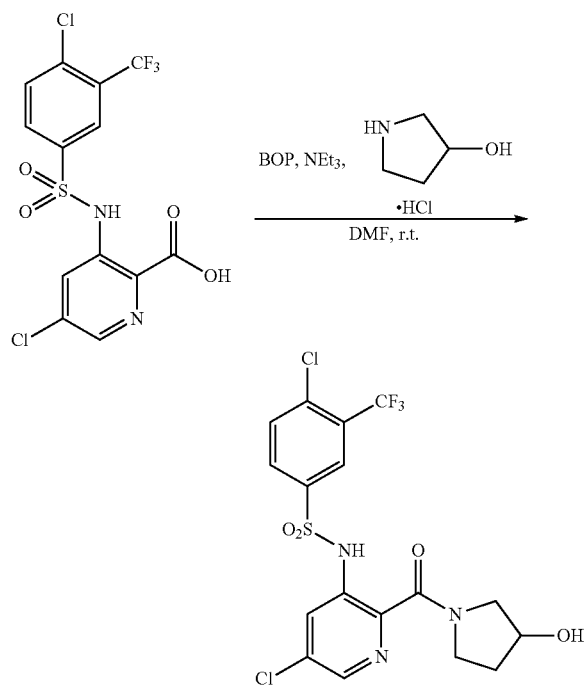

To a vial containing 5-chloro-3-(4-chloro-3-trifluoromethyl benzenesulfonylamino)-pyridine-2-carboxylic acid (20 mg, 0.05 mmol) were added 3-(±)-pyrrolidinol hydrochloride (13 mg, 0.11 mmol), BOP (25 mg, 0.06 mmol), DMF (0.3 mL) and NEt₃ (40 µL, 0.29 mmol). The solution was maintained at room temperature for 24 h, then diluted with EtOAc (30 mL), washed with saturated aqueous NaCl (3×5 mL), and dried over MgSO₄. The volatiles were removed in vacuo. The resulting residue was purified by preparative HPLC (20→95% gradient of MeCN-H₂O with 0.1% TFA) and the pure fractions lyophilized to afford the title compound (10 mg, 43% yield): HPLC retention time=2.49 minutes. MS (ES) [M+H]⁺ expected 484.0, found 484.0. ¹H NMR (400 MHz, CDCl₃) δ 11.38 (s, 1H), 8.21-8.24 (m, 1H), 8.11-8.13 (m, 1H), 8.02-8.04 (m, 1H), 7.91-7.93 (m, 1H), 7.60-7.62 (m, 1H), 4.50-4.53 (m, 1H), 3.82-4.01 (m, 2H), 3.65-3.76 (m, 3H), 1.95-2.04 (m, 2H).

Example 288: N-{5-chloro-2-[2-chloro-3-(3-methylureido)benzoyl]pyridin-3-yl}-4-methyl-3-trifluoromethylbenzenesulfonamide

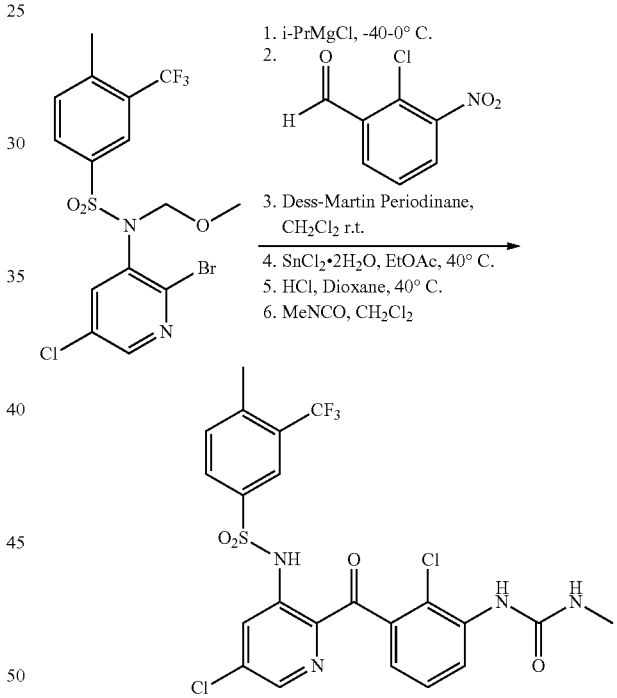

To an oven-dried vial containing N-(2-bromo-5-chloropyridin-3-yl)-N-methoxymethyl-4-methyl-3-trifluoromethylbenzenesulfonamide (1.00 g, 2.1 mmol) was added anhydrous THF (4 mL) under positive nitrogen pressure. The vial was cooled to −40° C. (dry ice-MeCN) and a 2.0 M solution of i-PrMgCl in THF (2.2 mL, 4.4 mmol) was added. After 5 min, the solution was warmed to 0° C. After a further 30 min, 2-chloro-3-nitrobenzaldehyde (600 mg, 3.2 mmol) was added, and the reaction mixture was warmed to room temperature over 1 h. The solution was maintained at room temperature for 48 h, after which time it was poured into EtOAc (50 mL). The organic phase was washed with 0.1 N HCl (1×25 mL), saturated aqueous NaCl (2×25 mL), and dried over MgSO₄. The volatiles were removed in vacuo to afford a brown oil that was used without further purification.

The preceding oil was dissolved in CH$_2$Cl$_2$ (2 mL) and treated with a 15 wt % solution of Dess-Martin Periodinane in CH$_2$Cl$_2$ (6 mL, 2.1 mmol). After 18 h, the reaction mixture was diluted with EtOAc (50 mL) and washed with saturated aqueous NaCl (1×25 mL) and 10% aqueous NaHCO$_3$ (1×25 mL). The organic phase was dried over MgSO$_4$, and concentrated in vacuo to afford a brown oil. Purification by flash chromatography on 12 g of silica gel (0→33% EtOAc-Hexanes) afforded N-[5-chloro-2-(2-chloro-3-nitrobenzoyl)pyridin-3-yl]-N-methoxymethyl-4-methyl-3-trifluoromethyl benzene-sulfonamide (490 mg, 40% yield over two steps). HPLC retention time=3.10 minutes. MS (ES) [M+Na]$^+$ expected 600.0, found 599.9. $^1$H NMR (400 MHz, CDCl$_3$) δ 8.52 (d, J=2.0 Hz, 1H), 7.91 (d, J=2.0 Hz, 1H), 7.86 (dd, J=1.6, 7.6 Hz, 1H), 7.75 (dd, J=2.0, 8.0 Hz, 1H), 7.64 (d, J=2.0 Hz, 1H), 7.54 (dd, J=1.6, 7.6 Hz, 1H), 7.46 (t, J=7.6 Hz, 1H), 7.38 (d, J=8.0 Hz, 1H), 5.31 (s, 2H), 3.41 (s, 3H), 2.53 (s, 3H).

To a vial containing a magnetic stir bar and N-[5-chloro-2-(2-chloro-3-nitro-benzoyl)-pyridin-3-yl]-N-methoxymethyl-4-methyl-3-trifluoromethylbenzenesulfonamide (100 mg, 0.17 mmol) was added EtOAc (0.5 mL). SnCl$_2$*2H$_2$O (240 mg, 1.06 mmol) was added, and the mixture heated to 40° C. with vigorous stirring. After 1 h, the mixture was diluted with Et$_2$O (30 mL) and treated with KF (120 mg, 2.07 mmol) and H$_2$O (3 mL). After stirring for 1 h, the organic phase was filtered through Celite and concentrated in vacuo to afford a yellow oil which was used without further purification.

To the preceding oil were added a 4.0 N solution of HCl in dioxane (4 mL, 16 mmol), and H$_2$O (2 mL). The solution was heated to 40° C. for 18 h. After cooling to room temperature, the mixture was partitioned between EtOAc (30 mL) and a 1.0 M solution of Na$_2$HPO$_4$ (10 mL). The organic phase was washed with saturated aqueous NaCl (1×10 mL) and dried over MgSO$_4$. The volatiles were removed in vacuo, and the crude product used without further purification.

The preceding product was dissolved in CH$_2$Cl$_2$ (0.1 mL) and treated with methyl isocyanate (20 μL, 0.34 mmol). After 6 h, the reaction mixture was diluted with EtOAc (5 mL) and treated with saturated aqueous NaHCO$_3$ (1 mL). The organic phase was dried over MgSO$_4$ and concentrated in vacuo. The resulting product was purified by flash chromatography on 4 g of silica gel (20→100% EtOAc-Hexanes) to afford the title compound (20 mg, 21% yield over 3 steps): HPLC retention time=2.75 minutes. MS (ES) [M+H]$^+$ expected 561.0, found 560.9. $^1$H NMR (400 MHz, CDCl$_3$) δ 10.97 (s, 1H), 8.51 (d, J=2.0 Hz, 1H), 8.26 (dd, J=0.8, 8.0 Hz, 1H), 8.10-8.12 (m, 1H), 7.96 (dd, J=2.0, 8.0 Hz, 1H), 7.71 (dd, J=1.4, 7.8 Hz, 1H), 7.67 (d, J=2.0 Hz, 1H), 7.17-7.32 (m, 2H), 6.89 (bs, 1H), 6.76 (bs, 1H), 2.87 (bs, 3H), 2.54 (s, 3H).

Example 289: 8-Formyl-2,3-dihydro-benzo[1,4]oxazine-4-carboxylic acid tert-butyl Ester

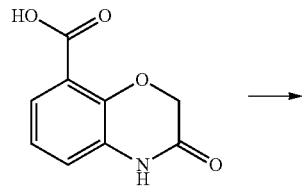

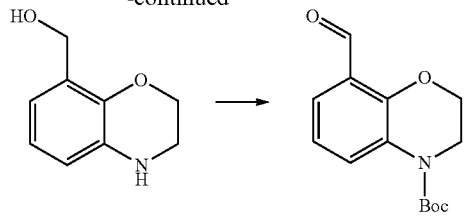

To a suspension of 3-oxo-3,4-dihydro-2H-benzo[1,4]oxazine-8-carboxylic acid (1.51 g, 7.8 mmol) in anhydrous THF (10 mL) was added BH$_3$.Me$_2$S (2 M in THF, 10 mL, 20 mmol) dropwise under nitrogen at 0° C. The resulted mixture was allowed to rise to r.t., and the reaction was continued to be carried out at this temperature overnight. Then, saturated aqueous NH$_4$Cl (30 mL) was added in, and the resulted mixture was extracted with EtOAc (200 mL×2). The combined organic layers were washed with saturated aqueous NaHCO$_3$ solution (30 mL), brine (30 mL), dried (Na$_2$SO$_4$) and filtered before it was concentrated under reduced pressure. The resulted crude product (3,4-dihydro-2H-benzo[1,4]oxazin-8-yl)-methanol, which was utilized in the following step without further purification. MS m/z: 166.2 (M+H)$^+$.

To a suspension of (3,4-dihydro-2H-benzo[1,4]oxazin-8-yl)-methanol (1.49 g, 7.8 mmol) in dioxane (10 mL) was added Et$_3$N (1 mL), and Boc$_2$O (3.41 g, 15.6 mmol), the resulted mixture was stirred at r.t. for 2 h. Then, saturated aqueous NaHCO$_3$ (30 mL) was added in, and the resulted mixture was extracted with EtOAc (150 mL×2). The combined organic layers were washed with brine (30 mL), dried (Na$_2$SO$_4$) and filtered before it was concentrated under reduced pressure. The residue was purified by flash column chromatography on silica gel to provide 8-hydroxymethyl-2,3-dihydro-benzo[1,4]oxazine-4-carboxylic acid tert-butyl ester (1.11 g) as a white solid. ESMS m/z: 288.1 (M+Na)$^+$.

To a solution of 8-hydroxymethyl-2,3-dihydro-benzo[1,4]oxazine-4-carboxylic acid tert-butyl ester (591.2 mg, 2.2 mmol) in dioxane (4 mL) was added preactivated MnO$_2$ (2.00 g, 22.3 mmol), and the resulted mixture was heated at 80° C. for overnight. The resulted mixture was then cooled to r.t., and filtered. The solid was washed with EtOAc (20 mL×3). EtOAc washing solution was combined with dioxane filtrate, and concentrated under reduced pressure. The residue was purified by flash column chromatography on silica gel to provide 8-formyl-2,3-dihydro-benzo[1,4]oxazine-4-carboxylic acid tert-butyl ester (491.5 mg) as a white solid. MS m/z: 286.0 (M+Na)$^+$.

Example 290: 4-Chloro-N-[5-chloro-2-(3,4-dihydro-2H-benzo[1,4]oxazine-8-carbonyl)-pyridin-3-yl]-3-trifluoromethyl-benzenesulfonamide

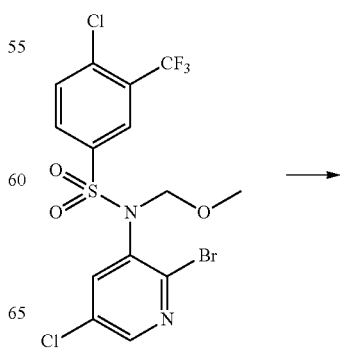

-continued

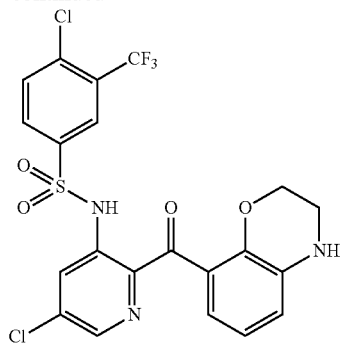

To a solution of N-(2-bromo-5-chloro-pyridin-3-yl)-4-chloro-N-methoxymethyl-3-trifluoromethyl-benzenesulfonamide (2.92 g, 6.18 mmol) in THF (12 mL) under nitrogen atmosphere at −20° C. was added isopropylmagnesium chloride (2 M solution in THF, 6.5 mL, 13.0 mmol) via dropwise addition. The mixture was then stirred for 1 hour at 0° C. followed by the addition of a solution of 8-formyl-2,3-dihydro-benzo[1,4]oxazine-4-carboxylic acid tert-butyl ester (273.5 mg, 1.54 mmol) in THF (2 mL) at −20° C. The mixture was stirred at room temperature overnight, quenched with saturated aqueous NH$_4$Cl solution (5 mL), and extracted with EtOAc (2×200 mL). The combined organic extracts were washed with saturated aqueous NH$_4$Cl solution (40 mL) and brine (40 mL), dried (Na$_2$SO$_4$), and concentrated under reduced pressure. The obtained residue was purified by flash column chromatography on silica gel (10% EtOAc-hexanes to 90% EtOAc-hexanes) to obtain 8-({5-chloro-3-[(4-chloro-3-trifluoromethyl-benzenesulfonyl)-methoxymethyl-amino]-pyridin-2-yl}-hydroxy-methyl)-2,3-dihydro-benzo[1,4]oxazine-4-carboxylic acid tert-butyl ester (590.2 mg) as yellow syrup. MS m/z: 678.0 (M+H)$^+$.

To a solution of 8-({5-chloro-3-[(4-chloro-3-trifluoromethyl-benzenesulfonyl)-methoxymethyl-amino]-pyridin-2-yl}-hydroxy-methyl)-2,3-dihydro-benzo[1,4]oxazine-4-carboxylic acid tert-butyl ester (562.7 mg, 0.91 mmol) in dioxane (4 mL) was added preactivated MnO$_2$ (932.9 mg, 9.12 mmol), and the resulted mixture was heated at 80° C. for two hour. The resulted mixture was cooled to r.t., and filtered. The solid was washed with EtOAc (20 mL×3). EtOAc washing solution was combined with dioxane filtrate, and concentrated under reduced pressure. The residue was purified by flash column chromatography on silica gel to provide 8-{5-chloro-3-[(4-chloro-3-trifluoromethyl-benzenesulfonyl)-methoxymethyl-amino]-pyridine-2-carbonyl}-2,3-dihydro-benzo[1,4]oxazine-4-carboxylic acid tert-butyl ester (510.2 mg) as yellow syrup. MS m/z: 676.0 (M+H)$^+$.

A solution of 8-{5-chloro-3-[(4-chloro-3-trifluoromethyl-benzenesulfonyl)-methoxymethyl-amino]-pyridine-2-carbonyl}-2,3-dihydro-benzo[1,4]oxazine-4-carboxylic acid tert-butyl ester (510.2 mg) in 3 mL HCl (4 M in dioxane) and water (1 mL) was heated at 80° C. for overnight. Upon cooling to room temperature, the mixture was concentrated and the residue was purified by flash column chromatography on silica gel to afford 4-chloro-N-[5-chloro-2-(3,4-dihydro-2H-benzo[1,4]oxazine-8-carbonyl)-pyridin-3-yl]-3-trifluoromethyl-benzenesulfonamide (210.2 mg) as white solid. MS m/z: 531.9 (M+H)$^+$.

Example 291: (3-formyl-pyridin-2-yl)-carbamic Acid Tert-Butyl Ester

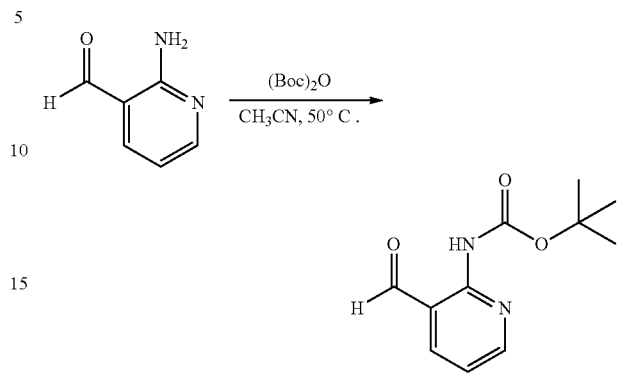

To 2-amino-pyridine-3-carbaldehyde (500 mg, 4.09 mmol) in CH$_3$CN (5 mL) was added (Boc)$_2$O (1.34 g, 6.14 mmol) and stirred at 50° C. for 24 hours. Reaction mixture was diluted with EtOAc (50 mL), washed with brine (3×25 mL), dried (Na$_2$SO$_4$), evaporated and purified by column chromatography (SiO$_2$, 50% EtOAc in hexanes) to obtain (3-formyl-pyridin-2-yl)-carbamic acid tert-butyl ester (655 mg) in 72% yield. ESMS m/z (relative intensity): 123 [(M−100)+H]$^+$ (100).

Example 292: [3-({5-chloro-3-[(4-chloro-3-trifluoromethyl-benzene sulfonyl)-methoxymethyl-amino]-pyridin-2-yl}-hydroxy-methyl)-pyridin-2-yl]-carbamic Acid Tert-Butyl Ester

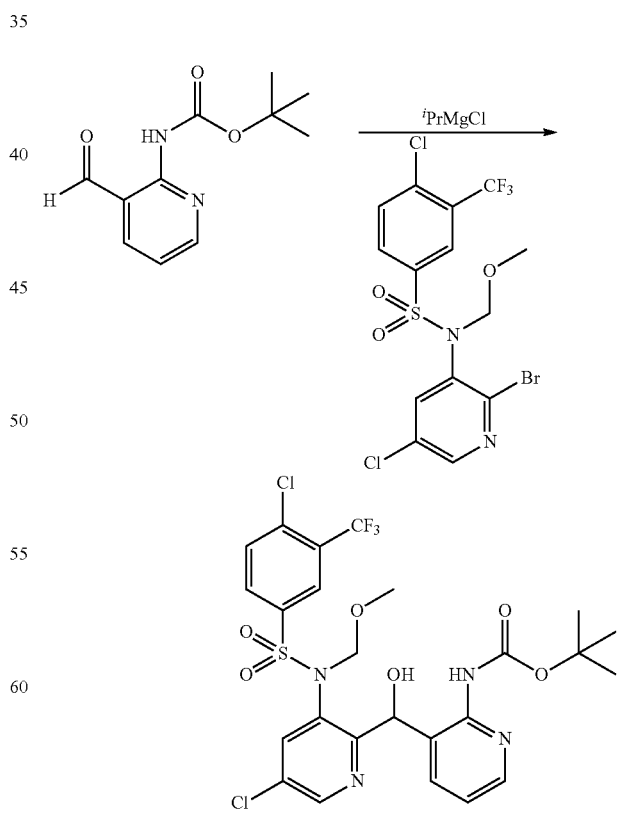

To a solution of N-(2-bromo-5-chloro-pyridin-3-yl)-4-chloro-N-methoxymethyl-3-trifluoromethyl-benzenesulfonamide (3.27 g, 6.64 mmol) in THF (20 mL) under nitrogen atmosphere at 0° C. was added dropwise isopropylmagnesium chloride (2 M solution in THF, 6.62 mL, 13.25 mmol). The mixture was then stirred for 30 min at 0° C. followed by the addition of a solution of (3-formyl-pyridin-2-yl)-carbamic acid tert-butyl ester (590 mg, 2.65 mmol) in THF (3 mL) at 0° C. The mixture was stirred at room temperature for 3 hours, quenched with saturated aqueous NH$_4$Cl solution (10 mL) and extracted with EtOAc (2×50 mL). Combined organic layers were washed with saturated aqueous NH$_4$Cl solution (50 mL), brine (50 mL), dried (anhydrous Na$_2$SO$_4$) and concentrated under reduced pressure. Obtained residue was column purified (SiO$_2$, 50% EtOAc-hexanes) to obtain [3-({5-chloro-3-[(4-chloro-3-trifluoromethyl-benzene sulfonyl)-methoxymethyl-amino]-pyridin-2-yl}-hydroxymethyl)-pyridin-2-yl]-carbamic acid tert-butyl ester (750 mg) in 44% yield as yellow solid. ESMS m/z (relative intensity): 637 (M+H)$^+$ (100).

Example 293: 3-{5-chloro-3-[(4-chloro-3-trifluoromethyl-benzenesulfonyl)-methoxymethyl-amino]-pyridine-2-carbonyl}-pyridin-2-yl)-carbamic Acid Tert-Butyl Ester

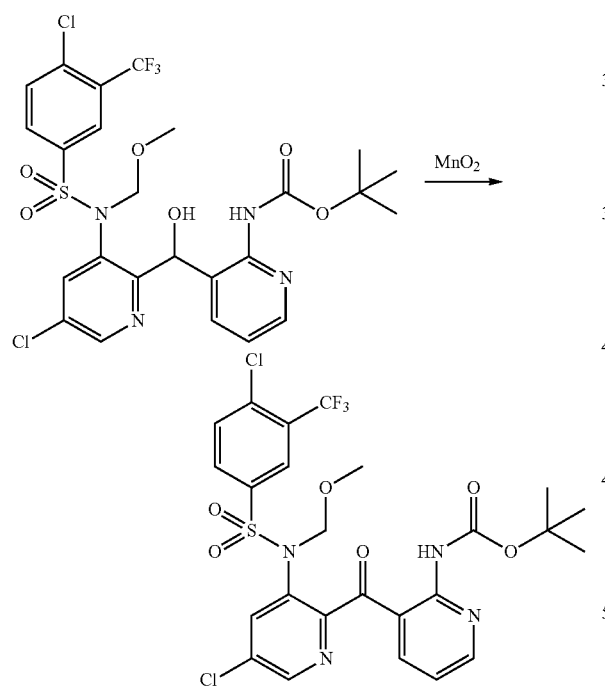

A mixture of [3-({5-chloro-3-[(4-chloro-3-trifluoromethyl-benzene sulfonyl)-methoxymethyl-amino]-pyridin-2-yl}-hydroxy-methyl)-pyridin-2-yl]-carbamic acid tert-butyl ester (750 mg, 1.18 mmol) and MnO$_2$ (512.6 mg, 5.9 mmol) in THF (10 mL) was stirred at 50° C. for overnight. The reaction mixture was cooled to room temperature, filtered through sintered funnel, washed with THF (2×10 mL), dried (anhydrous Na$_2$SO$_4$) and concentrated. The obtained residue was column purified (SiO$_2$, 50% EtOAc-hexanes) to afford (3-{5-chloro-3-[(4-chloro-3-trifluoromethyl-benzenesulfonyl)-methoxymethyl-amino]-pyridine-2-carbonyl}-pyridin-2-yl)-carbamic acid tert-butyl ester (456 mg) 61% in yield. ESMS m/z (relative intensity): 635 (M+H)$^+$ (100).

Example 294: N-[2-(2-amino-pyridine-3-carbonyl)-5-chloro-pyridin-3-yl]-4-chloro-3-trifluoromethyl-benzenesulfonamide

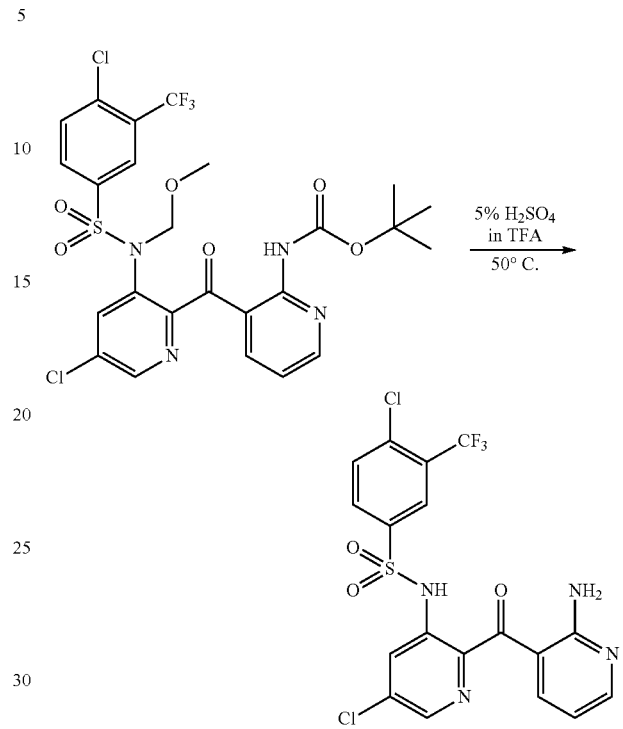

A mixture of (3-{5-chloro-3-[(4-chloro-3-trifluoromethyl-benzenesulfonyl)-methoxymethyl-amino]-pyridine-2-carbonyl}-pyridin-2-yl)-carbamic acid tert-butyl ester (25 mg, 0.0394 mmol) in 5% H$_2$SO$_4$ in TFA (4 mL) and water (1 mL) was stirred at 50° C. for 6 h. The reaction mixture was cooled to room temperature, evaporated to dryness and treated with saturated aqueous NaHCO$_3$ solution until pH 7-8. The mixture was extracted with EtOAc (2×15 mL), dried (anhydrous Na$_2$SO$_4$) and concentrated. The obtained residue was column purified to afford N-[2-(2-amino-pyridine-3-carbonyl)-5-chloro-pyridin-3-yl]-4-chloro-3-trifluoromethyl-benzenesulfonamide (9.3 mg) in 48% yield. ESMS m/z (relative intensity): 491 (M+H)$^+$ (100).

Example 295: 4-chloro-N-{2-[(2-chloro-5-nitrophenyl)-hydroxy-methyl]-5-methyl-pyridin-3-yl}-N-methoxymethyl-3-trifluoromethyl-benzenesulfonamide

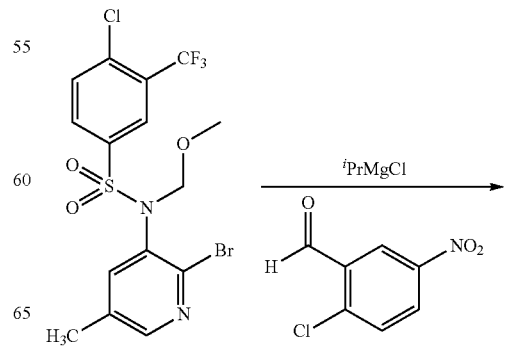

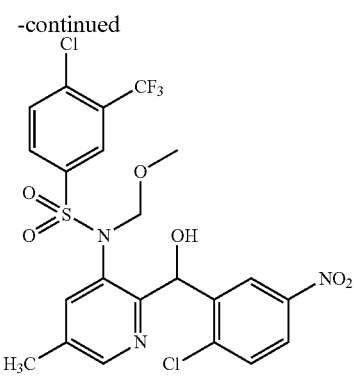

To a solution of N-(2-bromo-5-methyl-pyridin-3-yl)-4-chloro-N-methoxymethyl-3-trifluoromethyl-benzenesulfonamide (472 mg, 1.0 mmol) in THF (3 mL) under nitrogen atmosphere at 0° C. was added dropwise isopropylmagnesium chloride (2 M solution in THF, 1.2 mL, 2.4 mmol). The mixture was then stirred for 30 min at 0° C. followed by the addition of a solution of 2-chloro-5-nitro-benzaldehyde (352.6 mg, 1.9 mmol) at 0° C. The mixture was stirred at room temperature for 3 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 50% EtOAc-hexanes) to obtain 4-chloro-N-{2-[(2-chloro-5-nitro-phenyl)-hydroxy-methyl]-5-methyl-pyridin-3-yl}-N-methoxymethyl-3-trifluoromethyl-benzenesulfonamide (441 mg) in 76% yield. ESMS m/z (relative intensity): 580 (M+H)$^+$ (100), 602 (M+Na)+(20).

Example 296: 4-chloro-N-[2-(2-chloro-5-nitro-benzoyl)-5-methyl-pyridin-3-yl]-N-methoxymethyl-3-trifluoromethyl-benzenesulfonamide

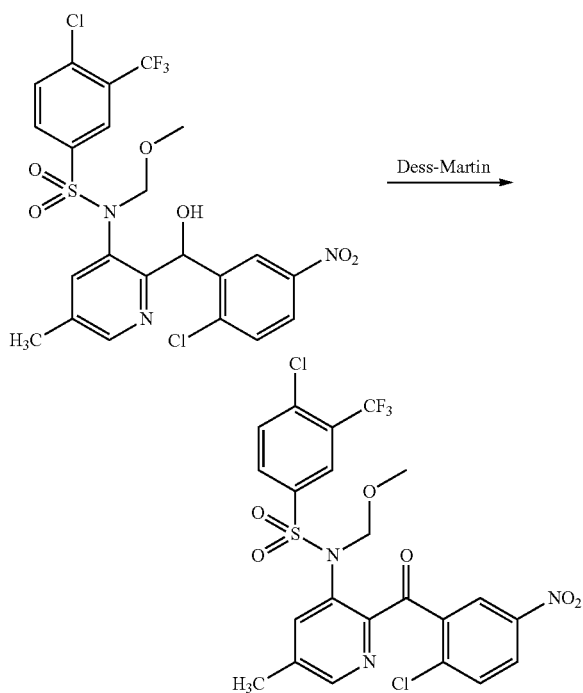

To a solution of 4-chloro-N-{2-[(2-chloro-5-nitro-phenyl)-hydroxy-methyl]-5-methyl-pyridin-3-yl}-N-methoxymethyl-3-trifluoromethyl-benzenesulfonamide (441 mg, 0.76 mmol) in CH$_2$CO$_2$ (5 mL) was added Dess-Martin periodinane (645 mg, 1.52 mmol) and stirred for 6 h at room temperature. 10% Na$_2$S$_2$O$_3$ (5 mL) and saturated aqueous NaHCO$_3$ solution (5 mL) was added and stirred for 30 min. Aqueous layer was separated and extracted with EtOAc (2×25 mL). Combined organic layers were washed with saturated aqueous NaHCO$_3$ solution (20 mL), brine (20 mL), dried (anhydrous Na$_2$SO$_4$), concentrated and purified (SiO$_2$, 40% EtOAc-hexanes) to obtain 4-chloro-N-[2-(2-chloro-5-nitro-benzoyl)-5-methyl-pyridin-3-yl]-N-methoxymethyl-3-trifluoromethyl-benzenesulfonamide (230 mg) as yellow syrup in 52% yield. ESMS m/z (relative intensity): 545.9 (M−31)+(100), 578 (M+H)$^+$ (50), 599.9 (M+Na)$^+$ (65).

Example 297: 4-chloro-N-[2-(2-chloro-5-nitro-benzoyl)-5-methyl-pyridin-3-yl]-3-trifluoromethyl-benzenesulfonamide

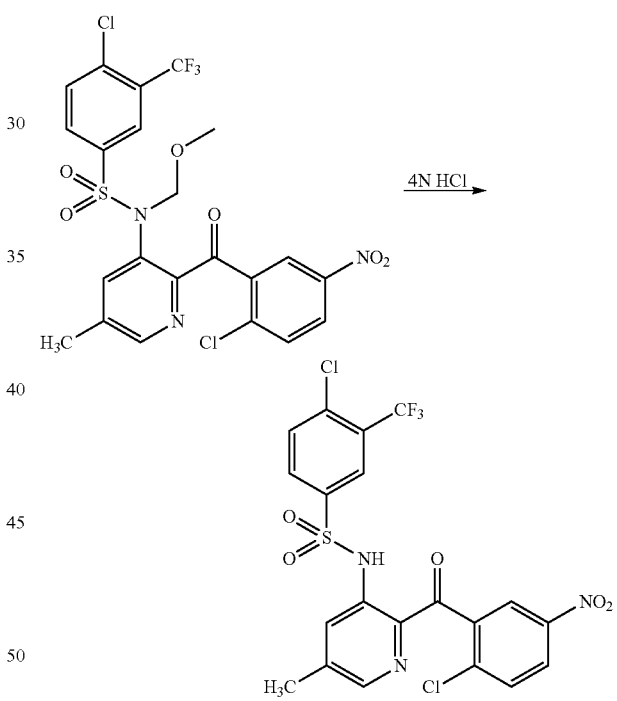

A mixture of 4-chloro-N-[2-(2-chloro-5-nitro-benzoyl)-5-methyl-pyridin-3-yl]-N-methoxymethyl-3-trifluoromethyl-benzenesulfonamide (230 mg, 0.398 mmol) in 4 M HCl in dioxane (4 mL) and water (1 mL) was 50° C. for overnight. Reaction mixture was cooled to room temperature, evaporated to dryness and treated slowly with saturated aqueous NaHCO$_3$ solution until pH 7-8. The mixture was extracted with EtOAc (2×25 mL), dried (anhydrous Na$_2$SO$_4$) and concentrated. The obtained residue was purified by flash chromatography (SiO$_2$, 50% EtOAc-hexanes) to afford 4-chloro-N-[2-(2-chloro-5-nitro-benzoyl)-5-methyl-pyridin-3-yl]-3-trifluoromethyl-benzenesulfonamide (136 mg) in 64% yield. ESMS m/z (relative intensity): 533.9 (M+H)$^+$ (90), 555.9 (M+Na)$^+$ (100).

Example 298: N-[2-(5-amino-2-chloro-benzoyl)-5-methyl-pyridin-3-yl]-4-chloro-3-trifluoromethyl-benzenesulfonamide

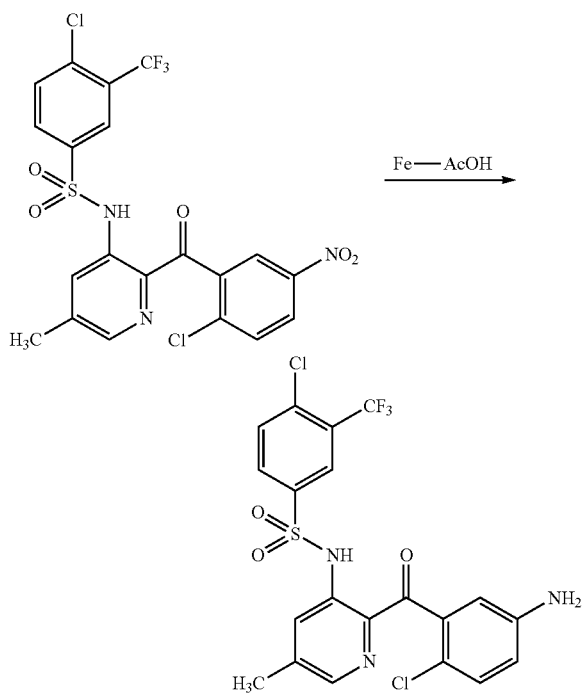

To Fe powder (61.3 mg, 1.09 mmol), AcOH (2 mL) was added dropwise and heated to 80° C. To it, a solution of 4-chloro-N-[2-(2-chloro-5-nitro-benzoyl)-5-methyl-pyridin-3-yl]-3-trifluoromethyl-benzenesulfonamide (136 mg, 0.255 mmol) in AcOH (2 mL) was added slowly. After 30 min, reaction mixture was allowed to cool to room temperature and diluted with EtOAc (25 mL), filtered through a pad of Celite. The filter cake was washed with EtOAc (25 mL) and the filtrate was concentrated. The residual liquid was slowly treated with saturated aqueous NaHCO₃ solution, followed by small portions of solid NaHCO₃ to neutralize the AcOH, extracted with EtOAc (2×25 mL) and the extracts were dried (anhydrous Na₂SO₄), concentrated under reduced pressure and purified (SiO₂, EtOAc) to get N-[2-(5-amino-2-chloro-benzoyl)-5-methyl-pyridin-3-yl]-4-chloro-3-trifluoromethyl-benzenesulfonamide (118 mg) in 92.2% yield. ESMS m/z (relative intensity): 504 (M+H)⁺ (100).

Example 299: 4-chloro-N-{2-[2-chloro-5-(3-methyl-ureido)-benzoyl]-5-methyl-pyridin-3-yl}-3-trifluoromethyl-benzenesulfonamide

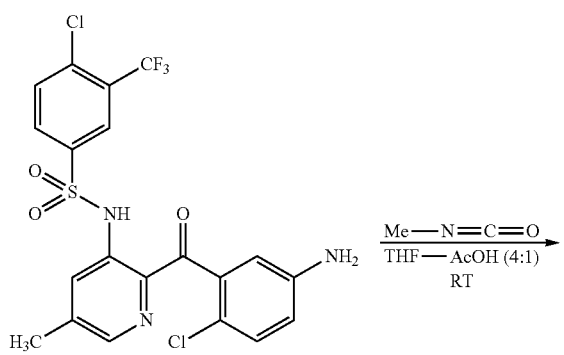

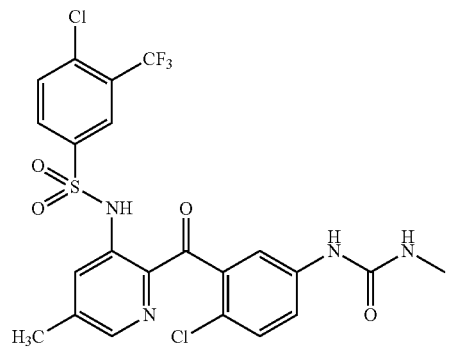

Methylisocyanate (17 μL, 0.235 mmol) was added to N-[2-(5-amino-2-chloro-benzoyl)-5-methyl-pyridin-3-yl]-4-chloro-3-trifluoromethyl-benzene sulfonamide (59 mg, 0.117 mmol) in THF (2 mL) and AcOH (0.5 mL) and stirred at room temperature for 4 h. The reaction mixture was directly purified by preparative HPLC (20-80% acetonitrile in water) to afford 4-chloro-N-{2-[2-chloro-5-(3-methyl-ureido)-benzoyl]-5-methyl-pyridin-3-yl}-3-trifluoromethyl-benzene sulfonamide (25 mg) in 38% yield. ¹H NMR (400 MHz, CDCl₃+CD₃OD) δ 8.14 (m, 2H), 7.95 (m, 2H), 7.63 (d, 1H), 7.58 (dd, 1H), 7.41 (dd, 1H), 7.19 (d, 1H), 2.76 (s, 3H), 2.42 (s, 3H); ESMS m/z (relative intensity): 561 (M+H)⁺ (100).

Example 300: 4-Chloro-N-[5-chloro-2-(2-chloro-pyridine-4-carbonyl)-pyridin-3-yl]-3-trifluoromethyl-benzenesulfonamide

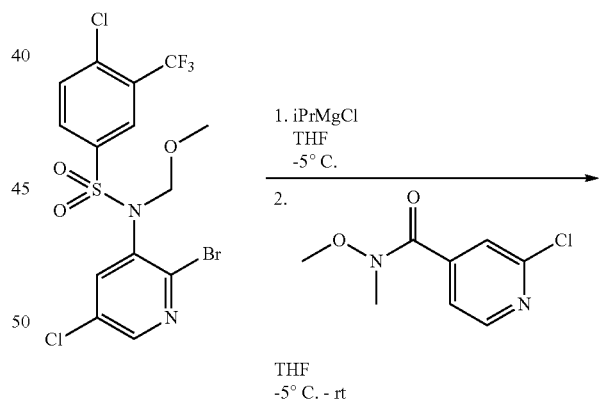

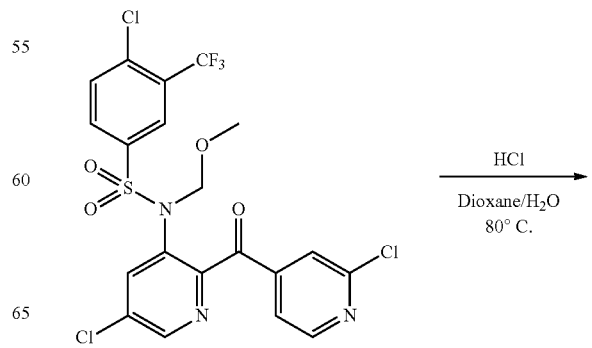

-continued

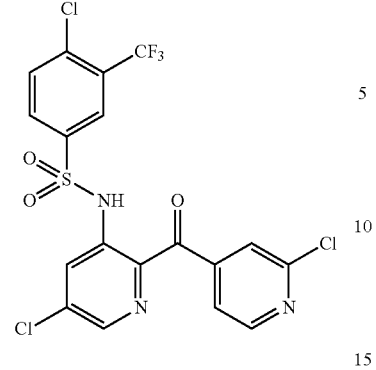

N-(2-Bromo-5-chloro-pyridin-3-yl)-4-chloro-N-methoxymethyl-3-trifluoromethyl-benzenesulfonamide (250 mg, 0.506 mmol) was placed in a dry 2-neck 10 mL round-bottom flask. The flask was evacuated and purged with nitrogen, followed by the addition of THF (1.27 mL). The homogeneous mixture was lowered to −5° C. and i-PrMgCl (0.53 mL, 2.0 M) was added dropwise. Upon completion of the addition, the reaction was stirred 90 minutes, followed by the addition of 2-chloro-N-methoxy-N-methyl-isonicotinamide (203 mg, 1.01 mmol). The reaction was stirred overnight, during which the ice-bath warmed to room temperature. The resultant solution was quenched with 10% HCl and diluted with EtOAc. The organics were washed with 10% HCl and saturated sodium bicarbonate, dried with sodium sulfate, and concentrated in vacuo to afford the protected diaryl ketone.

A 10 mL round-bottom flask was charged with the crude ketone, HCl in dioxane (2.15 mL, 4.0M), and water (0.72 mL). The solution was warmed to 80° C. and stirred overnight. The following day, the reaction was neutralized with saturated sodium bicarbonate and diluted with EtOAc. The organics were washed with 10% HCl and saturated sodium bicarbonate, dried with sodium sulfate, concentrated in vacuo, and purified via automated silica gel chromatography to afford the desired deprotected chloropyridine: $^1$H NMR (400 MHz, CDCl$_3$) δ 8.54 (d, 1H), 8.36 (d, 1H), 8.20 (d, 1H), 8.18 (d, 1H), 8.00 (dd, 1H), 7.66-7.80 (m, 2H), 7.56 (dd, 1H); MS (ES) M+H expect 509.9, found 509.9.

Example 301: 4-Chloro-N-[5-chloro-2-(pyridine-2-carbonyl)-pyridin-3-yl]-3-trifluoromethyl-benzenesulfonamide

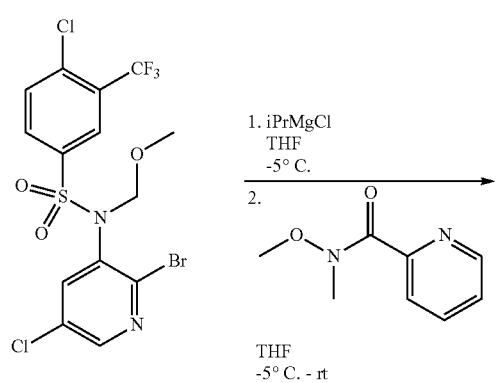

-continued

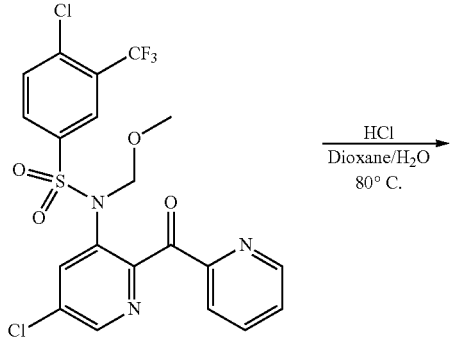

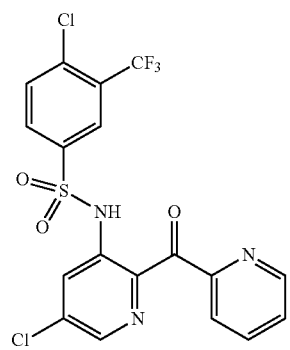

Following the procedure for example 300, 4-chloro-N-[5-chloro-2-(pyridine-2-carbonyl)-pyridin-3-yl]-3-trifluoromethyl-benzenesulfonamide was produced from N-(2-bromo-5-chloro-pyridin-3-yl)-4-chloro-N-methoxymethyl-3-trifluoromethyl-benzenesulfonamide (200 mg, 0.405 mmol) and pyridine-2-carboxylic acid methoxy-methyl-amide (135 mg, 0.810 mmol): $^1$H NMR (400 MHz, CDCl$_3$) δ 8.64 (dd, 1H), 8.36 (dd, 1H), 8.18 (dd, 1H), 8.07 (s, 1H), 7.78-7.88 (m, 3H), 7.54 (d, 1H), 7.45-7.51 (m, 1H); MS (ES) (M+H)$^+$ expected 476.0, found 475.9.

Example 302: 4-Chloro-N-[5-chloro-2-(6-chloro-pyridine-2-carbonyl)-pyridin-3-yl]-3-trifluoromethyl-benzenesulfonamide

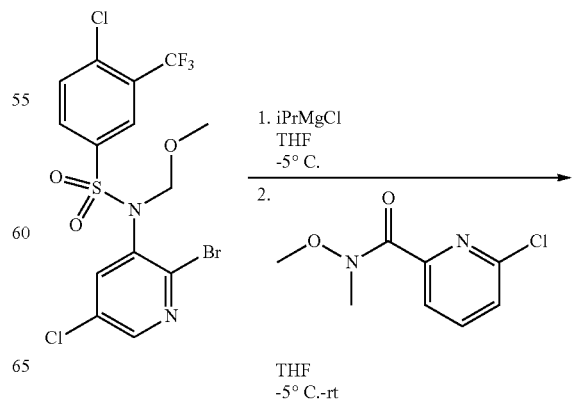

-continued

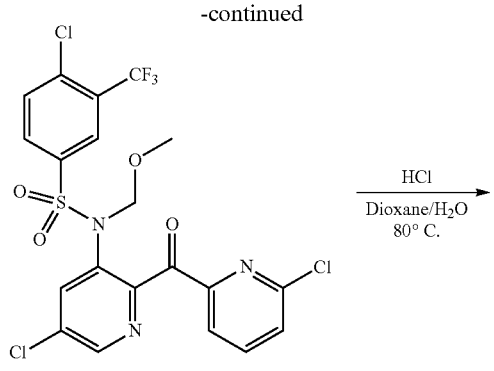

HCl
Dioxane/H₂O
80° C.

-continued

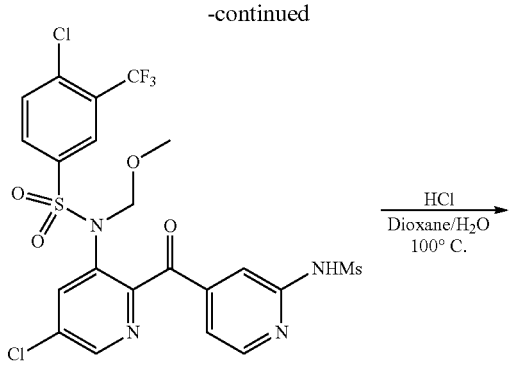

HCl
Dioxane/H₂O
100° C.

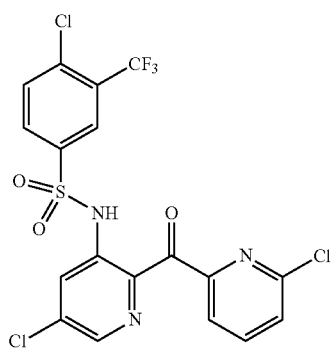

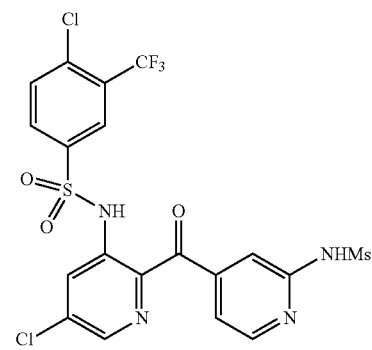

Following the procedure for example 300, 4-chloro-N-[5-chloro-2-(6-chloro-pyridine-2-carbonyl)-pyridin-3-yl]-3-trifluoromethyl-benzenesulfonamide was produced from N-(2-bromo-5-chloro-pyridin-3-yl)-4-chloro-N-methoxymethyl-3-trifluoromethyl-benzenesulfonamide (250 mg, 0.506 mmol) and 6-chloro-pyridine-2-carboxylic acid methoxymethyl-amide (203 mg, 1.01 mmol).

Following the procedure for 300, 4-chloro-N-[5-chloro-2-(2-methanesulfonylamino-pyridine-4-carbonyl)-pyridin-3-yl]-3-trifluoromethyl-benzenesulfonamide was produced from N-(2-bromo-5-chloro-pyridin-3-yl)-4-chloro-N-methoxymethyl-3-trifluoromethyl-benzenesulfonamide (784 mg, 1.59 mmol) and 2-methanesulfonylamino-N-methoxy-N-methyl-isonicotinamide (165 mg, 0.635 mmol): MS (ES) (M+H)⁺ expected 569.0, found 568.9.

Example 303: 4-Chloro-N-[5-chloro-2-(2-methanesulfonylamino-pyridine-4-carbonyl)-pyridin-3-yl]-3-trifluoromethyl-benzenesulfonamide Example 304: 4-Chloro-N-[5-chloro-2-(6-hydroxy-pyridine-2-carbonyl)-pyridin-3-yl]-3-trifluoromethyl-benzenesulfonamide

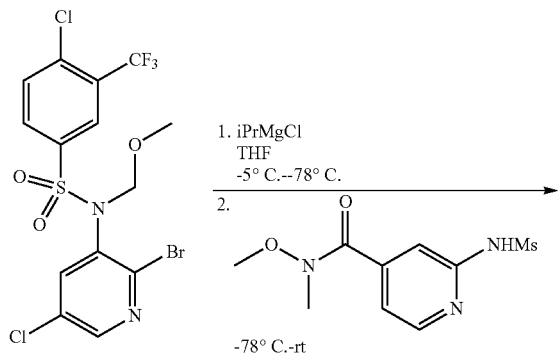

1. iPrMgCl
THF
−5° C.−−78° C.
2.

−78° C.-rt

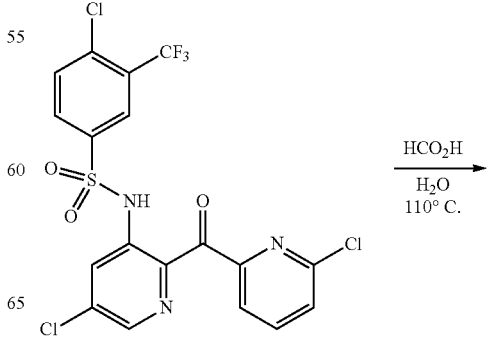

HCO₂H
H₂O
110° C.

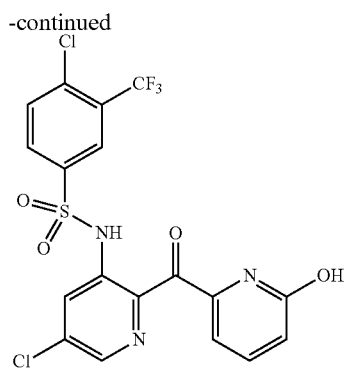

A 2 dram vial was charged with 4-chloro-N-[5-chloro-2-(6-chloro-pyridine-2-carbonyl)-pyridin-3-yl]-3-trifluoromethyl-benzenesulfonamide (65 mg, 0.127 mmol), formic acid (2.0 mL) and water (0.50 mL). The heterogeneous solution was warmed to 110° C. and stirred overnight. The following day, the resultant mixture was neutralized with saturated aqueous sodium bicarbonate, diluted with EtOAc, and the organic layer washed with saturated sodium bicarbonate. The combined organics were dried with sodium sulfate, concentrated in vacuo, and purified via automated silica gel chromatography to afford the desired hydroxypyridine: MS (ES) (M+H)$^+$ expected 492.0, found 491.9.

Example 305: 4-Chloro-N-[5-chloro-2-(2-hydroxy-pyridine-4-carbonyl)-pyridin-3-yl]-3-trifluoromethyl

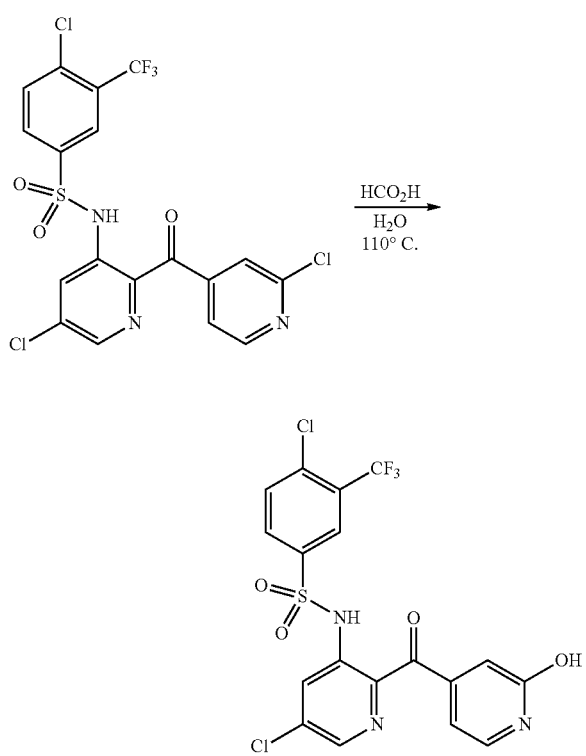

A 1 dram vial was charged with 4-chloro-N-[5-chloro-2-(2-chloro-pyridine-4-carbonyl)-pyridin-3-yl]-3-trifluoromethyl-benzenesulfonamide (25 mg, 0.045 mmol), formic acid (0.39 mL) and water (0.13 mL). The heterogeneous solution was warmed to 100° C. and stirred overnight. The following day, starting material remained; therefore, an additional 0.26 mL of formic acid was added. The reaction was subsequently warmed to 110° C. and stirred overnight. The resultant mixture was neutralized with saturated aqueous sodium bicarbonate, diluted with EtOAc, and the organic layer washed with saturated sodium bicarbonate. The combined organics were dried with sodium sulfate, concentrated in vacuo, and purified via automated silica gel chromatography to afford the desired hydroxypyridine: $^1$H NMR (400 MHz, C$_2$D$_6$SO) δ 11.95 (bs, 1H), 8.46 (s, 1H), 8.14 (s, 1H), 7.92 (d, 1H), 7.80-7.88 (m, 2H), 7.75 (d, 1H), 6.37 (s, 1H), 6.29 (d, 1H); MS (ES) (M+H)$^+$ expected 492.0, found 491.9.

Example 306: N-[2-(2-Amino-pyridine-4-carbonyl)-5-chloro-pyridin-3-yl]-4-chloro-3-trifluoromethyl-benzenesulfonamide

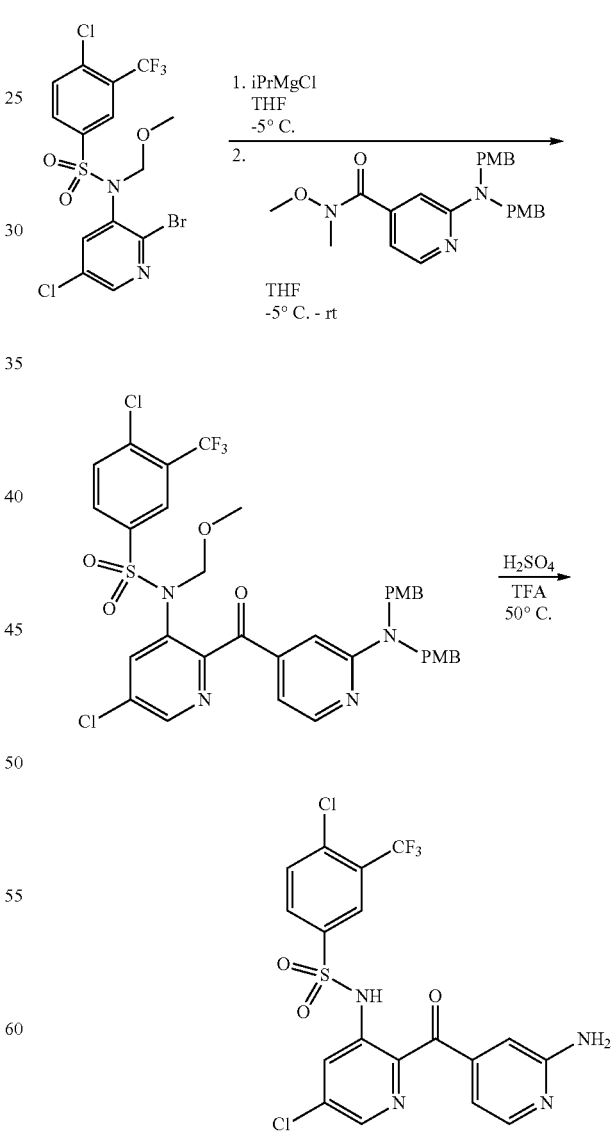

N-(2-Bromo-5-chloro-pyridin-3-yl)-4-chloro-N-methoxymethyl-3-trifluoromethyl-benzenesulfonamide (250 mg, 0.506 mmol) was placed in a dry 2-neck 10 mL round-bottom flask. The flask was evacuated and purged with nitrogen, followed by the addition of THF (1.0 mL). The homogeneous mixture was lowered to −5° C. and iPrMgCl (0.53 mL, 2.0 M) was added dropwise. Upon completion of the addition, the reaction was stirred 90 minutes, followed by the slow addition of 2-[bis-(4-methoxy-benzyl)-amino]-N-methoxy-N-methyl-isonicotinamide (427 mg, 1.01 mmol) dissolved in 1 mL THF. The reaction was stirred overnight, during which the ice-bath warmed to room temperature. The resultant solution was quenched with 10% HCl and diluted with EtOAc. The organics were washed with 10% HCl and saturated sodium bicarbonate, dried with sodium sulfate, and concentrated in vacuo to afford the protected diaryl ketone.

A 25 mL round-bottom flask was charged with the crude ketone, concentrated sulfuric acid (0.075 mL), and TFA (2.5 mL). The flask was sealed and stirred overnight. The following day, significant partially hydrolyzed N-hydroxymethyl sulfonamide remained; therefore, an additional 0.15 mL of sulfuric acid was added and the flask was heated to 50° C. for 8 h. The reaction was subsequently diluted with THF and neutralized with 2 M NaOH to pH 7-8. The resultant mixture was further diluted with EtOAc and the organics were washed with 10% HCl and saturated sodium bicarbonate, dried with sodium sulfate, concentrated in vacuo, and purified via automated silica gel chromatography then reverse phase HPLC to afford the desired aminopyridine: $^1$H NMR (400 MHz, CD$_3$OD) δ 8.42 (d, 1H), 8.10-8.14 (m, 2H), 7.86-7.94 (m, 2H), 7.70 (d, 1H), 6.91 (d, 1H), 6.80 (dd, 1H); MS (ES) (M+H)$^+$ expected 491.0, found 490.9.

Example 307: N-[2-(2-Amino-pyridine-4-carbonyl)-5-chloro-pyridin-3-yl]-4-methyl-3-trifluoromethyl-benzenesulfonamide

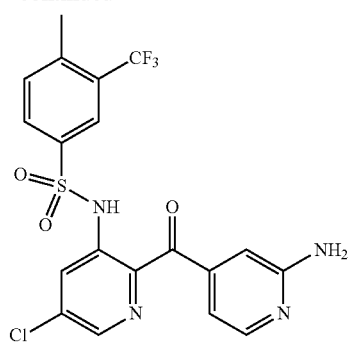

Following the procedure for example 306, N-[2-(2-amino-pyridine-4-carbonyl)-5-chloro-pyridin-3-yl]-4-methyl-3-trifluoromethyl-benzenesulfonamide was generated from N-(2-bromo-5-chloro-pyridin-3-yl)-4-methyl-N-methoxymethyl-3-trifluoromethyl-benzenesulfonamide (225 mg, 0.477 mmol) and 2-[bis-(4-methoxy-benzyl)-amino]-N-methoxy-N-methyl-isonicotinamide (427 mg, 1.01 mmol): $^1$H NMR (400 MHz, CDCl$_3$) δ 8.32 (d, 1H), 8.16 (s, 1H), 8.15 (d, 1H), 8.04 (s, 1H), 7.88 (dd, 1H), 7.38 (d, 1H), 6.84 (dd, 1H), 6.74 (s, 1H), 4.57 (s, 2H), 2.50 (s, 3H); MS (ES) (M+H)$^+$ expected 491.0, found 490.9.

Example 308: N-[5-Chloro-2-(2-methanesulfonylamino-pyridine-4-carbonyl)-pyridin-3-yl]-4-methyl-3-trifluoromethyl-benzenesulfonamide

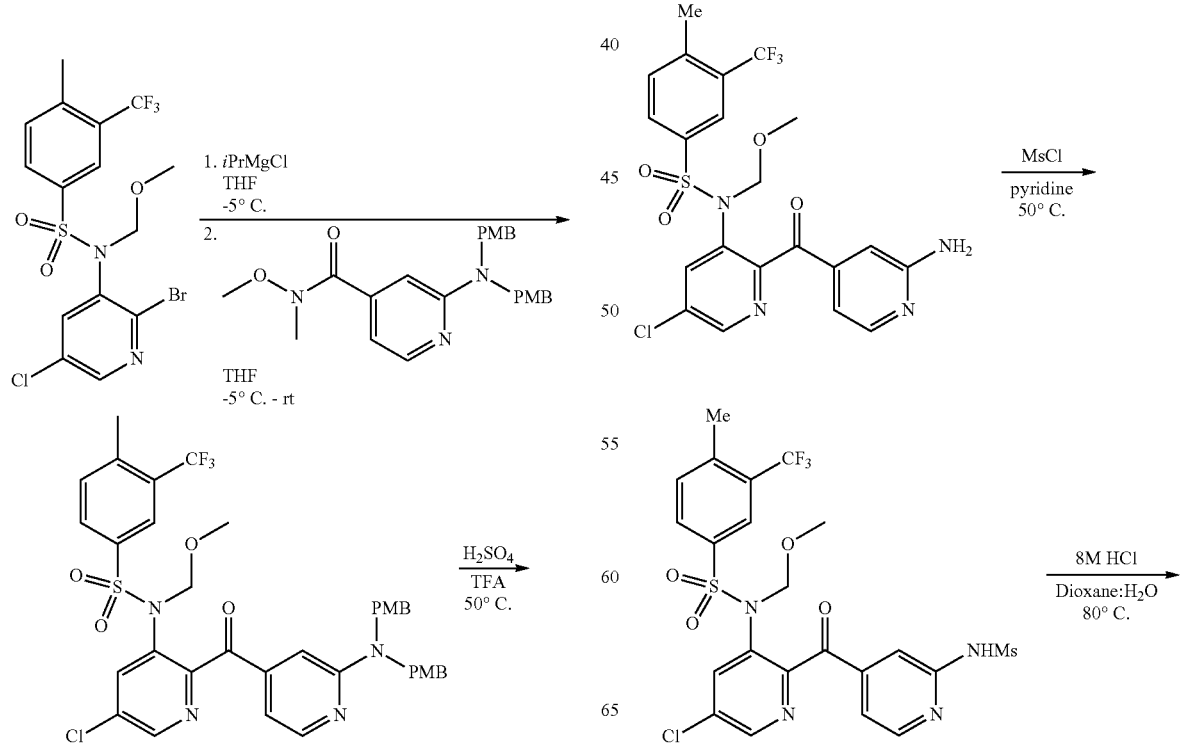

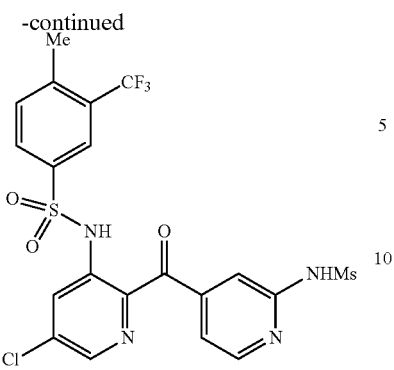

To a solution of N-[2-(2-amino-pyridine-4-carbonyl)-5-chloro-pyridin-3-yl]-N-methoxymethyl-4-methyl-3-trifluoromethyl-benzenesulfonamide (140 mg, 0.272 mmol) in pyridine (0.75 mL) was added methanesulfonyl chloride (0.042 mL, 0.544 mmol). The reaction was warmed to 50° C. and stirred 2.5 h. The resultant mixture was quenched with 10% HCl, diluted with EtOAc, and the organic layer washed with 10% HCl and saturated sodium bicarbonate. The combined organics were dried with sodium sulfate, concentrated in vacuo, and purified via automated silica gel chromatography to produce the desired sulfonamide.

A 10 mL round-bottom flask was charged with the protected sulfonamide (57 mg, (0.096 mmol), aqueous HCl (0.11 mL, 8.0 M), and dioxane (0.21 mL). The solution was warmed to 80° C. and stirred overnight. The following day, the reaction was neutralized with saturated sodium bicarbonate and diluted with EtOAc. The organics were washed with 10% HCl and saturated sodium bicarbonate, dried with sodium sulfate, concentrated in vacuo, and purified via automated silica gel chromatography to afford the desired methanesulfonamidino pyridine: $^1$H NMR (400 MHz, CD$_3$OD) δ 8.24 (d, 1H), 7.96 (d, 1H), 7.92 (d, 1H), 7.85 (d, 1H), 7.63 (d, 1H), 7.36 (d, 1H), 7.07-7.11 (m, 2H), 3.26 (s, 3H), 2.46 (s, 3H); MS (ES) (M+H)$^+$ expected 549.0, found 549.0.

Example 309: 2-Amino-N-{4-[5-chloro-3-(4-methyl-3-trifluoromethyl-benzenesulfonylamino)-pyridine-2-carbonyl]-pyridin-2-yl}-acetamide To a mixture of N-[2-(2-amino-pyridine-4-carbonyl)-5-chloro-pyridin-3-yl]-4-methyl-3-trifluoromethyl-benzenesulfonamide (800 mg, 1.69 mmol), Boc-glycine (742 mg, 4.24 mmol), diisopropylethylamine (1.9 mL, 10.14 mmol) in methylene chloride (4 mL) was added propylphosphonic anhydride (2.68 mL, 50% solution in EtOAc, 4.24 mmol) was added slowly. The resultant heterogeneous solution was allowed to stir overnight at 45° C. The following day, the reaction was diluted with EtOAc, the organics were washed with saturated sodium bicarbonate, aqueous saturated NH$_4$Cl and dried with sodium sulfate, concentrated in vacuo, and purified via automated silica gel chromatography to provide ({4-[5-chloro-3-(4-methyl-3-trifluoromethyl-benzenesulfonylamino)-pyridine-2-carbonyl]-pyridin-2-yl-carbamoyl}-methyl)-carbamic acid tert-butyl ester.

A solution of ({4-[5-chloro-3-(4-methyl-3-trifluoromethyl-benzenesulfonylamino)-pyridine-2-carbonyl]-pyridin-2-ylcarbamoyl}-methyl)-carbamic acid tert-butyl ester (45 mg) in CH$_2$Cl$_2$ was added TFA (200 ⌈L). The resulting mixture was stirred at room temperature for 3 h, concentrated under reduced pressure and the residue was re-dissolved in MeCN and purified by HPLC to provide 2-amino-N-{4-[5-chloro-3-(4-methyl-3-trifluoromethyl-benzenesulfonylamino)-pyridine-2-carbonyl]-pyridin-2-yl}-acetamide. $^1$H NMR (400 MHz, DMSO-d$_6$) δ 11.16 (s, 1H), 8.48-8.46 (m, 1H), 8.19 (s, 1H), 8.08 (br m, 3H), 7.89 (s, 1H), 7.78-7.76 (m, 2H), 7.55 (d, J=7.6 Hz, 1H), 7.28-7.26 (m, 1H), 3.85 (s, 2H), 2.43 (s, 3H); MS m/z 528.0 (M+H)$^+$.

Example 310: 4-chloro-N-{2-[2-(dimethylamino-methyleneamino)-pyridine-4-carbonyl]-5-methyl-pyridin-3-yl}-N-methoxymethyl-3-trifluoromethyl-benzenesulfonamide

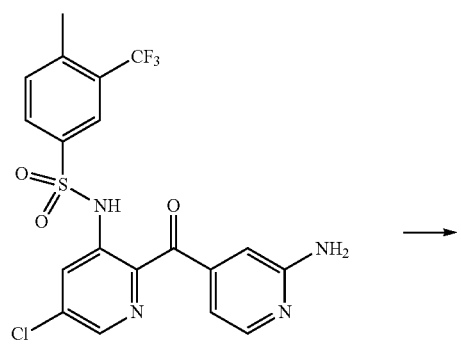

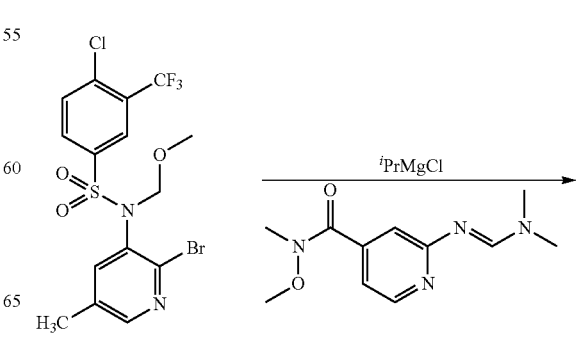

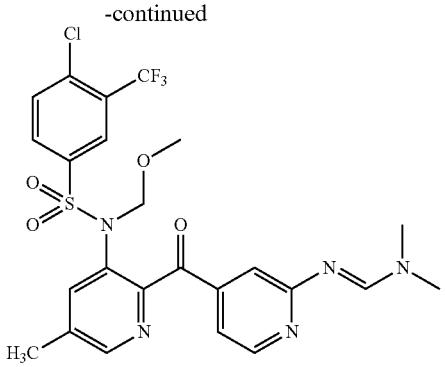

To a solution of N-(2-bromo-5-methyl-pyridin-3-yl)-4-chloro-N-methoxymethyl-3-trifluoromethyl-benzenesulfonamide (367 mg, 0.775 mmol) in THF (2 mL) under nitrogen atmosphere at 0° C. was added dropwise isopropylmagnesium chloride (2 M solution in THF, 0.94 mL, 1.866 mmol). The mixture was then stirred for 30 min at 0° C. followed by the addition of a solution of 2-(dimethyl-amino-methyleneamino)-N-methoxy-N-methyl-isonicotinamide (349 mg, 1.47 mmol) in THF (1 mL) at 0° C. The mixture was stirred at room temperature for 6 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 50% EtOAc-hexanes) to obtain 4-chloro-N-{2-[2-(dimethylamino-methyleneamino)-pyridine-4-carbonyl]-5-methyl-pyridin-3-yl}-N-methoxymethyl-3-trifluoromethyl-benzene sulfonamide (230 mg) in 52% yield. ESMS m/z (relative intensity): 570.1 (M+H)$^+$ (100).

Example 311: N-[2-(2-amino-pyridine-4-carbonyl)-5-methyl-pyridin-3-yl]-4-chloro-3-trifluoromethyl-benzenesulfonamide

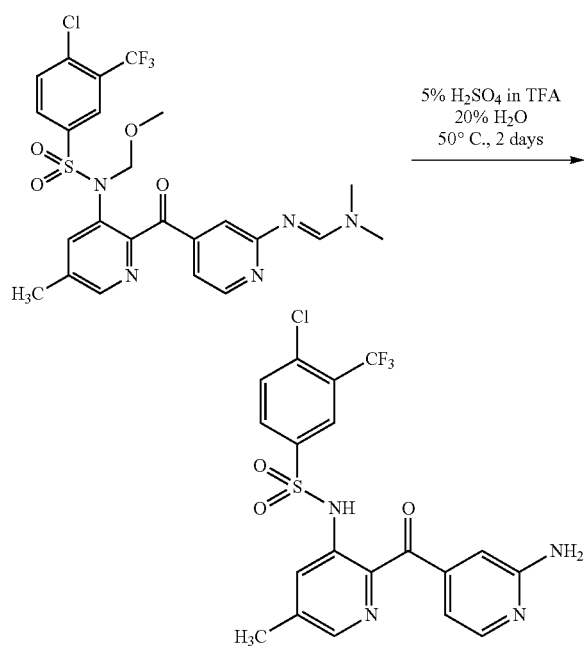

A mixture of 4-chloro-N-{2-[2-(dimethylamino-methyleneamino)-pyridine-4-carbonyl]-5-methyl-pyridin-3-yl}-N-methoxymethyl-3-trifluoromethyl-benzene sulfonamide (23 mg, mmol) in 5% H$_2$SO$_4$ in TFA (4 mL) and water (1 mL) was stirred at 50° C. for 2 days. The reaction mixture was cooled to room temperature, diluted with water (5 mL) and treated with saturated aqueous NaHCO$_3$ solution slowly till pH 7-8. The mixture was extracted with EtOAc (2×25 mL), dried (anhydrous Na$_2$SO$_4$) and concentrated. The obtained residue was column purified (SiO$_2$, 10% MeOH—CH$_2$Cl$_2$) to afford N-[2-(2-amino-pyridine-4-carbonyl)-5-methyl-pyridin-3-yl]-4-chloro-3-trifluoro methyl-benzenesulfonamide (12 mg) in 63% yield. $^1$H NMR (400 MHz, CDCl$_3$) 510.75 (s, 1H), 8.24 (s, 1H), 8.18 (m, 1H), 8.07 (dd, 1H), 7.95 (d, 1H), 7.75 (d, 1H), 7.63 (d, 1H), 7.15 (s, 1H), 6.95 (d, 1H), 2.25 (s, 3H); ESMS m/z (relative intensity): 471.0 (M+H)$^+$ (100).

Example 312: 4-Chloro-N-(2-formyl-5-methyl-pyridin-3-yl)-N-methoxymethyl-3-trifluoromethyl-benzenesulfonamide

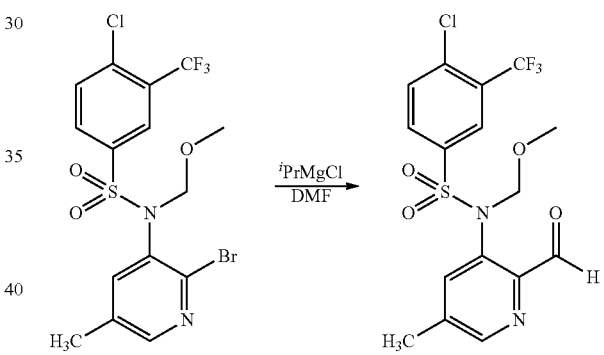

To a solution of N-(2-bromo-5-methyl-pyridin-3-yl)-4-chloro-N-methoxymethyl-3-trifluoromethyl-benzenesulfonamide (750 mg, 1.59 mmol) in THF (3 mL) under nitrogen atmosphere at 0° C. was added dropwise isopropylmagnesium chloride (2 M solution in THF). The mixture was then stirred for 30 min at 0° C. followed by the addition of N,N-dimethylformamide (1.19 mL, excess) at 0° C. The mixture was stirred at room temperature for 3 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 30% EtOAc-hexanes) to obtain 4-chloro-N-(2-formyl-5-methyl-pyridin-3-yl)-N-methoxymethyl-3-trifluoromethyl-benzenesulfonamide (300 mg) in 44.7% yield. ESMS m/z (relative intensity): 390.9 (M−32+H)$^+$ (40), 423 (M+H)$^+$ (40), 444.9 (M+Na)$^+$ (40).

Example 313: 4-Chloro-N-{5-chloro-2-[hydroxy-(1H-pyrazolo[3,4-b]pyridin-4-yl)-methyl]-pyridin-3-yl}-3-trifluoromethyl-benzenesulfonamide

Example 314: 4-Chloro-N-methoxymethyl—N-[5-methyl-2-(1H-pyrazolo[3,4-b]pyridine-4-carbonyl)-pyridin-3-yl]-3-trifluoromethyl-benzenesulfonamide

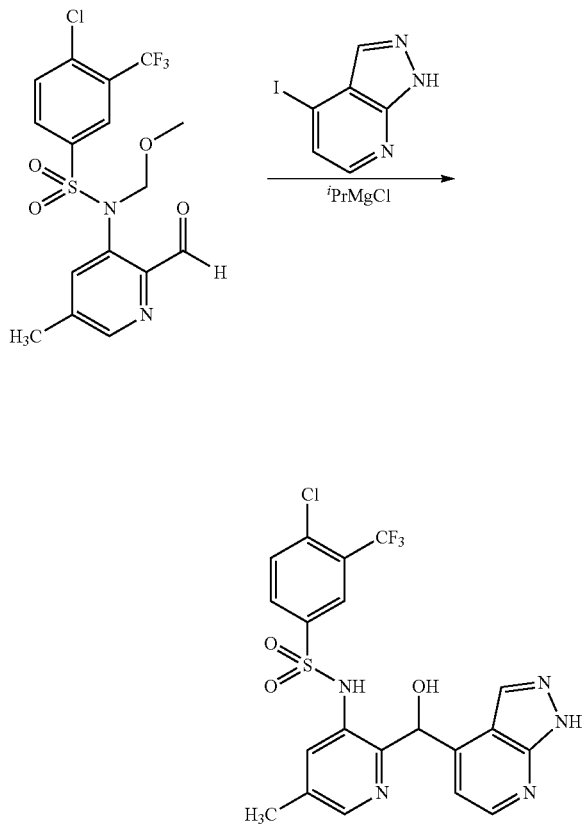

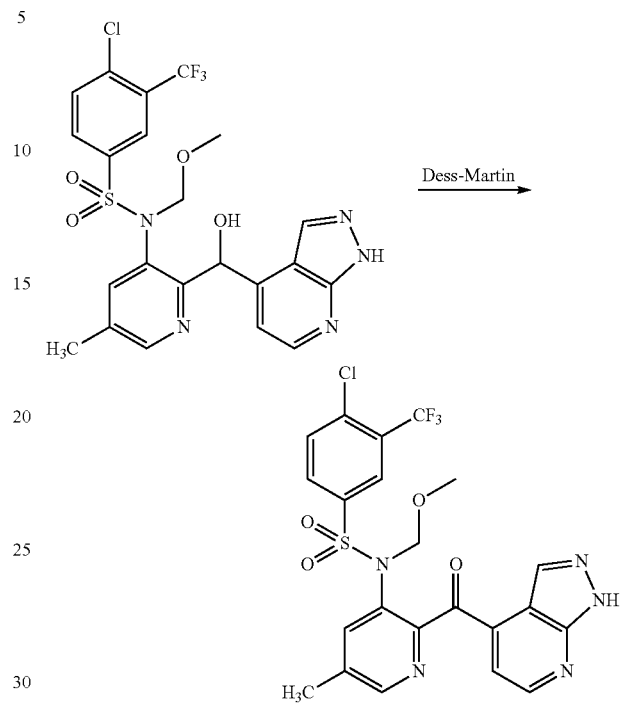

To a solution of 4-iodo-1H-pyrazolo[3,4-b]pyridine (174.2 mg, 0.71 mmol) in THF (3 mL) under nitrogen atmosphere at 0° C. was added dropwise isopropylmagnesium chloride (2 M solution in THF, 1.06 mL, 2.13 mmol). The resulting yellow suspension was then stirred for 30 min at 0° C. followed by the addition of a solution of 4-chloro-N-(2-formyl-5-methyl-pyridin-3-yl)-N-methoxymethyl-3-trifluoromethyl-benzenesulfonamide (300 mg, 0.71 mmol) in THF (2 mL) at 0° C. The mixture was stirred at room temperature for 3 hours, quenched with saturated aqueous NH$_4$Cl solution (5 mL) and extracted with EtOAc (2×25 mL). Combined organic layers were washed with saturated aqueous NH$_4$Cl solution (25 mL), brine (25 mL), dried (anhydrous Na$_2$SO$_4$) and concentrated under reduced pressure. Obtained residue was column purified (SiO$_2$, 50% EtOAc-hexanes) to obtain 4-chloro-N-{5-chloro-2-[hydroxy-(1H-pyrazolo[3,4-b]pyridin-4-yl)-methyl]-pyridin-3-yl}-3-trifluoromethyl-benzene sulfonamide (192 mg) in 50% yield. ESMS m/z (relative intensity): 542 (M+H)$^+$ (100), 564 (M+Na)$^+$ (10).

To a solution of 4-chloro-N-{5-chloro-2-[hydroxy-(1H-pyrazolo[3,4-b]pyridin-4-yl)-methyl]-pyridin-3-yl}-3-trifluoromethyl-benzene sulfonamide (192 mg, 0.355 mmol) in CH$_2$Cl$_2$ (5 mL) was added Dess-Martin periodinane (302 mg, 0.71 mmol) and stirred for 24 h at room temperature. 10% Na$_2$S$_2$O$_3$ (5 mL) and saturated aqueous NaHCO$_3$ solution (5 mL) was added and stirred for 30 min. Aqueous layer was separated and extracted with EtOAc (2×25 mL). Combined organic layers were washed with saturated aqueous NaHCO$_3$ solution (20 mL), brine (20 mL), dried (anhydrous Na$_2$SO$_4$), concentrated and purified (SiO$_2$, 50% EtOAc-hexanes) to obtain 4-chloro-N-methoxymethyl-N-[5-methyl-2-(1H-pyrazolo[3,4-b]pyridine-4-carbonyl)-pyridin-3-yl]-3-trifluoromethyl-benzenesulfonamide (128 mg) in 67% yield. ESMS m/z (relative intensity): 508 (M−32+H)$^+$ (40), 540 (M+H)$^+$ (40), 562 (M+Na)+(40).

Example 315: 4-Chloro-N-[5-methyl-2-(1H-pyrazolo[3,4-b]pyridine-4-carbonyl)-pyridin-3-yl]-3-trifluoromethyl-benzenesulfonamide

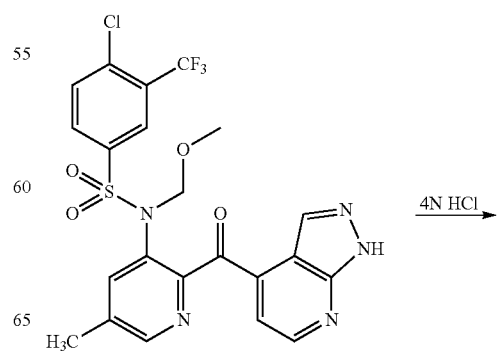

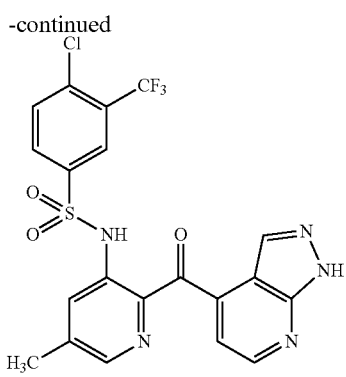

A mixture of 4-chloro-N-methoxymethyl-N-[5-methyl-2-(1H-pyrazolo[3,4-b]pyridine-4-carbonyl)-pyridin-3-yl]-3-trifluoromethyl-benzenesulfonamide (50 mg, 0.092 mmol) in 4M HCl in dioxane (4 mL) and water (1 mL) was stirred at 70° C. for overnight. Reaction mixture was cooled to room temperature, evaporated to dryness and treated with saturated aqueous NaHCO₃ solution till pH 7-8. The mixture was extracted with EtOAc (2×25 mL), dried (anhydrous Na₂SO₄) and concentrated. The obtained residue was purified by flash chromatography (SiO₂, 70% EtOAc-hexanes) to afford 4-chloro-N-[5-methyl-2-(1H-pyrazolo[3,4-b]pyridine-4-carbonyl)-pyridin-3-yl]-3-trifluoromethyl-benzenesulfonamide (28.9 mg) as yellow solid (after lyophilization) in 63% yield. $^1$H NMR (400 MHz, CDCl$_3$) δ10.75 (s, 1H), 8.65 (d, 1H), 8.24 (m, 1H), 8.14 (d, 1H), 8.08 (s, 1H), 7.94-7.99 (m, 2H), 7.59 (d, 1H), 7.58 (d, 1H), 2.48 (s, 3H); ESMS m/z (relative intensity): 496 (M+H)$^+$ (100).

Example 316: (S)-4-Chloro-N-(5-chloro-2-(4-hydroxy-3,3-dimethylpiperidine-1-carbonyl)pyridine-3-yl)-3-(trifluoromethyl)benzenesulfonamide

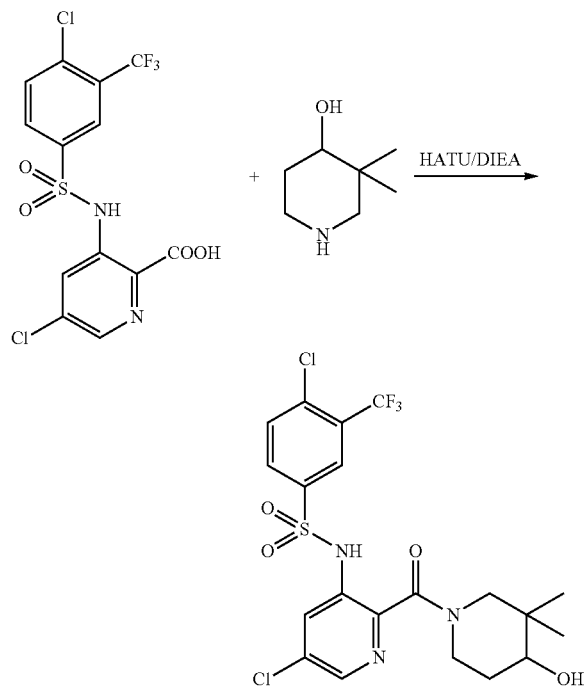

General synthesis of amides: A 10 mL scintillation vial was charged with the 5-chloro-3-(4-chloro-3-trifluoromethyl-benzenesulfonylamino)-pyridine-2-carboxylic acid (164 mg, 0.4 mmol), freshly prepared 3,3-dimethylpiperidin-4-ol (0.56 mmol) ((M+H+), 130.1), HATU (192 mg, 0.5 mmol), DIEA (260 mg, 2 mmol) and anhydrous DMF (1.5 mL). The resultant solution was heated to 70° C. and stirred for 2 h. After cooled to room temperature, the mixture was purified via preparative HPLC and dried (lyophilizer) to afford (S)-4-chloro-N-(5-chloro-2-(4-hydroxy-3,3-dimethylpiperidine-1-carbonyl)pyridine-3-yl)-3-(trifluoromethyl) benzenesulfonamide (1:2 mixture of rotamers): $^1$H NMR (400 MHz, CDCl$_3$) (major rotamer) δ 9.54 (s, 1H), 8.26 (d, 1H), 8.12 (d, 1H), 8.00 (d, 1H), 7.88 (dd, 1H), 7.62 (d, 1H), 4.05 (m, 1H), 3.70 (d, 1H), 3.50 (m, 2H), 3.40 (m, 1H), 3.10 (d, 1H), 1.82 (m, 2H), 1.00 (s, 3H), 0.92 (s, 3H); MS (ES) (M+H)$^+$ expected 526.0, found 526.0.

Example 317: 5-Chloro-3-(4-chloro-3-(trifluoromethyl)phenylsulfonamido)-N-methyl-N-(pyridin-3-yl)picolinamide

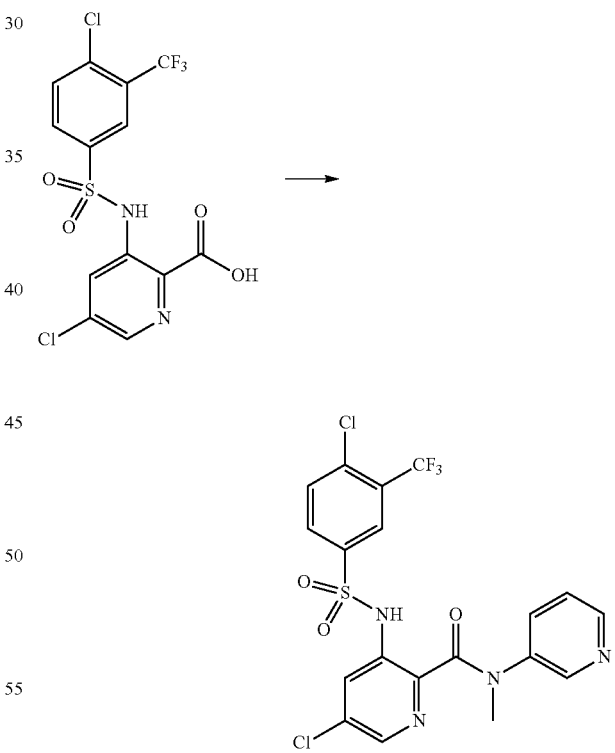

5-Chloro-3-(4-chloro-3-(trifluoromethyl)phenylsulfonamido)-N-methyl-N-(pyridin-3-yl)picolinamide was prepared according to method described in example 316: $^1$H NMR (400 MHz, CDCl$_3$) δ 8.62 (dd, 1H), 8.52 (s, 1H), 8.22 (d, 1H), 8.02 (dd, 1H), 7.96 (d, 1H), 7.80 (s, 1H), 7.68 (m, 3H), 3.50 (s, 3H); MS (ES) (M+H)$^+$ expect 505.0, found 505.0.

Example 318: N-[5-Chloro-2-(5-methoxy-1H-pyrrolo[2,3-b]pyridine-4-carbonyl)-pyridin-3-yl]-4-methyl-3-trifluoromethyl-benzenesulfonamide

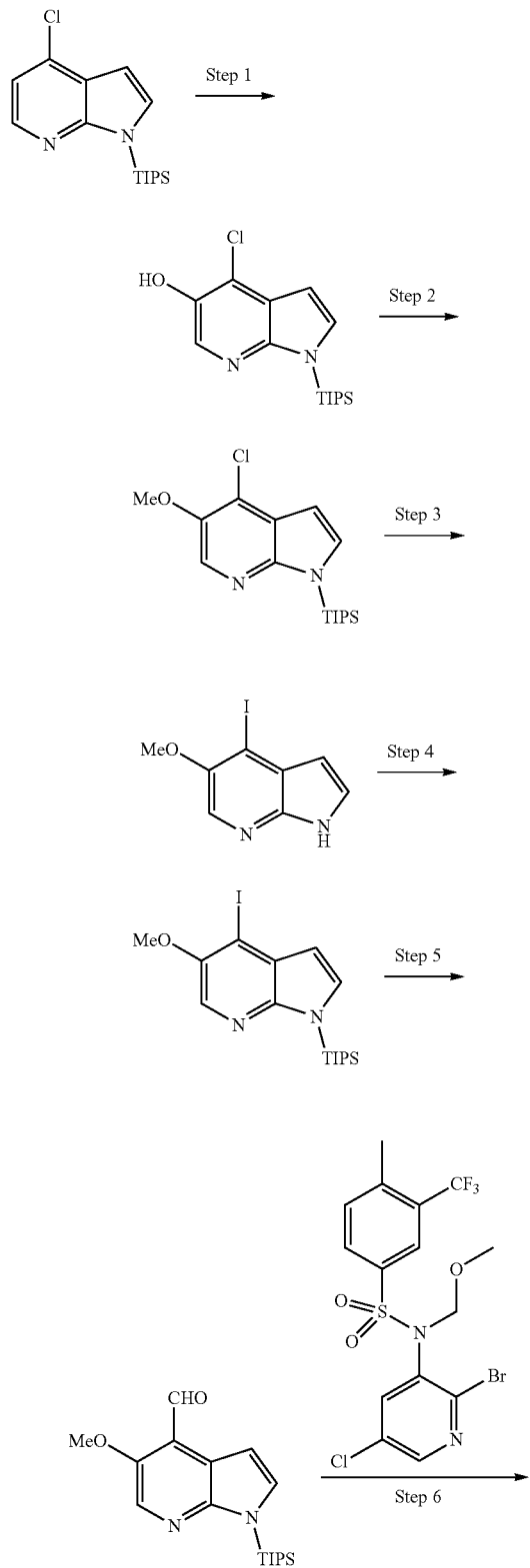

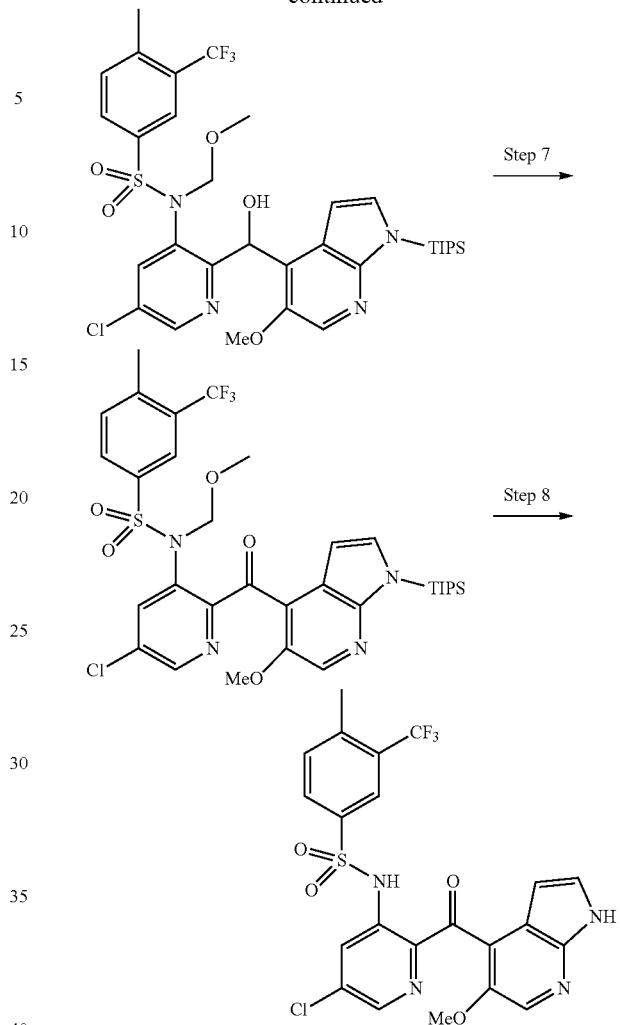

Step 1: A 25 mL round-bottom flask was charged with 4-chloro-1-triisopropylsilanyl-1H-pyrrolo[2,3-b]pyridine (308 mg, 1.0 mmol), THF (4 mL) and the mixture was cooled to −78° C. A sec-butyllithium solution (1.4 M in cyclohexane, 1.6 mL, 2.2 equiv.) was added dropwise and after 30 minutes, a solution of (R)-camphorsulfonyl oxaziridine (573 mg, 2.5 equiv.) in 4 mL of THF was added rapidly. The reaction mixture was then stirred for another 25 minutes at −78° C. and quenched with saturated ammonium chloride solution. The mixture was allowed to reach room temperature and then extracted with ethyl acetate. The combined organic layers were washed with brine and dried over MgSO$_4$. Solvent was removed and the crude material was purified by flash chromatography on silica gel (10% EtOAc/hexanes). The desired product was obtained as a colorless liquid (160 mg, 49%). MS: (M+H)/z=325.

Step 2: The product obtained from step 1 above (60 mg, 0.18 mmol) was dissolved in 2 mL of methanol. Trimethylsilyl diazomethane (2.0 M in ether, 1 mL) was added and the reaction mixture was stirred overnight at room temperature. Solvent was removed and the crude material was purified by flash chromatography on silica gel (10% EtOAc/hexanes). The desired product was obtained as a colorless liquid (58 mg, 93%). MS: (M+H)/z=339.

Step 3: The product obtained from step 2 above (106 mg, 0.31 mmol) was dissolved in 5 mL of acetonitrile. Then NaI (470 mg, 10 equiv.) was added followed by acetyl chloride (67 FL, 3 equiv.). The reaction mixture was allowed to stir at 80° C. for 2 hours, and then excess acetonitrile was removed in vacuo. A mixture of 10% $K_2CO_3$ (10 mL) and 10% sodium bisulfite (10 mL) was added to the residue and the mixture was extracted with ethyl acetate and washed with brine. The combined organic layer was dried over $MgSO_4$ and concentrated in vacuo to give the crude product. To a solution of this crude product in THF (3 mL) was added 1 M NaOH (0.5 mL). The mixture was stirred for 1 hour at room temperature and quenched with saturated ammonium chloride solution. The mixture was extracted with ethyl acetate, and the extracts were washed with brine, dried over $MgSO_4$ and concentrated in vacuo. The crude material was purified by flash chromatography on silica gel (20% EtOAc/hexanes). The desired product was obtained as a white solid (60 mg, 86%). MS: (M+H)/z=275.

Step 4: The product obtained from step 3 above (157 mg, 0.57 mmol) was dissolved in 5 mL of anhydrous DMF. Then NaH (25 mg, 60% dispersion in mineral oil) was added. After 30 minutes, triisopropylsilyl chloride (133 FL, 1.1 equiv.) was added and the reaction mixture was stirred overnight at room temperature. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (10% EtOAc/hexanes). The desired product was obtained as an oil (222 mg, 90%). MS: (M+H)/z=431.

Step 5: The product obtained from step 4 above (120 mg, 0.28 mmol) was dissolved in 3 mL of anhydrous THF and cooled to 0° C. Then isopropylmagnesium chloride (280 FL, 2.0 M in THF) was added. After 45 minutes, anhydrous DMF (215 FL, 10 equiv.) was added and the reaction mixture was warmed up to room temperature and stirred overnight. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (5% EtOAc/hexanes). The desired product was obtained as a pale yellow solid (46 mg, 50%). MS: (M+H)/z=333.

Step 6: To a solution of N-(2-bromo-5-chloro-pyridin-3-yl)-N-methoxymethyl-4-methyl-3-trifluoromethyl-benzenesulfonamide (97 mg, 0.21 mmol) in THF (3 mL) at 0° C. was added isopropylmagnesium chloride (187 FL, 2.0 M in THF) dropwise. After 45 minutes, a solution of the product obtained from step 5 above (62 mg, 0.19 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (20% EtOAc/hexanes). The desired product was obtained as a foaming yellow solid (95 mg, 70%). MS: (M+H)/z=727.

Step 7: The product obtained from step 6 above (77 mg, 0.11 mmol) was dissolved in 3 mL of dichloromethane. To the resultant solution was added Dess-Martin periodinane (72 mg, 1.6 equiv.) and stirred overnight at room temperature. The reaction was quenched with 10% $Na_2S_2O_3$, and the mixture was extracted with ethyl acetate. The extracts were washed with saturated $NaHCO_3$, brine, dried over $MgSO_4$ and concentrated in vacuo. The crude material was purified by flash chromatography on silica gel (20% EtOAc/hexanes). The desired product was obtained as a foaming yellow solid (59 mg, 77%). MS: (M+H)/z=725.

Step 8: The product obtained from step 7 above (59 mg, 0.081 mmol) was dissolved in 4 mL of HCl-dioxane (4.0 M) and 1 mL of water. The mixture was heated at 85° C. for 30 minutes and quenched with saturated $NaHCO_3$. The mixture was extracted with ethyl acetate. The extracts were washed with brine, dried over $MgSO_4$ and concentrated in vacuo. The crude material was purified by flash chromatography on silica gel (80% EtOAc/hexanes). The desired product was obtained as a yellow solid (34 mg, 80%). $^1$HNMR: (400 MHz, $CDCl_3$) δ 8.17 (dd, J=7.2, 2.4 Hz, 2H), 8.13 (d, J=1.6 Hz, 1H), 8.12 (s, 1H), 7.97 (dd, J=8.0, 2.0 Hz, 1H), 7.43 (d, J=8.0 Hz, 1H), 7.34 (t, J=2.8 Hz, 1H), 6.10 (dd, J=3.6, 2.0 Hz, 1H), 3.68 (s, 3H), 2.54 (s, 3H); MS: (M+H)/z=525.

Example 319: N-[5-Chloro-2-(7-hydroxy-5-methoxy-1H-pyrrolo[2,3-b]pyridine-4-carbonyl)-pyridin-3-yl]-4-methyl-3-trifluoromethyl benzenesulfonamide

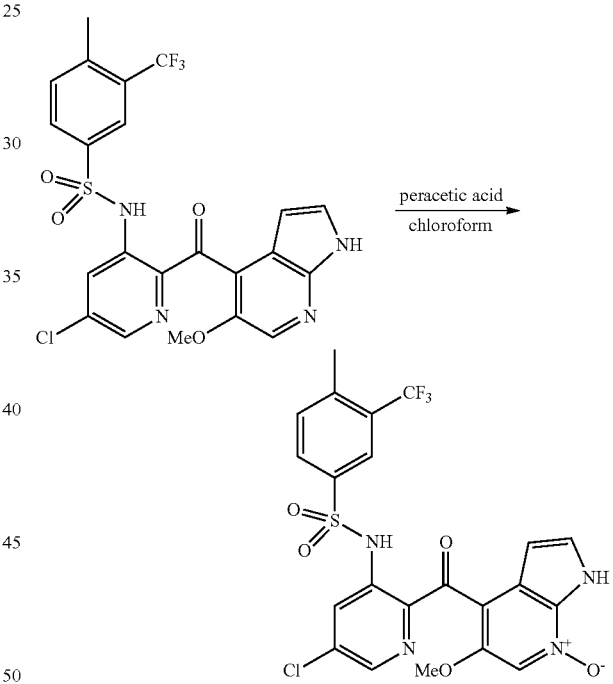

To a stirred solution of N-[5-chloro-2-(5-methoxy-1H-pyrrolo[2,3-b]pyridine-4-carbonyl)-pyridin-3-yl]-4-methyl-3-trifluoromethyl-benzenesulfonamide (13 mg, 0.025 mmol) in chloroform (5 mL) was added peracetic acid (20 FL, 32% wt in acetic acid). The reaction mixture was stirred for 2 days at room temperature and quenched with saturated $NaHCO_3$. The mixture was extracted with ethyl acetate. The extracts were washed with brine, dried over $MgSO_4$ and concentrated in vacuo. The crude material was purified by flash chromatography on silica gel (80% EtOAc/hexanes). The desired product was obtained as a yellow solid (11 mg, 80%). $^1$H NMR: (400 MHz, $CDCl_3$) δ 8.16 (s, 2H), 8.11 (s, 1H), 8.00 (s, 1H), 7.96 (dd, J=8.4, 2.0 Hz, 1H), 7.43 (d, J=8.4 Hz, 1H), 7.34 (d, J=3.6 Hz, 1H), 6.25 (d, J=3.2 Hz, 1H), 3.61 (s, 3H), 2.53 (s, 3H); MS: (M+H)/z=541.

Example 320: 5-Chloro-3-(4-chloro-3-trifluoromethyl-benzenesulfonylamino)-pyridine-2-carboxylic acid ethyl-(1H-pyrazol-3-yl)-amide

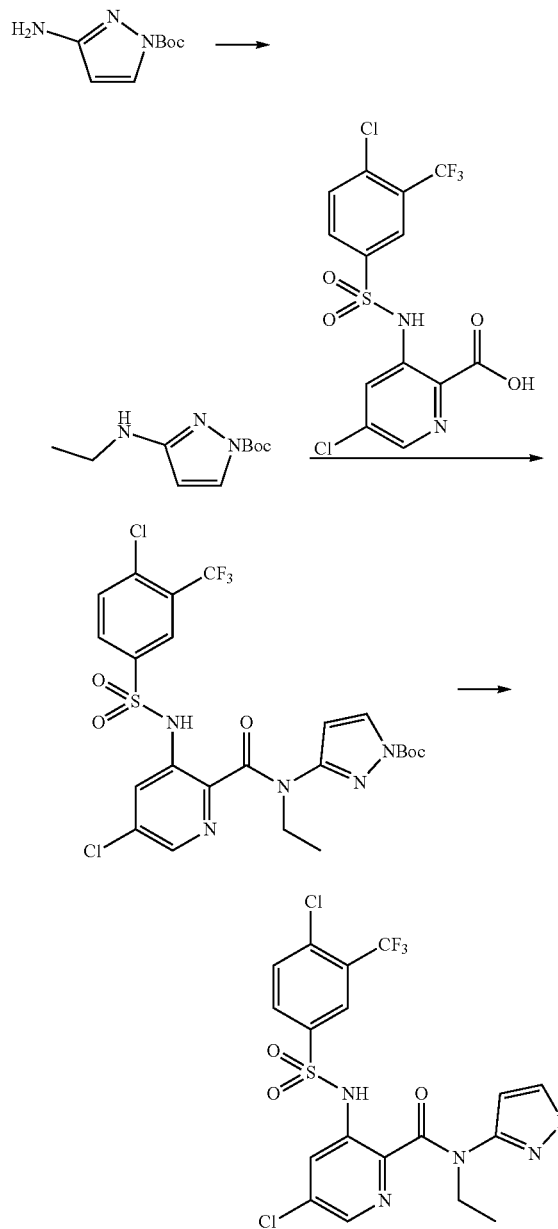

Step 1: A mixture of acetaldehyde (0.074 mL, 1.32 mmol), acetic acid (0.078 mL, 1.32 mmol) and 3-amino-pyrazole-1-carboxylic acid tert-butyl ester (200 mg, 1.1 mmol) in DCM (5 mL) was stirred at RT for 1 hour. To the mixture was added sodium triacetoxyborohydride (467 mg, 2.2 mmol), stirred overnight. The mixture was extracted with ethyl acetate, washed with water, dried and concentrated. The residue was purified by flash column to afford 3-amino-pyrazole-1-carboxylic acid tert-butyl ester.

Step 2: A mixture of 5-chloro-3-(4-chloro-3-trifluoromethyl-benzenesulfonylamino)-pyridine-2-carboxylic acid (100 mg, 0.24 mmol), 3-amino-pyrazole-1-carboxylic acid tert-butyl ester (51 mg, 0.24 mmol), HATU (160 mg, 0.42 mmol), and TEA (0.13 mL) in DMF (1.5 mL) was stirred at room temperature overnight. It was purified with HPLC to give 3-{[5-chloro-3-(4-chloro-3-trifluoromethyl-benzenesulfonylamino)-pyridine-2-carbonyl]-ethyl-amino}-pyrazole-1-carboxylic acid tert-butyl ester.

Step 3: 3-{[5-chloro-3-(4-chloro-3-trifluoromethyl-benzenesulfonylamino)-pyridine-2-carbonyl]-ethyl-amino}-pyrazole-1-carboxylic acid tert-butyl ester from step 2 was dissolved in a mixture of DCM and TFA (1:1) (5 mL). It was stirred at RT for 1 hour, concentrated, purified with HPLC to give 5-chloro-3-(4-chloro-3-trifluoromethyl-benzenesulfonylamino)-pyridine-2-carboxylic acid ethyl-(1H-pyrazol-3-yl)-amide: 1H NMR (400 MHz, CDCl$_3$) δ 8.11 (d, 1H), 8.0 (d, 1H), 7.94 (m, 1H), 7.88 (br, 1H), 7.6 (d, 1H), 7.37 (br, 1H), 5.8 (s, 1H), 3.8 (m, 2H), 1.1 (m, 3H); MS m/z: 508 (M+H)$^+$.

Example 321: 5-Chloro-3-(4-methyl-3-trifluoromethyl-benzenesulfonylamino)-pyridine-2-carboxylic acid ethyl-(1H-pyrazol-3-yl)-amide

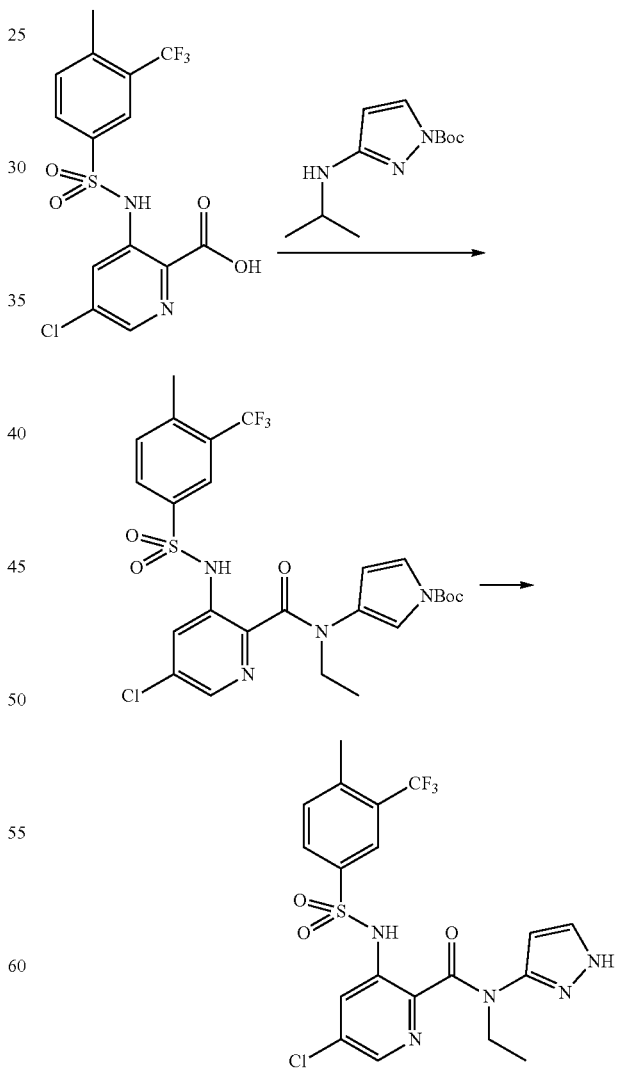

The title compound was prepared by procedure analogous to that described in Example 320 using 5-chloro-3-(4- methyl-3-trifluoromethyl-benzenesulfonylamino)-pyridine-2-carboxylic acid: ¹H NMR (400 MHz, CDCl₃) δ 8.1 (d, 2H), 7.9 (d, 2H), 7.3 (m, 2H), 5.5 (s, 1H), 3.8 (m, 2H), 2.5 (s, 3H), 1.1 (m, 3H); MS m/z: 488 (M+H)⁺.

Example 322: Chloro-3-(4-chloro-3-trifluoromethyl-benzenesulfonylamino)-pyridine-2-carboxylic acid isopropyl-(1H-pyrazol-3-yl)-amide

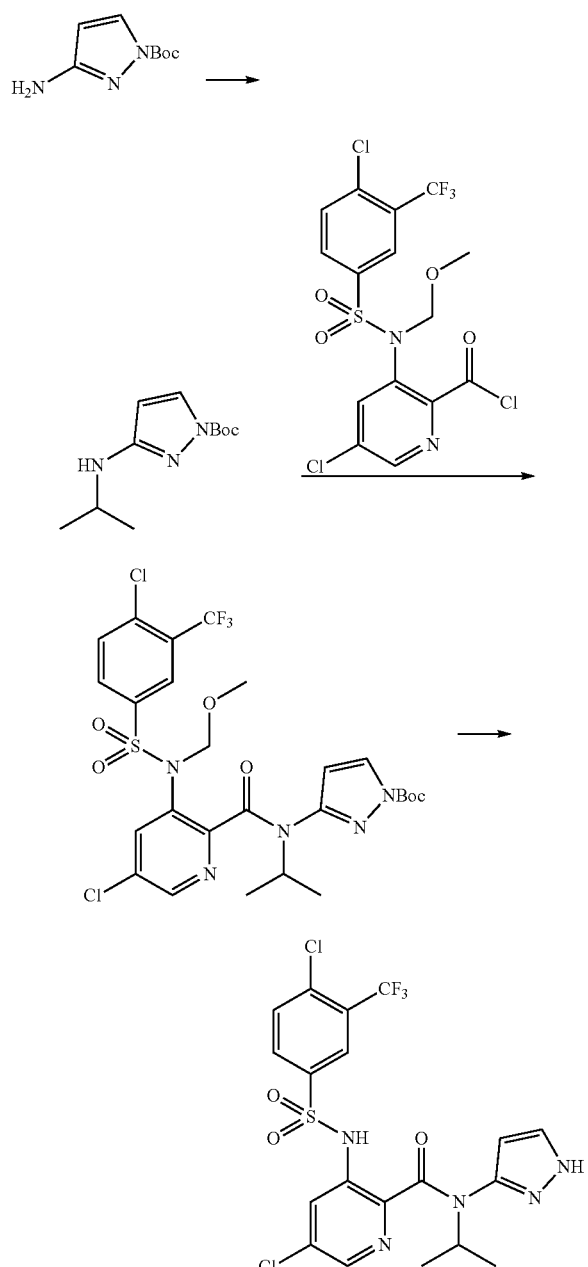

Step 1: A mixture of acetone (0.1 mL, 1.4 mmol), acetic acid (0.078 mL, 1.43 mmol) and 3-amino-pyrazole-1-carboxylic acid tert-butyl ester (200 mg, 1.1 mmol) in DCM (5 mL) was stirred at RT for 1 hour. Sodium triacetoxyborohydride (467 mg, 2.2 mmol) was added and the mixture stirred overnight. The mixture was extracted with ethyl acetate, washed with water, dried and concentrated. The residue was purified by flash column to give 3-Isopropylamino-pyrazole-1-carboxylic acid tert-butyl ester.

Step 2: A mixture of 5-chloro-3-(4-chloro-3-trifluoromethyl-benzenesulfonylamino)-pyridine-2-carboxylic acid (100 mg, 0.24 mmol), oxalyl chloride (2 N in DCM, 0.24 mL, 0.48 mmol), TEA (0.064 mL) in THF (1 mL) was stirred at RT for 2 hours and then evaporated to dryness to give 5-chloro-3-[(4-chloro-3-trifluoromethyl-benzenesulfonyl)-methoxymethyl-amino]-pyridine-2-carbonyl chloride.

A mixture of 5-chloro-3-[(4-chloro-3-trifluoromethyl-benzenesulfonyl)-methoxymethyl-amino]-pyridine-2-carbonyl chloride (100 mg, 0.2 mmol), 3-isopropylamino-pyrazole-1-carboxylic acid tert-butyl ester (54 mg, 0.24 mmol), TEA (0.88 mL) in THF was stirred at RT for 2 hours and then purified by flash column to give 3-({5-chloro-3-[(4-chloro-3-trifluoromethyl-benzenesulfonyl)-methoxymethyl-amino]-pyridine-2-carbonyl}-isopropyl-amino)-pyrazole-1-carboxylic acid tert-butyl ester.

Step 3: 3-({5-chloro-3-[(4-chloro-3-trifluoromethyl-benzenesulfonyl)-methoxymethyl-amino]-pyridine-2-carbonyl}-isopropyl-amino)-pyrazole-1-carboxylic acid tert-butyl ester from step 2 was dissolved in a mixture of 4 M HCl in dioxane (4 mL) and water (1 mL), heated to 85° C. for 2 h. The solvent was evaporated and the residue was purified with HPLC to give 5-chloro-3-(4-chloro-3-trifluoromethyl-benzenesulfonylamino)-pyridine-2-carboxylic acid isopropyl-(1H-pyrazol-3-yl)-amide. MS m/z: 522 (M+H)⁺.

Example 323: 5-Chloro-3-(4-chloro-3-methyl-benzenesulfonylamino)-pyridine-2-carboxylic acid ethyl-(1H-pyrazol-3-yl)-amide

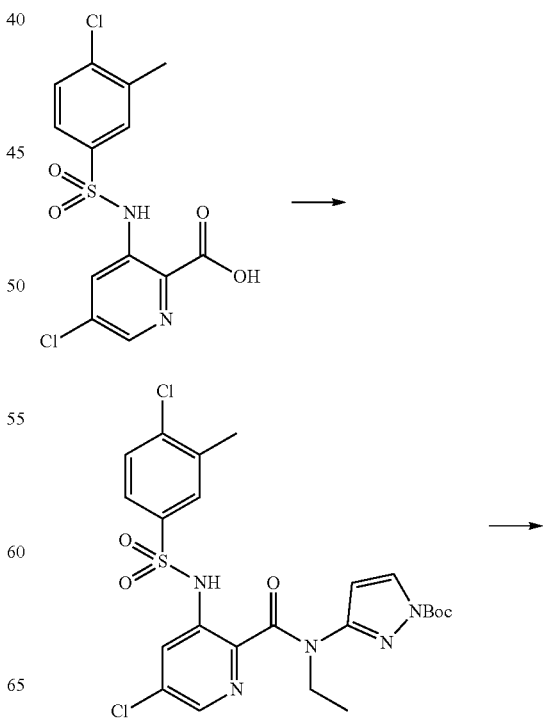

347

-continued

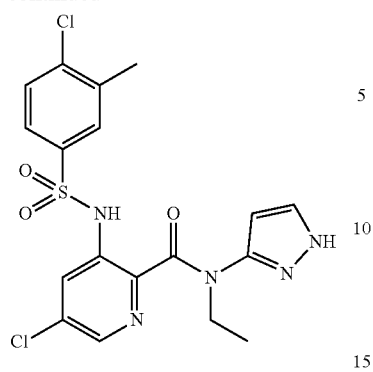

5-Chloro-3-(4-chloro-3-methyl-benzenesulfonylamino)-pyridine-2-carboxylic acid ethyl-(1H-pyrazol-3-yl)-amide was prepared by procedure analogous to that described in Example 320 using 5-chloro-3-(4-chloro-3-methyl-benzenesulfonylamino)-pyridine-2-carboxylic acid. MS m/z: 454 (M+H)⁺.

Example 324: 5-Chloro-3-(4-chloro-3-trifluoromethyl-benzenesulfonylamino)-pyridine-2-carboxylic acid ethyl-(1H-indazol-3-yl)-amide

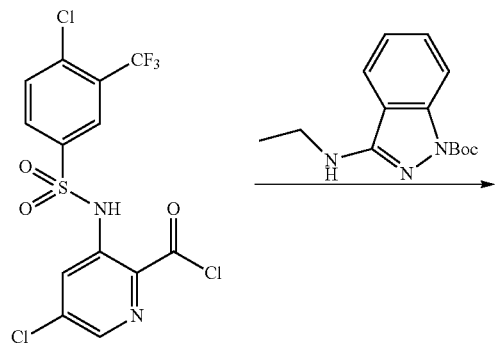

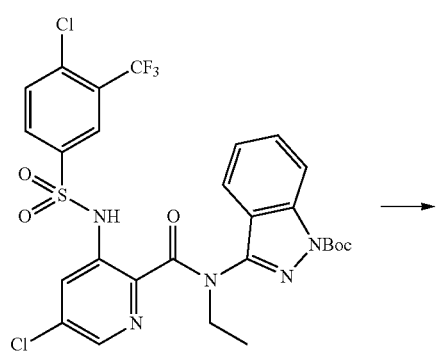

348

-continued

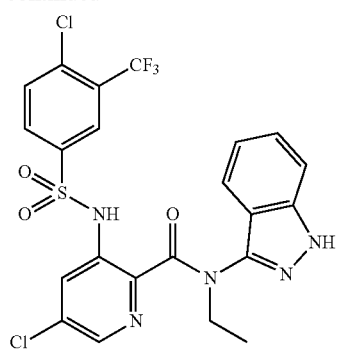

Step 1: A mixture of 5-chloro-3-(4-chloro-3-trifluoromethyl-benzenesulfonylamino)-pyridine-2-carbonyl chloride (100 mg, 0.24 mmol), 3-ethylamino-indazole-1-carboxylic acid tert-butyl ester (62.6 mg, 0.24 mmol), and TEA (0.64 mL) in THF (1 mL) was stirred at 60° C. for 2 hours and then purified by flash column to give 3-{[5-chloro-3-(4-chloro-3-trifluoromethyl-benzenesulfonylamino)-pyridine-2-carbonyl]-ethyl-amino}-indazole-1-carboxylic acid tert-butyl ester.

Step 2: 3-{[5-Chloro-3-(4-chloro-3-trifluoromethyl-benzenesulfonylamino)-pyridine-2-carbonyl]-ethyl-amino}-indazole-1-carboxylic acid tert-butyl ester was dissolved in a mixture of DCM and TFA (1:1) (5 mL). It was stirred at RT for 1 hour, concentrated, purified with HPLC to give 5-chloro-3-(4-chloro-3-trifluoromethyl-benzenesulfonylamino)-pyridine-2-carboxylic acid ethyl-(1H-indazol-3-yl)-amide. MS m/z: 557.9 (M+H)⁺.

Example 325: 5-Chloro-3-(4-chloro-3-trifluoromethyl-benzenesulfonylamino)-pyridine-2-carboxylic acid (6-amino-pyridin-2-yl)-ethyl-amide

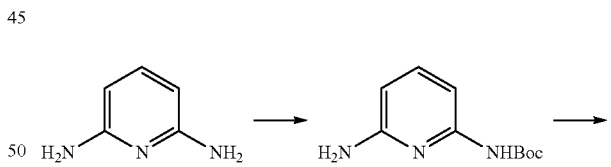

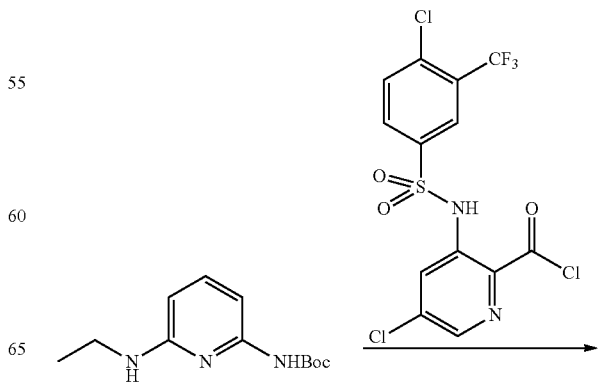

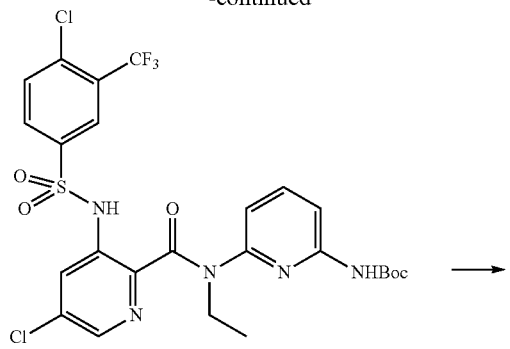

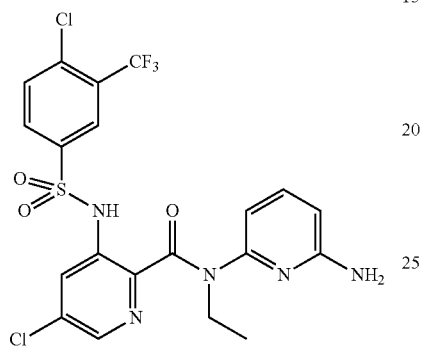

Step 1: To a solution of pyridine-2,6-diamine (2 g, 18.3 mmol) was added LiHMDS (20 mL, 20 mmol). The resultant solution was stirred at ambient temperature for 30 minutes, followed by the addition of (Boc)₂O (4.8 g, 22 mmol) and stirred for 3 hours. The mixture was stirred 3 h, diluted with ethyl acetate, washed with water, and purified by flash column to give (6-amino-pyridin-2-yl)-carbamic acid tert-butyl ester.

Step 2: The title compound was prepared by reductive amination procedure analogous to that described in step 1 of example 320 using (6-amino-pyridin-2-yl)-carbamic acid tert-butyl ester.

Step 3: The title compound was prepared by procedure analogous to that described in example 325, step 2 using 5-chloro-3-(4-chloro-3-trifluoromethyl-benzenesulfonylamino)-pyridine-2-carbonyl chloride and (6-ethylamino-pyridin-2-yl)-carbamic acid tert-butyl ester.

Step 4: The title compound was prepared by procedure analogous to that described in example 322, step 3 using (6-{[5-chloro-3-(4-chloro-3-trifluoromethyl-benzenesulfonylamino)-pyridine-2-carbonyl]-ethyl-amino}-pyridin-2-yl)-carbamic acid tert-butyl ester. MS m/z: 534 (M+H).

Example 326: 5-Chloro-3-(4-chloro-3-trifluoromethyl-benzenesulfonylamino)-pyridine-2-carboxylic acid (3-amino-phenyl)-isopropyl-amide

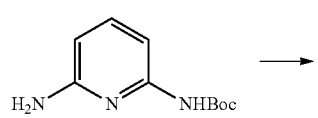

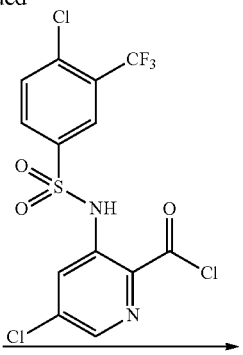

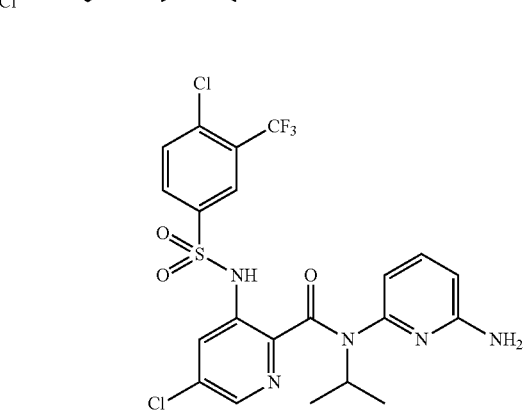

Step 1: The functionalized amine was prepared according to the procedure described in step 1 of Example 322 using (6-amino-pyridin-2-yl)-carbamic acid tert-butyl ester in reductive amination to give(6-Isopropylamino-pyridin-2-yl)-carbamic acid tert-butyl ester.

Step 2: The secondary amide was prepared according to the procedure described in step 1 of Example 323 using (6-isopropylamino-pyridin-2-yl)-carbamic acid tert-butyl ester to give (6-{[5-chloro-3-(4-chloro-3-trifluoromethyl-benzenesulfonylamino)-pyridine-2-carbonyl]-isopropyl-amino}-pyridin-2-yl)-carbamic acid tert-butyl ester.

Step 3: The title compound was prepared according to the procedure described in step 2 of Example 323 to give 5-chloro-3-(4-chloro-3-trifluoromethyl-benzenesulfonylamino)-pyridine-2-carboxylic acid (6-amino-pyridin-2-yl)-isopropyl-amide. MS m/z: 548 (M+H)⁺.

Example 327: 5-Chloro-3-(4-methyl-3-trifluoromethyl-benzenesulfonylamino)-pyridine-2-carboxylic acid (6-amino-pyridin-2-yl)-ethyl-amide

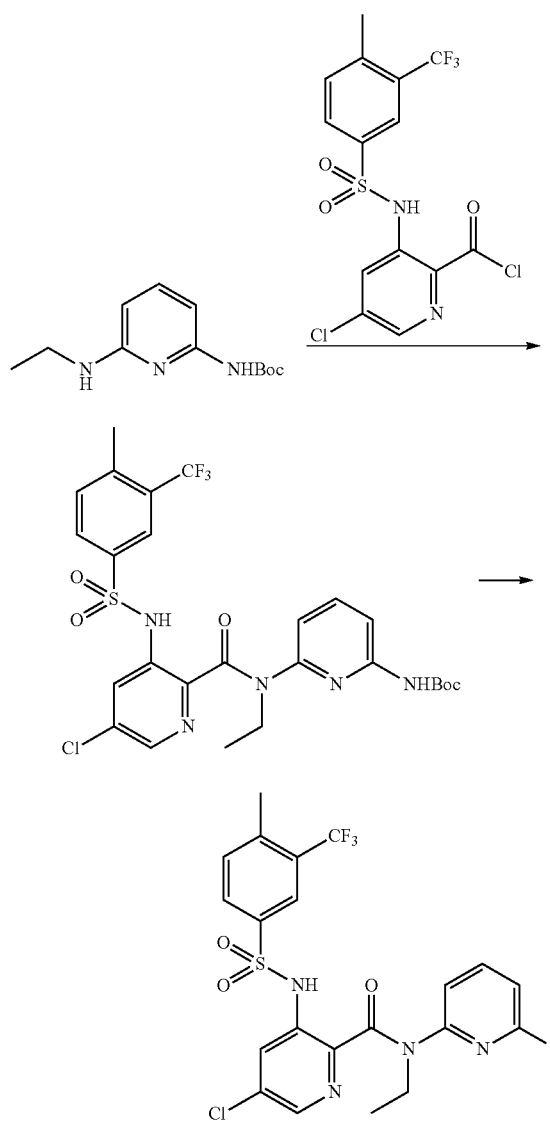

Step 1: The acid chloride was prepared according to the procedure described in Example 323, step 2 using 5-chloro-3-(4-methyl-3-trifluoromethyl-benzenesulfonylamino)-pyridine-2-carboxylic acid to give the desired product.

The corresponding amide was prepared according to the procedure described in step 1 of example 325 using 5-chloro-3-(4-methyl-3-trifluoromethyl-benzenesulfonylamino)-pyridine-2-carbonyl chloride to give (6-{[5-chloro-3-(4-methyl-3-trifluoromethyl-benzenesulfonylamino)-pyridine-2-carbonyl]-ethyl-amino}-pyridin-2-yl)-carbamic acid tert-butyl ester.

Step 2: The title compound was prepared by procedure analogous to that described in example 325, step 2 using (6-{[5-chloro-3-(4-methyl-3-trifluoromethyl-benzenesulfo-nylamino)-pyridine-2-carbonyl]-ethyl-amino}-pyridin-2-yl)-carbamic acid tert-butyl ester to give 5-chloro-3-(4-methyl-3-trifluoromethyl-benzenesulfonylamino)-pyridine-2-carboxylic acid (6-amino-pyridin-2-yl)-ethyl-amide. MS m/z: 514 (M+H)$^+$.

Example 328: 4-Chloro-N-[5-chloro-2-(2-chloro-5-pyrazol-1-yl-benzoyl)-pyridin-3-yl]-3-trifluoromethyl-benzenesulfonamide

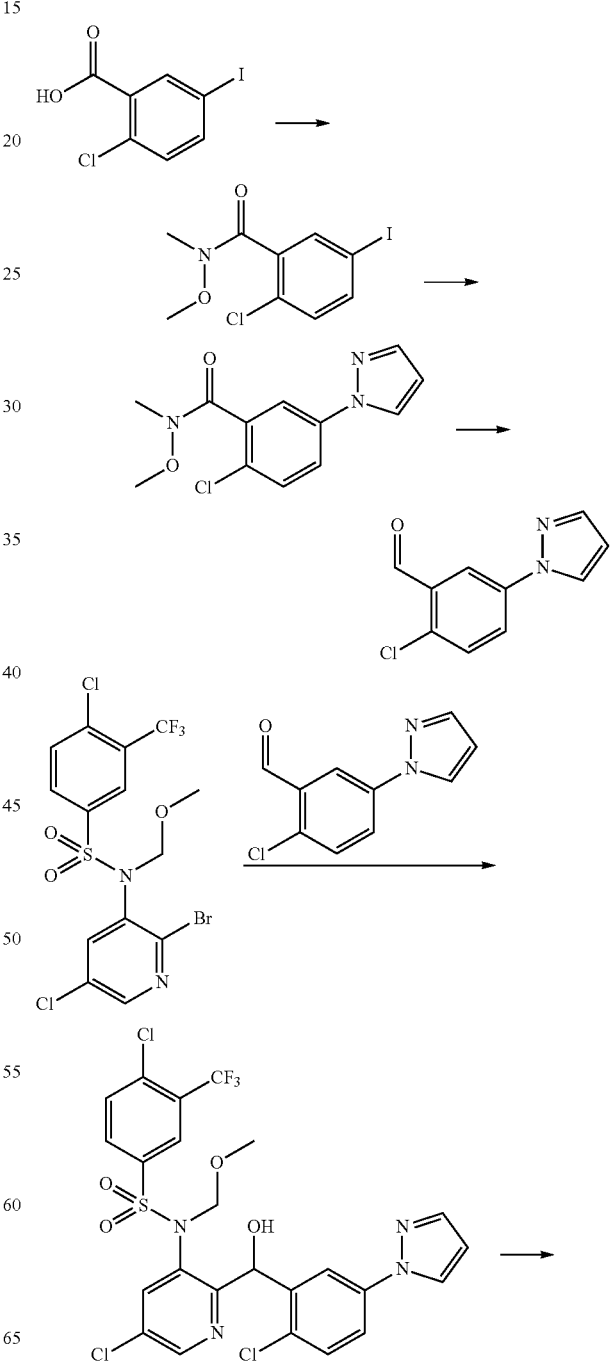

353

-continued

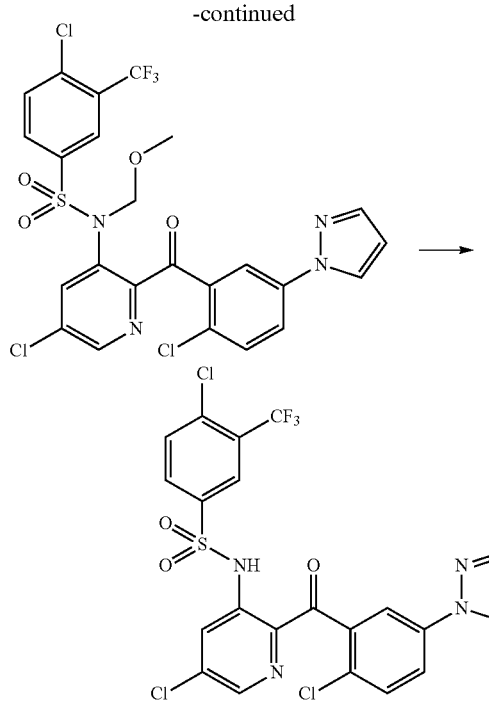

Step 1: 2-Chloro-5-iodo-N-methoxy-N-methyl-benzamide was synthesized from 2-chloro-5-iodobenzoic acid according to example 214.

Step 2: A mixture of 2-chloro-5-iodo-N-methoxy-N-methyl-benzamide (700 mg, 2.15 mmol), pyrazole (439 mg, 6.45 mmol), 8-hydroxyquinoline (62.7 mg, 0.43 mmol), copper iodide (81.7 mg, 0.43 mmol), and potassium carbonate (445 mg, 3.22 mmol) in DMSO (2 mL) was stirred at 115° C. overnight. The resultant solution was diluted with ethyl acetate, washed with water, dried over sodium sulfate, and purified by HPLC to give the desired product. (M+H)$^+$: 266.

Step 3: To a solution of 2-chloro-N-methoxy-N-methyl-5-pyrazol-1-yl-benzamide (280 mg, 1.05 mmol) was added DIBAL-H (1.16 mL, 1.16 mmol) slowly at −78° C. The reaction was stirred 2 h, quenched with water, extracted with ether, concentrated, and purified by flash chromatography to give 2-chloro-5-pyrazol-1-yl-benzaldehyde.

Step 4: To a solution of N-(2-bromo-5-chloro-pyridin-3-yl)-4-chloro-N-methoxymethyl-3-trifluoromethyl-benzenesulfonamide (356 mg, 0.68 mmol) in THF was added isopropylmagnesium chloride (0.75 mL, 1.5 mmol) slowly at 0° C. One hour later 2-chloro-5-pyrazol-1-yl-benzaldehyde (140 mg, 0.68 mmol) was added and warmed up the reaction mixture to RT for 2 hours, quenched with water, extracted with ethyl acetate, concentrated and purified by flash column to give 4-chloro-N-{5-chloro-2-[(2-chloro-5-pyrazol-1-yl-phenyl)-hydroxy-methyl]-pyridin-3-yl}-N-methoxymethyl-3-trifluoromethyl-benzenesulfonamide.

Step 5: A mixture of 4-chloro-N-{5-chloro-2-[(2-chloro-5-pyrazol-1-yl-phenyl)-hydroxy-methyl]-pyridin-3-yl}-N-methoxymethyl-3-trifluoromethyl-benzenesulfonamide (400 mg, 0.64 mol), Dess-Martin periodinane (409 mg, 0.96 mmol), in DCM was stirred at RT for 2 hours and then purified by flash column to give 4-chloro-N-[5-chloro-2-(2-chloro-5-pyrazol-1-yl-benzoyl)-pyridin-3-yl]-N-methoxymethyl-3-trifluoromethyl-benzenesulfonamide.

Step 6: 4-Chloro-N-[5-chloro-2-(2-chloro-5-pyrazol-1-yl-benzoyl)-pyridin-3-yl]-N-methoxymethyl-3-trifluorom-

354 ethyl-benzenesulfonamide from step 5 was dissolved in a mixture of 4 M HCl in dioxane (8 mL) and water (2 mL) and heated at 85° C. for 2 h. The solvent was evaporated and the residue was purified via HPLC to give 4-chloro-N-[5-chloro-2-(2-chloro-5-pyrazol-1-yl-benzoyl)-pyridin-3-yl]-3-trifluoromethyl-benzenesulfonamide: $^1$H NMR (400 MHz, CDCl$_3$) (8.2 (m, 3H), 8.0 (m, 1H), 7.9 (s, 1H), 7.7 (m, 4H), 7.45 (d, 1H), 6.45 (s, 1H); MS m/z: 576.9 (M+H)$^+$.

Example 329: 4-Chloro-N-[5-chloro-2-(2-morpholin-4-yl-pyridine-4-carbonyl)-pyridin-3-yl]-3-trifluoromethyl-benzenesulfonamide

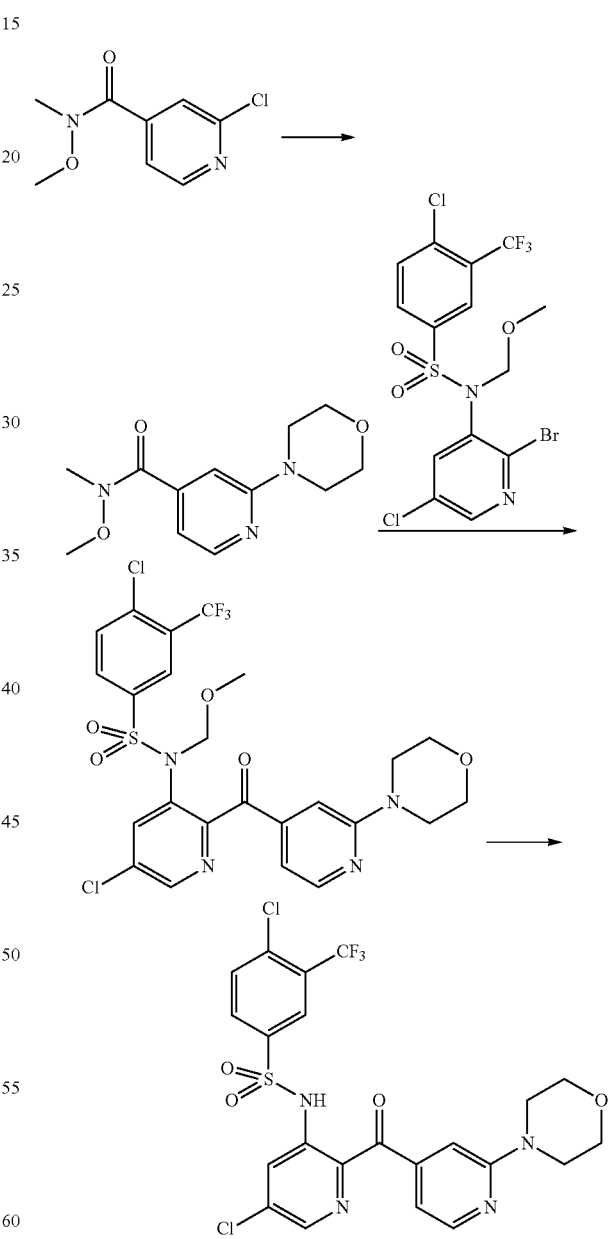

Step 1: A mixture of 2-chloro-N-methoxy-N-methyl-isonicotinamide (800 mg, 4 mmol), morpholine (452 mg, 5.2 mmol), sodium tert-butoxide (500 mg, 5.2 mmol), 1,3-bis(2,6-di-isopropylphenyl)imidazol-2-ylidene(1,4-naphthoquinone palladium(0) dimer in dioxane (4 mL) was stirred at 80° C. overnight. The mixture was diluted with ethyl acetate, washed with water and purified by flash column to give N-methoxy-N-methyl-2-morpholin-4-yl-isonicotinamide.

Step 2: To a solution of N-(2-bromo-5-chloro-pyridin-3-yl)-4-chloro-N-methoxymethyl-3-trifluoromethyl-benzenesulfonamide (590 mg, 1.2 mmol) in THF (2 mL) was added isopropylmagnesium chloride (1.3 mL, 2.6 mmol) slowly at 0° C. One hour later, N-methoxy-N-methyl-2-morpholin-4-yl-isonicotinamide (300 mg, 1.2 mmol) was added and warmed up to RT while stirring overnight, quenched with water, extracted with ethyl acetate, concentrated and purified by flash column to give 4-chloro-N-[5-chloro-2-(2-morpholin-4-yl-pyridine-4-carbonyl)-pyridin-3-yl]-N-methoxymethyl-3-trifluoromethyl-benzenesulfonamide.

Step 3: 4-Chloro-N-[5-chloro-2-(2-morpholin-4-yl-pyridine-4-carbonyl)-pyridin-3-yl]-N-methoxymethyl-3-trifluoromethyl-benzenesulfonamide from step 2 was dissolved in a mixture of 4 M HCl in dioxane (8 mL) and water (2 mL), heated to 85° C. for 2 h. The solvent was evaporated and the residue was purified with HPLC to give 4-chloro-N-[5-chloro-2-(2-morpholin-4-yl-pyridine-4-carbonyl)-pyridin-3-yl]-3-trifluoromethyl-benzenesulfonamide. MS m/z: 561 (M+H)$^+$.

Example 330: N-{5-Chloro-2-[2-(2-hydroxy-ethyl-amino)-pyridine-4-carbonyl]-pyridin-3-yl}-4-methyl-3-trifluoromethyl-benzenesulfonamide Step 1: A mixture of (tert-butyl-dimethyl-silanyloxy)-acetaldehyde (177.7 mg, 1.02 mmol), acetic acid (0.051 mL, 0.85 mmol) and N-[2-(2-amino-pyridine-4-carbonyl)-5-chloro-pyridin-3-yl]-4-methyl-3-trifluoromethyl-benzenesulfonamide (400 mg, 0.85 mmol) in DCM (3 mL) was stirred at RT for 1 hour. To the mixture was added sodium triacetoxyborohydride (360.8 mg, 1.7 mmol), stirred overnight. The mixture was extracted with ethyl acetate, washed with water, dried and concentrated. The residue was purified by flash column to afford N-[2-({2-[2-(tert-butyl-dimethyl-silanyloxy)-ethylamino]-pyridin-4-yl}-hydroxy-methyl)-5-chloro-pyridin-3-yl]-4-methyl-3-trifluoromethyl-benzenesulfonamide.

Step 2: To the dioxane (1 mL) solution of N-[2-({2-[2-(tert-butyl-dimethyl-silanyloxy)-ethylamino]-pyridin-4-yl}-hydroxy-methyl)-5-chloro-pyridin-3-yl]-4-methyl-3-trifluoromethyl-benzenesulfonamide from step 1, was added MnO$_2$ (440 mg, 5 mmol). The mixture was stirred at 80° C. for 1 hour, filtered, concentrated. The deprotection was performed in 4 M HCl in dioxane (4 mL) and water (1 mL) for 1 hour at RT. The solvent was evaporated and the residue was purified with HPLC to give N-{5-chloro-2-[2-(2-hydroxy-ethylamino)-pyridine-4-carbonyl]-pyridin-3-yl}-4-methyl-3-trifluoromethyl-benzenesulfonamide: $^1$H NMR (400 MHz, CDCl$_3$) δ 8.3 (s, 1H), 8.15 (d, 2H), 8.05 (s, 1H), 7.9 (d, 1H), 7.4 (d, 1H), 6.7 (m, 2H), 3.8 (m, 2H), 3.5 (m, 2H), 2.5 (s, 3H); MS m/z: 515 (M+H)$^+$.

Example 331: 5-Chloro-3-(4-chloro-3-trifluoromethyl-benzenesulfonylamino)-pyridine-2-carboxylic acid (2H-pyrazol-3-yl)-amide

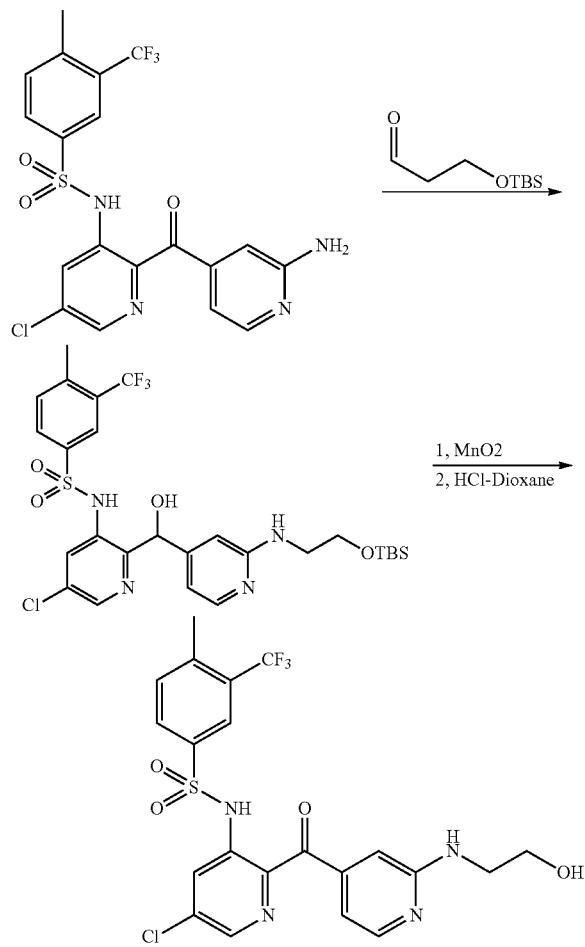

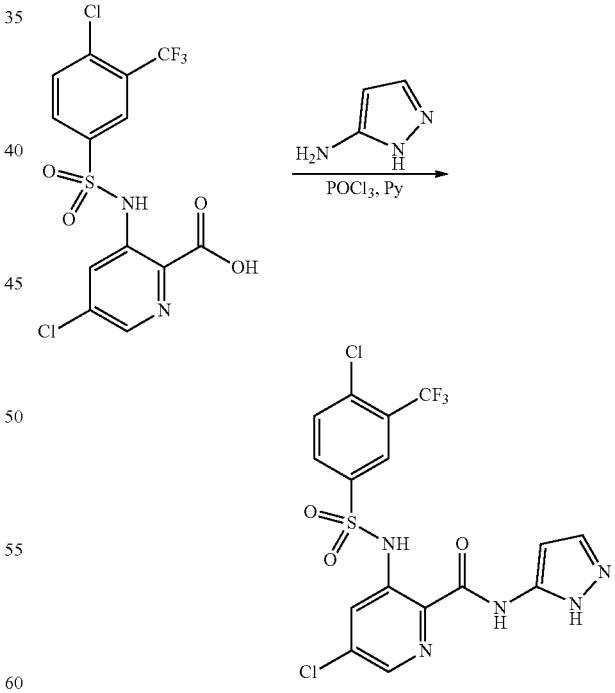

A 0° C. mixture of 5-chloro-3-(4-chloro-3-trifluoromethyl-benzenesulfonylamino)-pyridine-2-carboxylic acid (41 mg, 0.1 mmol, 1 equiv) and 3-aminopyrazole (21 mg, 2.5 equiv) in 0.5 mL of pyridine was treated with 11 FL (1.1 equiv) of POCl$_3$ for 5 minutes. After addition of 1 mL of water, the mixture was subjected to preparative reverse phase HPLC to give 5-chloro-3-(4-chloro-3-trifluoromethyl-benzenesulfonylamino)-pyridine-2-carboxylic acid (2H-pyrazol-3-yl)-amide. $^1$H NMR (400 MHz, CDCl$_3$) δ 11.95 (s, 1H), 10.37 (s, 1H), 8.24 (m, 2H), 8.18 (s, 1H), 8.00 (dd, 1H), 7.63 (d, 1H), 7.60 (d, 1H), 6.80 (d, 1H); MS (ES) (M+H)$^+$ expected 480.0, found 480.0.

Example 332: 5-Chloro-thiophene-2-sulfonic acid [2-(2-amino-pyridine-4-carbonyl)-5-chloro-pyridin-3-yl]-amide

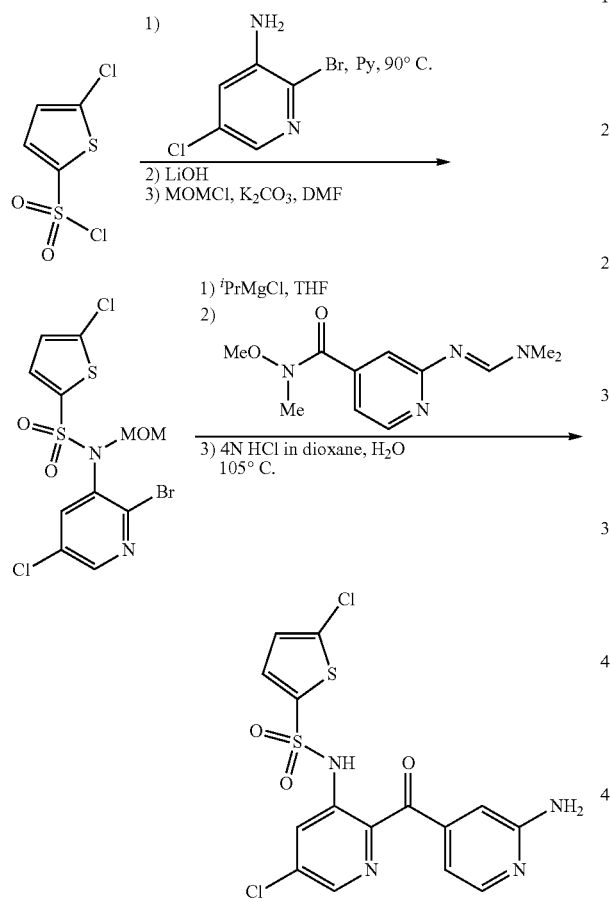

Following the procedure for example 24, 5-chloro-thiophene-2-sulfonic acid (2-bromo-5-chloro-pyridin-3-yl)-amide was synthesized from 5-chloro-thiophene-2-sulfonyl chloride and 2-bromo-5-chloro-pyridin-3-ylamine.

5-Chloro-thiophene-2-sulfonic acid (2-bromo-5-chloro-pyridin-3-yl)-methoxymethyl-amide was synthesized according to procedure described in example 25.

5-Chloro-thiophene-2-sulfonic acid [2-(2-amino-pyridine-4-carbonyl)-5-chloro-pyridin-3-yl]-amide was prepared according to procedure described in example 29. $^1$H NMR (400 MHz, DMSO-d$_6$) δ 8.45 (s, 1H), 8.00 (d, 1H), 7.8 (d, 1H), 7.39 (d, 1H), 7.18 (dd, 1H), 7.05 (s, 1H), 6.96 (dd, 1H); MS (ES) (M$^+$+H) expected 429.0, found 429.0.

Example 333: N-[2-(2-Amino-pyridine-4-carbonyl)-5-chloro-pyridin-3-yl]-4-chloro-3-isopropoxy-benzenesulfonamide

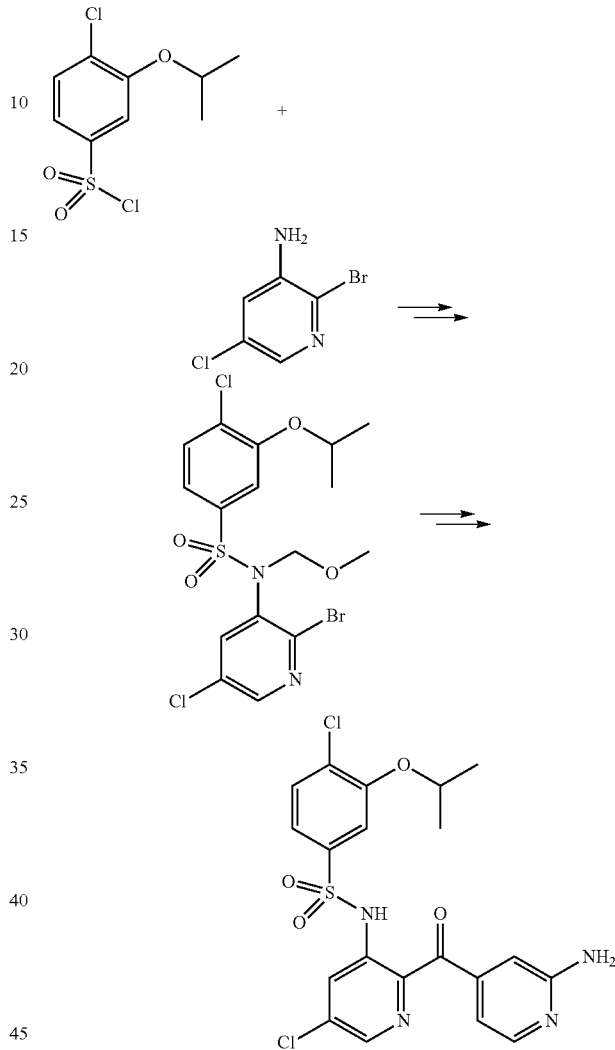

N-[2-(2-Amino-pyridine-4-carbonyl)-5-chloro-pyridin-3-yl]-4-chloro-3-isopropoxy-benzenesulfonamide was prepared following the procedures described in example 332. Mass spectrum m/z 481.0 (M+1), expected 481.0.

Example 334: N-[2-(2-Amino-pyridine-4-carbonyl)-5-chloro-pyridin-3-yl]-4-chloro-3-ethoxy-benzenesulfonamide

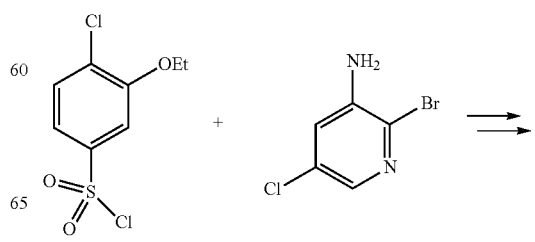

359

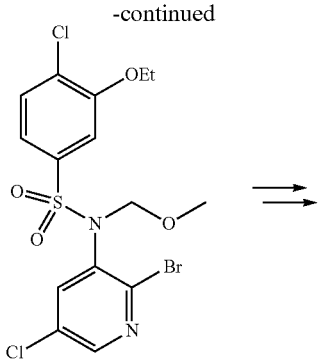

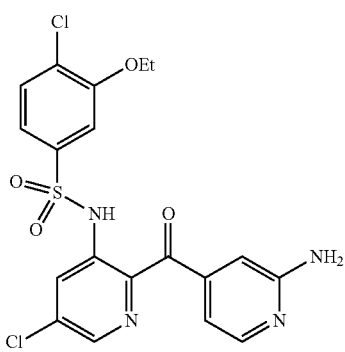

N-[2-(2-Amino-pyridine-4-carbonyl)-5-chloro-pyridin-3-yl]-4-chloro-3-ethoxy-benzenesulfonamide was prepared following the procedures described in example 332. Mass spectrum m/z 481.0 (M+1), expected 481.0.

Example 335: N-[2-(2-Amino-pyridine-4-carbonyl)-pyridin-3-yl]-4-methyl-3-trifluoromethyl-benzene-sulfonamide

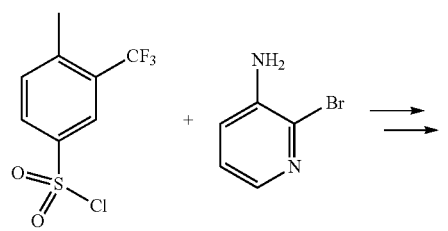

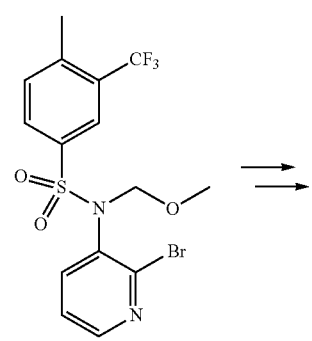

360

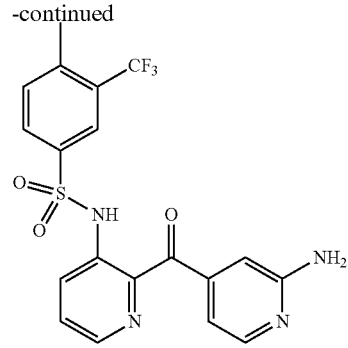

N-[2-(2-Amino-pyridine-4-carbonyl)-pyridin-3-yl]-4-methyl-3-trifluoromethyl-benzenesulfonamide was prepared following the procedures described in example 332. Mass spectrum m/z 437.0 (M+1), expected 437.0.

Example 336: 4-Chloro-N-[5-chloro-2-((R)-3-methyl-morpholine-4-carbonyl)-pyridin-3-yl]-3-trifluoromethyl-benzenesulfonamide

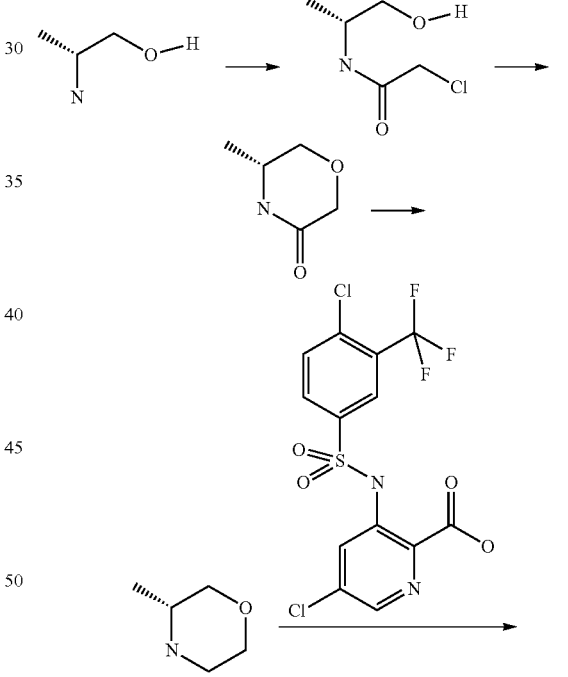

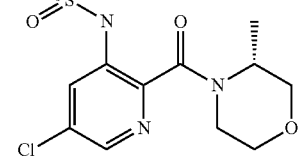

Step 1: To a mixture of (R)-2-amino-propan-1-ol (2.0 g, 26.6 mmol) in 150 mL of DCM at −40° C. under nitrogen atmosphere was added dropwise chloroacetyl chloride (2.3 mL, 29.2 mmol) in 60 mL of DCM. The mixture was gradually warmed to 0° C. and was stirred for 2 hours. After the removal of the solvents the residue was diluted with 50 mL of 1:1 ethyl acetate/hexane, stirred for 30 min and filtered. The filtrate was concentrated to afford 2-chloro-N-((R)-2-hydroxy-1-methyl-ethyl)-acetamide as a liquid.

Step 2: To a mixture of 2-chloro-N-((R)-2-hydroxy-1-methyl-ethyl)-acetamide obtained above in 175 mL of isopropanol and 120 mL of DCM was added t-BuOK (6 g) in 120 mL of isopropanol over 40 min. The mixture was stirred for another 40 min and was neutralized with concentrated HCl until pH was 6.5. The mixture was concentrated and the residue was diluted with 150 mL of water and 150 mL of ethyl acetate. The aqueous layer was extracted with ethyl acetate, the organic layers were combined and dried. Removal of the solvents afforded the desired (R)-5-methyl-morpholin-3-one which was used directly at next step.

Step 3: To a mixture of (R)-5-methyl-morpholin-3-one (237 mg. 2.0 mmol) in 2 mL of THF was added 4.0 mL of LAH/THF (1.0M), the resulting mixture was stirred overnight at room temperature. To the mixture was slowly added ice-cooled water and then was dried over Na$_2$SO$_4$. Removal of the solvents afforded (R)-3-methyl-morpholine as a liquid.

Step 4: A mixture of 5-chloro-3-(4-chloro-3-trifluoromethyl-benzenesulfonylamino)-pyridine-2-carboxylic acid (63 mg, 0.152 mmol), (R)-3-methyl-morpholine (100 mg, 1.0 mmol), DIEA (0.132 mL, 0.76 mmol) and HATU (86 mg, 0.23 mmol) in 1.5 mL of DMF was stirred at room temperature for 4 hours. The mixture was directly applied for preparative HPLC (20-80% acetonitrile in water) to afford the title compound as a white solid: $^1$H NMR: (CDCl$_3$, ppm) δ 8.24 (d, 1H), 8.11 (m, 1H), 8.02 (m, 1H), 7.93 (m, 1H), 7.63 (d, 1H), 4.60 (m, 1H), 4.29 (m, 1H), 3.77 (m, 2H), 3.59 (m, 1H), 3.38 (m, 2H), 1.28 (m, 3H); MS: (M+H)/z=498.0.

Example 337: 2-[5-Chloro-3-(4-chloro-3-trifluoromethyl-benzenesulfonylamino)-pyridine-2-carbonyl]benzoic acid methyl ester

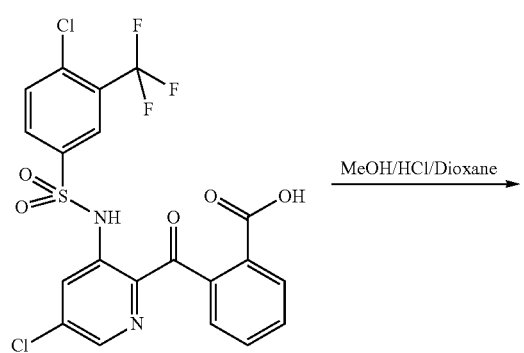

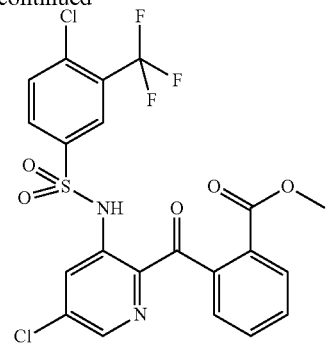

A mixture of 2-[5-chloro-3-(4-chloro-3-trifluoromethyl-benzenesulfonylamino)-pyridine-2-carbonyl]benzoic acid (20 mg), 4N HCll/dioxane (1 mL) and 1.5 mL of methanol was refluxed overnight. After cooled to room temperature, the mixture was concentrated and the residue was diluted with ethyl acetate, washed with sodium bicarbonate and brine and dried. Removal of the solvents afforded the title compound as an off white solid: $^1$H NMR: (CDCl$_3$, ppm) δ 11.20 (s, 1H), 8.22 (m, 2H), 8.04 (m, 2H), 7.94 (m, 1H), 7.62 (m, 2H), 7.54 (m, 1H), 7.31 (m, 1H), 3.54 (s, 3H); MS: (M+H)/z=533.0.

Example 338: 4-Chloro-N-[5-chloro-2-(4-oxo-piperidine-1-carbonyl)-pyridin-3-yl]-3-trifluoromethyl-benzenesulfonamide

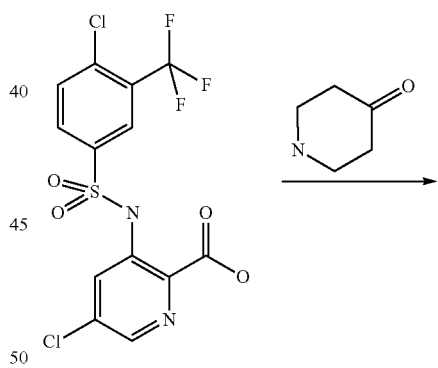

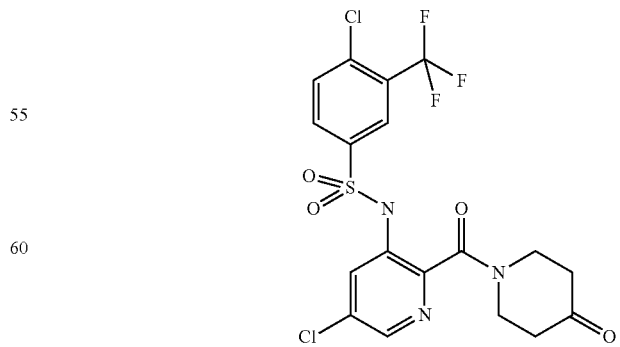

A mixture of 5-chloro-3-(4-chloro-3-methyl-benzenesulfonylamino)-pyridine-2-carboxylic acid (415 mg, 1.0 mmol), piperidin-4-one hydrochloride (500 mg, 3.0 mmol), DIEA (0.695 mL, 4.0 mmol), and 1-propane phosphonic acid cyclic anhydride (T₃P, 0.783 mL, 4.5 mmol) in 5.0 mL of DCM was stirred at room temperature for 4 hours. The mixture was directly applied for flash column (40% ethyl acetate in hexane) to afford the title compound as a white solid: ¹H NMR: (CDCl₃, ppm) δ 9.80 (s, 1H), 8.27 (d, 1H), 8.13 (d, 1H), 8.02 (d, 1H), 7.92 (dd, 1H), 7.63 (d, 1H), 3.91 (t, 2H), 3.75 (t, 2H), 2.57 (t, 4H); MS: (M+H)/z=496.0.

Example 339: 4-Chloro-N-[5-chloro-2-(4-hydroxy-piperidine-1-carbonyl)-pyridin-3-yl]-3-trifluoromethyl-benzenesulfonamide

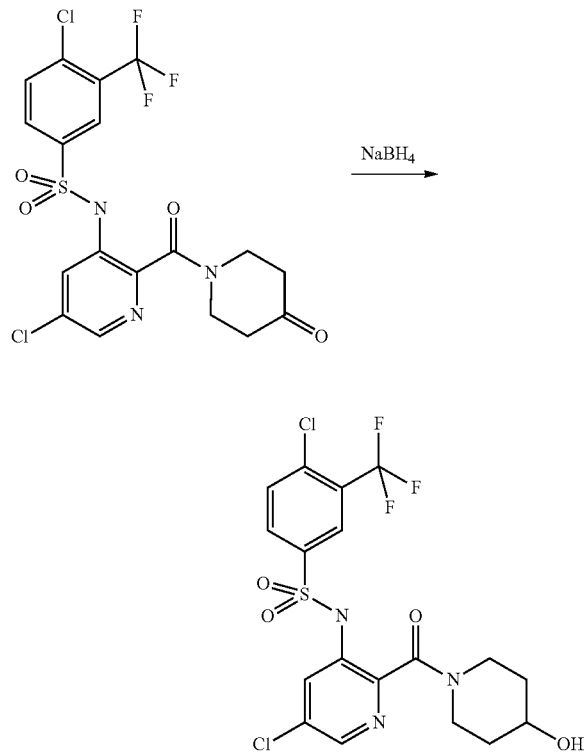

A mixture of 4-chloro-N-[5-chloro-2-(4-oxo-piperidine-1-carbonyl)-pyridin-3-yl]-3-trifluoromethyl-benzenesulfonamide (20 mg), sodium borohydride (10 mg) in 1 mL of methanol was stirred at room temperature overnight. To the mixture was added water and the resulting mixture was extracted with ethyl acetate three times. The organic layer was washed with brine and dried. After the removal of solvents the residue was further purified by flash column (50% ethyl acetate in hexane) to afford the title compound as a white solid: ¹H NMR: (CDCl₃, ppm) δ 8.12 (d, 1H), 8.09 (d, 1H), 7.95 (dd, 1H), 7.80 (d, 1H), 7.62 (d, 1H), 4.05 (m, 1H), 3.88 (m, 1H), 3.47 (m, 1H), 3.36 (m, 1H), 3.02 (m, 1H), 1.94 (m, 1H), 1.73 (m, 1H), 1.58 (m, 1H), 1.48 (m, 2H); MS: (M+H)/z=498.0.

Example 340: (S)-1-[5-Chloro-3-(4-chloro-3-trifluoromethyl-benzenesulfonylamino)-pyridine-2-carbonyl]-pyrrolidine-2-carboxylic Acid Methyl Ester

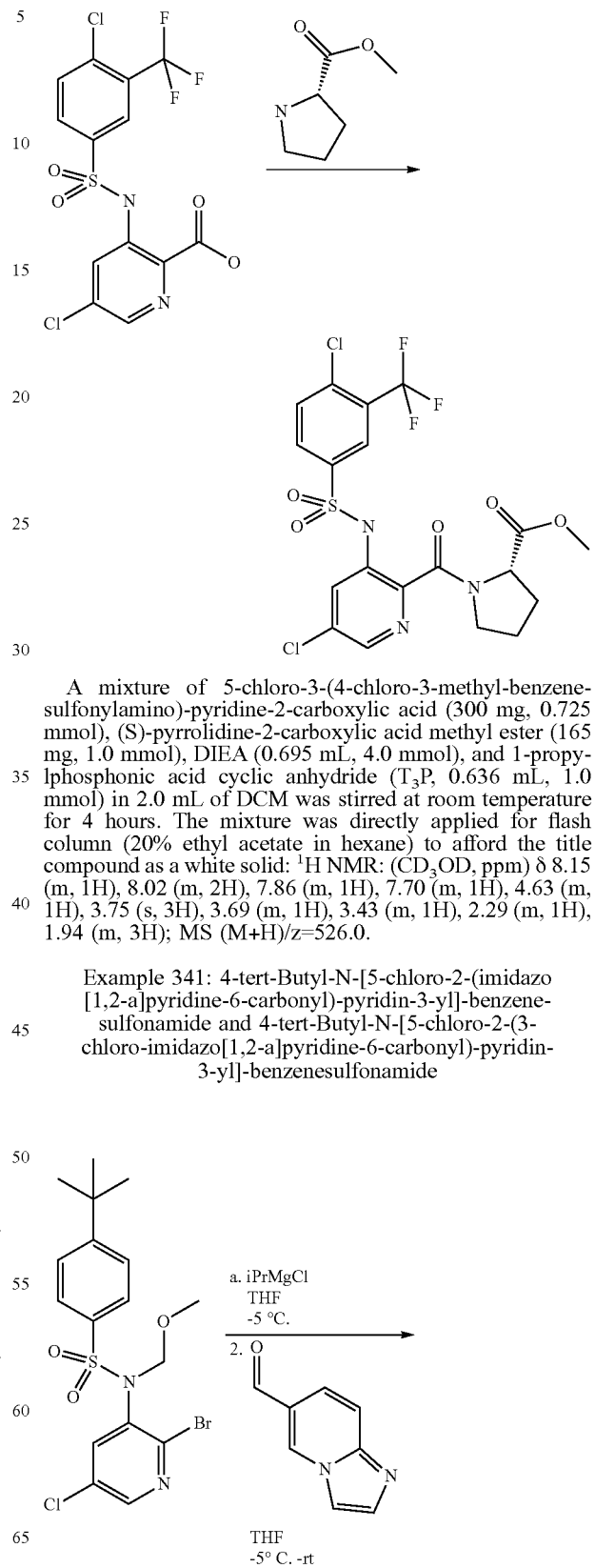

A mixture of 5-chloro-3-(4-chloro-3-methyl-benzenesulfonylamino)-pyridine-2-carboxylic acid (300 mg, 0.725 mmol), (S)-pyrrolidine-2-carboxylic acid methyl ester (165 mg, 1.0 mmol), DIEA (0.695 mL, 4.0 mmol), and 1-propylphosphonic acid cyclic anhydride (T₃P, 0.636 mL, 1.0 mmol) in 2.0 mL of DCM was stirred at room temperature for 4 hours. The mixture was directly applied for flash column (20% ethyl acetate in hexane) to afford the title compound as a white solid: ¹H NMR: (CD₃OD, ppm) δ 8.15 (m, 1H), 8.02 (m, 2H), 7.86 (m, 1H), 7.70 (m, 1H), 4.63 (m, 1H), 3.75 (s, 3H), 3.69 (m, 1H), 3.43 (m, 1H), 2.29 (m, 1H), 1.94 (m, 3H); MS (M+H)/z=526.0.

Example 341: 4-tert-Butyl-N-[5-chloro-2-(imidazo[1,2-a]pyridine-6-carbonyl)-pyridin-3-yl]-benzenesulfonamide and 4-tert-Butyl-N-[5-chloro-2-(3-chloro-imidazo[1,2-a]pyridine-6-carbonyl)-pyridin-3-yl]-benzenesulfonamide -continued

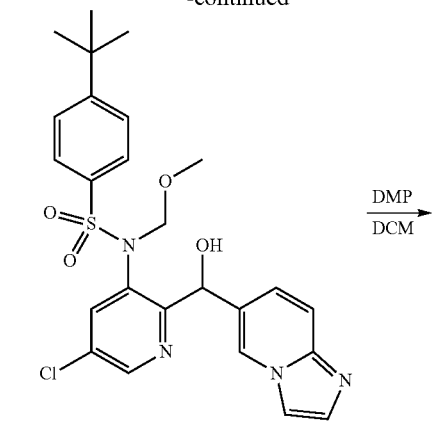

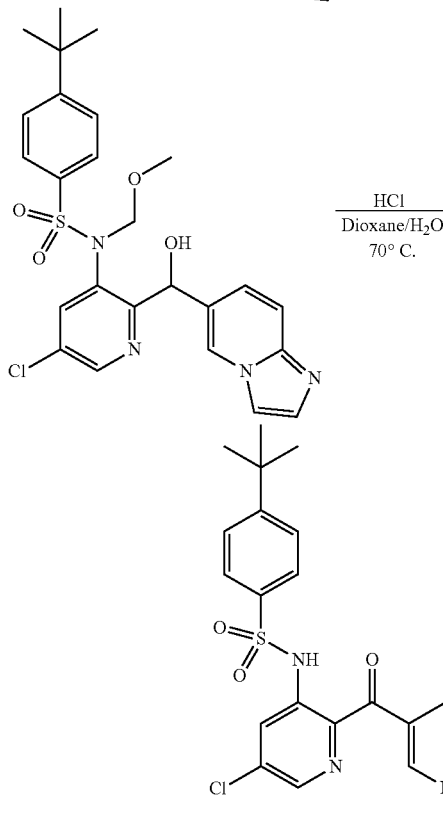

Following the procedure for 26, 4-tert-butyl-N-[5-chloro-2-(hydroxy-imidazo[1,2-a]pyridin-6-yl-methyl)-pyridin-3-yl]-N-methoxymethyl-benzenesulfonamide was produced from N-(2-bromo-5-chloro-pyridin-3-yl)-4-tert-butyl-N-methoxymethyl-benzenesulfonamide (250 mg, 0.558 mmol) and imidazo[1,2-a]pyridine-6-carbaldehyde (179 mg, 1.23 mmol).

The crude alcohol was dissolved in methylene chloride (2.5 mL), followed by the addition of the Dess-Martin periodinane (592 mg, 1.40 mmol). The resultant solution was stirred 4 h and then quenched with aqueous sodium thiosulfate. The mixture was diluted with EtOAc and the organics were washed with aqueous sodium thiosulfate and saturated sodium bicarbonate, dried with sodium sulfate, concentrated in vacuo, and purified via automated silica gel chromatography to afford the biaryl ketone.

A 10 mL round-bottom flask was charged with the above protected sulfonamide (40 mg, 0.078 mmol), HCl in dioxane (1.6 mL, 4.0 M), and water (0.50 mL). The solution was warmed to 70° C. and stirred overnight. The following day, the reaction was neutralized with saturated sodium bicarbonate and diluted with EtOAc. The organics were washed with 10% HCl and saturated sodium bicarbonate, dried with sodium sulfate, concentrated in vacuo, and purified via automated silica gel chromatography to generate the desired imidazo[1,2-a]pyridine: $^1$H NMR (400 MHz, CDCl$_3$) δ 10.82 (bs, 1H), 9.22 (s, 1H), 8.33 (d, 1H), 8.21 (d, 1H), 7.77 (d, 2H), 7.69-7.76 (m, 2H), 7.59-7.64 (m, 2H), 7.43 (d, 2H), 1.21 (s, 9H); MS (ES) (M+H)$^+$ expected 469.1, found 469.1.

Example 342: N-{2-[(6-Amino-pyridin-3-yl)-methoxyimino-methyl]-5-chloro-pyridin-3-yl}-4-tert-butyl-benzenesulfonamide and N-{2-[(6-Amino-pyridin-3-yl)-methoxyimino-methyl]-5-chloro-pyridin-3-yl}-4-tert-butyl-benzenesulfonamide

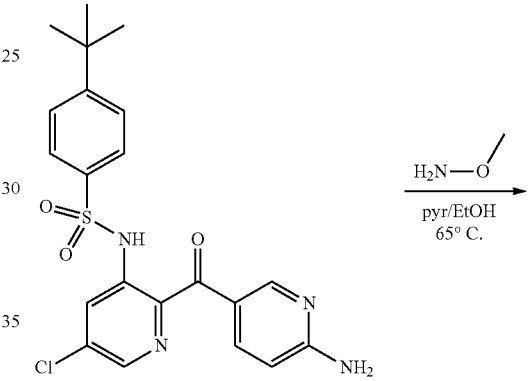

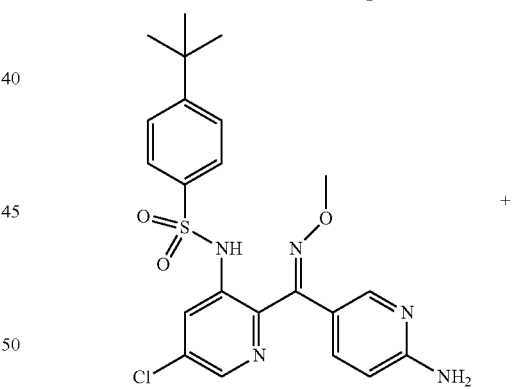

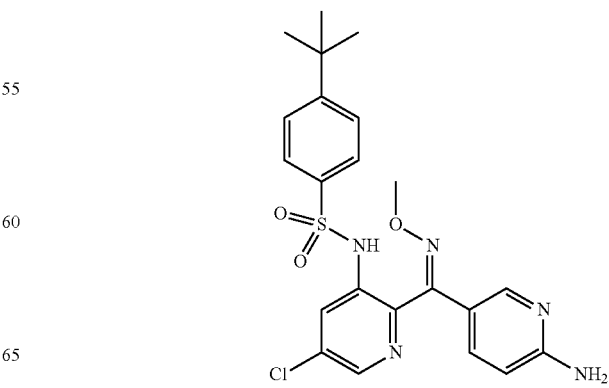

A 1-dram vial was charged with N-[2-(6-amino-pyridine-3-carbonyl)-5-chloro-pyridin-3-yl]-4-tert-butyl-benzenesulfonamide (12.5 mg, 0.056 mmol), methoxylamine hydrochloride (14 mg, 0.327 mmol), pyridine (0.05 mL), and ethanol (0.05 mL). The reaction vessel was warmed to 60° C. and stirred overnight. The following day, the mixture was acidified with 0.1% aqueous TFA/0.1% TFA in acetonitrile and purified via preparatory HPLC to afford a mixture of the cis and trans methoxime: (More polar isomer)$^1$H NMR (400 MHz, CD$_3$OD) δ 8.46 (d, 1H), 8.18 (dd, 1H), 7.50-7.68 (m, 6H), 6.98 (dd, 1H), 3.90 (s, 3H), 1.33 (s, 9H); MS (ES) (M+H)$^+$ expected 474.1, found 474.1; (Less polar isomer)$^1$H NMR (400 MHz, CD$_3$OD) δ 8.24 (d, 1H), 8.03 (d, 1H), 7.88 (dd, 1H), 7.74 (d, 2H), 7.55-7.60 (m, 3H), 6.93 (dd, 1H), 4.11 (s, 3H), 1.30 (s, 9H); MS (ES) (M+H)$^+$ expected 474.1, found 474.1.

Example 343: N-[4-Chloro-2-(pyridine-4-carbonyl)-phenyl]-methanesulfonamide

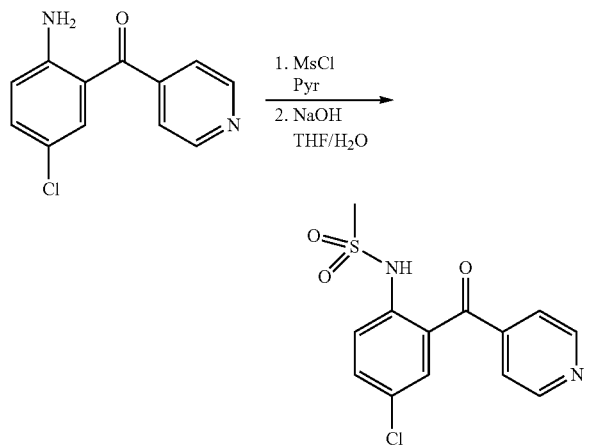

A 250 mL flask was charged with (2-amino-5-chlorophenyl)-pyridin-4-yl-methanone (10.0 g, 43.1 mmol) and pyridine (43 mL) under nitrogen. To the resultant solution was added methanesulfonyl chloride (7.06 mL, 90.5 mmol) and the reaction was stirred at room temperature overnight. The following morning, the organics were concentrated in vacuo at 60° C., followed by hydrolysis of the bis-sulfonamide employing THF (65 mL) and sodium hydroxide (65 mL, 4.0 M). The resultant homogeneous solution was stirred at room temperature for 120 min. Upon completion of the hydrolysis, the THF was removed under reduced pressure and the pH of the aqueous layer was adjusted to 5-6 with 6 M HCl. The resultant solution was diluted with EtOAc and the organics were washed with 10% HCl and saturated sodium bicarbonate, dried with sodium sulfate, concentrated in vacuo, and purified via automated silica gel chromatography to generate the desired methanesulfonamide: MS (ES) (M+H)$^+$ expected 311.0, found 311.1.

Example 344: N-{2-[(6-Amino-pyridin-3-yl)-ethoxyimino-methyl]-5-chloro-pyridin-3-yl}-4-tert-butyl-benzenesulfonamide

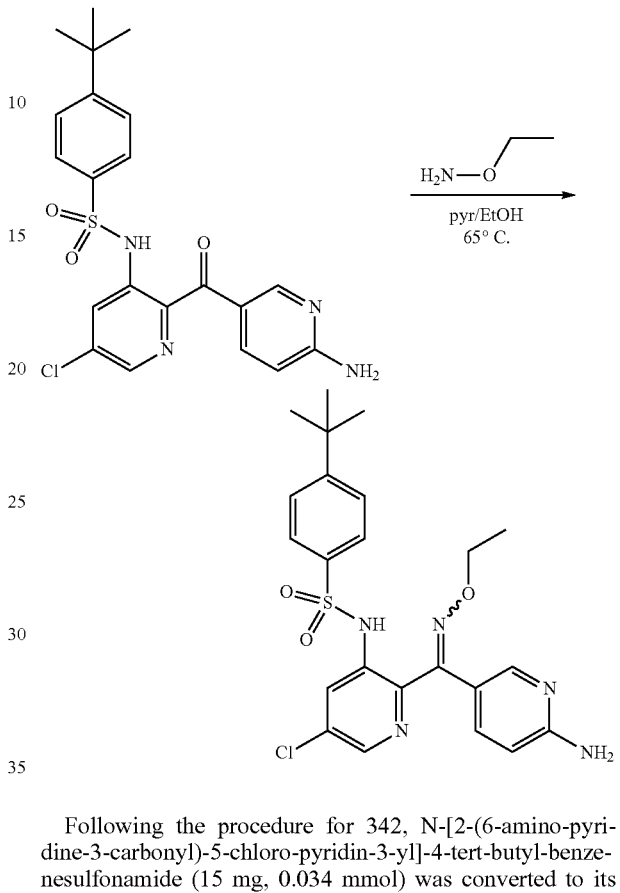

Following the procedure for 342, N-[2-(6-amino-pyridine-3-carbonyl)-5-chloro-pyridin-3-yl]-4-tert-butyl-benzenesulfonamide (15 mg, 0.034 mmol) was converted to its corresponding ethoxime: (Less polar isomer)$^1$H NMR (400 MHz, CD$_3$OD) δ 8.22 (d, 1H), 8.03 (d, 1H), 7.89 (dd, 1H), 7.74 (d, 2H), 7.58-7.60 (m, 3H), 6.93 (dd, 1H), 4.37 (q, 2H), 1.41 (t, 3H), 1.30 (s, 9H); MS (ES) (M+H)$^+$ expected 488.1, found 488.1.

Example 345: N-{2-[(6-Amino-pyridin-3-yl)-isopropoxyimino-methyl]-5-chloro-pyridin-3-yl}-4-tert-butyl-benzenesulfonamide

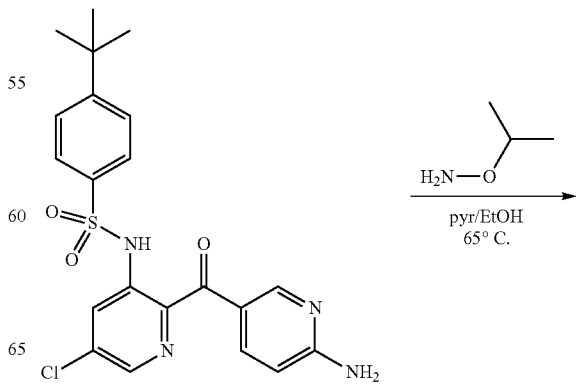

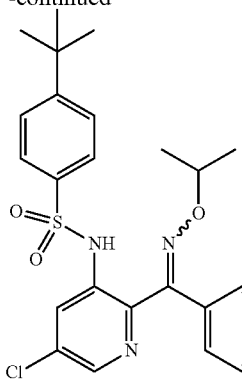

Following the procedure for 342, N-[2-(6-amino-pyridine-3-carbonyl)-5-chloro-pyridin-3-yl]-4-tert-butyl-benzenesulfonamide (15 mg, 0.034 mmol) was converted to its corresponding isopropyl oxime: (Less polar isomer) $^1$H NMR (400 MHz, CD$_3$OD) δ 8.21 (d, 1H), 8.04 (d, 1H), 7.89 (dd, 1H), 7.74 (d, 2H), 7.57-7.64 (m, 3H), 6.94 (dd, 1H), 4.60 (quint, 1H), 1.40 (d, 6H), 1.30 (s, 9H); MS (ES) (M+H)$^+$ expected 502.1, found 502.1.

Example 346: N-{2-[(6-Amino-pyridin-3-yl)-hydroxyimino-methyl]-5-chloro-pyridin-3-yl}-4-tert-butyl-benzenesulfonamide

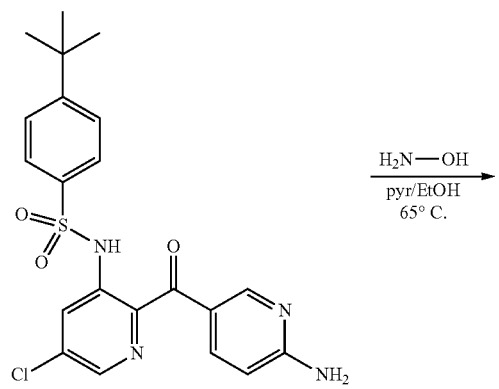

Following the procedure for 342, N-[2-(6-amino-pyridine-3-carbonyl)-5-chloro-pyridin-3-yl]-4-tert-butyl-benzenesulfonamide (15 mg, 0.034 mmol) was converted to its corresponding hydroxime: (Less polar isomer) $^1$H NMR (400 MHz, CD$_3$OD) δ 8.20 (d, 1H), 8.06 (d, 1H), 7.87 (dd, 1H), 7.71 (d, 2H), 7.51-7.58 (m, 3H), 6.92 (dd, 1H), 1.29 (s, 9H); MS (ES) (M+H)$^+$ expected 460.1, found 460.0.

Example 347: 3-(4-tert-Butyl-benzenesulfonylamino)-5-chloro-pyridine-2-carboxylic acid (2-fluoro-phenyl)-methyl-amide

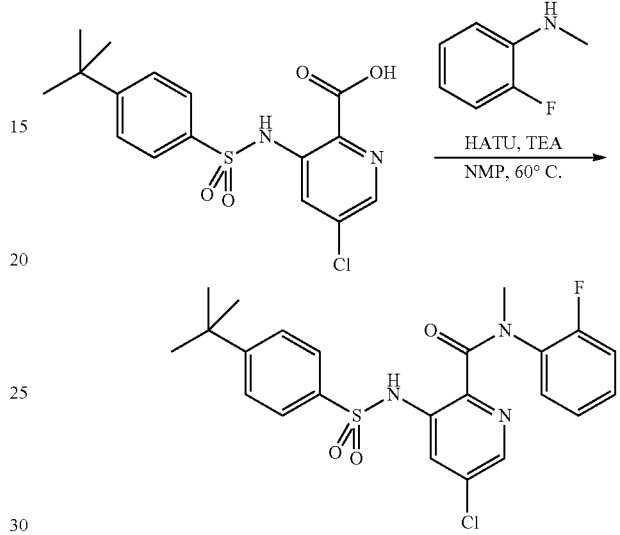

3-(4-tert-Butyl-benzenesulfonylamino)-5-chloro-pyridine-2-carboxylic acid (75 mg, 0.20 mmol), (2-fluoro-phenyl)-methyl-amine (23 mg, 0.61 mmol), HATU (193 mg, 0.51 mmol), TEA (114 μL, 0.81 mmol) and 0.5 mL NMP were combined in a 4 mL vial and stirred overnight at 60° C. HPLC purification (10 to 95% gradient of MeCN-water) provided 3-(4-tert-butyl-benzenesulfonylamino)-5-chloro-pyridine-2-carboxylic acid (2-fluoro-phenyl)-methyl-amide: $^1$H NMR (400 MHz, CDCl$_3$) 9.98 (s, 1H), 8.01 (s, 1H), 7.82 (d, 2H), 7.63 (s, 1H), 7.51 (d, 2H), 7.13 (m, 1H), 6.92 (t, 1H), 6.84 (t, 1H), 6.37 (m, 1H), 3.38 (t, 3H), 1.26 (s, 9H); MS m/z 476.1.

Example 348: 4-tert-Butyl-N-[5-chloro-2-(6-cyano-pyridine-3-carbonyl)-pyridin-3-yl]-N-methoxymethyl-benzenesulfonamide

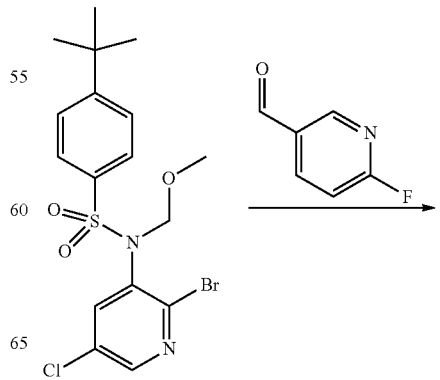

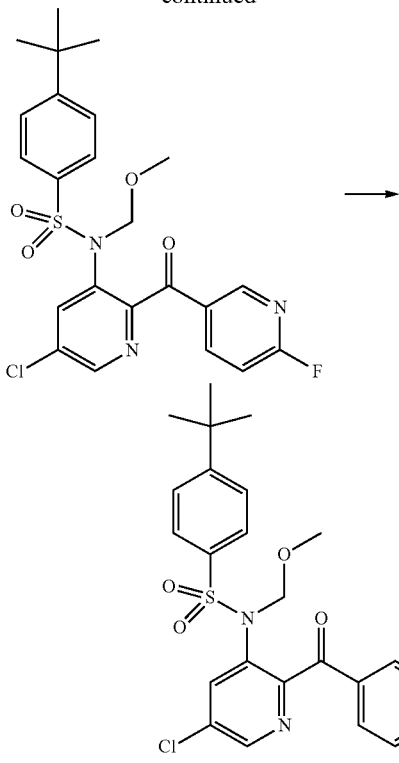

4-tert-Butyl-N-[5-chloro-2-(6-fluoro-pyridine-3-carbonyl)-pyridin-3-yl]-N-methoxymethyl-benzenesulfonamide was prepared from N-(2-bromo-5-chloro-pyridin-3-yl)-4-tert-butyl-N-methoxymethyl-benzenesulfonamide and 6-fluoro-pyridine-3-carbaldehyde using the procedure described in examples 35 and 36.

4-tert-Butyl-N-[5-chloro-2-(6-fluoro-pyridine-3-carbonyl)-pyridin-3-yl]-N-methoxymethyl-benzenesulfonamide (444 mg, 0.899 mmol) was dissolved in DMF (5 mL). KCN (300 mg, 4.6 mmol) was then added and the reaction mixture was heated to 60° C. for 2 hours. Additional KCN (110 mg, 1.7 mmol) was then added and the reaction was stirred for another 2 hours. The solvent was removed under reduced pressure and the resulting brown oil purified by column (1:4 EtOAc/hexanes) to give 172 mg (0.345 mmol, 38% yield). MS calc'd for $C_{24}H_{24}ClN_4O_4S$ (MH$^+$): 499.1, found 499.1.

Example 349: 4-tert-Butyl-N-[5-chloro-2-(6-cyano-pyridine-3-carbonyl)-pyridin-3-yl]-benzenesulfonamide

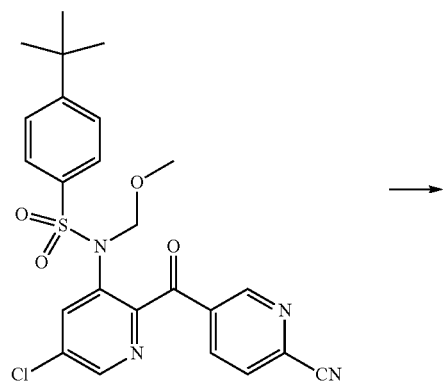

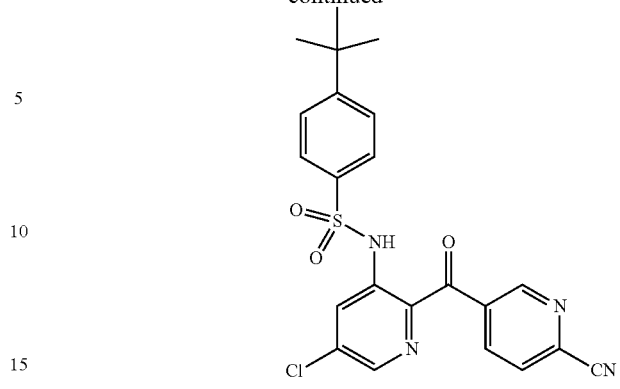

4-tert-Butyl-N-[5-chloro-2-(6-cyano-pyridine-3-carbonyl)-pyridin-3-yl]-N-methoxymethyl-benzenesulfonamide (15 mg, 0.030 mmol) was dissolved in 4N HCl (500 FL) and dioxane (1 mL). The reaction was then stirred at 90° C. for 12 hours. The solvent was removed under reduced pressure and the crude solid was purified by preparatory TLC (1:4 EtOAc/hexanes) to give 5 mg (0.01 mmol, 40% yield) of the desired product as a white solid. MS calc'd for $C_{22}H_{20}ClN_4O_3S$ (MH$^+$): expected 455.1, found 455.0.

Example 350: 6-Fluoro-pyridine-2-carboxylic acid methoxy-methyl-amide

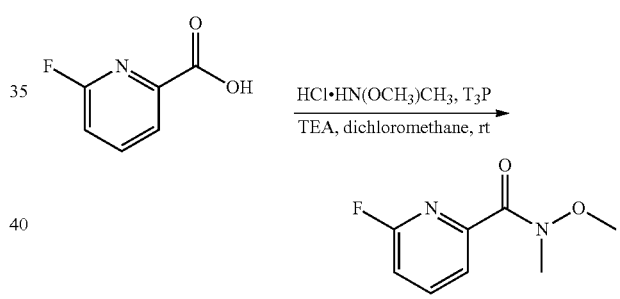

To a cooled mixture of 6-fluoro picolinic acid (1.19 g, 8.43 mmol), N,O-dimethylhydroxyl amine (860 mg, 8.82 mmol) and Et$_3$N (3.27 mL, 23.52 mmol) in CH$_2$Cl$_2$ (10 mL) was added 1-propane phosphonic acid cyclic anhydride (4.49 mL, 7.05 mmol; 50 wt % solution in EtOAc) dropwise and stirred at room temperature for 3 h. The reaction mixture was filtered, washed with CH$_2$Cl$_2$ (2×10 mL), evaporated to dryness, and subjected to column chromatography (SiO$_2$, 40% EtOAc-hexanes) to obtain 6-fluoro-pyridine-2-carboxylic acid methoxy-methyl-amide (1.19 g) in 73% yield. ESMS m/z (relative intensity): 185 (M+H)$^+$ (100).

Example 351: 6-Azido-pyridine-2-carboxylic acid methoxy-methyl-amide

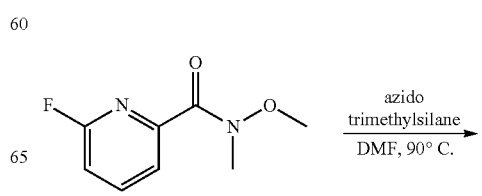

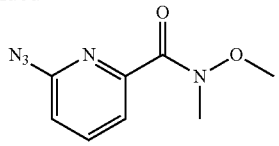

A mixture of 6-fluoro-pyridine-2-carboxylic acid methoxy-methyl-amide (1.19 g, 6.47 mmol) and azido-trimethylsilane (2.0 g, 16.8 mmol) in DMF (10 mL) was stirred at 110° C. for 72 h. The reaction mixture was diluted with 50 mL of dichloromethane and washed with water (3×50 mL). The organic layer was separated, evaporated to dryness, and subjected to column chromatography (SiO$_2$, 40% EtOAc-hexanes) to obtain 6-azido-pyridine-2-carboxylic acid methoxy-methyl-amide (0.335 g) in 25% yield. ESMS m/z (relative intensity): 208 (M+H)$^+$ (100).

Example 352: N-[2-(6-Azido-pyridine-2-carbonyl)-5-chloro-pyridin-3-yl]-4-tert-butyl-N-methoxymethyl-benzenesulfonamide

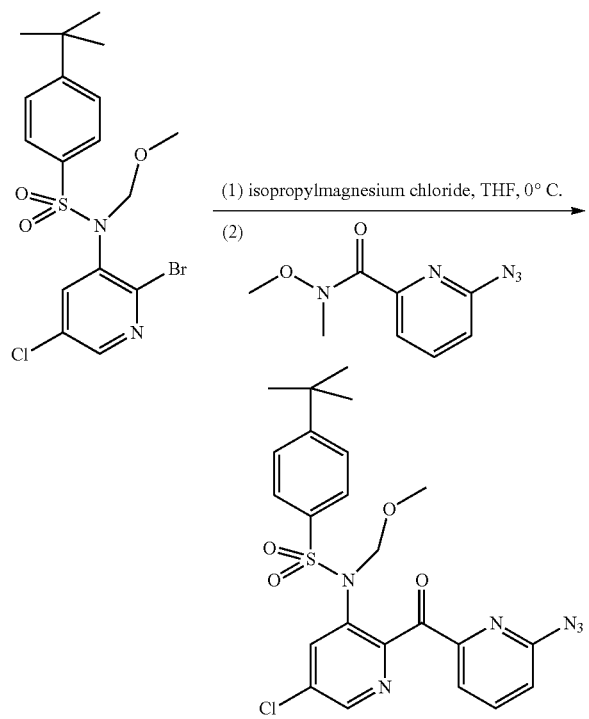

N-[2-(6-Azido-pyridine-2-carbonyl)-5-chloro-pyridin-3-yl]-4-tert-butyl-N-methoxymethyl-benzenesulfonamide was prepared from N-(2-bromo-5-chloro-pyridin-3-yl)-4-tert-butyl-N-methoxymethyl-benzene sulfonamide according to previously described procedure in example 29, step 1. The product was purified by flash column chromatography on silica gel using ethyl acetate-hexane. MS m/z: 515.1 (M+H)$^+$.

Example 353: N-[2-(6-Amino-pyridine-2-carbonyl)-5-chloro-pyridin-3-yl]-4-tert-butyl-N-methoxymethyl-benzenesulfonamide

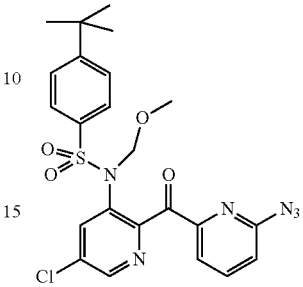
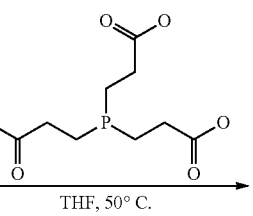

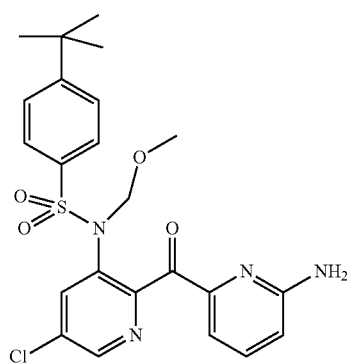

To a mixture of N-[2-(6-azido-pyridine-2-carbonyl)-5-chloro-pyridin-3-yl]-4-tert-butyl-N-methoxymethyl-benzenesulfonamide (0.3 mmol, 155 mg) in THF (3 mL) was added 3-[bis-(2-carboxy-ethyl)-phosphanyl]-propionic acid (1 mmol, 250 mg). The mixture was stirred at 50° C. for 3 h. Upon completion of the reduction, the THF was removed under reduced pressure. The residue was diluted with EtOAc and the organics were washed with saturated sodium bicarbonate, dried with sodium sulfate, concentrated in vacuo, and purified via automated silica gel chromatography to generate the desired product. MS m/z: 489.1 (M+H)$^+$.

Example 354: N-[2-(6-Amino-pyridine-2-carbonyl)-5-chloro-pyridin-3-yl]-4-tert-butyl-benzenesulfonamide

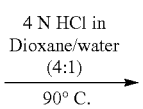

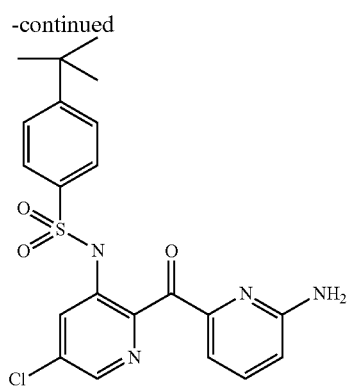

A mixture of N-[2-(6-amino-pyridine-2-carbonyl)-5-chloro-pyridin-3-yl]-4-tert-butyl-N-methoxymethyl-benzenesulfonamide (58.6 mg, 1.03 mmol) in 4 N HCl in dioxane (4 mL) and water (1 mL) was stirred at 90° C. overnight. The reaction mixture was cooled to room temperature, evaporated to dryness, and treated with saturated aqueous NaHCO₃ solution until pH 7-8. The mixture was extracted with EtOAc (2×25 mL), dried (anhydrous Na₂SO₄), and concentrated in vacuo. The obtained residue was purified via column chromatography (SiO₂, 70% EtOAc in hexanes) to afford N-[2-(6-amino-pyridine-2-carbonyl)-5-chloro-pyridin-3-yl]-4-tert-butyl-benzenesulfonamide (34.5 mg) in 64% yield. $^1$H NMR (400 MHz, CDCl₃) δ11.1 (s, 1H), 8.26 (d, 1H), 8.18 (d, 1H), 7.76 (d, 2H), 7.51 (t, 1H), 7.44 (d, 2H), 7.03 (d, 1H), 6.66 (d, 1H), 4.67 (s, 2H), 1.22 (s, 9H); ESMS m/z (relative intensity): 445.1 (M+H)⁺ (100).

Example 355: N-{6-[3-(4-tert-Butyl-benzenesulfonylamino)-5-chloro-pyridine-2-carbonyl]-pyridin-2-yl}-acetamide

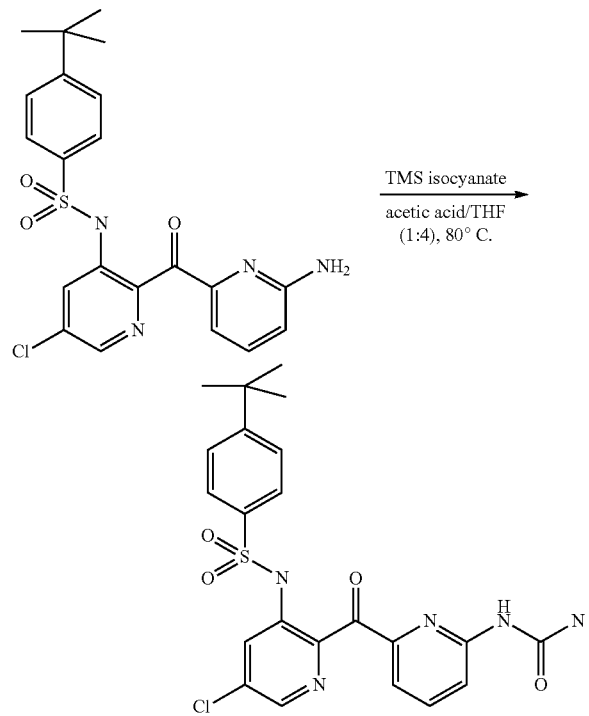

N-[2-(6-Amino-pyridine-2-carbonyl)-5-chloro-pyridin-3-yl]-4-tert-butyl-benzenesulfonamide (26 mg, 0.05 mmol) in THF (2 mL) was treated with TMS-isocyanate (100 mg) and AcOH (0.5 mL), and then stirred at 80° C. for 2 h. The mixture was subsequently diluted with acetonitrile (1 mL) and purified via HPLC to afford the title compound: $^1$H NMR (400 MHz, CDCl₃) δ 11.1 (s, 1H), 8.48 (d, 1H), 8.32 (d, 1H), 8.24 (m, 2H), 7.86 (m, 3H), 7.55 (d, 2H), 5.30 (s, 2H), 4.75 (s, 2H), 1.22 (s, 9H); ESMS m/z (relative intensity): 488.1 (M+H)⁺ (100).

Example 356: 4-tert-Butyl-N-[5-chloro-2-(6-methanesulfonylamino-pyridine-2-carbonyl)-pyridin-3-yl]-benzenesulfonamide

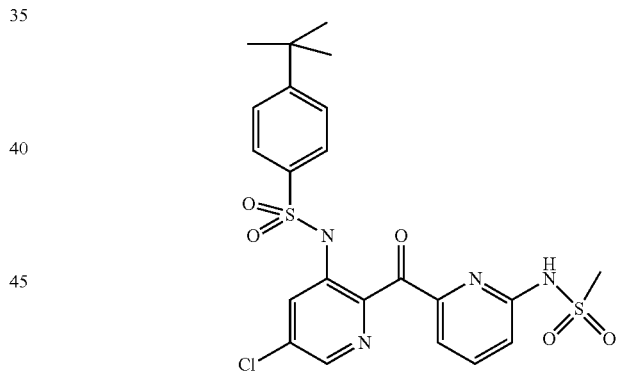

N-[2-(6-Amino-pyridine-2-carbonyl)-5-chloro-pyridin-3-yl]-4-tert-butyl-benzenesulfonamide (52 mg, 0.1 mmol) in pyridine was treated with methanesulfonyl chloride (100 mg) and then stirred at 70° C. for 2 h. After evaporation of solvent under reduced pressure, to the mixture was added THF (5 mL), followed by NaOH (2 N, 2 mL) and stirred at room temperature for another 2 h. The mixture was dissolved in EtOAc and washed with 1N HCl, NaHCO₃(saturated), brine, dried over MgSO₄, concentrated under reduced pressure, and purified through automated normal-phase chromatography to afford the title compound: 1H NMR (400 MHz, CDCl3) δ 11.0 (s, 1H), 8.37 (d, 1H), 8.25 (d, 1H), 7.82 (d, 2H), 7.72 (m, 1H), 7.61 (d, 1H), 7.42 (d, 2H), 7.17 (d, 1H), 3.15 (s, 3H), 1.23 (s, 9H); MS (ES) (M+H)⁺ expected 523.1, found 523.1.

Example 357: N-{6-[3-(4-tert-Butyl-benzenesulfonylamino)-5-chloro-pyridine-2-carbonyl]-pyridin-2-yl}-acetamide

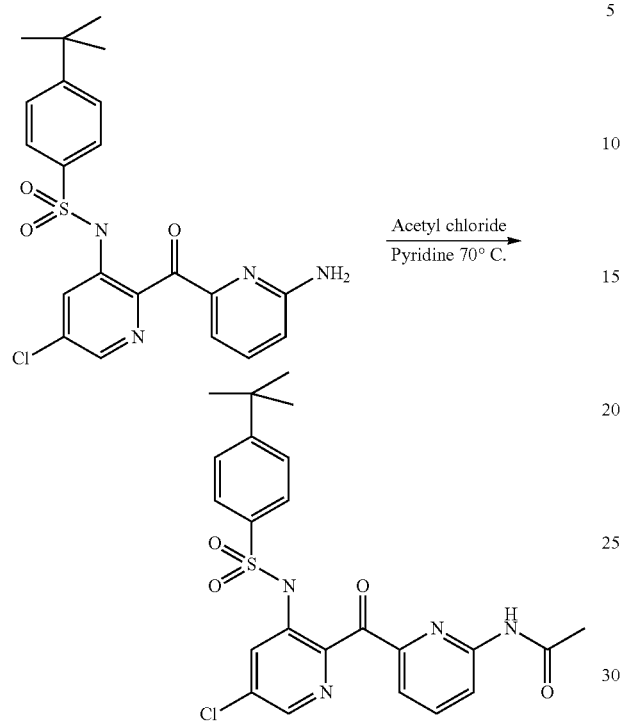

N-[2-(6-amino-pyridine-2-carbonyl)-5-chloro-pyridin-3-yl]-4-tert-butyl-benzenesulfonamide (52 mg, 0.1 mmol) in pyridine/1,4-dioxane (1:1, 4 mL) was treated with acetyl chloride (100 mg) and then stirred at 60° C. for 2 h. After evaporation of solvent under reduced pressure, to the mixture was added THF (5 mL), followed by NaOH (2 N, 2 mL) and stirred at room temperature for another 2 h. The mixture was diluted with EtOAc and the organics were washed with 1 N HCl, NaHCO$_3$(saturated), and brine; dried over MgSO$_4$, concentrated under reduced pressure, and purified through automated normal-phase chromatography to afford the title compound: $^1$H NMR (400 MHz, CDCl$_3$) δ 10.80 (s, 1H), 8.37 (d, 1H), 8.22 (m, 2H), 8.14 (s, 1H), 7.80 (m, 3H), 7.46 (m, 3H), 2.20 (s, 3H), 1.23 (s, 9H); MS (ES) (M+H)$^+$ expected 487.1, found 487.1.

Example 358: Preparation of (3-amino-5-chloro-pyridin-2-yl)-(1H-pyrrolo[2,3-b]pyridin-4-yl)-methanone

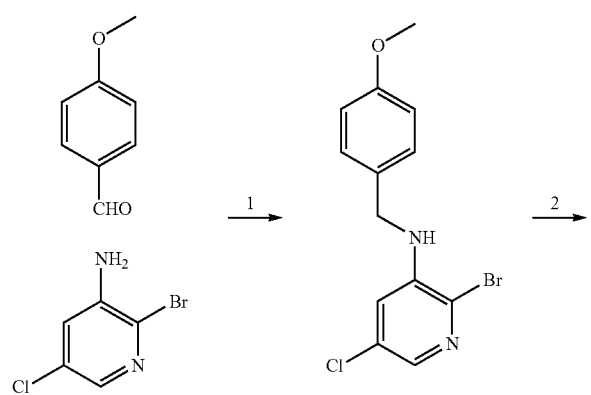

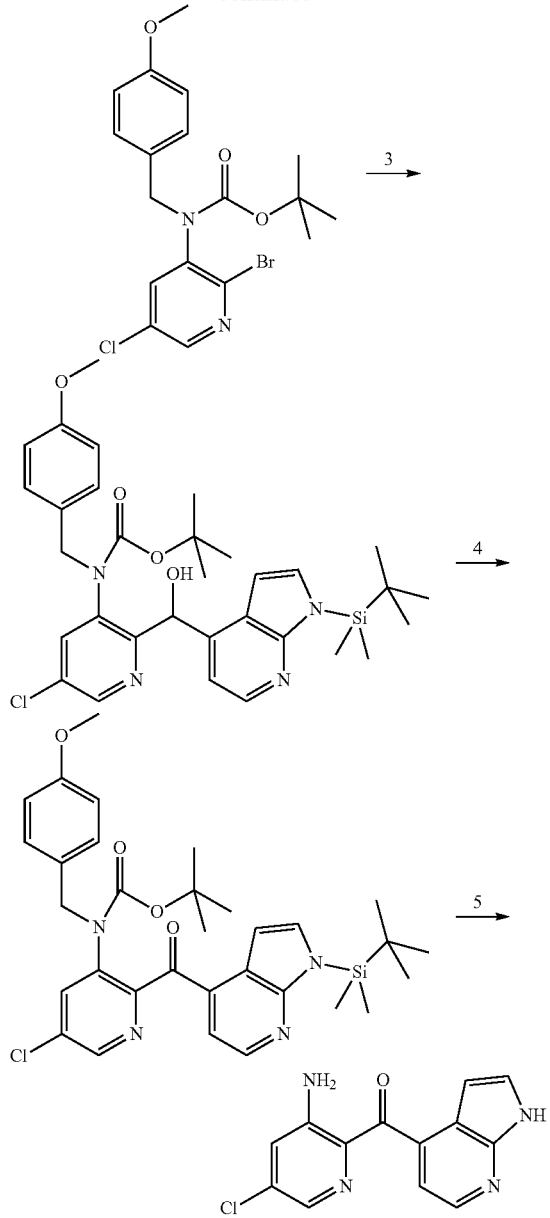

Step 1: (2-Bromo-5-chloro-pyridin-3-yl)-(4-methoxy-benzyl)-amine 5.16 g (24.8 mmol) of 2-bromo-5-chloro-pyridin-3-ylamine, 7.09 g (52.1 mmol) of p-anisaldehyde and 13.1 g (62.0 mmol) of sodium triacetoxyborohydride were dissolved in 100 mL of DCM and stirred at r.t. overnight. The next day DCM was replaced with chloroform, 5 g excess of sodium triacetoxyborohydride and 3 g excess of p-anisaldehyde were added and the reaction was conducted at 65° C. for 3 h. The mixture was worked up with aqueous sodium bicarbonate and purified on silica followed by recrystallization from ethyl acetate/hexanes mixture to give 3.40 g (42%) of the product as a white solid. MS (M+H)/z=328.9

Step 2: (2-Bromo-5-chloro-pyridin-3-yl)-(4-methoxy-benzyl)-carbamic acid tert-butyl ester: 2.19 g (6.66 mmol) of (2-bromo-5-chloro-pyridin-3-yl)-(4-methoxy-benzyl)-amine, 2.90 g (13.3 mmol) of di-tert-butyl dicarbonate and 82 mg (0.67 mmol) of DMAP were dissolved in 5 mL of DCM and heated to 60° C. letting DCM to evaporate. After 1 h 5 g of di-tert-butyl dicarbonate were added and the mixture stirred at 80° C. for 30 minutes. Flash chromatography of such mixture afforded 2.7 g (95%) of the product as a white solid. LC-MSD, m/z for $C_{18}H_{20}BrClN_2O_3[M+H]^+$=426.9, 428.9, 430.9.

Step 3: (2-{[1-(tert-Butyl-dimethyl-silanyl)-1H-pyrrolo[2,3-b]pyridin-4-yl]-hydroxy-methyl}-5-chloro-pyridin-3-yl)-(4-methoxy-benzyl)-carbamic acid tert-butyl ester: 2.12 g (4.96 mmol) of (2-bromo-5-chloro-pyridin-3-yl)-(4-methoxy-benzyl)-carbamic acid tert-butyl ester were dissolved in 12 mL THF and cooled down under nitrogen atmosphere to 0° C. 5.2 mL of 2 M solution of isopropyl-magnesium chloride solution in THF were added dropwise. Stirring at 00° C. for 15 minutes resulted in a complete bromine-magnesium exchange. The solution was cooled down to −20° C. and 1.29 g (4.96 mmol) of solid 1-(tert-butyl-dimethyl-silanyl)-1H-pyrrolo[2,3-b]pyridine-4-carbaldehyde was added. After 5 minutes the mixture was allowed to warm up to r.t. and was stirred at r.t. for 1 h. Aqueous ammonium chloride solution was added and the mixture was extracted with DCM. Organic layer was evaporated under reduced pressure. Flash chromatography on silica using 5-60% ethyl acetate in hexanes afforded 1.76 g (58%) of the product as a white solid. LC-MSD, m/z for $C_{32}H_{41}ClN_4O_4Si$ [M+H]$^+$=609.2, 611.2

Step 4: {2-[1-(tert-Butyl-dimethyl-silanyl)-1H-pyrrolo[2,3-b]pyridine-4-carbonyl]-5-chloro-pyridin-3-yl}-(4-methoxy-benzyl)-carbamic acid tert-butyl ester: 1.76 g (2.89 mmol) of (2-{[1-(tert-Butyl-dimethyl-silanyl)-1H-pyrrolo[2,3-b]pyridin-4-yl]-hydroxy-methyl}-5-chloro-pyridin-3-yl)-(4-methoxy-benzyl)-carbamic acid tert-butyl ester and 3.08 g (7.22 mmol) of Dess-Martin periodinane were dissolved in 10 mL of DCM and stirred at r.t. for 2 h. The reaction was worked up with aqueous sodium bicarbonate and sodium thiosulfate followed by purification on silica with 0-50% ethyl acetate in hexanes to afford 0.97 g of a mixture of the expected product and its desilylated analog as a yellow solid. LC-MSD, m/z for $C_{32}H_{39}ClN_4O_4Si$ [M+H]$^+$=607.2, 609.2;

Step 5: (3-Amino-5-chloro-pyridin-2-yl)-(1H-pyrrolo[2,3-b]pyridin-4-yl)-methanone: 0.97 g of {2-[1-(tert-Butyl-dimethyl-silanyl)-1H-pyrrolo[2,3-b]pyridine-4-carbonyl]-5-chloro-pyridin-3-yl}-(4-methoxy-benzyl)-carbamic acid tert-butyl ester and desilylated analog mixture was dissolved in 5 mL of TFA, stirred at r.t. for 2 h and evaporated. The residue was partitioned into a mixture of aqueous sodium bicarbonate solution and ethyl acetate. The organic layer was evaporated under reduced pressure. The solid residue was triturated with 200 mL of a 1:3 mixture of ethyl acetate-hexanes to afford 372 mg of the product as a brown solid. LC-MSD, m/z for $C_{13}H9ClN_4O$ [M+H]$^+$=273.0, 275.0;

Example 359:
1-Chloro-2-(1,1-difluoro-ethyl)-4-nitro-benzene

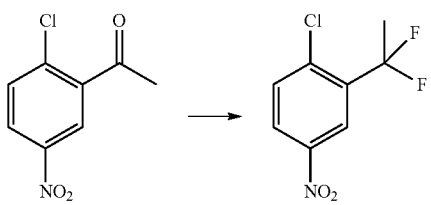

650 mg (3.27 mmol) of 1-(2-chloro-5-nitro-phenyl)-ethanone was combined with 855 µL (6.54 mmol) of DAST (diethylaminosulfur trifluoride) and heated to 50° C. for 5 h. The mixture was cooled down and diluted with 50 mL DCM. The solution was washed with 10 mL of water. The organic layer was evaporated on silica and purified on silica gel eluting with a 0-20% ethyl acetate in hexanes to give 490 mg (68%) of the pure product as a white solid. LC-MSD spectrum not observed;

Example 360:
4-Chloro-3-(1,1-difluoro-ethyl)-phenylamine

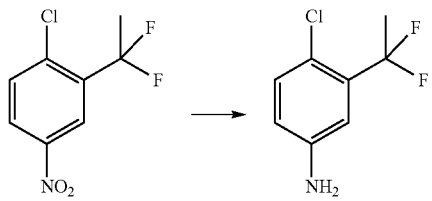

480 mg (2.17 mmol) of 1-chloro-2-(1,1-difluoro-ethyl)-4-nitro-benzene, 464 mg (8.67 mmol) of ammonium chloride and 365 mg (6.51 mmol) of iron powder were added to a mixture of 1.5 mL of water and 3 mL of methanol. The slurry was stirred at 70° C. for 1 h, and then cooled down, filtered through a pad of celite washing with excess methanol and concentrated down under reduced pressure. The residue was dissolved in ethyl acetate, evaporated under reduced pressure on silica gel and purified on silica eluting with a 5-30% ethyl acetate in hexanes to give 365 mg of the pure product as a white solid. LC-MSD, m/z for $C_8H8ClF_2N$ [M+H]$^+$=192.0, 194.0;

Example 361:
1-(5-Amino-2-chloro-phenyl)-ethanone

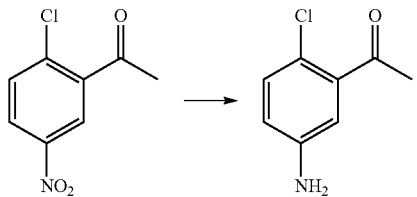

2.01 g (10.1 mmol) of 1-(2-chloro-5-nitro-phenyl)-ethanone, 2.54 g (47.5 mmol) of ammonium chloride and 1.99 g (35.7 mmol) of iron powder were added to a mixture of 6 mL of water and 12 mL of methanol. The slurry was stirred at 70° C. for 1 h, and then cooled down, filtered through a pad of celite and concentrated down under reduced pressure. The residue was taken up in 60 mL ethyl acetate and 60 mL of water. The aqueous layer was extracted with 40 mL of ethyl acetate and the combined organic layers were evaporated under reduced pressure. The residue was filtered through a pad of silica gel eluting with a 7:3 mixture of ethyl acetate-hexanes to give 1.6 g (94%) of the pure product as a white solid. LC-MSD, m/z for $C_8H_8ClNO$ [M+H]+=170.0, 172.0;

Example 362: General Procedure for Para-Chlorination of Anilines

Aniline (23 mmol) is dissolved in 100 mL of isopropanol and 23 mmol of NCS is added in one portion. After 30 minutes of stirring at r.t. silica gel is added and the solution is evaporated under reduced pressure. Flash chromatography using ethyl acetate/hexanes affords the product.

Example 363: 3-tert-Butyl-4-chloro-phenylamine

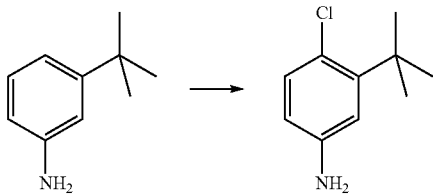

Prepared from 3.48 g of 3-tert-butyl-phenylamine and 3.12 g NCS. Yield: 1.5 g. LC-MSD, m/z for $C_{10}H_{14}ClN$ $[M+H]^+$=184.1, 186.1;

Example 364: 4-Chloro-3-iso-propyl-phenylamine

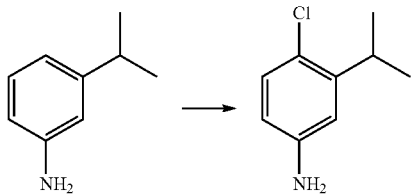

Prepared from 7.84 g of 3-iso-propyl-phenylamine and 7.75 g NCS. Yield: 4.6 g. LC-MSD, m/z for $C_9H_{12}ClN$ $[M+H]^+$=170.2, 172.0;

Example 365: 4-Chloro-3-ethyl-phenylamine

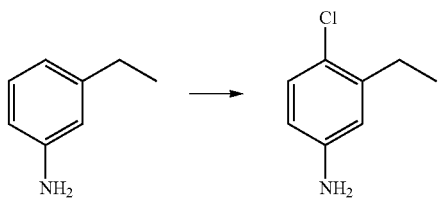

Prepared from 7.36 g of 3-ethyl-phenylamine and 8.12 g NCS. Yield: 4.4 g. LC-MSD, m/z for $C_8H_{10}ClN$ $[M+H]^+$=156.0, 158.0;

Example 366: 4-Ethyl-3-trifluoromethyl-phenylamine

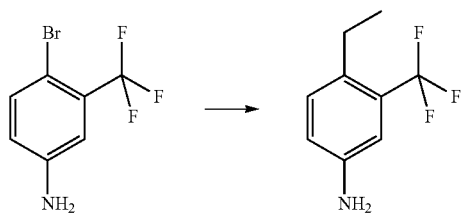

6.52 g (27.2 mmol) of 4-bromo-3-trifluoromethyl-phenylamine was dissolved in 30 mL of diethylamine in a sealed tube. To this solution sequentially were added 5.32 g (54.4 mmol) of trimethylsilylacetylene, 382 mg (0.54 mmol) of bis(triphenylphosphine)dichloropalladium(II) and 103 mg (0.54 mmol) of copper(I) iodide. The vessel was flushed with nitrogen, sealed and heated to 120° C. for 2 days. The solution was evaporated under reduced pressure, redissolved in DCM and evaporated on silica gel. Flash chromatography on silica using 0-40% ethyl acetate in hexanes afforded a mixture of 3-trifluoromethyl-4-trimethylsilanylethynyl-phenylamine and starting material. The mixture was dissolved in 30 mL methanol and heated to 60° C. for 30 minutes with 5 g of potassium carbonate. To this silica gel was added and the solvent was evaporated under reduced pressure. Flash chromatography on silica using 10-50% ethyl acetate in hexanes afforded 2.85 g of a mixture of 4-ethynyl-3-trifluoromethyl-phenylamine and 4-bromo-3-trifluoromethyl-phenylamine. It was dissolved in 50 mL of methanol, followed by the addition of 220 mg of 10% wet palladium on carbon catalyst and reduction under atmospheric pressure of hydrogen gas at r.t. for 16 h. To this mixture 10 mL of 2M ammonia solution in methanol was added, followed by silica gel, and it was evaporated under reduced pressure. Flash chromatography on silica using 5-30% ethyl acetate in hexanes afforded 1.45 g of the product as a white solid. LC-MSD, m/z for $C_9H_{10}F_3N$ $[M+H]^+$=190.1.

Example 367: General Procedure for Conversion of Anilines to Sulfonyl Chlorides

Followed the procedure described in *Org. Syn. Coll.* Vol. 7 p. 508. Flash chromatography using ethyl acetate in hexanes affords the product.

Example 368: 3-tert-Butyl-4-chloro-benzenesulfonyl Chloride

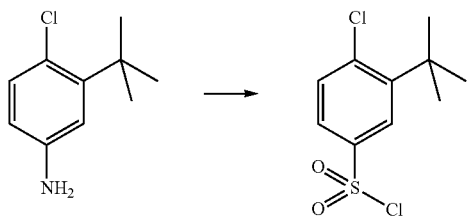

Amounts used: 10 mL of acetic acid was saturated with sulfur dioxide, 220 mg of copper(I) chloride, 1.5 g (8.20 mmol) of 3-tert-butyl-4-chloro-phenylamine dissolved in a mixture of 3 mL of acetic acid and 3 mL of concentrated hydrochloric acid, 0.622 g of sodium nitrite in 3 mL of water. Flash chromatography on silica using 0-15% ethyl acetate in hexanes afforded 0.42 g of the product as a white solid. LC-MSD spectrum not observed.

Example 369:
4-Chloro-3-iso-propyl-benzenesulfonyl Chloride

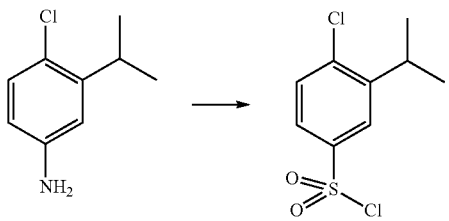

Amounts used: 25 mL of acetic acid was saturated with sulfur dioxide, 671 mg of copper(I) chloride, 4.60 g (27.1 mmol) of 4-chloro-3-isopropyl-phenylamine dissolved in a mixture of 4 mL of acetic acid and 9 mL of concentrated hydrochloric acid, 2.3 g of sodium nitrite in 10 mL of water. Flash chromatography on silica using 3-20% ethyl acetate in hexanes afforded 2.18 g of the product as a white solid. LC-MSD spectrum not observed.

Example 370: 4-Chloro-3-ethyl-benzenesulfonyl Chloride

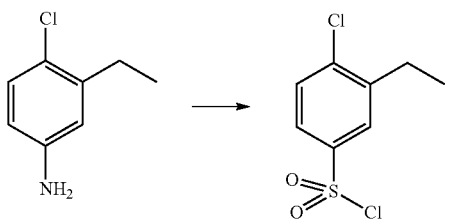

Amounts used: 25 mL of acetic acid was saturated with sulfur dioxide, 700 mg of copper(I) chloride, 4.40 g (28.3 mmol) of 4-chloro-3-ethyl-phenylamine dissolved in a mixture of 9 mL of acetic acid and 9 mL of concentrated hydrochloric acid, 2.20 g of sodium nitrite in 10 mL of water. Flash chromatography on silica using 0-20% ethyl acetate in hexanes afforded 3.4 g of the product as a white solid. LC-MSD spectrum not observed;

Example 371: 3-Acetyl-4-chloro-benzenesulfonyl Chloride

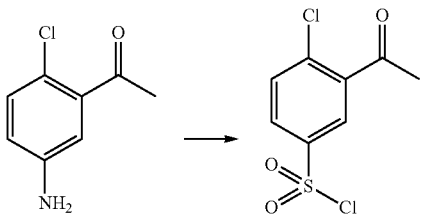

Amounts used: 8 mL of acetic acid was saturated with sulfur dioxide, 233 mg of copper(I) chloride, 1.60 g (9.41 mmol) of 1-(5-amino-2-chloro-phenyl)-ethanone dissolved in a mixture of 3 mL of acetic acid and 3 mL of concentrated hydrochloric acid, 714 mg of sodium nitrite in 3 mL of water. Flash chromatography on silica using 20-50% ethyl acetate in hexanes afforded 1.6 g of the product as a white solid. LC-MSD, m/z for $C_8H_6Cl_2O_3S$ $[M+H]^+$=252.9, 254.9, 256.9;

Example 372:
4-Chloro-3-(1,1-difluoro-ethyl)-benzenesulfonyl Chloride

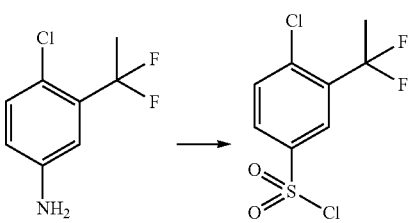

Amounts used: 2 mL of acetic acid was saturated with sulfur dioxide, 47 mg of copper(I) chloride, 365 mg (1.91 mmol) of 4-chloro-3-(1,1-difluoro-ethyl)-phenylamine dissolved in a mixture of 1.2 mL of acetic acid and 0.6 mL of concentrated hydrochloric acid, 145 mg of sodium nitrite in 1 mL of water. Flash chromatography on silica using 0-15% ethyl acetate in hexanes afforded 377 mg of the product as a white solid. LC-MSD spectrum not observed;

Example 373:
4-Ethyl-3-trifluoromethyl-benzenesulfonyl Chloride

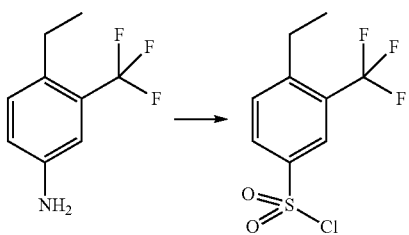 [SMILES: CCc1ccc(N)cc1C(F)(F)F ; CCc1ccc(S(=O)(=O)Cl)cc1C(F)(F)F]

Amounts used: 8 mL of acetic acid was saturated with sulfur dioxide, 190 mg of copper(I) chloride, 1.45 g (7.67 mmol) of 4-ethyl-3-trifluoromethyl-phenylamine dissolved in a mixture of 3 mL of acetic acid and 3 mL of concentrated hydrochloric acid, 0.635 g of sodium nitrite in 3 mL of water. Flash chromatography on silica using 0-20% ethyl acetate in hexanes afforded 0.9 g of the product as a white solid. LC-MSD spectrum not observed; HPLC retention time: 2.9 min.

Example 374: General Procedure for the Preparation of Sulfonamides without the Azaindole Moiety

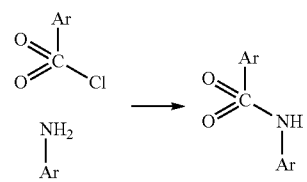

Sulfonyl chloride (1 equiv.) and amine (1.1 equiv.) are dissolved in pyridine and heated to 80° C. overnight. The solvent is evaporated under reduced pressure and the residue purified by flash chromatography to produce the sulfonamide.

Example 375: General Procedure for the Preparation of Sulfonamides with the Azaindole Moiety

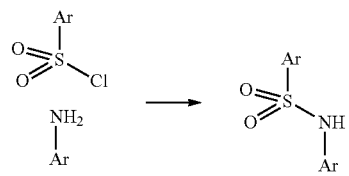

Sulfonyl chloride (3.5 equiv.) and amine (1 equiv.) are dissolved in pyridine and heated to 80° C. overnight. The temperature is lowered to 65° C. and methanol and aqueous sodium hydroxide solution are added and the mixture is stirred for 30 minutes. The solvent is evaporated under reduced pressure and the residue purified by reverse-phase HPLC followed by flash chromatography to produce the sulfonamide.

Example 376: N-(2-Bromo-5-chloro-pyridin-3-yl)-4-ethyl-3-trifluoromethyl-benzenesulfonamide

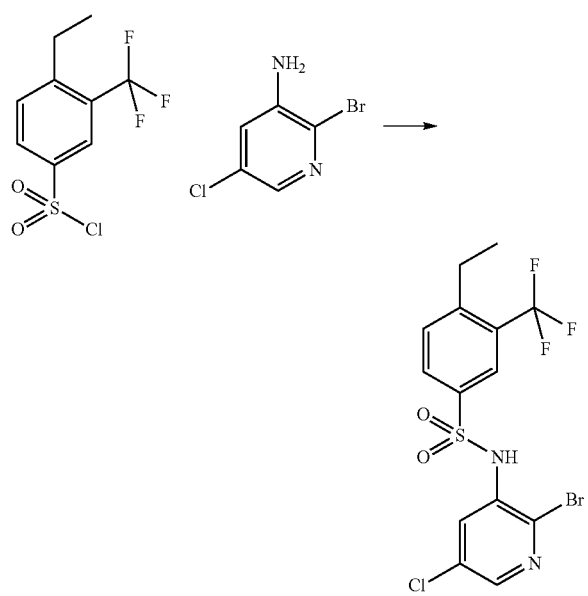

Prepared from 1.04 g (3.82 mmol) of 4-ethyl-3-trifluoromethyl-benzenesulfonyl chloride and 0.87 g (4.20 mmol) of 2-bromo-5-chloro-pyridin-3-ylamine in 3 mL pyridine using procedure x. Yield: 0.45 g of a white solid. LC-MSD, m/z for $C_{14}H_{11}BrClF_3N_2O_2S$ [M+H]$^+$=442.9, 444.9, 446.9

Example 377: N-(2-Bromo-5-chloro-pyridin-3-yl)-4-chloro-3-ethyl-benzenesulfonamide

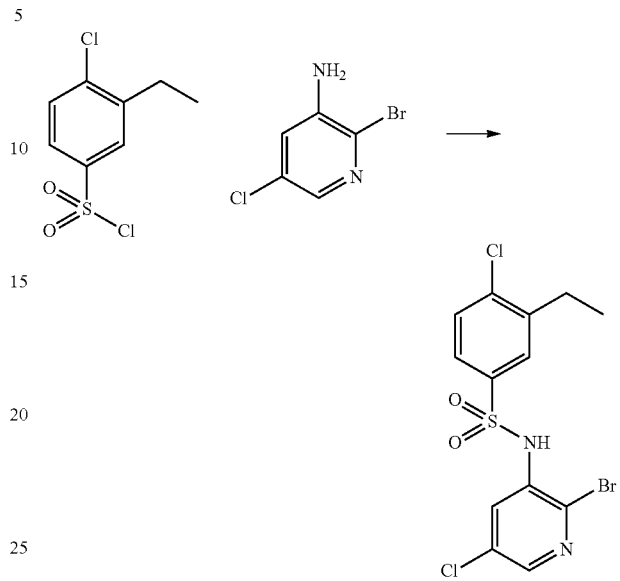

Prepared from 1.71 g (7.15 mmol) of 4-chloro-3-ethyl-benzenesulfonyl chloride and 1.34 g (6.47 mmol) of 2-bromo-5-chloro-pyridin-3-ylamine in 4 mL pyridine using procedure x. Yield: 2.35 g of a white solid. LC-MSD, m/z for $C_{13}H_{11}BrCl_2N_2O_2S$ [M+H]$^+$=408.8, 410.8, 412.8

Example 378: N-(2-Bromo-5-chloro-pyridin-3-yl)-3-tert-butyl-4-chloro-benzenesulfonamide

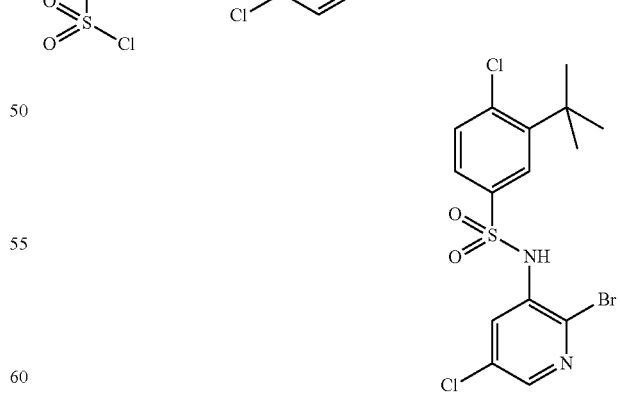

Prepared from 420 mg (1.57 mmol) of 3-tert-butyl-4-chloro-benzenesulfonyl chloride and 326 mg (1.57 mmol) of 2-bromo-5-chloro-pyridin-3-ylamine in 3 mL pyridine using procedure x. Yield: 0.48 g of a white solid. LC-MSD, m/z for $C_{15}H_{15}BrCl_2N_2O_2S$ [M+H]$^+$=436.9, 438.8, 440.8.

Example 379: 3-Acetyl-N-(2-bromo-5-chloro-pyridin-3-yl)-4-chloro-benzenesulfonamide

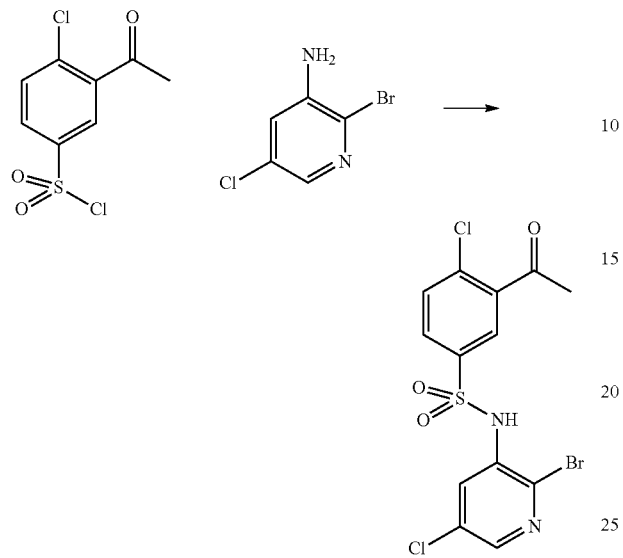

Prepared from 1.6 g (6.32 mmol) of 3-acetyl-4-chloro-benzenesulfonyl chloride and 1.3 g (6.28 mmol) of 2-bromo-5-chloro-pyridin-3-ylamine in 8 mL pyridine using procedure x. Yield: 1.3 g of a white solid. LC-MSD, m/z for $C_{13}H_9BrCl_2N_2O_3S$ [M+H]$^+$=422.8, 424.8, 426.8.

Example 380: N-(2-Bromo-5-chloro-pyridin-3-yl)-4-chloro-3-(1,1-difluoro-ethyl)-benzenesulfonamide

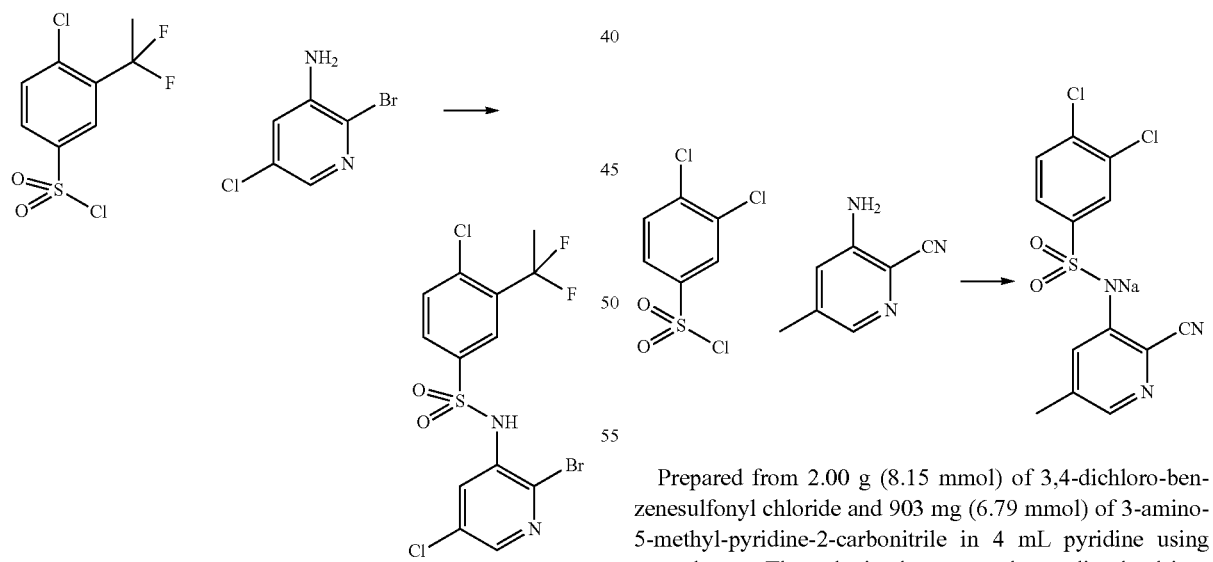

Prepared from 377 mg (1.37 mmol) of 4-chloro-3-(1,1-difluoro-ethyl)-benzenesulfonyl chloride and 270 mg (1.30 mmol) of 2-bromo-5-chloro-pyridin-3-ylamine in 2 mL pyridine using procedure x. Yield: 460 mg of a white solid. LC-MSD, m/z for $C_{13}H_9BrCl_2F_2N_2O_2S$ [M+H]$^+$=444.8, 446.8, 448.8.

Example 381: N-(2-Cyano-5-methyl-pyridin-3-yl)-4-methyl-3-trifluoromethyl-benzenesulfonamide

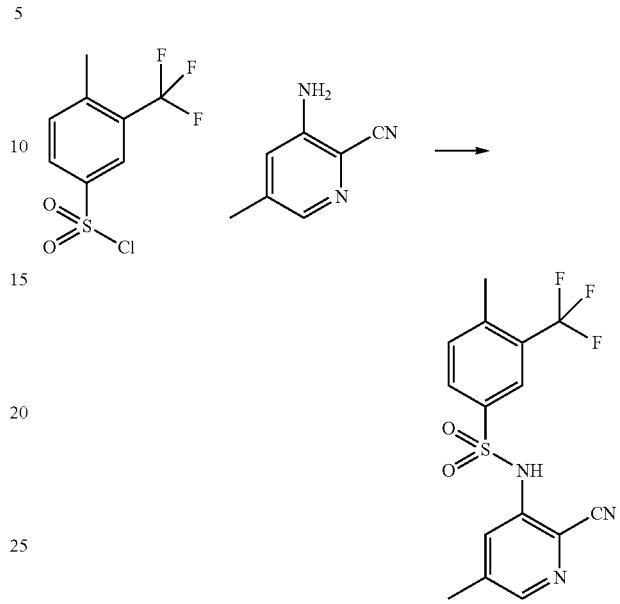

Prepared from 2.92 g (11.3 mmol) of 4-methyl-3-trifluoromethyl-benzenesulfonyl chloride and 1.25 g (9.41 mmol) of 3-amino-5-methyl-pyridine-2-carbonitrile in 4 mL pyridine using procedure x. Yield: 1.13 g of a white solid. LC-MSD, m/z for $C_{15}H_{12}F_3N_3O_2S$ [M+H]$^+$=356.0

Example 382: 3,4-Dichloro-N-(2-cyano-5-methyl-pyridin-3-yl)-benzenesulfonamide Sodium Salt Prepared from 2.00 g (8.15 mmol) of 3,4-dichloro-benzenesulfonyl chloride and 903 mg (6.79 mmol) of 3-amino-5-methyl-pyridine-2-carbonitrile in 4 mL pyridine using procedure x. Thus obtained compound was dissolved in a mixture of 20 mL THF and 10 mL of water with 326 mg (8.15 mmol) of sodium hydroxide and stirred at r.t. for 1 h, then evaporated under reduced pressure to dryness and washed with 10 mL of water. The solid was dried under vacuum at 110° C. Yield: 1.34 g of a white solid. LC-MSD, m/z for $C_{13}H_{10}Cl_2N_3O_2S$ [M+H]$^+$=341.9, 343.9.

Example 383: N-(2-Bromo-5-chloro-pyridin-3-yl)-4-chloro-3-(1-hydroxy-1-methyl-ethyl)-benzenesulfonamide

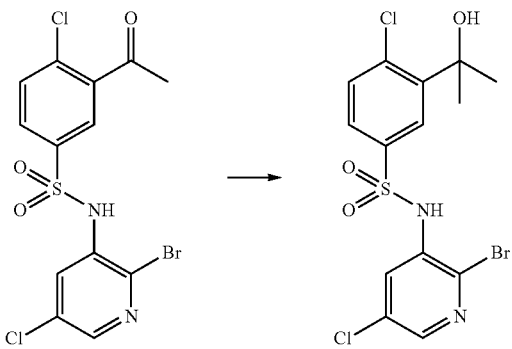 [SMILES: CC(=O)c1cc(S(=O)(=O)Nc2cc(Cl)cnc2Br)ccc1Cl ; CC(C)(O)c1cc(S(=O)(=O)Nc2cc(Cl)cnc2Br)ccc1Cl]

365 mg (0.86 mmol) of 3-acetyl-N-(2-bromo-5-chloro-pyridin-3-yl)-4-chloro-benzenesulfonamide was dissolved in 3 mL of anhydrous THF and cooled down under nitrogen atmosphere to −78° C. To that solution 0.86 mL of 3M methylmagnesium bromide solution in diethyl ether was added dropwise. The solution was allowed to warm up to 0° C. and was then quenched with aqueous ammonium chloride and extracted with DCM. The organic layer was evaporated under reduced pressure and purified on silica using 5-40% ethyl acetate in hexanes to yield 288 mg of a white solid. LC-MSD, m/z for $C_{14}H_{13}BrCl_2N_2O_3S$ [M+H]$^+$=438.9, 440.9, 442.9.

Example 384: General Procedure for the Protection of Sulfonamides

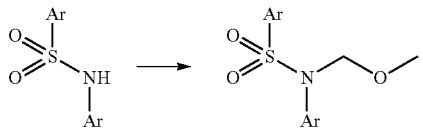

Sulfonamide (1 eqiuv.) and methoxymethyl chloride (2.5 equiv.) are dissolved in THF, 3 equiv. of potassium carbonate are added and the mixture is stirred overnight at r.t. The solvent is evaporated under reduced pressure and the residue purified by flash chromatography to produce the MOM-protected sulfonamide.

Example 385: N-(2-Bromo-5-chloro-pyridin-3-yl)-4-chloro-3-ethyl-N-methoxymethyl-benzenesulfonamide

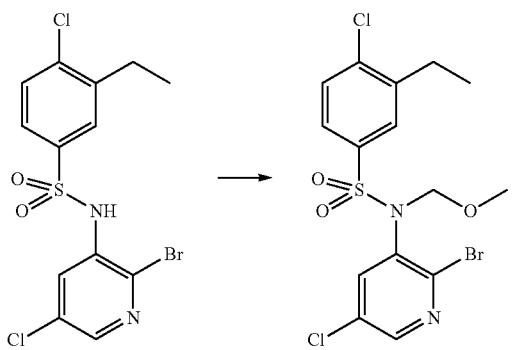 [SMILES: CCc1cc(S(=O)(=O)Nc2cc(Cl)cnc2Br)ccc1Cl ; CCc1cc(S(=O)(=O)N(COC)c2cc(Cl)cnc2Br)ccc1Cl]

Prepared from 2.35 g (5.73 mmol) of N-(2-bromo-5-chloro-pyridin-3-yl)-4-chloro-3-ethyl-benzenesulfonamide, 2.76 g of potassium carbonate and 1.3 mL of methoxymethyl chloride in 10 mL THF using procedure x. Yield: 980 mg of a white solid. LC-MSD, m/z for $C_{15}H_{15}BrCl_2N_2O_3S$ [M+H]$^+$=452.9, 454.9, 456.9

Example 386: N-(2-Bromo-5-chloro-pyridin-3-yl)-3-tert-butyl-4-chloro-N-methoxymethyl-benzenesulfonamide

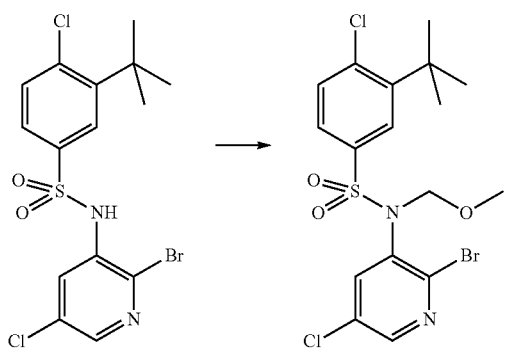 [SMILES: CC(C)(C)c1cc(S(=O)(=O)Nc2cc(Cl)cnc2Br)ccc1Cl ; COCN(c1cc(Cl)cnc1Br)S(=O)(=O)c1ccc(Cl)c(C(C)(C)C)c1]

Prepared from 480 mg (1.10 mmol) of N-(2-bromo-5-chloro-pyridin-3-yl)-3-tert-butyl-4-chloro-benzenesulfonamide, 400 mg of potassium carbonate and 170 μL (1.57 mmol) of methoxymethyl chloride in 2 mL THF using procedure x. Yield: 160 mg of a white solid. LC-MSD, m/z for $C_{17}H_{19}BrCl_2N_2O_3S$ [M+H]$^+$=480.9, 482.9, 484.9

Example 387: N-(2-Bromo-5-chloro-pyridin-3-yl)-4-chloro-3-(1-hydroxy-1-methyl-ethyl)-N-methoxymethyl-benzenesulfonamide

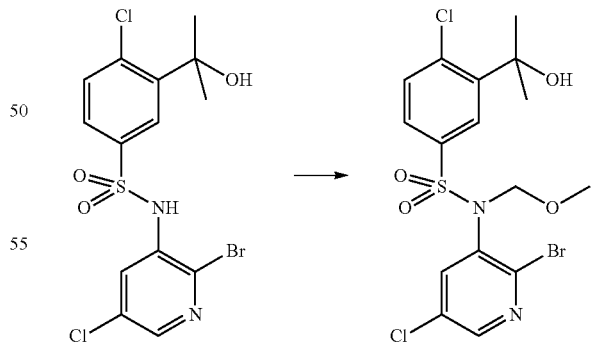

Prepared from 285 mg (0.648 mmol) of N-(2-bromo-5-chloro-pyridin-3-yl)-4-chloro-3-(1-hydroxy-1-methyl-ethyl)-benzenesulfonamide, 268 mg of potassium carbonate and 150 μL of methoxymethyl chloride in 2 mL THF using procedure x. Yield: 153 mg of a white solid. LC-MSD, m/z for $C_{16}H_{17}BrCl_2N_2O_4S$ [M+H]$^+$=482.9, 484.9, 486.9

Example 388: N-(2-Bromo-5-chloro-pyridin-3-yl)-4-chloro-3-(1,1-difluoro-ethyl)-N-methoxymethyl-benzenesulfonamide

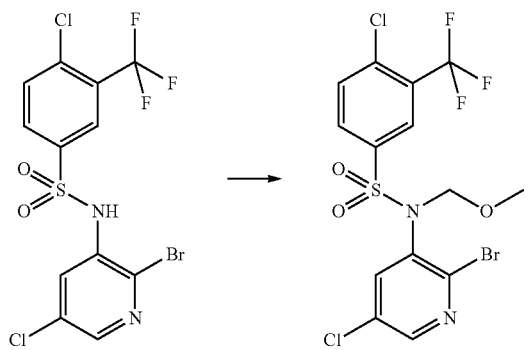 [SMILES: O=S(=O)(Nc1cc(Cl)cnc1Br)c1ccc(Cl)c(C(F)(F)F)c1 ; COCN(c1cc(Cl)cnc1Br)S(=O)(=O)c1ccc(Cl)c(C(F)(F)F)c1]

Prepared from 460 mg (1.03 mmol) of N-(2-bromo-5-chloro-pyridin-3-yl)-4-chloro-3-(1,1-difluoro-ethyl)-benzenesulfonamide, 355 mg of potassium carbonate and 195 µL of methoxymethyl chloride in 2 mL THF using procedure x. Yield: 162 mg of a white solid. LC-MSD, m/z for $C_{15}H_{13}BrCl_2F_2N_2O_3S$ [M+H]$^+$=488.8, 490.8, 492.8; HPLC retention time: 2.9 min.

Example 389: General Procedure for the preparation of N-[5-chloro-2-(1H-pyrrolo[2,3-b]pyridine-4-carbonyl)-pyridin-3-yl]-arylsulfonamides from N-(2-Bromo-5-chloro-pyridin-3-yl)-N-methoxymethyl-arylsulfonamides

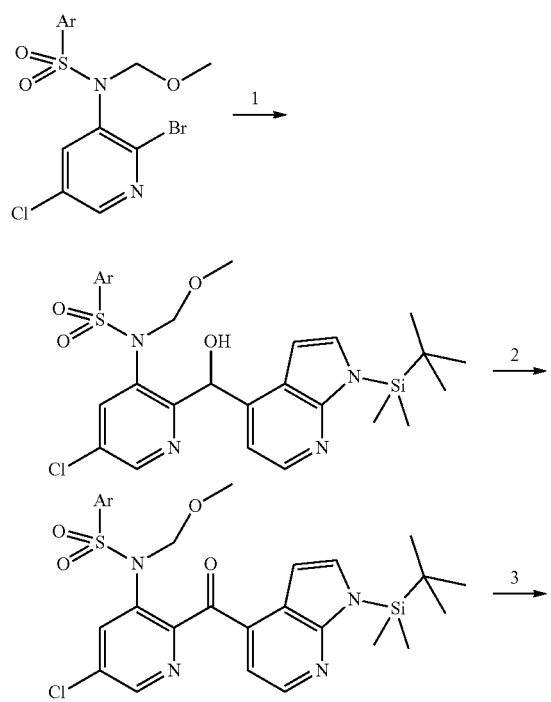

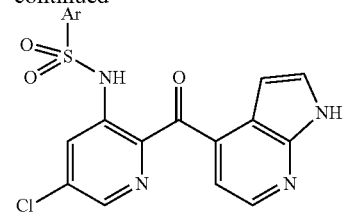

Step 1: N-(2-{[1-(tert-Butyl-dimethyl-silanyl)-1H-pyrrolo[2,3-b]pyridin-4-yl]-hydroxy-methyl}-5-chloro-pyridin-3-yl)-N-methoxymethyl-arylsulfonamide: 1 mmol of N-(2-bromo-5-chloro-pyridin-3-yl)-N-methoxymethyl-arylsulfonamide was dissolved under nitrogen atmosphere in 3 mL THF. 1.05 mL of 2 M solution of isopropylmagnesium chloride solution in THF was added dropwise. Stirring at r.t. for 15 minutes resulted in a complete bromine-magnesium exchange. The solution was cooled down to −20° C. and 1.1 mmol of solid 1-(tert-butyl-dimethyl-silanyl)-1H-pyrrolo[2,3-b]pyridine-4-carbaldehyde was added. After 5 minutes the mixture was allowed to warm up to r.t. and was stirred at r.t. for 1 h. Aqueous ammonium chloride solution was added and the mixture was extracted with DCM. Organic layer was evaporated under reduced pressure. Flash chromatography on silica using ethyl acetate in hexanes afforded the products.

Step 2: N-{2-[1-(tert-Butyl-dimethyl-silanyl)-1H-pyrrolo[2,3-b]pyridine-4-carbonyl]-5-chloro-pyridin-3-yl}-N-methoxymethyl-arylsulfonamide: 1 mmol of N-(2-{[1-(tert-butyl-dimethyl-silanyl)-1H-pyrrolo[2,3-b]pyridin-4-yl]-hydroxy-methyl}-5-chloro-pyridin-3-yl)-N-methoxymethyl-arylsulfonamide and 2.5 mmol of Dess-Martin periodinane were dissolved in 1 mL of DCM and stirred at r.t. for 2 h. The reaction was worked up with aqueous sodium bicarbonate and sodium thiosulfate and purified on silica with ethyl acetate in hexanes to afford a mixture of the expected product and its desilylated analog as a yellow solid.

Step 3: N-[5-chloro-2-(1H-pyrrolo[2,3-b]pyridine-4-carbonyl)-pyridin-3-yl]-arylsulfonamide: 1 mmol of N-{2-[1-(tert-butyl-dimethyl-silanyl)-1H-pyrrolo[2,3-b]pyridine-4-carbonyl]-5-chloro-pyridin-3-yl}-N-methoxymethyl-arylsulfonamide mixture with its desilylated analog was dissolved in a mixture of 20 mL of methanol and 20 mL of 6N hydrochloric acid. The solution was heated in a sealed tube at 80° C. for 8 h, then cooled down and evaporated. The residue was dissolved in methanolic ammonia and evaporated on silica gel under reduced pressure. Flash chromatography on silica using ethyl acetate in hexanes afforded the products as yellow solids. In some cases additional reverse-phase HPLC purification step was necessary to obtain pure products.

Example 390: 1H-Pyrrolo[2,3-b]pyridine-4-boronic Acid

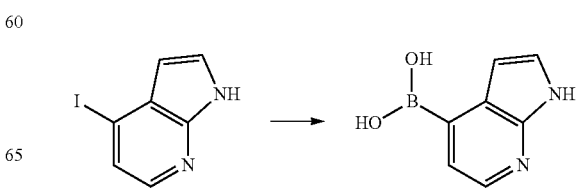

199 mg (0.816 mmol) of 4-iodo-1H-pyrrolo[2,3-b]pyridine, 203 mg (0.897 mmol) of bis(neopentyl glycolato)diboron, 240 mg (2.45 mmol) of potassium acetate and 20 mg (0.024 mmol) of bis(triphenylphosphine)dichloropalladium(II) were dissolved/suspended in 1 mL of DMSO and reacted at 90° C. for 4 h. The mixture was separated using reverse-phase HPLC to give 140 mg of a mixture of the desired boronic acid, its neopentyl glycolate and 1H-pyrrolo[2,3-b]pyridine. LC-MSD, m/z for $C_7H7BN_2O_2[M+H]^+=162.1$, 163.0 (boronic acid). LC-MSD, m/z for $C_{12}H_{15}BN_2O_2 [M+H]^+=230.1$, 231.0; HPLC retention time: 0.2 min (boronic ester). LC-MSD, m/z for $C_7H6N_2 [M+H]^+=119.0$

Example 391: 4-Chloro-2-(4-chloro-3-trifluoromethyl-benzenesulfonylamino)-benzoic Acid

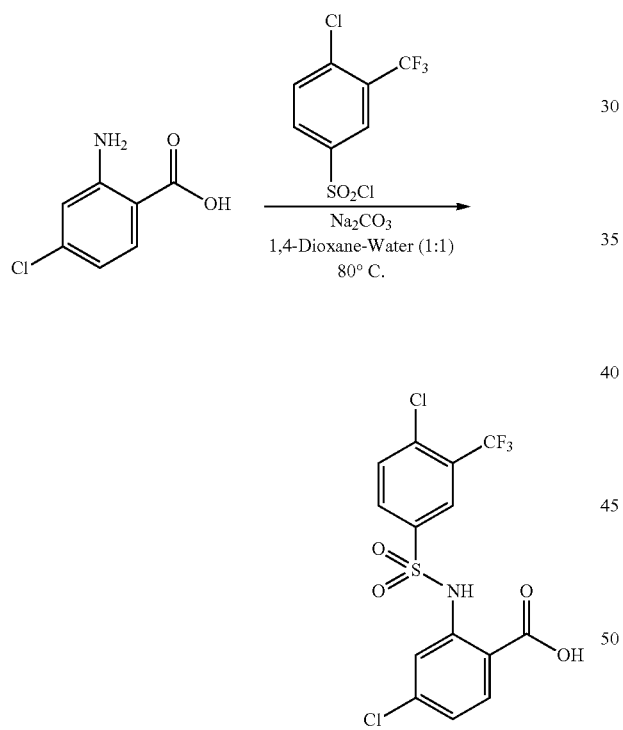

To a solution of $Na_2CO_3$ (11.7 g, 110.7 mmol) in water (50 mL) and 1,4-dioxane (50 mL) at 60° C. was added 2-amino-4-chloro-benzoic acid (5.0 g, 29.14 mmol) followed by 4-chloro-3-trifluoromethyl-benzenesulfonyl chloride (20.15 g, 72.48 mmol) in 3 portions and heated the resulting reaction mixture at 80° C. for 4 h. 2N HCl Was added until the reaction mixture became acidic (pH=2) and obtained white solid was filtered, washed with water, dried under high vacuum to obtain title compound (7.8 g) in 65% yield. MS (ES) M+Na expected 436.0, found 435.8.

Example 392: 4-Chloro-2-(4-chloro-3-trifluoromethyl-benzenesulfonylamino)-N-methoxy-N-methyl-benzamide

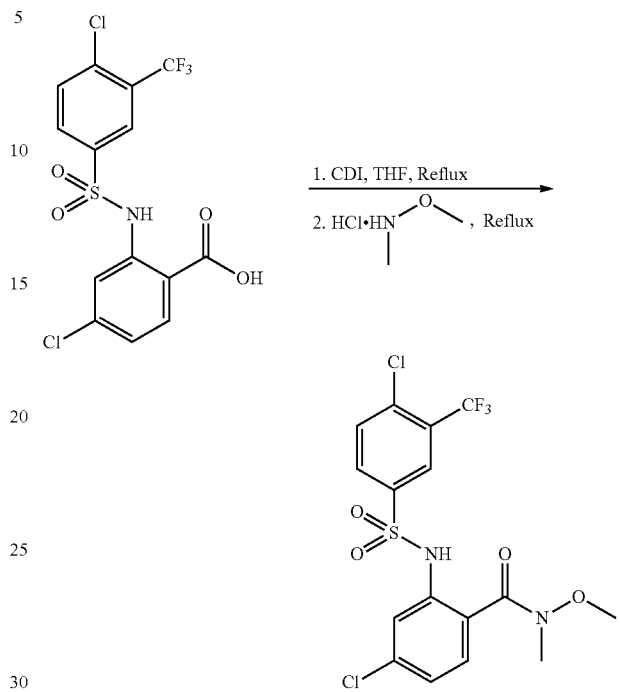

To a solution of 4-chloro-2-(4-chloro-3-trifluoromethyl-benzenesulfonylamino)-benzoic acid (5.0 g, 12.1 mmol) in THF (20 mL) was added N,N'-carbonyldiimidazole (CDI, 2.45 g, 15.13 mmol) in portions (Caution!: $CO_2$). The resulting reaction mixture was then heated at reflux. After 4 hours, reaction mixture was cooled to room temperature and charged with N,O-dimethylhydroxylamine hydrochloride (1.3 g, 13.31 mmol) and heated at reflux for 1 hour. Water (100 mL) was added followed by EtOAc (100 mL) with stirring. EtOAc layer was separated and aqueous layer was further extracted with EtOAc (2×50 mL). Combined EtOAc layers were washed with aq. 2N HCl (50 mL), saturated $NaHCO_3$ solution (50 mL), brine (50 mL), dried ($Na_2SO_4$) and evaporated. Obtained crude product was purified by automated normal-phase chromatography (50% EtOAc in hexanes) to afford title compound (4.0 g) in 73% yield. MS (ES) M+H expected 457.0, found 456.9.

Example 393: 4-chloro-N-(5-chloro-2-formyl-phenyl)-N-methoxymethyl-3-trifluoromethyl-benzenesulfonamide

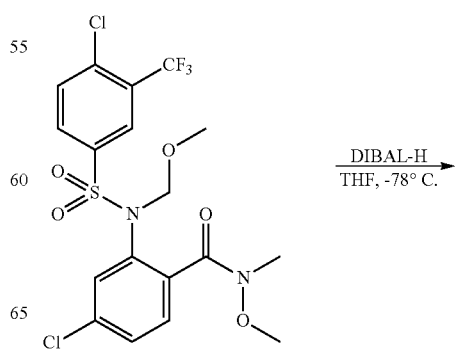

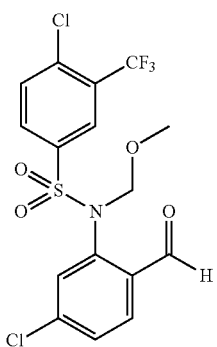

Diisobutylaluminium hydride (DIBAL-H, 1.5 M solution in toluene, 0.73 mL, 1.1 mmol) was added drop wise to a solution of 4-chloro-2-[(4-chloro-3-trifluoromethyl-benzenesulfonyl)-methoxymethyl-amino]-N-methoxy-N-methyl-benzamide (220 mg, 0.44 mmol) in THF (3 mL) at −78° C. and stirred at the same temperature for an hour. Saturated aqueous sodium potassium tartarate solution (10 mL) was added slowly, warmed to room temperature, extracted with EtOAc (2×25 mL), dried (anhydrous Na₂SO₄) and concentrated. Obtained residue was purified by column chromatography (SiO₂, 50% EtOAc-hexanes) to obtain 4-chloro-N-(5-chloro-2-formyl-phenyl)-N-methoxymethyl-3-trifluoromethyl-benzene sulfonamide (120 mg) in 62% yield. ESMS m/z (relative intensity): 410 (M−31)⁺ (95), 464 (M+Na)⁺ (100).

Example 394: 2-Bromo-5-methyl-3-nitropyridine

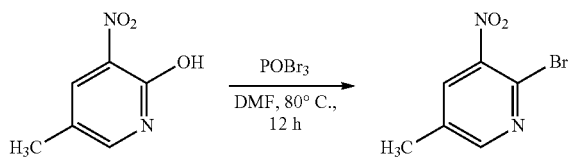

POBr₃ (222.8 g, 0.78 mol) was added in portions to 2-hydroxy-5-methyl-3-nitropyridine (100 g, 0.65 mol) in DMF (500 mL) with stirring at 0-10° C. then the reaction mixture was stirred at 80° C. under nitrogen for 12 h. Reaction mixture was cooled and poured into crushed ice (1 Kg), obtained solid was filtered, washed thoroughly with ice-cold water (2×500 mL), dried in a desiccator under high vacuum for one day to obtain 2-bromo-5-methyl-3-nitropyridine as yellow solid (121 g) in 86% yield. (M+H) Expected: 217; found 216.9.

Example 395: 2-Cyano-5-methyl-3-nitropyridine

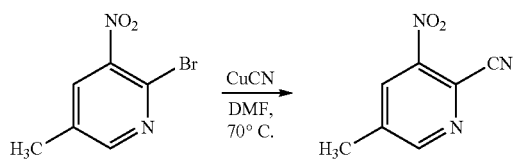

A round bottom flask was charged with 2-bromo-5-methyl-3-nitropyridine (60.53 g, 278.9 mmol) and CuCN (27.52 g, 307.3 mmol) The flask was evacuated, and back-filled with nitrogen. DMF (150 mL) was added via cannula. The solution was heated to 70° C. for 1.5 h. After cooling to room temperature, the reaction mixture was poured into EtOAc (500 mL) and water (250 mL). Both phases were filtered through a 1 cm bed of celite. The layers were separated, and the organic phase washed with water (2×100 mL) then with a solution of 1:1 sat. aq. NH₄Cl/NH₄OH (2×100 mL). The combined aqueous layers were extracted with EtOAc (2×200 mL). The combined organic layers were dried over MgSO₄ and concentrated in vacuo to afford the title compound (36.10 g, 79% yield).

Example 396: 3-Amino-2-cyano-5-methylpyridine

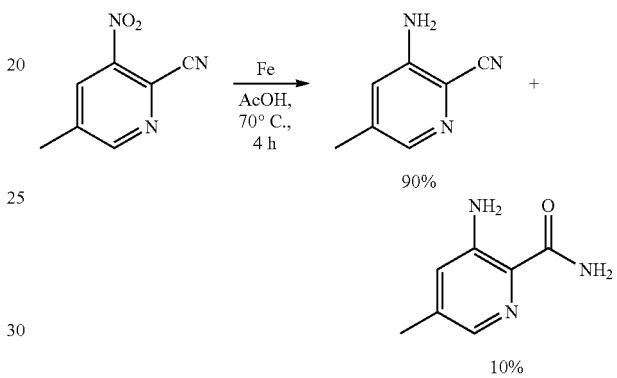

To acetic acid (300 mL) in a 3-neck 2 liter round bottom flask equipped with mechanical stirrer and a thermometer was added Fe powder (99.6 g, 1.78 mol) with stirring at 60° C. 2-Cyano-5-methyl-3-nitropyridine (97 g, 0.59 mol) was dissolved in acetic acid (400 mL) with gentle warming and added to the above reaction mixture drop wise with efficient stirring so that the reaction temperature kept below 80° C. over 3.5 hours. The reaction mixture was further stirred for an addition 30 min, cooled, diluted with EtOAc (750 mL), filtered through celite and washed with EtOAc (lx 500 mL, 3×250 mL). Combined EtOAc layers were evaporated to dryness to obtain dark brown solid which was neutralized with saturated NaHCO₃ solution (850 mL), after addition of water (250 mL) to obtain homogeneous, this aqueous layer was extracted with EtOAc (1×750 mL, 2×500 mL). Combined EtOAc layers were filtered through small pad of silica gel (sand-SiO₂-sand in sintered funnel), dried (Na₂SO₄) and evaporated to obtain 3-amino-2-cyano-5-methylpyridine (60 g) as yellow solid in 76% yield including ~10% corresponding amide.

To the crude 3-amino-2-cyano-5-methylpyridine (containing ~10% carboxamide) (49 g) was added EtOAc (441 mL, 9:1 volume ratio to aniline), the resulting suspension was heated to reflux to form a clean solution. After cooling to room temperature, the resulting crystal was collected by filtration, washed with small amount of cold EtOAc (44 mL (1/10 the initial volume)×2), and dried in vacuo to afford the pure 3-amino-2-cyano-5-methylpyridine (35 g) as pale yellow needles. The mother liquor was concentrated under reduced pressure, the resulting yellow solid was added EtOAc (136 mL) and repeated the above process to afford another 4 g of pure 3-amino-2-cyano-5-methylpyridine; total recovery yield 79.5%. ¹H NMR (400 MHz, CDCl₃) δ

7.89 (1H, s), 6.90 (1H, s), 4.39 (2H, br), 2.30 (3H, s). MS (ES) M+H expect 134.0, found 134.0.

Example 397: 3-(4-Chloro-3-trifluoromethyl-benzenesulfonylamino)-5-methyl-pyridine-2 carboxylic Acid

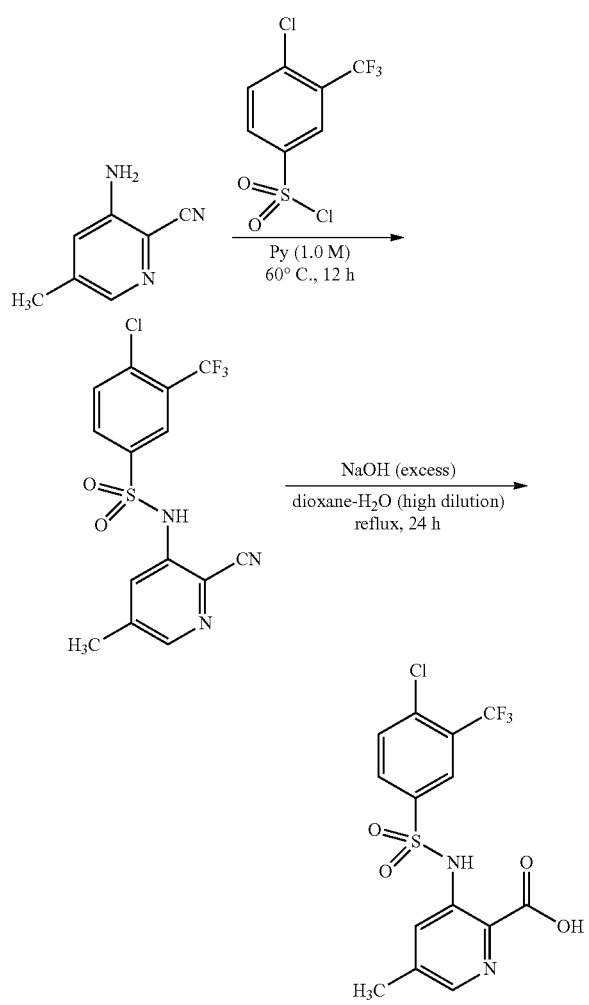

To 3-amino-5-methylpicolinonitrile (9.6 g, 72 mmol) in pyridine (63 mL) was added 4-chloro-3-trifluoromethyl-benzenesulfonyl chloride (19.6 g, 80 mmol) in one portion and the resulting reaction mixture was stirred at 60° C. for overnight. Pyridine was removed in vacuo, added 2N HCl (100 mL), extracted with EtOAc (3×300 mL; Note: due to the amide presence, solubility in EtOAc is low). Combined EtOAc layers were dried (Na$_2$SO$_4$), evaporated to obtain 26.3 g of crude product which contained a small amount of bis-sulfonamide which was subjected to hydrolysis in THF (200 mL) with 2N NaOH (100 mL) at room temperature for 2 h. 2 N HCl (100 mL) Was added, extracted with EtOAc (1×700 mL, 1x 250 mL), combined EtOAc layers were washed with saturated NaHCO$_3$ solution (2×250 mL), dried (Na$_2$SO$_4$) and evaporated to obtain 22 g of monosulfonamide. To this dioxane (350 mL), water (450 mL) (Note: requires high dilution for fast reaction) was added, followed by NaOH (30 g, 0.75 mol) and stirred under reflux for 24 h. Dioxane was removed in vacuo and conc. HCl (75 mL) was added slowly with cooling. The resultant solid was filtered, washed with water and dried in vacuo to afford title compound (22 g, 88% for 2 steps) as light yellow solid. (M+H) Expected: 395.0; found 394.9.

Example 398: 5-Chloro-3-(4-chloro-3-(trifluoromethyl)phenyl-sulfonamido)picolinic Acid

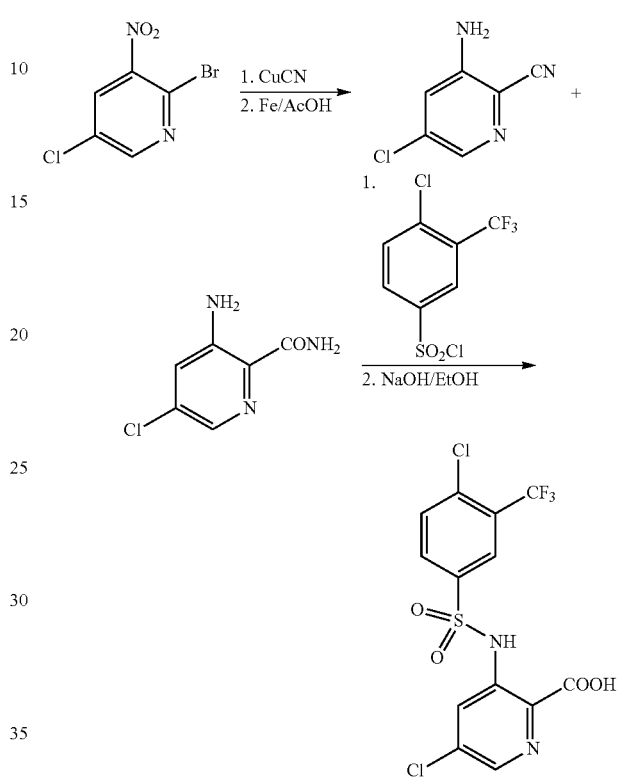

Step 1: A dry 250 mL flask was charged with 2-bromo-5-chloro-3-nitropyridine (24 g, 101 mmol), CuCN (19 g, 212 mmol) and DMF (100 mL). The resultant mixture was stirred at 110° C. for 2 h. The mixture was concentrated under reduced pressure. Water (100 mL) was added and extracted with EtOAc (3×250 mL). The combined organic layer was washed with brine, dried (MgSO$_4$) and filtered. The solvent was evaporated the solvent in vacuo to afford a light yellow solid (15 g) which was used directly for the next step.

Step 2: A 250 mL round-bottom flask with a magnetic stir bar was charged with iron powder (15.6 g, 0.3 mol) in acetic acid (80 mL) and heated to 80° C. (oil bath) under N$_2$. To this mixture was added slowly the above nitrocyanopyridine (10 g, 55 mmol) from step 1 in acetic acid (80 mL) via dropping funnel over 15 min. The mixture was stirred at 80° C. for another 30 min after the addition. After cooling, the reaction mixture was diluted with EtOAc, filtered through celite and the solvent evaporated in vacuo. The residue was dissolved in EtOAc and washed with 3 N NaOH, brine, dried over MgSO$_4$, and concentrated in vacuo to afford a 4:1 mixture (7.7 g) of 3-amino-2-cyano-5-chloropyridine (major) and the 2-amide. The mixture was used directly for the next step: MS (ES) (M+H)$^+$ expected 154.0, found 154.0.

Step 3: A 100 mL round-bottom flask was charged with the above 3-amino-2-cyano-5-chloropyridine mixture (7.7 g, 50 mmol), 4-chloro-3-trifluoromethylbenzenesulfonyl chloride (28 g, 100 mmol), and pyridine (50 mL). The resultant solution was heated to 70° C. and stirred for 5 h. The pyridine was removed in vacuo and 80% aq. EtOH (260 mL) was added, followed by NaOH (30 g, 0.75 mol). The mixture was stirred under reflux for 12 h. The solvent was subsequently removed in vacuo and ice (100 g) was added. The pH adjusted to 2-3 with conc. HCl. The resultant aqueous solution was extracted with EtOAc, washed with brine, dried over MgSO$_4$, and concentrated in vacuo. The resulting light yellow solid was recrystallized from EtOAc/hexane (1:1) to afford the desired acid as white needles (10 g, 44% overall yield): $^1$H NMR (400 MHz, CDCl$_3$) δ 10.80 (s, 1H), 8.23 (m, 3H), 8.00 (d, 1H), 7.63 (d, 1H); MS (ES) (M+H)$^+$ expected 415.0, found 415.0.

Example 399: 5-Chloro-3-(4-chloro-3-trifluoromethyl-benzenesulfonylamino)-pyridine-2-carboxylic acid methoxy-methyl-amide

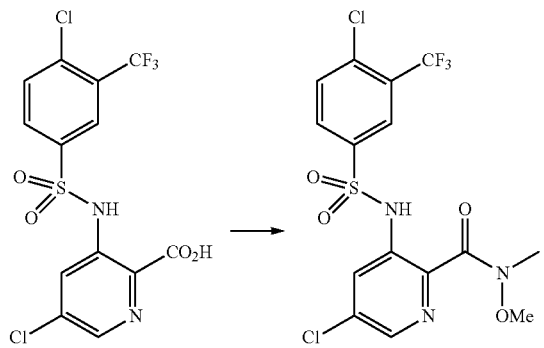 [SMILES: O=C(O)c1ncc(Cl)cc1NS(=O)(=O)c1ccc(Cl)c(C(F)(F)F)c1 ; CON(C)C(=O)c1ncc(Cl)cc1NS(=O)(=O)c1ccc(Cl)c(C(F)(F)F)c1]

5-Chloro-3-(4-chloro-3-trifluoromethyl-benzenesulfonylamino)-pyridine-2-carboxylic acid (15.8, 38 mmol), N,O-dimethyl hydroxylamine hydrochloride (11.1 mg, 114 mmol), DIEA (41 mL, 228 mmol) methyl-m-tolyl-amine (44 mg, 0.36 mmol), and BOP (69 mg, 49 mmol), were reacted according to the procedure D for the synthesis of 5-chloro-3-(4-chloro-3-(trifluoromethyl)phenylsulfonamido)-picolinic amides at 50° C. The reaction mixture was quenched with 1 (M) HCl, extracted with EtOAc, and the organic portions were washed with 1 (M) aqueous HCl, NaHCO$_3$ and brine. The combined organic extracts were dried (Na$_2$SO$_4$), filtered and concentrated under reduced pressure. The resulting residue was purified by flash column chromatography to afford 5-chloro-3-(4-chloro-3-trifluoromethyl-benzenesulfonylamino)-pyridine-2-carboxylic acid methoxy-methyl-amide: MS m/z: (M+H) 458.0.

Example 400: 5-Chloro-3-(4-methyl-3-trifluoromethyl-benzenesulfonylamino)-pyridine-2-carboxylic acid methoxy-methyl-amide

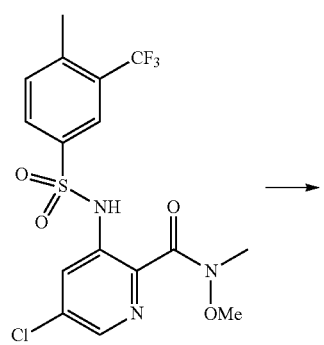

-continued

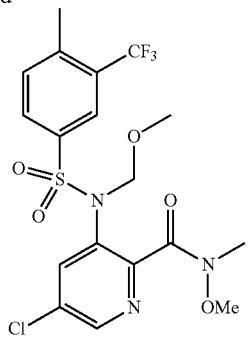

5-Chloro-3-(4-methyl-3-trifluoromethyl-benzenesulfonylamino)-pyridine-2-carboxylic acid methoxy-methyl-amide was prepared from 5-Chloro-3-(4-methyl-3-trifluoromethyl-benzenesulfonylamino)-pyridine-2-carboxylic acid as described in example 144.

Example 401: 5-Chloro-3-[methoxymethyl-(4-methyl-3-trifluoromethyl-benzenesulfonyl)-amino]-pyridine-2-carboxylic acid methoxy-methyl-amide

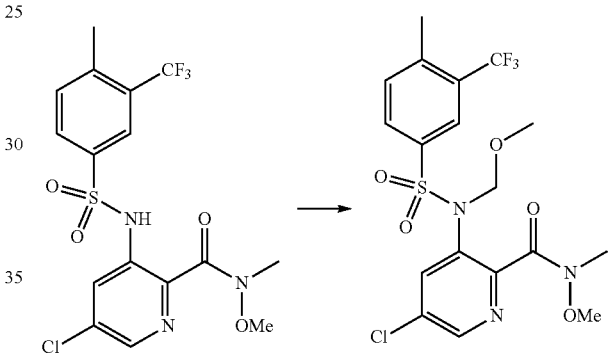

To a mixture of sodium hydride (164 mg, 4.10 mmol) in 5 mL of THF was added a mixture of 5-chloro-3-(4-methyl-3-trifluoromethyl-benzenesulfonylamino)-pyridine-2-carboxylic acid methoxy-methyl-amide (1.50 g, 3.42 mmol) and chloromethyl methyl ether (0.388 mL, 5.13 mmol) in 5 mL of THF. The mixture was stirred at room temperature overnight. After the removal of the solvents the residue was purified by flash column (20% ethyl acetate in hexane) to afford 1.50 grams of the title compound as a white solid: (M$^+$+H) expect 482.0, found 482.0.

Example 402: 5-Chloro-3-[methoxymethyl-(4-chloro-3-trifluoromethyl-benzenesulfonyl)-amino]-pyridine-2-carboxylic acid methoxy-methyl-amide

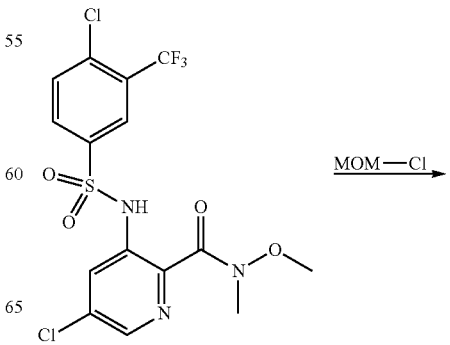

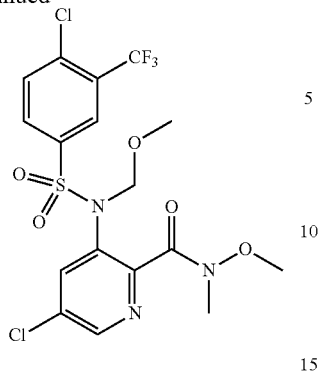

To a suspension of sodium hydride (314 mg, 7.86 mmol) in 8 mL of THF was added a mixture of 5-chloro-3-(4-chloro-3-trifluoromethyl-benzenesulfonylamino)-pyridine-2-carboxylic acid methoxy-methyl-amide (3.0 g, 6.55 mmol) and chloromethyl methyl ether (0.741 mL, 9.825 mmol) in 8 mL of THF. The mixture was stirred at room temperature overnight. After the removal of the solvents the residue was purified by flash column (20% ethyl acetate in hexane) to afford 2.70 grams of the title compound as a white solid. $(M+H)^+$ expect 502.0, found 502.0.

Example 403: 3-Amino-pyridine-2-carboxylic Acid Methyl Ester

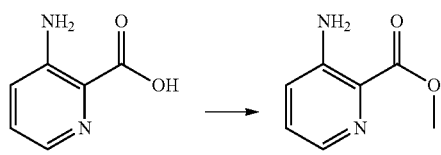

400 mg (2.9 mmol) of 3-amino-pyridine-2-carboxylic acid was dissolved in 3 mL of methanol. To this solution 1.6 mL of 2 M (trimethylsilyl)diazomethane solution in diethyl ether was added dropwise at 00° C., followed by stirring of the mixture for 2 h at r.t. The solution was diluted with ethyl acetate and washed with aqueous sodium bicarbonate solution. Flash chromatography afforded the ester product. LC-MSD, m/z for $C_7H8N_2O_2[M+H]^+=153.0$; HPLC retention time: 0.2 min.

Example 404: 3-(4-Chloro-3-trifluoromethyl-benzenesulfonylamino)-pyridine-2-carboxylic Acid

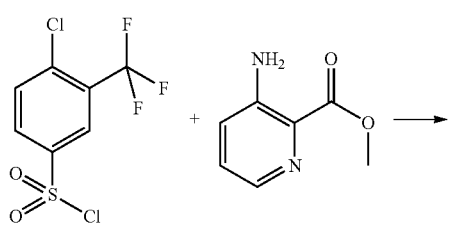

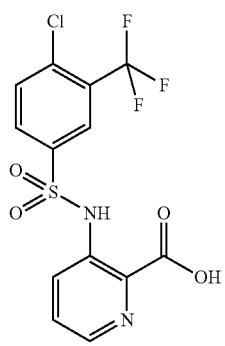

Prepared from 0.60 g (2.17 mmol) of 4-chloro-3-trifluoromethyl-benzenesulfonyl chloride and 0.30 g (1.97 mmol) of 3-amino-pyridine-2-carboxylic acid methyl ester in 3 mL pyridine using procedure x. The solvent was switched to THF, followed by the addition of 1 M aqueous LiOH and the mixture stirred for 1 h. The pH of the mixture was adjusted to neutral and the product was extracted with ethyl acetate. LC-MSD, m/z for $C_{13}H_8ClF_3N_2O_4S$ $[M+H]^+=380.9, 383.0$; HPLC retention time: 1.8 min.

Example 405: 3-[(4-Chloro-3-trifluoromethyl-benzenesulfonyl)-methoxymethyl-amino]-pyridine-2-carboxylic acid methoxy-methyl-amide

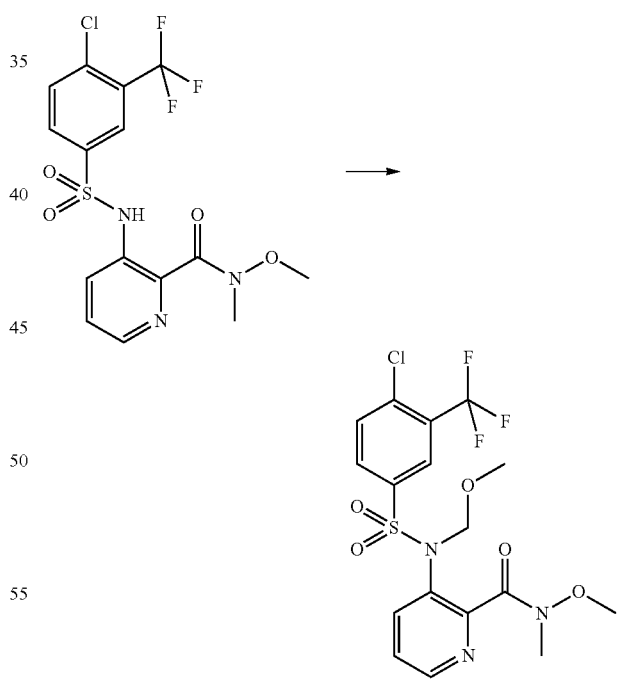

Prepared from 1.05 g (2.48 mmol) of 3-(4-chloro-3-trifluoromethyl-benzenesulfonylamino)-pyridine-2-carboxylic acid methoxy-methyl-amide, 1.71 g of potassium carbonate and 566 µL of methoxymethyl chloride in 7 mL THF using procedure x. Yield: 420 mg of a white solid. LC-MSD, m/z for $C_{17}H_{17}ClF_3N_3O_5S$ $[M+Na]+=490.0, 491.9$; HPLC retention time: 2.5 min.

Example 406: 4-Chloro-N-(2-(5-methoxy-1H-pyrrolo[2,3-b]pyridine-4-carbonyl)-5-(methoxymethyl)pyridin-3-yl)-3-(trifluoromethyl)benzenesulfonamide

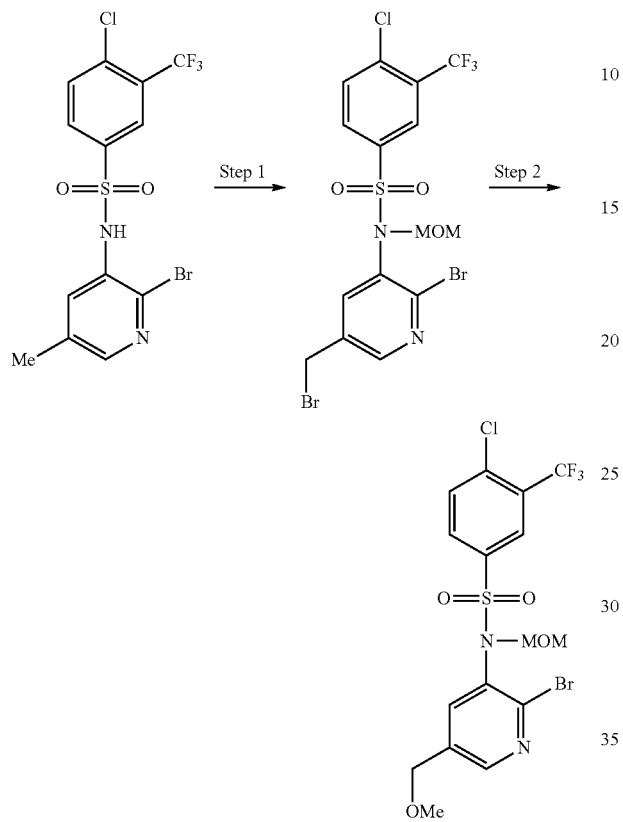

Step 1: To a solution of the bromopyridine (132 mg, 0.28 mmol) in carbon tetrachloride (4 mL) was added N-bromosuccinimide (60 mg, 1.2 equiv.), followed by 2, 2'-azobisisobutyronitrile (AIBN, 4.6 mg, 0.1 equiv.). The reaction mixture was heated at 60° C. overnight. After cooling down to room temperature, excessive carbon tetrachloride was removed and the residue was purified by flash chromatography on silica gel (33% EtOAc/hexanes). The desired product was obtained as a white solid (107 mg, 70%). MS: (M+H)/z=551.

Step 2: The product obtained from step 1 above (51 mg, 0.093 mmol) was dissolved in 3 mL of methanol. To the resultant solution was added sodium methoxide (10 mg, 2.0 equiv.). The reaction mixture was heated at 50° C. overnight. After cooling down to room temperature, the reaction was quenched with saturated ammonium chloride solution, and the mixture was extracted with ethyl acetate. The extracts were washed with brine, dried over MgSO4 and concentrated in vacuo. The crude material was purified by flash chromatography on silica gel (33% EtOAc/hexanes). The desired product was obtained as a white solid (42 mg, 90%). MS: (M+H)/z=503.

Example 407: 3-(4-Chloro-3-trifluoromethyl-benzenesulfonylamino)-5-methyl-pyridine-2-carboxylic acid methoxy-methyl-amide

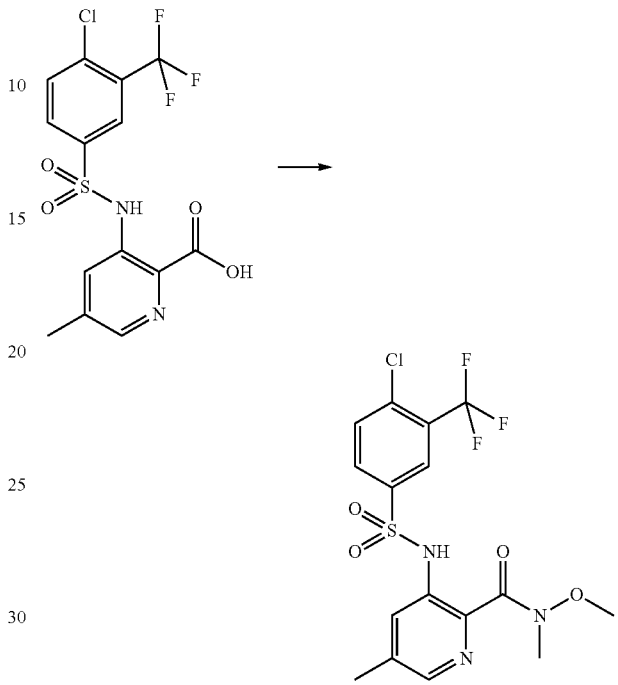

10.49 g (26.6 mmol) of 3-(4-chloro-3-trifluoromethyl-benzenesulfonylamino)-5-methyl-pyridine-2-carboxylic acid was reacted with 5.40 g (33.2 mmol) of N,N'-carbonyldiimidazole in 40 mL of refluxing THF for 3 h. The temperature was lowered to 50° C., 2.86 g (29.3 mmol) of O,N-dimethyl-hydroxylamine hydrochloride was added and the reaction was stirred overnight at 50° C. Half of the solvent was removed under reduced pressure and the reaction mixture was diluted with 200 mL of cold water. The solids were filtered off, washed with 100 mL of water and dried to give 9.8 g (84%) of the product as a tan powder.

Example 408: 3-[(4-Chloro-3-trifluoromethyl-benzenesulfonyl)-methoxymethyl-amino]-5-methyl-pyridine-2-carboxylic acid methoxy-methyl-amide

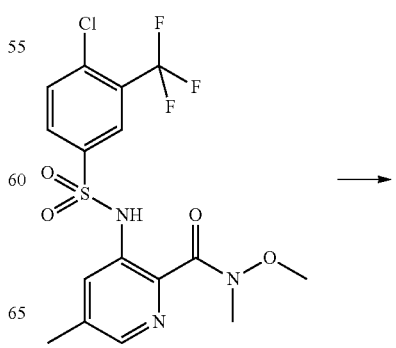

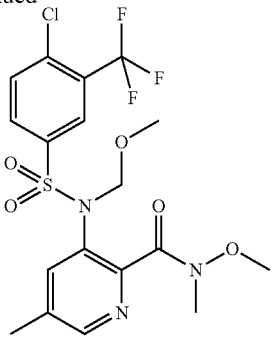

Prepared from 223 mg (0.51 mmol) of 3-(4-chloro-3-trifluoromethyl-benzenesulfonylamino)-5-methyl-pyridine-2-carboxylic acid methoxy-methyl-amide, 352 mg of potassium carbonate and 116 µL of methoxymethyl chloride in 1 mL THF using procedure x. Yield: 200 mg of a white solid. LC-MSD, m/z for $C_{18}H_{19}ClF_3N_3O_5S$ $[M+H]^+$=482.0, 484.0; HPLC retention time: 2.5 min.

Example 409: 7-Chloro-3H-imidazo[4,5-b]pyridine

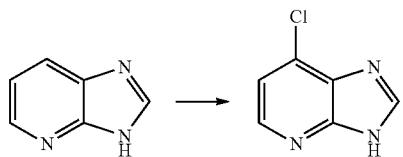 [SMILES: c1cnc2[nH]cnc2c1 ; Clc1ccnc2[nH]cnc12]

The product was prepared following the procedure from *Bioorg. Med. Chem. Lett.* 2004, 3165-3168.

Example 410: 6-Iodo-9H-purine

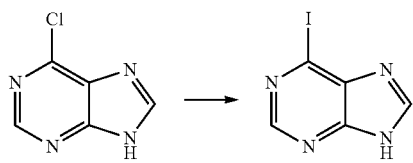 [SMILES: Clc1ncnc2[nH]cnc12 ; Ic1ncnc2[nH]cnc12]

A mixture of 6-chloro-9H-purine (684 mg, 4.46 mmol) and 6 mL of 57% hydriodic acid were stirred at 0° C. for 1.5 h. The reaction yielded 840 mg of the product as a white powder. The solid was filtered off, suspended in 5 mL of water and brought to pH=8 with aqueous ammonia solution. The suspension was cooled down to 0° C. and the solid was filtered off, washed with cold water and dried to give the product.

Example 411: 4-Iodo-7H-pyrrolo[2,3-d]pyrimidine

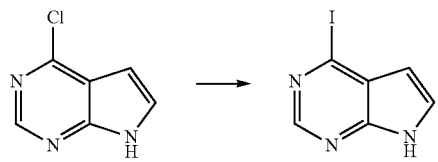 [SMILES: Clc1ncnc2[nH]ccc12 ; Ic1ncnc2[nH]ccc12]

A mixture of 4-chloro-7H-pyrrolo[2,3-d]pyrimidine (673 mg, 4.41 mmol) and 7 mL of 57% hydriodic acid was stirred at room temperature for 16 h. The solid was filtered off, suspended in 5 mL of water and brought to pH=8 with aqueous ammonia solution. The suspension was cooled down to 00° C. and the solid was filtered off, washed with cold water and dried to give the product to yield 970 mg of the product as a white powder. The product contains about 10% of the starting material.

Example 412: 7-Iodo-3H-imidazo[4,5-b]pyridine

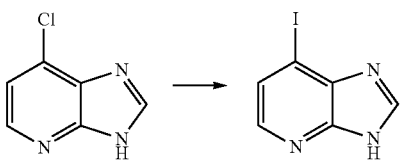 [SMILES: Clc1ccnc2[nH]cnc12 ; Ic1ccnc2[nH]cnc12]

A mixture of 7-chloro-3H-imidazo[4,5-b]pyridine (1.47 g, 9.64 mmol) and 15 mL of 57% hydriodic acid were reacted at 80° C. for 4 h. After the solid was filtered off it was resubmitted to the reaction with 10 mL of fresh 57% hydriodic acid. The reaction yielded 1.3 g of the product as a black powder, 90% pure.

Example 413: General Procedure for N-Protection of the Iodoheterocycles 1.65 mmol of the iodoheterocycle was dissolved in 2 mL DMF and cooled down to 0° C. To this solution 1.81 mmol of 60% sodium hydride was added followed by dropwise addition of 1.81 mmol of trimethylsilylethoxymethyl chloride over the period of 5 minutes. The solution was stirred at 0° C. for 0.5 h, followed by 0.5 h at r.t. To this solution 10 mL of water was added and the mixture was extracted twice with 10 mL of diethyl ether. The organic layers were washed with 10 mL of water, then dried over anhydrous magnesium sulfate, evaporated under reduced pressure and purified on silica using ethyl acetate in hexanes.

Example 414: 6-Iodo-9-(2-trimethylsilanyl-ethoxymethyl)-9H-purine

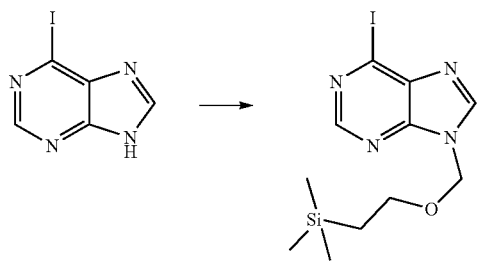 [SMILES: Ic1ncnc2[nH]cnc12 ; C[Si](C)(C)CCOCn1cnc2c(I)ncnc21]

405 mg (1.65 mmol) of 6-iodo-9H-purine was dissolved in 2 mL DMF. 72 mg (1.81 mmol) of 60% sodium hydride was added followed by 320 µL (1.81 mmol) of trimethylsilylethoxymethyl chloride. Yield: 343 mg of an oily product.

Example 415: 4-Iodo-7-(2-trimethylsilanyl-ethoxymethyl)-7H-pyrrolo[2,3-d]pyrimidine

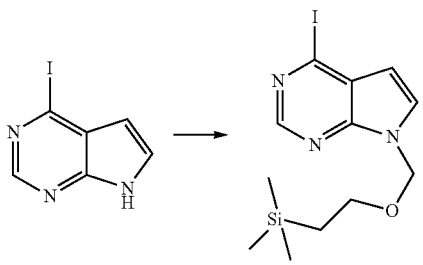 [SMILES: Ic1ncnc2[nH]ccc12 ; C[Si](C)(C)CCOCn1ccc2c(I)ncnc21]

610 mg (2.49 mmol) of 4-iodo-7H-pyrrolo[2,3-d]pyrimidine was dissolved in 2.5 mL DMF. 110 mg (2.74 mmol) of 60% sodium hydride was added followed by 480 μL (2.74 mmol) of trimethylsilylethoxymethyl chloride. Yield: 750 mg of an oily product, 90% pure.

Example 416: 4-Iodo-7-methyl-7H-pyrrolo[2,3-d]pyrimidine

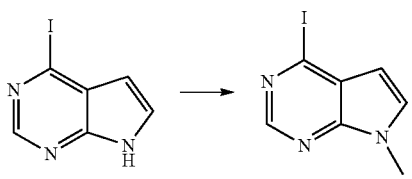

206 mg (0.84 mmol) of 4-iodo-7H-pyrrolo[2,3-d]pyrimidine was dissolved in 1 mL DMF. 37 mg (0.92 mmol) of 60% sodium hydride was added followed by 58 μL (0.92 mmol) of iodomethane. The reaction was quenched by adding 10 mL of water, the solid filtered off, washed with 10 mL of water, then 10 mL of hexanes and dried. Yield: 142 mg of a tan powder, 90% pure.

Example 417: 7-Iodo-3-(2-trimethylsilanyl-ethoxymethyl)-3H-imidazo[4,5-b]pyridine

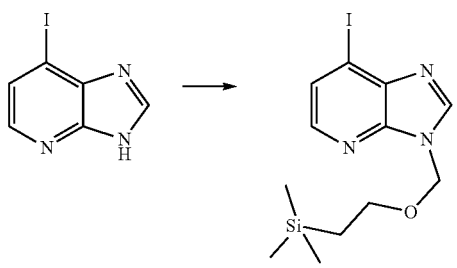 [SMILES: Ic1ccnc2[nH]cnc12 ; C[Si](C)(C)CCOCn1cnc2c(I)ccnc21]

850 mg (3.47 mmol) of 7-iodo-3H-imidazo[4,5-b]pyridine was dissolved in 3.5 mL DMF. 153 mg (3.82 mmol) of 60% sodium hydride was added followed by 670 μL (3.82 mmol) of trimethylsilylethoxymethyl chloride. Yield: 424 mg of an oily product, 90% pure.

Example 418: General Procedure for Ketones from Weinreb Amides

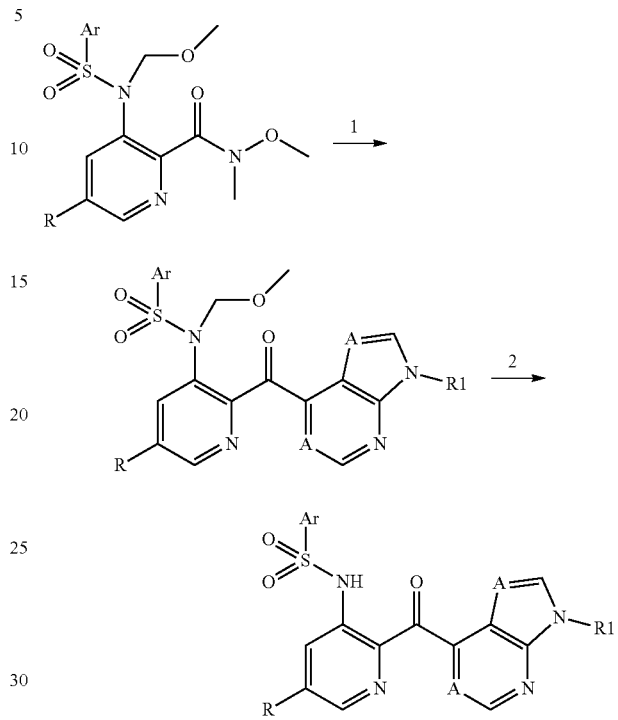

Step 1: Addition of the Grignard reagent: 1 mmol of the iodoheterocycle was dissolved under nitrogen atmosphere in 4 mL THF and cooled down to −30° C. 0.50 mL of 2 M solution of isopropylmagnesium chloride solution in THF was added dropwise. The mixture was warmed up to −10° C. and stirred for 10 minutes, which resulted in a complete iodine-magnesium exchange. The solution was then cooled down to −20° C. and 1.0 mmol of solid Weinreb amide was added. After 5 minutes the mixture was allowed to warm up to r.t. and was stirred at r.t. for 1 h. Aqueous ammonium chloride solution was added and the mixture was extracted with DCM. Organic layer was evaporated under reduced pressure. Flash chromatography on silica using ethyl acetate in hexanes afforded the products.

Step 2: Deprotection: 1 mmol of the protected ketone intermediate was dissolved in a mixture of 20 mL of methanol and 20 mL of 6N hydrochloric acid. The solution was heated in a sealed tube at 95° C. for 8 h, then cooled down and evaporated. The residue was dissolved in methanolic ammonia and evaporated on silica gel under reduced pressure. Flash chromatography on silica using ethyl acetate in hexanes afforded the products as a yellow solids. In some cases additional reverse-phase HPLC purification step was necessary to obtain pure products.

Example 419: General Procedure for the Preparation of Ketones from Nitriles

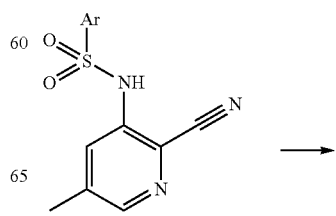

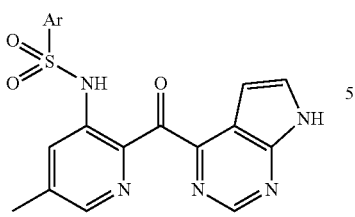

1 mmol of 4-iodo-7H-pyrrolo[2,3-d]pyrimidine was dissolved under nitrogen atmosphere in 2.8 mL THF and cooled down to −10° C. 0.50 mL of 2 M solution of phenylmagnesium chloride solution in THF was added dropwise followed by 0.50 mL of 2 M solution of isopropylmagnesium chloride solution in THF. The mixture was warmed up to r.t. and stirred for 1 h, which resulted in a complete iodine-magnesium exchange. A separate solution of 0.77 mmol of the corresponding nitrile in 1 mL THF was prepared and 0.96 mmol of 60% sodium hydride was added to it. The solutions were combined and the mixture was stirred at 45° C. for 8 h. The reaction mixture was cooled down to r.t., 0.52 mL of concentrated hydrochloric acid was added and the mixture was stirred at 50° C. for 0.5 h. The solids were filtered off and washed with three 10 mL portions of THF, followed by 10 mL of diethyl ether and four portions of 1N hydrochloric acid. The solids were taken up in the mixture of aqueous sodium bicarbonate and ethyl acetate. The organic layer was passed through a pad of silica gel and evaporated under reduced pressure to give the products.

Example 420: 4-Chloro-N-[5-chloro-2-(7H-pyrrolo[2,3-d]pyrimidine-4-carbonyl)-phenyl]-3-trifluoromethyl-benzenesulfonamide

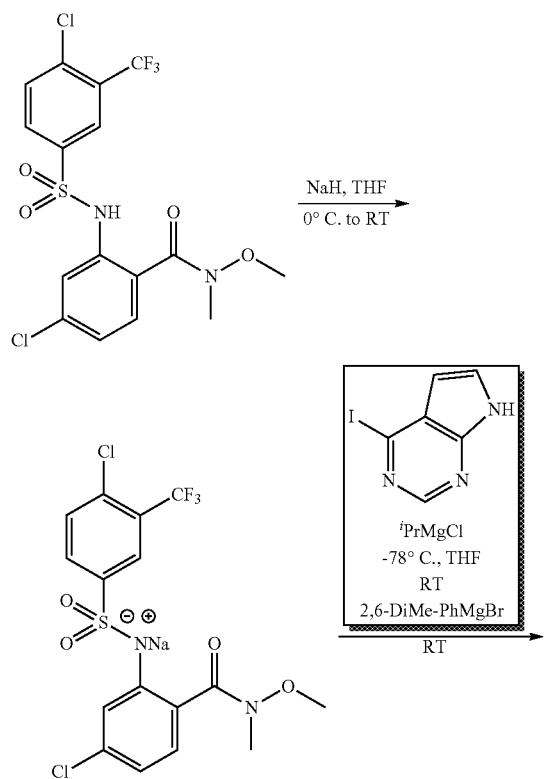

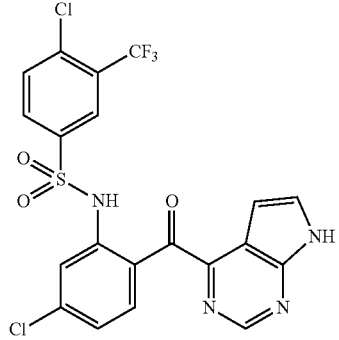

$^i$PrMgCl (3.84 mL, 7.56 mmol; 1.97 M solution in THF) was added to iodo-pyrrolopyrimidine (0.882 g, 3.6 mmol) in THF (5 mL) at −78° C. After 15 min, it was warmed to room temperature and added 2,6-dimethylphenymagnesium bromide (2.4 mL, 2.4 mmol; 1.0 M solution in diethyl ether). To this reaction mixture at room temperature was added a sodium salt THF solution of 4-chloro-2-(4-chloro-3-trifluoromethyl-benzenesulfonylamino)-N-methoxy-N-methyl-benzamide [prepared separately by adding 60% NaH (0.144 g, 3.6 mmol) in THF (5 mL)] and stirred overnight. Saturated NH$_4$Cl solution (5 mL) was added and extracted with EtOAc (2×50 mL). EtOAc layer was washed with brine (25 mL), dried (Na$_2$SO$_4$) and evaporated. Crude product was purified by column purification (silica gel, 60% EtOAc in hexanes) followed by recrystallization from CH$_3$CN to obtain title compound (1 g) as a crystalline yellow solid in 67% yield. MS (ES) M+H expected 515.0, found 514.9. $^1$H NMR (CDCl$_3$, 400 MHz): δ 10.75 (s, 1H), 9.92 (brs., 1H), 8.92 (d, 1H), 8.05 (s, 1H), 7.92 (dd, 1H), 7.81 (m, 2H), 7.58 (m, 1H), 7.45 (dd, 1H), 7.3 (d, 1H), 6.9 (m, 1H).

Example 421: 4-Chloro-N-[2-(7H-pyrrolo[2,3-d]pyrimidine-4-carbonyl)-pyridin-3-yl]-3-trifluoromethyl-benzenesulfonamide

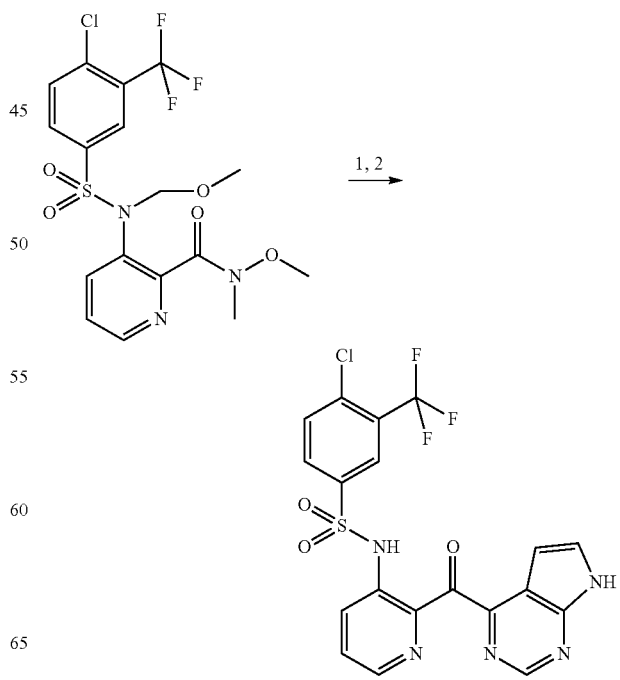

Prepared from 248 mg (0.53 mmol) of 3-[(4-chloro-3-trifluoromethyl-benzenesulfonyl)-methoxymethyl-amino]-pyridine-2-carboxylic acid methoxy-methyl-amide, 239 mg (0.58 mmol) of 90% 4-iodo-7-(2-trimethylsilanyl-ethoxymethyl)-7H-pyrrolo[2,3-d]pyrimidine dissolved in 2 mL THF with 0.32 mL of 2 M isopropylmagnesium chloride solution in THF added. All of the resulting intermediate ketone was used in the second step with 4 mL methanol and 4 mL 6N hydrochloric acid mixture to give after purification 29 mg of the final product as a yellow solid.

Example 422: 4-Chloro-N-[5-chloro-2-(7-methyl-7H-pyrrolo[2,3-d]pyrimidine-4-carbonyl)-pyridin-3-yl]-3-trifluoromethyl-benzenesulfonamide Prepared from 227 mg (0.45 mmol) of 5-chloro-3-[(4-chloro-3-trifluoromethyl-benzenesulfonyl)-methoxymethyl-amino]-pyridine-2-carboxylic acid methoxy-methyl-amide, 129 mg (0.45 mmol) of 90% 4-iodo-7-methyl-7H-pyrrolo[2,3-d]pyrimidine dissolved in 2 mL THF with 0.23 mL of 2 M isopropylmagnesium chloride solution in THF added. All of the resulting intermediate ketone (80 mg) was used in the second step with 2 mL ethanol and 2 mL 6N hydrochloric acid mixture to give after purification 45 mg of the final product as a yellow solid.

Example 423: Preparation of 4-Chloro-N-(5-(methoxymethyl)-2-(7H-pyrrolo[2,3-d]pyrimidine-4-carbonyl)pyridin-3-yl)-3-(trifluoromethyl)benzenesulfonamide

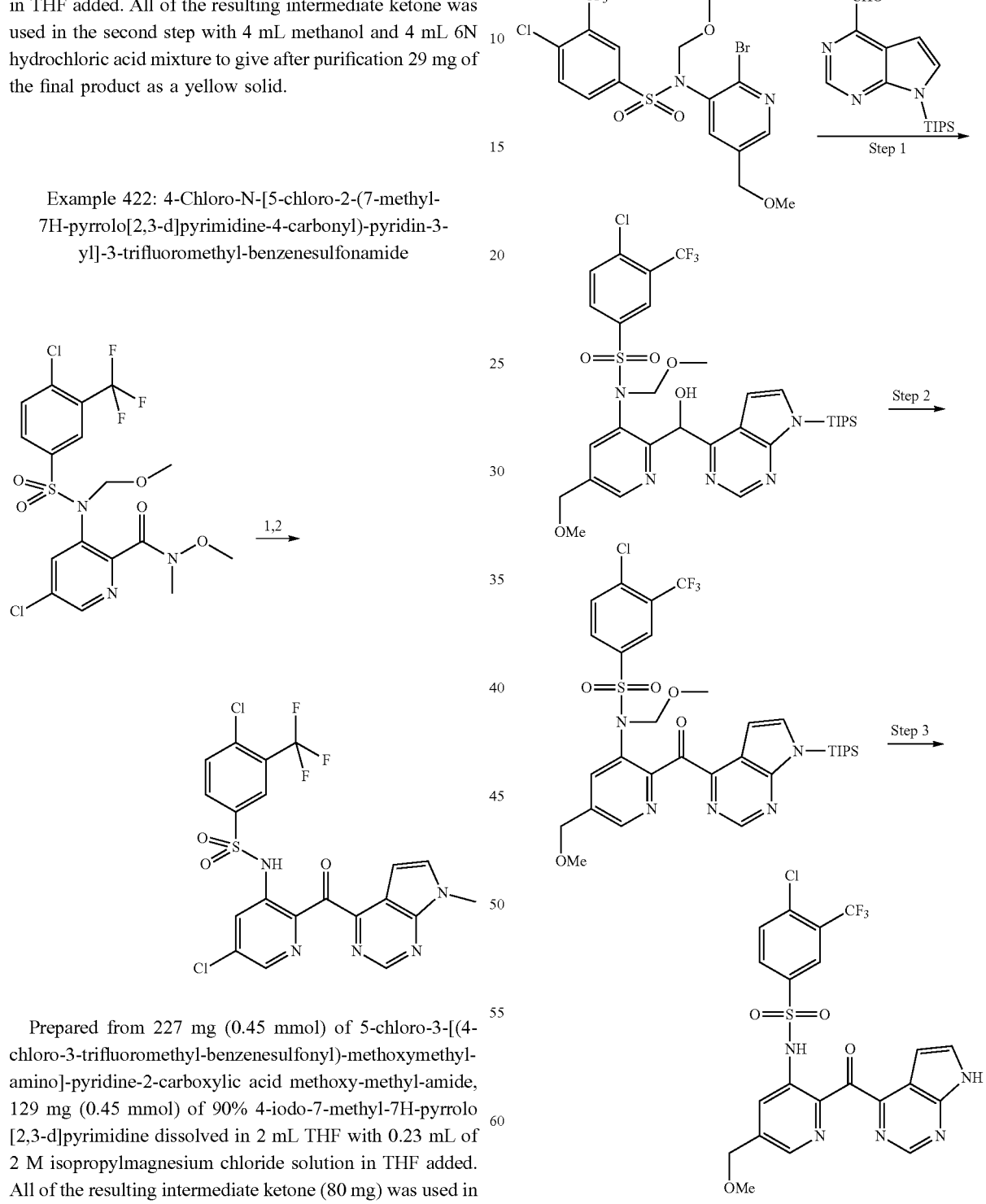

Step 1: To a solution of the bromopyridine obtained from Example 13 (step 2) (74 mg, 0.15 mmol) in THF (1 mL) at 0° C. was added isopropylmagnesium chloride (147 μL, 2.0 M in THF) dropwise. After 45 minutes, a solution of 7-(triisopropylsilyl)-7H-pyrrolo[2,3-d]pyrimidine-4-carbaldehyde (67 mg, 0.22 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO₄ and concentrated in vacuo. The crude material was purified by flash chromatography on silica gel (33% EtOAc/hexanes). The desired product was obtained as a foaming yellow solid (45 mg, 42%). MS: (M+H)/z=728.

Step 2: The product obtained from step 1 above (45 mg, 0.062 mmol) was dissolved in 3 mL of dichloromethane. To the resultant solution was added Dess-Martin periodinane (42 mg, 1.6 equiv.) and stirred overnight at room temperature. The reaction was quenched with 10% Na₂S₂O₃, and the mixture was extracted with ethyl acetate. The extracts were washed with saturated NaHCO₃, brine, dried over MgSO₄ and concentrated in vacuo. The crude material was purified by flash chromatography on silica gel (33% EtOAc/hexanes). The desired product was obtained as a foaming yellow solid (35 mg, 78%). MS: (M+H)/z=726.

Step 3: The product obtained from step 2 above (35 mg, 0.048 mmol) was dissolved in 4 mL of HCl-dioxane (4.0 M) and 1 mL of water. The mixture was heated at 85° C. for 30 minutes and quenched with saturated NaHCO₃. The mixture was extracted with ethyl acetate. The extracts were washed with brine, dried over MgSO₄ and concentrated in vacuo. The crude material was purified by flash chromatography on silica gel (10% methanol/DCM). The desired product was obtained as a yellow solid (15 mg, 60%). MS: (M+H)/z=526.

Example 424: 4-Chloro-N-[5-methyl-2-(7H-pyrrolo[2,3-d]pyrimidine-4-carbonyl)-pyridin-3-yl]-3-trifluoromethyl-benzenesulfonamide

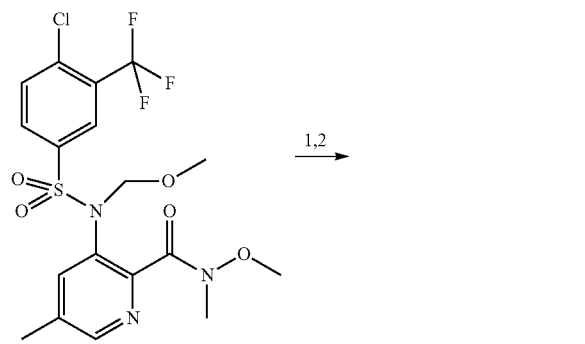

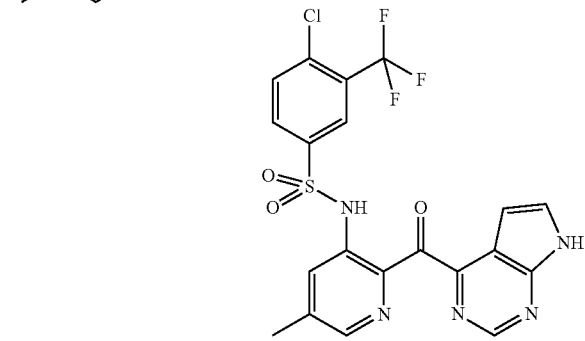

Prepared from 200 mg (0.42 mmol) of 3-[(4-chloro-3-trifluoromethyl-benzenesulfonyl)-methoxymethyl-amino]-5-methyl-pyridine-2-carboxylic acid methoxy-methyl-amide, 202 mg (0.50 mmol) of 90% 4-iodo-7-(2-trimethylsilanyl-ethoxymethyl)-7H-pyrrolo[2,3-d] pyrimidine dissolved in 2 mL THF with 0.25 mL of 2 M isopropylmagnesium chloride solution in THF added. All of the resulting intermediate ketone was used in the second step with 2 mL methanol and 2 mL 6N hydrochloric acid mixture to give after purification 29 mg of the final product as a yellow solid.

Example 425: 4-Methyl-N-[5-methyl-2-(7H-pyrrolo[2,3-d]pyrimidine-4-carbonyl)-pyridin-3-yl]-3-trifluoromethyl-benzenesulfonamide

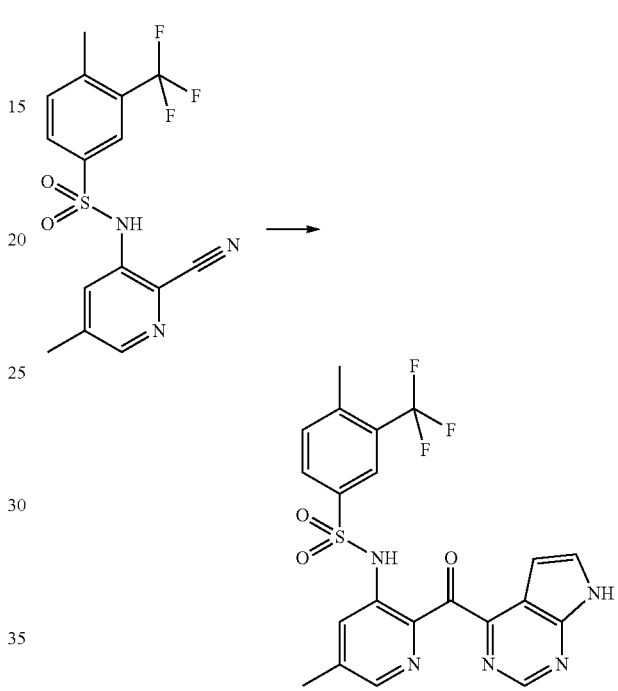

Prepared from 496 mg (1.40 mmol) of N-(2-cyano-5-methyl-pyridin-3-yl)-4-methyl-3-trifluoromethyl-benzenesulfonamide and 70 mg (1.75 mmol) of 60% sodium hydride in 2 mL THF. The Grignard solution was prepared from 467 mg (1.82 mmol) of 95% 4-iodo-7H-pyrrolo[2,3-d]pyrimidine dissolved in 5 mL THF with 0.98 mL of 2 M phenylmagnesium chloride solution in THF and 0.98 mL of 2 M isopropylmagnesium chloride solution in THF added. The reaction yielded 340 mg of the final product as a yellow solid.

Example 426: 3,4-Dichloro-N-[5-methyl-2-(7H-pyrrolo[2,3-d]pyrimidine-4-carbonyl)-pyridin-3-yl]-benzenesulfonamide

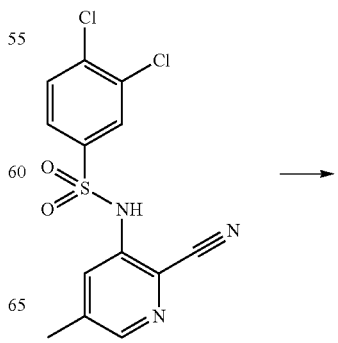

-continued

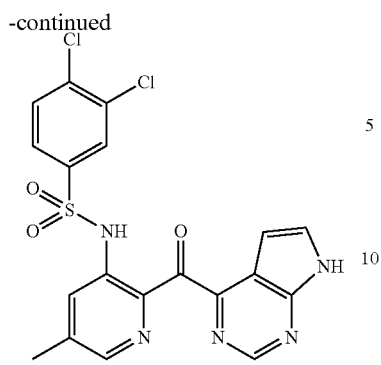

Prepared from 563 mg (1.55 mmol) of 3,4-dichloro-N-(2-cyano-5-methyl-pyridin-3-yl)-benzenesulfonamide sodium salt, 506 mg (2.01 mmol) of 97% 4-iodo-7H-pyrrolo[2,3-d]pyrimidine dissolved in 6 mL THF with 1.16 mL of 1.8 M phenylmagnesium chloride solution in THF and 1.06 mL of 2 M isopropylmagnesium chloride solution in THF added. The reaction yielded 471 mg of the final product as a yellow solid.

Example 427: Preparation of 4-Chloro-N-(5-methyl-2-(2-methyl-7H-pyrrolo[2,3-d]pyrimidine-4-carbonyl)pyridin-3-yl)-3-(trifluoromethyl)benzenesulfonamide

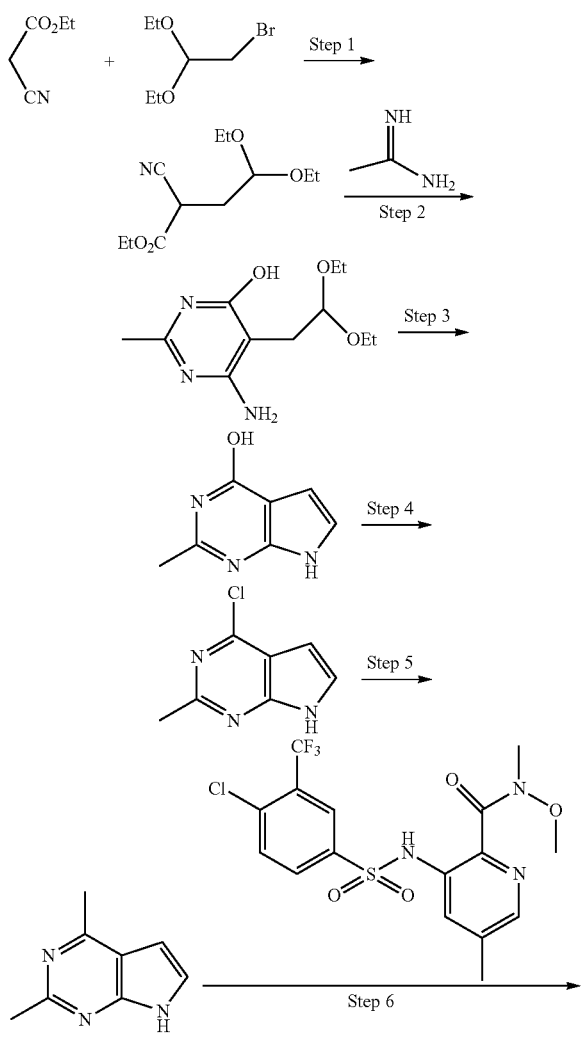

-continued

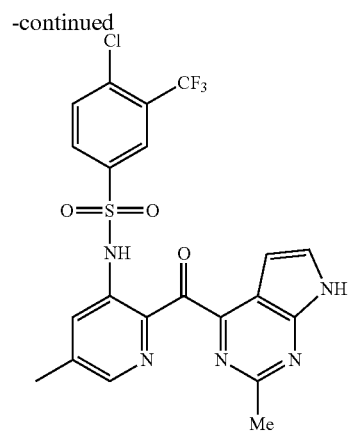

Step 1: To a suspension of NaH (60% dispersion in mineral oil, 1.62 g, 40.5 mmol) in DMF (35 mL) and benzene (12 mL) was added ethyl cyanoacetate (4.7 mL, 44.2 mmol) dropwise at −10° C. After stirring for 1 hour at room temperature, 2-bromo-1,1-diethoxyethane (5.6 mL, 0.82 equiv.) was added and the reaction mixture was heated at 100° C. for 2 hours. The reaction mixture was then cooled to room temperature and filtered. The filtrate was condensed, and water was added. The mixture was extracted with ether. The extracts were washed with brine, dried over MgSO$_4$ and concentrated in vacuo. The crude material was purified by flash chromatography on silica gel (20% EtOAc/hexanes). The desired product was obtained as colorless oil (5 g, 60%). MS: (M+Na)/z=252.

Step 2: Acetamidine hydrochloride (413 mg, 4.4 mmol) was added to a solution of sodium ethoxide (594 mg, 2.0 equiv.) in ethanol (8 mL). After stirring for half an hour at room temperature, the resultant sodium chloride was removed by filtration. The filtrate was added to ethyl 2-cyano-4,4-diethoxybutanoate (1.0 g, 4.4 mmol) and the mixture was refluxed for 5 hours. Most of the solvent was removed and the remaining slurry was dissolved in ice water, and extracted with ethyl acetate. The extracts were washed with brine, dried over MgSO$_4$ and concentrated in vacuo. The crude material was purified by flash chromatography on silica gel (100% methanol). The desired product was obtained as a red solid (421 mg, 40%). MS: (M+H)/z=242.

Step 3: The above pyrimidine (2.0 g, 8.30 mmol) was added to a solution of sulfuric acid (0.9 mL) in 50 mL of ethanol and refluxed for 2 hours. After cooling down to room temperature, the mixture was concentrated in vacuo. The crude material (soluble in water) was used directly for the next step. MS: (M+H)/z=150.

Step 4: A suspension of 90 mg (0.60 mmol) of the above hydroxypyrrolopyrimidine in 2 mL of phosphorous oxychloride was refluxed for 2 hours. The excess phosphorous oxychloride was removed and the residue was quenched carefully with ice. The mixture was extracted with ethyl acetate. The extracts were washed with brine, dried over MgSO$_4$ and concentrated in vacuo. The crude material was purified by flash chromatography on silica gel (10% methanol/DCM). The desired product was obtained as a colorless solid (86 mg, 85%). MS: (M+H)/z=168.

Step 5: The above chloropyrrolopyrimidine (40 mg, 0.24 mmol) was added to an aqueous solution of hydroiodic acid (57 wt. % in water, 1.5 mL) and the mixture was heated at 35° C. overnight. After cooling down to room temperature, a solution of hydroxylamine was added and the mixture was extracted with ethyl acetate. The extracts were washed with brine, dried over MgSO$_4$ and concentrated in vacuo. The desired product was obtained as a brown solid (50 mg, 80%). MS: (M+H)/z=260.

Step 6: To a solution of 3-(4-chloro-3-(trifluoromethyl) phenylsulfonamido)-N-methoxy-N,5-dimethylpicolinamide (56 mg, 0.13 mmol) in THF (1 mL) at 0° C. was added NaH (60% dispersion in mineral oil, 6 mg, 1.2 equiv.). The reaction was then warmed up to room temperature and stirred for 0.5 hour. In a separate flask was charged the above iodopyrrolopyrimidine (40 mg, 1.2 equiv.) in 0.5 mL of THF. The solution was cooled to −78° C., and a solution of isopropylmagnesium chloride in THF (2.0 M, 167 μL) was added dropwise. The reaction mixture was then warmed up to room temperature and a solution of 2, 6-dimethylphenyl magnesium bromide solution (1.0 M, 167 μL, 1.3 equiv.) in THF was added. After stirring for half an hour, the mixture was added to the above Weinreb amide solution and the reaction was stirred for an additional hour before quenching with saturated ammonium chloride solution. The mixture was extracted with ethyl acetate. The extracts were washed with brine, dried over MgSO₄ and concentrated in vacuo. The crude material was purified by flash chromatography on silica gel (33% EtOAc/hexanes). The desired product was obtained as a yellow solid (31 mg, 40%). MS: (M+H)/ z=510.

Example 428: 4-Chloro-N-[5-chloro-2-(9H-purine-6-carbonyl)-pyridin-3-yl]-3-trifluoromethyl-benzenesulfonamide

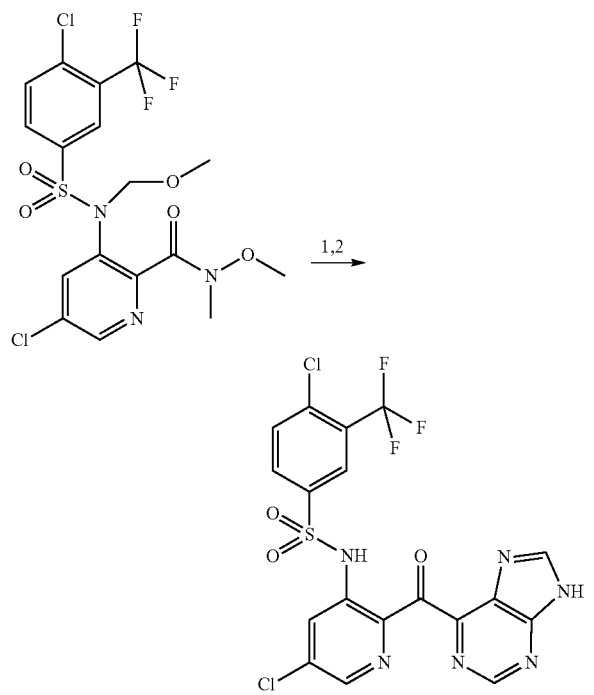

Prepared from 256 mg (0.51 mmol) of 5-chloro-3-[(4-chloro-3-trifluoromethyl-benzenesulfonyl)-methoxymethyl-amino]-pyridine-2-carboxylic acid methoxy-methyl-amide, 191 mg (0.51 mmol) of 6-iodo-9-(2-trimethylsilanyl-ethoxymethyl)-9H-purine dissolved in 2 mL THF with 0.25 mL of 2 M isopropylmagnesium chloride solution in THF added. All of the resulting intermediate ketone was used in the second step with 1 mL methanol and 1 mL 6N hydrochloric acid mixture to give after purification 2.05 mg of the final product as a yellow solid.

Example 429: 4-Chloro-N-[5-chloro-2-(1H-pyrrolo [2,3-c]pyridine-4-carbonyl)-pyridin-3-yl]-3-trifluoromethyl-benzenesulfonamide

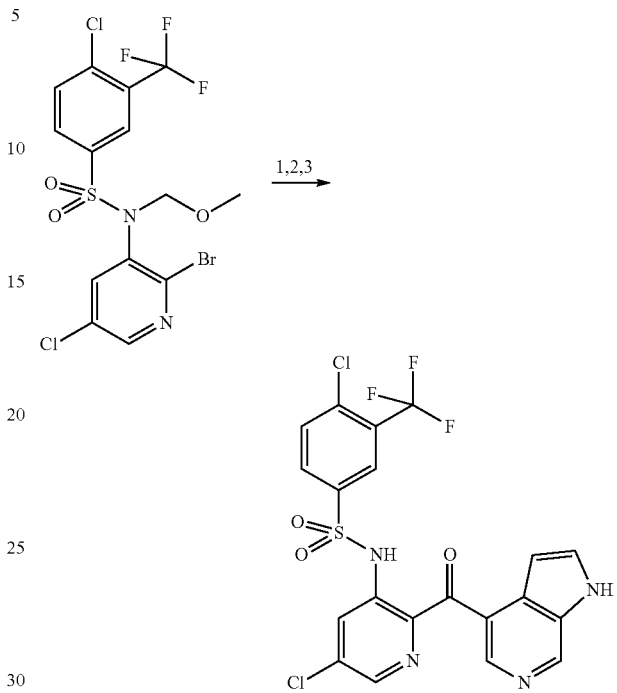

Prepared from 494 mg (1.00 mmol) of N-(2-bromo-5-chloro-pyridin-3-yl)-4-chloro-N-methoxymethyl-3-trifluoromethyl-benzenesulfonamide dissolved in 2 mL THF, 1.05 mL of 2 M isopropylmagnesium chloride solution in THF. 146 mg (1.00 mmol) of 1H-pyrrolo[2,3-c]pyridine-4-carbaldehyde was dissolved in 1 mL THF and treated sequentially at r.t. with 44 mg (1.1 mmol) of 60% sodium hydride and 177 uL (1 mmol) of trimethylsilylethoxymethyl chloride prior to addition to the Grignard reagent solution. Yield: 40 mg of the intermediate alcohol. All of it was used in the second step with 74 mg of Dess-Martin periodinane dissolved in 1 mL of DCM. The 31 mg of the resulting protected ketone was subjected to step 3 in 2 mL methanol and 2 mL 6N hydrochloric acid mixture at 100° C. to give after purification 17 mg of the final product as a yellow solid. LC-MSD, m/z for $C_{20}H_{11}Cl_2F_3N_4O_3S$ [M+H]⁺=514.9, 516.9; HPLC retention time: 2.3 min.

Example 430: 3,4-Dichloro-N-[5-methyl-2-(1H-pyrrolo[2,3-c]pyridine-4-carbonyl)-pyridin-3-yl]-benzenesulfonamide

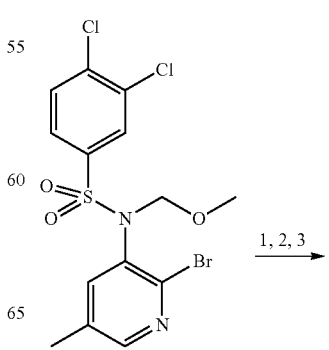

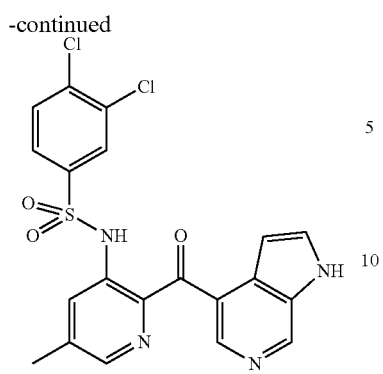

Prepared from 204 mg (0.464 mmol) of N-(2-bromo-5-methyl-pyridin-3-yl)-3,4-dichloro-N-methoxymethyl-benzenesulfonamide dissolved in 1 mL THF, 0.49 mL of 2 M isopropylmagnesium chloride solution in THF. 75 mg (0.510 mmol) of 1H-pyrrolo[2,3-c]pyridine-4-carbaldehyde was dissolved in 1 mL THF and treated at r.t. with 22 mg (0.557 mmol) of 60% sodium hydride prior to addition to the Grignard reagent solution. All of the intermediate alcohol was used in the second step with 300 mg of Dess-Martin periodinane dissolved in 2 mL of DCM. The resulting protected ketone was subjected to step 3 in 6 mL methanol and 6 mL 6N hydrochloric acid mixture at 90° C. to give after purification 22 mg of the final product as a yellow solid. LC-MSD, m/z for $C_{20}H_{14}Cl_2N_4O_3S$ [M+H]⁺=460.9, 462.9; HPLC retention time: 2.3 min.

Example 431: 4-Chloro-N-[5-chloro-2-(7H-pyrrolo[2,3-d]pyrimidine-4-carbonyl)-pyridin-3-yl]-3-trifluoromethyl-benzenesulfonamide

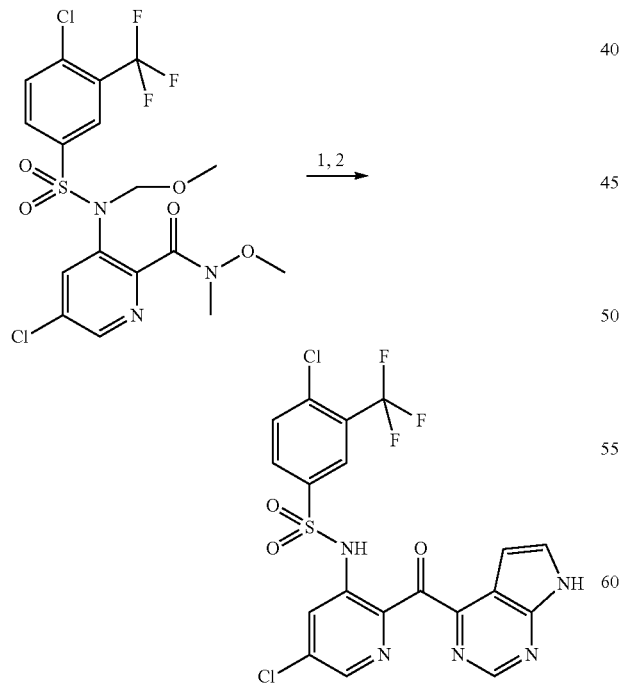

Prepared from 259 mg (0.52 mmol) of 5-chloro-3-[(4-chloro-3-trifluoromethyl-benzenesulfonyl)-methoxymethyl-amino]-pyridine-2-carboxylic acid methoxy-methyl-amide, 213 mg (0.52 mmol) of 90% 4-iodo-7-(2-trimethylsilanyl-ethoxymethyl)-7H-pyrrolo[2,3-d]pyrimidine dissolved in 2 mL THF with 0.26 mL of 2 M isopropylmagnesium chloride solution in THF added. All of the resulting intermediate ketone was used in the second step with 2 mL methanol and 2 mL 6N hydrochloric acid mixture to give after purification 40 mg of the final product as a yellow solid.

Example 432: Synthesis of 4-chloro-N-{5-chloro-2-[hydroxy-(1-(tert-butyl-dimethyl-silanyl)-1H-pyrrolo[2,3-b]pyridin-4-yl)-methyl]-phenyl}-N-methoxymethyl-3-trifluoromethyl-benzenesulfonamide

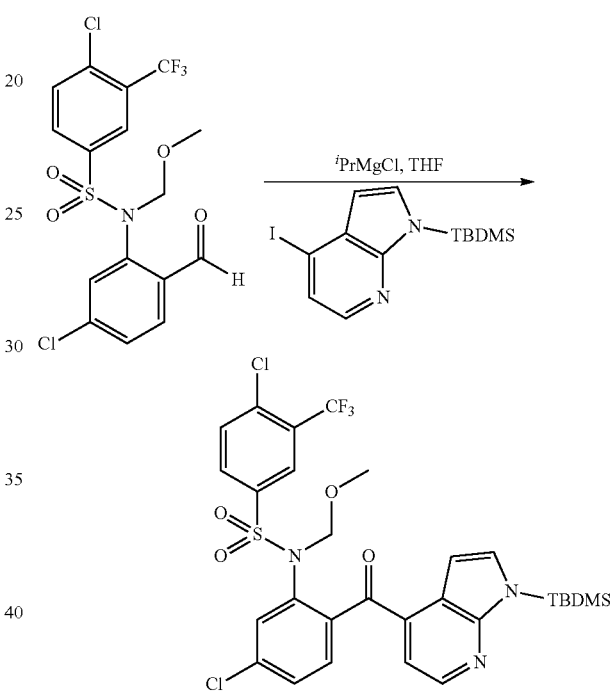

To a solution of 1-(tert-butyl-dimethyl-silanyl)-4-iodo-1H-pyrrolo[2,3-b]pyridine (97.4 mg, 0.27 mmol) in THF (2 mL) under nitrogen atmosphere at 0° C. was added drop wise isopropylmagnesium chloride (2 M solution in THF, 0.27 mL, 0.54 mmol). The mixture was then stirred for 30 min at 0° C. followed by the addition of a solution of 4-chloro-N-(5-chloro-2-formyl-phenyl)-N-methoxymethyl-3-trifluoromethyl-benzene sulfonamide (120 mg, 0.27 mmol) in THF (2 mL) at 0° C. The mixture was stirred at room temperature for overnight, quenched with saturated aqueous NH₄Cl solution (5 mL) and extracted with EtOAc (2×25 mL). Combined organic layers were washed with saturated aqueous NH₄Cl solution (25 mL), brine (25 mL), dried (anhydrous Na₂SO₄) and concentrated under reduced pressure. Obtained residue was column purified (SiO₂, 30% EtOAc-hexanes) to obtain 4-chloro-N-{5-chloro-2-[hydroxy-(1-(tert-butyl-dimethyl-silanyl)-1H-pyrrolo[2,3-b]pyridin-4-yl)-methyl]-phenyl}-N-methoxymethyl-3-trifluoromethyl-benzenesulfonamide (88 mg) in 48% yield. ESMS m/z (relative intensity): 674 (M+H)⁺ (100).

Example 433: Synthesis of 4-chloro-N-[5-chloro-2-(1-(tert-butyl-dimethyl-silanyl)-1H-pyrrolo[2,3-b]pyridine-4-carbonyl)-phenyl]-N-methoxymethyl-3-trifluoromethyl-benzenesulfonamide

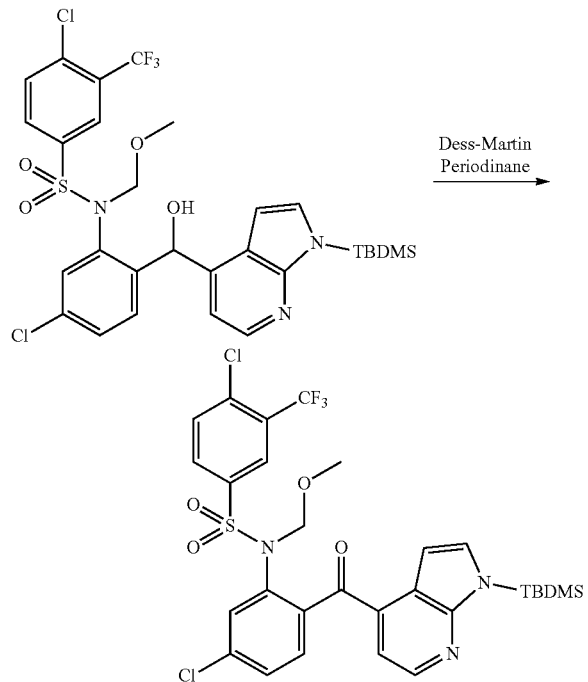

To a solution of 4-chloro-N-{5-chloro-2-[hydroxy-(1-(tert-butyl-dimethyl-silanyl)-1H-pyrrolo[2,3-b]pyridin-4-yl)-methyl]-phenyl}-N-methoxymethyl-3-trifluoromethyl-benzenesulfonamide (88 mg, 0.13 mmol) in $CH_2Cl_2$ (3 mL) was added Dess-Martin periodinane (99.8 mg, 0.235 mmol) and stirred for 5 h at room temperature. 10% $Na_2S_2O_3$ (3 mL) and saturated aqueous $NaHCO_3$ solution (3 mL) was added and stirred for 30 min. Aqueous layer was separated and extracted with EtOAc (2×25 mL). Combined organic layers were washed with saturated aqueous $NaHCO_3$ solution (20 mL), brine (20 mL), dried (anhydrous $Na_2SO_4$), concentrated and column purified ($SiO_2$, 30% EtOAc-hexanes) to obtain 4-chloro-N-[5-chloro-2-(1-(tert-butyl-dimethyl-silanyl)-1H-pyrrolo[2,3-b]pyridine-4-carbonyl)-phenyl]-N-methoxymethyl-3-trifluoromethyl-benzenesulfonamide (80 mg) in 92% yield. ESMS m/z (relative intensity): 672 $(M+H)^+$ (100).

Example 434: Synthesis of 4-chloro-N-[5-chloro-2-(1H-pyrrolo[2,3-b]pyridine-4-carbonyl)-phenyl]-3-trifluoromethyl-benzenesulfonamide

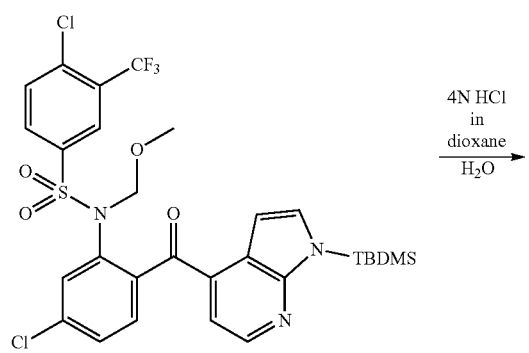

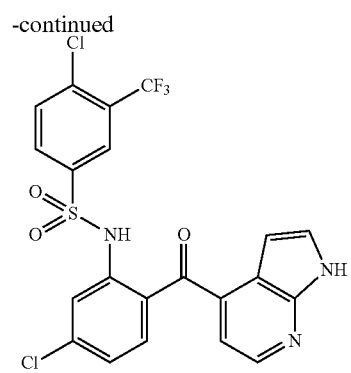

A mixture of 4-chloro-N-[5-chloro-2-(1-(tert-butyl-dimethyl-silanyl)-1H-pyrrolo[2,3-b]pyridine-4-carbonyl)-phenyl]-N-methoxymethyl-3-trifluoromethyl-benzenesulfonamide (20 mg, 0.029 mmol) in 4N HCl in dioxane (2 mL) and water (0.5 mL) was stirred at 70° C. for overnight. MeOH (0.5 mL) was added and further stirred at the same temperature for 30 min. Then reaction mixture was cooled to room temperature, evaporated to dryness and treated with saturated aqueous $NaHCO_3$ solution till pH 7-8. The mixture was extracted with EtOAc (2×25 mL), dried (anhydrous $Na_2SO_4$) and concentrated. The obtained residue was purified by HPLC to afford 4-chloro-N-[5-chloro-2-(1H-pyrrolo[2,3-b]pyridine-4-carbonyl)-phenyl]-3-trifluoromethyl-benzenesulfonamide in 60% yield. ESMS m/z (relative intensity): 514 $(M+H)^+$ (100).

Example 435: 4-Chloro-N-[5-chloro-2-(1H-pyrrolo[2,3-b]pyridine-4-carbonyl)-pyridin-3-yl]-3-isopropyl-benzenesulfonamide

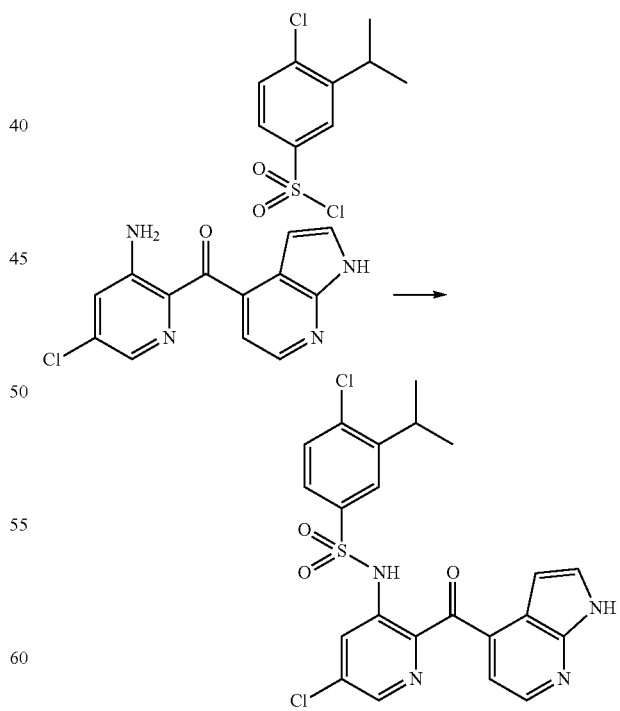

Prepared from 25 mg (0.092 mmol) of (3-amino-5-chloro-pyridin-2-yl)-(1H-pyrrolo[2,3-b]pyridin-4-yl)-methanone and 81 mg (0.32 mmol) of 4-chloro-3-iso-propyl-benzenesulfonyl chloride in 0.2 mL pyridine using procedure x. After the sulfonylation was complete, 3 mL methanol, 0.5 mL water and 44 mg sodium hydroxide were used. Yield: 18 mg of a yellow solid. LC-MSD, m/z for $C_{22}H_{18}Cl_2N_4O_3S$ $[M+H]^+$=489.0, 491.0

Example 436: N-[5-Chloro-2-(1H-pyrrolo[2,3-b]pyridine-4-carbonyl)-pyridin-3-yl]-4-cyano-3-trifluoromethyl-benzenesulfonamide

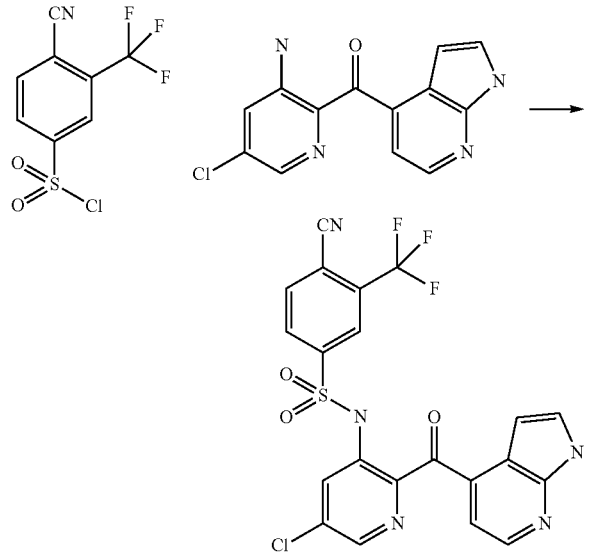

Prepared from 40 mg (0.15 mmol) of (3-amino-5-chloro-pyridin-2-yl)-(1H-pyrrolo[2,3-b]pyridin-4-yl)-methanone and 137 mg (0.51 mmol) of 4-cyano-3-trifluoromethyl-benzenesulfonyl chloride in 0.3 mL pyridine using procedure x. After the sulfonylation was complete, 3 mL methanol, 0.5 mL water and 71 mg sodium hydroxide were used. Yield: 10 mg of a yellow solid. LC-MSD, m/z for $C_{21}H_{12}ClF_3N_5O_3S$ $[M+H]^+$=505.9, 507.9

Example 437: 3-Chloro-N-[5-chloro-2-(1H-pyrrolo[2,3-b]pyridine-4-carbonyl)-pyridin-3-yl]-4-methyl-benzenesulfonamide

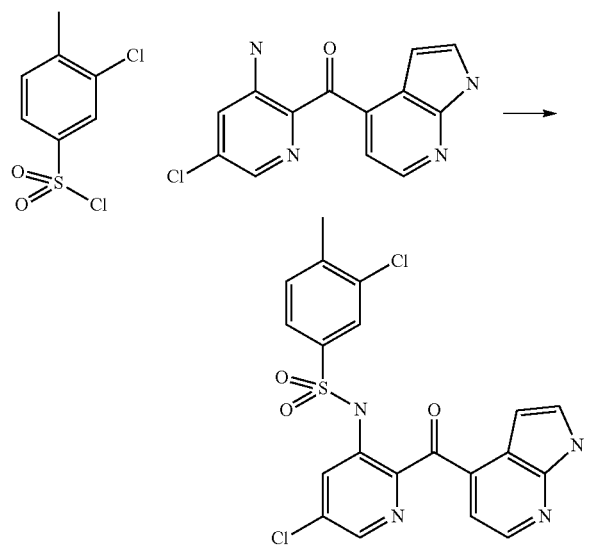 [SMILES: Cc1ccc(S(=O)(=O)Cl)cc1Cl ; Nc1cc(Cl)cnc1C(=O)c1ccnc2[nH]ccc12 ; Cc1ccc(S(=O)(=O)Nc2cc(Cl)cnc2C(=O)c2ccnc3[nH]ccc23)cc1Cl]

Prepared from 20 mg (0.075 mmol) of (3-amino-5-chloro-pyridin-2-yl)-(1H-pyrrolo[2,3-b]pyridin-4-yl)-methanone and 58 mg (0.25 mmol) of 3-chloro-4-methyl-benzenesulfonyl chloride in 0.15 mL pyridine using procedure x. After the sulfonylation was complete, 3 mL methanol, 0.5 mL water and 35 mg sodium hydroxide were used. Yield: 9 mg of a yellow solid. LC-MSD, m/z for $C_{20}H_{14}Cl_2N_4O_3S$ $[M+H]^+$=460.9, 462.9

Example 438: N-[5-Chloro-2-(1H-pyrrolo[2,3-b]pyridine-4-carbonyl)-pyridin-3-yl]-3-fluoro-4-methyl-benzenesulfonamide

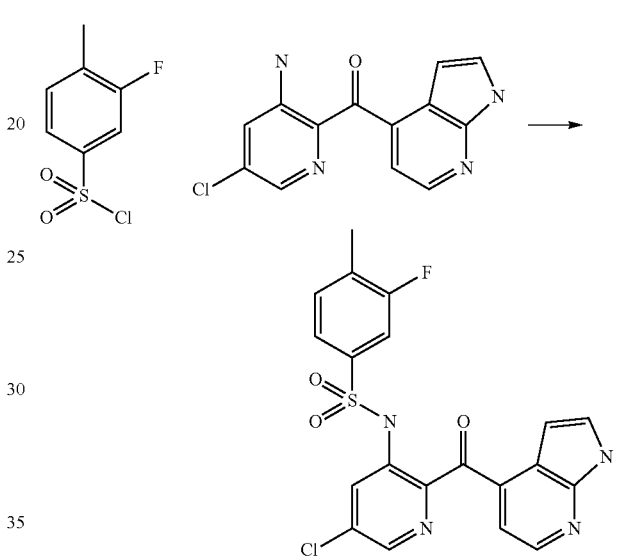

Prepared from 18 mg (0.066 mmol) of (3-amino-5-chloro-pyridin-2-yl)-(1H-pyrrolo[2,3-b]pyridin-4-yl)-methanone and 48 mg (0.25 mmol) of 3-fluoro-4-methyl-benzenesulfonyl chloride in 0.10 mL pyridine using procedure x. After the sulfonylation was complete, 2 mL methanol, 0.5 mL water and 32 mg sodium hydroxide were used. Yield: 20 mg of a yellow solid. LC-MSD, m/z for $C_{20}H_{14}ClFN_4O_3S$ $[M+H]^+$=445.0, 447.0.

Example 439: 3-tert-Butyl-4-chloro-N-[5-chloro-2-(1H-pyrrolo[2,3-b]pyridine-4-carbonyl)-pyridin-3-yl]-benzenesulfonamide

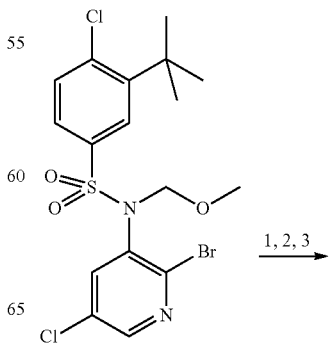

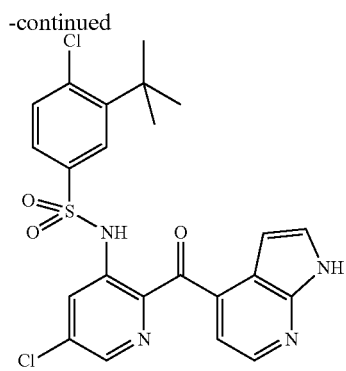

Prepared from 160 mg (0.332 mmol) of N-(2-bromo-5-chloro-pyridin-3-yl)-3-tert-butyl-4-chloro-N-methoxymethyl-benzenesulfonamide dissolved in 1 mL THF, 0.35 mL of 2 M isopropylmagnesium chloride solution in THF and 95 mg (0.365 mmol) of 1-(tert-butyl-dimethyl-silanyl)-1H-pyrrolo[2,3-b]pyridine-4-carbaldehyde. Yield: 180 mg of the intermediate alcohol. All of it was used in the second step with 180 mg of Dess-Martin periodinane dissolved in 5 mL of DCM. 55 mg of the resulting protected ketone was subjected to step 3 in 2 mL methanol and 2 mL 6N hydrochloric acid mixture to give after purification 20 mg of the final product as a yellow solid. LC-MSD, m/z for $C_{23}H_{20}Cl_2N_4O_3S$ [M+H]$^+$=503.0, 505.0.

Example 440: 4-Chloro-N-[5-chloro-2-(1H-pyrrolo[2,3-b]pyridine-4-carbonyl)-pyridin-3-yl]-3-(1-hydroxy-1-methyl-ethyl)-benzenesulfonamide

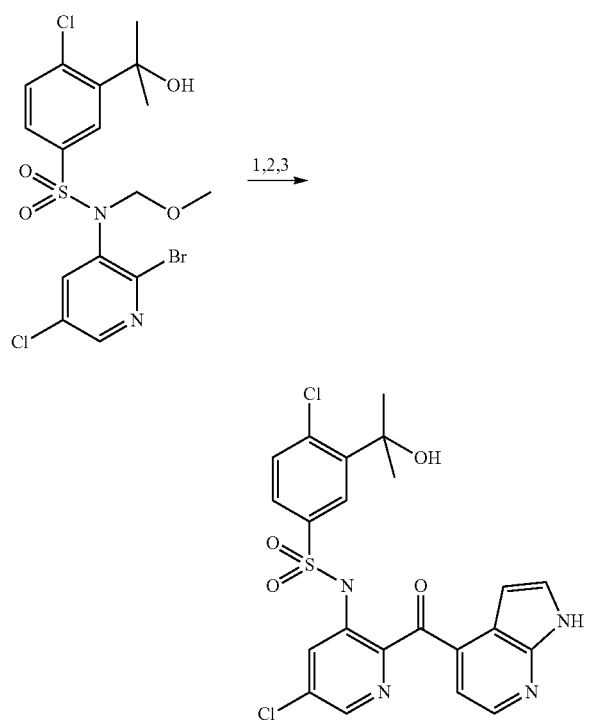

Prepared from 147 mg (0.30 mmol) of N-(2-bromo-5-chloro-pyridin-3-yl)-4-chloro-3-(1-hydroxy-1-methyl-ethyl)-N-methoxymethyl-benzenesulfonamide dissolved in 1 mL THF (in this case the solution was cooled down to −40° C. prior to the addition of the Grignard reagent), 0.47 mL of 2 M isopropylmagnesium chloride solution in THF and 86 mg (0.33 mmol) of 1-(tert-butyl-dimethyl-silanyl)-1H-pyrrolo[2,3-b]pyridine-4-carbaldehyde. Yield: 132 mg of the intermediate alcohol. All of it was used in the second step with 210 mg of Dess-Martin periodinane dissolved in 2 mL of DCM. 96 mg of the resulting protected ketone was subjected to step 3 in 4 mL methanol and 4 mL 6N hydrochloric acid mixture to give after purification 37 mg of the final product as a yellow solid. LC-MSD, m/z for $C_{22}H_{18}Cl_2N_4O_4S$ [M+H]$^+$=505.0, 507.0.

Example 441: 4-Chloro-N-[5-chloro-2-(1H-pyrrolo[2,3-b]pyridine-4-carbonyl)-pyridin-3-yl]-3-(1,1-difluoro-ethyl)-benzenesulfonamide

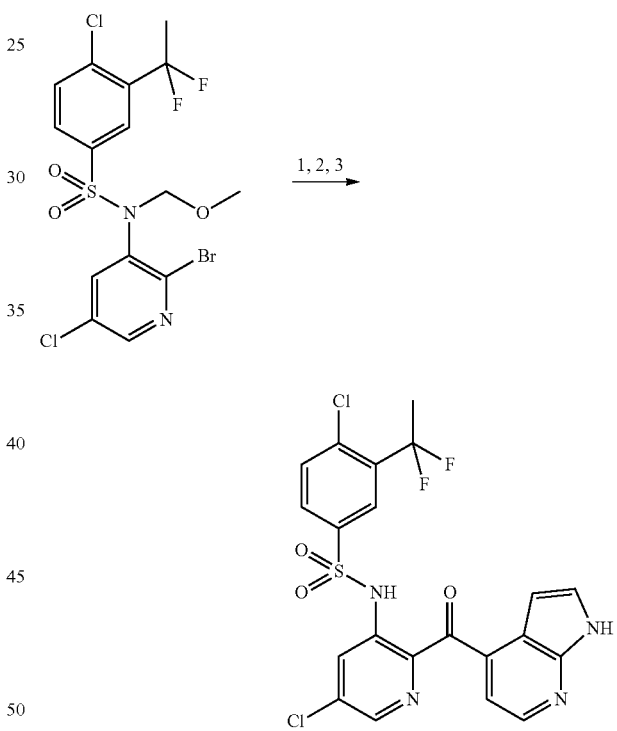

Prepared from 162 mg (0.331 mmol) of N-(2-bromo-5-chloro-pyridin-3-yl)-4-chloro-3-(1,1-difluoro-ethyl)-N-methoxymethyl-benzenesulfonamide dissolved in 1 mL THF, 0.35 mL of 2 M isopropylmagnesium chloride solution in THF and 95 mg (0.364 mmol) of 1-(tert-butyl-dimethyl-silanyl)-1H-pyrrolo[2,3-b]pyridine-4-carbaldehyde. All of the intermediate alcohol was used in the second step with 350 mg of Dess-Martin periodinane dissolved in 2 mL of DCM. 95 mg of the resulting protected ketone was subjected to step 3 in 3 mL methanol and 3 mL 6N hydrochloric acid mixture to give after purification 50 mg of the final product as a yellow solid. LC-MSD, m/z for $C_{21}H_{14}Cl_2F_2N_4O_3S$ [M+H]$^+$=510.9, 512.9.

Example 442: 4-Chloro-N-[5-chloro-2-(1H-pyrrolo[2,3-b]pyridine-4-carbonyl)-pyridin-3-yl]-3-ethyl-benzenesulfonamide

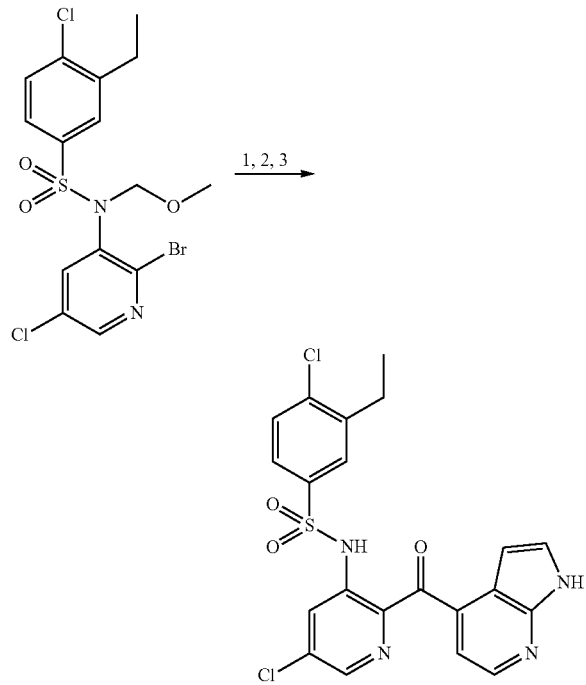

Prepared from 186 mg (0.41 mmol) of N-(2-bromo-5-chloro-pyridin-3-yl)-4-chloro-3-ethyl-N-methoxymethyl-benzenesulfonamide dissolved in 1 mL THF, 0.43 mL of 2 M isopropylmagnesium chloride solution in THF and 117 mg (0.45 mmol) of 1-(tert-butyl-dimethyl-silanyl)-1H-pyrrolo[2,3-b]pyridine-4-carbaldehyde. Yield: 152 mg of the intermediate alcohol. All of it was used in the second step with 255 mg of Dess-Martin periodinane dissolved in 1 mL of DCM. The resulting protected ketone was subjected to step 3 in 3 mL methanol and 3 mL 6N hydrochloric acid mixture to give after purification 50 mg of the final product as a yellow solid. LC-MSD, m/z for $C_{21}H_{16}Cl_2N_4O_3S$ [M+H]$^+$=474.9, 476.9; HPLC retention time: 2.8 min.

Example 443: N-[5-Chloro-2-(1H-pyrrolo[2,3-b]pyridine-4-carbonyl)-pyridin-3-yl]-4-ethyl-3-trifluoromethyl-benzenesulfonamide

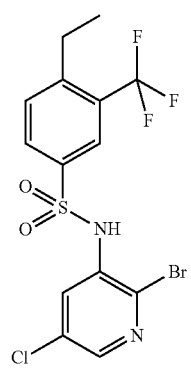

→

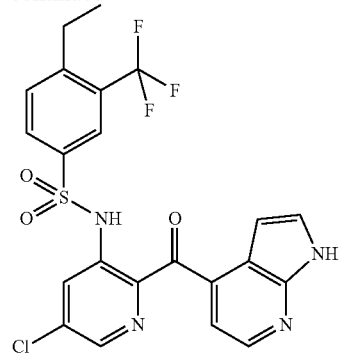

A solution/suspension made of 97 mg (0.22 mmol) of N-(2-bromo-5-chloro-pyridin-3-yl)-4-ethyl-3-trifluoromethyl-benzenesulfonamide, 140 mg (0.87 mmol) of 1H-pyrrolo[2,3-b]pyridine-4-boronic acid (mixture with its neopentyl glycolate ester and 1H-pyrrolo[2,3-b]pyridine), 240 mg (1.74 mmol) of potassium carbonate and 15 mg (0.022 mmol) of bis(triphenylphosphine)dichloropalladium(II) in 1 mL of anisole was stirred at 150° C. under 10 atm pressure of carbon monoxide for 2 h. After cooling down and decompression the mixture was introduced onto a flash column and eluted with 50-100% ethyl acetate in hexanes. Fractions containing the product were repurified on reverse-phase HPLC and free based to give 3.5 mg of the product as a yellow solid. LC-MSD, m/z for $C_{22}H_{16}ClF_3N_4O_3S$ [M+H]$^+$=509.0, 511.0.

Example 444: N-(2-{[1-(tert-Butyl-dimethyl-silanyl)-1H-pyrrolo[2,3-b]pyridin-4-yl]-hydroxymethyl}-5-chloro-6-methyl-pyridin-3-yl)-4-chloro-N-methoxymethyl-3-trifluoromethylbenzenesulfonamide

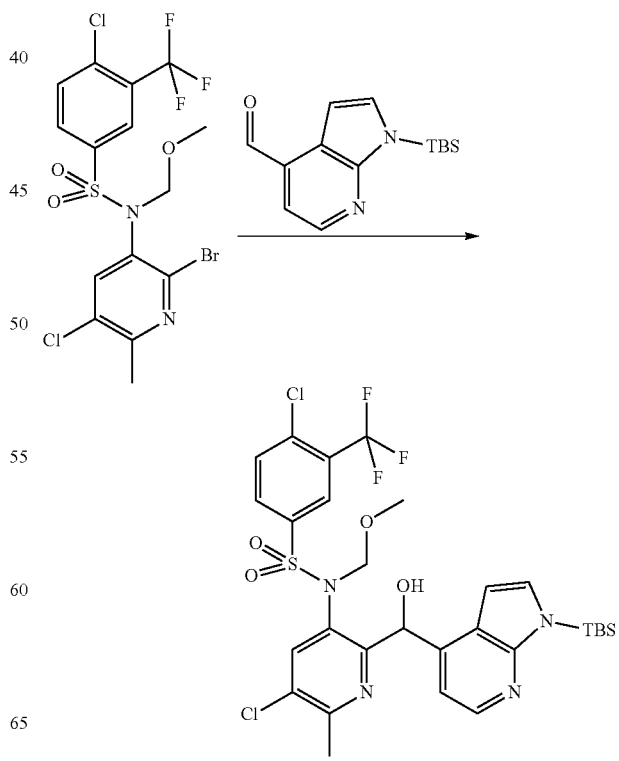

To a solution of N-(2-Bromo-5-chloro-6-methyl-pyridin-3-yl)-4-chloro-N-methoxymethyl-3-trifluoromethyl-benzenesulfonamide (152.7 mg, 0.3 mmol) in 2 ml of THF under nitrogen atmosphere at 00° C. was added via syringe 2.0M isopropyl magnesium chloride (0.36 ml, 0.72 mmol). The reaction mixture was stirred for about 45 minutes and 1-(tert-Butyl-dimethyl-silanyl)-1H-pyrrolo[2,3-b]pyridine-4-carbaldehyde (54 mg, 0.21 mmol) was added and the resultant mixture was stirred for 30 minutes at 00° C. and then 2 hours at room temperature. The mixture was quenched with saturated ammonium chloride and extracted with ethyl acetate. The organic layer was separated and washed with water twice and dried. Concentration of this mixture afforded the crude product (210 mg) which was used in the next step without any further purification. MS (ES) (M$^+$+H) expect 689, found 688.9

Example 445: N-{2-[1-(tert-Butyl-dimethyl-silanyl)-1H-pyrrolo[2,3-b]pyridine-4-carbonyl]-5-chloro-6-methyl-pyridin-3-yl}-4-chloro-N-methoxymethyl-3-trifluoromethyl-benzenesulfonamide

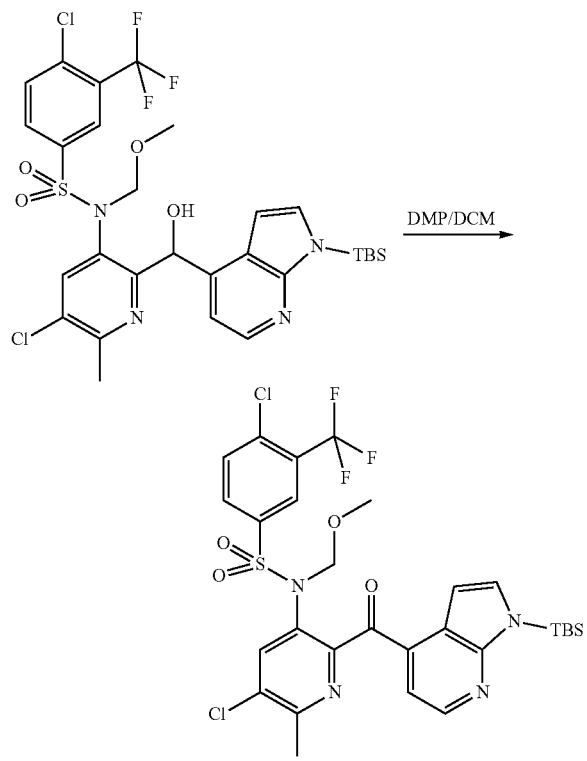

A mixture of N-(2-{[1-(tert-Butyl-dimethyl-silanyl)-1H-pyrrolo[2,3-b]pyridin-4-yl]-hydroxy-methyl}-5-chloro-6-methyl-pyridin-3-yl)-4-chloro-N-methoxymethyl-3-trifluoromethylbenzenesulfonamide (from above step), Dess-Martin periodinane (424 mg, 1.0 mmol) in 3 ml of DCM was stirred at room temperature for overnight. The mixture was directly purified by flash chromatography (25% ethyl acetate in hexane) to afford the desired title compound. MS (ES) (M$^+$+H) expect 687, found 686.9

Example 446: 4-Chloro-N-[5-chloro-6-methyl-2-(1H-pyrrolo[2,3-b]pyridine-4-carbonyl)-pyridin-3-yl]-3-trifluoromethyl-benzenesulfonamide

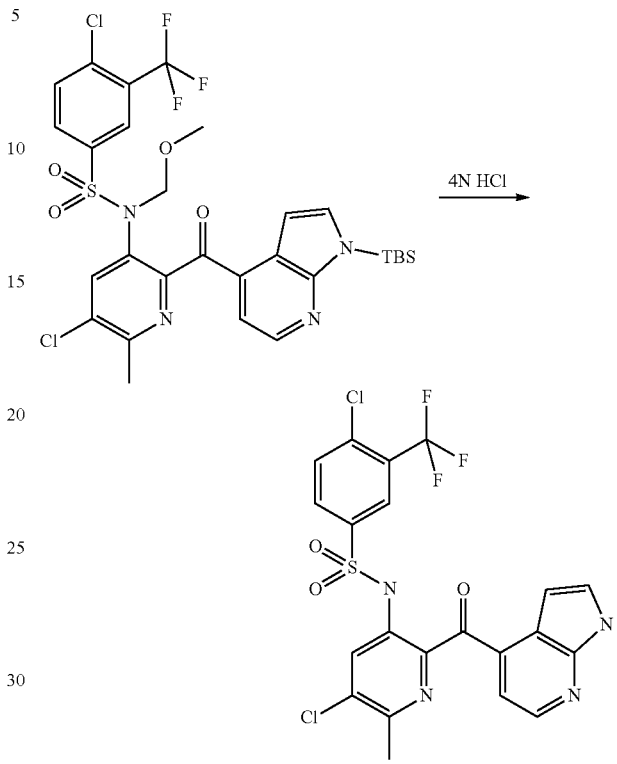

A mixture of N-{2-[1-(tert-Butyl-dimethyl-silanyl)-1H-pyrrolo[2,3-b]pyridine-4-carbonyl]-5-chloro-6-methyl-pyridin-3-yl}-4-chloro-N-methoxymethyl-3-trifluoromethyl-benzenesulfonamide (from above step) in 2 ml of 4M HCl and 2 ml of dioxane was stirred at 90° C. for 2 hours. The mixture was concentrated and the residue was diluted with ethyl acetate, this organic layer was washed with saturated sodium bicarbonate and followed by brine and then dried over sodium sulfate. After filtration and concentration the residue was purified by preparative TLC to afford the title compound. 1H NMR: (CD$_3$OD, ppm): 8.15 (d, 1H), 7.98 (s, 1H), 7.84 (m, 1H), 7.53 (m, 1H), 7.40 (d, 1H), 7.26 (d, 1H), 7.07 (d, 1H), 6.23 (d, 1H), 2.47 (s, 3H); MS (ES) (M$^+$+H) expect 529, found 528.9

Example 447: 4-Chloro-N-[5-chloro-2-(1H-pyrrolo[2,3-b]pyridine-4-carbonyl)-pyridin-3-yl]-3-methyl-benzenesulfonamide

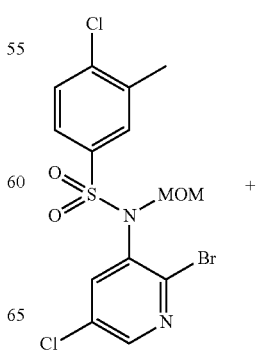

431
-continued
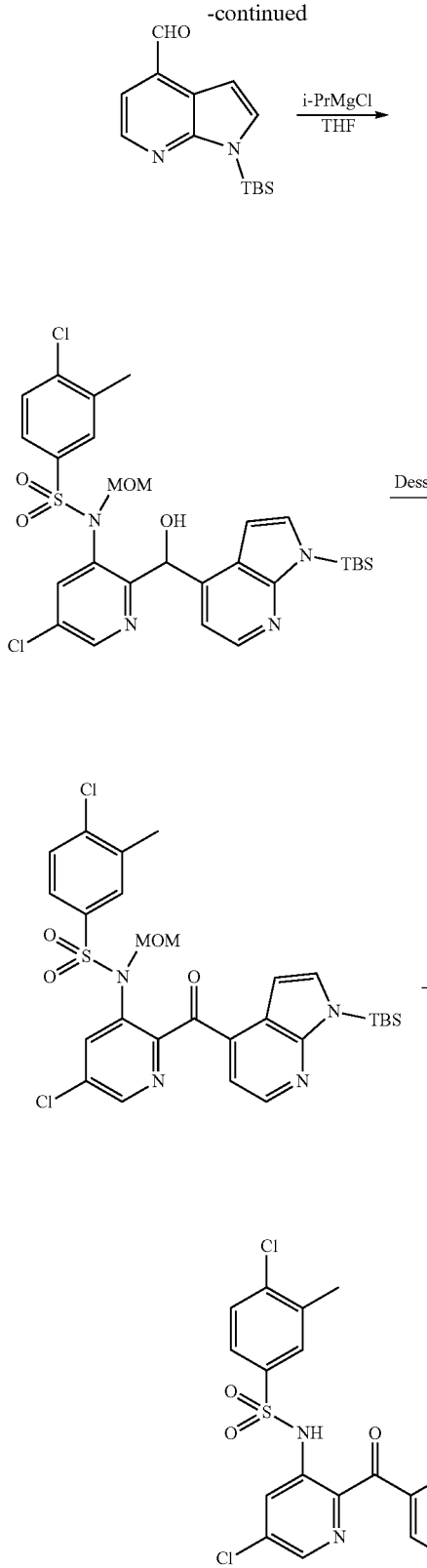
The title compound was synthesized according to procedures outlined above using 1-(tert-Butyl-dimethyl-silanyl)-1H-pyrrolo[2,3-b]pyridine-4-carbaldehyde MS (M+H): 461.0.
432
Example 448: 4-Chloro-N-[5-methyl-2-(1H-pyrrolo[2,3-b]pyridine-4-carbonyl)-pyridin-3-yl]-3-trifluoromethyl-benzenesulfonamide
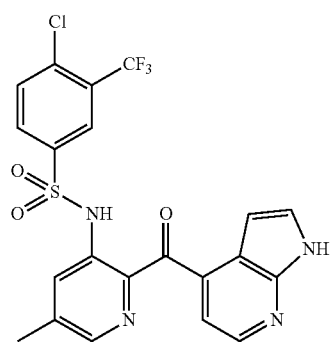

The title compound was synthesized according to procedures outlined above using 1-(tert-Butyl-dimethyl-silanyl)-1H-pyrrolo[2,3-b]pyridine-4-carbaldehyde. MS (M+H): 495.0.

Example 449: N-[5-Chloro-2-(1H-pyrrolo[2,3-b]pyridine-4-carbonyl)-pyridin-3-yl]-3-trifluoromethyl-benzenesulfonamide Example 450: 3,4-Dichloro-N-[5-chloro-2-(1H-pyrrolo[2,3-b]pyridine-4-carbonyl)-pyridin-3-yl]-benzenesulfonamide

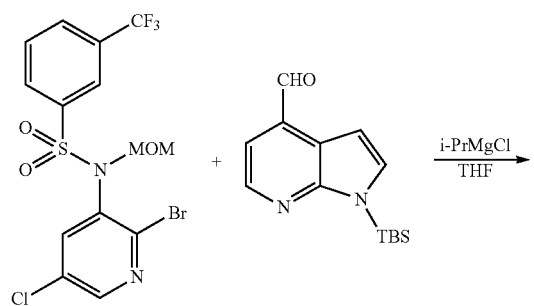

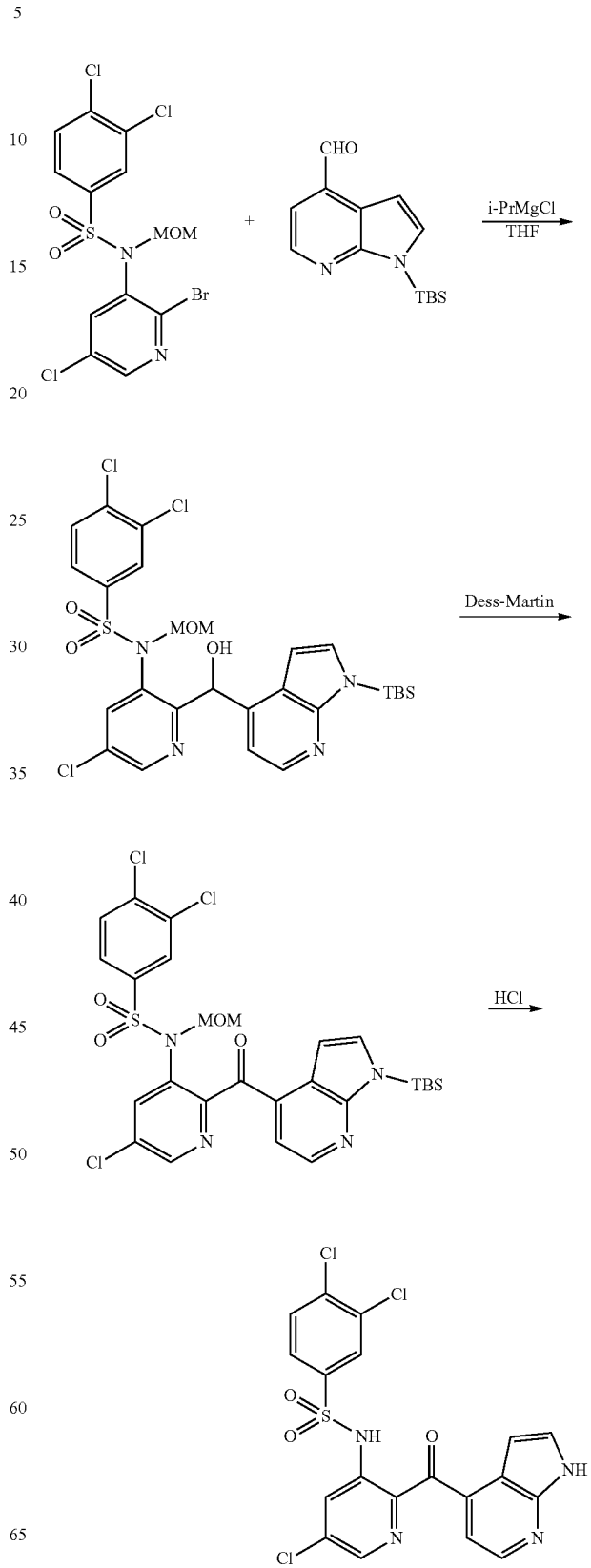

The title compound was synthesized according to procedures outlined using 1-(tert-Butyl-dimethyl-silanyl)-1H-pyrrolo[2,3-b]pyridine-4-carbaldehyde. MS (M+H): 481.0.

The title compound was synthesized according to procedures outlined above using 1-(tert-Butyl-dimethyl-silanyl)-1H-pyrrolo[2,3-b]pyridine-4-carbaldehyde. MS (M+H): 480.9.

Example 451: 3,4-Dichloro-N-[2-(1H-pyrrolo[2,3-b]pyridine-4-carbonyl)-5-trifluoromethyl-pyridin-3-yl]-benzenesulfonamide

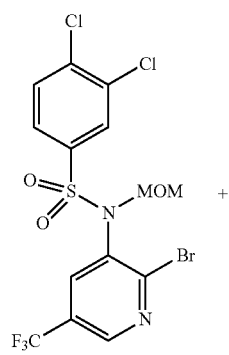

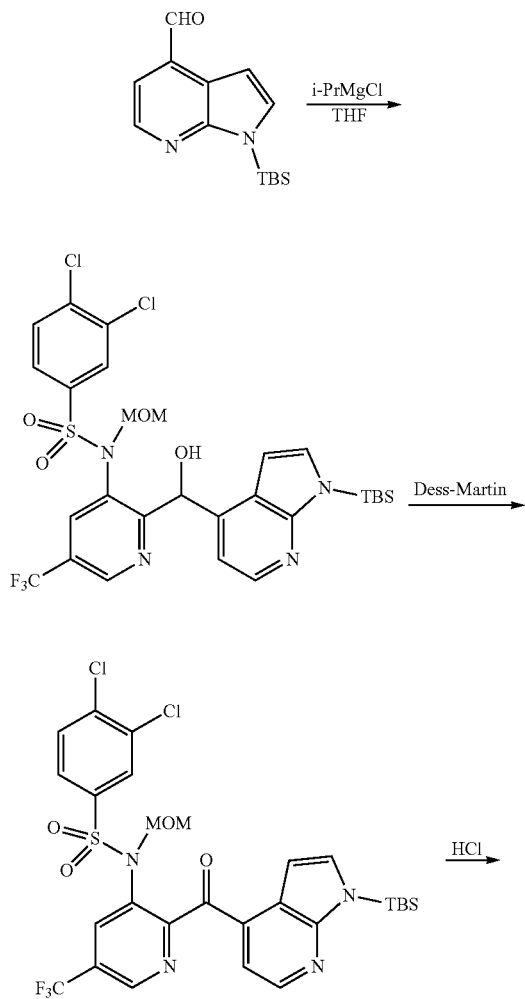

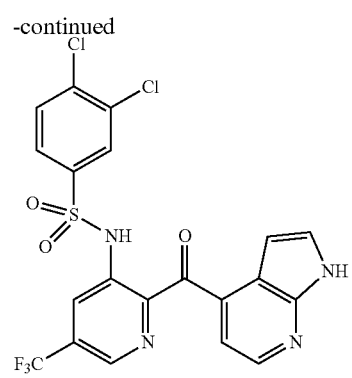

The title compound was synthesized according to procedures outlined above using 1-(tert-Butyl-dimethyl-silanyl)-1H-pyrrolo[2,3-b]pyridine-4-carbaldehyde. MS (M+H): 514.9.

Example 452: Preparation of 4-(5-Chloro-3-(4-methyl-3-(trifluoromethyl) phenylsulfonamido)picolinoyl)-5-methoxy-1H-pyrrolo[2,3-b]pyridine 7-oxide

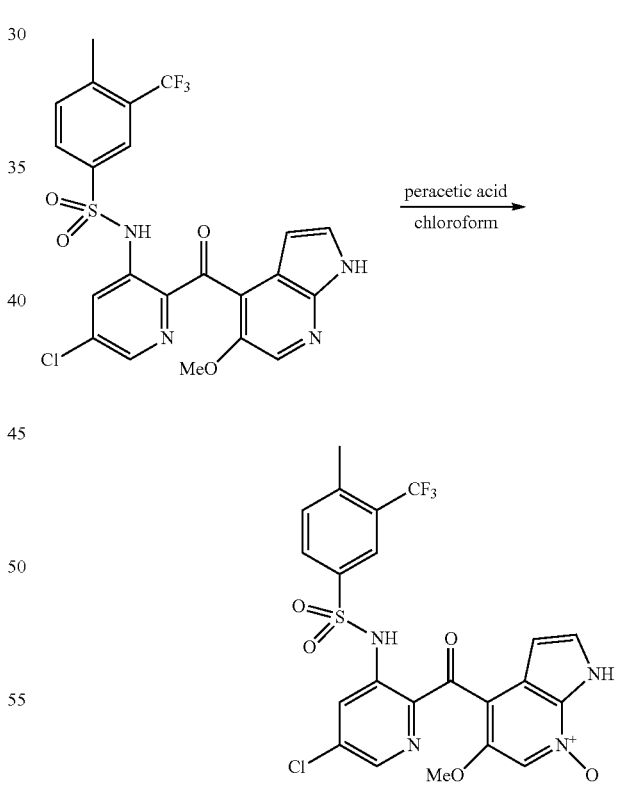

To a stirred solution of the azaindole obtained from Example 1 (13 mg, 0.025 mmol) in chloroform (5 mL) was added peracetic acid (20 μL, 32% wt in acetic acid). The reaction mixture was stirred for 2 days at room temperature and quenched with saturated NaHCO₃. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (11 mg, 80%). $^1$HNMR: (400 MHz, CDCl$_3$) δ 8.16 (s, 2H), 8.11 (s, 1H), 8.00 (s, 1H), 7.96 (dd, J=8.4, 2.0 Hz, 1H), 7.43 (d, J=8.4 Hz, 1H), 7.34 (d, J=3.6 Hz, 1H), 6.25 (d, J=3.2 Hz, 1H), 3.61 (s, 3H), 2.53 (s, 3H); MS: (M+H)/z=541.

Example 453: Preparation of 4-Chloro-N-(2-(5-methoxy-1H-pyrrolo[2,3-b]pyridine-4-carbonyl)-5-methylpyridin-3-yl)-3-(trifluoromethyl)benzenesulfonamide

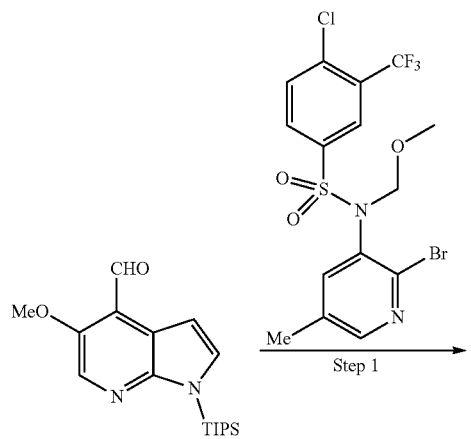

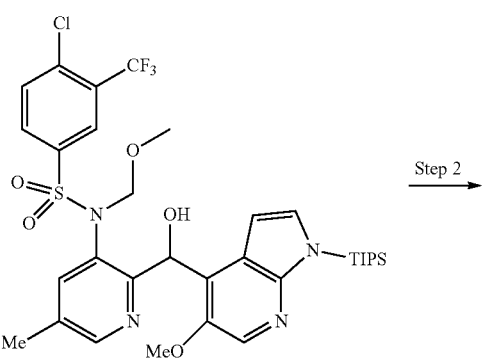

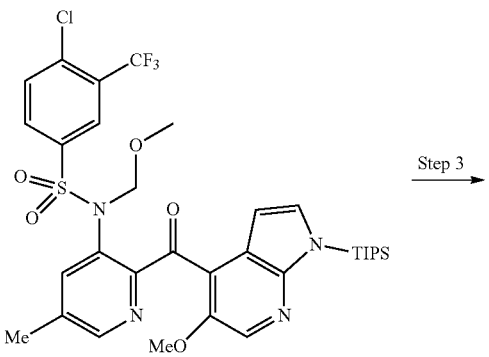

-continued

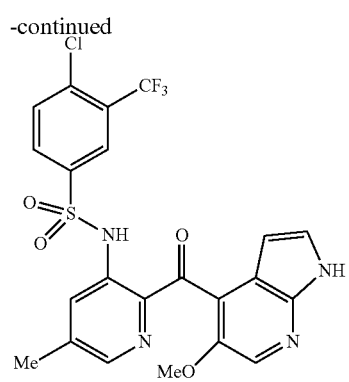

Step 1: To a solution of the bromopyridine (74 mg, 0.16 mmol) in THF (1 mL) at 0° C. was added isopropylmagnesium chloride (156 μL, 2.0 M in THF) dropwise. After 45 minutes, a solution of the aldehyde obtained from step 5, example 1 above (54 mg, 0.16 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (25% EtOAc/hexanes). The desired product was obtained as a foaming yellow solid (62 mg, 55%). MS: (M+H)/z=727.

Step 2: The product obtained from step 1 above (45 mg, 0.062 mmol) was dissolved in 2 mL of dichloromethane. To the resultant solution was added Dess-Martin periodinane (42 mg, 1.6 equiv.) and stirred overnight at room temperature. The reaction was quenched with 10% Na$_2$S$_2$O$_3$, and the mixture was extracted with ethyl acetate. The extracts were washed with saturated NaHCO$_3$, brine, dried over MgSO$_4$ and concentrated in vacuo. The crude material was purified by flash chromatography on silica gel (20% EtOAc/hexanes). The desired product was obtained as a foaming yellow solid (28 mg, 62%). MS: (M+H)/z=725.

Step 3: The product obtained from step 2 above (28 mg, 0.039 mmol) was dissolved in 4 mL of HCl-dioxane (4.0 M) and 1 mL of water. The mixture was heated at 85° C. for 30 minutes and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (12 mg, 59%). MS: (M+H)/z=525.

Example 454: Preparation 4-(3-(4-Chloro-3-(trifluoromethyl)phenylsulfonamido)-5-methylpicolinoyl)-5-methoxy-1H-pyrrolo[2,3-b]pyridine 7-oxide

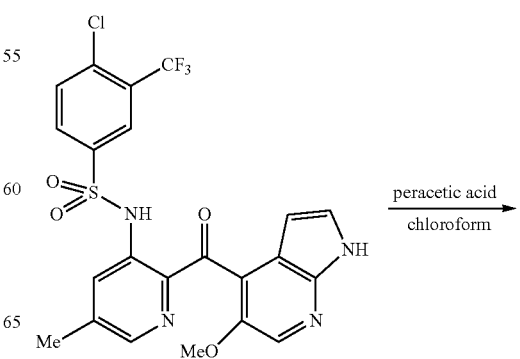

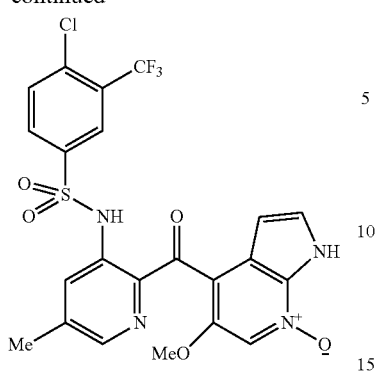

To a stirred solution of the azaindole from Example 4 (20 mg, 0.038 mmol) in chloroform (5 mL) was added peracetic acid (31 µL, 32% wt in acetic acid). The reaction mixture was stirred for 2 days at room temperature and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (15 mg, 73%). MS: (M+H)/z=541.

Example 455: Preparation of N-(2-(5-Methoxy-1H-pyrrolo[2,3-b]pyridine-4-carbonyl)-5-methylpyridin-3-yl)-4-methyl-3-(trifluoromethyl)benzenesulfonamide

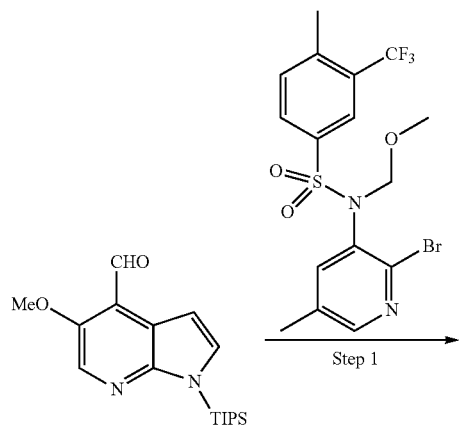

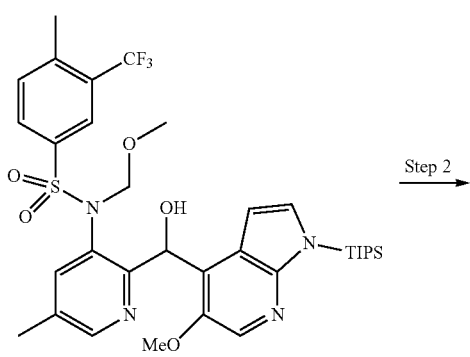

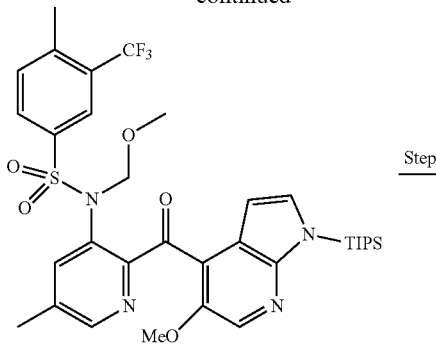

Step 1: To a solution of the bromopyridine (68 mg, 0.15 mmol) in THF (1 mL) at 0° C. was added isopropylmagnesium chloride (150 µL, 2.0 M in THF) dropwise. After 45 minutes, a solution of the aldehyde obtained from step 5, Example 1 above (50 mg, 0.15 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a foaming yellow solid (60 mg, 57%). MS: (M+H)/z=707.

Step 2: The product obtained from step 1 above (56 mg, 0.079 mmol) was dissolved in 2 mL of dichloromethane. To the resultant solution was added Dess-Martin periodinane (54 mg, 1.6 equiv.) and stirred overnight at room temperature. The reaction was quenched with 10% Na$_2$S$_2$O$_3$, and the mixture was extracted with ethyl acetate. The extracts were washed with saturated NaHCO$_3$, brine, dried over MgSO$_4$ and concentrated in vacuo. The crude material was purified by flash chromatography on silica gel (20% EtOAc/hexanes). The desired product was obtained as a foaming yellow solid (40 mg, 71%). MS: (M+H)/z=705.

Step 3: The product obtained from step 2 above (41 mg, 0.057 mmol) was dissolved in 4 mL of HCl-dioxane (4.0 M) and 1 mL of water. The mixture was heated at 85° C. for 30 minutes and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (20 mg, 68%). MS: (M+H)/z=505.

Example 456: Preparation of 5-Methoxy-4-(5-methyl-3-(4-methyl-3-(trifluoromethyl) phenylsulfonamido)picolinoyl)-1H-pyrrolo[2,3-b]pyridine 7-oxide

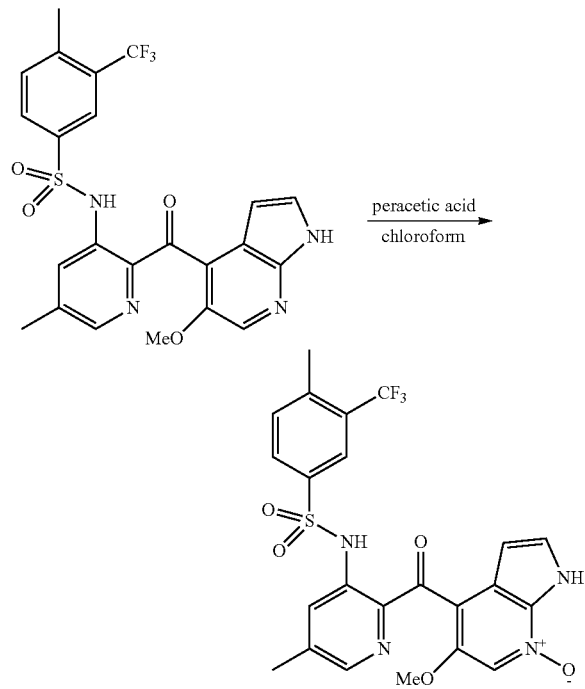

To a stirred solution of the azaindole from Example 5 (20 mg, 0.040 mmol) in chloroform (5 mL) was added peracetic acid (28 μL, 32% wt in acetic acid). The reaction mixture was stirred for 2 days at room temperature and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (12 mg, 58%). MS: (M+H)/z=521.

Example 457: Preparation of 4-Chloro-N-(2-(5-methoxy-1H-pyrrolo[2,3-b]pyridine-4-carbonyl)pyridin-3-yl)-3-(trifluoromethyl)benzenesulfonamide

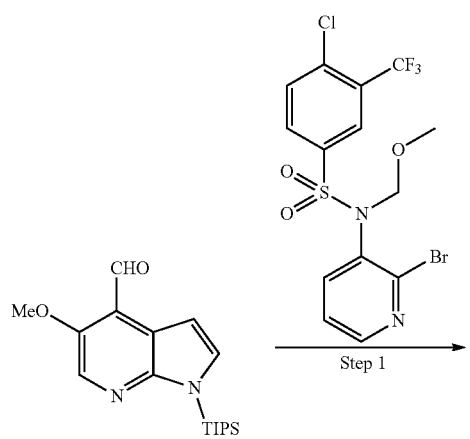

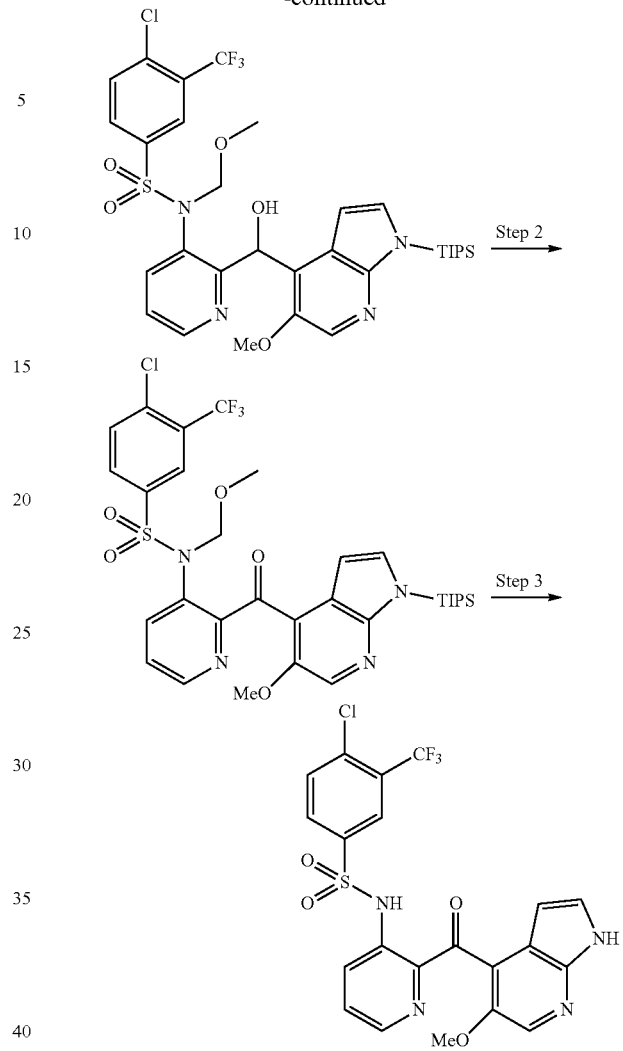

Step 1: To a solution of the bromopyridine (152 mg, 0.33 mmol) in THF (1 mL) at 0° C. was added isopropylmagnesium chloride (330 μL, 2.0 M in THF) dropwise. After 45 minutes, a solution of the aldehyde obtained from step 5, Example 1 above (110 mg, 0.33 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a foaming yellow solid (120 mg, 51%). MS: (M+H)/z=713.

Step 2: The product obtained from step 1 above (120 mg, 0.17 mmol) was dissolved in 2 mL of dichloromethane. To the resultant solution was added Dess-Martin periodinane (114 mg, 1.6 equiv.) and stirred overnight at room temperature. The reaction was quenched with 10% Na$_2$S$_2$O$_3$, and the mixture was extracted with ethyl acetate. The extracts were washed with saturated NaHCO$_3$, brine, dried over MgSO$_4$ and concentrated in vacuo. The crude material was purified by flash chromatography on silica gel (33% EtOAc/hexanes). The desired product was obtained as a foaming yellow solid (100 mg, 83%). MS: (M+H)/z=711.

Step 3: The product obtained from step 2 above (50 mg, 0.070 mmol) was dissolved in 4 mL of HCl-dioxane (4.0 M)

and 1 mL of water. The mixture was heated at 85° C. for 30 minutes and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (20 mg, 56%). MS: (M+H)/z=511.

Example 458: Preparation of 4-(3-(4-Chloro-3-(trifluoromethyl)phenylsulfonamido) picolinoyl)-5-methoxy-1H-pyrrolo[2,3-b]pyridine 7-oxide

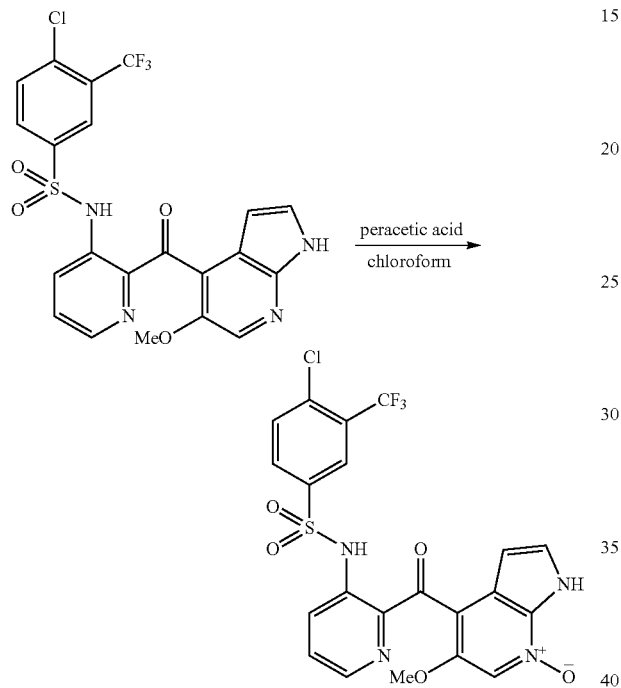

To a stirred solution of the azaindole from Example 7 (32 mg, 0.063 mmol) in chloroform (5 mL) was added peracetic acid (45 μL, 32% wt in acetic acid). The reaction mixture was stirred for 2 days at room temperature and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (20 mg, 61%). MS: (M+H)/z=527.

Example 459: Preparation of 4-Chloro-N-(5-methyl-2-(5-propoxy-1H-pyrrolo[2,3-b]pyridine-4-carbonyl)pyridin-3-yl)-3-(trifluoromethyl)benzenesulfonamide

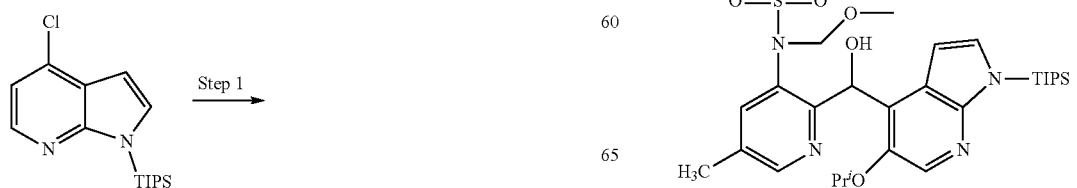

-continued

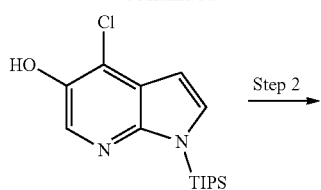

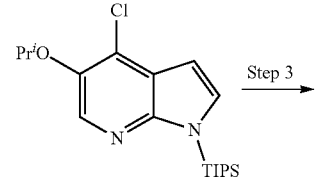

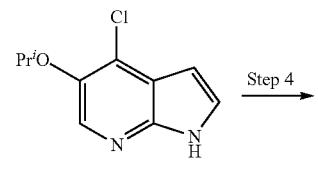

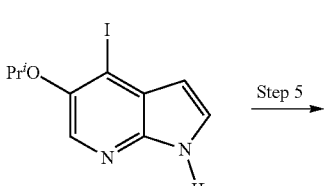

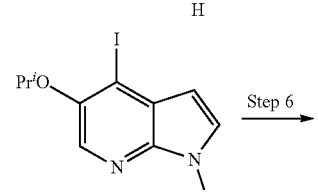

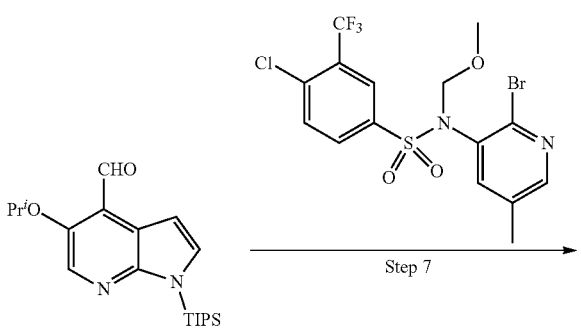

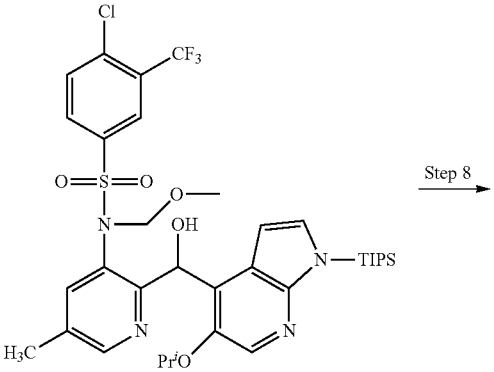

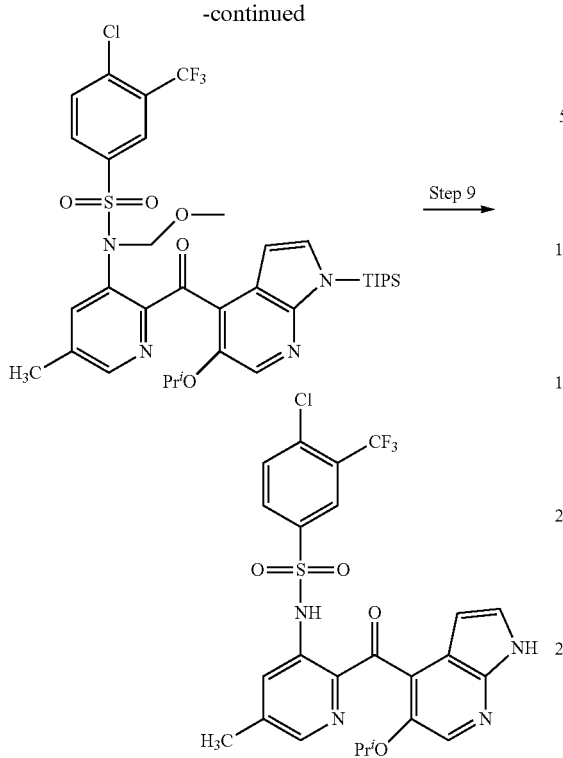

Step 1: A 100 mL round-bottom flask was charged with 4-chloro-1-triisopropylsilanyl-1H-pyrrolo [2, 3-b] pyridine (1.2 g, 3.9 mmol), THF (20 mL) and the mixture was cooled to −78° C. A sec-butyllithium solution (1.4 M in cyclohexane, 4.2 mL, 1.5 equiv.) was added dropwise and after 30 minutes, titanium isopropoxide (2.2 mL, 2.0 equiv.) was added rapidly. The reaction mixture was warmed up to 0° C. for 15 minutes and then cooled to −78° C. and a solution of tert-butylhydrogen peroxide in decane (5.5 M, 0.71 mL, 1.0 equiv.) was added. After 1 hour, the reaction mixture was quenched with saturated ammonium chloride solution. The mixture was allowed to reach room temperature and then extracted with ethyl acetate. The combined organic layers were washed with brine and dried over MgSO$_4$. Solvent was removed and the crude material was purified by flash chromatography on silica gel (10% EtOAc/hexanes). The desired product was obtained as a colorless liquid (760 mg, 60%). MS: (M+H)/z=325.

Step 2: To a solution of triphenylphosphine (288 mg, 1.10 mmol) in 2 mL of THF was added diisopropyl azodicarboxylate (DIAD, 213 μL, 1.1 equiv.) at room temperature. After 10 minutes, isopropanol (84 μL, 1.1 equiv.) was added. After another 5 minutes, the product obtained from step 1 above (324 mg, 1.00 mmol) was added in one portion. The reaction mixture was stirred for half an hour before it was quenched with saturated ammonium chloride solution. The mixture was extracted with ethyl acetate. The extracts were washed with brine, dried over MgSO$_4$ and concentrated in vacuo. The crude material was purified by flash chromatography on silica gel (10% EtOAc/hexanes). The desired product was obtained as a solid (320 mg, 87%). MS: (M+H)/z=367.

Step 3: The product obtained from step 2 above (110 mg, 0.30 mmol) dissolved in 3 mL of THF. To this mixture was added TBAF (1.0 M in THF, 0.60 mL, 2.0 equiv.). The reaction mixture was stirred overnight at room temperature, quenched with saturated ammonium chloride solution, and extracted with ethyl acetate. The extracts were washed with brine, dried over MgSO$_4$ and concentrated in vacuo. The crude material was purified by flash chromatography on silica gel (50% EtOAc/hexanes). The desired product was obtained as a solid (55 mg, 87%). MS: (M+H)/z=211.

Step 4: The product obtained from step 3 above (100 mg, 0.48 mmol) was dissolved in 4 mL of acetonitrile. Then NaI (357 mg, 5 equiv.) was added followed by acetyl chloride (71 μL, 2.1 equiv.). The reaction mixture was allowed to stir at 80° C. for 1 hour, and then excessive acetonitrile was removed in vacuo. A mixture of 10% K$_2$CO$_3$ (10 mL) and 10% sodium bisulfite (10 mL) was added to the residue and the mixture was extracted with ethyl acetate and washed with brine. The combined organic layer was dried over MgSO$_4$ and concentrated in vacuo to give the crude product. To a solution of this crude product in THF (3 mL) was added 1 M NaOH (0.5 mL). The mixture was stirred for 1 hour at room temperature and quenched with saturated ammonium chloride solution. The mixture was extracted with ethyl acetate, and the extracts were washed with brine, dried over MgSO$_4$ and concentrated in vacuo. The crude material was purified by flash chromatography on silica gel (50% EtOAc/hexanes). The desired product was obtained as a white solid (122 mg, 85%). MS: (M+H)/z=303.

Step 5: The product obtained from step 4 above (150 mg, 0.50 mmol) was dissolved in 4 mL of anhydrous DMF. Then NaH (24 mg, 60% dispersion in mineral oil, 1.2 equiv.) was added. After 30 minutes, triisopropylsilyl chloride (116 μL, 1.1 equiv.) was added and the reaction mixture was stirred overnight at room temperature. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (10% EtOAc/hexanes). The desired product was obtained as colorless oil (205 mg, 90%). MS: (M+H)/z=459.

Step 6: The product obtained from step 5 above (210 mg, 0.46 mmol) was dissolved in 3 mL of anhydrous THF and cooled to 0° C. Then isopropylmagnesium chloride (460 μL, 2.0 M in THF) was added. After 45 minutes, anhydrous DMF (1 mL) was added and the reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (5% EtOAc/hexanes). The desired product was obtained as a pale yellow solid (88 mg, 53%). MS: (M+H)/z=361.

Step 7: To a solution of the bromopyridine (116 mg, 0.24 mmol) in THF (1 mL) at 0° C. was added isopropylmagnesium chloride (250 μL, 2.0 M in THF) dropwise. After 45 minutes, a solution of the product obtained from step 6 above (88 mg, 0.24 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (20% EtOAc/hexanes). The desired product was obtained as a foaming yellow solid (112 mg, 61%). MS: (M+H)/z=755.

Step 8: The product obtained from step 7 above (95 mg, 0.13 mmol) was dissolved in 3 mL of dichloromethane. To the resultant solution was added Dess-Martin periodinane (85 mg, 1.6 equiv.) and stirred overnight at room temperature. The reaction was quenched with 10% $Na_2S_2O_3$, and the mixture was extracted with ethyl acetate. The extracts were washed with saturated $NaHCO_3$, brine, dried over $MgSO_4$ and concentrated in vacuo. The crude material was purified by flash chromatography on silica gel (20% EtOAc/hexanes). The desired product was obtained as a foaming yellow solid (71 mg, 75%). MS: (M+H)/z=753.

Step 9: The product obtained from step 8 above (100 mg, 0.13 mmol) was dissolved in 4 mL of HCl-dioxane (4.0 M) and 1 mL of water. The mixture was heated at 85° C. for 30 minutes and quenched with saturated $NaHCO_3$. The mixture was extracted with ethyl acetate. The extracts were washed with brine, dried over $MgSO_4$ and concentrated in vacuo. The crude material was purified by flash chromatography on silica gel (80% EtOAc/hexanes). The desired product was obtained as a yellow solid (40 mg, 55%). MS: (M+H)/z=553.

Example 460: Preparation of 4-(3-(4-Chloro-3-(trifluoromethyl)phenylsulfonamido)-5-methylpicolinoyl)-5-propoxy-1H-pyrrolo[2,3-b]pyridine 7-oxide To a stirred solution of the azaindole from Example 9 (15 mg, 0.027 mmol) in chloroform (5 mL) was added peracetic acid (20 µL, 32% wt in acetic acid). The reaction mixture was stirred for 2 days at room temperature and quenched with saturated $NaHCO_3$. The mixture was extracted with ethyl acetate. The extracts were washed with brine, dried over $MgSO_4$ and concentrated in vacuo. The crude material was purified by flash chromatography on silica gel (80% EtOAc/hexanes). The desired product was obtained as a yellow solid (11 mg, 70%). MS: (M+H)/z=569.

Example 461: Preparation of 4-Chloro-N-(2-(5-chloro-1H-pyrrolo[2,3-b]pyridine-4-carbonyl)pyridin-3-yl)-3-(trifluoromethyl)benzenesulfonamide

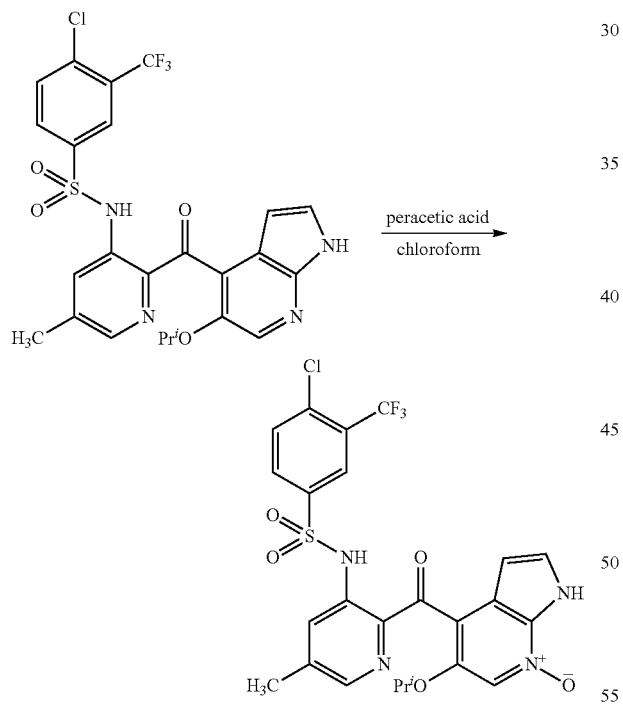

-continued

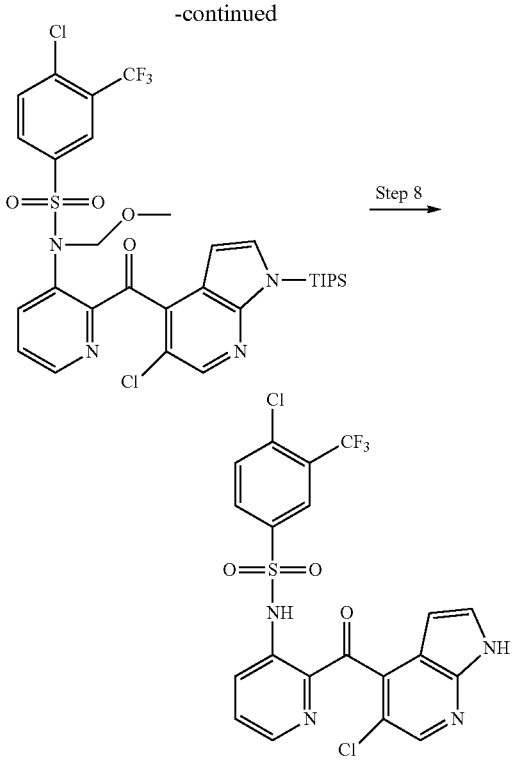

Step 8

Step 1: A 100 mL round-bottom flask was charged with 4-chloro-1-triisopropylsilanyl-1H-pyrrolo [2, 3-b] pyridine (308 mg, 1.0 mmol), THF (5 mL) and the mixture was cooled to −78° C. A sec-butyllithium solution (1.4 M in cyclohexane, 1.6 mL, 2.2 equiv.) was added dropwise and after 30 minutes, a solution of hexachloroethane (592 mg, 2.5 equiv.) in 4 mL of THF was added rapidly. The reaction mixture was then stirred for another 25 minutes at −78° C. and quenched with saturated ammonium chloride solution. The mixture was allowed to reach room temperature and then extracted with ethyl acetate. The combined organic layers were washed with brine and dried over $MgSO_4$. Solvent was removed and the crude material was purified by flash chromatography on silica gel (10% EtOAc/hexanes). The desired product was obtained as a yellow solid (171 mg, 50%). MS: (M+H)/z=343.

Step 2: The product obtained from step 1 above (342 mg, 1.0 mmol) dissolved in 3 mL of THF. To this mixture was added TBAF (1.0 M in THF, 2.0 mL, 2.0 equiv.). The reaction mixture was stirred overnight at room temperature, quenched with saturated ammonium chloride solution, and extracted with ethyl acetate. The extracts were washed with brine, dried over $MgSO_4$ and concentrated in vacuo. The crude material was purified by flash chromatography on silica gel (50% EtOAc/hexanes). The desired product was obtained as a solid (167 mg, 90%). MS: (M+H)/z=187.

Step 3: The product obtained from step 2 above (105 mg, 0.56 mmol) was dissolved in 4 mL of acetonitrile. Then NaI (423 mg, 5 equiv.) was added followed by acetyl chloride (84 μL, 2.1 equiv.). The reaction mixture was allowed to stir at 80° C. for 1 hour, and then excessive acetonitrile was removed in vacuo. A mixture of 10% $K_2CO_3$ (10 mL) and 10% sodium bisulfite (10 mL) was added to the residue and the mixture was extracted with ethyl acetate and washed with brine. The combined organic layer was dried over $MgSO_4$ and concentrated in vacuo to give the crude product. To a solution of this crude product in THF (3 mL) was added 1 M NaOH (0.5 mL). The mixture was stirred for 1 hour at room temperature and quenched with saturated ammonium chloride solution. The mixture was extracted with ethyl acetate, and the extracts were washed with brine, dried over $MgSO_4$ and concentrated in vacuo. The crude material was purified by flash chromatography on silica gel (50% EtOAc/hexanes). The desired product was obtained as a white solid (118 mg, 75%). MS: (M+H)/z=279.

Step 4: The product obtained from step 3 above (92 mg, 0.33 mmol) was dissolved in 4 mL of anhydrous DMF. Then NaH (16 mg, 60% dispersion in mineral oil, 1.2 equiv.) was added. After 30 minutes, triisopropylsilyl chloride (77 μL, 1.1 equiv.) was added and the reaction mixture was stirred overnight at room temperature. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (10% EtOAc/hexanes). The desired product was obtained as colorless oil (129 mg, 90%). MS: (M+H)/z=435.

Step 5: The product obtained from step 4 above (150 mg, 0.35 mmol) was dissolved in 2 mL of anhydrous THF and cooled to 0° C. Then isopropylmagnesium chloride (340 μL, 2.0 M in THF) was added. After 45 minutes, anhydrous DMF (1 mL) was added and the reaction mixture was warmed up to room temperature and stirred overnight. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (5% EtOAc/hexanes). The desired product was obtained as a pale yellow solid (70 mg, 60%). MS: (M+H)/z=337.

Step 6: To a solution of xxx (151 mg, 0.33 mmol) in THF (1 mL) at 0° C. was added isopropylmagnesium chloride (330 μL, 2.0 M in THF) dropwise. After 45 minutes, a solution of the product obtained from step 5 above (110 mg, 0.33 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over $MgSO_4$ and concentrated in vacuo. The crude material was purified by flash chromatography on silica gel (20% EtOAc/hexanes). The desired product was obtained as a foaming yellow solid (129 mg, 55%). MS: (M+H)/z=717.

Step 7: The product obtained from step 6 above (142 mg, 0.20 mmol) was dissolved in 3 mL of dichloromethane. To the resultant solution was added Dess-Martin periodinane (135 mg, 1.6 equiv.) and stirred overnight at room temperature. The reaction was quenched with 10% $Na_2S_2O_3$, and the mixture was extracted with ethyl acetate. The extracts were washed with saturated $NaHCO_3$, brine, dried over $MgSO_4$ and concentrated in vacuo. The crude material was purified by flash chromatography on silica gel (20% EtOAc/hexanes). The desired product was obtained as a foaming yellow solid (99 mg, 70%). MS: (M+H)/z=715.

Step 8: The product obtained from step 7 above (50 mg, 0.070 mmol) was dissolved in 4 mL of HCl-dioxane (4.0 M) and 1 mL of water. The mixture was heated at 85° C. for 30 minutes and quenched with saturated $NaHCO_3$. The mixture was extracted with ethyl acetate. The extracts were washed with brine, dried over $MgSO_4$ and concentrated in vacuo. The crude material was purified by flash chromatography on silica gel (80% EtOAc/hexanes). The desired product was obtained as a yellow solid (20 mg, 56%). MS: (M+H)/z=515.

Example 462: Preparation of 5-Chloro-4-(3-(4-chloro-3-(trifluoromethyl) phenylsulfonamido)picolinoyl)-1H-pyrrolo[2,3-b]pyridine 7-oxide

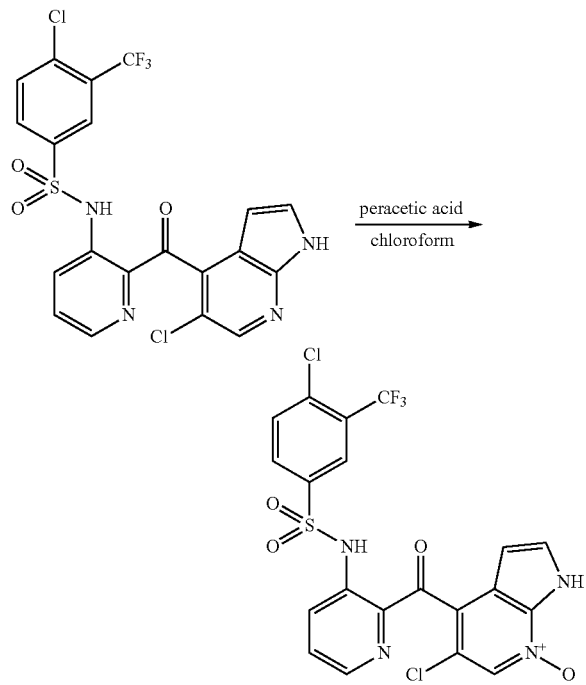

To a stirred solution of the azaindole from Example 11 (21 mg, 0.041 mmol) in chloroform (5 mL) was added peracetic acid (29 μL, 32% wt in acetic acid). The reaction mixture was stirred for 2 days at room temperature and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (15 mg, 70%). MS: (M+H)/z=531.

Example 463: Preparation of 4-Chloro-N-(2-(5-methoxy-1H-pyrrolo[2,3-b]pyridine-4-carbonyl)-5-(methoxymethyl)pyridin-3-yl)-3-(trifluoromethyl)benzenesulfonamide

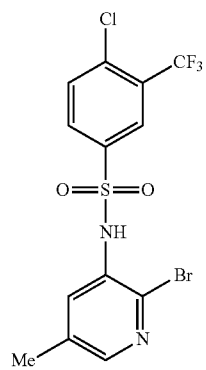

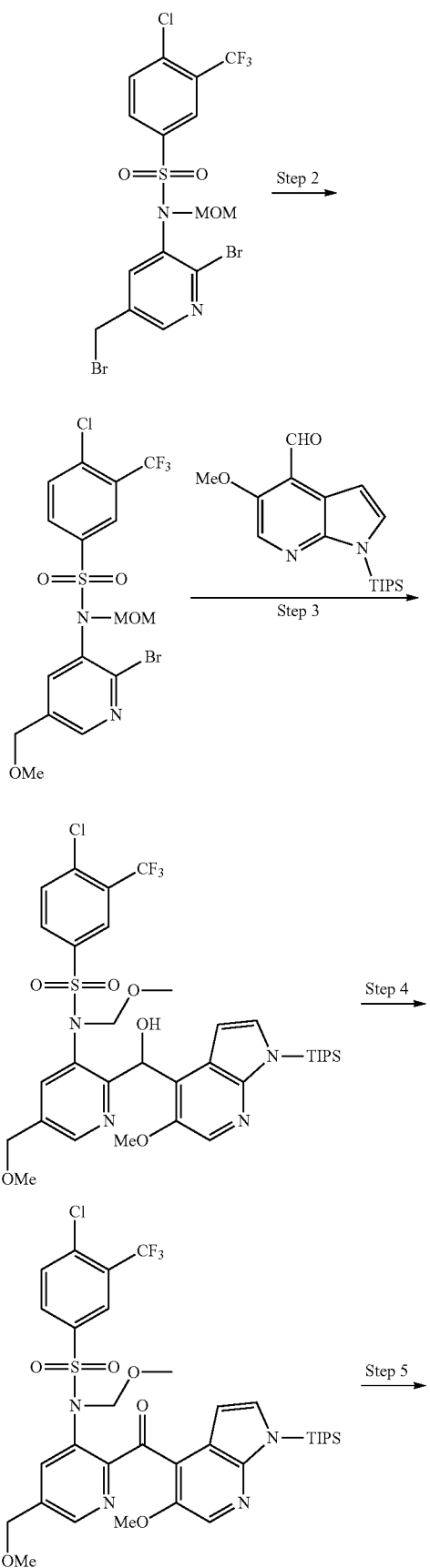

-continued

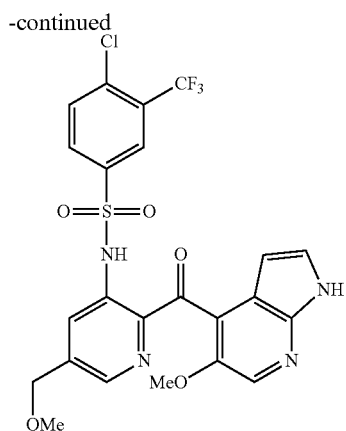

Step 1: To a solution of the bromopyridine (132 mg, 0.28 mmol) in carbon tetrachloride (4 mL) was added N-bromosuccinimide (60 mg, 1.2 equiv.), followed by 2, 2'-azobisisobutyronitrile (AIBN, 4.6 mg, 0.1 equiv.). The reaction mixture was heated at 60° C. overnight. After cooling down to room temperature, excessive carbon tetrachloride was removed and the residue was purified by flash chromatography on silica gel (33% EtOAc/hexanes). The desired product was obtained as a white solid (107 mg, 70%). MS: (M+H)/z=551.

Step 2: The product obtained from step 1 above (51 mg, 0.093 mmol) was dissolved in 3 mL of methanol. To the resultant solution was added sodium methoxide (10 mg, 2.0 equiv.). The reaction mixture was heated at 50° C. overnight. After cooling down to room temperature, the reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a white solid (42 mg, 90%). MS: (M+H)/z=503.

Step 3: To a solution of the bromopyridine obtained from step 2 (60 mg, 0.12 mmol) in THF (1 mL) at 0° C. was added isopropylmagnesium chloride (120 µL, 2.0 M in THF) dropwise. After 45 minutes, a solution of the aldehyde obtained from Example 1 (step 5) above (40 mg, 0.12 mmol) in THF was added. The reaction mixture was warmed up to room temperature and stirred overnight. The reaction was quenched with saturated ammonium chloride solution, and the mixture was extracted with ethyl acetate. The extracts were washed with brine, dried over MgSO$_4$ and concentrated in vacuo. The crude material was purified by flash chromatography on silica gel (33% EtOAc/hexanes). The desired product was obtained as a foaming yellow solid (45 mg, 50%). MS: (M+H)/z=757.

Step 4: The product obtained from step 3 above (25 mg, 0.032 mmol) was dissolved in 3 mL of dichloromethane. To the resultant solution was added Dess-Martin periodinane (22 mg, 1.6 equiv.) and stirred overnight at room temperature. The reaction was quenched with 10% Na$_2$S$_2$O$_3$, and the mixture was extracted with ethyl acetate. The extracts were washed with saturated NaHCO$_3$, brine, dried over MgSO$_4$ and concentrated in vacuo. The crude material was purified by flash chromatography on silica gel (33% EtOAc/hexanes). The desired product was obtained as a foaming yellow solid (18 mg, 70%). MS: (M+H)/z=755.

Step 5: The product obtained from step 4 above (10 mg, 0.013 mmol) was dissolved in 4 mL of HCl-dioxane (4.0 M) and 1 mL of water. The mixture was heated at 85° C. for 30 minutes and quenched with saturated NaHCO$_3$. The mixture was extracted with ethyl acetate. The extracts were washed with brine, dried over MgSO$_4$ and concentrated in vacuo. The crude material was purified by flash chromatography on silica gel (80% EtOAc/hexanes). The desired product was obtained as a yellow solid (4.4 mg, 70%). MS: (M+H)/z=555.

Measuring Efficacy of Chemokine Modulators

In Vitro Assays

A variety of assays can be used to evaluate the compounds provided herein, including signaling assays, migration assays, ligand binding assays, and other assays of cellular response. Chemokine receptor signaling assays can be used to measure the ability of a compound, such as a potential CCR2 antagonist, to block CCR2 ligand- (e.g. MCP-1)-induced signaling or a potential CCR9 antagonist, to block CCR9 ligand- (e.g. TECK)-induced signaling. A migration assay can be used to measure the ability of a compound of interest, such as a possible chemokine antagonist, to block chemokine-mediated cell migration in vitro. The latter is believed to resemble chemokine-induced cell migration in vivo. A ligand binding assay can be used to measure the ability of a compound, such as a potential CCR2 antagonist, to block the interaction of MCP-1 with its receptor or a potential CCR9 antagonist, to block the interaction of TECK with its receptor.

In a suitable assay, a chemokine protein (whether isolated or recombinant) is used which has at least one property, activity, or functional characteristic of a mammalian chemokine protein. The property can be a binding property (to, for example, a ligand or inhibitor), a signaling activity (e.g., activation of a mammalian G protein, induction of rapid and transient increase in the concentration of cytosolic free calcium ion), cellular response function (e.g., stimulation of chemotaxis or inflammatory mediator release by leukocytes), and the like.

The assay can be a cell-based assay that utilizes cells stably or transiently transfected with a vector or expression cassette having a nucleic acid sequence that encodes the chemokine receptor. Cell lines naturally expressing the chemokine can also be used. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., MCP-1 or TECK) as a competitor.

Binding inhibition assays can be used to evaluate the present compounds. In these assays, the compounds are evaluated as inhibitors of ligand binding using, for example, MCP-1 or TECK. In one embodiment, the CCR2 receptor is contacted with a ligand such as MCP-1 and a measure of ligand binding is made. The receptor is then contacted with a test agent in the presence of a ligand (e.g., MCP-1) and a second measurement of binding is made. In another embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express the chemokine, or a membrane fraction from cells which express the chemokine.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., Cell, 72:415425 (1993); Van Riper et al., J. Exp. Med., 177:851-856 (1993) and Dahinden et al., J. Exp. Med., 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer et al., WO 94/20142; Berman et al., Immunol. Invest., 17:625-677 (1988); and Kavanaugh et al., J. Immunol., 146:4149-4156 (1991)).

Calcium signaling assays measure calcium concentration over time, preferably before and after receptor binding. These assays can be used to quantify the generation of a receptor-signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between a chemokine receptor and a known chemokine ligand, chemokine receptor-expressing cells (CCR2-expressing cells such as THP-1 cells or CCR9-expressing cells such as T cell line MOLT-4 cells) are first incubated with a compound of interest, such as a potential chemokine antagonist, at increasing concentrations. The cell number can be from $10^5$ to $5 \times 10^5$ cells per well in a 96-well microtiter plate. The concentration of the compound being tested may range from 0 to 100 μM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the chemokine ligand (MCP-1 for CCR2 or TECK for CCR9) at 5-100 nM final concentration, and the signal of intracellular calcium increase (also called calcium flux) is recorded. The efficacy of a compound as an inhibitor of binding between the chemokine and the ligand can be calculated as an $IC_{50}$ (the concentration needed to cause 50% inhibition in signaling) or $IC_{90}$ (at 90% inhibition).

In vitro cell migration assays can be performed (but are not limited to this format) using the 96-well microchamber (called ChemoTX™). The ChemoTX™ system is well known to those skilled in the art as a type of chemotactic/cell migration instrument. In this assay, CCR2-expressing cells (such as THP-1) or CCR9-expressing cells (such as MOLT-4) are first incubated with a compound of interest, such as a possible CCR2 or CCR9 antagonist, respectively, at increasing concentrations. Typically, fifty thousand cells per well are used, but the amount can range from $10^3$-$10^6$ cells per well. The chemokine ligand (for example, CCR2 ligand MCP-1, typically at 0.1 nM (but can range from 5-100 nM); or CCR9 ligand TECK, typically at 50 nM (but can range from 5-100 nM)), is placed at the lower chamber and the migration apparatus is assembled. Twenty microliters of test compound-treated cells are then placed onto the membrane. Migration is allowed to take place at 37° C. for a period of time, typically 1.5 hours for CCR2 or 2.5 hours for CCR9. At the end of the incubation, the number of cells that migrated across the membrane into the lower chamber is then quantified. The efficacy of a compound as an inhibitor of chemokine-mediated cell migration is calculated as an $IC_{50}$ (the concentration needed to reduce cell migration by 50%) or $IC_{90}$ (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala et al., J Immunol., 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., J. Exp. Med., 184(1):241-51(1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., Int Immunol., 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Murine Models with Pathology Similar to Human Crohn's Disease

The TNF ARE(−/−) model. The role of TNF in Crohn's disease in human has been demonstrated more recently by success of treatment using anti-TNF alpha antibody by Targan et al., N. Engl. J. Med., 337(15):1029-35 (1997). Mice with aberrant production of TNF-alpha due to genetic alteration in the TNF gene (ARE−/−) develop Crohn's-like inflammatory bowel diseases (see Kontoyiannis et al., Immunity, 10(3):387-98 (1999)).

The SAMP/yit model. This is model described by Kosiewicz et al., J. Clin. Invest., 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Examples of In Vitro Assays

Reagents

THP-1 cells and MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine proteins MCP-1 and TECK were obtained from R&D Systems (Minneapolis, Minn.). $^{125}$I-labeled MCP-1 protein was obtained from Amersham (Piscataway, N.J.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Conventional Migration Assay

Conventional migration assay was used to determine the efficacy of potential receptor antagonists in blocking migration mediated through chemokines (such as CCR2 or CCR9). This assay was routinely performed using the ChemoTX® microchamber system with a 5-µm pore-sized polycarbonate membrane. To begin such an assay, chemokine expressing cells (such as THP-1 cells for CCR2 assay or MOLT-4 cells for CCR9 assay) were harvested by centrifugation of cell suspension at 1000 RPM on a GS-6R Beckman centrifuge. The cell pellet was resuspended in chemotaxis buffer (HBSS with 0.1% BSA) at $10 \times 10^6$ cells/mL for CCR2 assay ($5 \times 10^6$ cells/mL for CCR9 assay). Test compounds at desired concentrations were prepared from 10 mM stock solutions by serial dilutions in chemotaxis buffer. An equal volume of cells and compounds were mixed and incubated at room temperature for 15 minutes. Afterwards, 20 µL of the mixture was transferred onto the porous membrane of a migration microchamber, with 29 µL of chemokine ligand (0.1 nM chemokine MCP-1 protein for CCR2 assay or 50 nm chemokine TECK protein for CCR9 assay) placed at the lower chamber. Following an incubation at 37° C. (90-minute for CCR2; 150-minute for CCR9), during which cells migrated against the chemokine gradient, the assay was terminated by removing the cell drops from atop the filter. To quantify cells migrated across the membrane, 5 µL of 7× CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. $IC_{50}$ calculation was further performed by non-linear squares regression analysis using Graphpad Prism (Graphpad Software, San Diego, Calif.).

BiRAM Assay

The primary screen to identify chemokine antagonists was carried out using BiRAM assay (WO 02101350, US2004023286), which detects potential hits by their ability to activate cell migration under inhibitory chemokine concentration. To begin such an assay, chemokine expressing cells (such as THP-1 cells for CCR2 assay or MOLT-4 cells for CCR9 assay) were harvested by centrifugation of cell suspension at 1000 RPM on a GS-6R Beckman centrifuge. The cell pellet was resuspended in chemotaxis buffer (HBSS/0.1% BSA) at $10 \times 10^6$ cells/mL for CCR2 assay ($5 \times 10^6$ cells/mL for CCR9 assay). Twenty-five microliters of cells was mixed with an equal volume of a test compound diluted to 20 µM in the same buffer. Twenty microliters of the mixture was transferred onto the filter in the upper chemotaxis chamber, with 29 µL of chemokine solution containing chemokine ligand (100 nM chemokine MCP-1 and MIP-1α protein for CCR2 assay or 500 nm chemokine TECK protein for CCR9 assay) was placed in the lower chamber. Following an incubation at 37° C. (90-minute for CCR2; 150-minute for CCR9), the assay was terminated by removing the cell drops from atop the filter. To quantify cells migrated across the membrane, 5 µL of 7× CyQUANT® solution was added to each well in the lower chamber, and the fluorescence signal measured on a Spectrafluor Plus fluorescence plate reader (TECAN, Durham, N.C.).

For selection of potential hits, the level of migration activation was calculated as a RAM index—the ratio between the signal of a particular well and the median signal of the whole plate. Compounds with a RAM index of greater than 1.5 for CCR2 assay (1.8 for CCR9 assay) were regarded as RAM positive, and were selected for $IC_{50}$ determinations in conventional functional assays.

Calcium Flux Assay

Calcium flux assay measures an increase in intracellular calcium following ligand-induced receptor activation. In the screen of chemokine antagonists, it was used as a secondary assay carried out on a FLIPR® machine (Molecular Devices, Mountain View, Calif.). To begin an assay, chemokine expressing cells (such as THP-1 cells for CCR2 assay or MOLT-4 cells for CCR9 assay) were harvested by centrifugation of cell suspension, and resuspended to $1.5 \times 10^6$ cells/mL in HBSS (with 1% fetal calf serum). Cells were then labeled with a calcium indicator dye Fluo-4 AM for 45 minutes at 37° C. with gentle shaking. Following incubation, cells were pelletted, washed once with HBSS and resuspended in the same buffer at a density of $1.6 \times 10^6$ cells/mL. One hundred microliters of labeled cells were mixed with 10 µL of test compound at the appropriate concentrations on an assay plate. Chemokine protein (MCP-1 at a final concentration of 0.1 nM for CCR2 assay or TECK at a final concentration of 25 nM for CCR9 assay) to activate the receptor. The degree of inhibition was determined by comparing calcium signals between compound-treated and untreated cells. $IC_{50}$ calculations were further performed by non-linear squares regression analysis using Graphpad Prism (Graphpad Software, San Diego, Calif.).

Ligand Binding Assay

Ligand binding assay was used to determine the ability of potential CCR2 antagonists to block the interaction between CCR2 and its ligand MCP-1. CCR2 expressing THP-1 cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $2.2 \times 10^5$ cells/mL. Binding assays were set up as follows. First, 0.09 mL of cells ($1 \times 10^5$ THP-1 cells/well) was added to the assay plates containing the compounds, giving a final concentration of ~2-10 µM each compound for screening (or part of a dose response for compound $IC_{50}$ determinations). Then 0.09 mL of $^{125}I$ labeled MCP-1 (obtained from Amersham; Piscataway, N.J.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 µL; Microscint 20, Packard Instruments) was added to each well, the plates were sealed and radioactivity measured in a Top Count scintillation counter (Packard Instruments). Control wells containing either diluent only (for total counts) or excess MCP-1 (1 g/mL, for non-specific binding) were used to calculate the percent of total inhibition for compound. The computer program Prism from GraphPad, Inc. (San Diego, Ca) was used to calculate $IC_{50}$ values. $IC_{50}$ values are those concentrations required to reduce the binding of labeled MCP-1 to the receptor by 50%.

Discovery of Chemokine Antagonists

The discovery of chemokine antagonists was carried out in two steps: First, BiRAM assay was used to screen a compound library in a high-throughput manner. The assay detected compounds by their ability to cause a positive migration signal under BiRAM condition. Secondly, BiRAM positive compounds were tested to determine their $IC_{50}$ values using the conventional migration, calcium flux assays and ligand binding assays.

For instance, in a screen of approximately 100,000 compounds, 2000 individual wells representing approximately 2% of total compounds showed a desired RAM index (greater than 1.5 for CCR2; greater than 1.8 for CCR9). These compounds were cheery-picked and retested in duplicate wells by RAM assay. A total of 156 compounds were confirmed BiRAM positives.

Since a BiRAM positive signal indicates only the presence of a receptor antagonist and not how strongly it blocks receptor functions, the BiRAM positive compounds were further tested for potency in conventional migration, calcium flux and ligand binding assays. $IC_{50}$ determinations on this subset discovered several compounds with an $IC_{50}$ less than 1 µM and that did not inhibit other chemokine receptors examined at significant levels.

In Vivo Efficacy

A 17-day study of type II collagen-induced arthritis is conducted to evaluate the effects of a modulator on arthritis-induced clinical ankle swelling. Rat collagen-induced arthritis is an experimental model of polyarthritis that has been widely used for preclinical testing of numerous anti-arthritic agents (see Trentham et al., J. Exp. Med., 146(3):857-868 (1977), Bendele et al., Toxicologic Pathol., 27:134-142 (1999), Bendele et al., Arthritis Rheum., 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. The test modulator is dosed daily by sub-cutaneous injection from day 9 to day 17 at a dose of 100 mg/kg and a volume of 1 mL/kg in the following vehicle (24.5% Cremaphore EL, 24.5% common oil, 1% Benzylalcohol and 50% Distilled water). Caliper measurements of the ankle joint diameter are taken daily, and reducing joint swelling is taken as a measure of efficacy.

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, a CCR9 antagonist is evaluated by prophylactic administration for its ability to delay disease onset. Female mice (n=34) are dosed with 50 mg/kg twice a day by subcutaneous injections for 14 consecutive weeks starting at age 10 weeks. The study is evaluated for IBD-associated growth retardation.

Evaluation of a Test Modulator in a Rat Model of Thioglycollate-Induced Peritoneal Inflammation A 2-day study of thioglycollate-induced inflammation is conducted to evaluate the effects of the test modulator. The hallmarks of this model are reliable onset and progression of robust, easily measurable inflammatory cellular infiltrate. For the induction of inflammatory peritonitis in Lewis rats, Brewer-Thioglycollate (1.0 mL, 4% solution in distilled water) is injected intra peritoneal (i.p.). Before this injection, the treatment group received test modulator or vehicle and the control group received the same volume of PBS as i.p. injection. After 2 days, a peritoneal lavage is performed with ice-cold PBS containing 1 mM EDTA. The recovered cells are counted with a cell counter (Coulter Counter; Coulter Pharmaceutical, Palo Alto, Calif.) and monocytes/macrophages were identified by flow cytometry using light-scatter properties.

Evaluation of a Test Modulator in a Mouse Model of Bacterial Infection

A 1-day study of *Streptococcus pneumoniae* infection is conducted to evaluate the effects of the test modulator. The model measures bacterial infection and spread in an animal following pulmonary infection with live bacterial cultures, measured by inflammatory cellular infiltrate, and assessment of bacterial burden. C57/B6 mice are inoculated intra nasally with LD50 400 CFU at day 0. Groups are either test modulator or vehicle control treated 1 day prior to bacterial inoculation and twice daily throughout the study. Bacterial burden is measured at 24 hours by plating serial dilutions of homogenized lung tissue on agar plates and counting colonies.

Pharmacologics to be Used in Conjunction with CCR2 Compounds

Pharmacological agents that can be used in conjunction with the CCR2 antagonists of the current invention include those used for the treatments of atherosclerosis, restenosis, multiple sclerosis, pulmonary fibrosis, inflammatory bowel disease, rheumatoid arthritis, graft-versus-host disease, renal fibrosis, psoriasis, transplantation rejection, obesity, diabetes, hypercholesterolemia and cancer.

In the tables below, structures and activity are provided for representative compounds described herein. Activity is provided as follows for either or both of the chemotaxis assay and/or calcium mobilization assays, described above: +, $IC_{50}$>1000 nM; and ++, $IC_{50}$<1000 nM.

TABLE 1

Compounds with CCR2 activity in one of the chemotaxis, binding or calcium mobilization assays, with IC50 < 1000 nM

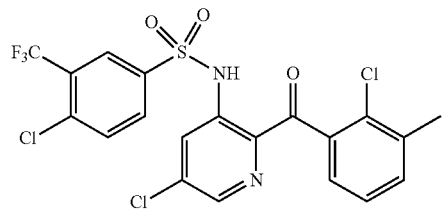 [SMILES: Cc1cccc(C(=O)c2ncc(Cl)cc2NS(=O)(=O)c2ccc(Cl)c(C(F)(F)F)c2)c1Cl]
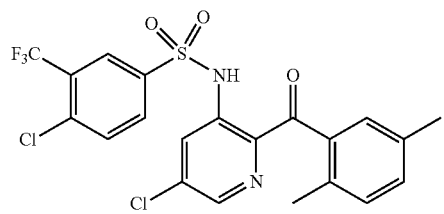 [SMILES: Cc1ccc(C)c(C(=O)c2ncc(Cl)cc2NS(=O)(=O)c2ccc(Cl)c(C(F)(F)F)c2)c1]
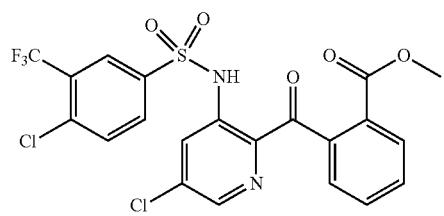 [SMILES: COC(=O)c1ccccc1C(=O)c1ncc(Cl)cc1NS(=O)(=O)c1ccc(Cl)c(C(F)(F)F)c1]
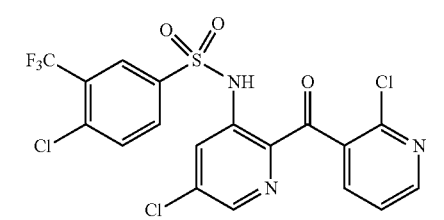 [SMILES: O=C(c1cccnc1Cl)c1ncc(Cl)cc1NS(=O)(=O)c1ccc(Cl)c(C(F)(F)F)c1]
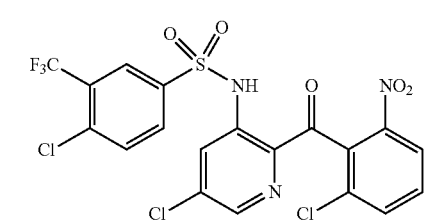 [SMILES: O=C(c1ncc(Cl)cc1NS(=O)(=O)c1ccc(Cl)c(C(F)(F)F)c1)c1c(Cl)cccc1[N+](=O)[O-]]
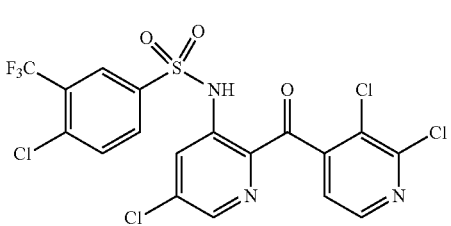 [SMILES: O=C(c1ccnc(Cl)c1Cl)c1ncc(Cl)cc1NS(=O)(=O)c1ccc(Cl)c(C(F)(F)F)c1]

TABLE 1-continued

Compounds with CCR2 activity in one of the chemotaxis, binding or calcium mobilization assays, with IC50 < 1000 nM

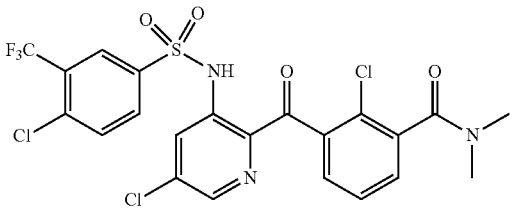 [SMILES: CN(C)C(=O)c1cccc(C(=O)c2ncc(Cl)cc2NS(=O)(=O)c2ccc(Cl)c(C(F)(F)F)c2)c1Cl]
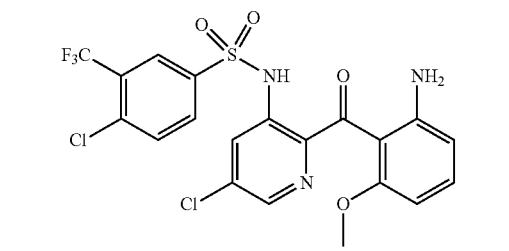 [SMILES: COc1cccc(N)c1C(=O)c1ncc(Cl)cc1NS(=O)(=O)c1ccc(Cl)c(C(F)(F)F)c1]
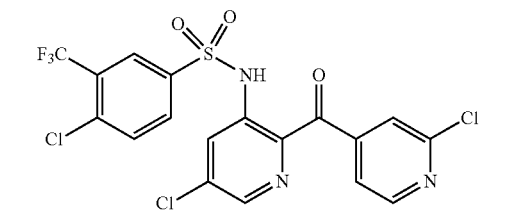 [SMILES: O=C(c1ccnc(Cl)c1)c1ncc(Cl)cc1NS(=O)(=O)c1ccc(Cl)c(C(F)(F)F)c1]
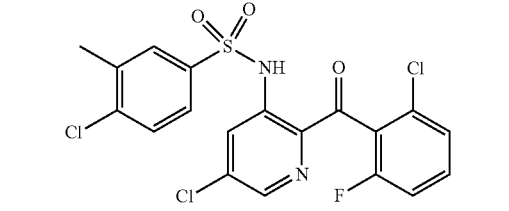 [SMILES: Cc1cc(S(=O)(=O)Nc2cc(Cl)cnc2C(=O)c2c(F)cccc2Cl)ccc1Cl]
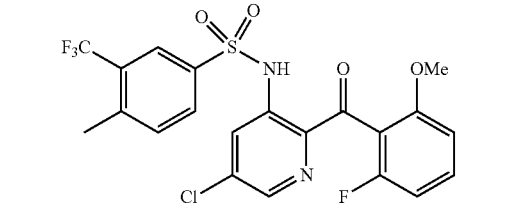 [SMILES: COc1cccc(F)c1C(=O)c1ncc(Cl)cc1NS(=O)(=O)c1ccc(C)c(C(F)(F)F)c1]
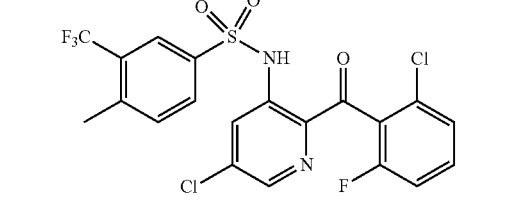
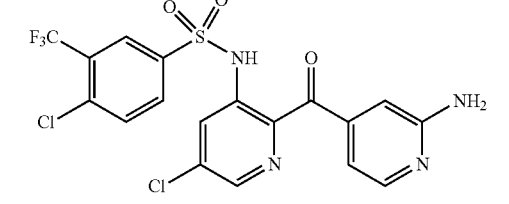

TABLE 1-continued
Compounds with CCR2 activity in one of the chemotaxis, binding or calcium mobilization assays, with IC50 < 1000 nM
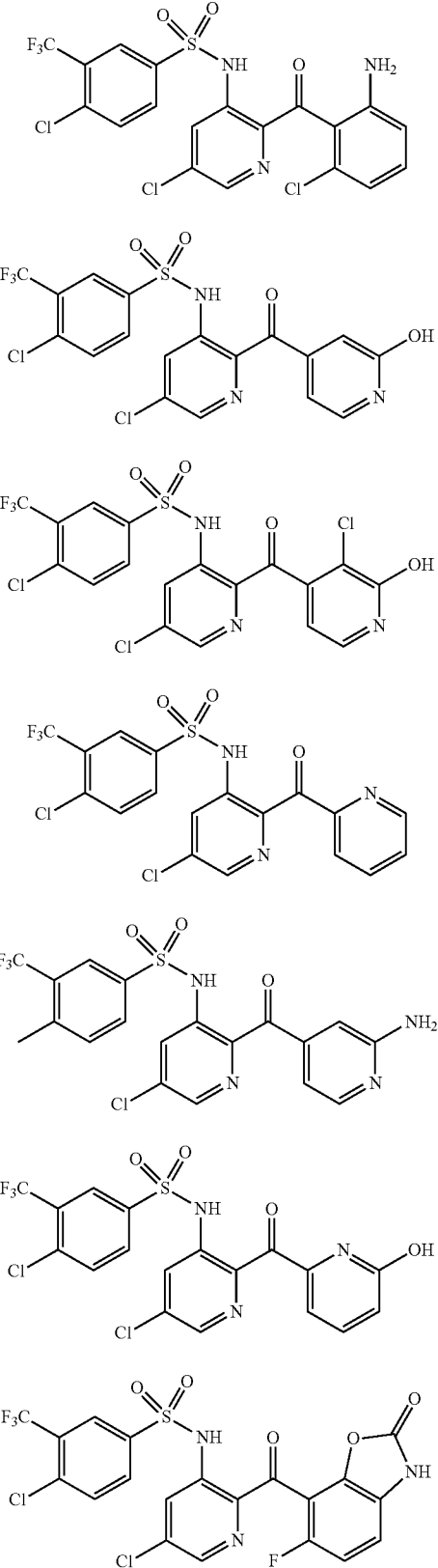
TABLE 1-continued
Compounds with CCR2 activity in one of the chemotaxis, binding or calcium mobilization assays, with IC50 < 1000 nM
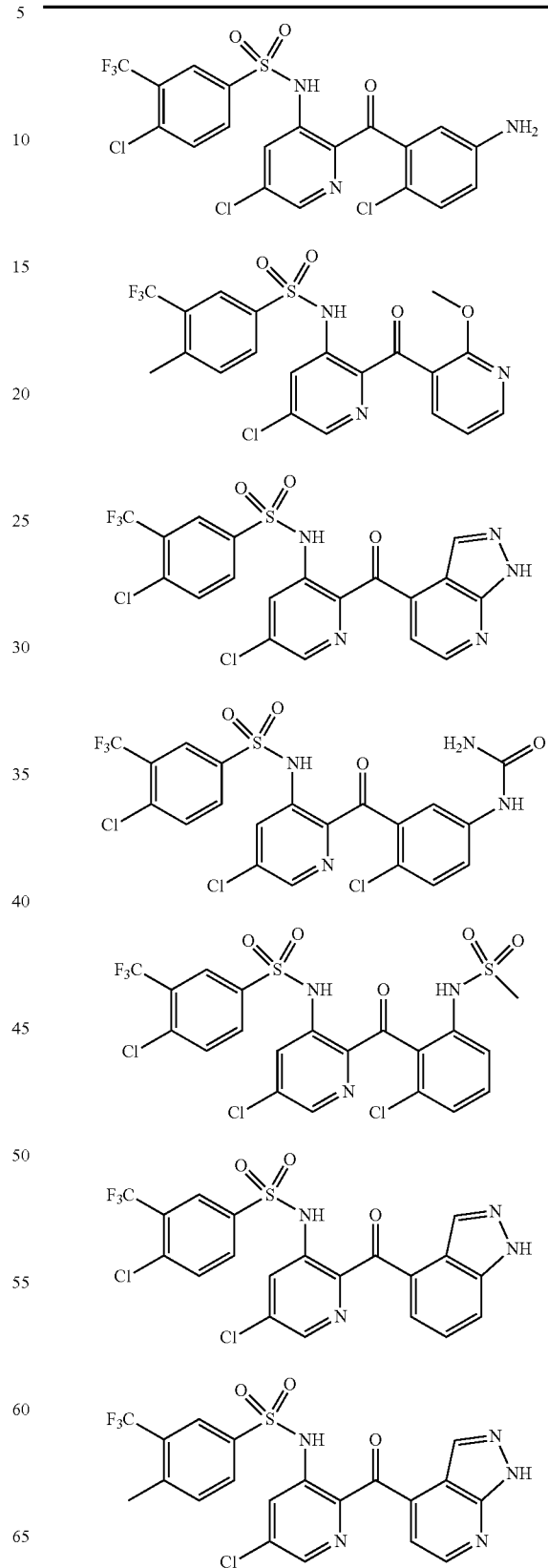

TABLE 1-continued
Compounds with CCR2 activity in one of the chemotaxis, binding or calcium mobilization assays, with IC50 < 1000 nM
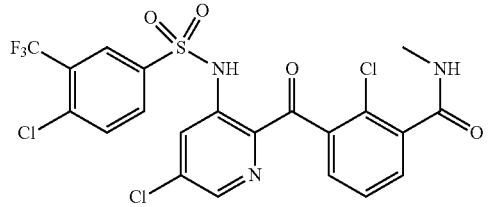 [SMILES: CNC(=O)c1cccc(C(=O)c2ncc(Cl)cc2NS(=O)(=O)c2ccc(Cl)c(C(F)(F)F)c2)c1Cl]
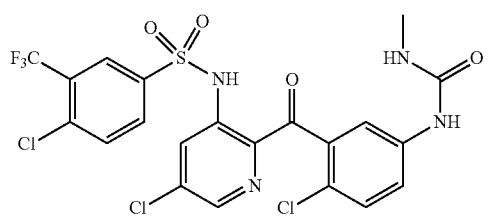 [SMILES: CNC(=O)Nc1ccc(Cl)c(C(=O)c2ncc(Cl)cc2NS(=O)(=O)c2ccc(Cl)c(C(F)(F)F)c2)c1]
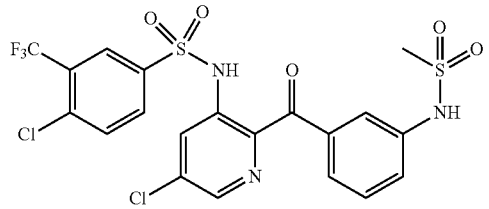 [SMILES: CS(=O)(=O)Nc1cccc(C(=O)c2ncc(Cl)cc2NS(=O)(=O)c2ccc(Cl)c(C(F)(F)F)c2)c1]
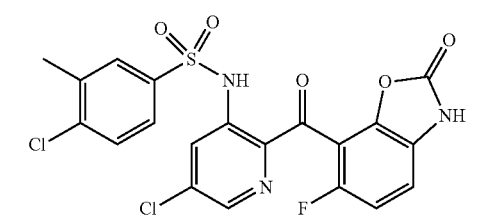 [SMILES: Cc1cc(S(=O)(=O)Nc2cc(Cl)cnc2C(=O)c2c(F)ccc3[nH]c(=O)oc23)ccc1Cl]
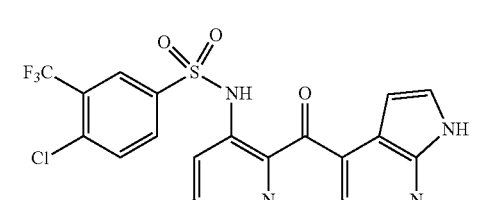
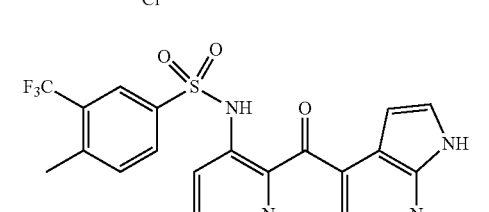
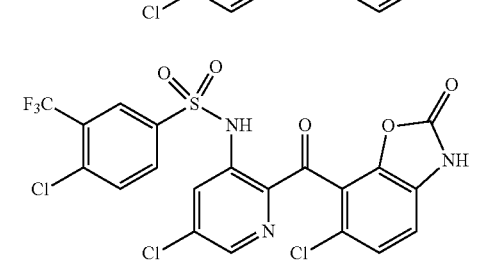
TABLE 1-continued
Compounds with CCR2 activity in one of the chemotaxis, binding or calcium mobilization assays, with IC50 < 1000 nM
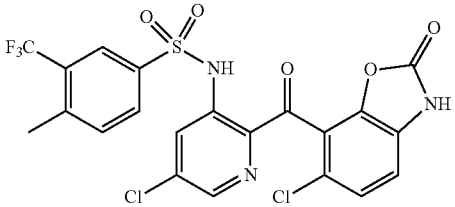 [SMILES: Cc1ccc(S(=O)(=O)Nc2cc(Cl)cnc2C(=O)c2c(Cl)ccc3[nH]c(=O)oc23)cc1C(F)(F)F]
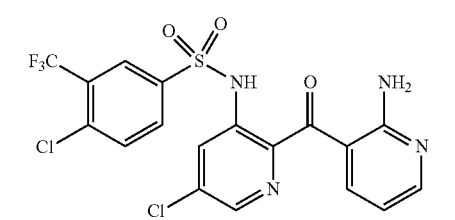 [SMILES: Nc1ncccc1C(=O)c1ncc(Cl)cc1NS(=O)(=O)c1ccc(Cl)c(C(F)(F)F)c1]
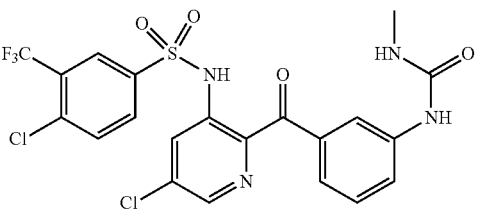 [SMILES: CNC(=O)Nc1cccc(C(=O)c2ncc(Cl)cc2NS(=O)(=O)c2ccc(Cl)c(C(F)(F)F)c2)c1]
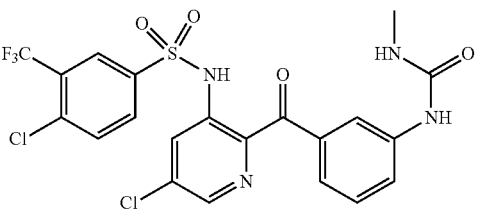 [SMILES: CNC(=O)Nc1cccc(C(=O)c2ncc(Cl)cc2NS(=O)(=O)c2ccc(Cl)c(C(F)(F)F)c2)c1]
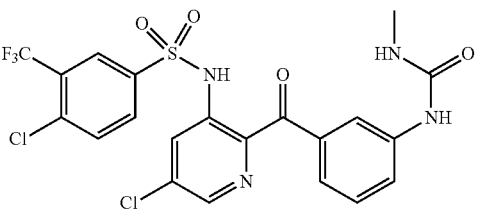 [SMILES: CNC(=O)Nc1cccc(C(=O)c2ncc(Cl)cc2NS(=O)(=O)c2ccc(Cl)c(C(F)(F)F)c2)c1]
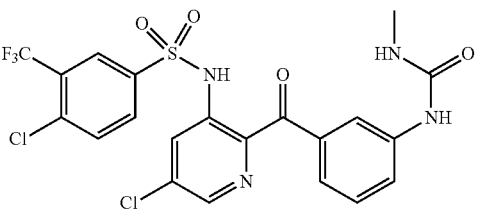 [SMILES: CNC(=O)Nc1cccc(C(=O)c2ncc(Cl)cc2NS(=O)(=O)c2ccc(Cl)c(C(F)(F)F)c2)c1]
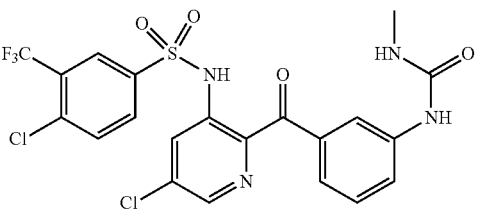 [SMILES: CNC(=O)Nc1cccc(C(=O)c2ncc(Cl)cc2NS(=O)(=O)c2ccc(Cl)c(C(F)(F)F)c2)c1]

TABLE 1-continued
Compounds with CCR2 activity in one of the chemotaxis, binding or calcium mobilization assays, with IC50 < 1000 nM
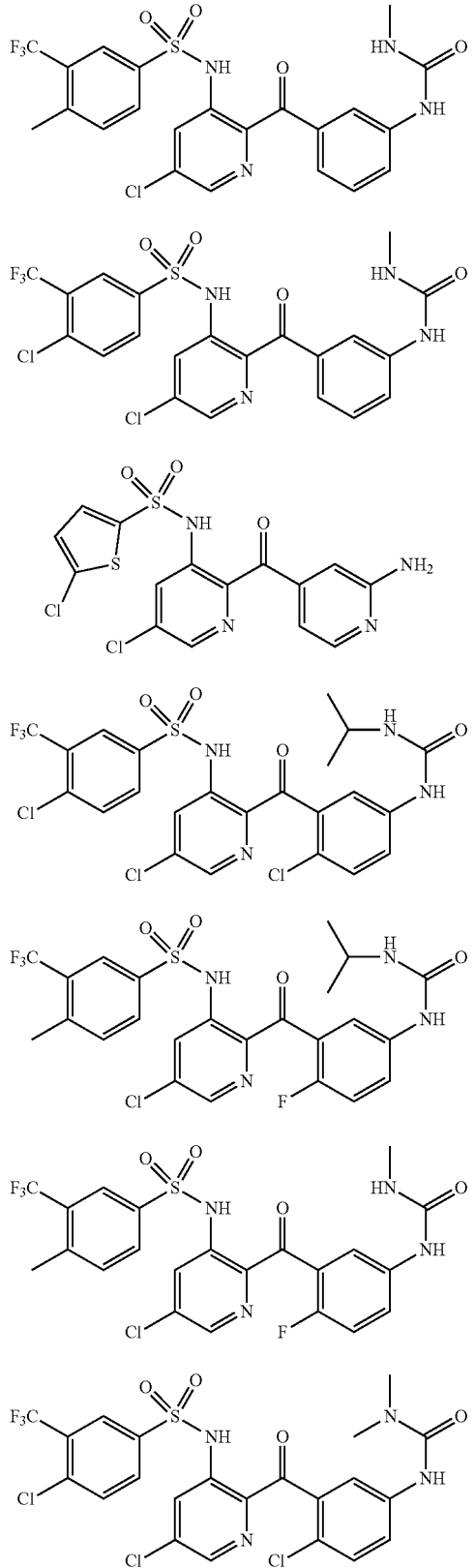
TABLE 1-continued
Compounds with CCR2 activity in one of the chemotaxis, binding or calcium mobilization assays, with IC50 < 1000 nM
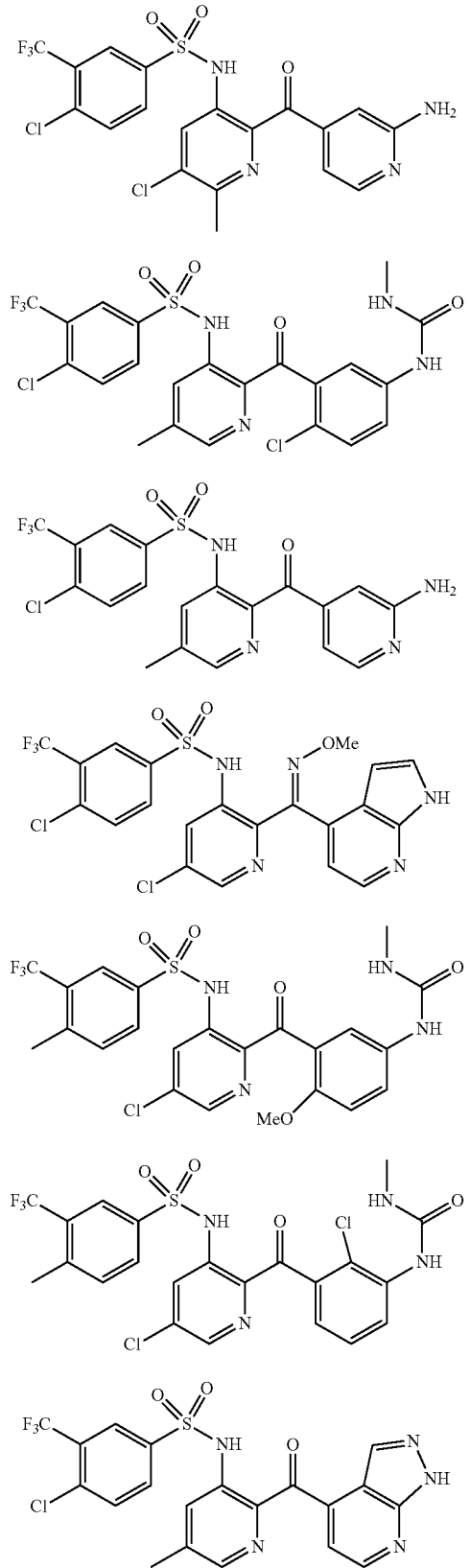

TABLE 1-continued
Compounds with CCR2 activity in one of the chemotaxis, binding or calcium mobilization assays, with IC50 < 1000 nM
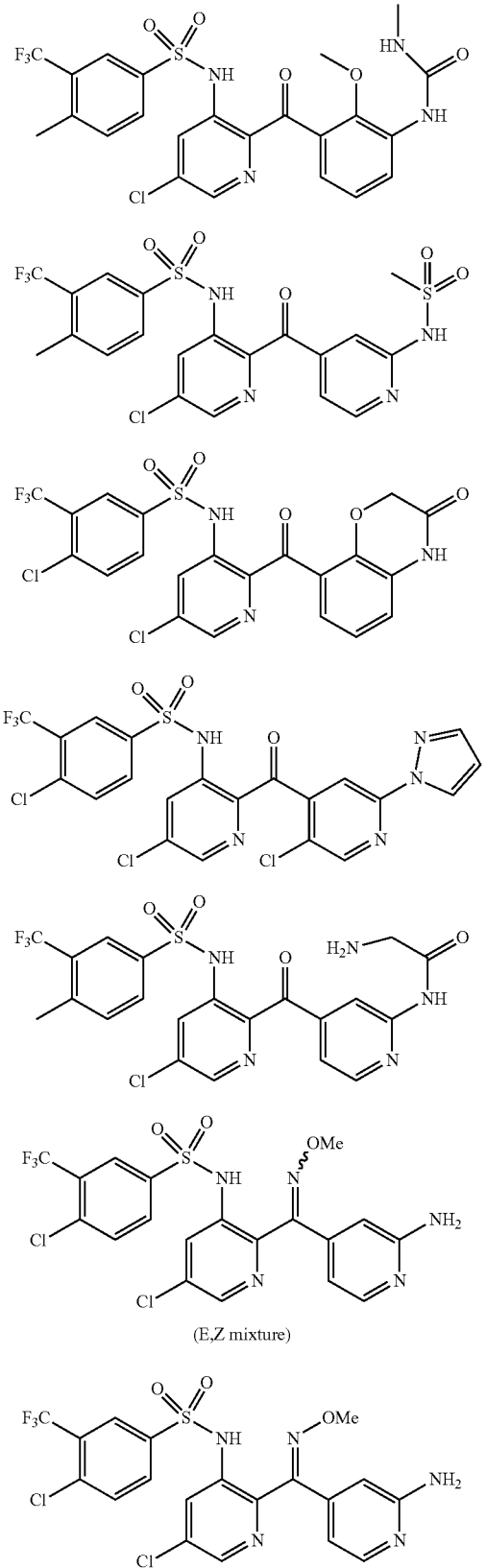
TABLE 1-continued
Compounds with CCR2 activity in one of the chemotaxis, binding or calcium mobilization assays, with IC50 < 1000 nM
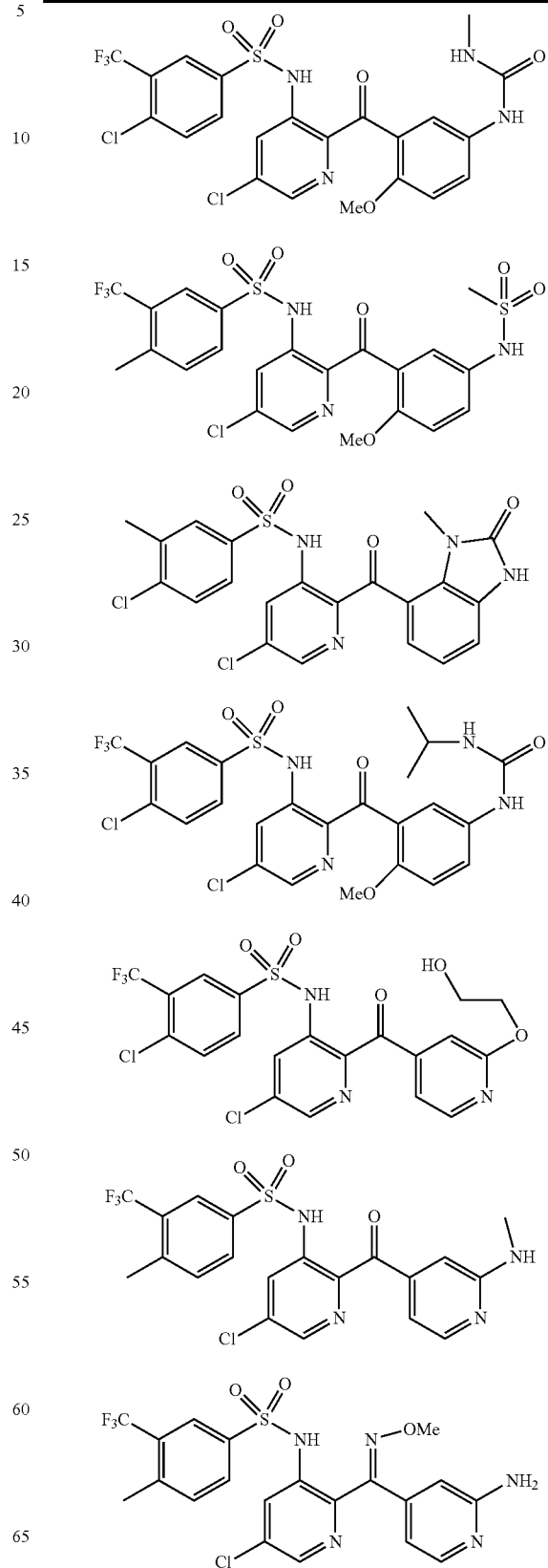

TABLE 1-continued
Compounds with CCR2 activity in one of the chemotaxis,
binding or calcium mobilization assays, with IC50 < 1000 nM
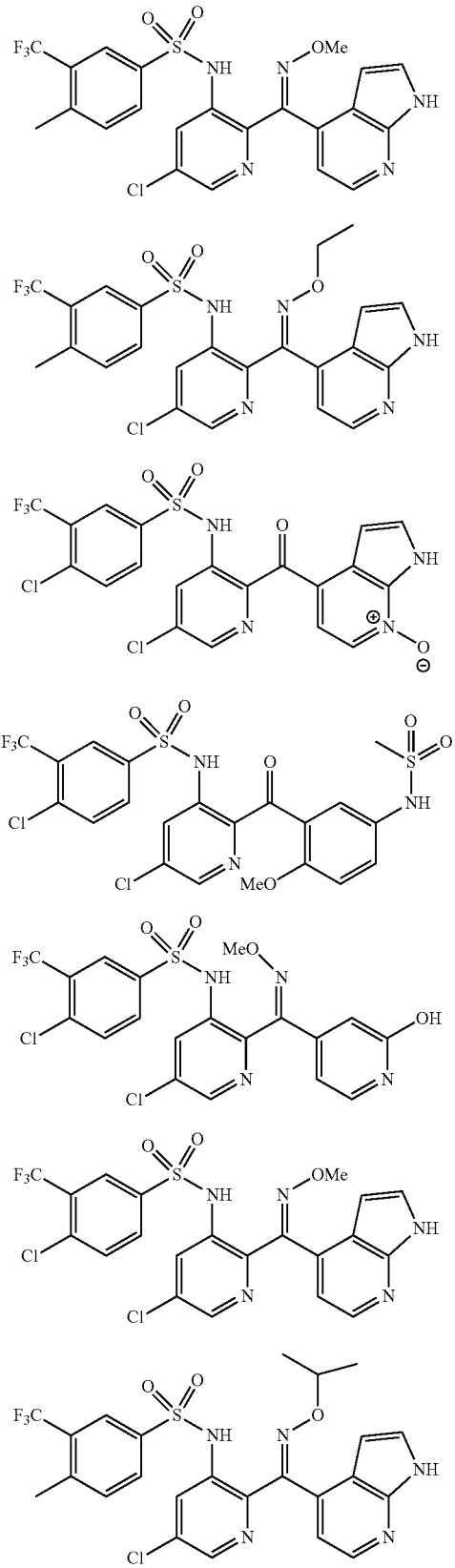
TABLE 1-continued
Compounds with CCR2 activity in one of the chemotaxis,
binding or calcium mobilization assays, with IC50 < 1000 nM
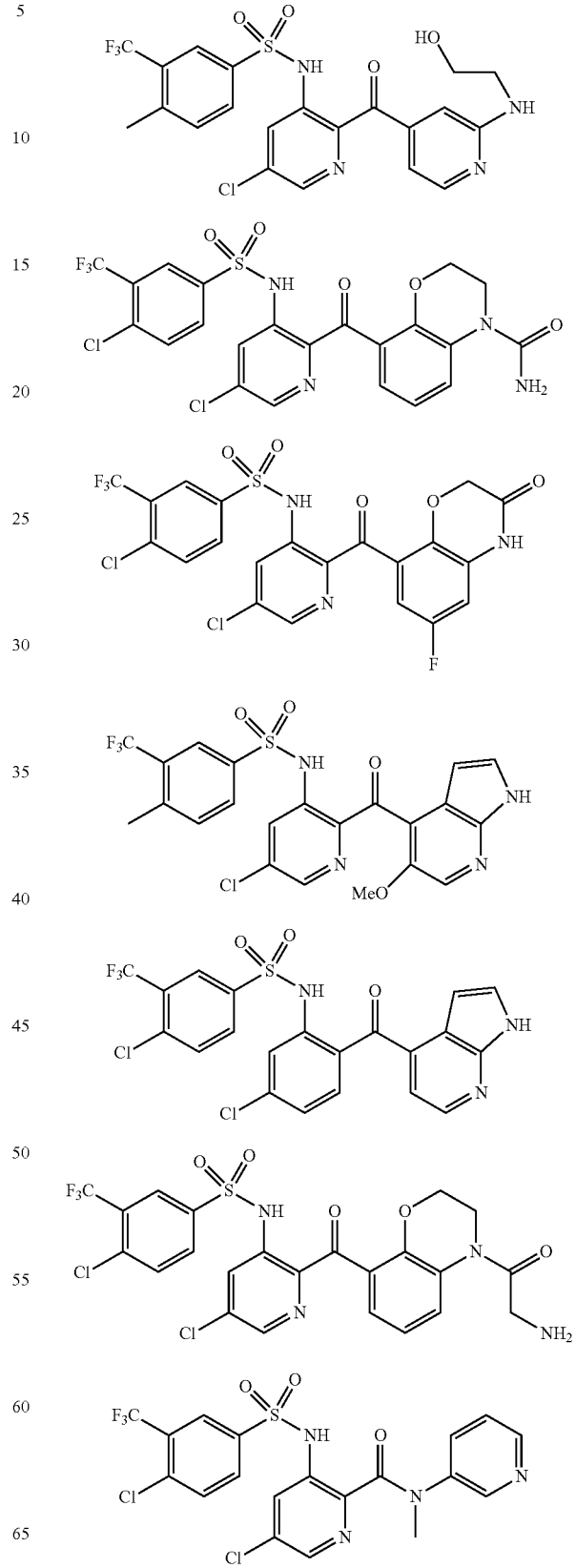

TABLE 1-continued
Compounds with CCR2 activity in one of the chemotaxis, binding or calcium mobilization assays, with IC50 < 1000 nM
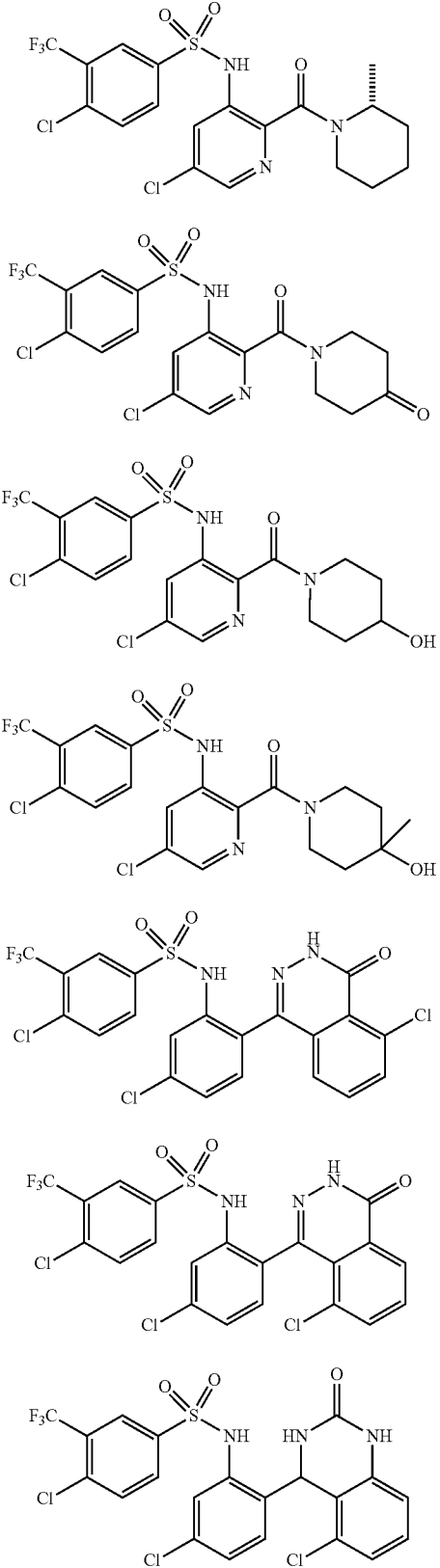
TABLE 1-continued
Compounds with CCR2 activity in one of the chemotaxis, binding or calcium mobilization assays, with IC50 < 1000 nM
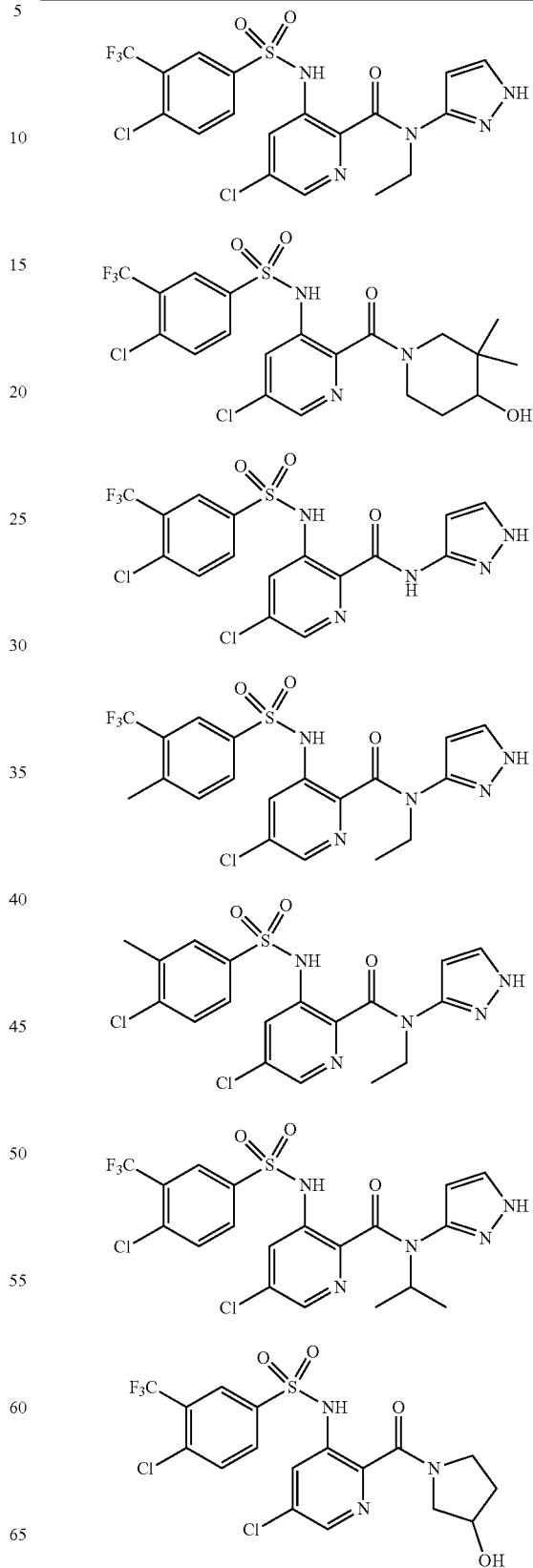

TABLE 1-continued
Compounds with CCR2 activity in one of the chemotaxis, binding or calcium mobilization assays, with IC50 < 1000 nM
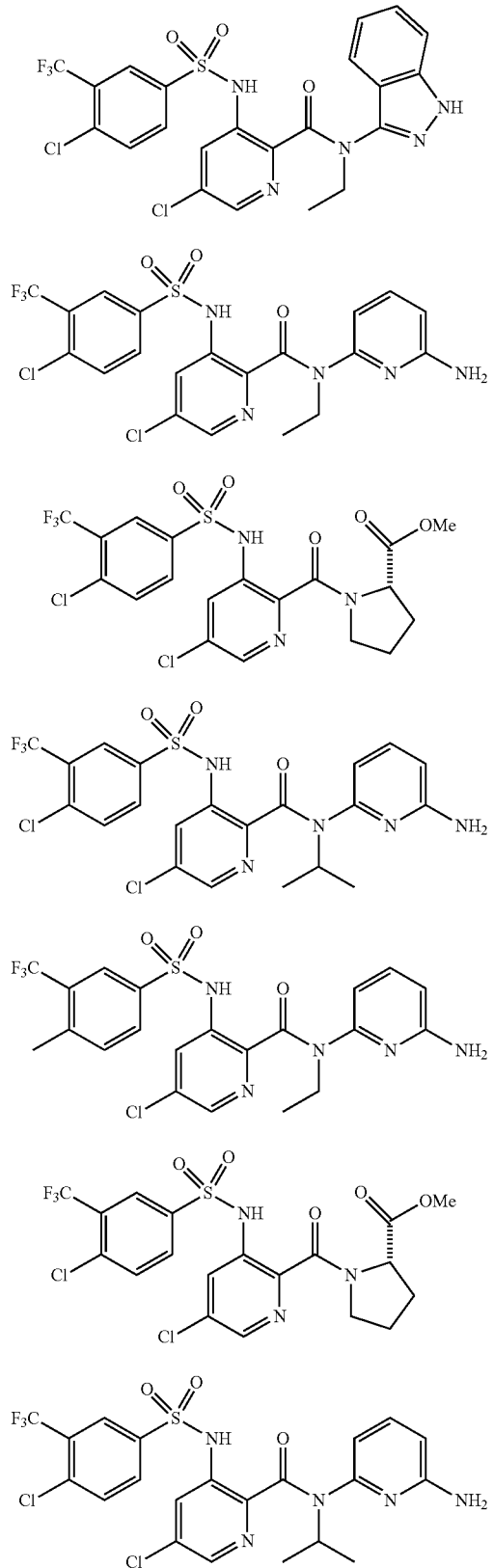
TABLE 1-continued
Compounds with CCR2 activity in one of the chemotaxis, binding or calcium mobilization assays, with IC50 < 1000 nM
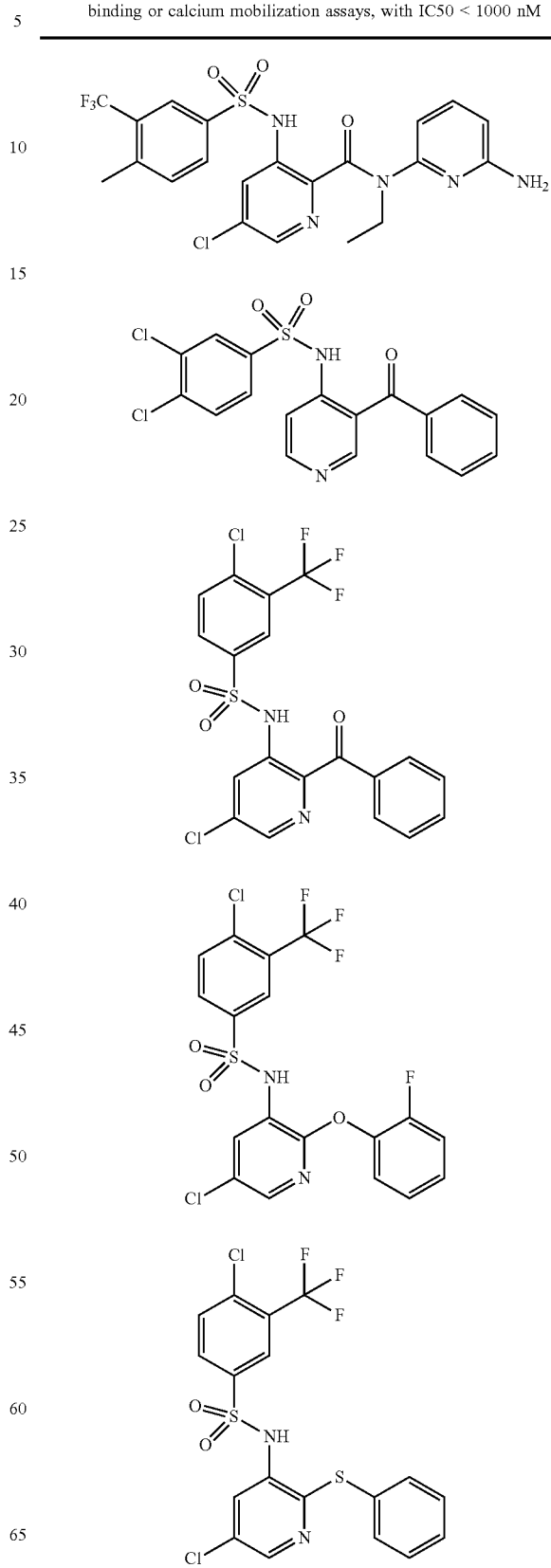

TABLE 1-continued
Compounds with CCR2 activity in one of the chemotaxis, binding or calcium mobilization assays, with IC50 < 1000 nM
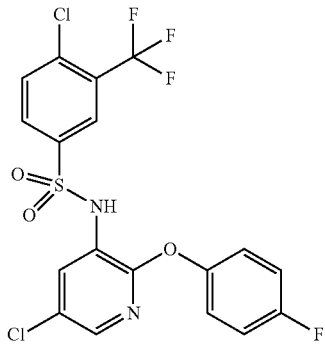 [SMILES: O=S(=O)(Nc1cc(Cl)cnc1Oc1ccc(F)cc1)c1ccc(Cl)c(C(F)(F)F)c1]
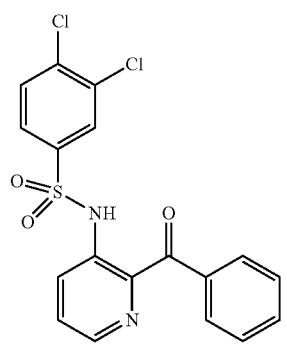 [SMILES: O=C(c1ccccc1)c1ncccc1NS(=O)(=O)c1ccc(Cl)c(Cl)c1]
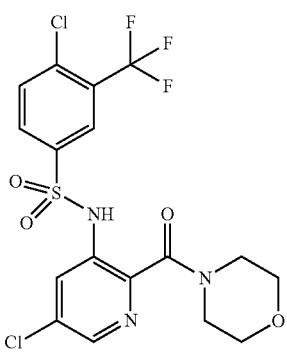 [SMILES: O=C(c1ncc(Cl)cc1NS(=O)(=O)c1ccc(Cl)c(C(F)(F)F)c1)N1CCOCC1]
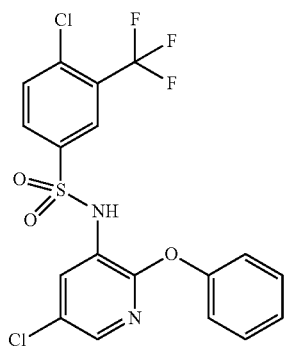 [SMILES: O=S(=O)(Nc1cc(Cl)cnc1Oc1ccccc1)c1ccc(Cl)c(C(F)(F)F)c1]
TABLE 1-continued
Compounds with CCR2 activity in one of the chemotaxis, binding or calcium mobilization assays, with IC50 < 1000 nM
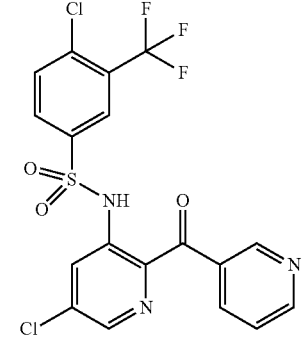 [SMILES: O=C(c1cccnc1)c1ncc(Cl)cc1NS(=O)(=O)c1ccc(Cl)c(C(F)(F)F)c1]
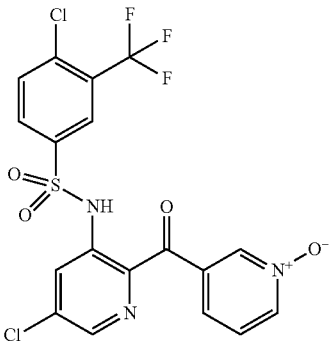 [SMILES: O=C(c1ccc[n+]([O-])c1)c1ncc(Cl)cc1NS(=O)(=O)c1ccc(Cl)c(C(F)(F)F)c1]
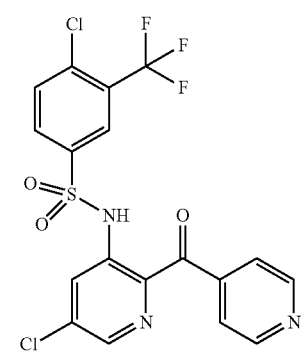 [SMILES: O=C(c1ccncc1)c1ncc(Cl)cc1NS(=O)(=O)c1ccc(Cl)c(C(F)(F)F)c1]
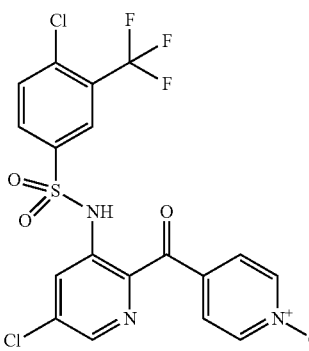

TABLE 1-continued
Compounds with CCR2 activity in one of the chemotaxis, binding or calcium mobilization assays, with IC50 < 1000 nM
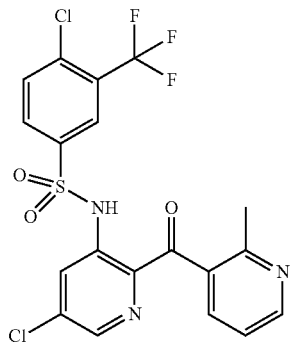 [SMILES: Cc1ncccc1C(=O)c1ncc(Cl)cc1NS(=O)(=O)c1ccc(Cl)c(C(F)(F)F)c1]
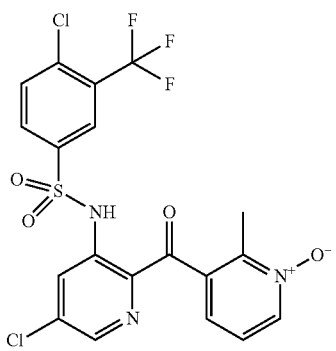 [SMILES: Cc1c(C(=O)c2ncc(Cl)cc2NS(=O)(=O)c2ccc(Cl)c(C(F)(F)F)c2)ccc[n+]1[O-]]
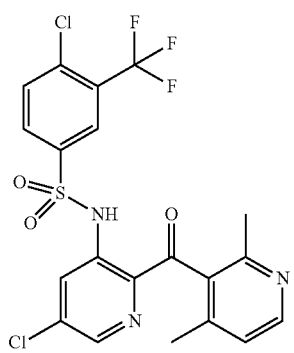 [SMILES: Cc1ccnc(C)c1C(=O)c1ncc(Cl)cc1NS(=O)(=O)c1ccc(Cl)c(C(F)(F)F)c1]
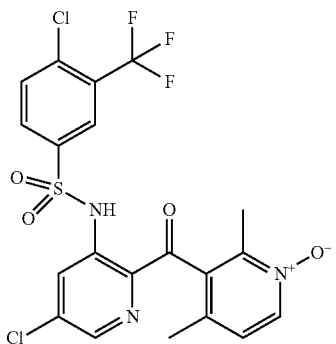 [SMILES: Cc1cc[n+]([O-])c(C)c1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
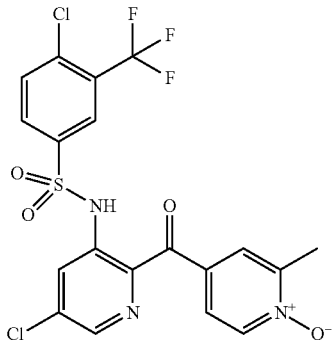 [SMILES: Cc1cc(C(=O)c2ncc(Cl)cc2NS(=O)(=O)c2ccc(Cl)c(C(F)(F)F)c2)cc[n+]1[O-]]
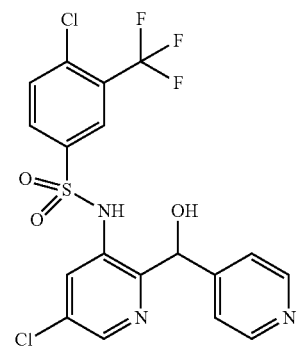 [SMILES: O=S(=O)(Nc1cc(Cl)cnc1C(O)c1ccncc1)c1ccc(Cl)c(C(F)(F)F)c1]
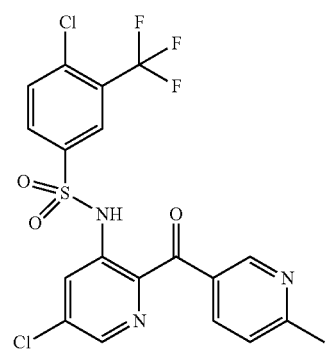 [SMILES: Cc1ccc(C(=O)c2ncc(Cl)cc2NS(=O)(=O)c2ccc(Cl)c(C(F)(F)F)c2)cn1]
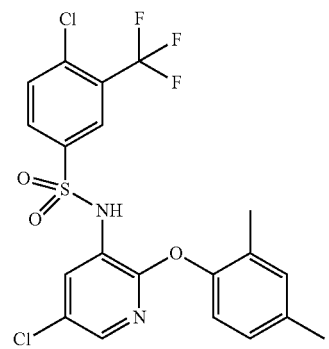 [SMILES: Cc1ccc(Oc2ncc(Cl)cc2NS(=O)(=O)c2ccc(Cl)c(C(F)(F)F)c2)c(C)c1]

TABLE 1-continued
Compounds with CCR2 activity in one of the chemotaxis, binding or calcium mobilization assays, with IC50 < 1000 nM
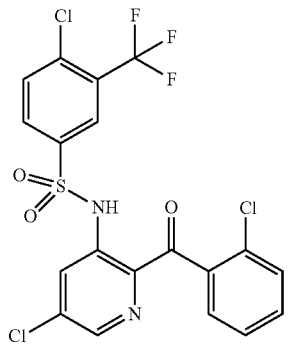
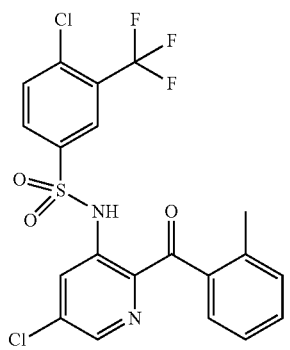 [SMILES: Cc1ccccc1C(=O)c1ncc(Cl)cc1NS(=O)(=O)c1ccc(Cl)c(C(F)(F)F)c1]
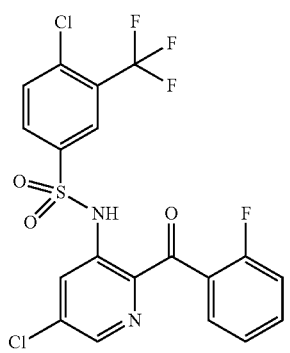
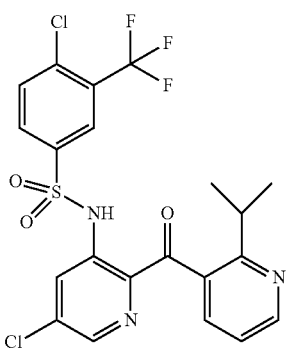 [SMILES: CC(C)c1ncccc1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
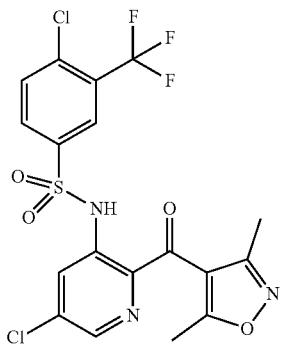 [SMILES: Cc1noc(C)c1C(=O)c1ncc(Cl)cc1NS(=O)(=O)c1ccc(Cl)c(C(F)(F)F)c1]
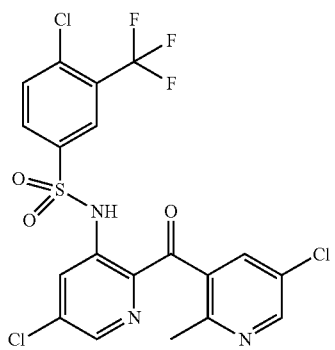 [SMILES: Cc1ncc(Cl)cc1C(=O)c1ncc(Cl)cc1NS(=O)(=O)c1ccc(Cl)c(C(F)(F)F)c1]
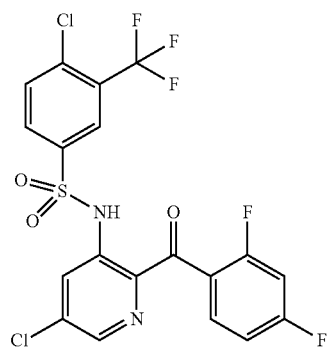 [SMILES: O=C(c1ccc(F)cc1F)c1ncc(Cl)cc1NS(=O)(=O)c1ccc(Cl)c(C(F)(F)F)c1]
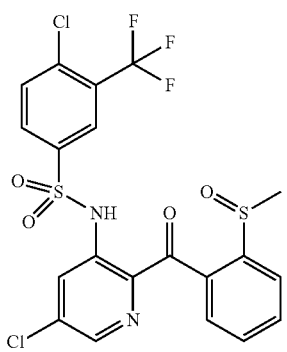 [SMILES: CS(=O)c1ccccc1C(=O)c1ncc(Cl)cc1NS(=O)(=O)c1ccc(Cl)c(C(F)(F)F)c1]

TABLE 1-continued
Compounds with CCR2 activity in one of the chemotaxis, binding or calcium mobilization assays, with IC50 < 1000 nM
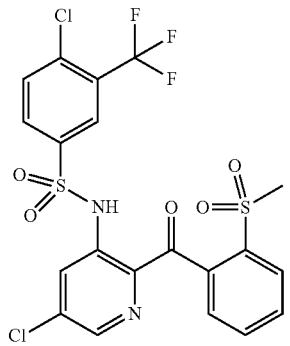 [SMILES: CS(=O)(=O)c1ccccc1C(=O)c1ncc(Cl)cc1NS(=O)(=O)c1ccc(Cl)c(C(F)(F)F)c1]
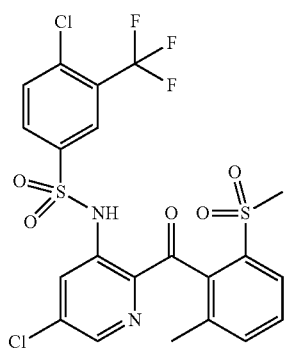 [SMILES: Cc1cccc(S(C)(=O)=O)c1C(=O)c1ncc(Cl)cc1NS(=O)(=O)c1ccc(Cl)c(C(F)(F)F)c1]
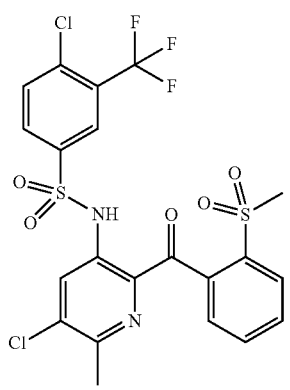 [SMILES: Cc1nc(C(=O)c2ccccc2S(C)(=O)=O)c(NS(=O)(=O)c2ccc(Cl)c(C(F)(F)F)c2)cc1Cl]
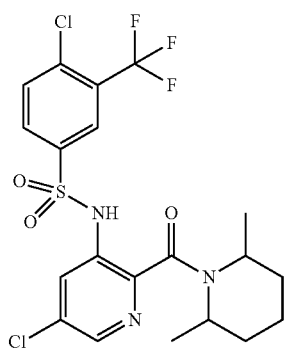 [SMILES: CC1CCCC(C)N1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
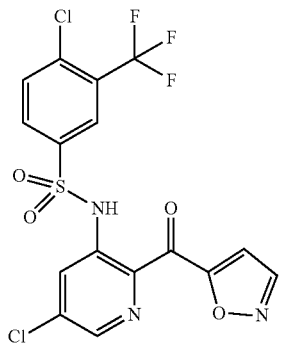 [SMILES: O=C(c1ccno1)c1ncc(Cl)cc1NS(=O)(=O)c1ccc(Cl)c(C(F)(F)F)c1]
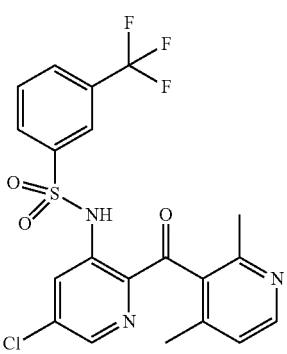 [SMILES: Cc1ccnc(C)c1C(=O)c1ncc(Cl)cc1NS(=O)(=O)c1cccc(C(F)(F)F)c1]
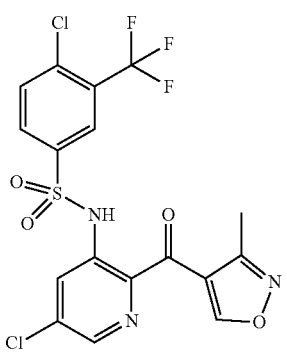 [SMILES: Cc1nocc1C(=O)c1ncc(Cl)cc1NS(=O)(=O)c1ccc(Cl)c(C(F)(F)F)c1]
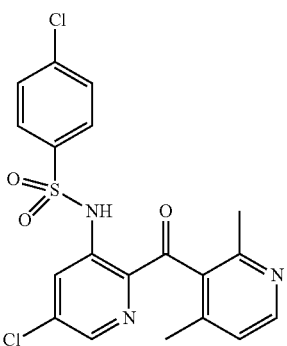 [SMILES: Cc1ccnc(C)c1C(=O)c1ncc(Cl)cc1NS(=O)(=O)c1ccc(Cl)cc1]

TABLE 1-continued
Compounds with CCR2 activity in one of the chemotaxis, binding or calcium mobilization assays, with IC50 < 1000 nM
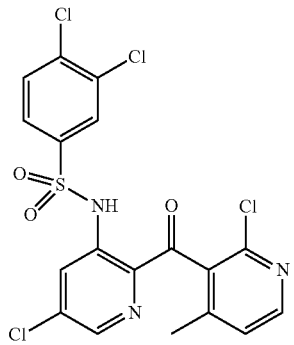
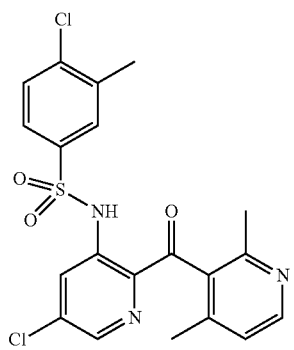 [SMILES: Cc1cc(S(=O)(=O)Nc2cc(Cl)cnc2C(=O)c2c(C)ccnc2C)ccc1Cl]
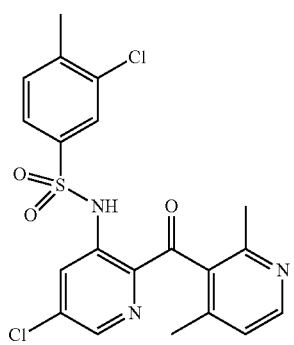 [SMILES: Cc1ccc(S(=O)(=O)Nc2cc(Cl)cnc2C(=O)c2c(C)ccnc2C)cc1Cl]
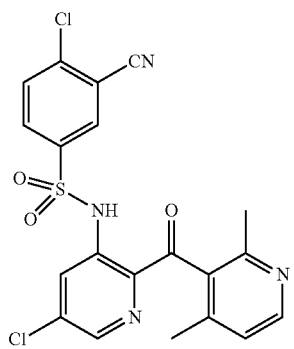 [SMILES: Cc1ccnc(C)c1C(=O)c1ncc(Cl)cc1NS(=O)(=O)c1ccc(Cl)c(C#N)c1]
TABLE 1-continued
Compounds with CCR2 activity in one of the chemotaxis, binding or calcium mobilization assays, with IC50 < 1000 nM
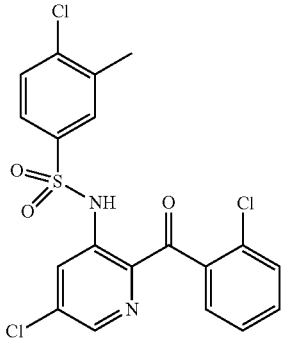 [SMILES: Cc1cc(S(=O)(=O)Nc2cc(Cl)cnc2C(=O)c2ccccc2Cl)ccc1Cl]
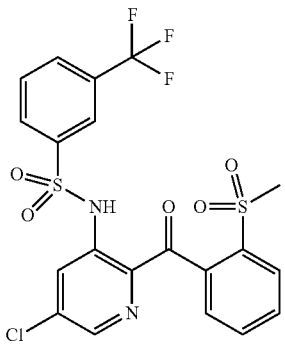 [SMILES: CS(=O)(=O)c1ccccc1C(=O)c1ncc(Cl)cc1NS(=O)(=O)c1cccc(C(F)(F)F)c1]
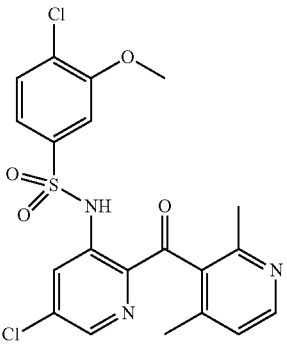 [SMILES: COc1cc(S(=O)(=O)Nc2cc(Cl)cnc2C(=O)c2c(C)ccnc2C)ccc1Cl]
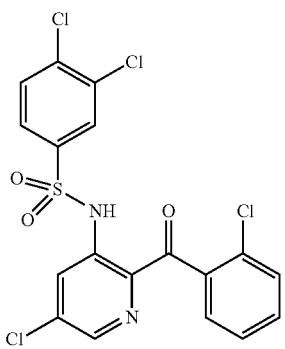 [SMILES: O=C(c1ccccc1Cl)c1ncc(Cl)cc1NS(=O)(=O)c1ccc(Cl)c(Cl)c1]

TABLE 1-continued
Compounds with CCR2 activity in one of the chemotaxis, binding or calcium mobilization assays, with IC50 < 1000 nM
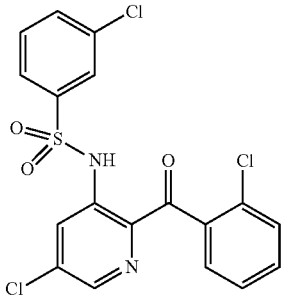 [SMILES: O=C(c1ccccc1Cl)c1ncc(Cl)cc1NS(=O)(=O)c1cccc(Cl)c1]
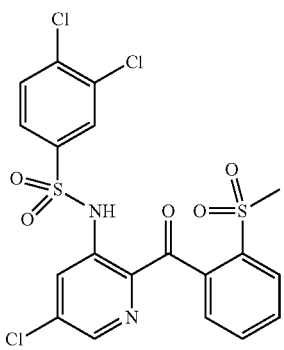 [SMILES: CS(=O)(=O)c1ccccc1C(=O)c1ncc(Cl)cc1NS(=O)(=O)c1ccc(Cl)c(Cl)c1]
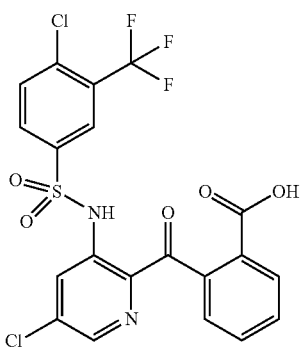 [SMILES: O=C(O)c1ccccc1C(=O)c1ncc(Cl)cc1NS(=O)(=O)c1ccc(Cl)c(C(F)(F)F)c1]
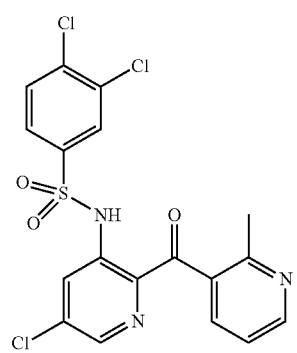 [SMILES: Cc1ncccc1C(=O)c1ncc(Cl)cc1NS(=O)(=O)c1ccc(Cl)c(Cl)c1]
TABLE 1-continued
Compounds with CCR2 activity in one of the chemotaxis, binding or calcium mobilization assays, with IC50 < 1000 nM
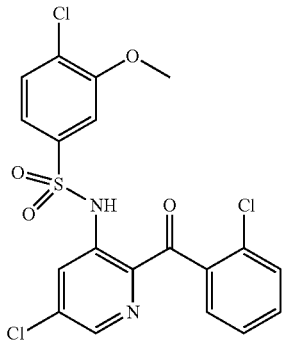 [SMILES: COc1cc(S(=O)(=O)Nc2cc(Cl)cnc2C(=O)c2ccccc2Cl)ccc1Cl]
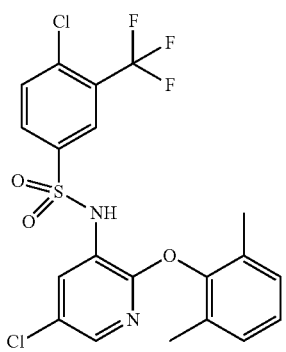 [SMILES: Cc1cccc(C)c1Oc1ncc(Cl)cc1NS(=O)(=O)c1ccc(Cl)c(C(F)(F)F)c1]
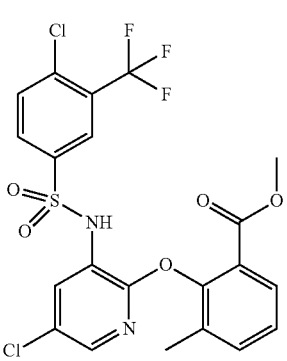 [SMILES: COC(=O)c1cccc(C)c1Oc1ncc(Cl)cc1NS(=O)(=O)c1ccc(Cl)c(C(F)(F)F)c1]
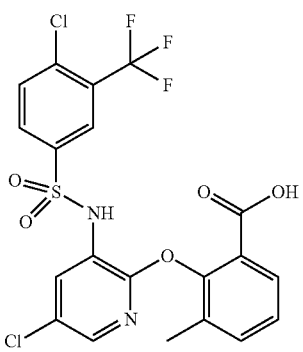 [SMILES: Cc1cccc(C(=O)O)c1Oc1ncc(Cl)cc1NS(=O)(=O)c1ccc(Cl)c(C(F)(F)F)c1]

TABLE 1-continued
Compounds with CCR2 activity in one of the chemotaxis, binding or calcium mobilization assays, with IC50 < 1000 nM
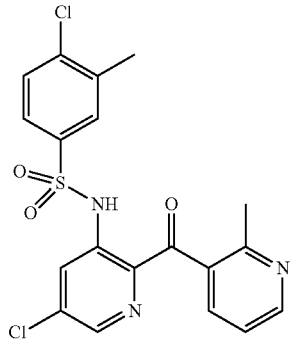 [SMILES: Cc1cc(S(=O)(=O)Nc2cc(Cl)cnc2C(=O)c2cccnc2C)ccc1Cl]
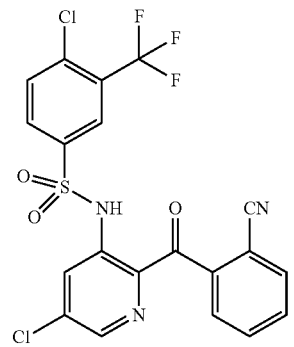 [SMILES: N#Cc1ccccc1C(=O)c1ncc(Cl)cc1NS(=O)(=O)c1ccc(Cl)c(C(F)(F)F)c1]
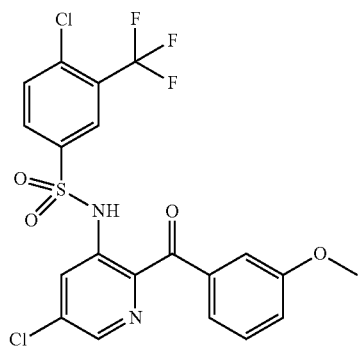 [SMILES: COc1cccc(C(=O)c2ncc(Cl)cc2NS(=O)(=O)c2ccc(Cl)c(C(F)(F)F)c2)c1]
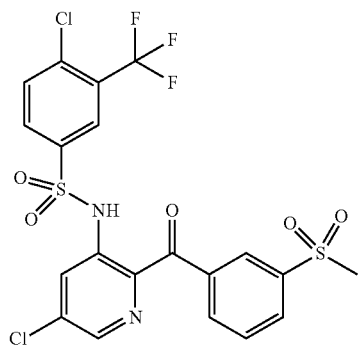 [SMILES: CS(=O)(=O)c1cccc(C(=O)c2ncc(Cl)cc2NS(=O)(=O)c2ccc(Cl)c(C(F)(F)F)c2)c1]
TABLE 1-continued
Compounds with CCR2 activity in one of the chemotaxis, binding or calcium mobilization assays, with IC50 < 1000 nM
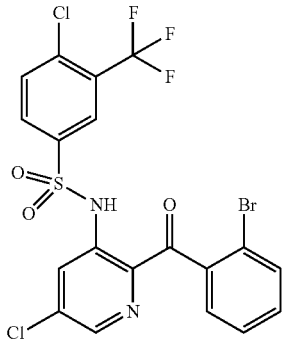 [SMILES: O=C(c1ccccc1Br)c1ncc(Cl)cc1NS(=O)(=O)c1ccc(Cl)c(C(F)(F)F)c1]
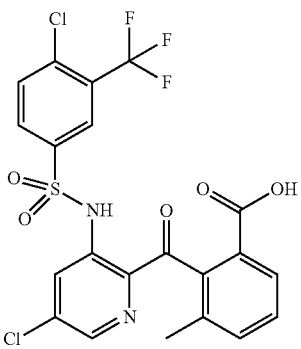 [SMILES: Cc1cccc(C(=O)O)c1C(=O)c1ncc(Cl)cc1NS(=O)(=O)c1ccc(Cl)c(C(F)(F)F)c1]
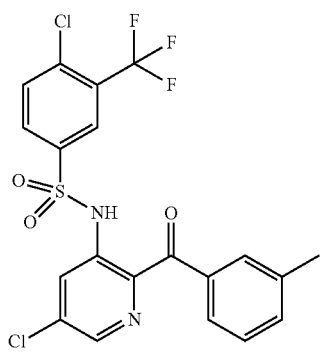 [SMILES: Cc1cccc(C(=O)c2ncc(Cl)cc2NS(=O)(=O)c2ccc(Cl)c(C(F)(F)F)c2)c1]
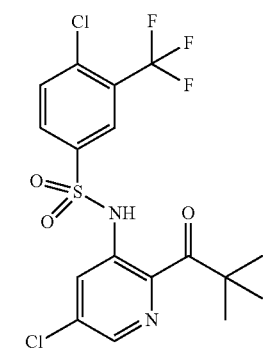 [SMILES: CC(C)(C)C(=O)c1ncc(Cl)cc1NS(=O)(=O)c1ccc(Cl)c(C(F)(F)F)c1]

TABLE 1-continued
Compounds with CCR2 activity in one of the chemotaxis, binding or calcium mobilization assays, with IC50 < 1000 nM
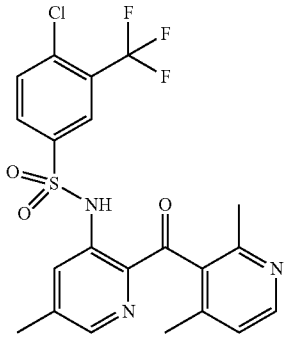 [SMILES: Cc1cnc(C(=O)c2c(C)ccnc2C)c(NS(=O)(=O)c2ccc(Cl)c(C(F)(F)F)c2)c1]
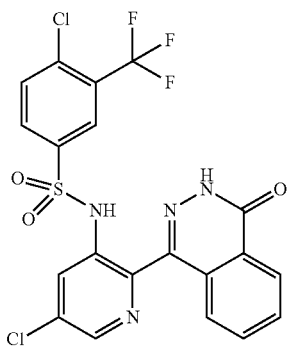 [SMILES: O=c1[nH]nc(-c2ncc(Cl)cc2NS(=O)(=O)c2ccc(Cl)c(C(F)(F)F)c2)c2ccccc12]
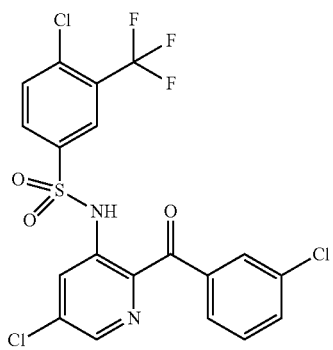 [SMILES: O=C(c1cccc(Cl)c1)c1ncc(Cl)cc1NS(=O)(=O)c1ccc(Cl)c(C(F)(F)F)c1]
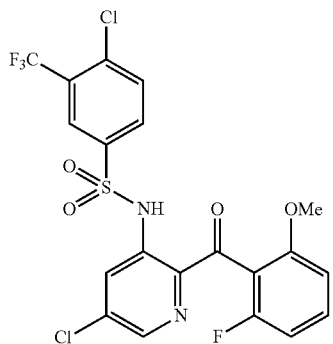 [SMILES: COc1cccc(F)c1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
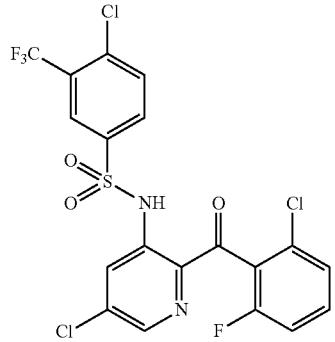
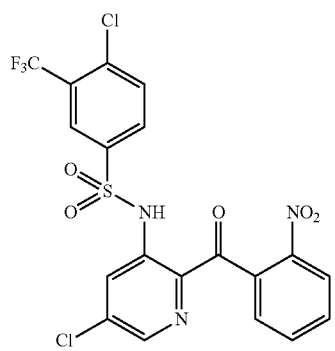
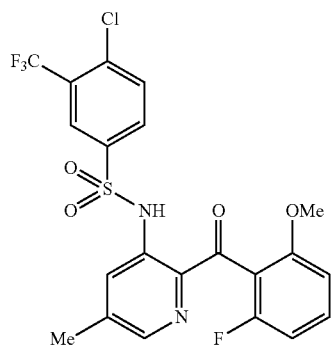
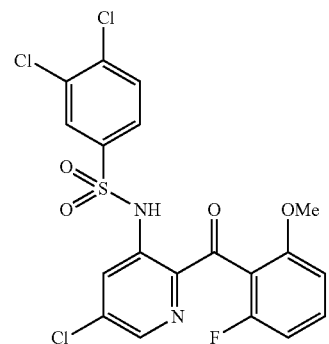 [SMILES: COc1cccc(F)c1C(=O)c1ncc(Cl)cc1NS(=O)(=O)c1ccc(Cl)c(Cl)c1]

TABLE 1-continued
Compounds with CCR2 activity in one of the chemotaxis, binding or calcium mobilization assays, with IC50 < 1000 nM
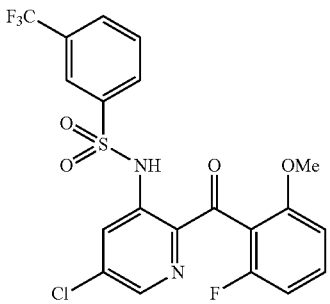 [SMILES: COc1cccc(F)c1C(=O)c1ncc(Cl)cc1NS(=O)(=O)c1cccc(C(F)(F)F)c1]
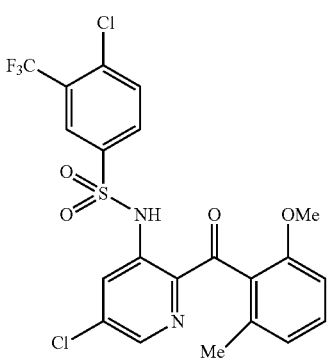
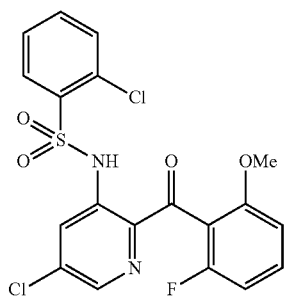 [SMILES: COc1cccc(F)c1C(=O)c1ncc(Cl)cc1NS(=O)(=O)c1ccccc1Cl]
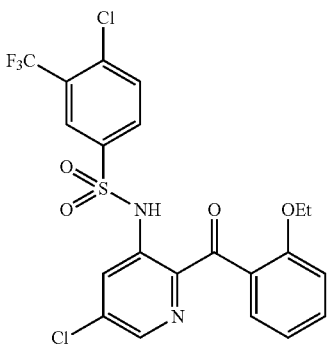 [SMILES: CCOc1ccccc1C(=O)c1ncc(Cl)cc1NS(=O)(=O)c1ccc(Cl)c(C(F)(F)F)c1]
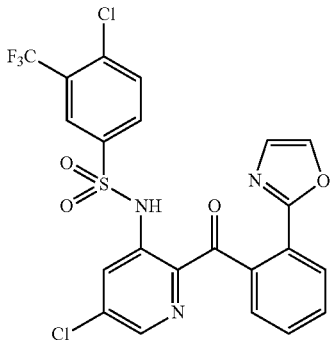
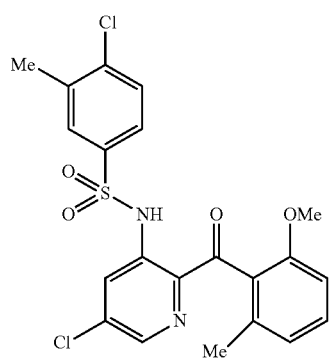 [SMILES: COc1cccc(C)c1C(=O)c1ncc(Cl)cc1NS(=O)(=O)c1ccc(Cl)c(C)c1]
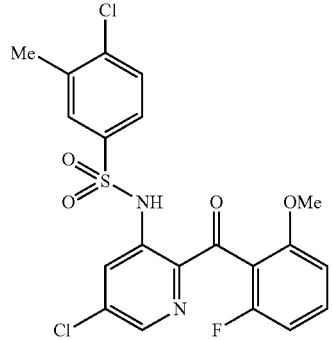 [SMILES: COc1cccc(F)c1C(=O)c1ncc(Cl)cc1NS(=O)(=O)c1ccc(Cl)c(C)c1]
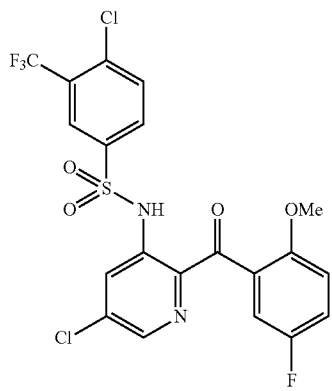 [SMILES: COc1ccc(F)cc1C(=O)c1ncc(Cl)cc1NS(=O)(=O)c1ccc(Cl)c(C(F)(F)F)c1]

TABLE 1-continued
Compounds with CCR2 activity in one of the chemotaxis, binding or calcium mobilization assays, with IC50 < 1000 nM
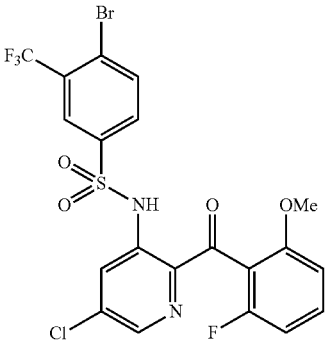 [SMILES: COc1cccc(F)c1C(=O)c1ncc(Cl)cc1NS(=O)(=O)c1ccc(Br)c(C(F)(F)F)c1]
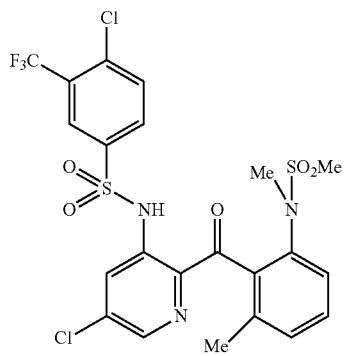 [SMILES: Cc1cccc(N(C)S(C)(=O)=O)c1C(=O)c1ncc(Cl)cc1NS(=O)(=O)c1ccc(Cl)c(C(F)(F)F)c1]
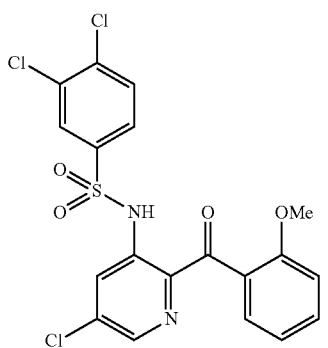
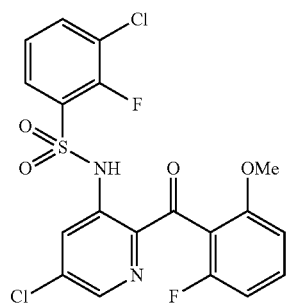 [SMILES: COc1cccc(F)c1C(=O)c1ncc(Cl)cc1NS(=O)(=O)c1cccc(Cl)c1F]
TABLE 1-continued
Compounds with CCR2 activity in one of the chemotaxis, binding or calcium mobilization assays, with IC50 < 1000 nM
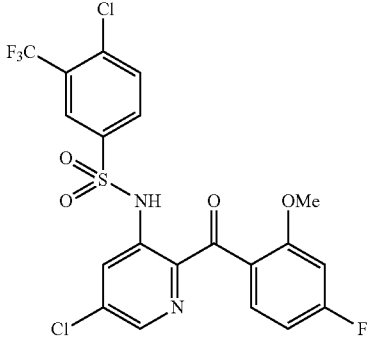 [SMILES: COc1cc(F)ccc1C(=O)c1ncc(Cl)cc1NS(=O)(=O)c1ccc(Cl)c(C(F)(F)F)c1]
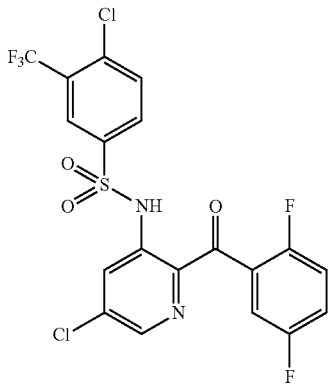 [SMILES: O=C(c1cc(F)ccc1F)c1ncc(Cl)cc1NS(=O)(=O)c1ccc(Cl)c(C(F)(F)F)c1]
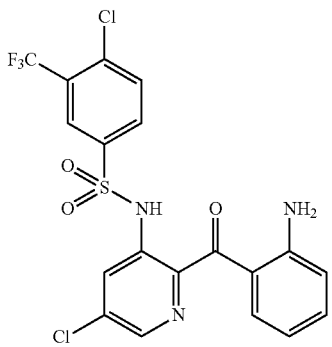
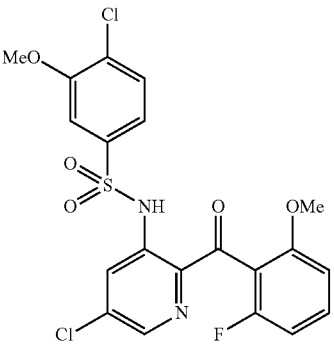 [SMILES: COc1cc(S(=O)(=O)Nc2cc(Cl)cnc2C(=O)c2c(F)cccc2OC)ccc1Cl]

TABLE 1-continued
Compounds with CCR2 activity in one of the chemotaxis, binding or calcium mobilization assays, with IC50 < 1000 nM
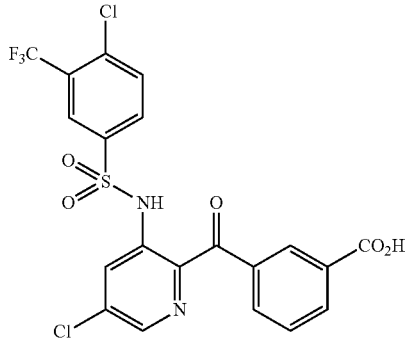 [SMILES: O=C(O)c1cccc(C(=O)c2ncc(Cl)cc2NS(=O)(=O)c2ccc(Cl)c(C(F)(F)F)c2)c1]
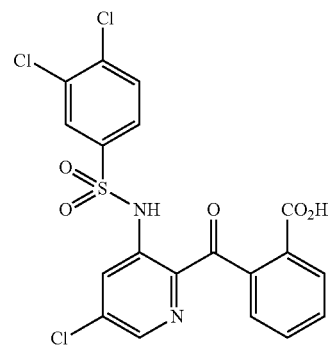 [SMILES: O=C(O)c1ccccc1C(=O)c1ncc(Cl)cc1NS(=O)(=O)c1ccc(Cl)c(Cl)c1]
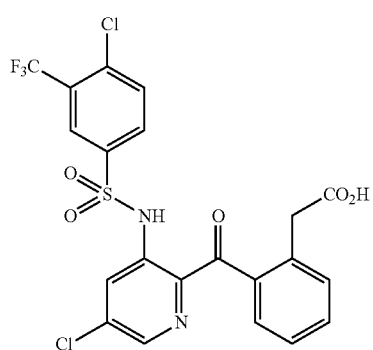 [SMILES: O=C(O)Cc1ccccc1C(=O)c1ncc(Cl)cc1NS(=O)(=O)c1ccc(Cl)c(C(F)(F)F)c1]
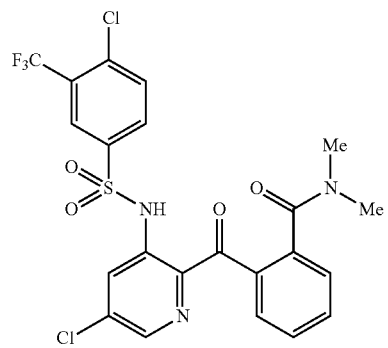 [SMILES: CN(C)C(=O)c1ccccc1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
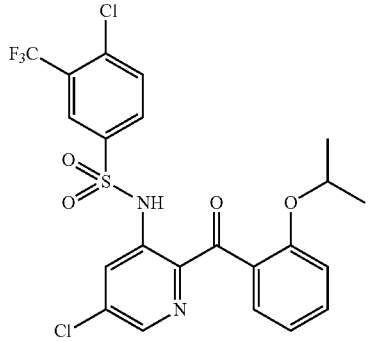 [SMILES: CC(C)Oc1ccccc1C(=O)c1ncc(Cl)cc1NS(=O)(=O)c1ccc(Cl)c(C(F)(F)F)c1]
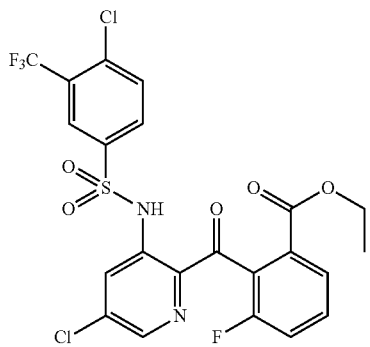 [SMILES: CCOC(=O)c1cccc(F)c1C(=O)c1ncc(Cl)cc1NS(=O)(=O)c1ccc(Cl)c(C(F)(F)F)c1]
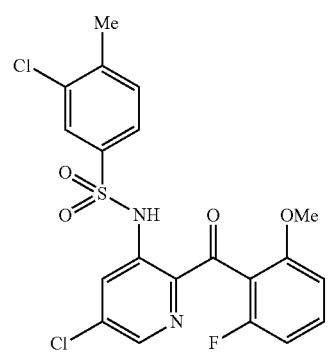
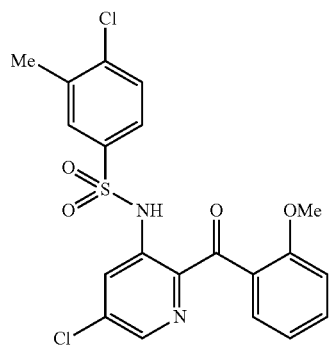 [SMILES: COc1ccccc1C(=O)c1ncc(Cl)cc1NS(=O)(=O)c1ccc(Cl)c(C)c1]

TABLE 1-continued
Compounds with CCR2 activity in one of the chemotaxis, binding or calcium mobilization assays, with IC50 < 1000 nM
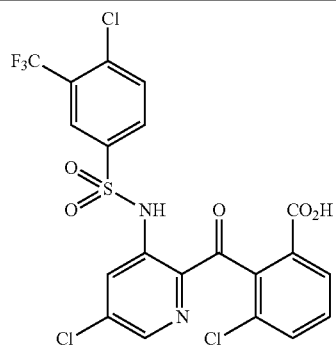
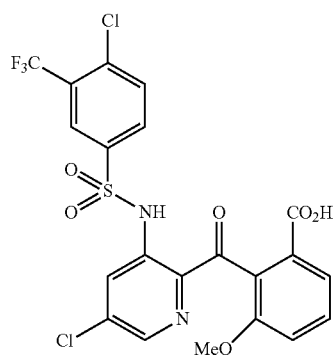 [SMILES: COc1cccc(C(=O)O)c1C(=O)c1ncc(Cl)cc1NS(=O)(=O)c1ccc(Cl)c(C(F)(F)F)c1]
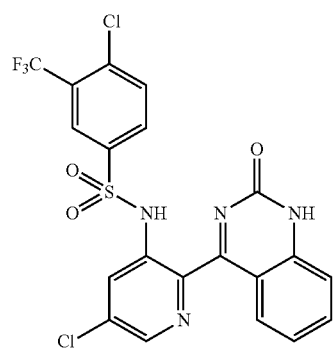 [SMILES: O=c1nc(-c2ncc(Cl)cc2NS(=O)(=O)c2ccc(Cl)c(C(F)(F)F)c2)c2ccccc2[nH]1]
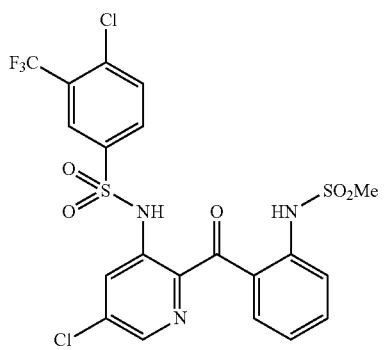 [SMILES: CS(=O)(=O)Nc1ccccc1C(=O)c1ncc(Cl)cc1NS(=O)(=O)c1ccc(Cl)c(C(F)(F)F)c1]
TABLE 1-continued
Compounds with CCR2 activity in one of the chemotaxis, binding or calcium mobilization assays, with IC50 < 1000 nM
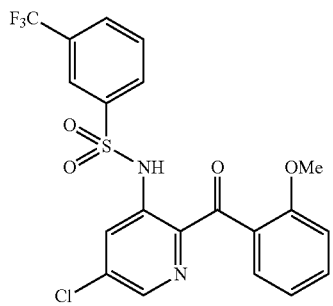 [SMILES: COc1ccccc1C(=O)c1ncc(Cl)cc1NS(=O)(=O)c1cccc(C(F)(F)F)c1]
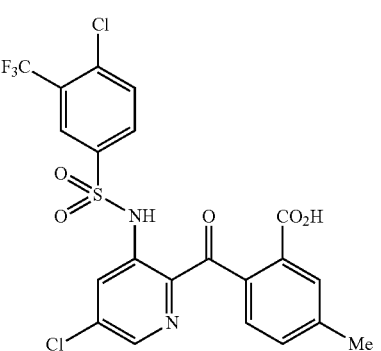 [SMILES: Cc1ccc(C(=O)c2ncc(Cl)cc2NS(=O)(=O)c2ccc(Cl)c(C(F)(F)F)c2)c(C(=O)O)c1]
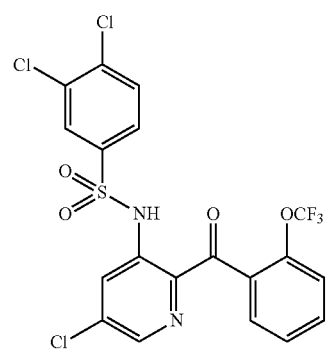 [SMILES: O=C(c1ccccc1OC(F)(F)F)c1ncc(Cl)cc1NS(=O)(=O)c1ccc(Cl)c(Cl)c1]
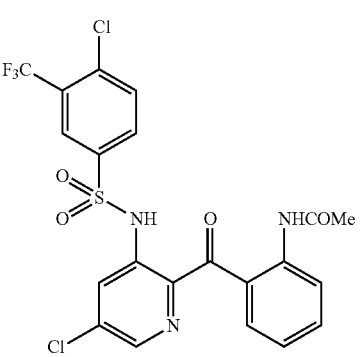

TABLE 1-continued
Compounds with CCR2 activity in one of the chemotaxis, binding or calcium mobilization assays, with IC50 < 1000 nM
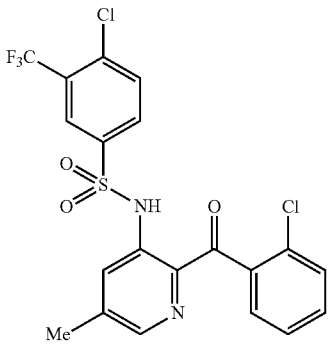 [SMILES: Cc1cnc(C(=O)c2ccccc2Cl)c(NS(=O)(=O)c2ccc(Cl)c(C(F)(F)F)c2)c1]
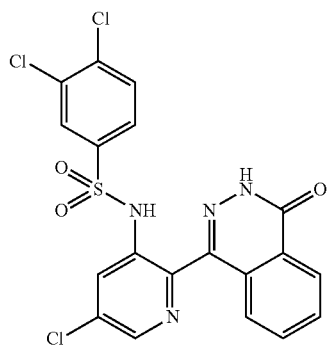
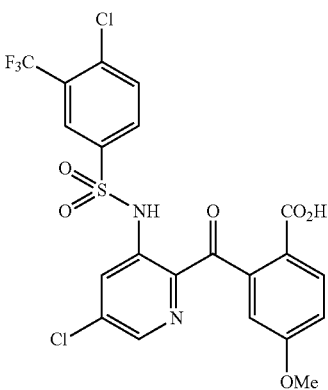 [SMILES: COc1ccc(C(=O)O)c(C(=O)c2ncc(Cl)cc2NS(=O)(=O)c2ccc(Cl)c(C(F)(F)F)c2)c1]
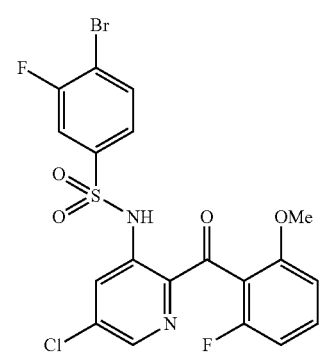 [SMILES: COc1cccc(F)c1C(=O)c1ncc(Cl)cc1NS(=O)(=O)c1ccc(Br)c(F)c1]
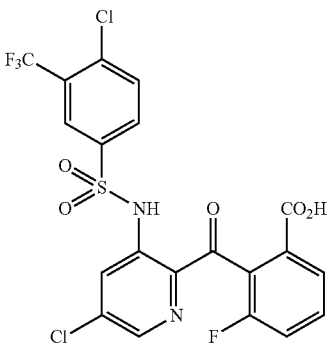
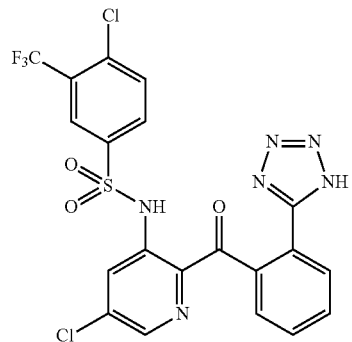 [SMILES: O=C(c1ccccc1-c1nnn[nH]1)c1ncc(Cl)cc1NS(=O)(=O)c1ccc(Cl)c(C(F)(F)F)c1]
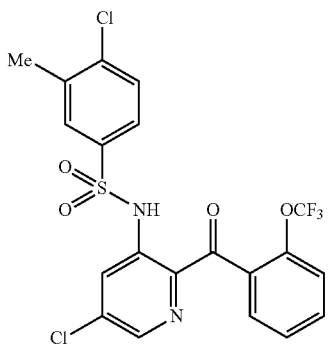
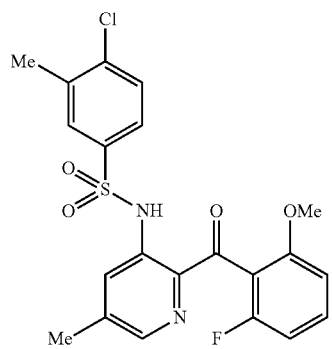 [SMILES: COc1cccc(F)c1C(=O)c1ncc(C)cc1NS(=O)(=O)c1ccc(Cl)c(C)c1]

503
TABLE 1-continued
Compounds with CCR2 activity in one of the chemotaxis,
binding or calcium mobilization assays, with IC50 < 1000 nM
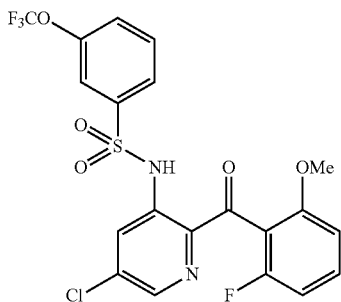 [SMILES: COc1cccc(F)c1C(=O)c1ncc(Cl)cc1NS(=O)(=O)c1cccc(OC(F)(F)F)c1]
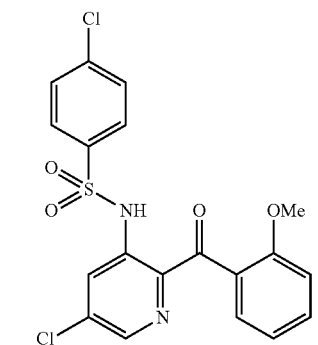 [SMILES: COc1ccccc1C(=O)c1ncc(Cl)cc1NS(=O)(=O)c1ccc(Cl)cc1]
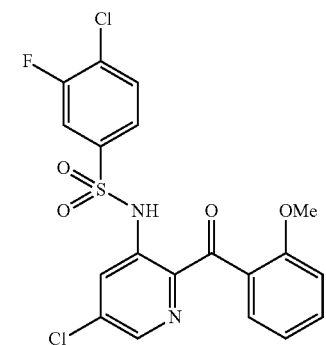 [SMILES: COc1ccccc1C(=O)c1ncc(Cl)cc1NS(=O)(=O)c1ccc(Cl)c(F)c1]
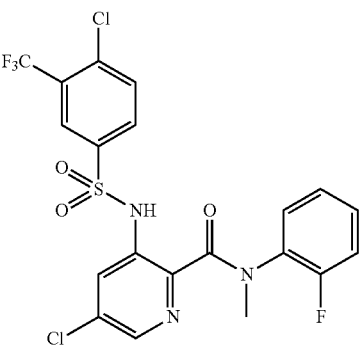
504
TABLE 1-continued
Compounds with CCR2 activity in one of the chemotaxis,
binding or calcium mobilization assays, with IC50 < 1000 nM
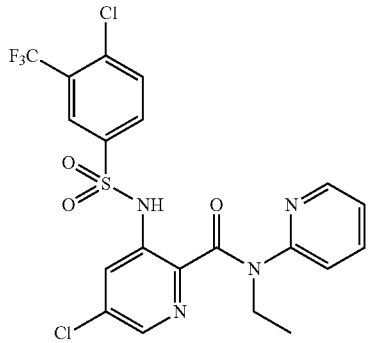 [SMILES: CCN(C(=O)c1ncc(Cl)cc1NS(=O)(=O)c1ccc(Cl)c(C(F)(F)F)c1)c1ccccn1]
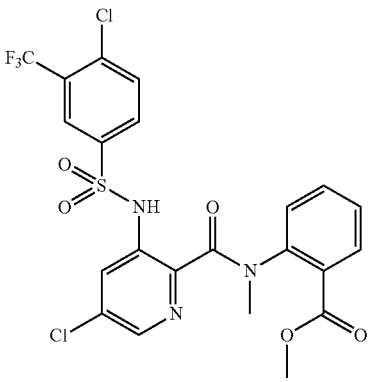 [SMILES: COC(=O)c1ccccc1N(C)C(=O)c1ncc(Cl)cc1NS(=O)(=O)c1ccc(Cl)c(C(F)(F)F)c1]
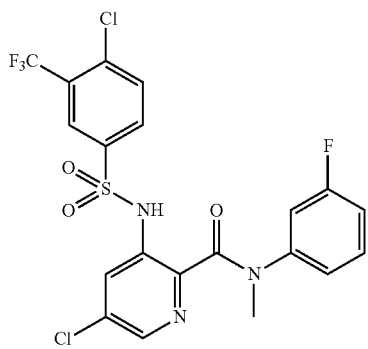 [SMILES: CN(C(=O)c1ncc(Cl)cc1NS(=O)(=O)c1ccc(Cl)c(C(F)(F)F)c1)c1cccc(F)c1]
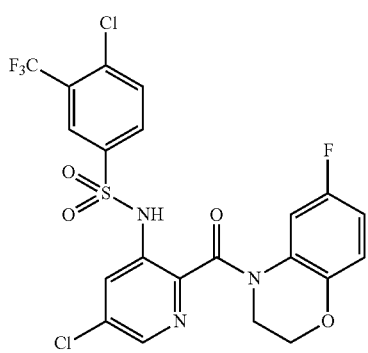 [SMILES: O=C(c1ncc(Cl)cc1NS(=O)(=O)c1ccc(Cl)c(C(F)(F)F)c1)N1CCOc2ccc(F)cc21]

TABLE 1-continued
Compounds with CCR2 activity in one of the chemotaxis, binding or calcium mobilization assays, with IC50 < 1000 nM
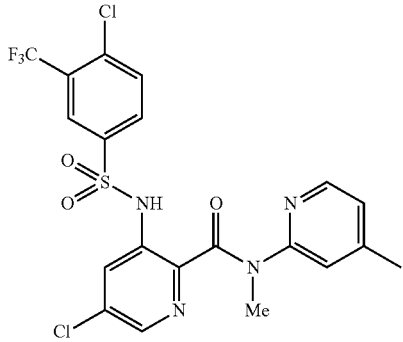 [SMILES: Cc1ccnc(N(C)C(=O)c2ncc(Cl)cc2NS(=O)(=O)c2ccc(Cl)c(C(F)(F)F)c2)c1]
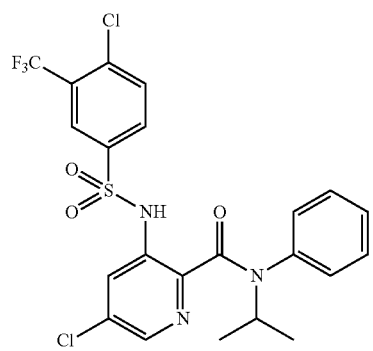 [SMILES: CC(C)N(C(=O)c1ncc(Cl)cc1NS(=O)(=O)c1ccc(Cl)c(C(F)(F)F)c1)c1ccccc1]
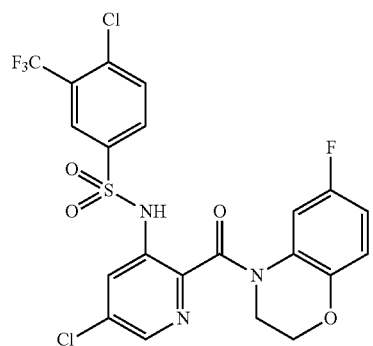 [SMILES: O=C(c1ncc(Cl)cc1NS(=O)(=O)c1ccc(Cl)c(C(F)(F)F)c1)N1CCOc2ccc(F)cc21]
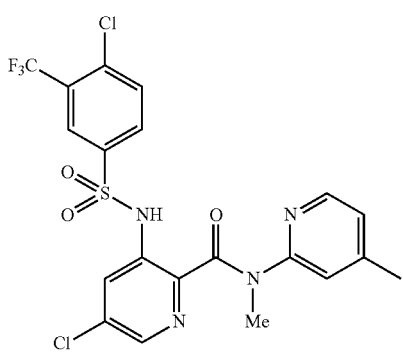 [SMILES: Cc1ccnc(N(C)C(=O)c2ncc(Cl)cc2NS(=O)(=O)c2ccc(Cl)c(C(F)(F)F)c2)c1]
TABLE 1-continued
Compounds with CCR2 activity in one of the chemotaxis, binding or calcium mobilization assays, with IC50 < 1000 nM
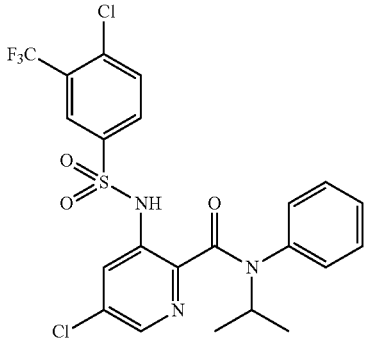
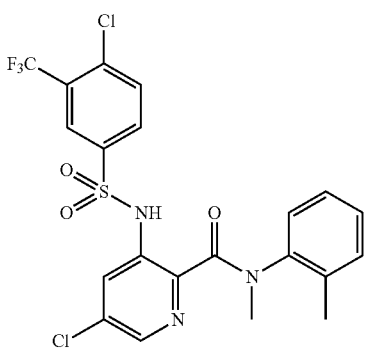 [SMILES: Cc1ccccc1N(C)C(=O)c1ncc(Cl)cc1NS(=O)(=O)c1ccc(Cl)c(C(F)(F)F)c1]
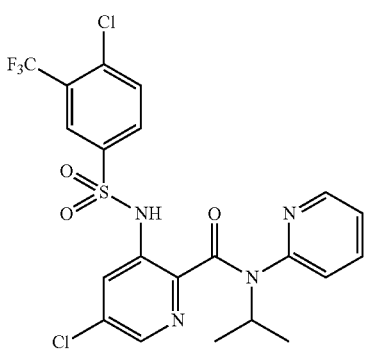 [SMILES: CC(C)N(C(=O)c1ncc(Cl)cc1NS(=O)(=O)c1ccc(Cl)c(C(F)(F)F)c1)c1ccccn1]
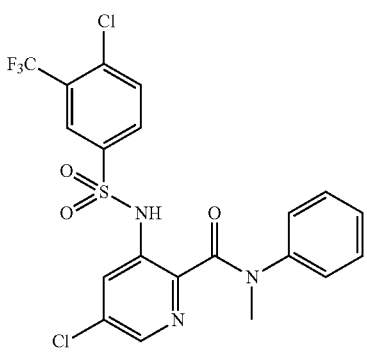 [SMILES: CN(C(=O)c1ncc(Cl)cc1NS(=O)(=O)c1ccc(Cl)c(C(F)(F)F)c1)c1ccccc1]

TABLE 1-continued
Compounds with CCR2 activity in one of the chemotaxis, binding or calcium mobilization assays, with IC50 < 1000 nM
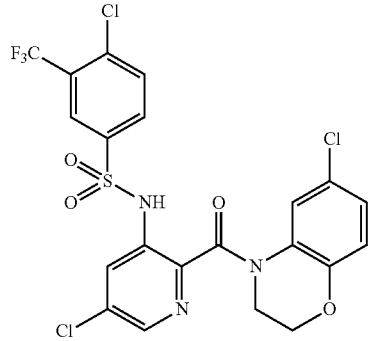
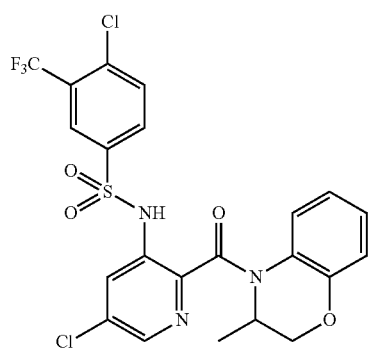
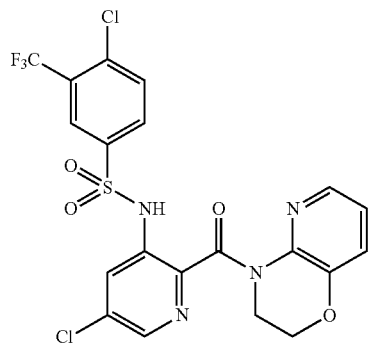 [SMILES: O=C(c1ncc(Cl)cc1NS(=O)(=O)c1ccc(Cl)c(C(F)(F)F)c1)N1CCOc2cccnc21]
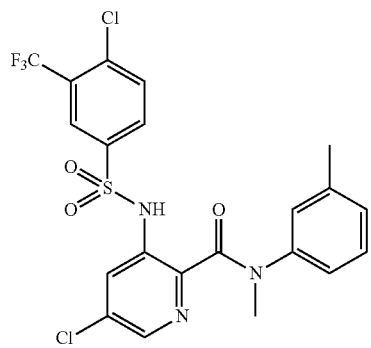
TABLE 1-continued
Compounds with CCR2 activity in one of the chemotaxis, binding or calcium mobilization assays, with IC50 < 1000 nM
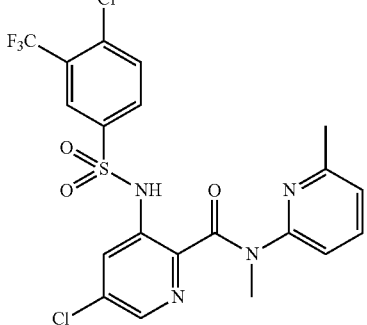
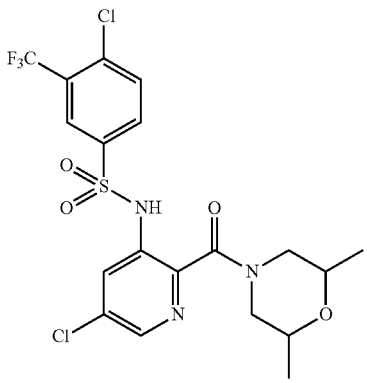 [SMILES: CC1CN(C(=O)c2ncc(Cl)cc2NS(=O)(=O)c2ccc(Cl)c(C(F)(F)F)c2)CC(C)O1]
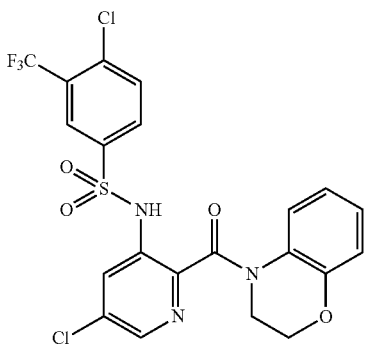 [SMILES: O=C(c1ncc(Cl)cc1NS(=O)(=O)c1ccc(Cl)c(C(F)(F)F)c1)N1CCOc2ccccc21]
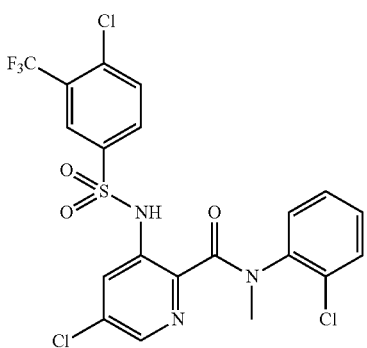

TABLE 1-continued
Compounds with CCR2 activity in one of the chemotaxis, binding or calcium mobilization assays, with IC50 < 1000 nM
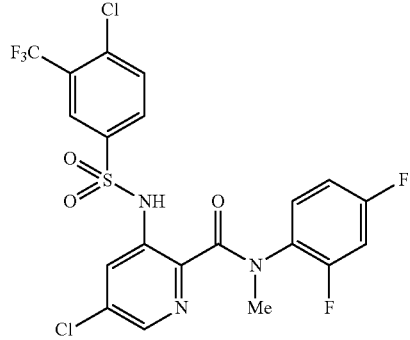 [SMILES: CN(C(=O)c1ncc(Cl)cc1NS(=O)(=O)c1ccc(Cl)c(C(F)(F)F)c1)c1ccc(F)cc1F]
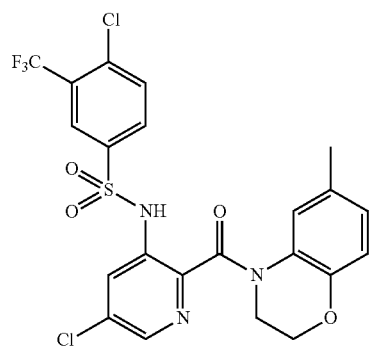
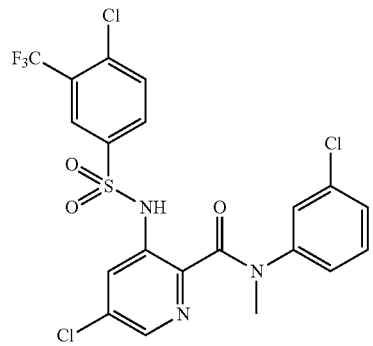
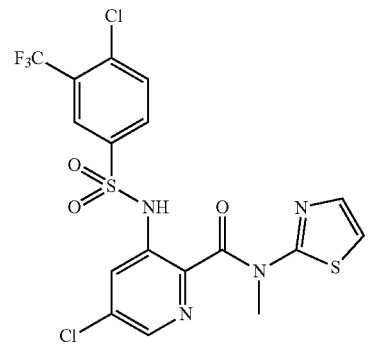 [SMILES: CN(C(=O)c1ncc(Cl)cc1NS(=O)(=O)c1ccc(Cl)c(C(F)(F)F)c1)c1nccs1]
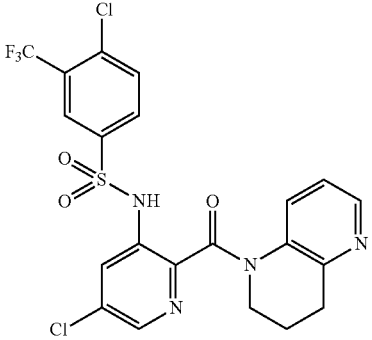 [SMILES: O=C(c1ncc(Cl)cc1NS(=O)(=O)c1ccc(Cl)c(C(F)(F)F)c1)N1CCCc2ncccc21]
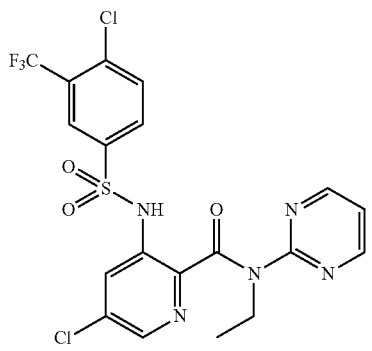 [SMILES: CCN(C(=O)c1ncc(Cl)cc1NS(=O)(=O)c1ccc(Cl)c(C(F)(F)F)c1)c1ncccn1]
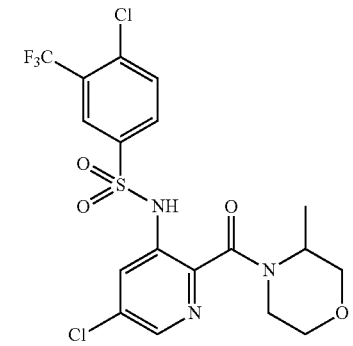
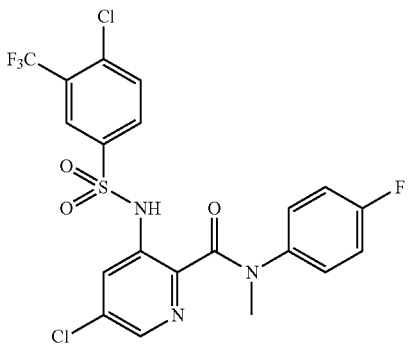 [SMILES: CN(C(=O)c1ncc(Cl)cc1NS(=O)(=O)c1ccc(Cl)c(C(F)(F)F)c1)c1ccc(F)cc1]

TABLE 1-continued
Compounds with CCR2 activity in one of the chemotaxis, binding or calcium mobilization assays, with IC50 < 1000 nM
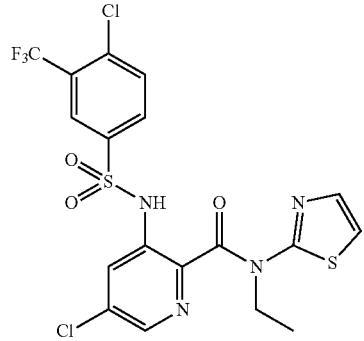 [SMILES: CCN(C(=O)c1ncc(Cl)cc1NS(=O)(=O)c1ccc(Cl)c(C(F)(F)F)c1)c1nccs1]
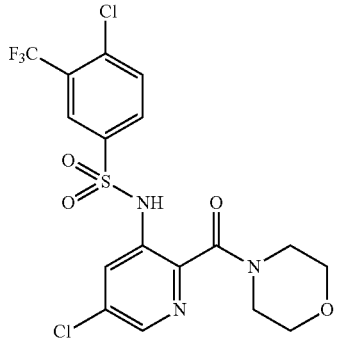
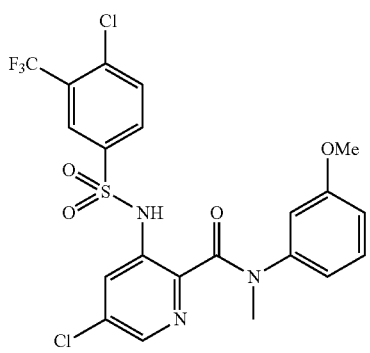 [SMILES: COc1cccc(N(C)C(=O)c2ncc(Cl)cc2NS(=O)(=O)c2ccc(Cl)c(C(F)(F)F)c2)c1]
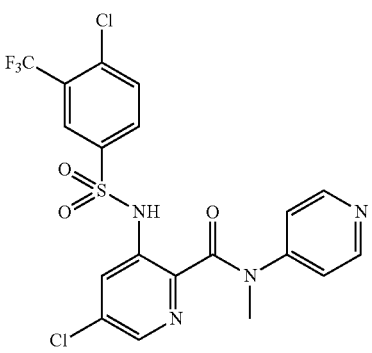
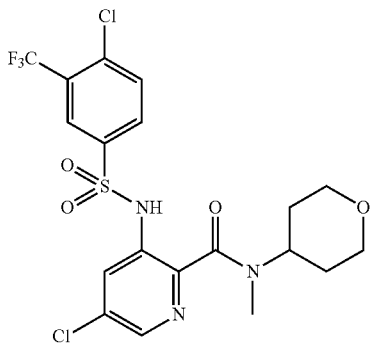 [SMILES: CN(C(=O)c1ncc(Cl)cc1NS(=O)(=O)c1ccc(Cl)c(C(F)(F)F)c1)C1CCOCC1]
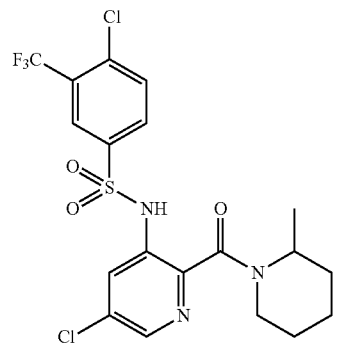
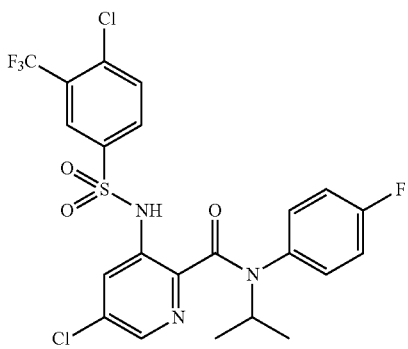 [SMILES: CC(C)N(C(=O)c1ncc(Cl)cc1NS(=O)(=O)c1ccc(Cl)c(C(F)(F)F)c1)c1ccc(F)cc1]
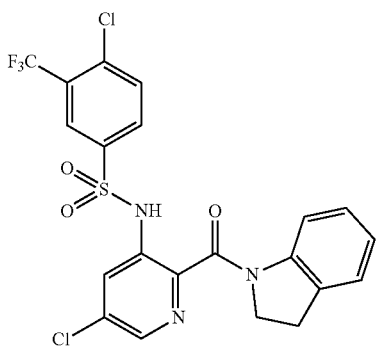 [SMILES: O=C(c1ncc(Cl)cc1NS(=O)(=O)c1ccc(Cl)c(C(F)(F)F)c1)N1CCc2ccccc21]

TABLE 1-continued
Compounds with CCR2 activity in one of the chemotaxis, binding or calcium mobilization assays, with IC50 < 1000 nM
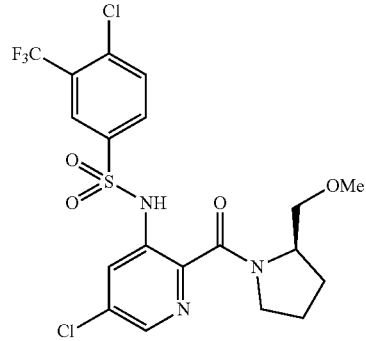 [SMILES: COC[C@H]1CCCN1C(=O)c1ncc(Cl)cc1NS(=O)(=O)c1ccc(Cl)c(C(F)(F)F)c1]
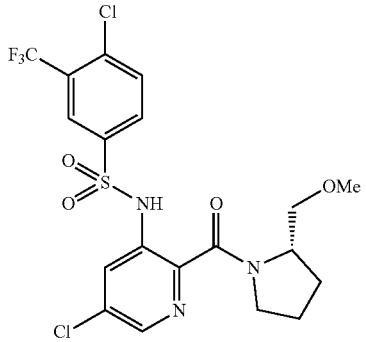
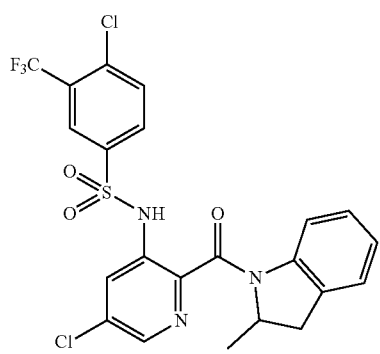 [SMILES: CC1Cc2ccccc2N1C(=O)c1ncc(Cl)cc1NS(=O)(=O)c1ccc(Cl)c(C(F)(F)F)c1]
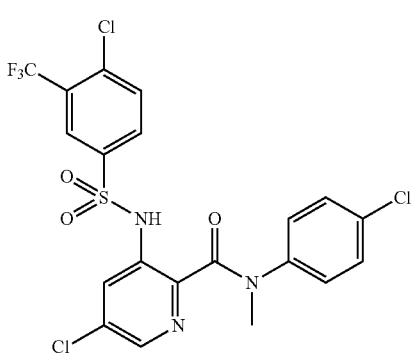
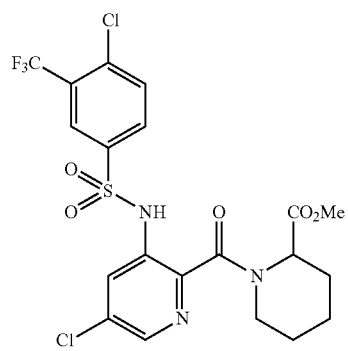 [SMILES: COC(=O)C1CCCCN1C(=O)c1ncc(Cl)cc1NS(=O)(=O)c1ccc(Cl)c(C(F)(F)F)c1]
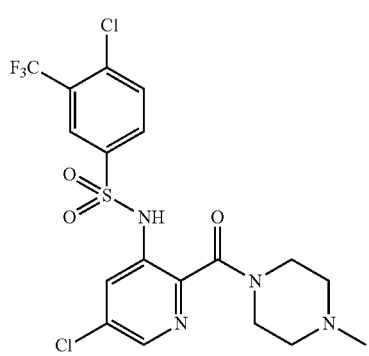
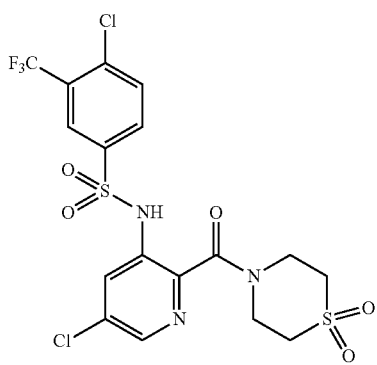 [SMILES: O=C(c1ncc(Cl)cc1NS(=O)(=O)c1ccc(Cl)c(C(F)(F)F)c1)N1CCS(=O)(=O)CC1]
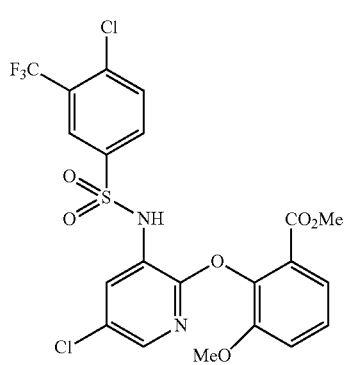 [SMILES: COC(=O)c1cccc(OC)c1Oc1ncc(Cl)cc1NS(=O)(=O)c1ccc(Cl)c(C(F)(F)F)c1]

TABLE 1-continued
Compounds with CCR2 activity in one of the chemotaxis, binding or calcium mobilization assays, with IC50 < 1000 nM
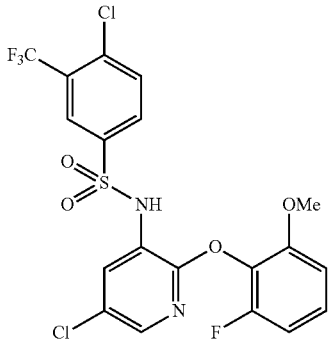 [SMILES: COc1cccc(F)c1Oc1ncc(Cl)cc1NS(=O)(=O)c1ccc(Cl)c(C(F)(F)F)c1]
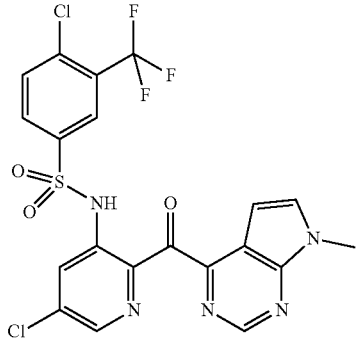
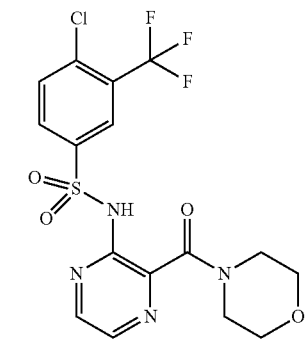 [SMILES: O=C(c1nccnc1NS(=O)(=O)c1ccc(Cl)c(C(F)(F)F)c1)N1CCOCC1]
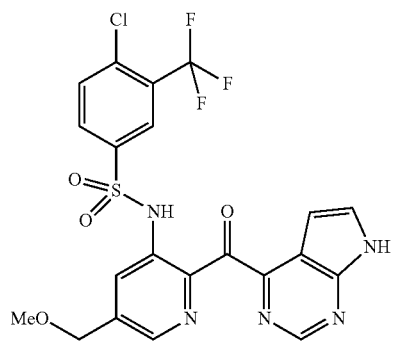
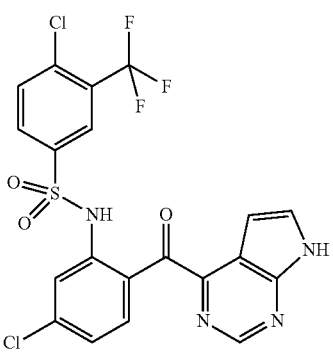 [SMILES: O=C(c1ccc(Cl)cc1NS(=O)(=O)c1ccc(Cl)c(C(F)(F)F)c1)c1ncnc2[nH]ccc12]
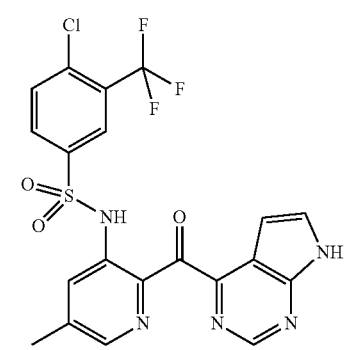
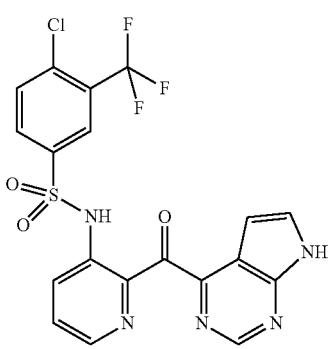 [SMILES: O=C(c1ncccc1NS(=O)(=O)c1ccc(Cl)c(C(F)(F)F)c1)c1ncnc2[nH]ccc12]
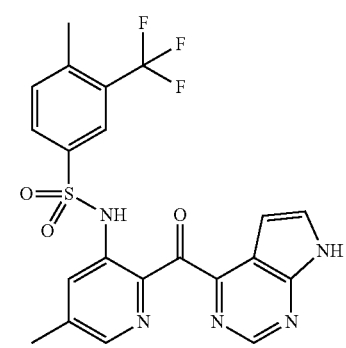 [SMILES: Cc1cnc(C(=O)c2ncnc3[nH]ccc23)c(NS(=O)(=O)c2ccc(C)c(C(F)(F)F)c2)c1]

TABLE 1-continued
Compounds with CCR2 activity in one of the chemotaxis, binding or calcium mobilization assays, with IC50 < 1000 nM
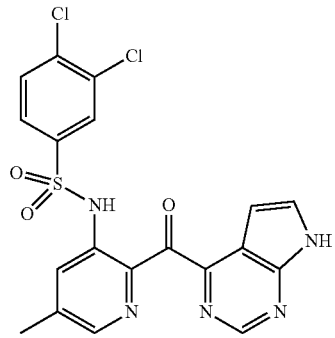 [SMILES: Cc1cnc(C(=O)c2ncnc3[nH]ccc23)c(NS(=O)(=O)c2ccc(Cl)c(Cl)c2)c1]
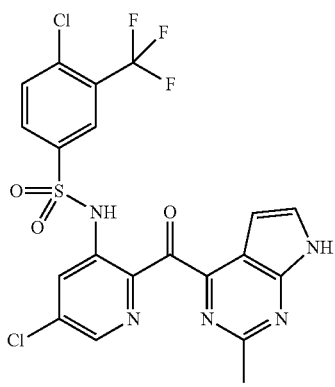 [SMILES: Cc1nc(C(=O)c2ncc(Cl)cc2NS(=O)(=O)c2ccc(Cl)c(C(F)(F)F)c2)c2cc[nH]c2n1]
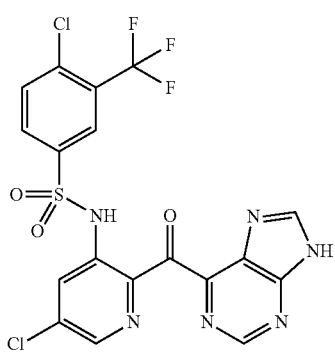 [SMILES: O=C(c1ncc(Cl)cc1NS(=O)(=O)c1ccc(Cl)c(C(F)(F)F)c1)c1ncnc2[nH]cnc12]
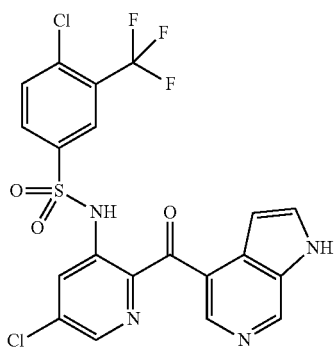 [SMILES: O=C(c1ncc(Cl)cc1NS(=O)(=O)c1ccc(Cl)c(C(F)(F)F)c1)c1cncc2[nH]ccc12]
TABLE 1-continued
Compounds with CCR2 activity in one of the chemotaxis, binding or calcium mobilization assays, with IC50 < 1000 nM
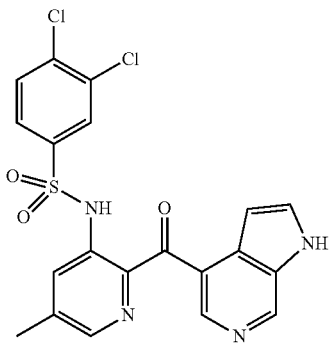 [SMILES: Cc1cnc(C(=O)c2cncc3[nH]ccc23)c(NS(=O)(=O)c2ccc(Cl)c(Cl)c2)c1]
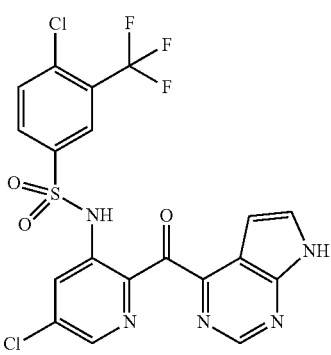 [SMILES: O=C(c1ncc(Cl)cc1NS(=O)(=O)c1ccc(Cl)c(C(F)(F)F)c1)c1ncnc2[nH]ccc12]
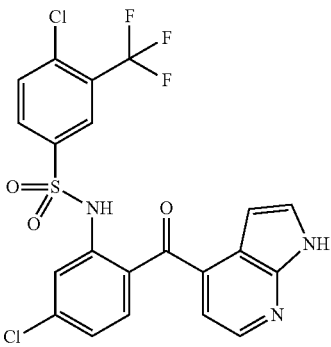 [SMILES: O=C(c1ccc(Cl)cc1NS(=O)(=O)c1ccc(Cl)c(C(F)(F)F)c1)c1ccnc2[nH]ccc12]
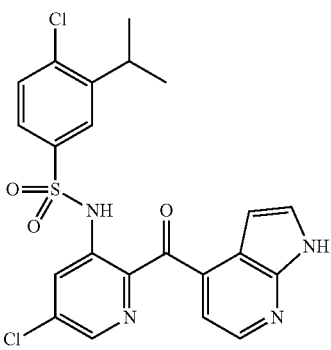 [SMILES: CC(C)c1cc(S(=O)(=O)Nc2cc(Cl)cnc2C(=O)c2ccnc3[nH]ccc23)ccc1Cl]

TABLE 1-continued
Compounds with CCR2 activity in one of the chemotaxis, binding or calcium mobilization assays, with IC50 < 1000 nM
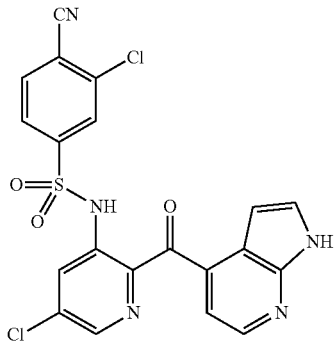 [SMILES: N#Cc1ccc(S(=O)(=O)Nc2cc(Cl)cnc2C(=O)c2ccnc3[nH]ccc23)cc1Cl]
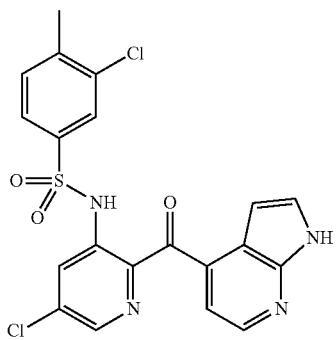 [SMILES: Cc1ccc(S(=O)(=O)Nc2cc(Cl)cnc2C(=O)c2ccnc3[nH]ccc23)cc1Cl]
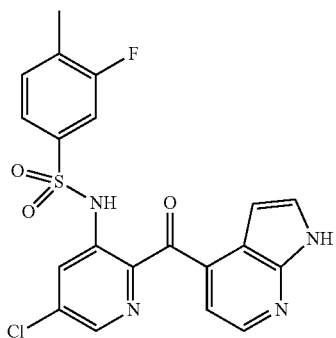 [SMILES: Cc1ccc(S(=O)(=O)Nc2cc(Cl)cnc2C(=O)c2ccnc3[nH]ccc23)cc1F]
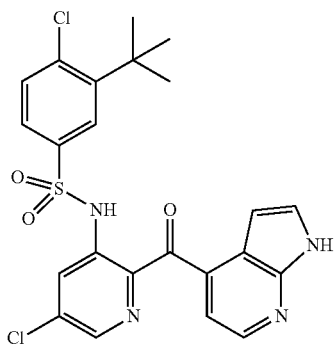 [SMILES: CC(C)(C)c1cc(S(=O)(=O)Nc2cc(Cl)cnc2C(=O)c2ccnc3[nH]ccc23)ccc1Cl]
TABLE 1-continued
Compounds with CCR2 activity in one of the chemotaxis, binding or calcium mobilization assays, with IC50 < 1000 nM
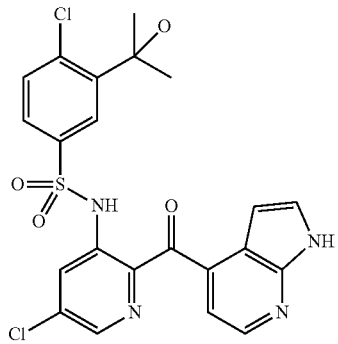 [SMILES: CC(C)(O)c1cc(S(=O)(=O)Nc2cc(Cl)cnc2C(=O)c2ccnc3[nH]ccc23)ccc1Cl]
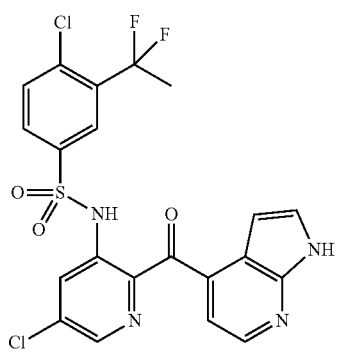 [SMILES: CC(F)(F)c1cc(S(=O)(=O)Nc2cc(Cl)cnc2C(=O)c2ccnc3[nH]ccc23)ccc1Cl]
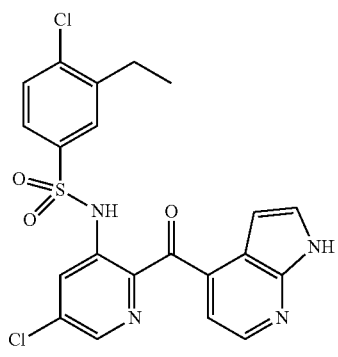
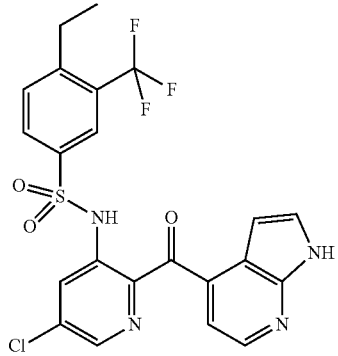 [SMILES: CCc1ccc(S(=O)(=O)Nc2cc(Cl)cnc2C(=O)c2ccnc3[nH]ccc23)cc1C(F)(F)F]

TABLE 1-continued
Compounds with CCR2 activity in one of the chemotaxis, binding or calcium mobilization assays, with IC50 < 1000 nM
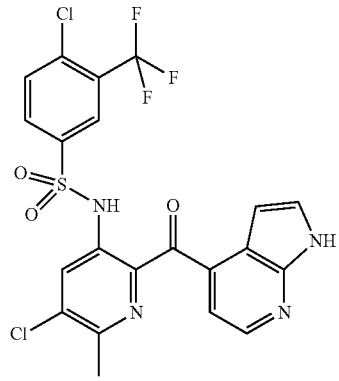 [SMILES: Cc1nc(C(=O)c2ccnc3[nH]ccc23)c(NS(=O)(=O)c2ccc(Cl)c(C(F)(F)F)c2)cc1Cl]
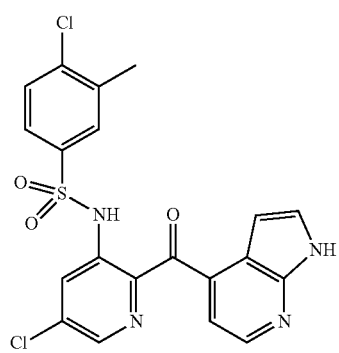 [SMILES: Cc1cc(S(=O)(=O)Nc2cc(Cl)cnc2C(=O)c2ccnc3[nH]ccc23)ccc1Cl]
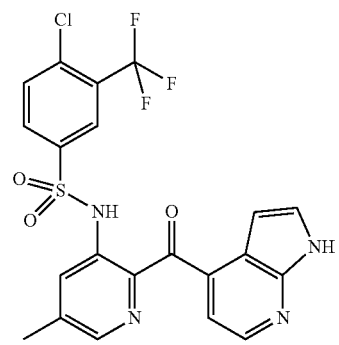
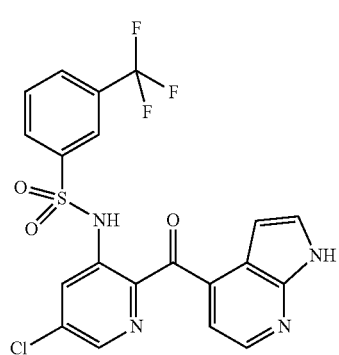 [SMILES: O=C(c1ncc(Cl)cc1NS(=O)(=O)c1cccc(C(F)(F)F)c1)c1ccnc2[nH]ccc12]
TABLE 1-continued
Compounds with CCR2 activity in one of the chemotaxis, binding or calcium mobilization assays, with IC50 < 1000 nM
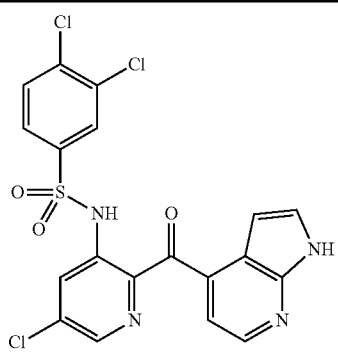
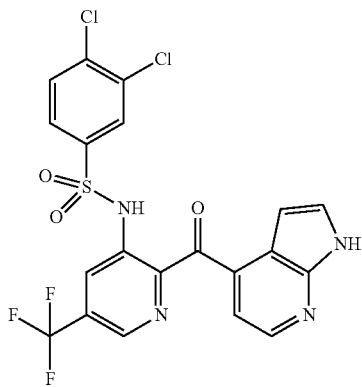 [SMILES: O=C(c1ncc(C(F)(F)F)cc1NS(=O)(=O)c1ccc(Cl)c(Cl)c1)c1ccnc2[nH]ccc12]
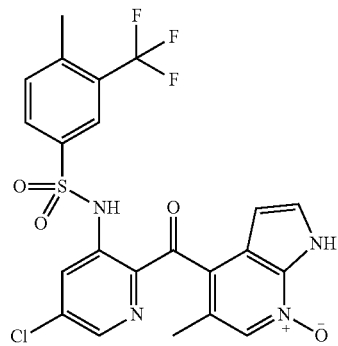
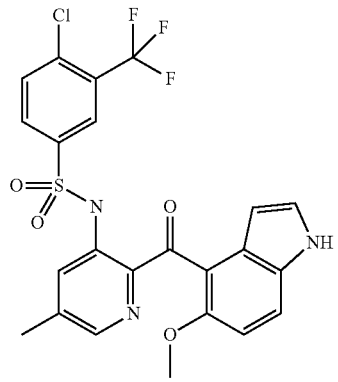 [SMILES: COc1ccc2[nH]ccc2c1C(=O)c1ncc(C)cc1NS(=O)(=O)c1ccc(Cl)c(C(F)(F)F)c1]

TABLE 1-continued
Compounds with CCR2 activity in one of the chemotaxis,
binding or calcium mobilization assays, with IC50 < 1000 nM
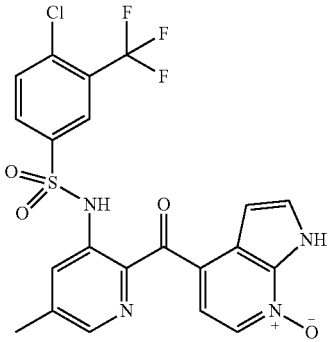
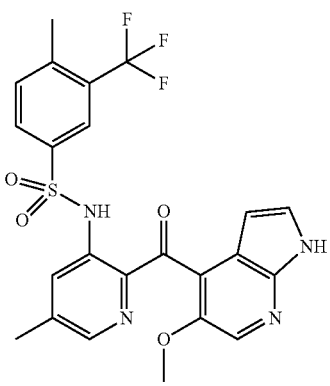 [SMILES: COc1cnc2[nH]ccc2c1C(=O)c1ncc(C)cc1NS(=O)(=O)c1ccc(C)c(C(F)(F)F)c1]
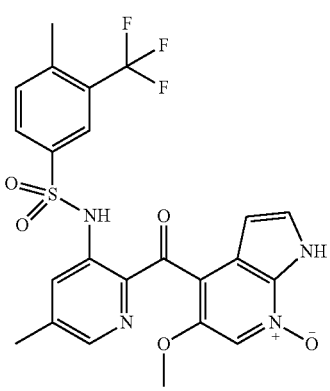
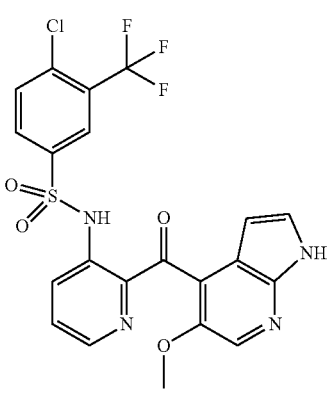 [SMILES: COc1cnc2[nH]ccc2c1C(=O)c1ncccc1NS(=O)(=O)c1ccc(Cl)c(C(F)(F)F)c1]
TABLE 1-continued
Compounds with CCR2 activity in one of the chemotaxis,
binding or calcium mobilization assays, with IC50 < 1000 nM
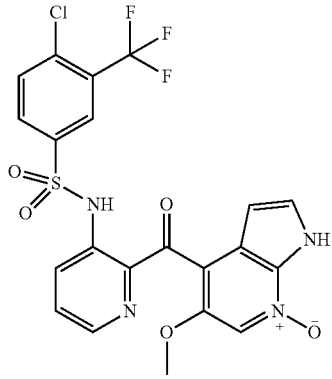
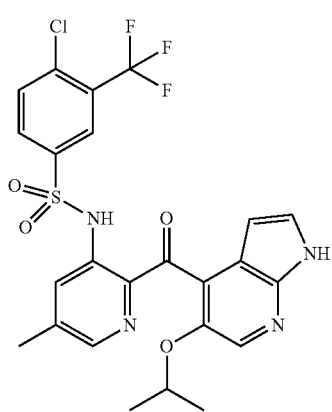 [SMILES: Cc1cnc(C(=O)c2c(OC(C)C)cnc3[nH]ccc23)c(NS(=O)(=O)c2ccc(Cl)c(C(F)(F)F)c2)c1]
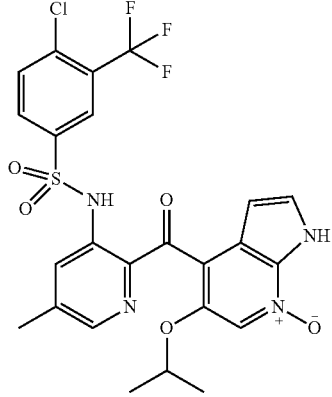
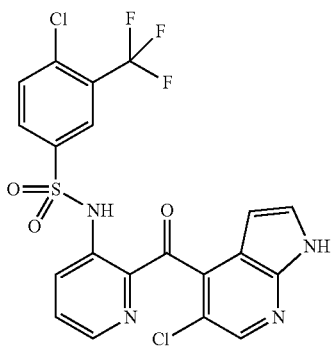 [SMILES: O=C(c1ncccc1NS(=O)(=O)c1ccc(Cl)c(C(F)(F)F)c1)c1c(Cl)cnc2[nH]ccc12]

TABLE 1-continued
Compounds with CCR2 activity in one of the chemotaxis, binding or calcium mobilization assays, with IC50 < 1000 nM
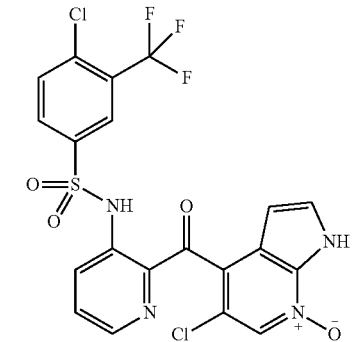
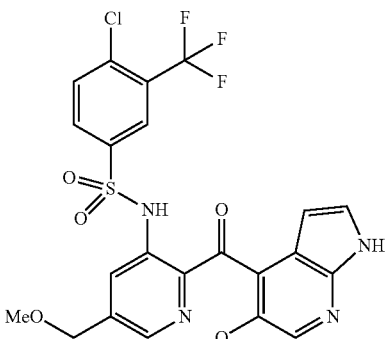
TABLE 2
Compounds with CCR9 activity in one of the chemotaxis, binding or calcium mobilization assays, with 1050 <1000 nM
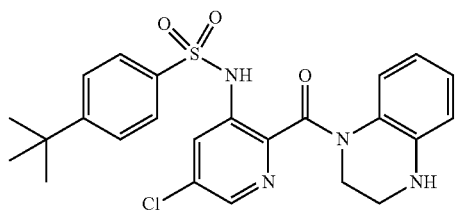 [SMILES: CC(C)(C)c1ccc(S(=O)(=O)Nc2cc(Cl)cnc2C(=O)N2CCNc3ccccc32)cc1]
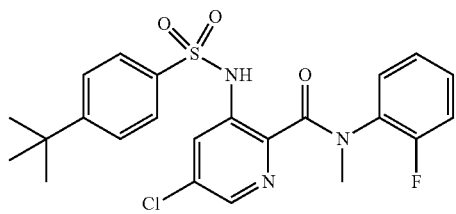 [SMILES: CN(C(=O)c1ncc(Cl)cc1NS(=O)(=O)c1ccc(C(C)(C)C)cc1)c1ccccc1F]
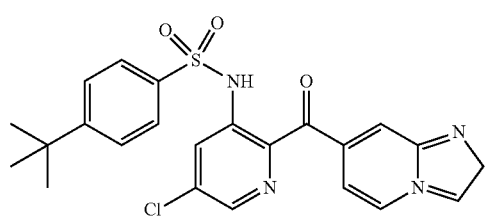
TABLE 2-continued
Compounds with CCR9 activity in one of the chemotaxis, binding or calcium mobilization assays, with 1050 <1000 nM
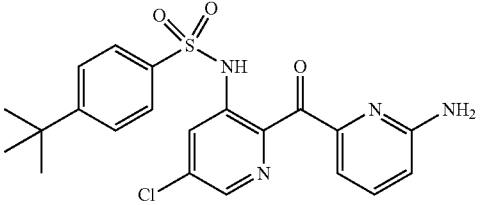 [SMILES: CC(C)(C)c1ccc(S(=O)(=O)Nc2cc(Cl)cnc2C(=O)c2cccc(N)n2)cc1]
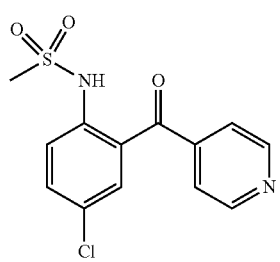 [SMILES: CS(=O)(=O)Nc1ccc(Cl)cc1C(=O)c1ccncc1]
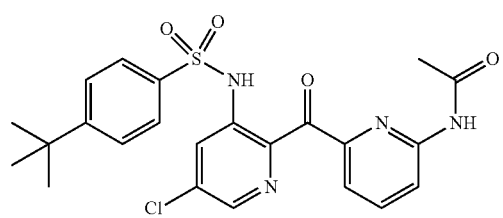 [SMILES: CC(=O)Nc1cccc(C(=O)c2ncc(Cl)cc2NS(=O)(=O)c2ccc(C(C)(C)C)cc2)n1]
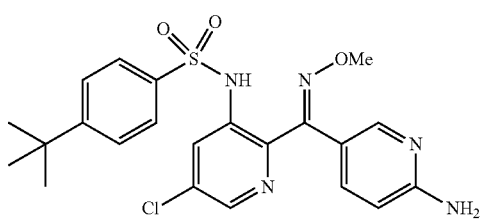 [SMILES: CO/N=C(\c1ccc(N)nc1)c1ncc(Cl)cc1NS(=O)(=O)c1ccc(C(C)(C)C)cc1]
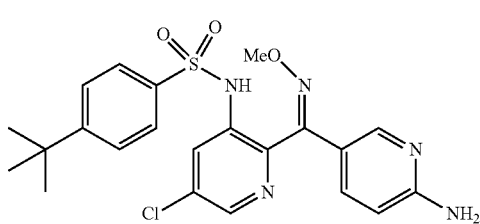 [SMILES: CO/N=C(/c1ccc(N)nc1)c1ncc(Cl)cc1NS(=O)(=O)c1ccc(C(C)(C)C)cc1]
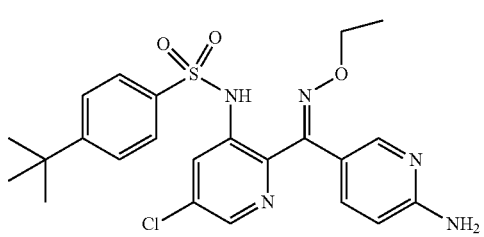

TABLE 2-continued
Compounds with CCR9 activity in one of the chemotaxis, binding or calcium mobilization assays, with IC50 <1000 nM
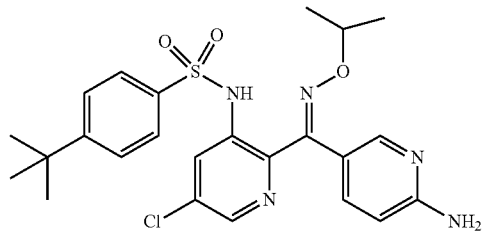 [SMILES: CC(C)O/N=C(\c1ccc(N)nc1)c1ncc(Cl)cc1NS(=O)(=O)c1ccc(C(C)(C)C)cc1]
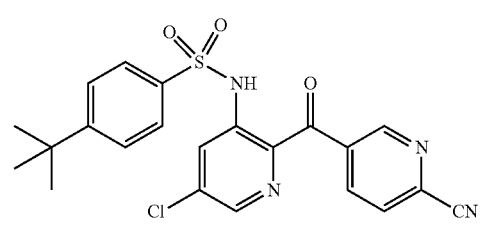 [SMILES: CC(C)(C)c1ccc(S(=O)(=O)Nc2cc(Cl)cnc2C(=O)c2ccc(C#N)nc2)cc1]
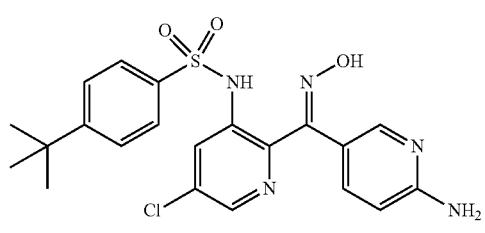 [SMILES: CC(C)(C)c1ccc(S(=O)(=O)Nc2cc(Cl)cnc2/C(=N/O)c2ccc(N)nc2)cc1]
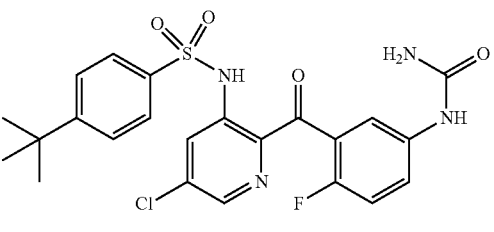 [SMILES: CC(C)(C)c1ccc(S(=O)(=O)Nc2cc(Cl)cnc2C(=O)c2cc(NC(N)=O)ccc2F)cc1]
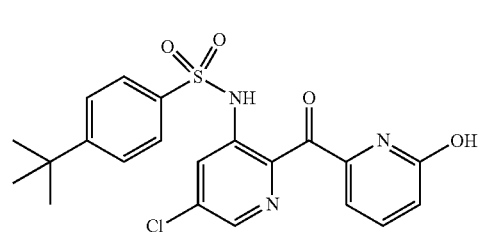 [SMILES: CC(C)(C)c1ccc(S(=O)(=O)Nc2cc(Cl)cnc2C(=O)c2cccc(O)n2)cc1]
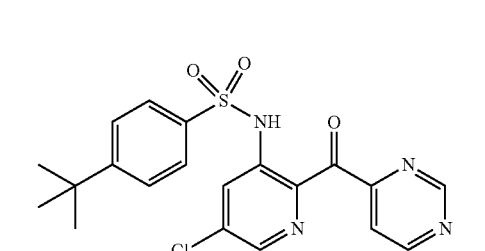
TABLE 2-continued
Compounds with CCR9 activity in one of the chemotaxis, binding or calcium mobilization assays, with IC50 <1000 nM
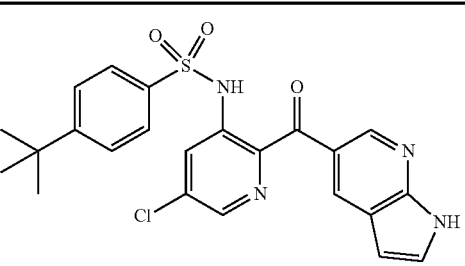
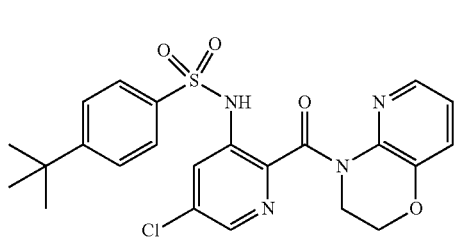 [SMILES: CC(C)(C)c1ccc(S(=O)(=O)Nc2cc(Cl)cnc2C(=O)N2CCOc3cccnc32)cc1]
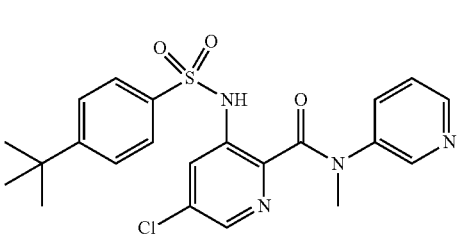 [SMILES: CN(C(=O)c1ncc(Cl)cc1NS(=O)(=O)c1ccc(C(C)(C)C)cc1)c1cccnc1]
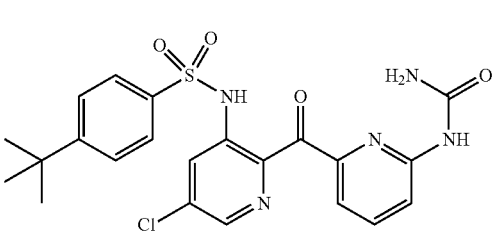 [SMILES: CC(C)(C)c1ccc(S(=O)(=O)Nc2cc(Cl)cnc2C(=O)c2cccc(NC(N)=O)n2)cc1]
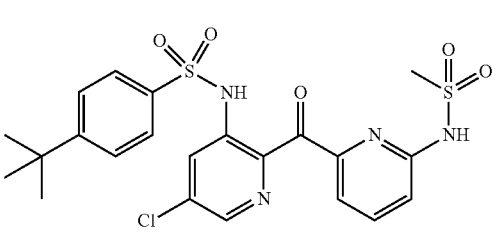 [SMILES: CC(C)(C)c1ccc(S(=O)(=O)Nc2cc(Cl)cnc2C(=O)c2cccc(NS(C)(=O)=O)n2)cc1]
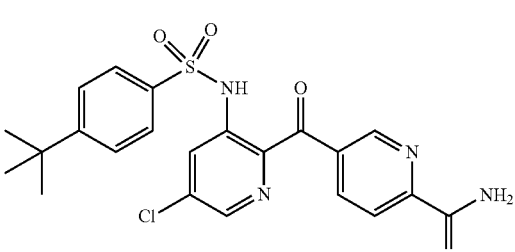

TABLE 2-continued
Compounds with CCR9 activity in one of the chemotaxis, binding or calcium mobilization assays, with IC50 <1000 nM
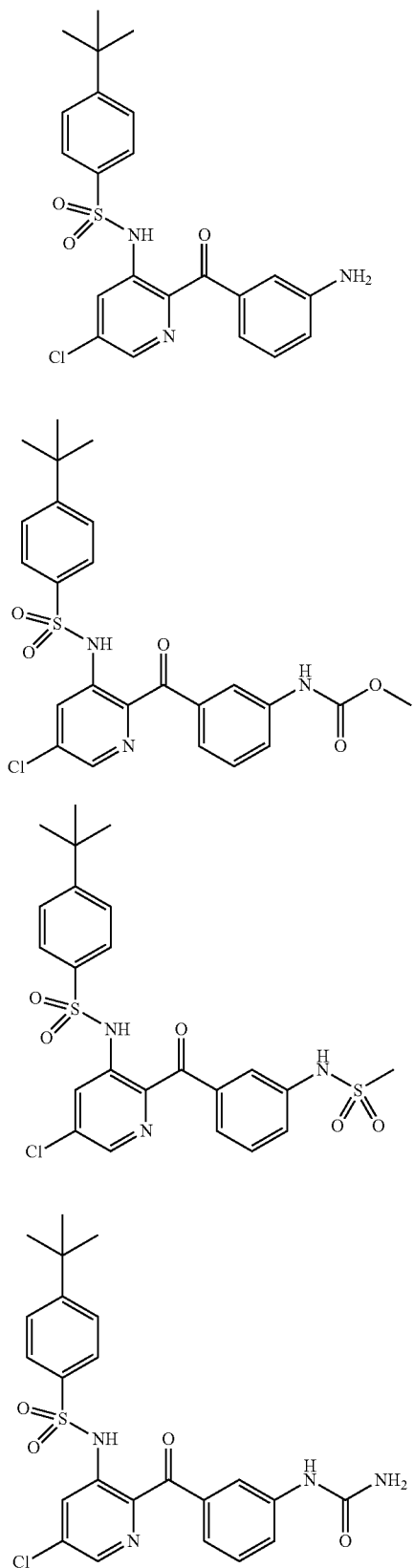
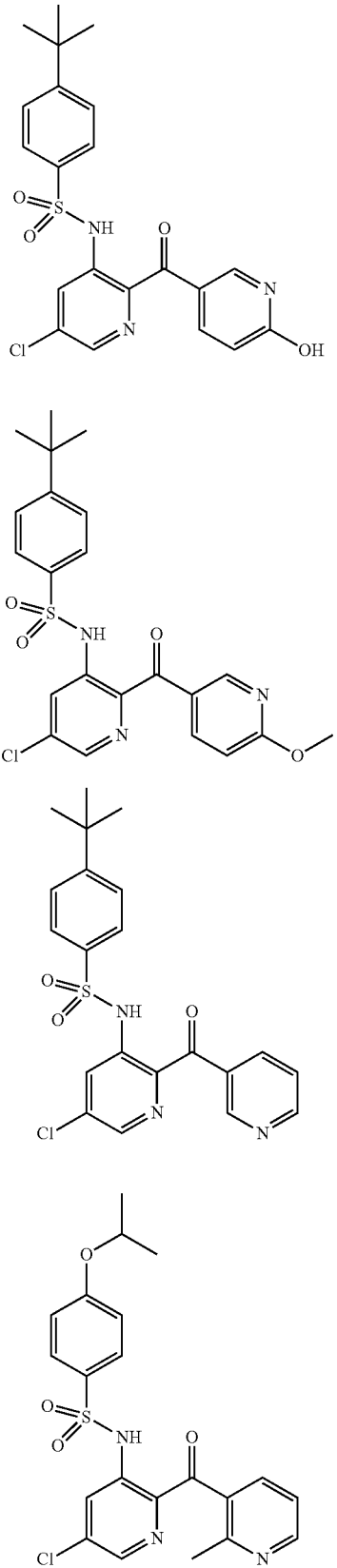

TABLE 2-continued
Compounds with CCR9 activity in one of the chemotaxis, binding or calcium mobilization assays, with 1050 <1000 nM
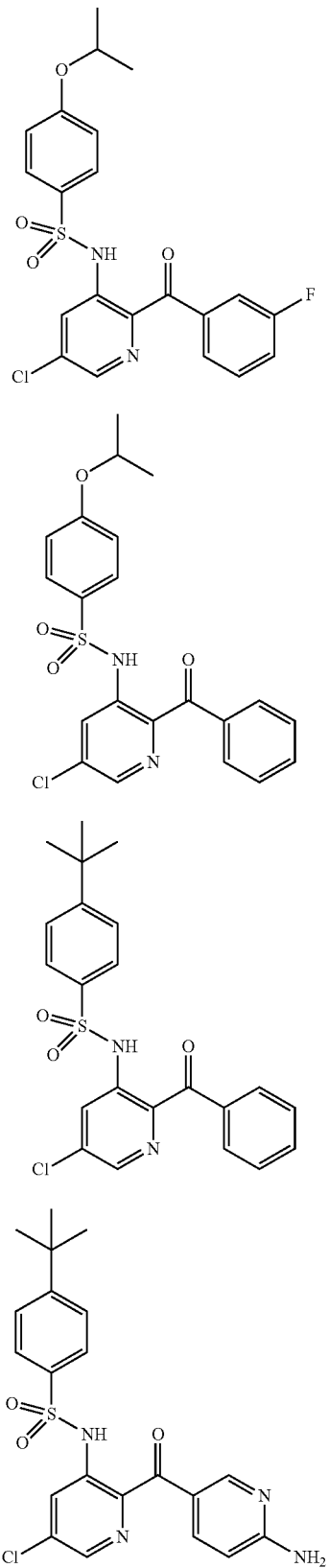
TABLE 2-continued
Compounds with CCR9 activity in one of the chemotaxis, binding or calcium mobilization assays, with 1050 <1000 nM
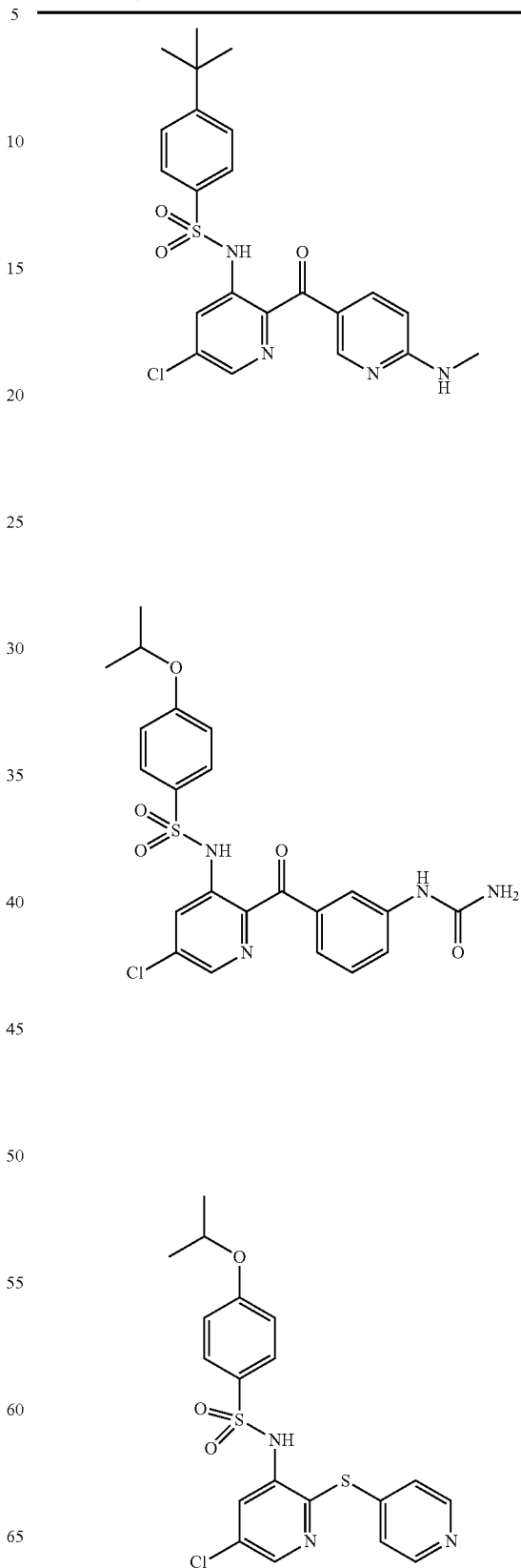

TABLE 2-continued
Compounds with CCR9 activity in one of the chemotaxis, binding or calcium mobilization assays, with 1050 <1000 nM
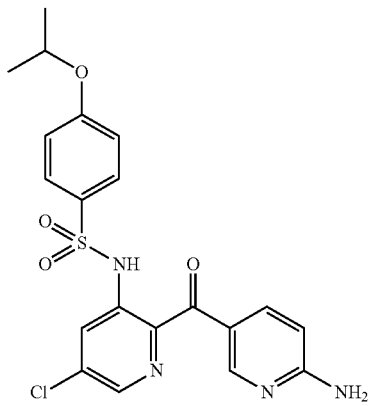 [SMILES: CC(C)Oc1ccc(S(=O)(=O)Nc2cc(Cl)cnc2C(=O)c2ccc(N)nc2)cc1]
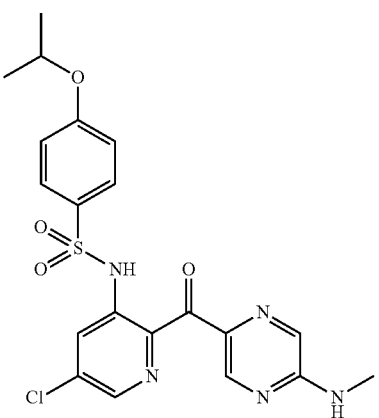 [SMILES: CNc1cnc(C(=O)c2ncc(Cl)cc2NS(=O)(=O)c2ccc(OC(C)C)cc2)cn1]
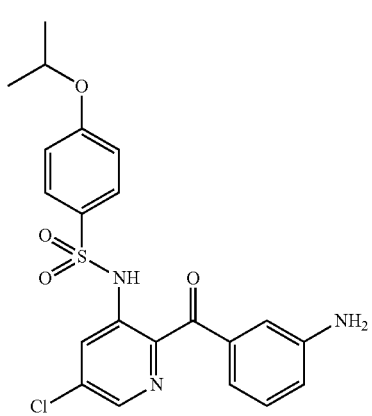 [SMILES: CC(C)Oc1ccc(S(=O)(=O)Nc2cc(Cl)cnc2C(=O)c2cccc(N)c2)cc1]
TABLE 2-continued
Compounds with CCR9 activity in one of the chemotaxis, binding or calcium mobilization assays, with 1050 <1000 nM
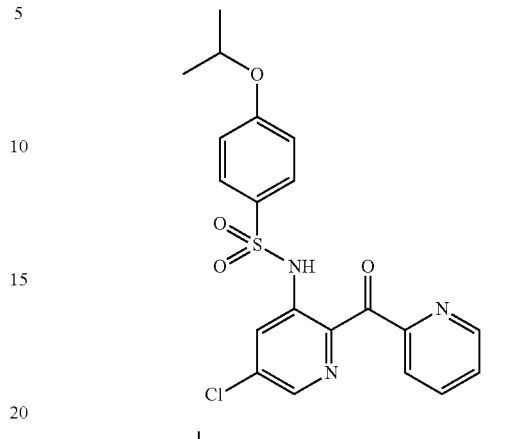
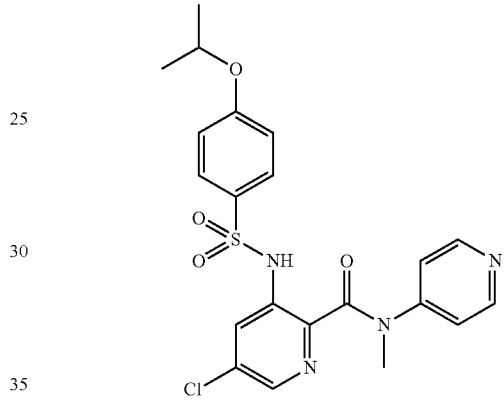
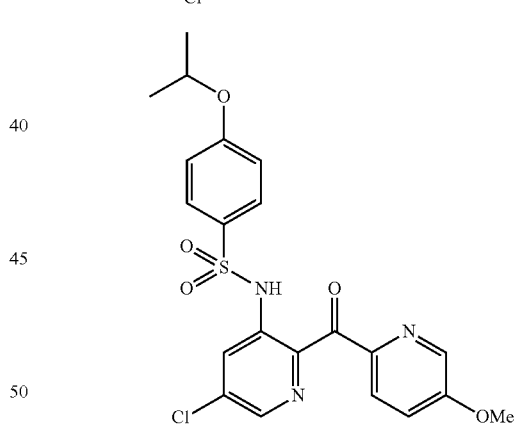
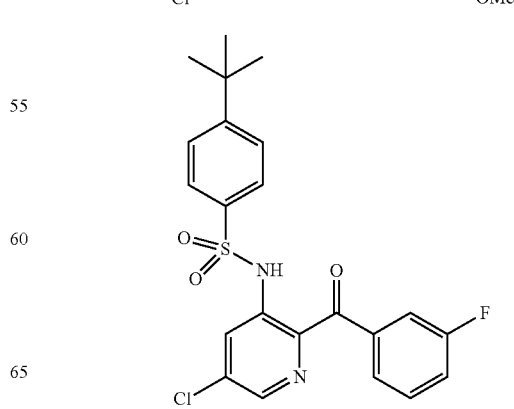

TABLE 2-continued
Compounds with CCR9 activity in one of the chemotaxis, binding or calcium mobilization assays, with 1050 <1000 nM
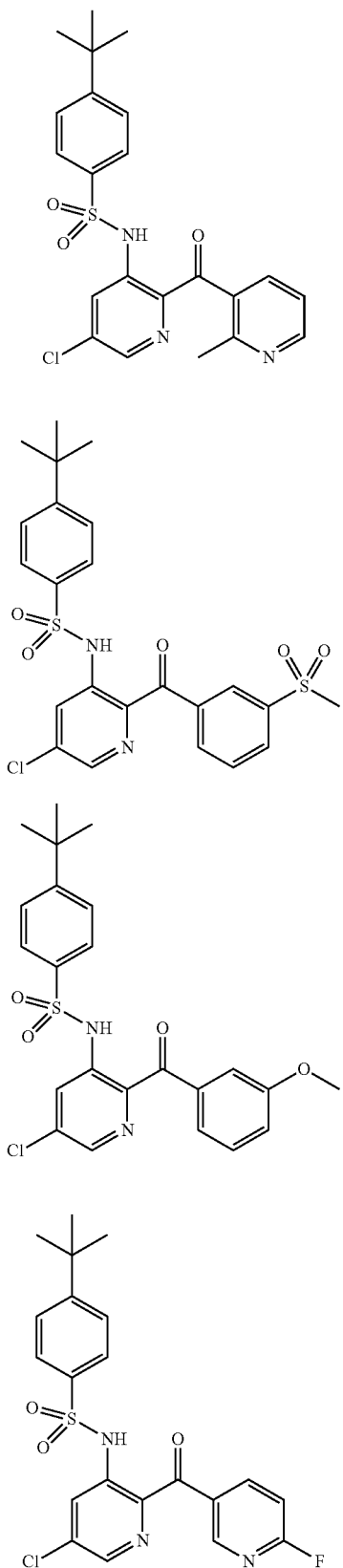
TABLE 2-continued
Compounds with CCR9 activity in one of the chemotaxis, binding or calcium mobilization assays, with 1050 <1000 nM
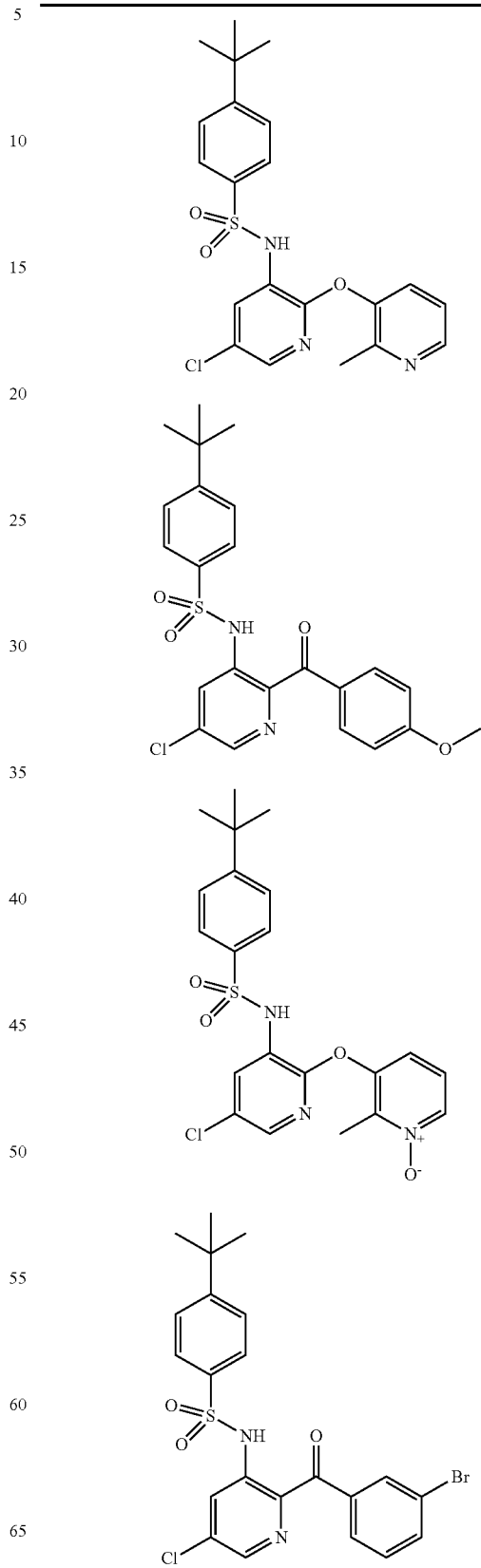

TABLE 2-continued
Compounds with CCR9 activity in one of the chemotaxis, binding or calcium mobilization assays, with I050 <1000 nM
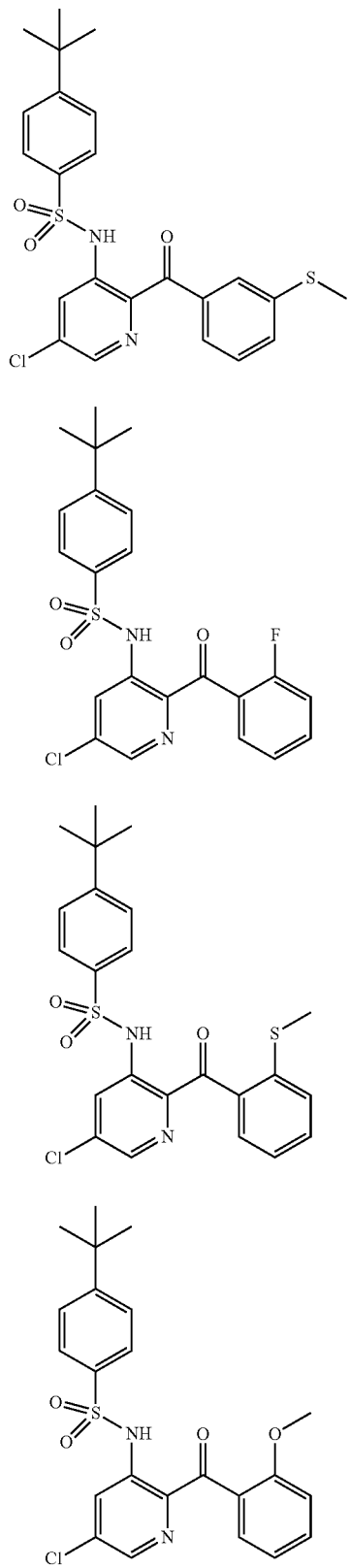
TABLE 2-continued
Compounds with CCR9 activity in one of the chemotaxis, binding or calcium mobilization assays, with I050 <1000 nM
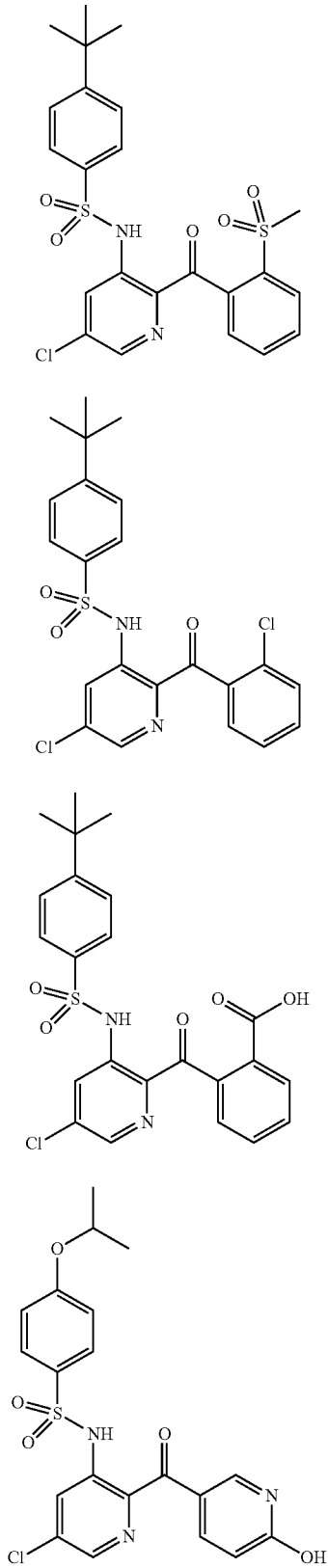

TABLE 2-continued
Compounds with CCR9 activity in one of the chemotaxis, binding or calcium mobilization assays, with I050 <1000 nM
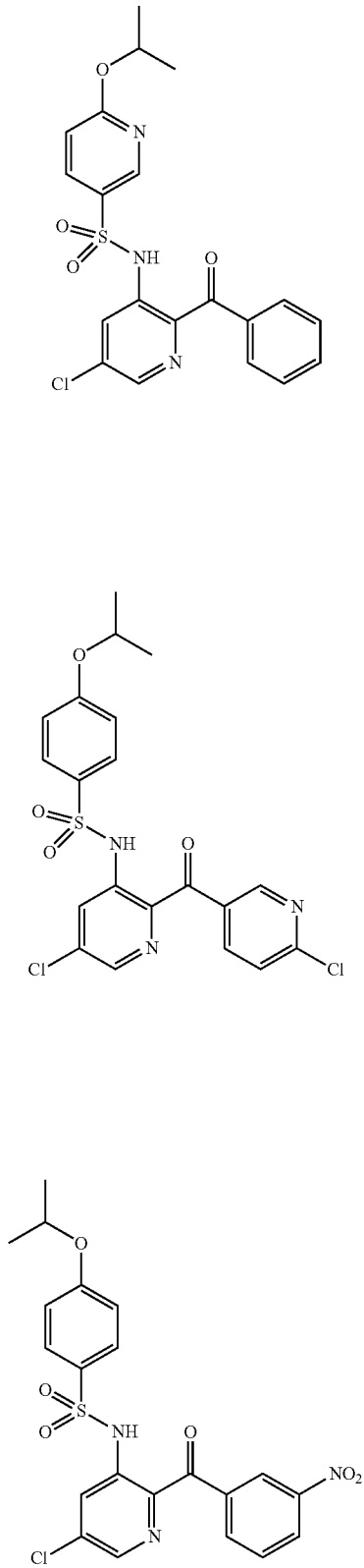

541
TABLE 2-continued
Compounds with CCR9 activity in one of the chemotaxis, binding or calcium mobilization assays, with 1050 <1000 nM
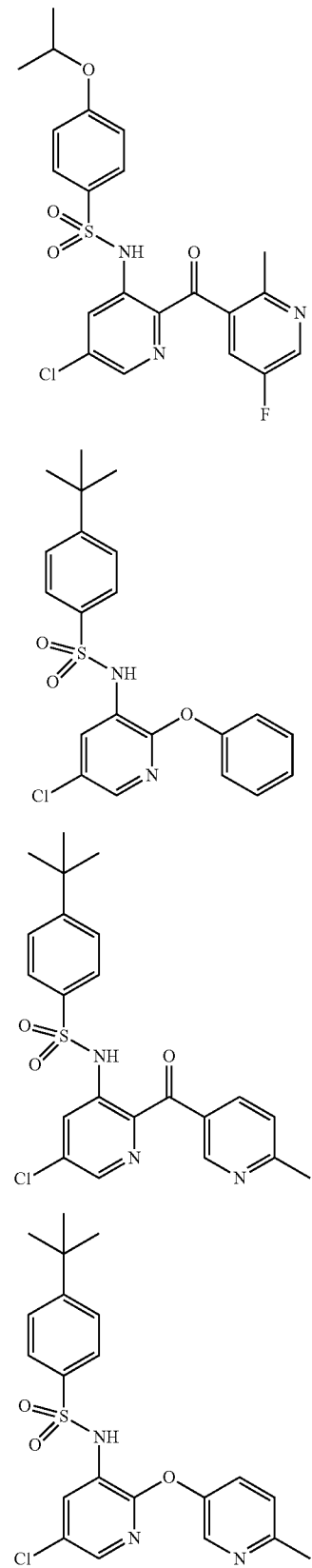
542
TABLE 2-continued
Compounds with CCR9 activity in one of the chemotaxis, binding or calcium mobilization assays, with 1050 <1000 nM
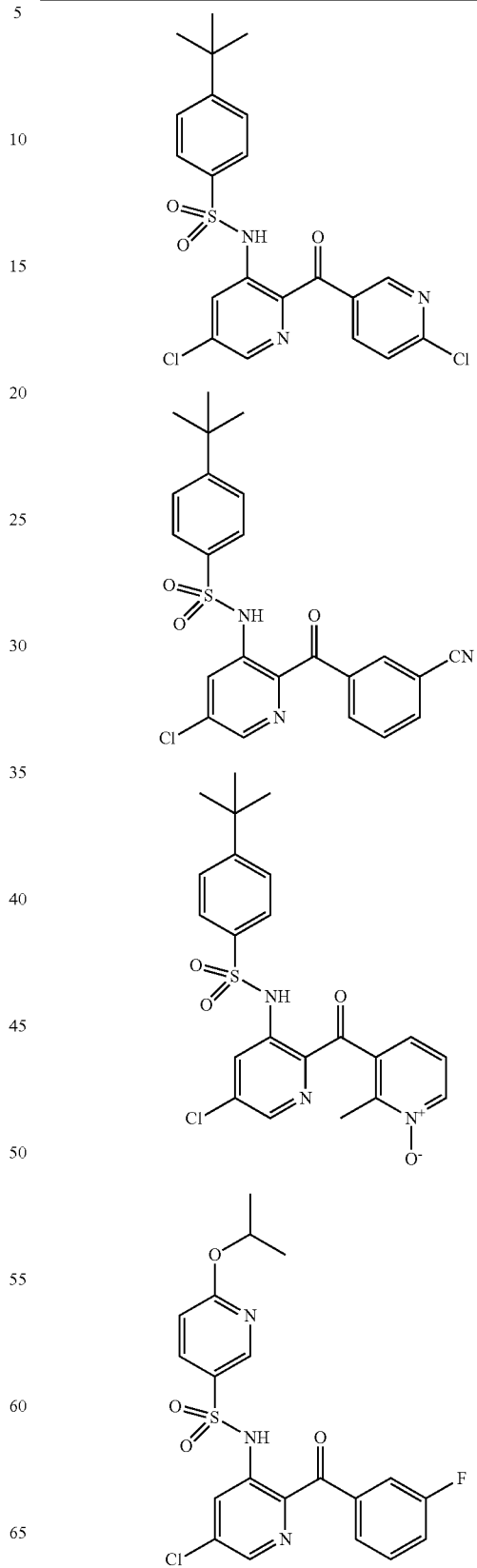

TABLE 2-continued
Compounds with CCR9 activity in one of the chemotaxis, binding or calcium mobilization assays, with IC50 <1000 nM
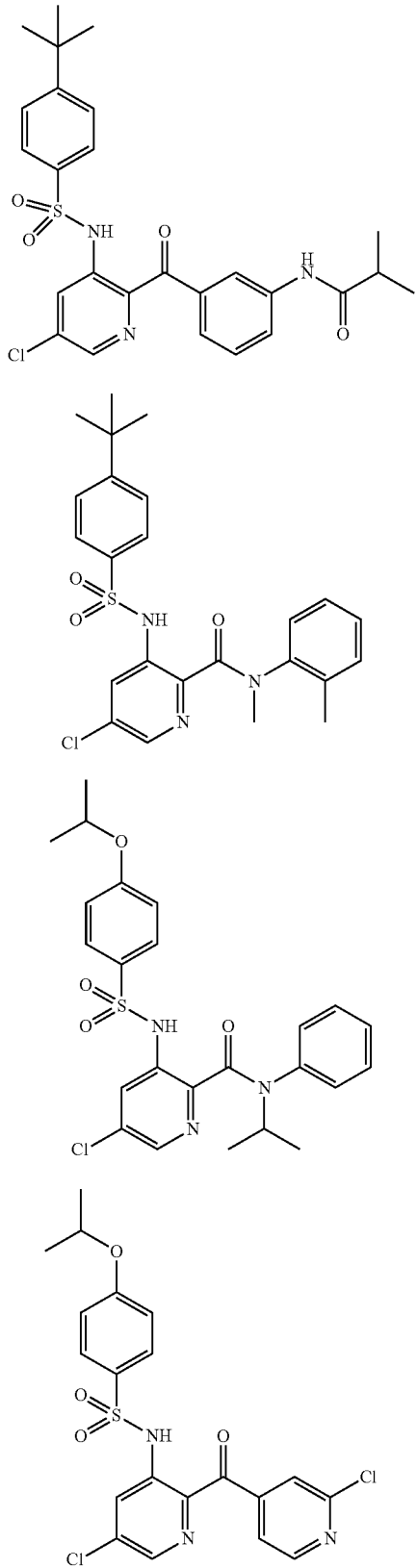
TABLE 2-continued
Compounds with CCR9 activity in one of the chemotaxis, binding or calcium mobilization assays, with IC50 <1000 nM
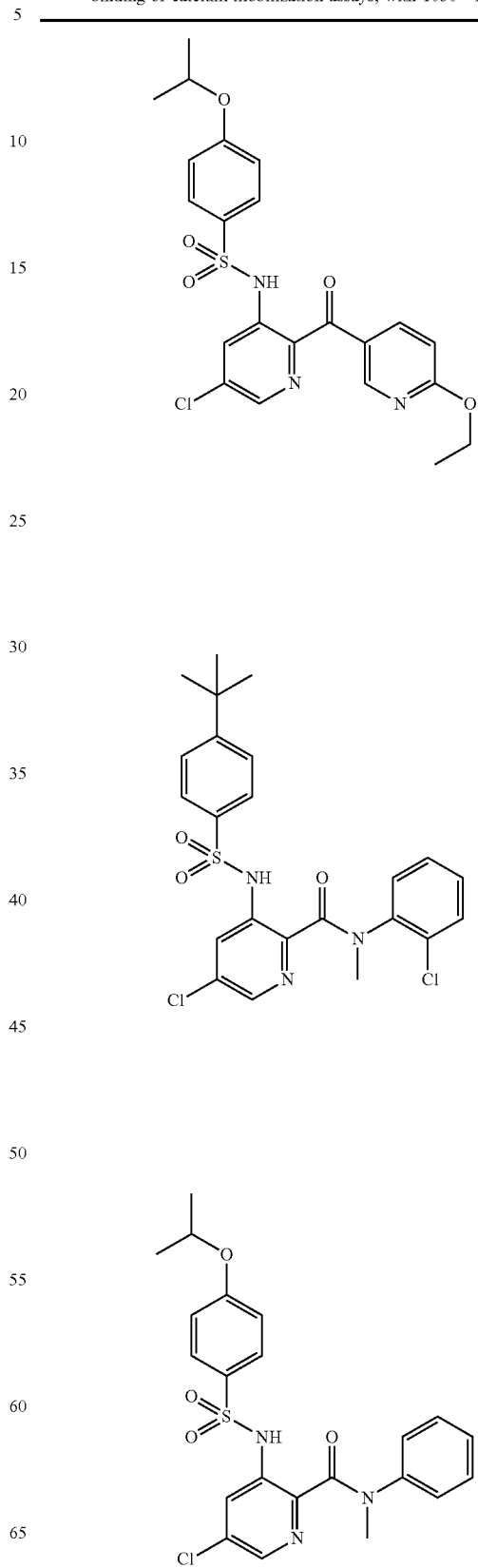

TABLE 2-continued
Compounds with CCR9 activity in one of the chemotaxis, binding or calcium mobilization assays, with 1050 <1000 nM
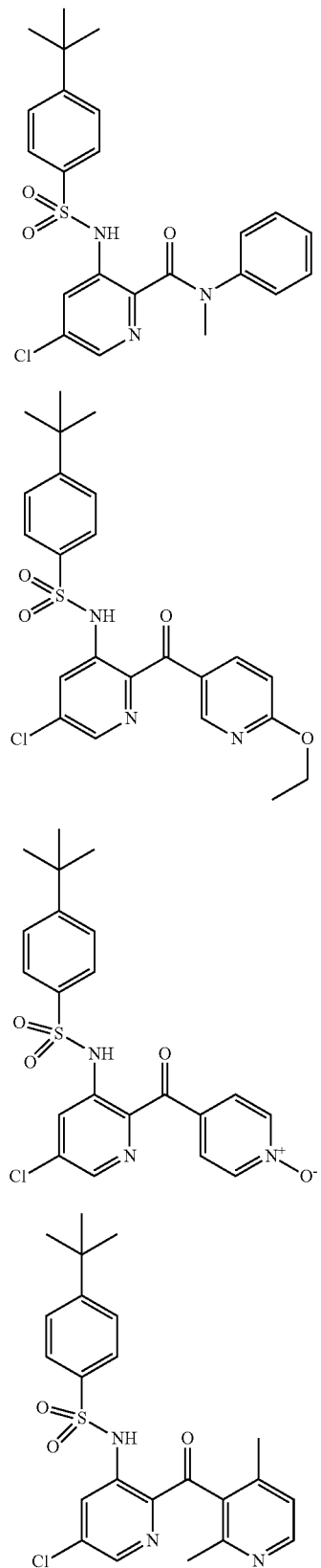
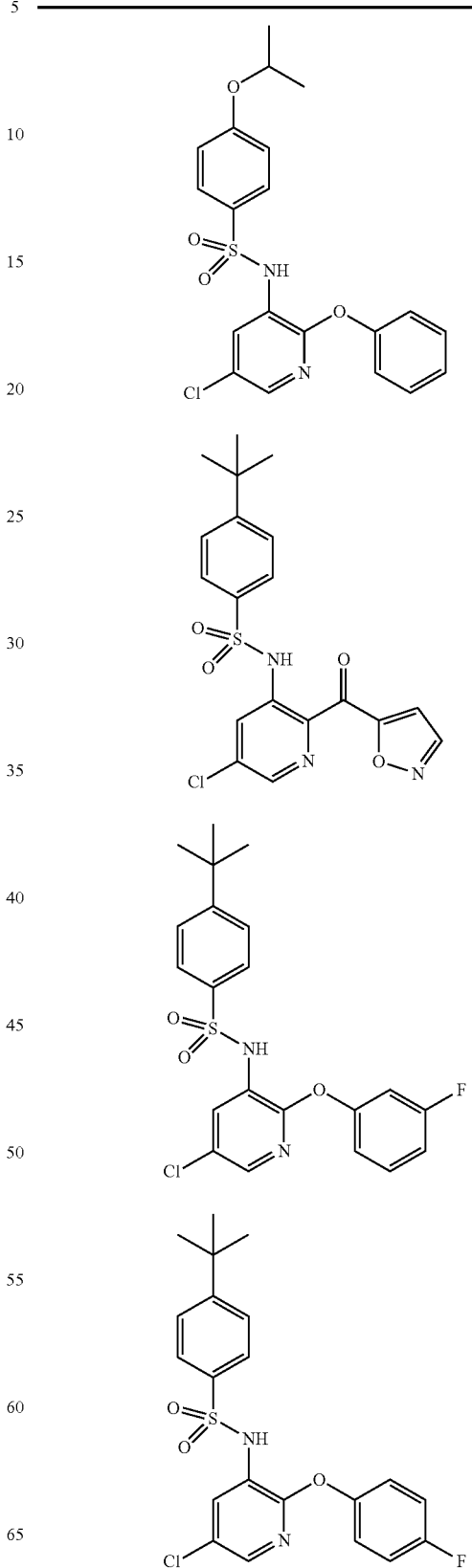

TABLE 2-continued
Compounds with CCR9 activity in one of the chemotaxis, binding or calcium mobilization assays, with IC50 <1000 nM
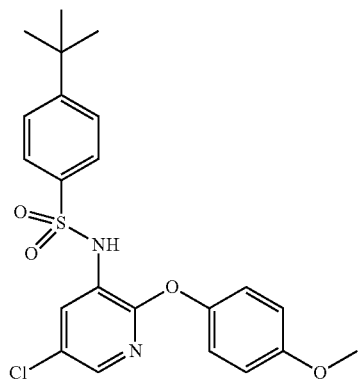 [SMILES: COc1ccc(Oc2ncc(Cl)cc2NS(=O)(=O)c2ccc(C(C)(C)C)cc2)cc1]
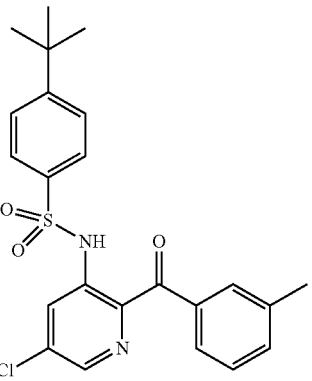
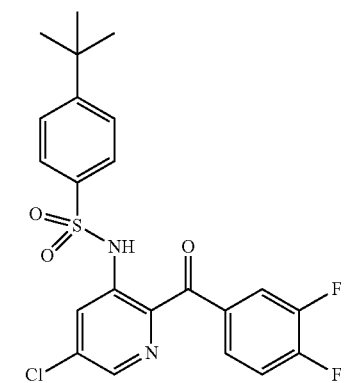 [SMILES: CC(C)(C)c1ccc(S(=O)(=O)Nc2cc(Cl)cnc2C(=O)c2ccc(F)c(F)c2)cc1]
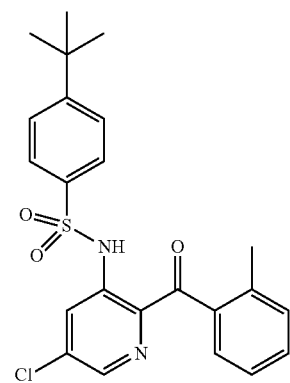
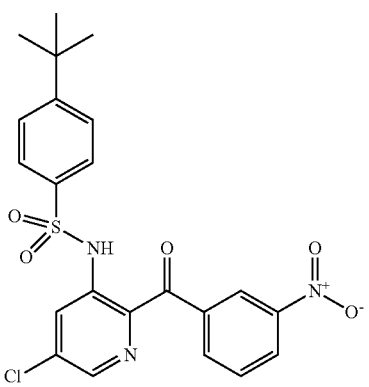 [SMILES: CC(C)(C)c1ccc(S(=O)(=O)Nc2cc(Cl)cnc2C(=O)c2cccc([N+](=O)[O-])c2)cc1]
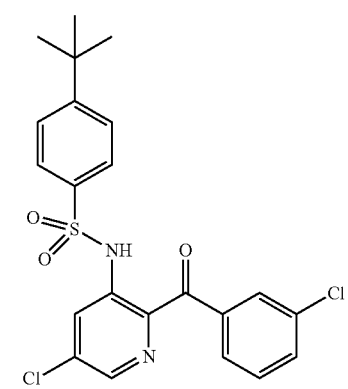 [SMILES: CC(C)(C)c1ccc(S(=O)(=O)Nc2cc(Cl)cnc2C(=O)c2cccc(Cl)c2)cc1]
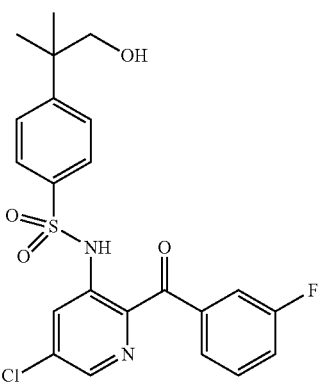 [SMILES: CC(C)(CO)c1ccc(S(=O)(=O)Nc2cc(Cl)cnc2C(=O)c2cccc(F)c2)cc1]
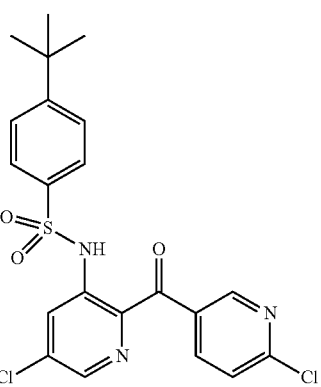

TABLE 2-continued
Compounds with CCR9 activity in one of the chemotaxis, binding or calcium mobilization assays, with IC50 <1000 nM
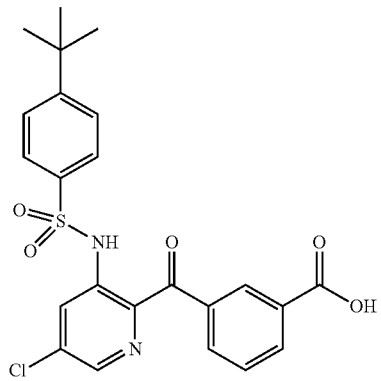 [SMILES: CC(C)(C)c1ccc(S(=O)(=O)Nc2cc(Cl)cnc2C(=O)c2cccc(C(=O)O)c2)cc1]
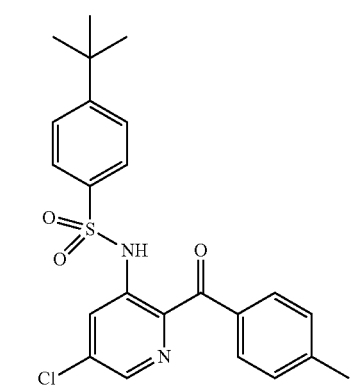 [SMILES: Cc1ccc(C(=O)c2ncc(Cl)cc2NS(=O)(=O)c2ccc(C(C)(C)C)cc2)cc1]
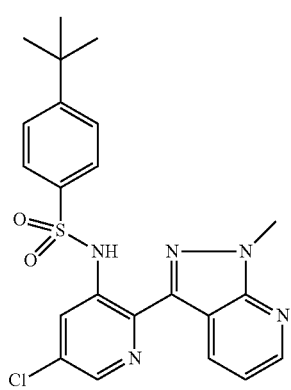 [SMILES: Cn1nc(-c2ncc(Cl)cc2NS(=O)(=O)c2ccc(C(C)(C)C)cc2)c2cccnc21]
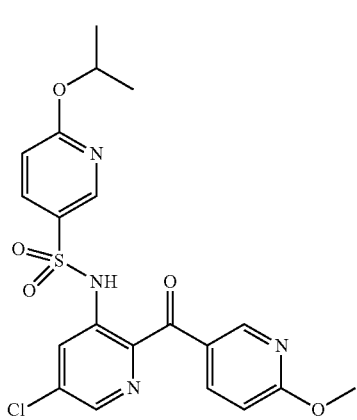 [SMILES: COc1ccc(C(=O)c2ncc(Cl)cc2NS(=O)(=O)c2ccc(OC(C)C)nc2)cn1]
TABLE 2-continued
Compounds with CCR9 activity in one of the chemotaxis, binding or calcium mobilization assays, with IC50 <1000 nM
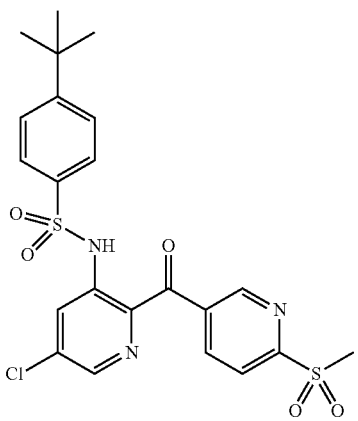 [SMILES: CC(C)(C)c1ccc(S(=O)(=O)Nc2cc(Cl)cnc2C(=O)c2ccc(S(C)(=O)=O)nc2)cc1]
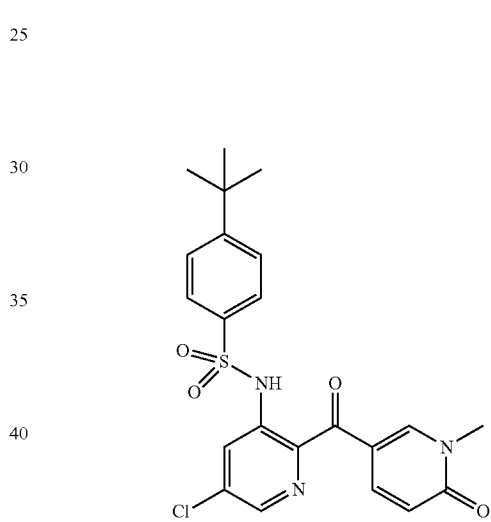
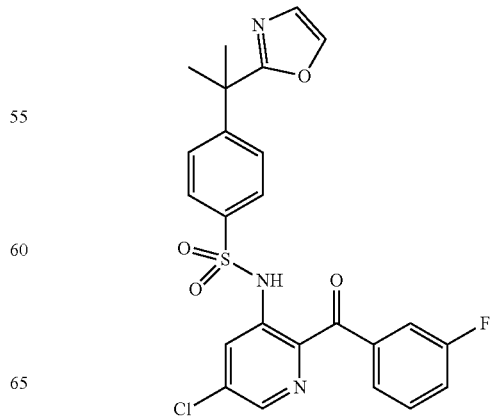

TABLE 2-continued
Compounds with CCR9 activity in one of the chemotaxis, binding or calcium mobilization assays, with IC50 <1000 nM
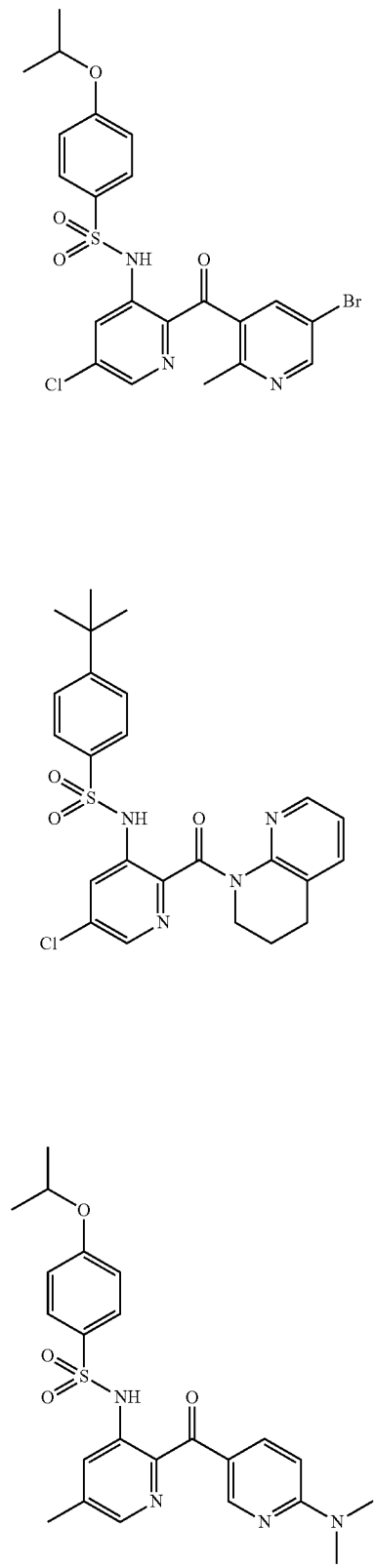
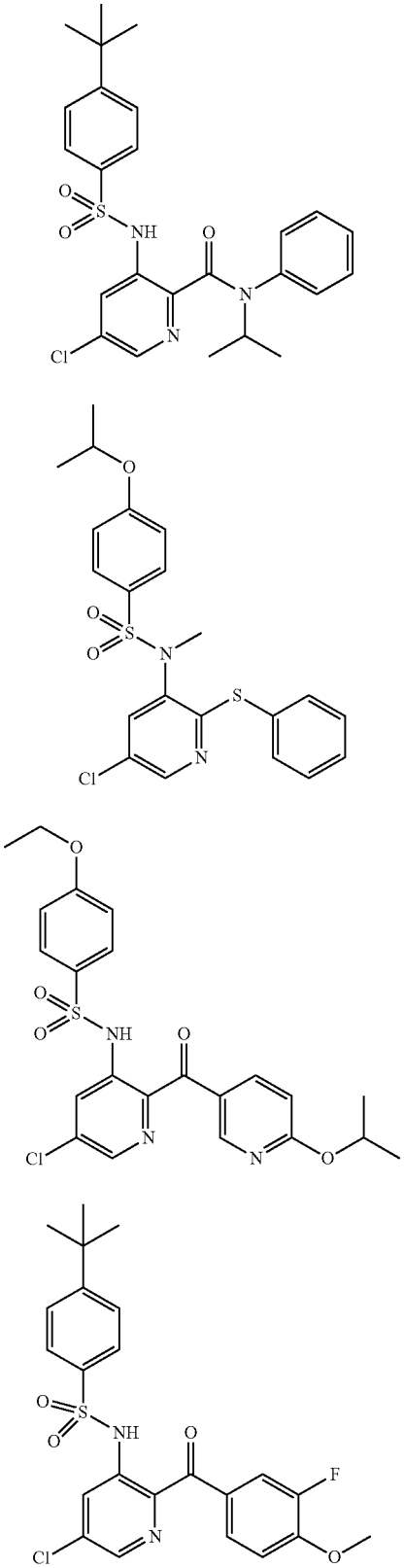

TABLE 2-continued

Compounds with CCR9 activity in one of the chemotaxis, binding or calcium mobilization assays, with 1050 <1000 nM

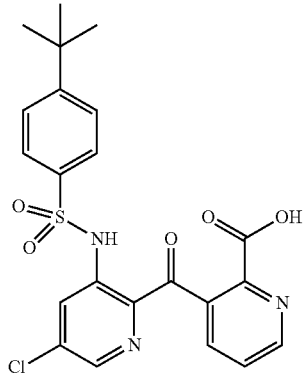 [SMILES: CC(C)(C)c1ccc(S(=O)(=O)Nc2cc(Cl)cnc2C(=O)c2cccnc2C(=O)O)cc1]

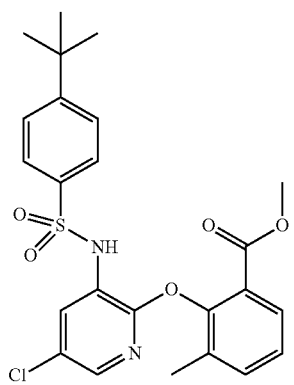 [SMILES: COC(=O)c1cccc(C)c1Oc1ncc(Cl)cc1NS(=O)(=O)c1ccc(C(C)(C)C)cc1]

It is therefore intended that the foregoing detailed description be regarded as illustrative rather than limiting, and that it be understood that it is the following claims, including all equivalents, that are intended to define the spirit and scope of this invention.

The invention claimed is:

1. A compound of formula (Ie), or a salt thereof:

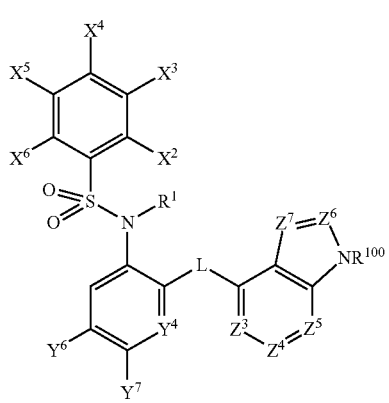

where:

$X^3$ and $X^4$ are each independently hydrogen, halogen, substituted or unsubstituted $C_{1-8}$ alkyl, —CN, or $C_{1-8}$ haloalkyl, provided that at least one of $X^3$ or $X^4$ is other than hydrogen;

each $X^2$, $X^5$, and $X^6$ is independently hydrogen, halogen, or substituted or unsubstituted $C_{1-4}$ alkyl;

$R^1$ is hydrogen or substituted or unsubstituted $C_{1-8}$ alkyl;

$Y^6$ is halogen or substituted or unsubstituted $C_{1-8}$ alkyl;

$Y^7$ is hydrogen or substituted or unsubstituted $C_{1-4}$ alkyl;

$R^{100}$ is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl and substituted or unsubstituted 3- to 10-membered heterocycle;

L is selected from the group consisting of a bond, —C(O)—, and —C(=N—O—$R^9$)—;

$Y^4$ is —$CR^{2a}$—, —N—, or —$N^+(O)^-$—;

$Z^3$ and $Z^4$ are each independently —$CR^{67}$—;

$Z^5$ is —N— or —$N^+(O)^-$—;

$Z^6$ and $Z^7$ are each independently —$CR^{67}$—, —N—, or —$N^+(O)^-$—; and each $R^{67}$ is independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^{68}$, —$OC(O)R^{68}$, —$CO_2R^{68}$, —$C(O)R^{68}$, —$C(O)NR^{69}R^{68}$, —$OC(O)NR^{69}R^{68}$, —$NR^{70}C(O)R^{68}$, —$NR^{70}C(O)NR^{69}R^{68}$, —$NR^{69}R^{68}$, —$NR^{70}CO2R^{68}$, —$SR^{68}$, —$S(O)R^{68}$, —$S(O)_2R^{68}$, —$S(O)_2NR^{69}R^{68}$, —$NR^{70}S(O)_2R^{68}$, substituted or unsubstituted $C_{6-10}$ aryl, substituted or unsubstituted 5- to 10-membered heteroaryl and substituted or unsubstituted 3- to 10-membered heterocyclyl;

each occurrence of $R^{68}$, $R^{69}$, and $R^{70}$ is independently selected from the group consisting of hydrogen, $C_{1-8}$ alkyl, $C_{2-8}$ alkenyl, $C_{2-8}$ alkynyl, aryl, or heteroaryl; or $R^{69}$ and $R^{68}$ or $R^{70}$ and $R^{68}$, together with the atom(s) to which they are attached, form an substituted or unsubstituted 5-, 6-, or 7-membered ring.

2. The compound of claim 1, wherein L is —C(O)—.

3. The compound of claim 1, wherein $X^3$ and $X^4$ are each independently halogen or $C_{1-8}$ haloalkyl.

4. The compound of claim 1, wherein $X^2$, $X^5$, and $X^6$ are each H.

5. The compound of claim 1, wherein $R^1$ is hydrogen.

6. The compound of claim 1, wherein $Y^6$ is unsubstituted $C_{1-8}$ alkyl.

7. The compound of claim 1, wherein $Y^7$ is hydrogen.

8. The compound of claim 1, wherein $Y^4$ is —N— or —$N_+(O)^-$—.

9. The compound of claim 1, wherein $Z^6$ and $Z^7$ are —CH—.

10. The compound of claim 1, wherein $Z^5$ is —N—.

11. The compound of claim 1, wherein $R^{100}$ is hydrogen.

12. The compound of claim 1, wherein each $R^{67}$ is hydrogen.

13. The compound of claim 1, which is of formula (If):
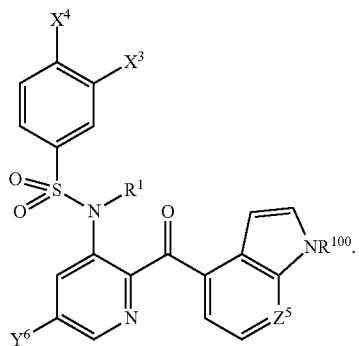
(If)
14. The compound of claim 1, which is of formula (Ig):
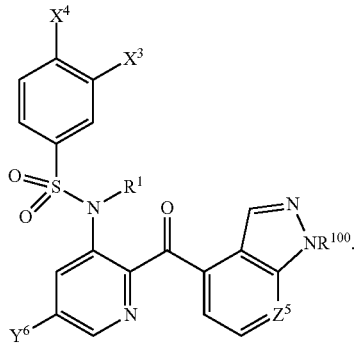
(Ig)
15. A compound selected from the group consisting of:
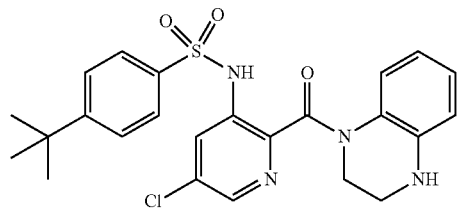
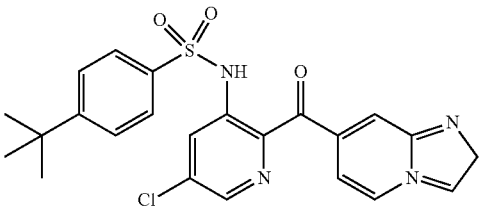
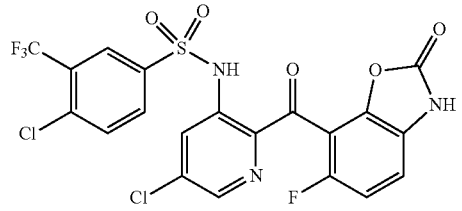
-continued
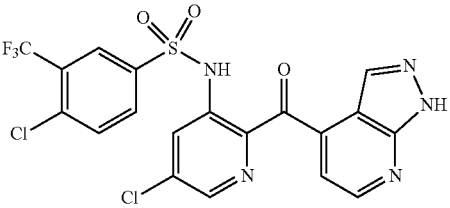
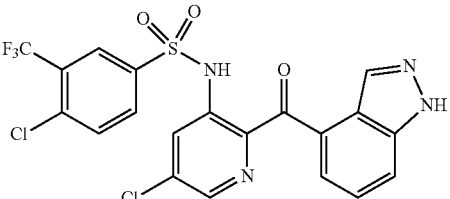
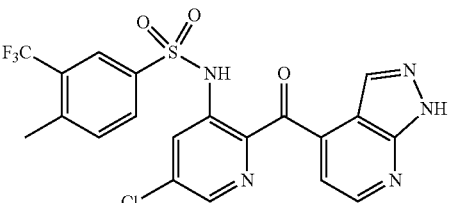
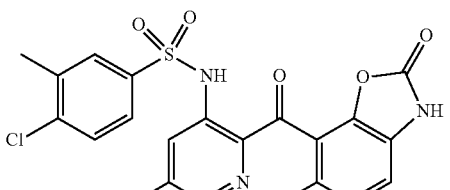
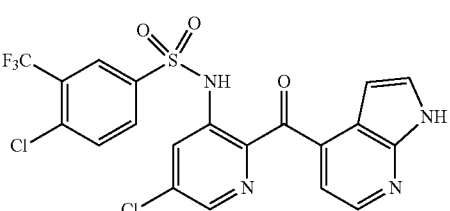
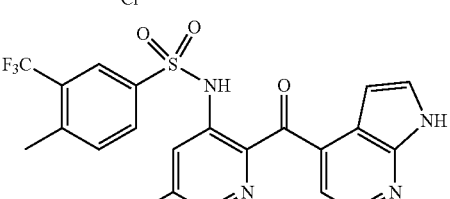
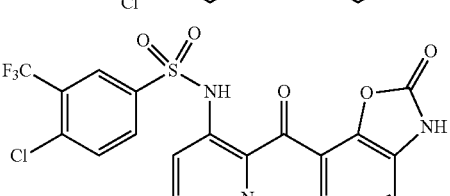
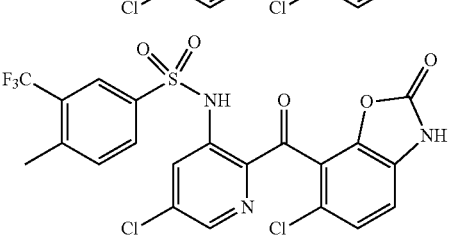

557
-continued
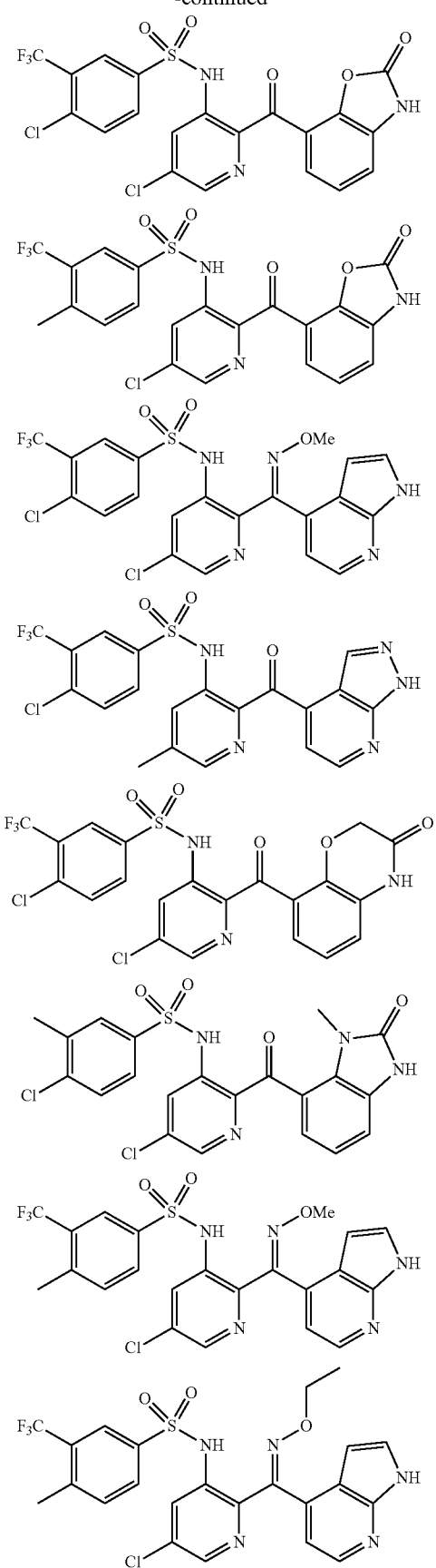
558
-continued
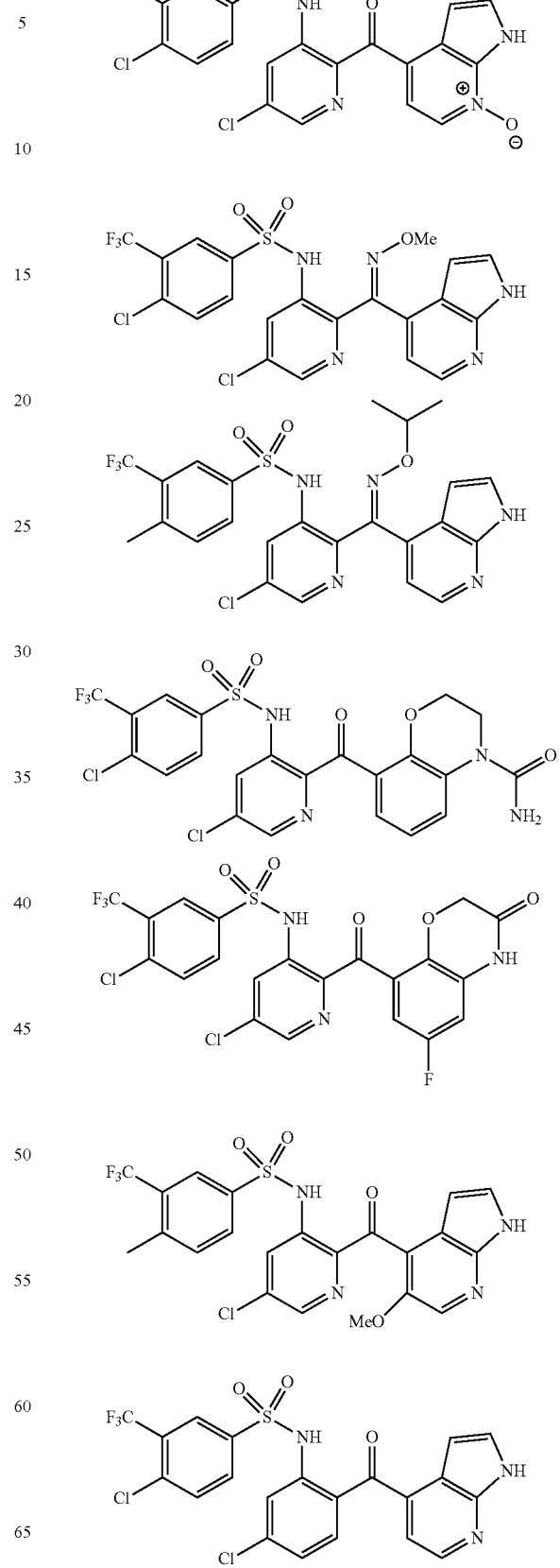

559
-continued
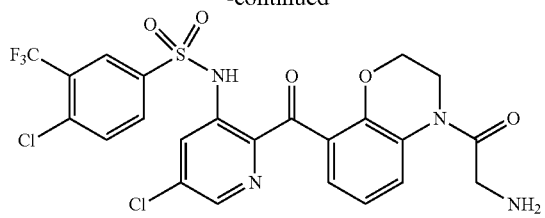
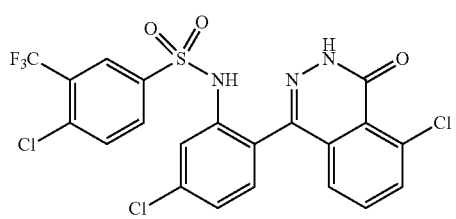
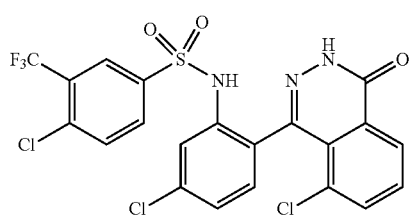
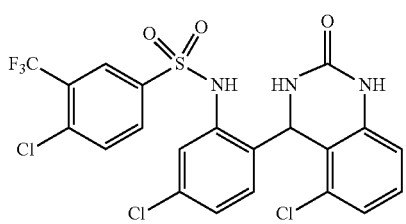
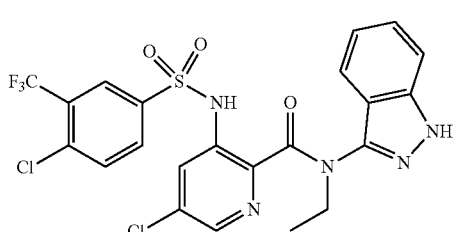
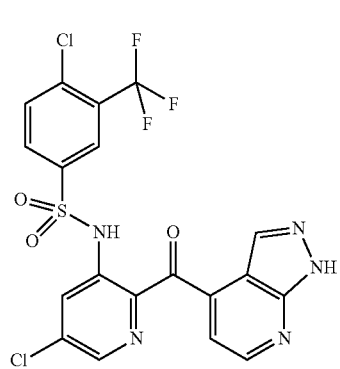
560
-continued
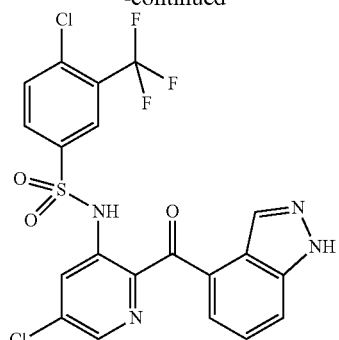
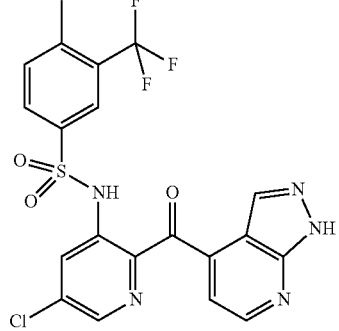
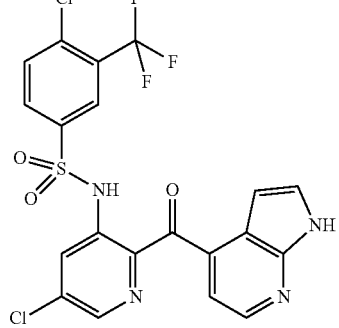
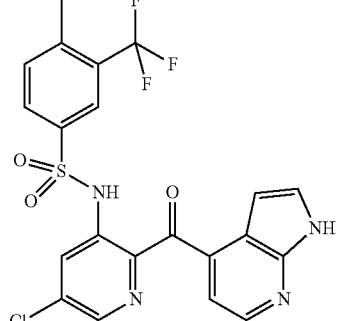
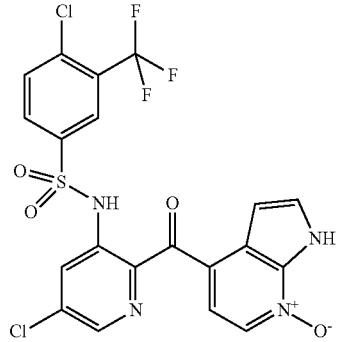

561
-continued
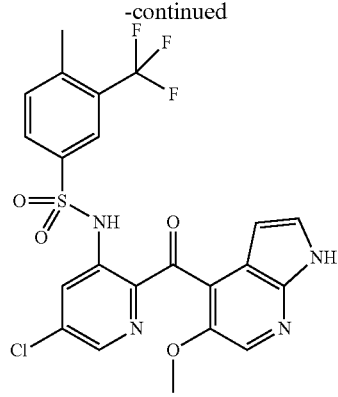
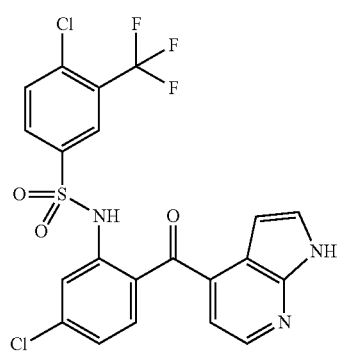
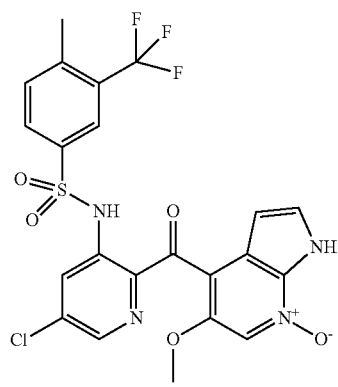
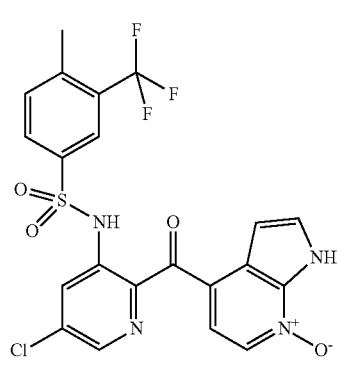
562
-continued
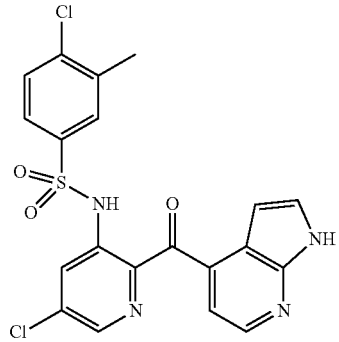
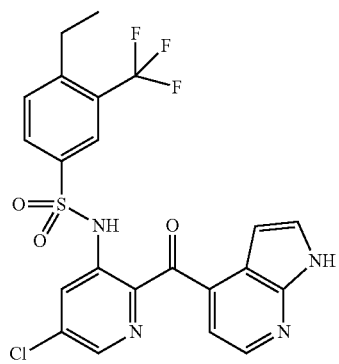
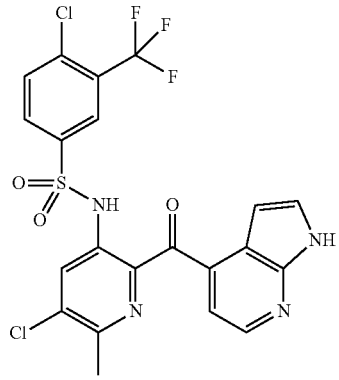
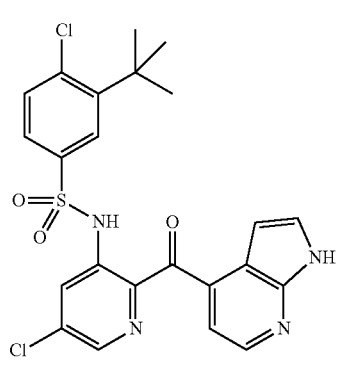

563
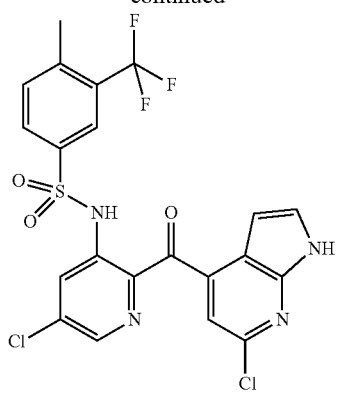
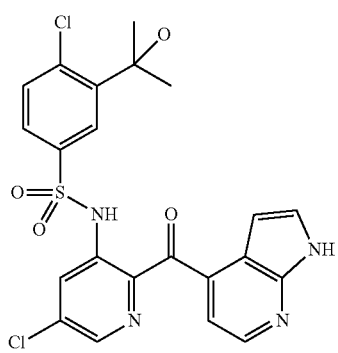
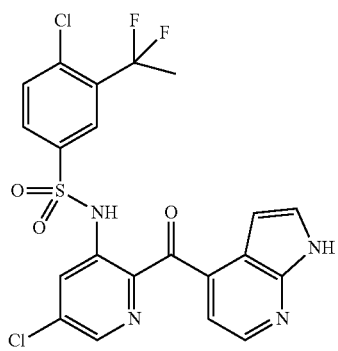
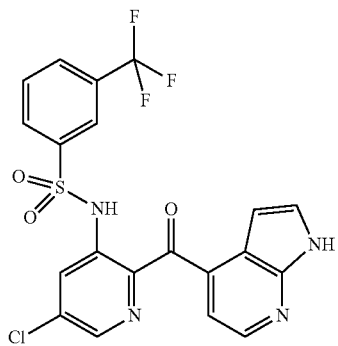
564
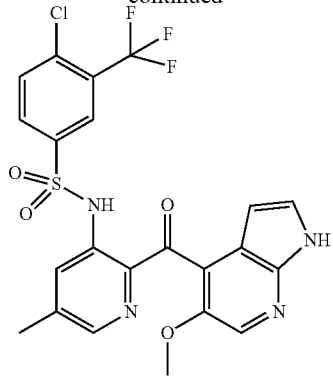
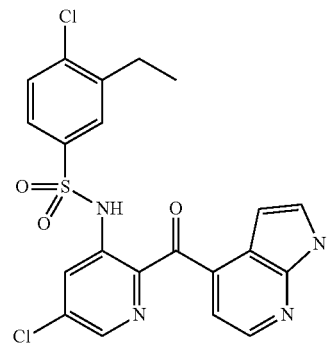
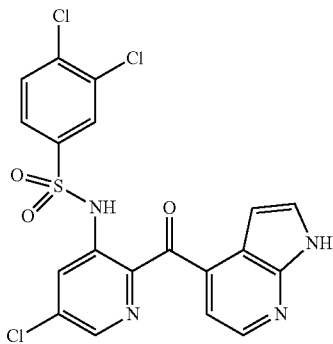
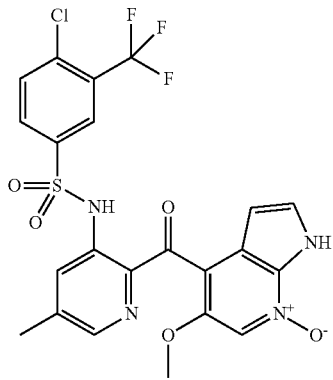

565
-continued
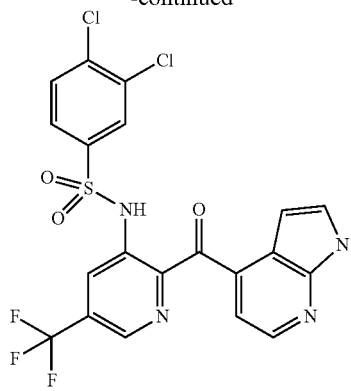
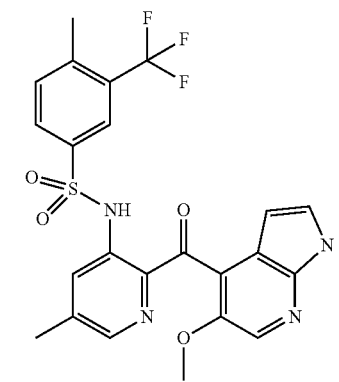
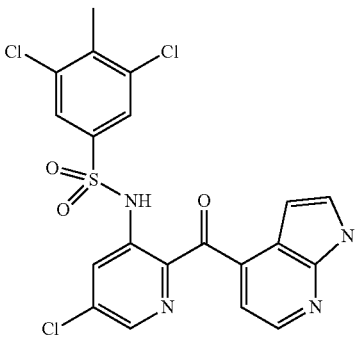
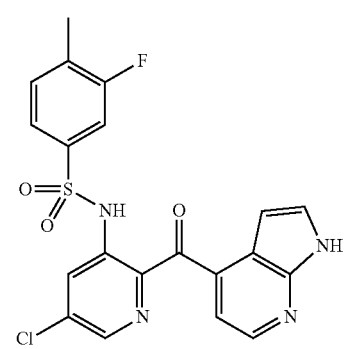
566
-continued
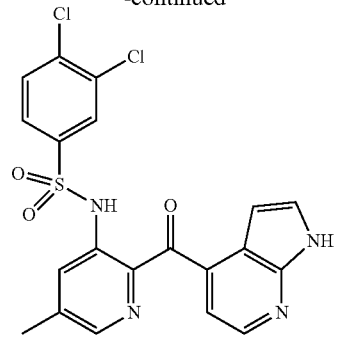
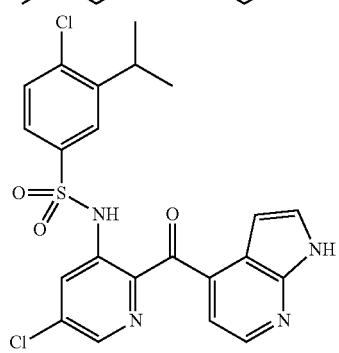
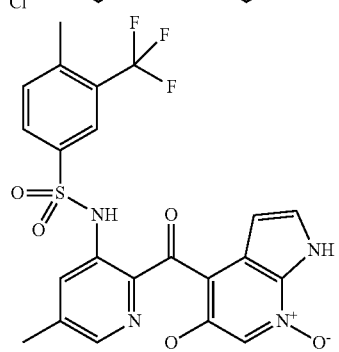
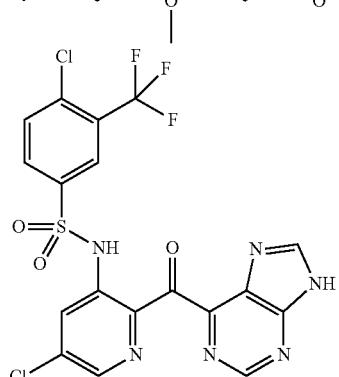
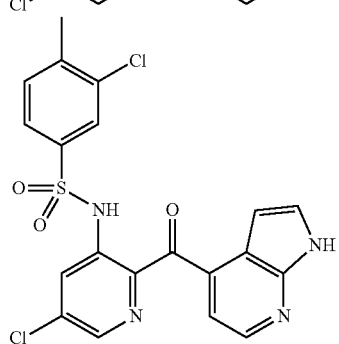

567
-continued
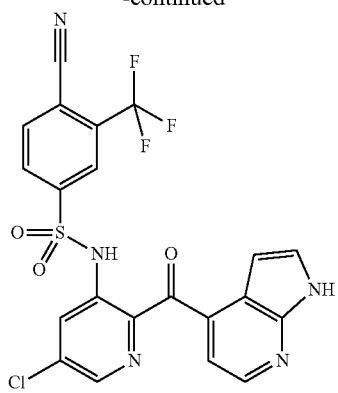
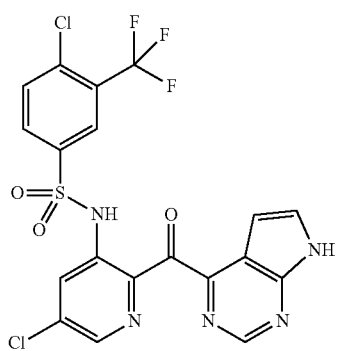
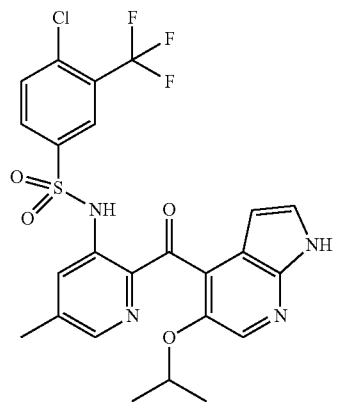
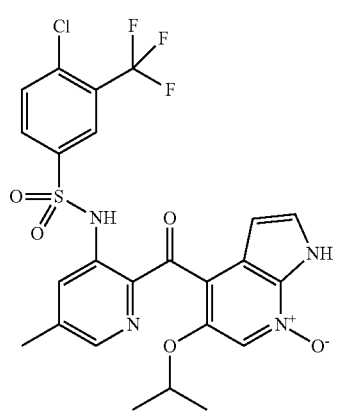
568
-continued
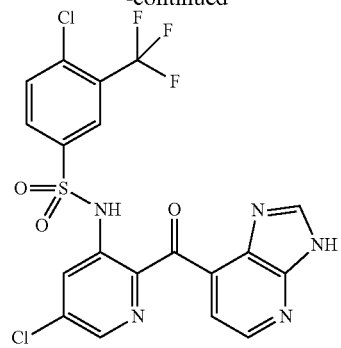
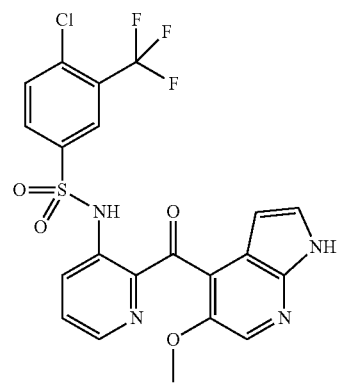
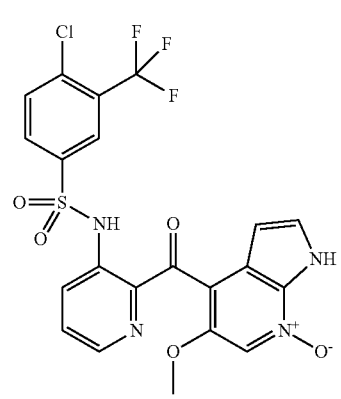
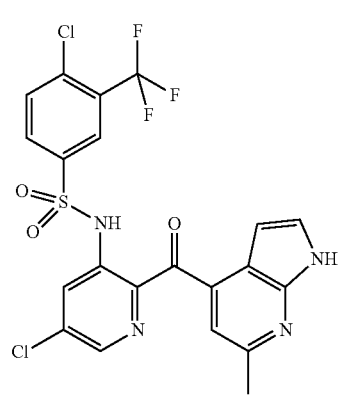

569
-continued
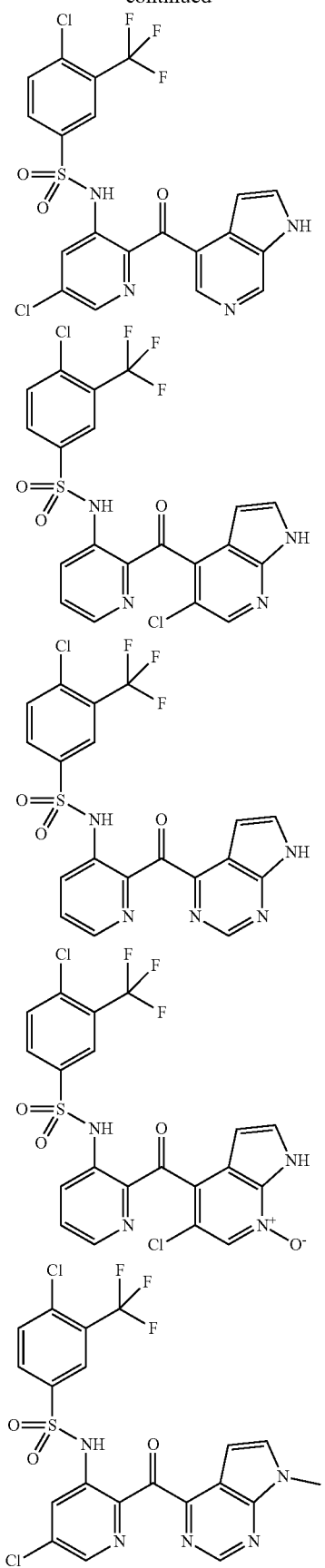
570
-continued
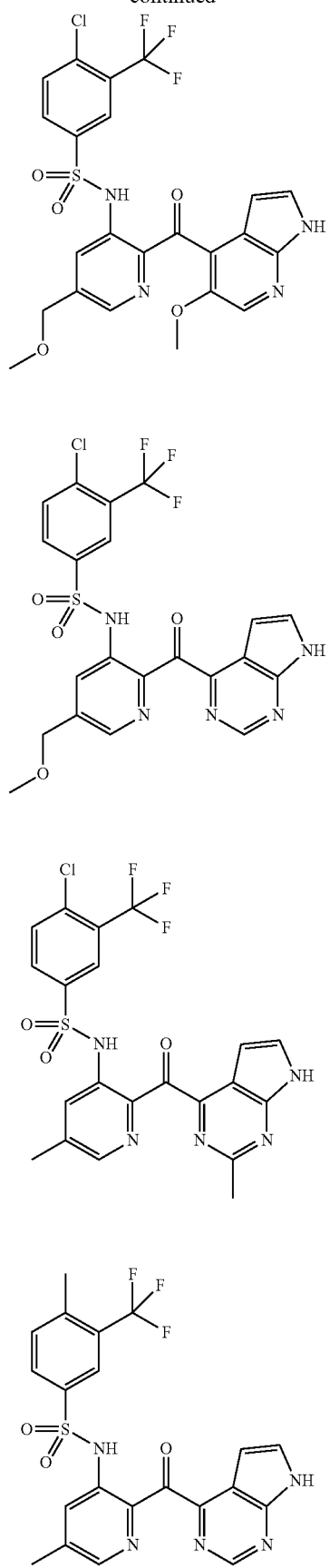

571
-continued
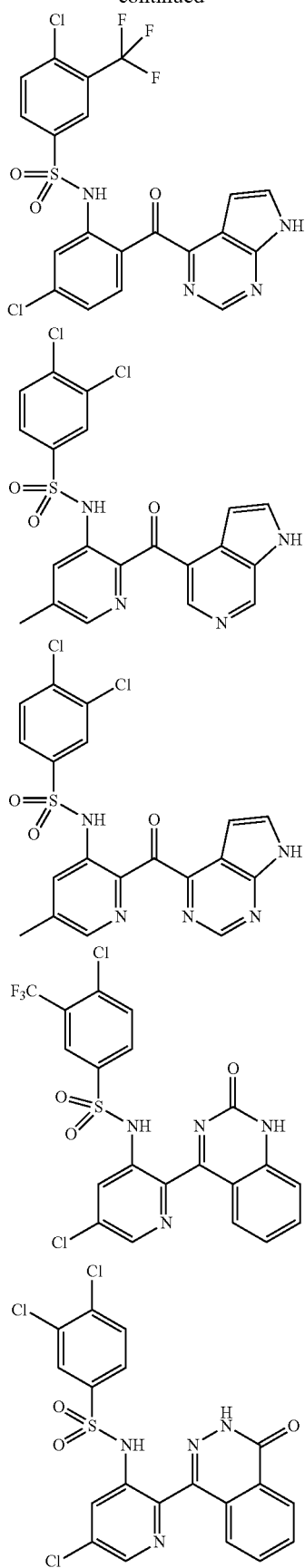
572
-continued
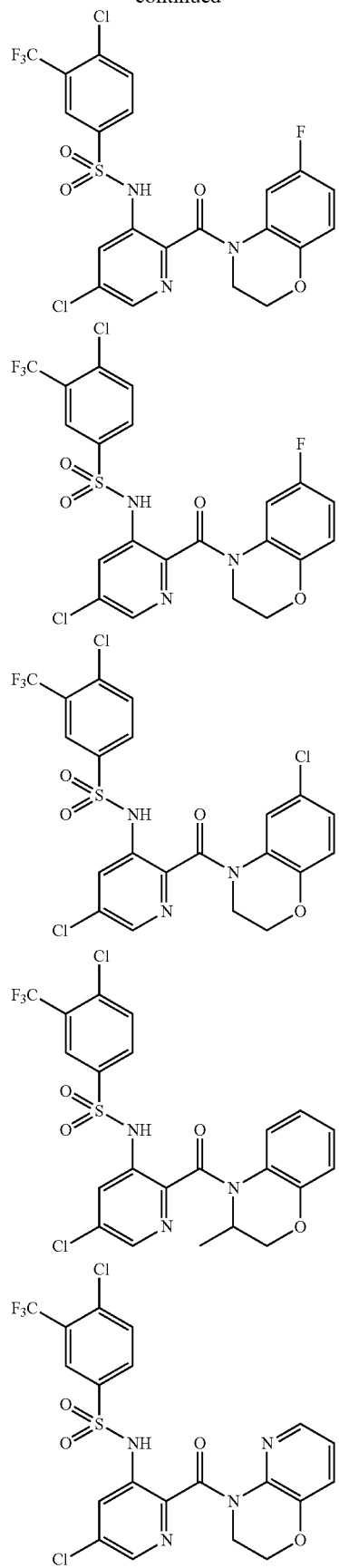

573
-continued
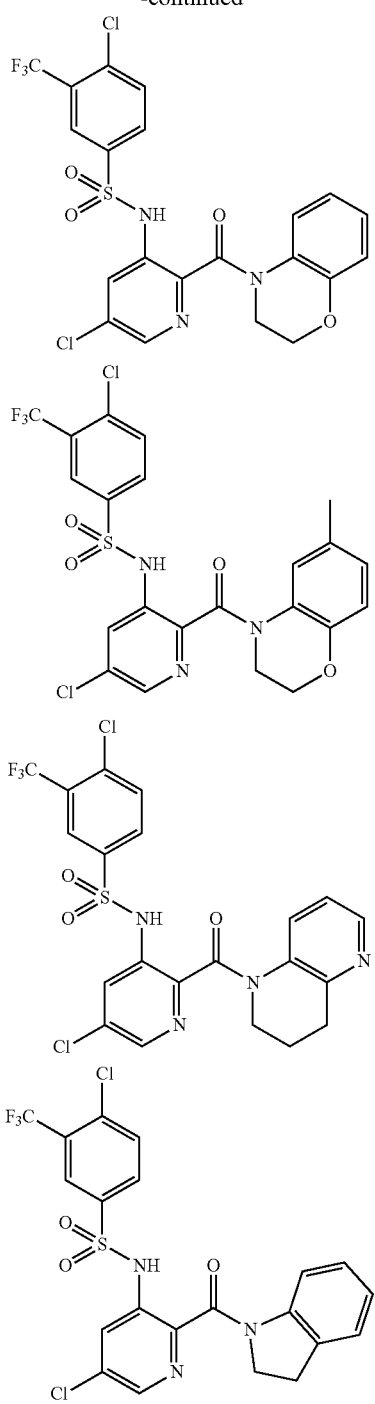
574
-continued
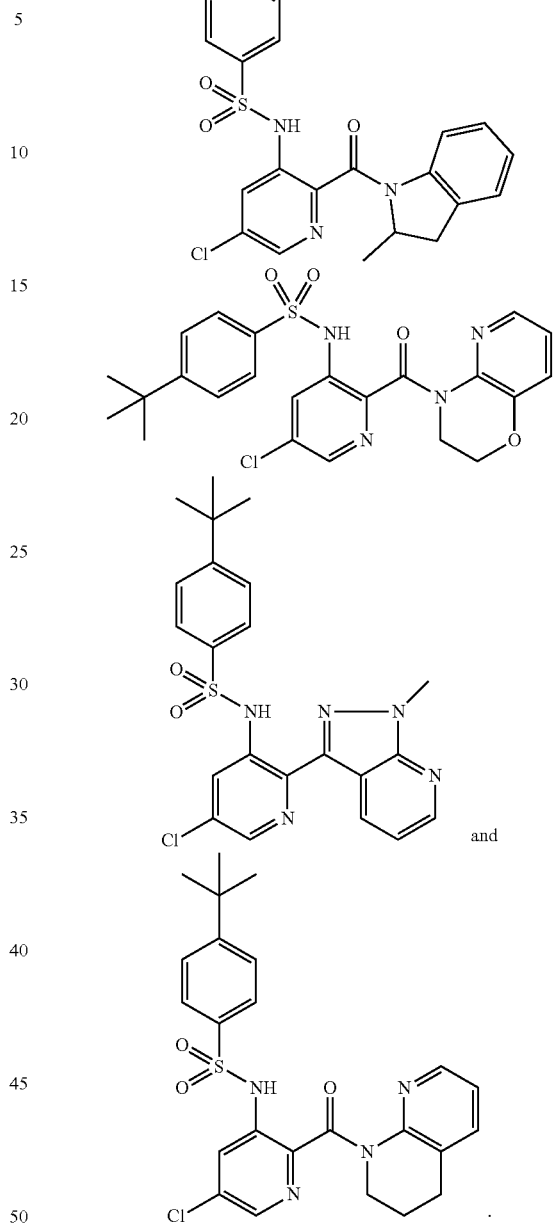
and
16. A composition comprising a pharmaceutically acceptable carrier and the compound or salt of claim 1.
* * * * *

UNITED STATES PATENT AND TRADEMARK OFFICE
CERTIFICATE OF CORRECTION

PATENT NO. : 11,433,061 B2
APPLICATION NO. : 16/739204
DATED : September 6, 2022
INVENTOR(S) : Solomon Ungashe et al.

It is certified that error appears in the above-identified patent and that said Letters Patent is hereby corrected as shown below:

In the Claims

In Claim 1, Column 554, Line 32, please delete "—$NR^{70}CO2R^{68}$—" and insert in place thereof -- —$NR^{70}CO_2R^{68}$— --
In Claim 8, Column 554, Line 58, please delete "—$N_+(O)^-$—" and insert in place thereof -- —$N^+(O)^-$— --

Signed and Sealed this
Twentieth Day of December, 2022

*Katherine Kelly Vidal*

Katherine Kelly Vidal
*Director of the United States Patent and Trademark Office*